(12) United States Patent
Chafeev et al.

(10) Patent No.: US 8,466,188 B2
(45) Date of Patent: Jun. 18, 2013

(54) USE OF SPIRO-OXINDOLE COMPOUNDS AS THERAPEUTIC AGENTS

(75) Inventors: Mikhail Chafeev, Burnaby (CA); Sultan Chowdhury, Surrey (CA); Robert Fraser, North Vancouver (CA); Jianmin Fu, Coquitlam (CA); Rajender Kamboj, Burnaby (CA); Duanjie Hou, Burnaby (CA); Shifeng Liu, Coquitlam (CA); Mehran Seid Bagherzadeh, Vancouver (CA); Serguei Sviridov, Burnaby (CA); Shaoyi Sun, Coquitlam (CA); Jianyu Sun, San Mateo, CA (US); Nagasree Chakka, Waltham, MA (US); Tom Hsieh, Toronto (CA); Vandna Raina, Gurgaon (IN)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 648 days.

(21) Appl. No.: 12/445,264

(22) PCT Filed: Oct. 12, 2007

(86) PCT No.: PCT/US2007/081247
§ 371 (c)(1),
(2), (4) Date: Mar. 4, 2010

(87) PCT Pub. No.: WO2008/060789
PCT Pub. Date: May 22, 2008

(65) Prior Publication Data
US 2011/0172282 A9    Jul. 14, 2011

Related U.S. Application Data

(60) Provisional application No. 60/851,787, filed on Oct. 12, 2006.

(51) Int. Cl.
*A61K 31/40* (2006.01)
*A61K 31/5377* (2006.01)

(52) U.S. Cl.
USPC ........ 514/409; 514/232.8; 514/256; 514/321; 514/338

(58) Field of Classification Search
None
See application file for complete search history.

(56) References Cited

U.S. PATENT DOCUMENTS

| | | | |
|---|---|---|---|
| 3,189,617 A | 6/1965 | Archer et al. | 260/319 |
| 3,723,459 A | 3/1973 | Paragamian | 260/325 |
| 3,845,770 A | 11/1974 | Theeuwes et al. | 128/260 |
| 4,045,576 A | 8/1977 | Welstead, Jr. et al. | 424/309 |
| 4,326,525 A | 4/1982 | Swanson et al. | 128/260 |
| 4,438,130 A | 3/1984 | Kaplan | 424/274 |
| 4,440,785 A | 4/1984 | Walsh | 424/317 |
| 4,670,566 A | 6/1987 | Walsh | 548/485 |
| 4,886,788 A | 12/1989 | Skuballa et al. | 514/58 |
| 4,935,446 A | 6/1990 | Imaki et al. | 514/530 |
| 5,023,265 A | 6/1991 | Scherlock et al. | 514/300 |
| 5,116,854 A | 5/1992 | Marfat | 514/365 |
| 5,182,289 A | 1/1993 | Ting et al. | 514/278 |
| 5,278,162 A | 1/1994 | Wilkerson | 514/252 |
| 5,296,478 A | 3/1994 | Teleha | 514/235.2 |
| 5,304,121 A | 4/1994 | Sahatjian | |
| 5,453,516 A | 9/1995 | Fischer et al. | 548/543 |
| 5,663,431 A | 9/1997 | Di Malta et al. | 562/828 |
| 5,686,624 A | 11/1997 | Di Malta et al. | 548/410 |
| 5,696,145 A | 12/1997 | Foulon et al. | 514/409 |
| 5,723,625 A | 3/1998 | Keplinger et al. | 548/408 |
| 5,726,322 A | 3/1998 | Di Malta et al. | 548/410 |
| 5,728,723 A | 3/1998 | Di Malta et al. | 514/418 |
| 5,763,471 A | 6/1998 | Fourtillan et al. | 514/409 |
| 5,767,128 A | 6/1998 | Guillaumet et al. | 514/300 |
| 5,776,936 A | 7/1998 | Lee et al. | 514/250 |
| 5,849,780 A | 12/1998 | Di Malta et al. | 514/409 |
| 5,886,026 A | 3/1999 | Hunter et al. | |

(Continued)

FOREIGN PATENT DOCUMENTS

| CA | 2095718 A1 | 5/1992 |
|---|---|---|
| CA | 2107348 A1 | 7/1993 |

(Continued)

OTHER PUBLICATIONS

Response to Official Action from European Patent Office re extended European search report, dated Dec. 13, 2012, for Patent Application No. 11009687.2, 9 pages.
Translation of Official Action from Israel Patent Office, dated Dec. 19, 2012, for Patent Application No. 186616, 3 pages.
Response to Official Action from European Patent Office, dated Dec. 14, 2012, for Patent Application No. 10 771 606.0, 25 pages.
Official Action from New Zealand Intellectual Property Office, dated Dec. 6, 2012, for Patent Application No. 599334, 2 pages.

(Continued)

*Primary Examiner* — Sreeni Padmanabhan
*Assistant Examiner* — Jody Karol
(74) *Attorney, Agent, or Firm* — Seed IP Law Group PLLC

(57) ABSTRACT

This invention is directed to methods of using spiro-oxindole compounds of formula (I): wherein k, j, Q, $R^1$, $R^{2a}$, $R^{2b}$, $R^{2c}$, $R^{2d}$, $R^{3a}$, $R^{3b}$, $R^{3c}$, and $R^{3d}$ are as defined herein, as a stereoisomer, enantiomer, tautomer thereof or mixtures thereof; or a pharmaceutically acceptable salt, solvate or prodrug thereof, for the treatment and/or prevention of hypercholesterolemia, benign prostatic hyperplasia, pruritis and cancer.

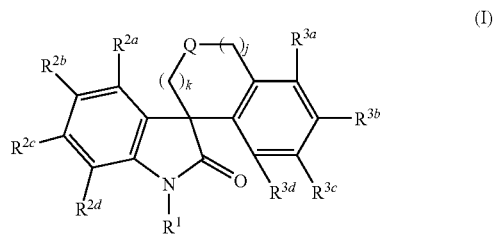

(I)

1 Claim, No Drawings

U.S. PATENT DOCUMENTS

| | | | |
|---|---|---|---|
| 5,994,350 A | 11/1999 | Foulon et al. | 514/232.8 |
| 6,046,341 A | 4/2000 | Foulon et al. | 548/411 |
| 6,090,818 A | 7/2000 | Foulon et al. | 514/278 |
| 6,099,562 A | 8/2000 | Ding et al. | |
| 6,110,969 A | 8/2000 | Tani et al. | 514/530 |
| 6,225,347 B1 | 5/2001 | Buchmann et al. | 514/530 |
| 6,235,780 B1 | 5/2001 | Ohuchida et al. | 514/530 |
| 6,262,293 B1 | 7/2001 | Tani et al. | 560/18 |
| 6,288,119 B1 | 9/2001 | Ohuchida et al. | 514/573 |
| 6,355,627 B1 | 3/2002 | Ishida et al. | 514/58 |
| 6,414,153 B1 | 7/2002 | Kelly et al. | 546/113 |
| 6,670,357 B2 | 12/2003 | Leftheris et al. | 514/218 |
| 6,964,973 B2 | 11/2005 | Zhi et al. | 514/312 |
| 7,368,470 B2 | 5/2008 | Sundermann et al. | 514/415 |
| 7,700,641 B2 | 4/2010 | Chafeev et al. | 514/409 |
| 7,799,798 B2 * | 9/2010 | Chafeev et al. | 514/278 |
| 8,101,647 B2 * | 1/2012 | Chafeev et al. | 514/412 |
| 8,106,087 B2 * | 1/2012 | Chafeev et al. | 514/409 |
| 8,263,606 B2 * | 9/2012 | Chafeev et al. | 514/278 |
| 2002/0039790 A1 | 4/2002 | Keplinger et al. | 435/371 |
| 2004/0038970 A1 | 2/2004 | Thurieau et al. | 514/234.2 |
| 2004/0167224 A1 | 8/2004 | Ozaki et al. | 514/616 |
| 2005/0004137 A1 | 1/2005 | Romano | 514/253.07 |
| 2005/0004138 A1 | 1/2005 | Romano | 514/253.07 |
| 2005/0014764 A1 | 1/2005 | Romano et al. | 514/253.06 |
| 2005/0020617 A1 | 1/2005 | Bastian et al. | 514/300 |
| 2005/0038036 A1 | 2/2005 | Romano et al. | 514/253.06 |
| 2005/0075351 A1 | 4/2005 | Berg et al. | 514/266.2 |
| 2005/0153998 A1 | 7/2005 | Ito et al. | 514/278 |
| 2005/0159473 A1 | 7/2005 | Sall et al. | 514/414 |
| 2005/0171186 A1 | 8/2005 | Fensome et al. | 514/418 |
| 2005/0256110 A1 | 11/2005 | Collins et al. | 514/224.2 |
| 2005/0256144 A1 | 11/2005 | Kath et al. | 514/275 |
| 2006/0247441 A1 | 11/2006 | Wilk | 548/408 |
| 2006/0252758 A1 | 11/2006 | Chafeev et al. | 514/249 |
| 2007/0049609 A1 | 3/2007 | Broka et al. | 514/269 |
| 2007/0072831 A1 | 3/2007 | Cai et al. | 514/80 |
| 2007/0105820 A1 | 5/2007 | Chafeev et al. | 514/80 |
| 2007/0299102 A1 | 12/2007 | Felding et al. | 514/299 |
| 2008/0103151 A9 | 5/2008 | Chafeev et al. | 514/248 |
| 2010/0099728 A1 | 4/2010 | Chafeev et al. | 514/409 |
| 2010/0125072 A1 | 5/2010 | Chafeev et al. | 514/232.8 |
| 2010/0130487 A1 | 5/2010 | Chafeev et al. | 514/232.8 |
| 2010/0137299 A1 | 6/2010 | Chafeev et al. | 514/232.8 |
| 2010/0160291 A1 | 6/2010 | Chafeev et al. | 514/211.09 |
| 2010/0160362 A1 | 6/2010 | Cadieux et al. | 514/278 |
| 2010/0331386 A1 | 12/2010 | Chafeev et al. | 514/409 |
| 2011/0034500 A1 | 2/2011 | Chafeev et al. | 514/278 |
| 2011/0086899 A1 | 4/2011 | Winters et al. | 514/409 |
| 2011/0087027 A1 | 4/2011 | Cadieux et al. | 546/15 |
| 2011/0251224 A1 | 10/2011 | Chafeev et al. | 514/278 |
| 2011/0269788 A1 | 11/2011 | Cadieux et al. | 514/278 |
| 2011/0294842 A9 | 12/2011 | Cadieux et al. | |
| 2012/0295897 A1 | 11/2012 | Chafeev et al. | |

FOREIGN PATENT DOCUMENTS

| | | | |
|---|---|---|---|
| CA | 2129215 A1 | 1/1995 | |
| CA | 2 274 898 A1 | 6/1998 | |
| CA | 2 450 550 A1 | 1/2003 | |
| CA | 2 466 915 A1 | 8/2003 | |
| CA | 2 487 494 A1 | 12/2003 | |
| CA | 2 235 686 C | 6/2007 | |
| DE | 1 956 237 A | 5/1971 | |
| DE | 2113343 A1 | 9/1972 | |
| EP | 0 147 805 A2 | 7/1985 | |
| EP | 0 164 860 A1 | 12/1985 | |
| EP | 0 175 551 A1 | 3/1986 | |
| EP | 0 608 058 A1 | 7/1994 | |
| EP | 1 422 217 A2 | 5/2004 | |
| EP | 1 557 166 A1 | 7/2005 | |
| FR | 2 722 195 A1 | 1/1996 | |
| JP | 10-95766 A | 4/1998 | |
| JP | 2003-505388 | 2/2003 | |
| WO | WO 86/03749 A1 | 7/1986 | |
| WO | WO 91/01306 A1 | 2/1991 | |
| WO | WO 91/04974 A1 | 4/1991 | |
| WO | WO 91/06545 A1 | 5/1991 | |
| WO | WO 92/09577 A1 | 6/1992 | |
| WO | WO 93/12786 A1 | 7/1993 | |
| WO | WO 93/15051 A1 | 8/1993 | |
| WO | WO 94/03427 A1 | 2/1994 | |
| WO | WO 95/06688 A1 | 3/1995 | |
| WO | WO 95/14667 A1 | 6/1995 | |
| WO | WO 97/15556 A1 | 5/1997 | |
| WO | WO 97/36895 A1 | 10/1997 | |
| WO | WO 98/25901 A1 | 6/1998 | |
| WO | WO 98/50016 A2 | 11/1998 | |
| WO | WO 00/06556 A1 | 2/2000 | |
| WO | WO 00/71129 A1 | 11/2000 | |
| WO | WO 01/05790 A1 | 1/2001 | |
| WO | WO 01/38564 A2 | 5/2001 | |
| WO | WO 01/38564 A3 | 5/2001 | |
| WO | WO 01/74775 A1 | 10/2001 | |
| WO | WO 02/30868 A1 | 4/2002 | |
| WO | WO 02/38544 A2 | 5/2002 | |
| WO | WO 03/000677 A1 | 1/2003 | |
| WO | WO 03/037274 A2 | 5/2003 | |
| WO | WO 03/037890 A2 | 5/2003 | |
| WO | WO 03/064425 A1 | 8/2003 | |
| WO | WO 03/078394 A1 | 9/2003 | |
| WO | WO 03/106457 A1 | 12/2003 | |
| WO | WO 2004/000225 A2 | 12/2003 | |
| WO | WO 2004/000227 A2 | 12/2003 | |
| WO | WO 2004/048320 A1 | 6/2004 | |
| WO | WO 2005/011657 A2 | 2/2005 | |
| WO | WO 2005/016913 A1 | 2/2005 | |
| WO | WO 2005/019208 A1 | 3/2005 | |
| WO | WO 2005/035498 A1 | 4/2005 | |
| WO | WO 2005/092304 A2 | 10/2005 | |
| WO | WO 2005/092895 A2 | 10/2005 | |
| WO | WO 2005/097107 A2 | 10/2005 | |
| WO | WO 2005/097122 A2 | 10/2005 | |
| WO | WO 2005/099689 A1 | 10/2005 | |
| WO | WO 2005/104711 A2 | 11/2005 | |
| WO | WO 2005/105753 A2 | 11/2005 | |
| WO | WO 2005/110992 A1 | 11/2005 | |
| WO | WO 2005/111024 A1 | 11/2005 | |
| WO | WO 2006/012173 A1 | 2/2006 | |
| WO | WO 2006/017075 A1 | 2/2006 | |
| WO | WO 2006/023107 A1 | 3/2006 | |
| WO | WO 2006/023109 A1 | 3/2006 | |
| WO | WO 2006/049290 A1 | 5/2006 | |
| WO | WO 2006/055752 A2 | 5/2006 | |
| WO | WO 2006/087019 A1 | 8/2006 | |
| WO | WO 2006/091646 A2 | 8/2006 | |
| WO | WO 2006/110654 A1 | 10/2006 | |
| WO | WO 2006/110917 A2 | 10/2006 | |
| WO | WO 2006/113864 A2 | 10/2006 | |
| WO | WO 2006/113875 A2 | 10/2006 | |
| WO | WO 2008/046046 A1 | 4/2008 | |
| WO | WO 2008/046049 A1 | 4/2008 | |
| WO | WO 2008/046065 A1 | 4/2008 | |
| WO | WO 2008/046082 A2 | 4/2008 | |
| WO | WO 2008/046083 A2 | 4/2008 | |
| WO | WO 2008/046084 A2 | 4/2008 | |
| WO | WO 2008/046087 A2 | 4/2008 | |
| WO | WO 2008/060789 A2 | 5/2008 | |
| WO | WO 2008/117050 A1 | 10/2008 | |
| WO | WO 2010/045197 A1 | 4/2010 | |
| WO | WO 2010/045251 A2 | 4/2010 | |
| WO | WO 2010/053998 A1 | 5/2010 | |
| WO | WO 2010/078307 A1 | 7/2010 | |
| WO | WO 2010/132352 A2 | 11/2010 | |
| WO | WO 2011/002708 A1 | 1/2011 | |
| WO | WO 2011/047173 A2 | 4/2011 | |
| WO | WO 2011/047174 A1 | 4/2011 | |
| WO | WO 2011/106729 A2 | 9/2011 | |

OTHER PUBLICATIONS

Cadieux et al., entitled Synthetic Methods for Spiro-Oxindole Compounds, Amendment mailed Nov. 16, 2012, for U.S. Appl. No. 12/904,880, 15 pages.

Official Action from European Patent Office, dated Sep. 11, 2012, for Patent Application No. 09 740 589.8, 5 pages.

Translation of Official Action from Korean Intellectual Property Office, dated Nov. 9, 2012, for Patent Application No. 10-2011-7011106, 9 pages.

Chafeev et al., entitled Spiro-Oxindole Compounds and Their Use As Therapeutic Agents, Restriction Requirement mailed Oct. 10, 2012, for U.S. Appl. No. 13/557,833, 9 pages.
International Search Report and Written Opinion, mailed Jun. 9, 2011, for PCTAN PCT/US2011/026359, 14 pages.
International Preliminary Report on Patentability, mailed Nov. 1, 2012, for PCTAN PCT/US2011/026359, 10 pages.
Winters et al., entitled Pharmaceutical Compositions of Spiro-oxindole Compound for Topical Administration and Their Use as Therapeutic Agents, Preliminary Amendment dated Oct. 30, 2012, for U.S. Appl. No. 13/580,129, 7 pages.
Official Action from Intellectual Property India, mailed Mar. 28, 2011, for India Patent Application No. 4596/CHENP/2007, 4 pages.
Official Action from Intellectual Property Australia, dated Jan. 12, 2011, for Patent Application No. 2006235593, 5 pages.
Official Action from State Intellectual Property Office of China, dated Dec. 25, 2009, for Patent Application No. 200680011733.9, 4 pages.
Official Action from State Intellectual Property Office of China, dated Oct. 9, 2010, for Patent Application No. 200680011733.9, 4 pages.
Official Action from European Patent Office, dated Apr. 9, 2010, for Patent Application No. 06 750 402.7, 4 pages.
Response to Official Action from European Patent Office, dated Aug. 19, 2010, for Patent Application No. 06 750 402.7, 105 pages.
Official Action from European Patent Office, dated Sep. 14, 2010, for Patent Application No. 06 750 402.7, 3 pages.
Response to Official Action from European Patent Office, dated Jul. 6, 2011, for Patent Application No. 06 750 402.7, 175 pages.
Official Action from Israel Patent Office, dated Jan. 17, 2011, for Patent Application No. 186616, 3 pages.
Response to Official Action from Israel Patent Office, mailed Jul. 14, 2011, for Patent Application No. 186616, 5 pages.
Official Action from Intellectual Property India, mailed Apr. 29, 2011, for India Patent Application No. 4597/CHENP/2007, 2 pages.
Official Action from Intellectual Property Office of New Zealand, dated Sep. 1, 2009, for Patent Application No. 561210, 2 pages.
Response to Official Action from Intellectual Property Office of New Zealand, dated Nov. 22, 2010, for Patent Application No. 561210, 2 pages.
Official Action from Intellectual Property Office of New Zealand, dated Nov. 30, 2010, for Patent Application No. 561210, 1 page.
Response to Official Action from Intellectual Property Office of New Zealand, dated Feb. 21, 2011, for Patent Application No. 561210, 2 pages.
Official Action from Intellectual Property Office of New Zealand, dated Feb. 25, 2011, for Patent Application No. 591268, 2 pages.
Official Action from Intellectual Property Office of Republic of the Philippines, dated Sep. 22, 2010, for Patent Application No. 1-2007-502050, 2 pages.
Response to Official Action from Intellectual Property Office of the Philippines, dated Jan. 20, 2011, for Patent Application No. 1-2007-502050, 85 pages.
Translation of Official Action from Intellectual Property Office of Russia, dated Mar. 16, 2010, for Patent Application No. 2007141632/04(045572), 7 pages.
Translation of Official Action from Intellectual Property Office of Russia, dated Sep. 22, 2010, for Patent Application No. 2007141632/04(045572), 7 pages.
Chafeev et al., entitled Spiro-Oxindole Compounds and Their Uses as Therapeutic Agents, Office Action mailed Jun. 14, 2011, for U.S. Appl. No. 12/650,196, 17 pages.
Sun et al., entitled Spiro-Oxindole Compounds and Their Uses as Therapeutic Agents, Preliminary Amendment dated Jun. 24, 2011, for U.S. Appl. No. 13/078,678, 32 pages.
Official Action from European Patent Office, dated Aug. 5, 2008, for Patent Application No. 06 758 436.7, 5 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from Israel Patent Office, dated Jan. 16, 2011, for Patent Application No. 186615, 3 pages.
Response to Official Action from Israel Patent Office, dated Jul. 13, 2011, for Patent Application No. 186615, 3 pages.
Official Action from Intellectual Property of India, dated May 18, 2009, for Patent Application No. 4598/CHENP/2007, 2 pages.
Response to Official Action from Intellectual Property of India, dated Mar. 15, 2010, for Patent Application No. 4598/CHENP/2007, 27 pages.
Official Action from Intellectual Property Office of New Zealand, dated Aug. 27, 2009, for Patent Application No. 561204, 2 pages.
Response to Official Action from Intellectual Property Office of New Zealand, dated Nov. 22, 2010, for Patent Application No. 561204, 2 pages.
Official Action from Intellectual Property Office of New Zealand, dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Official Action from State Intellectual Property Office of China, dated May 5, 2011, for Patent Application No. 200780038272.9, 9 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 2011, for Patent Application No. 07 868 434.7, 3 pages.
International Preliminary Report on Patentability, mailed May 10, 2011, for PCTAN PCT/US2009/063290, 7 pages.
Chafeev et al., entitled Enantiomers of Spiro-Oxindole Compounds and Their Uses as Therapeutic Agents, Restriction Requirement mailed Jun. 20, 2011, for U.S. Appl. No. 12/825,168, 8 pages.
Chafeev et al., entitled Enantiomers of Spiro-Oxindole Compounds and Their Uses as Therapeutic Agents, Response to Restriction Requirement and Preliminary Amendment, filed Jul. 20, 2011, for U.S. Appl. No. 12/825,168, 5 pages.
Chafeev et al., entitled Spiro-Oxindole Compounds and Their Use as Therapeutic Agents, Amendment dated Jul. 1, 2011, for U.S. Appl. No. 12/577,799, 21 pages.
International Preliminary Report on Patentability, mailed Jun. 29, 2011, for PCTAN PCT/US2009/069663, 6 pages.
International Search Report and Written Opinion, mailed Jul. 11, 2011, for PCTAN PCT/US2010/034223, 18 pages.
Arcangeli et al., "Targeting Ion Channels in Cancer: A Novel Frontier in Antineoplastic Therapy," *Current Medicinal Chemistry* 16: 66-93, 2009.
Dierks et al., "A Method for the Simultaneous Evaluation of the Activities of Seven Major Human Drug-Metabolizing Cytochrome P450S Using an in Vitro Cocktail of Probe Substrates and Fast Gradient Liquid Chromatography Tandem Mass Spectrometry," *Drug Metabolism and Disposition* 29(1): 23-29, 2001.
Diss et al., "Identification and characterization of the promoter region of the Nav1.7 voltage-gated sodium channel gene (SCN9A)," *Mol. Cell. Neurosci.* 37: 537-547, 2008.
Kis-Toth et al., "Voltage-Gated Sodium Channel Nav1.7 Maintains the Membrane Potential and Regulates the Activation and Chemokine-Induced Migration of a Monocyte-Derived Dendritic Cell Subset," *The Journal of Immunology* 187: 1273-1280, 2011.
Lange et al., "Regioselective Aminomethylations of Bicyclic Phenols," *Heterocycles* 53(1): 197-204, 2000.
Le Bourdonnec et al., "Medicinal Chemistry Strategies to Reduce CYP2D6 Inhibitory Activity of Lead Candidates," *Current Medicinal Chemistry* 16: 3093-3121, 2009.
Li et al., "A case of primary erythermalgia with prurigo," *Clinical and Experimental Dermatology* 34: e313-e314, 2009.
Lorenz et al., "Binary and ternary phase diagrams of two enantiomers in solvent systems," *Thermochimica Acta* 382: 129-142, 2002.
Namer et al., "Separate Peripheral Pathways for Pruritus in Man," *J. Neurophysiol.* 100: 2062-2069, 2008.

Shin et al., "Potent inhibition of CYP2D6 by haloperidol metabolites: stereoselective inhibition by reduced haloperidol," *J. Clin. Pharmacol.* 51: 45-52, 2001.

Stella and Nti-Addae, "Prodrug strategies to overcome poor water solubility," *Advanced Drug Delivery Reviews* 59: 677-694, 2007.

Wang and Yosipovitch, "New insights into the pathophysiology and treatment of chronic itch in patients with End-stage renal disease, Chronic liver disease and Lymphoma," *Int. J. Dermatol.* 49(1): 1-11, Jan. 2010.

Weaver et al., "Cytochrome P450 Inhibition Using Recombinant Proteins and Mass Spectrometry/Multiple Reaction Monitoring Technology in a Cassette Incubation," *Drug Metabolism and Disposition* 31(7): 955-966, 2003.

Xiao and Bennett, "C-fiber spontaneous discharge evoked by chronic inflammation is suppressed by a long-term infusion of lidocaine yielding nanogram per milliliter plasma levels," *Pain* 137: 218-228, 2008.

Zhao et al., "Voltage-gated sodium channel expression in rat and human epidermal keratinocytes: Evidence for a role in pain," *Pain* 139: 90-105, 2008.

Response to Official Action from Intellectual Property Australia, mailed May 28, 2012, for Patent Application No. 2006235593, 60 pages.

Official Action from State Intellectual Property Office of China, dated May 9, 2012, for Patent Application No. 201110027693.X, 6 pages.

Official Action from European Patent Office re extended European search report, dated Feb. 2, 2012, for Patent Application No. 11009687.2, 7 pages.

Response to Official Action from Intellectual Property India, mailed Apr. 18, 2012, for India Patent Application No. 4597/CHENP/2007, 86 pages.

Translation of Official Action from Patent Office of Japan, dated May 16, 2012, for Patent Application No. 2008-506802, 8 pages.

Sun et al., Entitled Spiro-Oxindole Compounds and Their Uses as Therapeutic Agents, Restriction Requirement dated Nov. 28, 2011, for U.S. Appl. No. 13/078,678, 7 pages.

Chafeev et al., entitled Tricyclic Spiro-Oxindole Derivatives and Their Uses as Therapeutic Agents, Restriction Requirement mailed Jan. 26, 2012, for U.S. Appl. No. 12/445,271, 7 pages.

Official Action from State Intellectual Property Office of China, dated Feb. 20, 2012, for Patent Application No. 200780038272.9, 5 pages.

Cadieux et al., entitled Spiro (FURO [3, 2-C] Pyridine-3-3'—Indol) -2' (1'H)-One Derivatives and Related Compounds for the Treatment of Sodium-Channel Mediated Diseases, Such as Pain, Restriction Requirement mailed Apr. 19, 2012, for U.S. Appl. No. 12/445,270, 6 pages.

International Preliminary Report on Patentability, mailed Apr. 17, 2012, for PCTAN PCT/US2010/052704, 6 pages.

Cadieux et al., entitled Synthetic Methods for Spiro-Oxindole Compounds, Restriction Requirement mailed May 7, 2012, for U.S. Appl. No. 12/904,880, 7 pages.

Cadieux et al., entitled Synthetic Methods for Spiro-Oxindole Compounds, Response to Restriction Requirement mailed Jun. 7, 2012, for U.S. Appl. No. 12/904,880, 1 page.

Cadieux et al., entitled Synthetic Methods for Spiro-Oxindole Compounds, Office Action mailed Aug. 16, 2012, for U.S. Appl. No. 12/904,880, 40 pages.

Official Action from Intellectual Property Australia, dated Mar. 22, 2012, for Patent Application No. 2007319580, 2 pages.

Translation of Official Action from Intellectual Property Office of Russia, dated Feb. 2, 2012, for Patent Application No. 2009117642, 8 pages.

Official Action from State Intellectual Property Office of China, dated Jun. 8, 2012, for Patent Application No. 200780038111.X, 7 pages.

International Preliminary Report on Patentability, mailed Apr. 17, 2012, for PCTAN PCT/US2010/052703, 9 pages.

Winters et al., Entitled Pharmaceutical Compositions for Oral Administration, Restriction Requirement, mailed May 7, 2012, for U.S. Appl. No. 12/905,048, 9 pages.

International Preliminary Report on Patentability, mailed Jan. 4, 2012, for PCTAN PCT/US2010/040187, 7 pages.

Response to Official Action from European Patent Office, dated Aug. 7, 2012, for Patent Application No. 10 731 662.2, 21 pages.

Response to Official Action from Philippines Intellectual Property Office, dated Jun. 15, 2012, for Patent Application No. 1-2011-502619, 3 pages.

Chafeev et al., entitled Enantiomers of Spiro-Oxindole Compounds and Their Uses as Therapeutic Agents, Amendment filed Jan. 30, 2012, for U.S. Appl. No. 12/825,168, 8 pages.

Chafeev et al., entitled Enantiomers of Spiro-Oxindole Compounds and Their Uses as Therapeutic Agents, Office Action, mailed Feb. 28, 2012, for U.S. Appl. No. 12/825,168, 13 pages.

Chafeev et al., entitled Enantiomers of Spiro-Oxindole Compounds and Their Uses as Therapeutic Agents, Amendment and Cadieux Declaration filed May 29, 2012, for U.S. Appl. No. 12/825,168, 17 pages.

Response to Official Action from European Patent Office, dated Jan. 10, 2012, for Patent Application No. 09 740 589.8, 4 pages.

Chafeev et al., entitled Spiro-Oxindole Compounds and Their Use as Therapeutic Agents, Response to Office Action dated Feb. 21, 2012, for U.S. Appl. No. 12/578,148, 46 pages.

Chafeev et al., entitled Spiro-Oxindole Compounds and Their Use as Therapeutic Agents, Notice of Allowance dated Apr. 27, 2012 for U.S. Appl. No. 12/578,148, 12 pages.

Response to Official Action from European Patent Office, dated Feb. 1, 2012, for Patent Application No. 09 741 118.5, 12 pages.

Byrn et al., "Chapter 11, Hydrates and Solvates," in *Solid-State Chemistry of Drugs*, Second Edition, 1999, pp. 233-247.

Catterall, "Molecular mechanisms of gating and drug block of sodium channels," 2002 *Sodium channels and neuronal hyperexcitability*, Wiley, Chichester (Novartis Foundation Symposium 241), p. 206-225.

Diss et al., "Expression Profiles of Voltage-Gated Na$^+$Channel α-Subunit Genes in Rat and Human Prostate Cancer Cell Lines," *The Prostate* 48:165-178, 2001.

Hille, "Local Anesthetics: Hydrophilic and Hydrophobic Pathways for the Drug-Receptor Reaction," *The Journal of General Physiology* 69: 497-515, 1977.

Hille, "The pH-Dependent Rate of Action of Local Anesthetics on the Node of Ranvier," *The Journal of General Physiology* 69: 475-496, 1977.

Hoffman, *Organic Chemistry: An Intermediate Text—Second Edition*, John Wiley & Sons, Inc., Hoboken, New Jersey, 2004, 124, 138-144.

Ikoma et al., "Neuronal Sensitization for Histamine-Induced Itch in Lesional Skin of Patients With Atopic Dermatitis," *Arch Dermatol.* 139: 1145-1458, Nov. 2003.

Laniado et al., "Short Communication: Expression and Functional Analysis of Voltage-Activated Na$^+$Channels in Human Prostate Cancer Cell Lines and their Contribution to Invasion in Vitro," *American Journal of Pathology* 150(4): 1213-1221, Apr. 1997.

Oaklander et al., "Intractable postherpetic itch and cutaneous deafferentation after facial shingles," *Pain* 96: 9-12, 2002.

Patani and LaVoie, "Bioisosterism: A Rational Approach in Drug Design," *Chem. Rev.* 96(8): 3147-3176, 1996.

Pearn, "Neurology of ciguatera," *J.Neurol. Neurosurg. Psychiatry* 70: 4-8, 2001.

Schmelz et al., "Specific C-Receptors for Itch in Human Skin," *The Journal of Neuroscience* 17(20): 8003-8008, Oct. 15, 1997.

Official Action from State Intellectual Property Office of China, dated Oct. 10, 2011, for Patent Application No. 201110027693.X, 5 pages.

Translation of Official Action from Patent Office of Japan, dated Nov. 22, 2011, for Patent Application No. 2008-506802, 11 pages.

Chafeev et al., entitled Spiro-Oxindole Compounds and Their Uses as Therapeutic Agents, Amendment dated Sep. 2, 2011, for U.S. Appl. No. 12/650,196, 15 pages.

Chafeev et al., entitled Spiro-Oxindole Compounds and Their Uses as Therapeutic Agents, Notice of Allowance dated Sep. 20, 2011, for U.S. Appl. No. 12/650,196, 11 pages.

Translation of Official Action from Patent Office of Japan, dated Nov. 4, 2011, for Patent Application No. 2008-506574, 10 pages.

Official Action from Intellectual Property Corporation of Malaysia, dated May 31, 2011, for Patent Application No. PI 20061651, 3 pages.

Response to Official Action from Intellectual Property Corporation of Malaysia, filed Aug. 11, 2011, for Patent Application No. PI 20061651, 30 pages.

Chafeev et al., Entitled Spiroheterocyclic Compounds and Their Uses as Therapeutic Agents, Office Action mailed Aug. 25, 2011, for U.S. Appl. No. 12/855,514, 43 pages.

Official Action from State Intellectual Property Office of China, dated Oct. 28, 2010, for Patent Application No. 200780038111.X, 5 pages.

Official Action from State Intellectual Property Office of China, dated Jul. 14, 2011, for Patent Application No. 200780038111.X, 5 pages.

Translation of Official Action from Intellectual Property Office of Russia, dated Aug. 31, 2011, for Patent Application No. 2009117642, 4 pages.

International Search Report and Written Opinion, mailed Dec. 1, 2011, for PCTAN PCT/US2010/052703, 13 pages.

Official Action from Intellectual Property Office of New Zealand, mailed Sep. 9, 2011, for New Zealand Patent Application No. 592275, 2 pages.

Chafeev et al., Entitled Enantiomers of Spiro-Oxindole Compounds and Their Uses as Therapeutic Agents, Office Action, mailed Aug. 29, 2011, for U.S. Appl. No. 12/825,168, 43 pages.

Chafeev et al., entitled Spiro-Oxindole Compounds and Their Use as Therapeutic Agents, Restriction Requirement mailed Aug. 15, 2011, for U.S. Appl. No. 12/578,148, 10 pages.

Chafeev et al., entitled Spiro-Oxindole Compounds and Their Use as Therapeutic Agents, Response to Restriction Requirement dated Sep. 14, 2011, for U.S. Appl. No. 12/578,148, 57 pages.

Chafeev et al., entitled Spiro-Oxindole Compounds and Their Use as Therapeutic Agents, Office Action mailed Oct. 21, 2011, for U.S. Appl. No. 12/578,148, 51 pages.

Chafeev et al., entitled Spiro-Oxindole Compounds and Their Use as Therapeutic Agents, Notice of Allowance mailed Oct. 7, 2011, for U.S. Appl. No. 12/577,799, 14 pages.

International Preliminary Report on Patentability, mailed Nov. 15, 2011, for PCTAN PCT/US2010/034223, 11 pages.

Al-Thebeiti and El-Zohry, "A Facile Route for the Synthesis of Some New Spiro[indoline-3,3'-indan]-2,1'-dione Derivatives," *Heterocycles* 41(11): 2475-2480, 1995.

Binder et al., "Disease mechanisms in neuropathic itch," *Nature Clinical Practice/Neurology* 4(6): 329-337, Jun. 2008.

Blair and Bean, "Roles of Tetrodotoxin (TTX)-Sensitive $Na^+$ Current, TTX-Resistant $Na^+$ Current, and $Ca^{2+}$ Current in the Action Potentials of Nociceptive Sensory Neurons," *Journal of Neuroscience* 22(23): 10277-10290, Dec. 1, 2002.

Brackenbury and Djamgoz, "Activity-dependent regulation of voltage-gated $Na^+$ channel expression in Mat-LyLu rat prostate cancer cell line," *J. Physiol.* 573.2: 343-356, 2006.

Caldwell et al., "Sodium channel $Na_v1.6$ is localized at nodes of Ranvier, dendrites, and synapses," *PNAS* 97(10): 5616-5620, May 9, 2000.

Chioni et al., "A novel adhesion molecule in human breast cancer cells: Voltage-gated $Na^+$ channel β1 subunit," *The International Journal of Biochemistry & Cell Biology* 41: 1216-1227, 2009.

Cox et al., "An SCN9A channelopathy causes congenital inability to experience pain," *Nature* 444: 894-898, Dec. 14, 2006.

Craner et al., "Molecular changes in neurons in multiple sclerosis: Altered axonal expression of $Na_v1.2$ and $Na_v1.6$ sodium channels and $Na^+/Ca^{2+}$ exchanger," *PNAS* 101(21): 8168-8173, May 25, 2004.

Dib-Hajj et al., "Genetics and Molecular Pathophysiology of $Na_v1.7$-Related Pain Syndromes," *Advances in Genetics* 63: 85-110, 2008.

Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.

Do and Bean, "Subthreshold Sodium Currents and Pacemaking of Subthalamic Neurons: Modulation by Slow Inactivation," *Neuron* 39: 109-120, Jul. 3, 2003.

Ettinger and Argoff, "Use of Antiepileptic Drugs for Nonepileptic Conditions: Psychiatric Disorders and Chronic Pain," *Neurotherapeutics: The Journal of the American Society for Experimental Neuro Therapeutics* 4:75-83, Jan. 2007.

Fishman et al., "Intravenous Lidocaine for Treatment-resistant Pruritus," *American Journal of Medicine* 102: 584-585, Jun. 1997.

Fuchs and See, "Basolateral amygdala inactivation abolishes conditioned stimulus- and heroin-induced reinstatement of extinguished heroin-seeking behavior in rats," *Psychopharmacology* 160: 425-433, 2002.

Goldberg et al., "Loss-of-function mutations in the $Na_v1.7$ gene underlie congenital indifference to pain in multiple human populations," *Clin. Genet.* 71: 311-319, 2007.

Goldberg, "The Significance of Molecular Type, Shape and Complementarity in Clathrate Inclusion," *Topics in Current Chemistry* 149: 1-44, 1988.

Guillaumet et al., "Synthese d'un analogue dioxinique du psoralene," *Tetrahedron Letters* 29(22): 2665-2666, 1988.

Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.

Hamann et al., "Motor disturbances in mice with deficiency of the sodium channel gene Scn8a show features of human dystonia," *Experimental Neurology* 184: 830-838, 2003.

Haufe et al., "The promiscuous nature of the cardiac sodium current," *Journal of Molecular and Cellular Cardiology* 42: 469-477, 2007.

Inan et al, "Inhibitory effect of lidocaine on pain and itch using formalin-induced nociception and 5'-guanidinonaltrindole-induced scratching models in mice: Behavioral and neuroanatomical evidence," *European Journal of Pharmacology* 616: 141-146, 2009.

Jarvis et al., "A-803467, a potent and selective $Na_v1.8$ sodium channel blocker, attenuates neuropathic and inflammatory pain in the rat," *PNAS* 104(20): 8520-8525, May 15, 2007.

Kamiya et al., "A Nonsense Mutation of the Sodium Channel Gene SCN2A in a Patient with Intractable Epilepsy and Mental Decline," *Journal of Neuroscience* 24(11): 2690-2698, Mar. 17, 2004.

Kim et al., "BACE1 regulates voltage-gated sodium channels and neuronal activity," *Nature Cell Biology* 9(7): 755-764, Jul. 2007.

Lai et al., "The role of voltage-gated sodium channels in neuropathic pain," *Current Opinion in Neurobiology* 13:291-297, 2003.

Liu et al., "Mutations in Cardiac Sodium Channels: Clinical Implications," *Am. J. Pharmacogenomics* 3(3): 173-179, 2003.

MacNicol, "Clathrates and Molecular Inclusion Phenomena," *Chemical Society Reviews* 7(1): 65-87, 1978.

Meisler et al., "Sodium channel gene family: epilepsy mutations, gene interactions and modifier effects," *J. Physiol.* 588.11: 1841-1848, 2010.

Morinville et al., "Distribution of the Voltage-Gated Sodium Channel $Na_v1.7$ in the Rat: Expression in the Autonomic and Endocrine Systems," *Journal of Comparative Neurology* 504: 680-689, 2007.

Papale et al., "Heterozygous mutations of the voltage-gated sodium channel SCN8A are associated with spike-wave discharges and absence epilepsy in mice," *Human Molecular Genetics* 18(9): 1633-1641, 2009.

Pereira et al., "Severe epilepsy, retardation, and dysmorphic features with a 2q deletion including SCN1A and SCN2A," *Neurology* 63: 191-192, 2004.

Pouton, "Lipid formulations for oral administration of drugs: non-emulsifying, self-emulsifying and 'self-microemulsifying' drug delivery systems," *European Journal of Pharmaceutical Sciences* 11(Suppl 2): S93-S98, 2000.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raymond et al., "Expression of Alternatively Spliced Sodium Channel α-Subunit Genes," *Journal of Biological Chemistry* 279(44): 46234-46241, Oct. 29, 2004.

Reimann et al., "Pain perception is altered by a nucleotide polymorphism in SCN9A," *PNAS* 107(11): 5148-5153, Mar. 16, 2010.

Rhodes et al., "Noninactivating voltage-gated sodium channels in severe myoclonic epilepsy of infancy," *PNAS* 101(30): 11147-11152, Jul. 27, 2004.

Ross et al., "Loss of Inhibitory Interneurons in the Dorsal Spinal Cord and Elevated Itch in Bhlhb5 Mutant Mice," *Neuron* 65: 886-898, Mar. 25, 2010.

Ruan et al., "Sodium channel mutations and arrhythmias," *Nature Reviews Cardiology* 6: 337-348, May 2009.

Saenger, "Cyclodextrin Inclusion Compounds in Research and Industry," *Angew. Chem. Int. Ed. Engl* 19: 344-362, 1980.

Sircar et al., "Synthesis and SAR of N-Benzoyl-1-Biphenylalanine Dervatives: Discovery of TR-14035, A Dual $\alpha_4\beta_7/\alpha_4\beta_1$ Integrin Antagonist," *Bioorganic & Medicinal Chemistry Letters* 10: 2051-2066, 2002.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Tamaoka, "Paramyotonia Congenita and Skeletal Sodium Channelopathy," *Internal Medicine* 42(9): 769-770, Sep. 2003.

Twycross et al., "Itch: scratching more than the surface," *Q. J. Med.* 96: 7-26, 2003.

Watanabe et al., "$Na_v2/NaG$ Channel is Involved in Control of Salt-Intake Behavior in the CNS," *Journal of Neuroscience* 20(20): 7743-7751, Oct. 15, 2000.

Weber and Czugler, "Functional Group Assisted Clathrate Formation—Scissor-Like and Roof-Shaped Host Molecules," *Topics in Current Chemistry* 149: 45-135, 1988.

Wood et al., "Voltage-Gated Sodium Channels and Pain Pathways," *J. Neurobiol.* 61: 55-71, 2004.

Chafeev et al., entitled Spiro-Oxindole Compounds and Their Uses as Therapeutic Agents, Office Action dated Feb. 4, 2011, for U.S. Appl. No. 12/650,196, 31 pages.

Chafeev et al., entitled Spiro-Oxindole Compounds and Their Uses as Therapeutic Agents, Amendment and Winther Declaration dated May 4, 2011, for U.S. Appl. No. 12/650,196, 197 pages.

Sun et al., entitled Spiro-Oxindole Compounds and Their Uses as Therapeutic Agents, Office Action dated Jul. 12, 2010, for U.S. Appl. No. 12/650,218, 26 pages.

Sun et al., entitled Spiro-Oxindole Compounds and Their Uses as Therapeutic Agents, Amendment dated Nov. 10, 2010, for U.S. Appl. No. 12/650,218, 28 pages.

Sun et al., entitled Spiro-Oxindole Compounds and Their Uses as Therapeutic Agents, Notice of Allowance mailed Dec. 13, 2010, for U.S. Appl. No. 12/650,218, 19 pages.

Sun et al., entitled Spiro-Oxindole Compounds and Their Uses as Therapeutic Agents, Supplemental Amendment dated Mar. 2, 2011, for U.S. Appl. No. 12/650,218, 3 pages.

Chafeev et al., entitled Spiroheterocyclic Compounds and Their Uses as Therapeutic Agents, Preliminary Amendment dated Oct. 25, 2010, for U.S. Appl. No. 12/855,514, 32 pages.

International Search Report and Written Opinion, mailed Apr. 1, 2011, for PCTAN PCT/US2010/052704, 12 pages.

Winters et al., entitled Pharmaceutical Compositions for Oral Administration, Preliminary Amendment dated Dec. 27, 2010, for U.S. Appl. No. 12/905,048, 9 pages.

International Search Report and Written Opinion, mailed Oct. 1, 2010, for PCTAN PCT/US2010/040187, 13 pages.

International Search Report and Written Opinion, mailed Oct. 6, 2010, for PCTAN PCT/US2009/060537, 18 pages.

International Preliminary Report on Patentability, mailed Apr. 19, 2011, for PCTAN PCT/US2009/060537, 11 pages.

International Preliminary Report on Patentability, mailed Apr. 19, 2011, for PCTAN PCT/US2009/060455, 7 pages.

Chafeev et al., entitled Spiro-Oxindole Compounds and Their Use as Therapeutic Agents, Office Action dated Apr. 1, 2011, for U.S. Appl. No. 12/577,799, 49 pages.

Invitation to Pay Additional Fees, mailed Aug. 18, 2010, for PCTAN PCT/US2010/034223, 7 pages.

Adams et al., "Bicyclic N-Hydroxyurea Inhibitors of 5-Lipoxygenase: Pharmacodynamic, Pharmacokinetic, and in Vitro Metabolic Studies Characterizing N-Hydroxy-N-(2,3-dihydro-6-(phenylmethoxy)-3-benzofuranyl)urea," *J. Med. Chem.* 39(26): 5035-5046, 1996.

Akai, "Development of Novel Asymmetric Reactions Oriented to Next-Generation Enzymatic Organic Syntheses," *Yakugaku Zasshi* 123(11): 919-931, 2003.

Alabaster et al., "The Synthesis of 5-Substituted 2,3-Dihydrobenzofurans," *Synthesis* 12: 950-952, Dec. 1988.

Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.

Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.

Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.

Anger et al., "Medicinal Chemistry of Neuronal Voltage-Gated Sodium Channel Blockers," *Journal of Medicinal Chemistry* 44(2): 115-137, Jan. 18, 2001.

Autrey and Tahk, "The Synthesis and Stereochemistry of Some Isatylideneacetic Acid Derivatives," *Tetrahedron* 23: 901-917, 1967.

Bacher et al., "Oxindole alkaloids from Uncaria tomentosa induce apoptosis in proliferating, G0/G1-arrested and bcl-2-expressing acute lymphoblastic leukaemia cells," *British Journal of Haematology* 132: 615-622, 2005.

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.

Basavaiah et al., "$TiCl_4$ catalyzed tandem construction of C-C and C-O bonds: a simplec and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol.* 81: 613-642, May 1983.

Bennett and Xie, "A peripheral mononeuropathy in rat that produces disorders of pain sensation like those seen in man," *Pain* 33: 87-107, 1988.

Beyersbergen Van Henegouwen et al., "First Total Synthesis of ent-Gelsedine via a Novel Iodide-Promoted Allene N-Acyliminium Ion Cyclization," *J. Org. Chem.* 65(24): 8317-8325, 2000.

Beyersbergen Van Henegouwen et al., "Total Synthesis of (+)-Gelsedine," *Angw. Chem. Int. Ed.* 38(15): 2214-2217, 1999.

Billert and Beckert, "Beiträge zur Chemie der Pyrido[1,2-α]pyrazine—Reaktivität gegenüber Heterocumulenen der Kohlensäurereihe und Ketenen," *J. Prakt. Chem.* 341(4): 332-341, 1999.

Bond et al., "Cyclopiamines A and B, Novel Oxindole Metabolites of Penicillium cyclopium Westling," *Journal of the Chemical Society, Perkin Transaction 1: Organic and Rio-Organic Chemistry* 7: 1751-1761, 1979.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Braude and Lindwall, "Condensations of Isatin with Acetone by the Knoevenagel Method," *Journal of the American Chemical Society* 55: 325-327, Jan. 1933.

Canas-Rodriguez and Leeming, "N-Phenyl-2-indolinones and N-Phenylindolines. A New Class of Antidepressant Agents," *Journal of Medicinal Chemistry* 15(7): 762-770, 1972.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Cestèle and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European Journal of Medicinal Chemistry* 40: 1143-1148, 2005.

Chaplan et al., "Quantitative assessment of tactile allodynia in the rat paw," *Journal of Neuroscience Methods* 53: 55-63, 1994.

Chung and Chung, "Sodium channels and neuropathic pain," *Novartis Found Symposium* 261: 19-31, 2004.

Clare et al., "Voltage-gated sodium channels as therapeutic targets," *Drug Discovery Today* 5(11): 506-520, Nov. 2000.

Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.

Coppola, "N-Arylation of Isatins. A Direct Route to N-Arylisatoic Anhydrides," *J. Heterocyclic Chem.* 24: 1249-1251, Sep./Oct. 1987.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cravotto et al., "Azomethine Ylide Cycloaddition/Reductive Heterocyclization Approach to Oxindole Alkaloids: Asymmetric Synthesis of (—)-Horsfiline," *J. Org. Chem.* 66(25): 8447-8453, 2001.

Creveling and Daly, "Batrachotoxinin A [$^3$H]Benzoate Binding to Sodium Channels," *Methods in Neurosciences* 8: 25-37, 1992.

Cube et al., "3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.

Dallacker and Sanders, "Darstellung and Reaktionen von 5-(3'-Hydroxy-oxindol-3'-yl)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of N-Aryldiazoamides. An Efficient Synthesis of 2(3H)-Indolinones," *J. Org. Chem* 53(5): 1017-1022, 1988.

Dubuisson and Dennis, "The Formalin Test: A Quantitative Study of the Analgesic Effects of Morphine, Meperidine, and Brain Stem Stimulation in Rats and Cats," *Pain* 4: 161-174, 1977.

Dutton et al., "A Total Synthesis of Gelsemine: Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)benzotriazoles," *Tetrahedron* 55: 11927-11942, 1999.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.

Feldman and Vidulova, "Extending Pummerer Reaction Chemistry. Application to the Oxidative Cyclization of Indole Derivatives," *Organic Letters* 6(11): 1869-1871, 2004.

Flanagan et al., "Radical cyclisation reactions with indoles," *Tetrahedron Letters* 44: 1795-1798, 2003.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.

Fujita et al., "The Beckmann Rearrangement by Means of Phosphoryl Chloride/N,N-Dimethylacetamide; A Novel and Convenient Method for Preparing Benzoxazoles," *Synthesis* 68-69, Jan. 1982.

Gálvez and García, "Synthesis of Isomeric β-Haloethylthienopyrroles," *J. Heterocyclic Chem.* 21: 393-395, Mar.-Apr. 1984.

Ganguly et al., "Solution- and solid-phase synthesis of enantiomerically pure spiro oxindoles," *Tetrahedron Letters* 43: 8981-8983, 2002.

Ganguly et al., "Synthesis of heterocyclic compounds using radical reactions and evidence for the formation of spiro radical intermediates," *Tetrahedron Letters* 45: 883-886, 2004. See also Ganguly et al., "Corrigendum to 'Synthesis of heterocyclic compounds using radical reactions and evidence for the formation of spiro radical intermediates,'"[*Tetrahedron Letters* 45: 883-886, 2004], *Tetrahedron Letters* 45: 3835, 2004.

Garden et al., "Investigation of the Selective reduction of isatin derivatives. Synthesis of α-hydroxyacetophenone derivatives and ethyl spiro-3,3-(ethylenedioxy)-2-hydroxyindoline carboxylates," *Tetrahedron Letters* 44: 7617-7621, 2003.

Garden et al., "A versatile synthetic methodology for the synthesis of tryptophols," *Tetrahedron* 58: 8399-8412, 2002.

González-López De Turiso and Curran, "Radical Cyclization Approach to Spirocyclohexadienones," *Organic Letters* 7(1): 151-154, 2005.

Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.

Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.

Grigoryan et al., "Synthesis and antispasmodic activity of spiro[β-carbolineindolones] and spiro[indoleindolo[2,3-c]azepinones]," *Hayastani Kimiakan Handes* 58(3): 100-104, 2005, CAPLUS Database Accession No. 2005:876436, 4 pages, Abstract only.

Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.

Ikoma et al., "The neurobiology of itch," *Nature Reviews Neuroscience* 7: 535-547, Jul. 2006.

Iranpoor et al., "A novel method for the highly efficient synthesis of 1,2-benzisoxazoles under neutral conditions using the $Ph_3P$/DDQ system," *Tetrahedron Letters* 47: 8247-8250, 2006.

Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.

Islip and White, "236. Some Reactions of 2-(3-Oxindolyl)ethylamines," *Journal of the Chemical Society* 1201-1204, 1964.

Itoh et al., "Introduction of a Hydroxy Group at the Para Position and N-Iodophenylation of N-Arylamides Using Phenyliodine(III) Bis(Trifluoracetate)," *J. Org. Chem.* 67: 7424-7428, 2002.

Jorgensen and Berteau, "Thyroxine Analogs. 21. o- and m-L-Thyroxine and Related Compounds," *Journal of Medicinal Chemistry* 14(12): 1199-1202, 1971.

Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.

Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.

Kaila et al., "Synthesis and Biological Evaluation of Quinoline Salicylic Acids as P-Selectin Antagonists," *J. Med. Chem.* 50: 21-39, 2007.

Kamara et al., "The First Direct Transformation of 2,2'-Dihydroxychalcones into Coumestans," *Tetrahedron* 55: 861-868, 1999.

Kang et al., "Pteropodine and isopteropodine positively modulate the function of rat muscarinic $M_1$ and $5-HT_2$ receptors expressed in *Xenopus* oocyte," *European Journal of Pharmacology* 444: 39-45, 2002.

Karp et al., "Preparation of 4-Hydroxy-2-trifluoromethylthiophene: A Novel Bioisostere of α,α,α-Trifluoro-*m*-cresol," *Synthesis* 8: 1078-1080, 2000.

Kende et al., "Intramolecular Radical Cyclization of Phenolic Enolates," *J. Am. Chem. Soc.* 110: 2210-2218, 1988.

Kim et al., "Design, synthesis, and evaluation of dioxane-based antiviral agents targeted against the Sindbis virus capsid protein," *Bioorganic & Medicinal Chemistry Letters* 15: 3207-3211, 2005.

King et al., "Hydroxy-quinoxalines and -phenazines, and Experiments on the Preparation of Hydroxyquinoxaline Di-*N*-oxides," *J. Chem. Soc.* 3012-3016, 1949.

Kirmse et al., "Intramolecular Reactivity of Arylcarbenes: Derivatives of *o*-Tolylcarbene," *J. Org. Chem.* 59: 3821-3829, 1994.

Klugbauer et al., "Structure and functional expression of a new member of the tetrodotoxin-sensitive voltage-activated sodium channel family from human neuroendocrine cells," *EMBO J.* 14(6): 1084-1090, 1995.

Kobayashi and Furukawa, "Studies on Indole Derivatives. I. Synthesis of 3-Phenyl-9*H*-pyridazino-[3,4-*b*]indole Derivatives," *Chemical & Pharmaceutical Bulletin* 12(10): 1129-1135, Oct. 1964.

Kollmar et al., "2-Amino-3-Fluorobenzoic Acid [Benzoic acid, 2-amino-3-fluoro-]," *Organic Syntheses, Coll.* 79: 196, 2002, 5 pages.

Kornet and Thio, "Oxindole-3-spiropyrrolidines and -piperidines. Synthesis and Local Anesthetic Activity," *Journal of Medicinal Chemistry* 19(7): 892-898, 1976.

Kotha et al., "Recent applications of the Suzuki-Miyaura cross-coupling reaction in organic synthesis," *Tetrahedron* 58: 9633-9695, 2002.

Kubo et al., "Michael Additions of Indoles to 2-oxoindolin-3-ylidene Ketones," *Heterocycles* 4(10), 1675-1680, 1976.

Kumar et al., "A New Route to Spiropyrrolidinyl-oxindole Alkaloids via Iodide Ion Induced Rearrangement of [(*N*-Aziridinomethylthio)methylene]-2-oxindoles," *Organic Letters* 3(26): 4193-4196, 2001.

Kuzma et al., "Progress in the Development of Ultra-Long-Acting Local Anesthetics," *Regional Anesthesia* 22(6): 543-551, Nov.-Dec. 1997.

Lackey and Sternbach, "Synthesis of Substituted Quinoline-4-carboxylic Acids," *Synthesis*: 993-997, Oct. 1993.

Laus, "Kinetics of isomerization of tetracyclic spiro oxindole alkaloids," *J. Chem. Soc., Perkin Trans.* 2: 315-317, 1998.

Laus et al., "Analysis of the kinetics of isomerization of spiro oxindole alkaloids," *J. Chem. Soc., Perkin Trans.* 2: 1931-1936, 1996.

Lee-Son et al., "Stereoselective Inhibition of Neuronal Sodium Channels by Local Anesthetics," *Anesthesiology* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.

Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.

Lindemann et al., "Zur Kenntnis der Indoxazene," *Justus Liebigs Annalen der Chemie* 456: 284-311, 1927.

Lindwall and Maclennan, "A Condensation of Acetophenone with Isatin by the Knoevenagel Method," *Journal of the American Chemical Society* 54: 4739-4744, Dec. 1932.

Lossin et al., "Molecular Basis of an Inherited Epilepsy," *Neuron* 34: 877-884, Jun. 13, 2002.

Loudon and Ogg, "2:3-Dihydro-3-oxobenz-1:4-oxazines," *J. Chem. Soc.*: 739-744, 1955.

Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.

Lyalin et al., [title unavailable], *Zhurnal Organicheskoi Khimii* 20(4): 846-849, 1984.

Ma and Cai, "*N*,*N*-Dimethyl Glycine-Promoted Ullmann Coupling Reaction of Phenols and Aryl Halides," *Organic Letters* 5(21): 3799-3802, 2003.

Maercker and Theysohn, "Versuche zur Umlagerung von 2-Cyclopropyl-äthyl-Anionen," *Liebigs Ann. Chem.* 759: 132-157, 1972.

Maginnity and Gaulin, "Derivatives of *o*-, *m*- and *p*-Aminobenzotrifluoride," *J. Am. Chem. Soc.* 73: 3579-3580, Aug. 1951.

Majumdar et al., "1-Alkylisatins via Aldol-Retro-aldol Condensation," *J. Chem. Research* (S), 460-461, 1996.

Mann et al., "The Synthesis of Lignans and Related Structures using Quinodimethanes and Isobenzofurans: Approaches to the Podophyllins," *J. Chem. Soc. Perkin Trans. I*: 2081-2088, 1984.

Mannaioni et al., "Tryptophan Metabolism and Hepatic Encephalopathy. Studies on the Sedative Properties of Oxindole," *Advances in experimental medicine and biology* 467: 155-167, 1999.

Mao and Baldwin, "New Spirocyclic Oxindole Synthesis Based on a Hetero Claisen Rearrangement," *Organic Letters* 6(14): 2425-2428, 2004.

Mao and Chen, "Systemic lidocaine for neuropathic pain relief," *Pain* 87: 7-17, 2000.

Marcantonio et al., "An Investigation into Causes and Effects of High Cyanide Levels in the Palladium-Catalyzed Cyanation Reaction," *Organic Letters* 6(21): 3723-3725, 2004.

Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.

Marti and Carreira, "Total Synthesis of (—)-Spirotryprostatin B: Synthesis and Related Studies," *J. Am. Chem. Soc.* 127(32): 11505-11515, 2005.

McMurtrey and Daves, Jr., "König's Adducts of *N*-Alkyl(aryl)aminoethanols and Quinones. 3,4-Dihydro-4-alkyl(aryl)-8a-hydroxy-2*H*-1,4,benzoxazin-6(8a*H*)-ones," *J. Org. Chem.* 35(12): 4252-4253, 1970.

McNeal et al., "[$^3$H]Batrachotoxinin A 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.

Morton et al., "Novel solid-phase synthesis of 1,5-benzothiazepine-4-one derivatives," *Tetrahedron Letters* 41: 3029-3033, 2000.

Muci and Buchwald, "Practical Palladium Catalysts for C-N and C-O Bond Formation," *Topics in Current Chemistry* 219: 131-209, 2002.

Muhammad et al., "Two stereoisomeric pentacyclic oxindole alkaloids from *Uncaria tomentosa*; uncarine C and uncarine E," *Acta Cyst.* C57: 480-482, 2001.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nair et al., "Formal dipolar cycloaddition of allylsilanes to *o*-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-*dl*-thyronine and Some of its Iodinated Derivatives," *J. Am. Chem. Soc.* 63: 609-611, Feb. 1941.

Oguri et al., "Amino Acids and Peptides. XXVIII. A New Synthesis of α-Amino Acid Derivatives by Alkylation of Schiff Bases derived from Glycine and Alanine," *Chem. Pharm. Bull.* 25(9): 2287-2291, 1977.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pages.

Overman and Watson, "Diaseroselection in the Formation of Spirocyclic Oxindoles by the Intramolecular Heck Reaction," *J. Org. Chem* 71: 2587-2599, 2006.

Pietra and Tacconi, "α-Alkyl- and α-aryl-N-methyltryptamines," *Farmaco, Edizione Scientifica* 14: 854-866, 1959, CAPLUS Database Accession No. 1960:50362, 1 page, Abstract only.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," *Journal of Pharmaceutical Sciences* 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7): 1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines," *Bioorganic & Medicinal Chemistry* 11: 407-419, 2003.

Reddy et al., "Synthesis and Pharmacological Evaluation of *N,N*-Diarylguanidines as Potent Sodium Channel Blockers and Anticonvulsant Agents," *J. Med. Chem.* 41(17): 3298-3302, 1998.

Rehn et al., "The Three-Component Reaction between Isatin, α-Amino Acids, and Dipolarophiles," *Eur. J. Org. Chem.* 413-418, 2004.

Ren and Dubner, "Enhanced Descending Modulation of Nociception in Rats With Persistent Hindpaw Inflamation," *Journal of Neurophysiology* 76(5): 3025-3037, Nov. 1996.

Rivalle and Bisagni, "Ethyl (4-*N*-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rosevear and Wilshire, "Cyclization Reactions in Azole Chemistry: The Reaction of Some Azoles with *o*-Fluoro-acetophenone, *o*-Fluorobenzaldehyde and *o*-Fluorobenzophenone," *Aust. J. Chem.* 44: 1097-1114, 1991.

Rossiter, "A convenient synthesis of 3-methyleneoxindoles: cytotoxic metabolites of indole-3-acetic acids," *Tetrahedron Letters* 43: 4671-4673, 2002.

Sadler, "Separation of Isomeric Isatins," *J. Org. Chem.* 21(2): 169-170, 1956.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sawyer, "Recent Advances in Diaryl Ether Synthesis," *Tetrahedron* 56: 5045-5065, 2000.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (—)-spirotryprostatin B via a diastereoselective azomethine glide [1,3]-dipolar cycloaddition reaction," *Tetrahedron* 58: 6311-6322, 2002.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono *O*-MOM- and *O*-Benzylresorcinols Prenylated at C-2 or C-4 Positions," *Synthesis* 6: 1017-1021, 1999.

Singh et al., "Novel cAMP PDE III Inhibitors: Imidazo[4,5-*b*]pyridine-2(3*H*)-ones and Thiazolo[4,5-*b*]pyridin-2(3*H*)-ones and Their Analogs," *J. Med. Chem.* 37: 248-254, 1994.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3']oxindole-spiro[3.7"] (3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (*S*)-(—)-Spirobrassinin, and Its Oxazoline Analog," *J. Org. Chem.* 66: 3940-3947, 2001.

Tacconi et al., "Heterodiene Syntheses—V 1,2- versus 1,4-cycloaddition reactions of enamines to n-substituted 3-oxindolideneacetopheones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2H-pyrrolo[2,3-b]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Usman et al., "1-Acetyl-3-(2-chloro-2,3-dihydrobenzofuran-3-yl)-1,2-dihydro-3-hydroxy-2-oxo-3H-indole," *Acta Cryst.* E58: o37-o39, 2002.

Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-b]pyridin-2(2H)-one Derivatives as Potential Non-opioid Analgesic Agents," *Pharmaceutical Sciences* 3: 283-287, 1997.

Viaud et al., "Acylation of Oxazolo[4,5-b]pyridin-2(3H)-ones, 2-Phenyloxazolo[4,5-b]pyridines and Pyrrolo[2,3-b]pyridin-2(2H)-ones," *Tetrahedron* 53(14): 5159-5168, 1997.

Villamil et al., "Efficacy of lidocaine in the treatment of pruritus in patients with chronic cholestatic liver diseases," *The American Journal of Medicine* 118: 1160-1163, 2005.

Vippagunta et al., "Crystalline solids," *Advanced Drug Delivery Reviews* 48: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

Wang and Ganesan, "A Biomimetic Total Synthesis of (—)-Spirotryprostatin B and Related Studies," *J. Org. Chem.* 65(15): 4685-4693, 2000.

Weidmann et al., "2-[(2-Pyridylmethyl)sulfinyl]-1H-thieno[3,4-d]imidazoles. A Novel Class of Gastric $H^+/K^+$-ATPase Inhibitors," *J. Med. Chem.* 35: 438-450, 1992.

Wolff (ed.), *Burger's Medicinal Chemistry and Drug Discovery, Fifth Edition, vol. I: Principles and Practice*, John Wiley & Sons, Inc., New York, New York, 1994, pp. 975-977.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Wu et al., "The Effect of Hypercholesterolemia on the Sodium Inward Currents in Cardiac Myocyte," *J. Mol. Cell. Cardiol.* 27: 1263-1269, 1995.

Yang and Williams, "Palladium-Catalyzed Cyanation of Aryl Bromides Promoted by Low-Level Organotin Compounds," *Organic Letters* 6(17): 2837-2840, 2004.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of syn-1-acetyl-9'aH-8'-methoxyspiro[indole-3,2'-oxeto[3',2':4,5]furo[3,2-g][1]benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans.* 1: 345-353, 2002.

Zinser et al., "Anthelmintic paraherquamides are cholinergic antagonists in gastrointestinal nematodes and mammals," *J. vet. Pharmacol. Therap.* 25: 241-250, 2002.

Invitation to Pay Additional Fees, mailed Aug. 23, 2006, for PCTAN PCT/US2006/014845, 11 pages.

International Search Report and Written Opinion, mailed Oct. 31, 2006, for PCTAN PCT/US2006/014865, 26 pages.

International Preliminary Report on Patentability, mailed Nov. 1, 2007, for PCTAN PCT/US2006/014865, 13 pages.

Chafeev et al., entitled Oxindole Compounds and Their Uses as Therapeutic Agents, Preliminary Amendment dated Jul. 14, 2006, for U.S. Appl. No. 11/408,269, 6 pages.

Chafeev et al., entitled Oxindole Compounds and Their Uses as Therapeutic Agents, Restriction Requirement mailed Sep. 9, 2008, for U.S. Appl. No. 11/408,269, 10 pages.

Chafeev et al., entitled Oxindole Compounds and Their Uses as Therapeutic Agents, Response to Restriction Requirement dated Oct. 9, 2008, for U.S. Appl. No. 11/408,269, 3 pages.

Chafeev et al., entitled Oxindole Compounds and Their Uses as Therapeutic Agents, Office Action mailed Dec. 15, 2008, for U.S. Appl. No. 11/408,269, 29 pages.

International Search Report and Written Opinion, mailed Oct. 6, 2006, for PCTAN PCT/US2006/014352, 11 pages.

International Preliminary Report on Patentability, mailed Oct. 16, 2007, for PCTAN PCT/US2006/014352, 6 pages.

Chafeev et al., entitled Spiro-Oxindole Compounds and Their Uses as Therapeutic Agents, Preliminary Amendment dated Jul. 5, 2006, for U.S. Appl. No. 11/402,310, 6 pages.

Chafeev et al., entitled Spiro-Oxindole Compounds and Their Uses as Therapeutic Agents, Restriction Requirement mailed Feb. 10, 2009, for U.S. Appl. No. 11/402,310, 7 pages.

Chafeev et al., entitled Spiro-Oxindole Compounds and Their Uses as Therapeutic Agents, Response to Restriction Requirement dated Feb. 25, 2009, for U.S. Appl. No. 11/402,310, 109 pages.

Chafeev et al., entitled Spiro-Oxindole Compounds and Their Uses as Therapeutic Agents, Office Action mailed May 15, 2009, for U.S. Appl. No. 11/402,310, 43 pages.

Chafeev et al., entitled Spiro-Oxindole Compounds and Their Uses as Therapeutic Agents, Amendment dated Aug. 17, 2009, for U.S. Appl. No. 11/402,310, 150 pages.

Chafeev et al., entitled Spiro-Oxindole Compounds and Their Uses as Therapeutic Agents, Notice of Allowance mailed Sep. 30, 2009, for U.S. Appl. No. 11/402,310, 9 pages.

Chafeev et al., entitled Spiro-Oxindole Compounds and Their Uses as Therapeutic Agents, Statement of the Substance of the Interview, mailed Oct. 30, 2009 for U.S. Appl. No. 11/402,310, 2 pages.

Chafeev et al., entitled Spiro-Oxindole Compounds and Their Uses as Therapeutic Agents, Communication dated Nov. 17, 2009, for U.S. Appl. No. 11/402,310, 4 pages.

Invitation to Pay Additional Fees, mailed Jan. 2, 2007, for PCTAN PCT/US2006/014887, 9 pages.

International Search Report and Written Opinion, mailed Mar. 15, 2007, for PCTAN PCT/US2006/014887, 22 pages.

International Preliminary Report on Patentability, mailed Nov. 1, 2007, for PCTAN PCT/US2006/014887, 12 pages.

Chafeev et al., entitled Heterocyclic Compounds and Their Uses as Therapeutic Agents, Preliminary Amendment dated Jul. 14, 2006, for U.S. Appl. No. 11/407,859, 6 pages.

Chafeev et al., entitled Heterocyclic Compounds and Their Uses as Therapeutic Agents, Restriction Requirement mailed Mar. 31, 2008, for U.S. Appl. No. 11/407,859, 9 pages.

Chafeev et al., entitled Heterocyclic Compounds and Their Uses as Therapeutic Agents, Response to Restriction Requirement dated Apr. 30, 2008, for U.S. Appl. No. 11/407,859, 39 pages.

Chafeev et al., entitled Heterocyclic Compounds and Their Uses as Therapeutic Agents, Office Action mailed Jun. 20, 2008, for U.S. Appl. No. 11/407,859, 46 pages.

Chafeev et al., entitled Heterocyclic Compounds and Their Uses as Therapeutic Agents, Amendment dated Oct. 17, 2008, for U.S. Appl. No. 11/407,859, 41 pages.

Chafeev et al., entitled Heterocyclic Compounds and Their Uses as Therapeutic Agents, Office Action mailed Jan. 15, 2009, for U.S. Appl. No. 11/407,859, 8 pages.

International Search Report and Written Opinion, mailed Aug. 11, 2006, for PCTAN PCT/US2006/013318, 15 pages.

International Preliminary Report on Patentability, mailed Oct. 16, 2007, for PCTAN PCT/US2006/013318, 9 pages.

Chafeev et al., entitled Spiroheterocyclic Compounds and Their Uses as Therapeutic Agents, Preliminary Amendment dated Jul. 7, 2006, for U.S. Appl. No. 11/402,200, 6 pages.

Chafeev et al., entitled Spiroheterocyclic Compounds and Their Uses as Therapeutic Agents, Restriction Requirement mailed Feb. 10, 2009, for U.S. Appl. No. 11/402,200, 6 pages.

Chafeev et al., entitled Spiroheterocyclic Compounds and Their Uses as Therapeutic Agents, Response to Restriction Requirement dated Feb. 27, 2009, for U.S. Appl. No. 11/402,200, 31 pages.

Chafeev et al., entitled Spiroheterocyclic Compounds and Their Uses as Therapeutic Agents, Office Action mailed Apr. 24, 2009, for U.S. Appl. No. 11/402,200, 30 pages.

Chafeev et al., entitled Spiroheterocyclic Compounds and Their Uses as Therapeutic Agents, Amendment dated Aug. 24, 2009, for U.S. Appl. No. 11/402,200, 36 pages.

Chafeev et al., entitled Spiroheterocyclic Compounds and Their Uses as Therapeutic Agents, Office Action mailed Nov. 17, 2009, for U.S. Appl. No. 11/402,200, 7 pages.

Chafeev et al., entitled Spiroheterocyclic Compounds and Their Uses as Therapeutic Agents, Amendment dated Mar. 17, 2010, for U.S. Appl. No. 11/402,200, 17 pages.

Chafeev et al., entitled Spiroheterocyclic Compounds and Their Uses as Therapeutic Agents, Notice of Allowance dated May 13, 2010, for U.S. Appl. No. 11/402,200, 16 pages.

International Search Report and Written Opinion, mailed Mar. 3, 2008, for PCTAN PCT/US2007/081240, 16 pages.

International Preliminary Report on Patentability mailed Apr. 23, 2009, for PCTAN PCT/US2007/081240, 9 pages.

International Search Report and Written Opinion, mailed Oct. 13, 2008, for PCTAN PCT/US2007/081323, 21 pages.

International Preliminary Report on Patentability, mailed Apr. 15, 2009, for PCTAN PCT/US2007/081323, 12 pages.

International Search Report and Written Opinion, mailed Mar. 3, 2008, for PCTAN PCT/US2007/081244, 21 pages.

International Preliminary Report on Patentability, mailed Apr. 23, 2009, for PCTAN PCT/US2007/081244, 12 pages.

Invitation to Pay Additional Fees, mailed Jul. 16, 2008, for PCTAN PCT/US2007/081319, 10 pages.

International Search Report and Written Opinion, mailed Dec. 29, 2008, for PCTAN PCT/US2007/081319, 18 pages.

International Preliminary Report on Patentability, mailed Apr. 15, 2009, for PCTAN PCT/US2007/081319, 8 pages.

International Search Report and Written Opinion, mailed May 19, 2008, for PCTAN PCT/US2007/081247, 18 pages.

International Preliminary Report on Patentability, mailed Apr. 15, 2009, for PCTAN PCT/US2007/081247, 10 pages.

Chafeev et al., entitled Use of Spiro-Oxindole Compounds as Therapeutic Agents, Preliminary Amendment dated Mar. 4, 2010, for U.S. Appl. No. 12/445,264, 18 pages.

International Search Report and Written Opinion, mailed May 13, 2008, for PCTAN PCT/US2007/081318, 12 pages.

International Preliminary Report on Patentability, mailed Apr. 15, 2009, for PCTAN PCT/US2007/081318, 5 pages.

International Search Report and Written Opinion, mailed Mar. 6, 2008, for PCTAN PCT/US2007/081297, 18 pages.

International Preliminary Report on Patentability, mailed Apr. 15, 2009, for PCTAN PCT/US2007/081297, 10 pages.

Invitation to Pay Additional Fees, mailed Jan. 27, 2009, for PCTAN PCT/US2007/081320, 7 pages.

Written Opinion of the International Searching Authority, mailed Jan. 5, 2009, for PCTAN PCT/US2007/081320, 11 pages.

International Preliminary Report on Patentability, mailed May 5, 2009, for PCTAN PCT/US2007/081320, 12 pages.

International Search Report and Written Opinion, mailed Feb. 9, 2010, for PCTAN PCT/US2009/063290, 13 pages.

Invitation to Pay Additional Fees, mailed Feb. 9, 2010, for PCTAN PCT/US2009/060537, 8 pages.

Chafeev et al., entitled Spiro-Oxindole Compounds and Their Use as Therapeutic Agents, Preliminary Amendment dated Jan. 12, 2010, for U.S. Appl. No. 12/578,148, 57 pages.

International Search Report and Written Opinion, mailed Jan. 22, 2010, for PCTAN PCT/US2009/060455, 14 pages.

International Search Report and Written Opinion, mailed Apr. 8, 2010, for PCTAN PCT/US2009/069663, 13 pages.

* cited by examiner

USE OF SPIRO-OXINDOLE COMPOUNDS AS THERAPEUTIC AGENTS

CROSS-REFERENCE TO RELATED APPLICATIONS

This application is a U.S. National Phase Application of International Application No. PCT/US2007/081247, filed Oct. 12, 2007; which claims the benefit of U.S. Provisional Patent Application No. 60/851,787, filed Oct. 12, 2006. These applications are incorporated herein by reference in their entireties.

FIELD OF THE INVENTION

The present invention is directed to methods of using spiro-oxindole compounds as therapeutic agents. In particular, this invention is directed to the use of certain spiro-oxindole compounds in treating diseases or conditions such as hypercholesterolemia, benign prostatic hyperplasia, pruritis and cancer.

BACKGROUND OF THE INVENTION

Voltage-gated sodium channels, transmembrane proteins that initiate action potentials in nerve, muscle and other electrically excitable cells, are a necessary component of normal sensation, emotions, thoughts and movements (Catterall, W. A., *Nature* (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., *Neuron* (2000), Vol. 28, pp. 365-368). Each alpha-subunit contains four homologous domains, I to IV, each with six predicted transmembrane segments. The alpha-subunit of the sodium channel, forming the ion-conducting pore and containing the voltage sensors regulating sodium ion conduction has a relative molecular mass of 260,000. Electrophysiological recording, biochemical purification, and molecular cloning have identified ten different sodium channel alpha subunits and four beta subunits (Yu, F. H., et al., *Sci. STKE* (2004), 253; and Yu, F. H., et al., *Neurosci.* (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., *Nature* (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. Implicit with function, this family of proteins are considered prime points of therapeutic intervention. $Na_v1.1$ and $Na_v1.2$ are highly expressed in the brain (Raymond, C. K., et al., *J. Biol. Chem.* (2004), 279(44):46234-41) and are vital to normal brain function. In humans, mutations in $Na_v1.1$ and $Na_v1.2$ result in severe epileptic states and in some cases mental decline (Rhodes, T. H., et al., *Proc. Natl. Acad. Sci. USA* (2004),101(30):11147-52; Kamiya, K., et al., *J. Biol. Chem.* (2004), 24(11):2690-8; Pereira, S., et al., *Neurology* (2004), 63(1):191-2). As such both channels have been considered as validated targets for the treatment of epilepsy (see PCT Published Patent Publication No. WO 01/38564).

$Na_v1.3$ is broadly expressed throughout the body (Raymond, C. K., et al., op. cit.). It has been demonstrated to have its expression upregulated in the dorsal horn sensory neurons of rats after nervous system injury (Hains, B. D., et al., *J. Neurosci.* (2003), 23(26):8881-92). Many experts in the field have considered $Na_v1.3$ as a suitable target for pain therapeutics (Lai, J., et al., *Curr. Opin. Neurobiol.* (2003), (3):291-72003; Wood, J. N., et al., *J. Neurobiol.* (2004), 61(1):55-71; Chung, J. M., et al., *Novartis Found Symp.* (2004), 261:19-27; discussion 27-31, 47-54).

$Na_v1.4$ expression is essentially limited to muscle (Raymond, C. K., et al., op. cit.). Mutations in this gene have been shown to have profound effects on muscle function including paralysis, (Tamaoka A., *Intern. Med.* (2003), (9):769-70). Thus, this channel can be considered a target for the treatment of abnormal muscle contractility, spasm or paralysis.

The cardiac sodium channel, $Na_v1.5$, is expressed mainly in the heart ventricles and atria (Raymond, C. K., et al., op. cit.), and can be found in the sinovial node, ventricular node and possibly Purkinje cells. The rapid upstroke of the cardiac action potential and the rapid impulse conduction through cardiac tissue is due to the opening of $Na_v1.5$. As such, $Na_v1.5$ is central to the genesis of cardiac arrhythmias. Mutations in human $Na_b1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H. et al., *Am. J. Pharmacogenomics* (2003), 3(3):173-9). Sodium channel blocker therapy has been used extensively in treating cardiac arrhythmias. The first antiarrhythmic drug, quinidine, discovered in 1914, is classified as a sodium channel blocker.

$Na_v1.6$ encodes an abundant, widely distributed voltage-gated sodium channel found throughout the central and peripheral nervous systems, clustered in the nodes of Ranvier of neural axons (Caldwell, J. H., et al., *Proc. Natl. Acad. Sci. USA* (2000), 97(10): 5616-20). Although no mutations in humans have been detected, $Na_v1.6$ is thought to play a role in the manifestation of the symptoms associated with multiple sclerosis and has been considered as a target for the treatment of this disease (Craner, M. J., et al., *Proc. Natl. Acad. Sci. USA* (2004), 101(21):8168-73).

$Na_v1.7$ was first cloned from the pheochromocytoma PC12 cell line (Toledo-Aral, J. J., et al., *Proc. Natl. Acad. Sci. USA* (1997), 94:1527-1532). Its presence at high levels in the growth cones of small-diameter neurons suggested that it could play a role in the transmission of nociceptive information. Although this has been challenged by experts in the field as $Na_v1.7$ is also expressed in neuroendocrine cells associated with the autonomic system (Klugbauer, N., et al., *EMBO J.* (1995), 14(6):1084-90) and as such has been implicated in autonomic processes. The implicit role in autonomic functions was demonstrated with the generation of $Na_v1.7$ null mutants; deleting $Na_v1.7$ in all sensory and sympathetic neurons resulted in a lethal perinatal phenotype. (Nassar, et al., *Proc. Natl. Acad. Sci. USA* (2004), 101(34):12706-11.). In contrast, by deleting the $Na_v1.7$ expression in a subset of sensory neurons that are predominantly nociceptive, a role in pain mechanisms, was demonstrated (Nassar, et al., op. cit.). Further support for $Na_v1.7$ blockers active in a subset of neurons is supported by the finding that two human heritable pain conditions, primary erythermalgia and familial rectal pain, have been shown to map to $Na_v1.7$ (Yang, Y., et al., *J. Med. Genet.* (2004), 41(3):171-4).

The expression of $Na_v1.8$ is essentially restricted to the DRG (Raymond, C. K., et al., op. cit.). There are no identified human mutations for $Na_v1.8$. However, $Na_v1.8$-null mutant mice were viable, fertile and normal in appearance. A pronounced analgesia to noxious mechanical stimuli, small deficits in noxious thermoreception and delayed development of inflammatory hyperalgesia suggested to the researchers that $Na_v1.8$ plays a major role in pain signalling (Akopian, A. N., et al., *Nat. Neurosci.* (1999), 2(6): 541-8). Blocking of this channel is widely accepted as a potential treatment for pain (Lai, J, et al., op. cit.; Wood, J. N., et al., op. cit.; Chung, J. M., et al., op. cit.). PCT Published Patent Application No. WO03/037274A2 describes pyrazole-amides and sulfonamides for the treatment of central or peripheral nervous system conditions, particularly pain and chronic pain by blocking sodium channels associated with the onset or recurrance of the indicated conditions. PCT Published Patent Application No. WO03/037890A2 describes piperidines for the treatment of central or peripheral nervous system conditions, particularly pain and chronic pain by blocking sodium channels associated with the onset or recurrence of the indicated conditions. The compounds, compositions and methods of these inventions are of particular use for treating neuropathic or inflammatory pain by the inhibition of ion flux through a channel that includes a PN3 ($Na_v1.8$) subunit.

The tetrodotoxin insensitive, peripheral sodium channel $Na_v1.9$, disclosed by Dib-Hajj, S. D., et al. (see Dib-Hajj, S. D., et al., *Proc. Natl. Acad. Sci. USA* (1998), 95(15):8963-8) was shown to reside solely in the dorsal root ganglia. It has been demonstrated that $Na_v1.9$ underlies neurotrophin (BDNF)-evoked depolarization and excitation, and is the only member of the voltage gated sodium channel superfamily to be shown to be ligand mediated (Blum, R., Kafitz, K. W., Konnerth, A., *Nature* (2002), 419 (6908):687-93). The limited pattern of expression of this channel has made it a candidate target for the treatment of pain (Lai, J, et al., op. cit.; Wood, J. N., et al., op. cit.; Chung, J. M. et al., op. cit.).

NaX is a putative sodium channel, which has not been shown to be voltage gated. In addition to expression in the lung, heart, dorsal root ganglia, and Schwann cells of the peripheral nervous system, NaX is found in neurons and ependymal cells in restricted areas of the CNS, particularly in the circumventricular organs, which are involved in body-fluid homeostasis (Watanabe, E., et al., *J. Neurosci.* (2000), 20(20):7743-51). NaX-null mice showed abnormal intakes of hypertonic saline under both water- and salt-depleted conditions. These findings suggest that the NaX plays an important role in the central sensing of body-fluid sodium level and regulation of salt intake behaviour. Its pattern of expression and function suggest it as a target for the treatment of cystic fibrosis and other related salt regulating maladies.

Studies with the sodium channel blocker tetrodotoxin (TTX) used to lower neuron activity in certain regions of the brain, indicate its potential use in the treatment of addiction. Drug-paired stimuli elicit drug craving and relapse in addicts and drug-seeking behavior in rats. The functional integrity of the basolateral amygdala (BLA) is necessary for reinstatement of cocaine-seeking behaviour elicited by cocaine-conditioned stimuli, but not by cocaine itself. BLA plays a similar role in reinstatement of heroin-seeking behavior. TTX-induced inactivation of the BLA on conditioned and heroin-primed reinstatement of extinguished heroin-seeking behaviour in a rat model (Fuchs, R. A. and See, R. E., *Psychopharmacology* (2002) 160(4):425-33).

This closely related family of proteins has long been recognised as targets for therapeutic intervention. Sodium channels are targeted by a diverse array of pharmacological agents. These include neurotoxins, antiarrhythmics, anticonvulsants and local anesthetics (Clare, J. J., et al., *Drug Discovery Today* (2000) 5:506-520). All of the current pharmacological agents that act on sodium channels have receptor sites on the alpha subunits. At least six distinct receptor sites for neurotoxins and one receptor site for local anesthetics and related drugs have been identified (Cestéle, S. et al., *Biochimie* (2000), Vol. 82, pp. 883-892).

The small molecule sodium channel blockers or the local anesthetics and related antiepileptic and antiarrhythmic drugs, interact with overlapping receptor sites located in the inner cavity of the pore of the sodium channel (Catterall, W. A., *Neuron* (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrignine, phenyloin and carbamazepine) and certain cardiac arrhythmias (e.g. lignocaine, tocamide and mexiletine). However, the potency and therapeutic index of these blockers is not optimal and have limited the usefulness of these compounds in a variety of therapeutic areas where a sodium channel blocker would be ideally suited.

SUMMARY OF THE INVENTION

The present invention is directed to the use of spiro-oxindole compounds for the treatment and/or prevention of diseases or conditions, such as hypercholesterolemia, benign prostatic hyperplasia, pruritis, and cancer.

Accordingly, in one aspect, the invention provides compounds of formula (I):

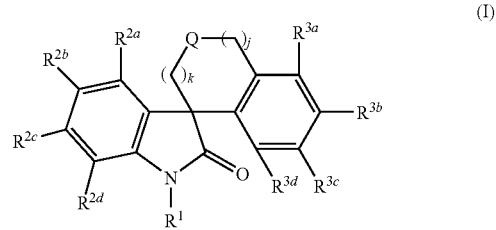

wherein:
j and k are each independently 0, 1, 2 or 3;
Q is —C($R^{1a}$)H—, —C(O)—, —O—, —S(O)$_m$— (where m is 0, 1 or 2), —$CF_2$—, —C(O)O—, —C(O)N($R^5$)— or —N($R^5$)C(O)—;
$R^{1a}$ is hydrogen or —$OR^5$;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)$OR^5$, —$R^8$—C(O)N($R^4$)$R^5$, —S(O)$_2$—$R^5$, —$R^9$—S(O)$_t$—$R^5$ (where m is 0, 1 or 2), —$R^8$—$OR^5$, —$R^8$—CN, —$R^9$—P(O)($OR^5$)$_2$, or —$R^9$—O—$R^9$—$OR^5$;

or $R^1$ is aralkyl substituted by —C(O)N($R^6$)$R^7$ where:
   $R^6$ is hydrogen, alkyl, aryl or aralkyl; and
   $R^7$ is hydrogen, alkyl, haloalkyl, —$R^9$—CN, —$R^9$—OR$^5$, —$R^9$—N($R^4$)$R^5$, aryl, aralkyl, cycloalkyl, cycloalkylalkyl, heterocyclyl, heterocyclylalkyl, heteroaryl, heteroarylalkyl;
   or $R^6$ and $R^7$, together with the nitrogen to which they are attached, form a heterocyclyl or heteroaryl;
   and wherein each aryl, aralkyl, cycloalkyl, cycloalkylalkyl, heterocyclyl, heterocyclylalkyl, heteroaryl and heteroaryl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—OR$^5$, heterocyclyl and heteroaryl;
or $R^1$ is aralkyl optionally substituted by one or more substituents selected from the group consisting of —$R^8$—OR$^5$, —C(O)OR$^5$, halo, haloalkyl, alkyl, nitro, cyano, aryl, aralkyl, heterocyclyl and heteroaryl;
or $R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ where:
   each $R^{10}$ is hydrogen, alkyl, aryl, aralkyl or heteroaryl;
   each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)R$^5$, —$R^9$—C(O)OR$^5$, —$R^9$—C(O)N($R^4$)$R^5$, —$R^9$—C(O)R$^5$, —$R^9$—N($R^4$)$R^5$, —$R^9$—OR$^5$, or —$R^9$—CN;
   $R^{12}$ is hydrogen, alkyl, aryl, aralkyl or —C(O)R$^5$;
   and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—OR$^5$, —$R^8$—C(O)R$^5$, heterocyclyl and heteroaryl;
or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—OR$^5$, —$R^8$—C(O)OR$^5$, —$R^8$—N($R^4$)$R^5$, —$R^8$—C(O)N($R^4$)$R^5$, —$R^8$—N($R^5$)C(O)R$^4$, —$R^8$—S(O)$_m$R$^4$ (where m is 0, 1 or 2), —$R^8$—CN, or —$R^8$—NO$_2$;
$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, —N=C($R^4$)$R^5$, —S(O)$_m$R$^4$, —OS(O)$_2$CF$_3$, —$R^8$—C(O)R$^4$, —C(S)R$^4$, —C($R^4$)$_2$C(O)R$^5$, —$R^8$—C(O)OR$^4$, —C(S)OR$^4$, —$R^8$—C(O)N($R^4$)$R^5$, —C(S)N($R^4$)$R^5$, —N($R^5$)C(O)R$^4$, —N($R^5$)C(S)R$^4$, —N($R^5$)C(O)OR$^4$, —N($R^5$)C(S)OR$^4$, —N($R^5$)C(O)N($R^4$)$R^5$, —N($R^5$)C(S)N($R^4$)$R^5$, —N($R^5$)S(O)$_n$R$^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$,
   wherein each m is independently 0, 1, or 2 and each n is independently 1 or 2;
   and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, S(O)$_m$R$^4$, —$R^8$—S(O)$_n$N($R^4$)$R^5$, —$R^8$—C(O)R$^4$, —$R^8$—C(O)OR$^4$, —$R^8$—C(O)N($R^4$)R$^5$, —N($R^5$)C(O)R$^4$, and —N($R^5$)S(O)$_n$R$^4$, wherein each m is independently 0, 1, or 2 and each n is independently 1 or 2;
or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;
or $R^{2b}$ and $R^{2c}$, together with the carbon ring atoms to which they are directly attached, may form a fused ring selected from cycloalkyl, aryl, heterocyclyl and heteroaryl, and $R^{2c}$ and $R^{2d}$ are as defined above;
or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;
$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, —N=C($R^4$)$R^5$, —S(O)$_m$R$^4$, —OS(O)$_2$CF$_3$, —$R^8$—C(O)R$^4$, —C(S)R$^4$, —C($R^4$)$_2$C(O)R$^5$, —$R^8$—C(O)OR$^4$, —C(S)OR$^4$, —$R^8$—C(O)N($R^4$)$R^5$, —C(S)N($R^4$)$R^5$, —N($R^5$)C(O)R$^4$, —N($R^5$)C(S)R$^4$, —N($R^5$)C(O)OR$^4$, —N($R^5$)C(S)OR$^4$, —N($R^5$)C(O)N($R^4$)$R^5$, —N($R^5$)C(S)N($R^4$)$R^5$, —N($R^5$)S(O)$_n$R$^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;
or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;
or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;
or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;
each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl; and
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain;
as a stereoisomer, enantiomer, tautomer thereof or mixtures thereof;
or a pharmaceutically acceptable salt, solvate or prodrug thereof.

In another aspect, the invention provides methods of treating or preventing hypercholesterolemia in a mammal, preferably a human, wherein the methods comprise administering to the mammal in need thereof a therapeutically effective amount of a compound of the invention as set forth above.

In another aspect, the invention provides methods of treating or preventing benign prostatic hyperplasia in a mammal, preferably a human, wherein the methods comprise administering to the mammal in need thereof a therapeutically effective amount of a compound of the invention as set forth above.

In another aspect, the invention provides methods of treating or preventing pruritis in a mammal, preferably a human, wherein the methods comprise administering to the mammal in need thereof a therapeutically effective amount of a compound of the invention as set forth above.

In another aspect, the invention provides methods of treating or preventing cancer in a mammal, preferably a human, wherein the methods comprise administering to the mammal in need thereof a therapeutically effective amount of a compound of the invention as set forth above.

In another aspect, the invention provides pharmaceutical compositions comprising the compounds of the invention, as set forth above, and pharmaceutically acceptable excipients.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed in the invention.

In another aspect, this invention is directed to the use of a compound of the invention, as set forth above, as a stereoisomer, enantiomer or tautomer or mixtures thereof, or a pharmaceutically acceptable salt, solvate or prodrug thereof, or the use of a pharmaceutical composition of the invention, comprising a pharmaceutically acceptable excipient and a compound of the invention, as set forth above, as a stereoisomer, enantiomer or tautomer or mixtures thereof, or a pharmaceutically acceptable salt, solvate or prodrug thereof, in the preparation of a medicament for the treatment and/or prevention of hypercholesterolemia, benign prostatic hyperplasia, pruritis, and/or cancer in a mammal.

DETAILED DESCRIPTION OF THE INVENTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described. For example, the following terms have the meaning indicated:

"$C_1$-$C_{10}$alkyl" refers to an alkyl radical as defined below containing one to ten carbon atoms. The $C_1$-$C_{10}$alkyl radical may be optionally substituted as defined below for an alkyl group.

"$C_2$-$C_{12}$alknyl" refers to an alknyl radical as defined below containing two to twelve carbon atoms. The $C_2$-$C_{12}$alknyl radical may be optionally substituted as defined below for an alkenyl group.

"$C_1$-$C_{12}$alkoxy" refers to an alkoxy radical as defined below containing one to twelve carbon atoms. The alkyl part of the $C_1$-$C_{12}$alkoxy radical may be optionally substituted as defined below for an alkyl group.

"$C_2$-$C_{12}$alkoxyalkyl" refers to an alkoxyalkyl radical as defined below containing two to twelve carbon atoms. Each alkyl part of the $C_2$-$C_{12}$alkoxyalkyl radical may be optionally substituted as defined below for an alkyl group.

"$C_7$-$C_{12}$aralkyl" refers to an aralkyl group as defined below containing seven to twelve carbon atoms. The aryl part of the $C_7$-$C_{12}$aralkyl radical may be optionally substituted as described below for an aryl group. The alkyl part of the $C_7$-$C_{12}$aralkyl radical may be optionally substituted as defined below for an alkyl group.

"$C_7$-$C_{12}$aralkenyl" refers to an aralkenyl group as defined below containing seven to twelve carbon atoms. The aryl part of the $C_7$-$C_{12}$aralkenyl radical may be optionally substituted as described below for an aryl group. The alkenyl part of the $C_7$-$C_{12}$aralkenyl radical may be optionally substituted as defined below for an alkenyl group.

"$C_3$-$C_{12}$cycloalkyl" refers to a cycloalkyl radical as defined below having three to twelve carbon atoms. The $C_3$-$C_{12}$cycloalkyl radical may be optionally substituted as defined below for a cycloalkyl group.

"$C_4$-$C_{12}$cycloalkylalkyl" refers to a cycloalkylalkyl radical as defined below having four to twelve carbon atoms. The $C_4$-$C_{12}$cycloalkylalkyl radical may be optionally substituted as defined below for a cycloalkylalkyl group.

In addition to the foregoing, as used in the specification and appended claims, unless specified to the contrary, the following terms have the meaning indicated:

"Amino" refers to the —$NH_2$ radical.
"Cyano" refers to the —CN radical.
"Hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Trifluoromethyl" refers to the —$CF_3$ radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —OC(O)—$R^{14}$, —$N(R^{14})_2$, —C(O)$R^{14}$, —C(O)$OR^{14}$, —C(O)N($R^{14})_2$, —N($R^{14}$)C(O)$OR^{16}$, —N($R^{14}$)C(O)$R^{16}$, —N($R^{14}$)S(O)$_tR^{16}$ (where t is 1 to 2), —S(O)$_tOR^{16}$ (where t is 1 to 2), —S(O)$_tR^{16}$ (where t is 0 to 2), and —S(O)$_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —N(R$^{14}$)C(O)OR$^{16}$, —N(R$^{14}$)C(O)R$^{16}$, —N(R$^{14}$)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms, preferably one to eight carbon atoms and which is attached to the rest of the molecule by a single bond, e.g., ethynyl, propynyl, butynyl, pentynyl, hexynyl, and the like. Unless stated otherwise specifically in the specification, an alkynyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from 6 to 18 carbon atoms, where the ring system may be partially saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl, akenyl, halo, haloalkyl, haloalkenyl, cyano, nitro, aryl, heteroaryl, heteroarylalkyl, —R$^{15}$—OR$^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)S(O)$_t$$R^{16}$ (where t is 1 to 2), —$R^{15}$—S(O)$_t$OR$^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aryloxy" refers to a radical of the formula —$OR_b$ where $R_b$ is an aryl group as defined above. The aryl part of the aryloxy radical may be optionally substituted as defined above.

"Aralkenyl" refers to a radical of the formula —$R_cR_b$, where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aralkyloxy" refers to a radical of the formula —$OR_b$ where $R_b$ is an aralkyl group as defined above. The aralkyl part of the aralkyloxy radical may be optionally substituted as defined above.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)S(O)$_t$$R^{16}$ (where t is 1 to 2), —$R^{15}$—S(O)$_t$OR$^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)S(O)$_t$$R^{16}$) (where t is 1 to 2), —$R^{15}$—S(O)$_t$OR$^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of one to seventeen carbon atoms and from one to ten heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, oxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—$N(R^{14})_2$, —$R^{15}$—C(O)$R^{14}$, —$R^{15}$—C(O)$R^{14}$, —$R^{15}$—C(O)$OR^{14}$, —$R^{15}$—C(O)$N(R^{14})_2$, —$R^{15}$—$N(R^{14})$C(O)$OR^{16}$, —$R^{15}$—$N(R^{14})$C(O)$R^{16}$, —$R^{15}$—$N(R^{14})$S(O)$_t R^{16}$ (where t is 1 to 2), —$R^{15}$—S(O)$_t OR^{16}$ (where t is 1 to 2), —$R^{15}$—S(O)$_t R^{16}$ (where t is 0 to 2), and —$R^{15}$—S(O)$_t N(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl.

"Heteroarylalkyl" refers to a radical of the formula —$R_a R_f$ where $R_a$ is an alkyl radical as defined above and $R_t$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —$R_b R_f$ where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"Trihaloalkoxy" refers to a radical of the formula —$OR_g$ where $R_g$ is a trihaloalkyl group as defined above. The trihaloalkyl part of the trihaloalkoxy group may be optionally substituted as defined above for a trihaloalkyl group.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reducation, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its coversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. When a functional group is described as "optionally substituted," and in turn, substitutents on the functional group are also "optionally substituted" and so on, for the purposes of this invention, such iterations are limited to five.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Also within the scope of the invention are intermediate compounds of formula (I) and all polymorphs of the aforementioned species and crystal habits thereof.

The chemical naming protocol and structure diagrams used herein are a modified form of the I.U.P.A.C. nomenclature system, using the ACD/Name Version 9.07 software program, wherein the compounds of the invention are named herein as derivatives of the central core structure, i.e., the 2-oxindole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I) wherein j is 0, k is 1, Q is —O—, $R^1$ is pentyl, $R^{2a}$ is 3,5-dichlorophenyl, $R^{2b}$, $R^{2c}$ and $R^{2d}$ are each hydrogen, $R^{3a}$ and $R^{3d}$ are each hydrogen, and $R^{3b}$ and $R^{3c}$, together with the carbon ring atoms to which they are attached, form a fused dioxolyl ring; i.e., a compound of the following formula:

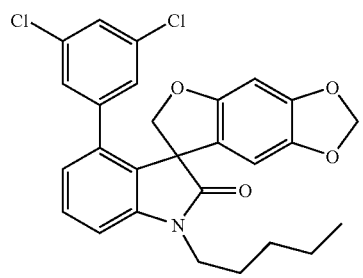 [SMILES: CCCCCN1C(=O)C2(COc3cc4c(cc32)OCO4)c2c(-c3cc(Cl)cc(Cl)c3)cccc21]

is named herein as 4'-(3,5-dichlorophenyl)-t-pentylspiro [furo[2,3-f][1,3]benzodioxole-7,3'-indol]-2'(1'H)-one.

Embodiments of the Invention

Of the various aspects of the invention set forth above in the Summary of the Invention, certain embodiments are preferred.

One embodiment of the invention are the compounds of formula (I) as set forth above in the Summary of the invention wherein:

at least one of j and k is 1 and the other is 0 or 1;
Q is —O—;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;
$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —S(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N(R$^4$)R$^5$, —N═C(R$^4$)R$^5$, —S(O)$_m$R$^4$, —OS(O)$_2$CF$_3$, —$R^8$—C(O)R$^4$, —C(S)R$^4$, —C(R$^4$)$_2$C(O)R$^5$, —$R^8$—C(O)OR$^4$, —C(S)OR$^4$, —$R^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —$R^8$—S(O)$_n$N(R$^4$)R$^5$, —N(R$^5$)C(═NR$^5$)N(R$^4$)R$^5$, and —N(R$^5$)C(N═C(R$^4$)R$^5$)N(R$^4$)R$^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is hydrogen, alkyl, alkenyl, alkynyl, haloalkyl, aryl, cycloalkyl, cycloalkylalkyl, heteroaryl, heterocyclyl, —$R^8$—C(O)R$^5$, —$R^8$—C(O)OR$^5$, —$R^8$—C(O)N(R$^4$)R$^5$, —S(O)$_2$—R$^5$, —$R^9$—S(O)$_m$—R$^5$ (where m is 0, 1 or 2), —$R^8$—OR$^5$, —$R^8$—CN, —$R^9$—P(O)(OR$^5$)$_2$, or —$R^9$—O—$R^9$—OR$^5$;

$R^{2a}$, $R^{2b}$, $R^{2c}$ and $R^{2d}$ are each independently selected from hydrogen, halo or alkyl;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N(R$^4$)R$^5$, —N═C(R$^4$)R$^5$, —S(O)$_m$R$^4$, —OS(O)$_2$CF$_3$, —$R^8$—C(O)R$^4$, —C(S)R$^4$, —C(R$^4$)$_2$C(O)R$^5$, —$R^8$—C(O)OR$^4$, —C(S)OR$^4$, —$R^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —$R^8$—S(O)$_n$N(R$^4$)R$^5$, —N(R$^5$)C(═NR$^5$)N(R$^4$)R$^5$, and —N(R$^5$)C(N═C(R$^4$)R$^5$)N(R$^4$)R$^5$, wherein each m is independently 0, 1, or 2 and each n is independently 1 or 2;

or $R^{3b}$ and $R^{3c}$, together with the carbon ring atoms to which they are directly attached, form a fused ring selected from cycloalkyl, heterocyclyl, aryl or heteroaryl, and $R^{3a}$ and $R^{3c}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl; or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

$R^1$ is hydrogen, alkyl, alkenyl, alkynyl, haloalkyl, cycloalkyl, cycloalkylalkyl, —$R^8$—OR$^5$, —$R^8$—C(O)R$^5$, —$R^8$—C(O)OR$^5$, —$R^8$—C(O)N(R$^4$)R$^5$, —S(O)$_2$—R$^5$, —$R^8$—CN, —$R^9$—P(O)(OR$^5$)$_2$, or —$R^9$—O—$R^9$—OR$^5$;

$R^{2a}$, $R^{2b}$, $R^{2c}$ and $R^{2d}$ are each independently selected from hydrogen, halo or alkyl;

$R^{3a}$ and $R^{3d}$ are both hydrogen;

$R^{3b}$ and $R^{3c}$, together with the carbon ring atoms to which they are directly attached, form a fused dioxolyl ring;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

1'-(2-cyclopropylethyl)spiro[furo[2,3-f][1,3]benzodioxole-7,3'-indol]-2'(1'H)-one;

1'-pentylspiro[furo[2,3-f][1,3]benzodioxole-7,3'-indol]-2'(1'H)-one;

4'-bromo-1'-pentylspiro[furo[2,3-f][1,3]benzodioxole-7,3'-indol]-2'(1'H)-one;

ethyl (2'-oxospiro[furo[2,3-f][1,3]benzodioxole-7,3'-indol]-1'(2'H)-yl)acetate;

spiro[furo[2,3-f][1,3]benzodioxole-7,3'-indol]-2'(1'H)-one;

1'-[3-(benzyloxy)propyl]spiro[furo[2,3-f][1,3]benzodioxole-7,3'-indol]-2'(1'H)-one;

4',7'-dichloro-1'-pentylspiro[furo[2,3-f][1,3]benzodioxole-7,3'-indol]-2'(1'H)-one;
4'-bromospiro[furo[2,3-f][1,3]benzodioxole-7,3'-indol]-2'(1'H)-one;
4'-bromo-5,6-dihydrospiro[benzo[1,2-b:5,4-b']difuran-3,3'-indol]-2'(1'H)-one;
5'-methylspiro[furo[2,3-f][1,3]benzodioxole-7,3'-indol]-2'(1'H)-one;
ethyl (4'-bromo-2'-oxo-5,6-dihydrospiro[benzo[1,2-b:5,4-b']difuran-3,3'-indol]-1'(2'H)-yl)acetate;
ethyl (4'-chloro-2'-oxo-5,6-dihydrospiro[benzo[1,2-b:5,4-b']difuran-3,3'-indol]-1'(2'H)-yl)acetate;
ethyl (5'-chloro-2'-oxo-5,6-dihydrospiro[benzo[1,2-b:5,4-b']difuran-3,3'-indol]-1'(2'H)-yl)acetate;
7'-fluorospiro[furo[2,3-f][1,3]benzodioxole-7,3'-indol]-2'(1'H)-one;
(2'-oxospiro[furo[2,3-f][1,3]benzodioxole-7,3'-indol]-1'(2'H)-yl)acetic acid;
N-(4-chlorobenzyl)-2-(2'-oxospiro[furo[2,3-f][1,3]benzodioxole-7,3'-indol]-1'(2'H)-yl)acetamide;
N-(3-fluorophenyl)-2-(2'-oxospiro[furo[2,3-f][1,3]benzodioxole-7,3'-indol]-1'(2'H)-yl)acetamide;
N-butyl-2-(2'-oxospiro[furo[2,3-f][1,3]benzodioxole-7,3'-indol]-1'(2'H)-yl)acetamide;
1'-(2-oxo-2-piperidin-1-ylethyl)spiro[furo[2,3-f][1,3]benzodioxole-7,3'-indol]-2'(1'H)-one;
N-butyl-N-methyl-2-(2'-oxospiro[furo[2,3-f][1,3]benzodioxole-7,3'-indol]-1'(2'H)-yl)acetamide;
2-(2'-oxospiro[furo[2,3-f][1,3]benzodioxole-7,3'-indol]-1'(2'H)-yl)-N-phenylacetamide;
N-(4-fluorophenyl)-2-(2'-oxospiro[furo[2,3-f][1,3]benzodioxole-7,3'-indol]-1'(2'H)-yl)acetamide;
N-(3-fluorobenzyl)-2-(2'-oxospiro[furo[2,3-f][1,3]benzodioxole-7,3'-indol]-1'(2'H)-yl)acetamide;
N-(3-chlorophenyl)-2-(2'-oxospiro[furo[2,3-f][1,3]benzodioxole-7,3'-indol]-1'(2'H)-yl)acetamide;
N-(2-fluorophenyl)-2-(2'-oxospiro[furo[2,3-f][1,3]benzodioxole-7,3'-indol]-1'(2'H)-yl)acetamide;
N-(2-ethylphenyl)-2-(2'-oxospiro[furo[2,3-f][1,3]benzodioxole-7,3'-indol]-1'(2'H)-yl)acetamide;
N-(4-ethylphenyl)-2-(2'-oxospiro[furo[2,3-f][1,3]benzodioxole-7,3'-indol]-1'(2'H)-yl)acetamide;
N-(3-methylphenyl)-2-(2'-oxospiro[furo[2,3-f][1,3]benzodioxole-7,3'-indol]-1'(2'H)-yl)acetamide;
N-(2,3-dimethylphenyl)-2-(2'-oxospiro[furo[2,3-f][1,3]benzodioxole-7,3'-indol]-1'(2'H)-yl)acetamide;
N-(3,5-dimethylphenyl)-2-(2'-oxospiro[furo[2,3-f][1,3]benzodioxole-7,3'-indol]-1'(2'H)-yl)acetamide;
2-(2'-oxospiro[furo[2,3-f][1,3]benzodioxole-7,3'-indol]-1'(2'H)-yl)-N-pentylacetamide;
2-(2'-oxospiro[furo[2,3-f][1,3]benzodioxole-7,3'-indol]-1'(2'H)-yl)-N-propylacetamide;
N-isopropyl-2-(2'-oxospiro[furo[2,3-f][1,3]benzodioxole-7,3'-indol]-1'(2'H)-yl)acetamide;
N-(3-methylbutyl)-2-(2'-oxospiro[furo[2,3-f][1,3]benzodioxole-7,3'-indol]-1'(2'H)-yl)acetamide;
N-isobutyl-2-(2'-oxospiro[furo[2,3-f][1,3]benzodioxole-7,3'-indol]-1'(2'H)-yl)acetamide;
N-hexyl-2-(2'-oxospiro[furo[2,3-f][1,3]benzodioxole-7,3'-indol]-1'(2'H)-yl)acetamide;
N-cyclohexyl-2-(2'-oxospiro[furo[2,3-f][1,3]benzodioxole-7,3'-indol]-1'(2'H)-yl)acetamide;
N-cyclopentyl-2-(2'-oxospiro[furo[2,3-f][1,3]benzodioxole-7,3'-indol]-1'(2'H)-yl)acetamide;
N-heptyl-2-(2'-oxospiro[furo[2,3-f][1,3]benzodioxole-7,3'-indol]-1'(2'H)-yl)acetamide;
N-(2-chlorobenzyl)-2-(2'-oxospiro[furo[2,3-f][1,3]benzodioxole-7,3'-indol]-1'(2'H)-yl)acetamide;
N-(2,6-dimethylphenyl)-2-(2'-oxospiro[furo[2,3-f][1,3]benzodioxole-7,3'-indol]-1'(2'H)-yl)acetamide;
N-(2-methoxyphenyl)-2-(2'-oxospiro[furo[2,3-f][1,3]benzodioxole-7,3'-indol]-1'(2'H)-yl)acetamide;
N-[(5-methyl-2-furyl)methyl]-2-(2'-oxospiro[furo[2,3-f][1,3]benzodioxole-7,3'-indol]-1'(2'H)-yl)acetamide;
N-ethyl-2-(2'-oxospiro[furo[2,3-f][1,3]benzodioxole-7,3'-indol]-1'(2'H)-yl)acetamide;
N-methyl-2-(2'-oxospiro[furo[2,3-f][1,3]benzodioxole-7,3'-indol]-1'(2'H)-yl)acetamide;
N-(2-fluorobenzyl)-2-(2'-oxospiro[furo[2,3-f][1,3]benzodioxole-7,3'-indol]-1'(2'H)-yl)acetamide;
N-[2-(3-methoxyphenyl)ethyl]-2-(2'-oxospiro[furo[2,3-f][1,3]benzodioxole-7,3'-indol]-1'(2'H)-yl)acetamide;
N-(2-ethoxyethyl)-2-(2'-oxospiro[furo[2,3-f][1,3]benzodioxole-7,3'-indol]-1'(2'H)-yl)acetamide;
N-(4-methoxybenzyl)-2-(2'-oxospiro[furo[2,3-f][1,3]benzodioxole-7,3'-indol]-1'(2'H)-yl)acetamide;
N-(2,4-dimethylphenyl)-2-(2'-oxospiro[furo[2,3-f][1,3]benzodioxole-7,3'-indol]-1'(2'H)-yl)acetamide;
N-(3-isopropoxypropyl)-2-(2'-oxospiro[furo[2,3-f][1,3]benzodioxole-7,3'-indol]-1'(2'H)-yl)acetamide;
N-(2-furylmethyl)-2-(2'-oxospiro[furo[2,3-f][1,3]benzodioxole-7,3'-indol]-1'(2'H)-yl)acetamide;
N-(cyclohexylmethyl)-2-(2'-oxospiro[furo[2,3-f][1,3]benzodioxole-7,3'-indol]-1'(2'H)-yl)acetamide;
N-(3-fluoro-2-methylphenyl)-2-(2'-oxospiro[furo[2,3-f][1,3]benzodioxole-7,3'-indol]-1'(2'H)-yl)acetamide;
N-(4-methoxyphenyl)-2-(2'-oxospiro[furo[2,3-f][1,3]benzodioxole-7,3'-indol]-1'(2'H)-yl)acetamide;
N-cyclobutyl-2-(2'-oxospiro[furo[2,3-f][1,3]benzodioxole-7,3'-indol]-1'(2'H)-yl)acetamide;
N-(2,5-difluorophenyl)-2-(2'-oxospiro[furo[2,3-f][1,3]benzodioxole-7,3'-indol]-1'(2'H)-yl)acetamide;
N-benzyl-2-(2'-oxospiro[furo[2,3-f][1,3]benzodioxole-7,3'-indol]-1'(2'H)-yl)acetamide;
N-(cyclopropylmethyl)-2-(2'-oxospiro[furo[2,3-f][1,3]benzodioxole-7,3'-indol]-1'(2'H)-yl)acetamide;
N-butyl-N-ethyl-2-(2'-oxospiro[furo[2,3-f][1,3]benzodioxole-7,3'-indol]-1'(2'H)-yl)acetamide;
N-octyl-2-(2'-oxospiro[furo[2,3-f][1,3]benzodioxole-7,3'-indol]-1'(2'H)-yl)acetamide;
N-(3,3-dimethylbutyl)-2-(2'-oxospiro[furo[2,3-f][1,3]benzodioxole-7,3'-indol]-1'(2'H)-yl)acetamide;
N-(4-chloro-2-methylphenyl)-2-(2'-oxospiro[furo[2,3-f][1,3]benzodioxole-7,3'-indol]-1'(2'H)-yl)acetamide;
N-(3-methoxyphenyl)-2-(2'-oxospiro[furo[2,3-f][1,3]benzodioxole-7,3'-indol]-1'(2'H)-yl)acetamide;
N-(2-fluoro-4-methylphenyl)-2-(2'-oxospiro[furo[2,3-f][1,3]benzodioxole-7,3'-indol]-1'(2'H)-yl)acetamide;
N-(3,4-dimethylphenyl)-2-(2'-oxospiro[furo[2,3-f][1,3]benzodioxole-7,3'-indol]-1'(2'H)-yl)acetamide;
N-(3-chlorobenzyl)-2-(2'-oxospiro[furo[2,3-f][1,3]benzodioxole-7,3'-indol]-1'(2'H)-yl)acetamide;
N-(3-methoxybenzyl)-2-(2'-oxospiro[furo[2,3-f][1,3]benzodioxole-7,3'-indol]-1'(2'H)-yl)acetamide;
N-(3,4-difluorophenyl)-2-(2'-oxospiro[furo[2,3-f][1,3]benzodioxole-7,3'-indol]-1'(2'H)-yl)acetamide;
N-(3-methylbenzyl)-2-(2'-oxospiro[furo[2,3-f][1,3]benzodioxole-7,3'-indol]-1'(2'H)-yl)acetamide;
N-(2-methoxybenzyl)-2-(2'-oxospiro[furo[2,3-f][1,3]benzodioxole-7,3'-indol]-1'(2'H)-yl)acetamide;
N-(4-isopropylphenyl)-2-(2-oxospiro[furo[2,3-f][1,3]benzodioxole-7,3'-indol]-1'(2'H)-yl)acetamide;

N-(2,3-difluorophenyl)-2-(2'-oxospiro[furo[2,3-f][1,3]benzodioxole-7,3'-indol]-1'(2'H)-yl)acetamide;
2-(2'-oxospiro[furo[2,3-f][1,3]benzodioxole-7,3'-indol]-1'(2'H)-yl)-N-(tetrahydrofuran-2-ylmethyl)acetamide;
N-[2-(4-methylphenyl)ethyl]-2-(2'-oxospiro[furo[2,3-f][1,3]benzodioxole-7,3'-indol]1'(2'H)-yl)acetamide;
N-[2-(3-chlorophenyl)ethyl]-2-(2'-oxospiro[furo[2,3-f][1,3]benzodioxole-7,3'-indol]-1'(2'H)-yl)acetamide;
N-(4-cyanophenyl)-2-(2-oxospiro[furo[2,3-f][1,3]benzodioxole-7,3'-indol]-1'(2'H)-yl)acetamide;
N-(2,3-dihydro-1H-inden-1-yl)-2-(2'-oxospiro[furo[2,3-f][1,3]benzodioxole-7,3'-indol]-1'(2'H)-yl)acetamide;
N-(2-methoxyethyl)-2-(2'-oxospiro[furo[2,3-f][1,3]benzodioxole-7,3'-indol]-1'(2'H)-yl)acetamide;
N-[2-(4-methoxyphenyl)ethyl]-2-(2'-oxospiro[furo[2,3-f][1,3]benzodioxole-7,3'-indol]-1'(2'H)-yl)acetamide;
N-(2-cyanoethyl)-2-(2'-oxospiro[furo[2,3-f][1,3]benzodioxole-7,3'-indol]-1'(2'H)-yl)acetamide;
N-(2,4-dichlorobenzyl)-2-(2'-oxospiro[furo[2,3-f][1,3]benzodioxole-7,3'-indol]-1'(2'H)-yl)acetamide;
N-(3,5-difluorobenzyl)-2-(2'-oxospiro[furo[2,3-f][1,3]benzodioxole-7,3'-indol]-1'(2'H)-yl)acetamide;
N-(2,4-difluorobenzyl)-2-(2'-oxospiro[furo[2,3-f][1,3]benzodioxole-7,3'-indol]-1'(2'H)-yl)acetamide;
N-(2-methylbenzyl)-2-(2-oxospiro[furo[2,3-f][1,3]benzodioxole-7,3'-indol]-1'(2'H)-yl)acetamide;
N-(3,4-difluorobenzyl)-2-(2'-oxospiro[furo[2,3-f][1,3]benzodioxole-7,3'-indol]-1'(2'H)-yl)acetamide;
N-(2,5-difluorobenzyl)-2-(2'-oxospiro[furo[2,3-f][1,3]benzodioxole-7,3'-indol]-1'(2'H)-yl)acetamide;
2-(2'-oxospiro[furo[2,3-f][1,3]benzodioxole-7,3'-indol]-1'(2'H)-yl)-N,N-dipropylacetamide;
N,N-dibutyl-2-(2'-oxospiro[furo[2,3-f][1,3]benzodioxole-7,3'-indol]-1'(2'H)-yl)acetamide;
N-(2,6-difluorobenzyl)-2-(2'-oxospiro[furo[2,3-f][1,3]benzodioxole-7,3'-indol]-1'(2'H)-yl)acetamide;
N-[2-(methylthio)phenyl]-2-(2'-oxospiro[furo[2,3-f][1,3]benzodioxole-7,3'-indol]-1'(2'H)-yl)acetamide;
N-(2-isopropylphenyl)-2-(2'-oxospiro[furo[2,3-f][1,3]benzodioxole-7,3'-indol]-1'(2'H)-yl)acetamide;
N-(4-bromophenyl)-2-(2'-oxospiro[furo[2,3-f][1,3]benzodioxole-7,3'-indol]-1'(2'H)-yl)acetamide;
N-(4-chlorophenyl)-2-(2'-oxospiro[furo[2,3-f][1,3]benzodioxole-7,3'-indol]-1'(2'H)-yl)acetamide;
N-(2,4-dichlorophenyl)-2-(2'-oxospiro[furo[2,3-f][1,3]benzodioxole-7,3'-indol]-1'(2'H)-yl)acetamide;
N-(3,5-dichlorophenyl)-2-(2'-oxospiro[furo[2,3-f][1,3]benzodioxole-7,3'-indol]-1'(2'H)-yl)acetamide;
N,N-diethyl-2-(2'-oxospiro[furo[2,3-f][1,3]benzodioxole-7,3'-indol]-1'(2'H)-yl)acetamide;
N-methyl-2-(2'-oxospiro[furo[2,3-f][1,3]benzodioxole-7,3'-indol]-1'(2'H)-yl)-N-phenylacetamide;
N-(4-hydroxybutyl)-2-(2'-oxospiro[furo[2,3-f][1,3]benzodioxole-7,3'-indol]-1'(2'H)-yl)acetamide;
N-allyl-2-(2'-oxospiro[furo[2,3-f][1,3]benzodioxole-7,3'-indol]-1'(2'H)-yl)acetamide;
N-(2-fluoro-5-methylphenyl)-2-(2'-oxospiro[furo[2,3-f][1,3]benzodioxole-7,3'-indol]-1'(2'H)-yl)acetamide;
N-(1,3-benzodioxol-5-ylmethyl)-2-(2'-oxospiro[furo[2,3-f][1,3]benzodioxole-7,3'-indol]-1'(2'H)-yl)acetamide;
N-cyclopropyl-2-(2'-oxospiro[furo[2,3-f][1,3]benzodioxole-7,3'-indol]-1'(2'H)-yl)acetamide;
N-(2-cyclopropylethyl)-2-(2'-oxospiro[furo[2,3-f][1,3]benzodioxole-7,3'-indol]-1'(2'H)-yl)acetamide;
N-(3,4-dichlorobenzyl)-2-(2'-oxospiro[furo[2,3-f][1,3]benzodioxole-7,3'-indol]-1'(2'H)-yl)acetamide;
N-(2,3-dichlorobenzyl)-2-(2'-oxospiro[furo[2,3-f][1,3]benzodioxole-7,3'-indol]-1'(2'H)-yl)acetamide;
N-(2,5-dimethylphenyl)-2-(2'-oxospiro[furo[2,3-f][1,3]benzodioxole-7,3'-indol]-1'(2'H)-yl)acetamide;
N-(3,4-dichlorophenyl)-2-(2'-oxospiro[furo[2,3-f][1,3]benzodioxole-7,3'-indol]-1'(2'H)-yl)acetamide;
N,N-dimethyl-2-(2'-oxospiro[furo[2,3-f][1,3]benzodioxole-7,3'-indol]-1'(2'H)-yl)acetamide;
N-methyl-2-(2'-oxospiro[furo[2,3-f][1,3]benzodioxole-7,3'-indol]-1'(2'H)-yl)-N-(2-phenylethyl)acetamide;
2-(2'-oxospiro[furo[2,3-f][1,3]benzodioxole-7,3'-indol]-1'(2'H)-yl)-N-(2-phenylpropyl)acetamide;
N-[(1R)-1-cyclohexylethyl]-2-(2'-oxospiro[furo[2,3-f][1,3]benzodioxole-7,3'-indol]-1'(2'H)-yl)acetamide;
N-[(1S)-1-cyclohexylethyl]-2-(2'-oxospiro[furo[2,3-f][1,3]benzodioxole-7,3'-indol]-1'(2'H)-yl)acetamide;
2-(2'-oxospiro[furo[2,3-f][1,3]benzodioxole-7,3'-indol]-1'(2'H)-yl)-N-(2-piperidin-1-ylethyl)acetamide;
2-(2'-oxospiro[furo[2,3-f][1,3]benzodioxole-7,3'-indol]-1'(2'H)-yl)-N-[3-(trifluoromethyl)phenyl]acetamide;
N-(3-cyanophenyl)-2-(2'-oxospiro[furo[2,3-f][1,3]benzodioxole-7,3'-indol]-1'(2'H)-yl)acetamide;
1'-(2-morpholin-4-yl-2-oxoethyl)spiro[furo[2,3-f][1,3]benzodioxole-7,3'-indol]-2'(1'H)-one;
2-(2'-oxospiro[furo[2,3-f][1,3]benzodioxole-7,3'-indol]-1'(2'H)-yl)-N-(2-phenylethyl)acetamide;
N-(4-bromo-2-chlorophenyl)-2-(2'-oxospiro[furo[2,3-f][1,3]benzodioxole-7,3'-indol]-1'(2'H)-yl)acetamide;
N-(2-biphenyl-4-ylethyl)-2-(2'-oxospiro[furo[2,3-f][1,3]benzodioxole-7,3'-indol]-1'(2'H)-yl)acetamide;
1'-prop-2-yn-1-ylspiro[furo[2,3-f][1,3]benzodioxole-7,3'-indol]-2'(1'H)-one;
1'-(2-ethoxyethyl)spiro[furo[2,3-f][1,3]benzodioxole-7,3'-indol]-2'(1'H)-one;
1-[(2E)-pent-2-en-1-yl]spiro[furo[2,3-f][1,3]benzodioxole-7,3'-indol]-2'(1'H)-one;
1'-hex-5-en-1-ylspiro[furo[2,3-f][1,3]benzodioxole-7,3'-indol]-2'(1'H)-one;
1'-(cyclobutylmethyl)spiro[furo[2,3-f][1,3]benzodioxole-7,3'-indol]-2'(1'H)-one;
1'-pent-2-yn-1-ylspiro[furo[2,3-f][1,3]benzodioxole-7,3'-indol]-2'(1'H)-one;
1'-(5-chloropentyl)spiro[furo[2,3-f][1,3]benzodioxole-7,3'-indol]-2'(1'H)-one;
1'-(4-fluorobutyl)spiro[furo[2,3-f][1,3]benzodioxole-7,3'-indol]-2'(1'H)-one;
1'-(5-methylhexyl)spiro[furo[2,3-f][1,3]benzodioxole-7,3'-indol]-2'(1'H)-one;
1'-[(3Z)-4-methylhex-3-en-1-yl]spiro[furo[2,3-f][1,3]benzodioxole-7,3'-indol]-2'(1'H)-one;
1'-(2-bromoethyl)spiro[furo[2,3-f][1,3]benzodioxole-7,3'-indol]-2'(1'H)-one;
5-(2'-oxospiro[furo[2,3-f][1,3]benzodioxole-7,3'-indol]-1'(2'H)-yl)pentanenitrile;
1'-[2-(2-methoxyethoxy)ethyl]spiro[furo[2,3-f][1,3]benzodioxole-7,3'-indol]-2'(1'H)-one;
1'-(cyclopropylmethyl)spiro[furo[2,3-f][1,3]benzodioxole-7,3'-indol]-2'(1'H)-one;
1'-(4,4,4-trifluorobutyl)spiro[furo[2,3-f][1,3]benzodioxole-7,3'-indol]-2'(1'H)-one;
diethyl [2-(2'-oxospiro[furo[2,3-f][1,3]benzodioxole-7,3'-indol]-1'(2'H)-yl)ethyl]phosphonate;
1'-[(2,2,3,3-tetrafluorocyclobutyl)methyl]spiro[furo[2,3-f][1,3]benzodioxole-7,3'-indol]-2'(1'H)-one;
1'-[(benzyloxy)methyl]spiro[furo[2,3-f][1,3]benzodioxole-7,3'-indol]-2'(1'H)-one;

1'-allylspiro[furo[2,3-f][1,3]benzodioxole-7,3'-indol]-2'(1'H)-one;
1'-(2-ethylbutyl)spiro[furo[2,3-f][1,3]benzodioxole-7,3'-indol]-2'(1'H)-one;
1'-(4-methylpentyl)spiro[furo[2,3-f][1,3]benzodioxole-7,3'-indol]-2'(1'H)-one;
1'-(3-methylbut-2-en-1-yl)spiro[furo[2,3-f][1,3]benzodioxole-7,3'-indol]-2'(1'H)-one;
1'-pent-4-en-1-ylspiro[furo[2,3-f][1,3]benzodioxole-7,3'-indol]-2'(1'H)-one;
4-(2'-oxospiro[furo[2,3-f][1,3]benzodioxole-7,3'-indol]-1'(2'H)-yl)butanenitrile;
1'-[(2-methylcyclopropyl)methyl]spiro[furo[2,3-f][1,3]benzodioxole-7,3'-indol]-2'(1'H)-one;
1'-(3-cyclopropylpropyl)spiro[furo[2,3-f][1,3]benzodioxole-7,3'-indol]-2'(1'H)-one;
1'-hexylspiro[furo[2,3-f][1,3]benzodioxole-7,3'-indol]-2'(1'H)-one;
1'-[(2-cyclopropyl-6-hydroxypyrimidin-4-yl)methyl]spiro[furo[2,3-f][1,3]benzodioxole-7,3'-indol]-2'(1'H)-one;
1'-[(2-methylcyclopropyl)methyl]spiro[furo[2,3-f][1,3]benzodioxole-7,3'-indol]-2'(1'H)-one;
1'-(3-cyclopropylpropyl)spiro[furo[2,3-f][1,3]benzodioxole-7,3'-indol]-2'(1'H)-one;
1'-butylspiro[furo[2,3-f][1,3]benzodioxole-7,3'-indol]-2'(1'H)-one;
1'[4-(trifluoromethoxy)benzyl]spiro[furo[2,3-f][1,3]benzodioxole-7,3'-indol]-2'(1'H)-one;
1'-Propylspiro[furo[2,3-f][1,3]benzodioxole-7,3'-indol]-2'(1'H)-one;
4'-bromo-1'-methylspiro[furo[2,3-f][1,3]benzodioxole-7,3'-indol]-2'(1'H)-one;
tert-butyl 4-[(4'-bromo-2'-oxospiro[furo[2,3-f][1,3]benzodioxole-7,3'-indol]-1'(2'H)-yl)methyl]piperidine-1-carboxylate;
ethyl 5-(2'-oxospiro[furo[2,3-f][1,3]benzodioxole-7,3'-indol]-1'(2'H)-yl)pentanoate;
ethyl 4-(2'-oxospiro[furo[2,3-f][1,3]benzodioxole-7,3'-indol]-1'(2'H)-yl)butanoate;
1-(3-chloropropyl)spiro[furo[2,3-f][1,3]benzodioxole-7,3'-indol]-2'(1'H)-one;
1'-(cyclohexylmethyl)spiro[furo[2,3-f][1,3]benzodioxole-7,3'-indol]-2'(1'H)-one;
1'-(methylsulfonyl)spiro[furo[2,3-f][1,3]benzodioxole-7,3'-indol]-2'(1'H)-one;
1'-(3-hydroxypropyl)spiro[furo[2,3-f][1,3]benzodioxole-7,3'-indol]-2'(1'H)-one;
3-(2'-oxospiro[furo[2,3-f][1,3]-benzodioxole-7,3'-indol]-1'(2'H)-yl)propanal; and
2'-oxo-1'-pentyl-1',2'-dihydrospiro[furo[2,3-f][1,3]benzodioxole-7,3'-indole]-4'-carbonitrile.

Another embodiment of the invention are the compounds of formula (I) as set forth above in the Summary of the Invention wherein:

$R^1$ is hydrogen, alkyl, alkenyl, alkynyl, haloalkyl, cycloalkyl, cycloalkylalkyl, —$R^8$—$OR^5$, —$R^8$—C(O)$R^5$, —$R^8$—C(O)$OR^5$, —$R^8$—C(O)N($R^4$)$R^5$, —S(O)$_2$—$R^5$, —$R^8$—CN, —$R^9$—P(O)(O$R^5$)$_2$, or —$R^9$—O—$R^9$—$OR^5$;

$R^{2a}$, $R^{2b}$, $R^{2c}$ and $R^{2d}$ are each independently selected from hydrogen, halo or alkyl;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —S(O)$_2$CF$_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

5,6-difluoro-1-pentylspiro[1-benzofuran-3,3'-indol]-2'(1'H)-one;
5-fluoro-1'-pentylspiro[1-benzofuran-3,3'-indol]-2'(1'H)-one;
5-bromo-1'-pentylspiro[1-benzofuran-3,3'-indol]-2'(1'H)-one;
5-chloro-6-fluoro-1'-pentylspiro[1-benzofuran-3,3'-indol]-2'(1'H)-one;
6-methoxy-1'-pentylspiro[1-benzofuran-3,3'-indol]-2'(1'H)-one;
6-chloro-5-fluoro-1'-pentylspiro[1-benzofuran-3,3'-indol]-2'(1'H)-one;
1'-pentyl-5-(trifluoromethyl)spiro[1-benzofuran-3,3'-indol]-2'(1'H)-one;
5,6-dichloro-1'-pentylspiro[1-benzofuran-3,3'-indol]-2'(1'H)-one;
6-bromo-1'-pentylspiro[1-benzofuran-3,3'-indol]-2'(1'H)-one;
5-bromospiro[1-benzofuran-3,3'-indol]-2'(1'H)-one;
6-(trifluoromethoxy)spiro[1-benzofuran-3,3'-indol]-2'(1'H)-one;
ethyl (4'-bromo-5,6-difluoro-2'-oxospiro[1-benzofuran-3,3'-indol]-1'(2'H)-yl)acetate;
methyl (6-chloro-2'-oxospiro[1-benzofuran-3,3'-indol]-1'(2'H)-yl)acetate;
ethyl (5,6-difluoro-2'-oxospiro[1-benzofuran-3,3'-indol]-1'(2'H)-yl)acetate;
2-(4'-bromo-5,6-difluoro-2'-oxospiro[1-benzofuran-3,3'-indol]-1'(2'H)-yl)-N-(2-fluorophenyl)acetamide;
2-(6-chloro-2'-oxospiro[1-benzofuran-3,3'-indol]-1'(2'H)-yl)-N-(2-fluorophenyl)acetamide;
2-(5,6-difluoro-2'-oxospiro[1-benzofuran-3,3'-indol]-1'(2'H)-yl)-N-(2-fluorophenyl)acetamide;
2-(5-bromo-2'-oxospiro[1-benzofuran-3,3'-indol]-1'(2'H)-yl)-N-(2-fluorophenyl)acetamide;
1'-pentylspiro[1-benzofuran-3,3'-indol]-2'(1'H)-one;
6-anilino-1'-pentylspiro[1-benzofuran-3,3'-indol]-2'(1'H)-one;
6-morpholin-4-yl-1'-pentylspiro[1-benzofuran-3,3'-indol]-2'(1'H)-one;
6-amino-1'-pentylspiro[1-benzofuran-3,3'-indol]-2'(1'H)-one;

1'-pentyl-6-phenoxyspiro[1-benzofuran-3,3'-indol]-2'(1'H)-one;
1'-pentyl-6-phenoxyspiro[1-benzofuran-3,3'-indol]-2'(1'H)-one;
1'-pentyl-6-pyridin-4-ylspiro[1-benzofuran-3,3'-indol]-2'(1'H)-one;
6-(methylsulfonyl)-1-pentylspiro[1-benzofuran-3,3'-indol]-2'(1'H)-one;
1'-pentyl-6-(phenylsulfonyl)spiro[1-benzofuran-3,3'-indol]-2'(1'H)-one;
1'-pentyl-5-phenoxyspiro[1-benzofuran-3,3'-indol]-2'(1'H)-one;
5-hydroxyspiro[1-benzofuran-3,3'-indol]-2'(1'H)-one;
2'-oxo-1',2'-dihydrospiro[1-benzofuran-3,3'-indol]-5-yl trifluoromethanesulfonate;
1'-pentyl-5-pyridin-3-ylspiro[1-benzofuran-3,3'-indol]-2'(1'H)-one;
1'-pentyl-5-pyrimidin-5-ylspiro[1-benzofuran-3,3'-indol]-2'(1'H)-one;
1-pentyl-5-pyridin-4-ylspiro[1-benzofuran-3,3'-indol]-2'(1'H)-one;
2'-oxo-1-pentyl-1',2'-dihydrospiro[1-benzofuran-3,3'-indole]-5-carbonitrile;
N-(2-fluorophenyl)-2-(2'-oxo-5-pyridin-3-ylspiro[1-benzofuran-3,3'-indol]-1'(2'H)-yl)acetamide;
tert-butyl 3-(2'-oxo-1',2'-dihydrospiro[1-benzofuran-3,3'-indol]-5-yl)piperidine-1-carboxylate;
5-methoxy-1'-methylspiro[1-benzofuran-3,3'-indol]-2'(1'H)-one.

Another embodiment of the invention are the compounds of formula (I) as set forth above in the Summary of the Invention wherein:

$R^1$ is hydrogen, alkyl, alkenyl, alkynyl, haloalkyl, cycloalkyl, cycloalkylalkyl, —$R^8$—$OR^5$, —$R^8$—$C(O)R^5$, —$R^8$—$C(O)OR^5$, —$R^8$—$C(O)N(R^4)R^5$, —$S(O)_2$—$R^5$, —$R^9$—$P(O)(OR^5)_2$, or —$R^9$—O—$R^9$—$OR^5$;

$R^{2a}$, $R^{2b}$, $R^{2c}$ and $R^{2d}$ are each independently selected from hydrogen, halo or alkyl;

$R^{3a}$ and $R^{3d}$ are both hydrogen;

$R^{3b}$ and $R^{3c}$, together with the carbon ring atoms to which they are directly attached, form a fused optionally substituted heterocyclyl ring or a fused optionally substituted cycloalkyl ring;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

5,5-dimethyl-5,6-dihydrospiro[benzo[1,2-b:5,4-b']difuran-3,3'-indol]-2'(1'H)-one;
ethyl (4'-bromo-6,6-dimethyl-2'-oxo-5,6-dihydrospiro[benzo[1,2-b:5,4-b']difuran-3,3'-indol]-1'(2'H)-yl)acetate;
ethyl (2'-oxo-6,7-dihydro-5H-spiro[indeno[5,6-b]furan-3,3'-indol]-1'(2'H)-yl)acetate;
ethyl (2-oxo-5',6',7',8'-tetrahydrospiro[indole-3,3'-naphtho[2,3-b']furan]-1(2H)-yl)acetate;
6,7-dihydrospiro[benzo[1,2-b:4,5-b']difuran-3,3'-indol]-2'(1'H)-one;
5,6-dihydrospiro[benzo[1,2-b:5,4-b']difuran-3,3'-indol]-2'(1'H)-one;
ethyl (2'-oxo-5,6-dihydrospiro[benzo[1,2-b:5,4-b']difuran-3,3'-indol]-1'(2'H)-yl)acetate;
(2'-oxo-6,7-dihydro-5H-spiro[indeno[5,6-b]furan-3,3'-indol]-1'(2'H)-yl)acetic acid;
(4'-chloro-2'-oxo-5,6-dihydrospiro[benzo[1,2-b:5,4-b']difuran-3,3'-indol]-1'(2'H)-yl)acetic acid;
(4'-bromo-2'-oxo-5,6-dihydrospiro[benzo[1,2-b:5,4-b']difuran-3,3'-indol]-1'(2'H)-yl)acetic acid;
(5'-chloro-2'-oxo-5,6-dihydrospiro[benzo[1,2-b:5,4-b']difuran-3,3'-indol]-1'(2'H)-yl)acetic acid;
(2-oxo-5',6',7',8'-tetrahydrospiro[indole-3,3'-naphtho[2,3-b']furan]-1(2H)-yl)acetic acid;
(2'-oxo-5,6-dihydrospiro[benzo[1,2-b:5,4-b']difuran-3,3'-indol]-1'(2'H)-yl)acetic acid;
N-(2-fluorophenyl)-2-(2'-oxo-6,7-dihydro-5H-spiro[indeno[5,6-b]furan-3,3'-indol]-1'(2'H)-yl)acetamide;
N-(2-fluorophenyl)-2-(2-oxo-5',6',7',8'-tetrahydrospiro[indole-3,3'-naphtho[2,3-b']furan]-1'(2'H)-yl)acetamide;
2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide;
2-(4'-chloro-2'-oxo-5,6-dihydrospiro[benzo[1,2-b:5,4-b']difuran-3,3'-indol]-1'(2'H)-yl)-N-(2-fluorophenyl)acetamide;
2-(5'-chloro-2'-oxo-5,6-dihydrospiro[benzo[1,2-b:5,4-b']difuran-3,3'-indol]-1'(2'H)-yl)-N-(2-fluorophenyl)acetamide;
2-(4'-fluoro-Z-oxo-5,6-dihydrospiro[benzo[1,2-b:5,4-b']difuran-3,3'-indol]-1'(2'H)-yl)-N-(2-fluorophenyl)acetamide;
2-(4'-bromo-2'-oxo-5,6-dihydrospiro[benzo[1,2-b:5,4-b']difuran-3,3'-indol]-1'(2'H)-yl)-N-(2-fluorophenyl)acetamide;
N-(2-fluorophenyl)-2-(2'-oxo-5,6-dihydrospiro[benzo[1,2-b:5,4-b']difuran-3,3'-indol]-1'(2'H)-yl)acetamide; and
2-(4'-fluoro-7'-methyl-2'-oxo-5,6-dihydrospiro[benzo[1,2-b:5,4-b']difuran-3,3'-indol]-1'(2'H)-yl)-N-(2-fluorophenyl)acetamide.

Another embodiment of the invention are the compounds of formula (I) as set forth above in the Summary of the Invention wherein:

$R^1$ is aryl, heteroaryl or heterocyclyl;

$R^{2a}$, $R^{2b}$, $R^{2c}$ and $R^{2d}$ are each hydrogen; and $R^{3b}$ and $R^{3c}$, together with the carbon ring atoms to which they are directly attached, form a fused dioxolyl ring.

Another embodiment of the invention are the compounds of formula (I) as set forth above in the Summary of the invention wherein:

at least one of j and k is 1 and the other is 0 or 1;

Q is —O—;

$R^1$ is hydrogen, alkyl, —$R^8$—$C(O)OR^5$ or —$R^8$—$C(O)N(R^4)R^5$;

$R^{2a}$ is selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_mR^4$, —$OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —R$^8$—S(O)$_n$N(R$^4$)R$^5$, —N(R$^5$)C(=NR$^5$)N(R$^4$)R$^5$, and —N(R$^5$)C(=N—CN)N(R$^4$)R$^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for R$^{2a}$ is optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —S(O)$_m$R$^4$, —R$^8$—S(O)$_n$N(R$^4$)R$^5$, —R$^8$—C(O)R$^4$, —R$^8$—C(O)OR$^4$, —R$^8$—C(O)N(R$^4$)R$^5$, —N(R$^5$)C(O)R$^4$, and —N(R$^5$)S(O)$_n$R$^4$, wherein each m is independently 0, 1, or 2 and each n is independently 1 or 2;

R$^{2b}$, R$^{2c}$ and R$^{2d}$ are each hydrogen;

R$^{3a}$, R$^{3b}$, R$^{3c}$ and R$^{3d}$ are each independently selected from hydrogen or halo;

or R$^{3b}$ and R$^{3c}$, together with the carbon ring atoms to which they are directly attached, form a fused ring selected from cycloalkyl, heterocyclyl, aryl or heteroaryl and R$^{3a}$ and R$^{3d}$ are as defined above;

each R$^4$ and R$^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R$^4$ and R$^5$ are each attached to the same nitrogen atom, then R$^4$ and R$^5$, together with the nitrogen atom to which they are attached, may form a heterocyclyl or heteroaryl; and each R$^8$ is a direct bond or a straight or branched alkylene chain, a straight or branched alkenylene chain or a straight or branched alkynylene chain; and each R$^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or j is 1 and k is 0;

Q is —O—;

R$^1$ is hydrogen or alkyl;

R$^{2a}$ is selected from the group consisting of alkyl, haloalkenyl, aryl, aralkyl, aralkenyl, heterocyclyl, heteroaryl, —R$^8$—C(O)N(R$^4$)R$^5$, and —R$^8$—N(R$^4$)R$^5$;

wherein each of the aryl, aralkyl, aralkenyl, heterocyclyl and heteroaryl groups for R$^{2a}$ is optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —S(O)$_m$R$^4$, —R$^8$—S(O)$_n$N(R$^4$)R$^5$, —R$^8$—C(O)R$^4$, —R$^8$—C(O)OR$^4$, —R$^8$—C(O)N(R$^4$)R$^5$, —N(R$^5$)C(O)R$^4$, and —N(R$^5$)S(O)$_n$R$^4$, wherein each m is independently 0, 1, or 2 and each n is independently 1 or 2;

R$^{2b}$, R$^{2c}$ and R$^{2d}$ are each hydrogen;

R$^{3a}$, R$^{3b}$, R$^{3c}$ and R$^{3d}$ are each independently selected from hydrogen or halo;

or R$^{3b}$ and R$^{3c}$, together with the carbon ring atoms to which they are directly attached, form a fused dioxolyl ring or a fused optionally substituted tetrahydrofuranyl ring, and R$^{3a}$ and R$^{3d}$ are as defined above;

each R$^4$ and R$^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R$^4$ and R$^5$ are each attached to the same nitrogen atom, then R$^4$ and R$^5$, together with the nitrogen atom to which they are attached, may form a heterocyclyl or heteroaryl; and each R$^8$ is a direct bond or a straight or branched alkylene chain, a straight or branched alkenylene chain or a straight or branched alkynylene chain.

Another embodiment of the invention are the compounds of formula (I) as set forth above in the Summary of the invention, selected from the group consisting of:

4'-[6-(dimethylamino)pyridin-3-yl]-1-pentylspiro[furo[2,3-f][1,3]benzodioxole-7,3'-indol]-2'(1H)-one;

4'-(3,5-dimethoxyphenyl)-1-pentylspiro[furo[2,3-f][1,3]benzodioxole-7,3'-indol]-2'(1'H)-one;

4'-(4-fluorophenyl)-1'-pentylspiro[furo[2,3-f][1,3]benzodioxole-7,3'-indol]-2'(1'H)-one;

4'-(3,5-dichlorophenyl)-1'-pentylspiro[furo[2,3-f][1,3]benzodioxole-7,3'-indol]-2'(1'H)-one;

4'-[4-(dimethylamino)phenyl]-1'-pentylspiro[furo[2,3-f][1,3]benzodioxole-7,3'-indol]-2'(1'H)-one;

1'-pentyl-4'-(3,4,5-trimethoxyphenyl)spiro[furo[2,3-f][1,3]benzodioxole-7,3'-indol]-2'(1'H)-one;

4-(2'-oxo-1'-pentyl-1',2'-dihydrospiro[furo[2,3-f][1,3]benzodioxole-7,3'-indol]-4'-yl)benzonitrile;

4'-dibenzo[b,d]furan-4-yl-1-pentylspiro[furo[2,3-f][1,3]benzodioxole-7,3'-indol]-2'(1'H)-one;

4'-(1-benzyl-1H-pyrazol-4-yl)-1'-pentylspiro[furo[2,3-f][1,3]benzodioxole-7,3'-indol]-2'(1'H)-one;

4'-(2-methoxypyrimidin-5-yl)-1'-pentylspiro[furo[2,3-f][1,3]benzodioxole-7,3'-indol]-2'(1'H)-one;

4'-(2,4-dimethoxypyrimidin-5-yl)-1'-pentylspiro[furo[2,3-f][1,3]benzodioxole-7,3'-indol]-2'(1'H)-one;

4-(2'-oxo-1'-pentyl-1',2'-dihydrospiro[furo[2,3-f][1,3]benzodioxole-7,3'-indol]-4'-yl)benzamide;

4'-{4-[(dimethylamino)methyl]phenyl}-1'-pentylspiro[furo[2,3-f][1,3]benzodioxole-7,3'-indol]-2'(1'H)-one;

4'-(1-benzofuran-2-yl)-1'-pentylspiro[furo[2,3-f][1,3]benzodioxole-7,3'-indol]-2'(1'H)-one;

4'-(6-methoxypyridin-3-yl)-1'-pentylspiro[furo[2,3-f][1,3]benzodioxole-7,3'-indol]-2'(1'H)-one;

N,N-dimethyl-4-(2'-oxo-1'-pentyl-1',2'-dihydrospiro[furo[2,3-f][1,3]benzodioxole-7,3'-indol]-4'-yl)benzamide;

4'-dibenzo[b,d]thien-4-yl-1'-pentylspiro[furo[2,3-f][1,3]benzodioxole-7,3'-indol]-2'(1'H)-one;

3-(2'-oxo-1'-pentyl-1',2'-dihydrospiro[furo[2,3-f][1,3]benzodioxole-7,3'-indol]-4'-yl)benzonitrile;

1-pentyl-4'-pyridin-3-ylspiro[furo[2,3-f][1,3]benzodioxole-7,3'-indol]-2'(1'H)-one;

4'-(3-fluoro-4-methoxyphenyl)-1'-pentylspiro[furo[2,3-f][1,3]benzodioxole-7,3'-indol]-2'(1'H)-one;

1'-pentyl-4'-[2-(trifluoromethoxy)phenyl]spiro[furo[2,3-f][1,3]benzodioxole-7,3'-indol]-2'(1'H)-one;

4'-[3,5-bis(trifluoromethyl)phenyl]-1'-pentylspiro[furo[2,3-f][1,3]benzodioxole-7,3'-indol]-2'(1'H)-one;

1'-pentyl-4'-[4-(trifluoromethyl)pyridin-3-yl]spiro[furo[2,3-f][1,3]benzodioxole-7,3'-indol]-2'(1'H)-one;

4'-(2-fluoro-5-methoxyphenyl)-1'-pentylspiro[furo[2,3-f][1,3]benzodioxole-7,3'-indol]-2'(1'H)-one;

4'-(4-ethoxy-3-fluorophenyl)-1'-pentylspiro[furo[2,3-f][1,3]benzodioxole-7,3'-indol]-2'(1'H)-one;

4'-(1-benzothien-2-yl)-1-pentylspiro[furo[2,3-f][1,3]benzodioxole-7,3'-indol]-2'(1'H)-one;

4'-isobutyl-1'-pentylspiro[furo[2,3-f][1,3]benzodioxole-7,3'-indol]-2'(1'H)-one;

1'-pentyl-4'-[4-(trifluoromethoxy)phenyl]spiro[furo[2,3-f][1,3]benzodioxole-7,3'-indol]-2'(1'H)-one;

4'-(5-fluoro-2-methoxyphenyl)-1'-pentylspiro[furo[2,3-f][1,3]benzodioxole-7,3'-indol]-2'(1'H)-one;

4'-(1,3-benzodioxol-5-yl)-1'-pentylspiro[furo[2,3-f][1,3]benzodioxole-7,3'-indol]-2'(1'H)-one;

1'-pentyl-4'-phenylspiro[furo[2,3-f][1,3]benzodioxole-7,3'-indol]-2'(1'H)-one;

1'-pentyl-4'-[2-(trifluoromethyl)phenyl]spiro[furo[2,3-f][1,3]benzodioxole-7,3'-indol]-2'(1'H)-one;

4'-(4-chlorophenyl)-1-pentylspiro[furo[2,3-f][1,3]benzodioxole-7,3'-indol]-2'(1'H)-one;

4'-(2,3-dihydro-1,4-benzodioxin-6-yl)-1'-pentylspiro[furo[2,3-f][1,3]benzodioxole-7,3'-indol]-2'(1'H)one;

1'-pentyl-4'-quinolin-3-ylspiro[furo[2,3-f][1,3]benzodioxole-7,3'-indol]-2'(1'H)-one;

4'-(3,5-difluorophenyl)-1'-pentylspiro[furo[2,3-f][1,3]benzodioxole-7,3'-indol]-2'(1'H)-one;

4'-isoquinolin-4-yl-1'-pentylspiro[furo[2,3-f][1,3]benzodioxole-7,3'-indol]-2'(1'H)-one;

4'-(6-methoxypyridin-2-yl)-1'-pentylspiro[furo[2,3-f][1,3]benzodioxole-7,3'-indol]-2'(1'H)-one;

4'-(1H-indol-5-yl)-1'-pentylspiro[furo[2,3-f][1,3]benzodioxole-7,3'-indol]-2'(1'H)-one;

N-[2-(2'-oxo-1'-pentyl-1',2'-dihydrospiro[furo[2,3-f][1,3]benzodioxole-7,3'-indol]-4'-yl)phenyl]acetamide;

4'-(4-fluoro-2-methylphenyl)-1-pentylspiro[furo[2,3-f][1,3]benzodioxole-7,3'-indol]-2'(1'H)-one;

1'-pentyl-4'-quinolin-6-ylspiro[furo[2,3-f][1,3]benzodioxole-7,3'-indol]-2'(1'H)-one;

N-[4-(2'-oxo-1'-pentyl-1',2'-dihydrospiro[furo[2,3-f][1,3]benzodioxole-7,3'-indol]-4'-yl)phenyl]methanesulfonamide;

4'-(5-chloro-2-methoxyphenyl)-1'-pentylspiro[furo[2,3-f][1,3]benzodioxole-7,3'-indol]-2'(1'H)-one;

1'-pentyl-4'-[3-(trifluoromethoxy)phenyl]spiro[furo[2,3-f][1,3]benzodioxole-7,3'-indol]-2'(1'H)-one;

1-pentyl-4'-(4-phenoxyphenyl)spiro[furo[2,3-f][1,3]benzodioxole-7,3'-indol]-2'(1'H)-one;

4'-(2,4-dimethoxyphenyl)-1'-pentylspiro[furo[2,3-f][1,3]benzodioxole-7,3'-indol]-2'(1'H)-one;

4'-(3-furyl)-1'-pentylspiro[furo[2,3-f][1,3]benzodioxole-7,3'-indol]-2'(1'H)-one;

4'-(3,4-dimethoxyphenyl)-1-pentylspiro[furo[2,3-f][1,3]benzodioxole-7,3'-indol]-2'(1'H)-one;

N-[4-(2'-oxo-1'-pentyl-1',2'-dihydrospiro[furo[2,3-f][1,3]benzodioxole-7,3'-indol]-4'-yl)phenyl]acetamide;

1'-pentyl-4'-[(E)-2-phenylvinyl]spiro[furo[2,3-f][1,3]benzodioxole-7,3'-indol]-2'(1'H)-one;

4'-(4-methoxyphenyl)-1-pentylspiro[furo[2,3-f][1,3]benzodioxole-7,3'-indol]-2'(1'H)-one;

4'-(6-fluoropyridin-3-yl)-1'-pentylspiro[furo[2,3-f][1,3]benzodioxole-7,3'-indol]-2'(1'H)-one;

4'-(3-chloro-4-fluorophenyl)-1'-pentylspiro[furo[2,3-f][1,3]benzodioxole-7,3'-indol]-2'(1'H)-one;

4'-(3-chlorophenyl)-1'-pentylspiro[furo[2,3-f][1,3]benzodioxole-7,3'-indol]-2'(1'H)-one;

4'-(1-benzothien-3-yl)-1-pentylspiro[furo[2,3-f][1,3]benzodioxole-7,3'-indol]-2'(1'H)-one;

1'-pentyl-4'-(2-phenoxyphenyl)spiro[furo[2,3-f][1,3]benzodioxole-7,3'-indol]-2'(1'H)-one;

4'-(4-isopropoxyphenyl)-1'-pentylspiro[furo[2,3-f][1,3]benzodioxole-7,3'-indol]-2'(1'H)-one;

4'-[(E)-2-(4-fluorophenyl)vinyl]-1'-pentylspiro[furo[2,3-f][1,3]benzodioxole-7,3'-indol]-2'(1'H)-one;

4'-(6-fluoropyridin-2-yl)-1-pentylspiro[furo[2,3-f][1,3]benzodioxole-7,3'-indol]-2'(1'H)-one;

1'-pentyl-4'-[1-(phenylsulfonyl)-1H-indol-3-yl]spiro[furo[2,3-f][1,3]benzodioxole-7,3'-indol]-2'(1'H)-one;

4'-(3-fluorophenyl)-1'-pentylspiro[furo[2,3-f][1,3]benzodioxole-7,3'-indol]-2'(1'H)-one;

4'-(3-acetylphenyl)-1-pentylspiro[furo[2,3-f][1,3]benzodioxole-7,3'-indol]-2'(1'H)-one;

4'-(2-furyl)-1'-pentylspiro[furo[2,3-f][1,3]benzodioxole-7,3'-indol]-2'(1'H)-one;

4'-(4-methylphenyl)-1'-pentylspiro[furo[2,3-f][1,3]benzodioxole-7,3'-indol]-2'(1'H)-one;

4'-(1-methyl-1H-pyrrol-3-yl)-1'-pentylspiro[furo[2,3-f][1,3]benzodioxole-7,3'-indol]-2'(1'H)-one;

4'-(2,5-difluorophenyl)-1-pentylspiro[furo[2,3-f][1,3]benzodioxole-7,3'-indol]-2'(1'H)-one;

4'-(2-fluorophenyl)-1'-pentylspiro[furo[2,3-f][1,3]benzodioxole-7,3'-indol]-2'(1'H)-one;

4'-(2-chlorophenyl)-1-pentylspiro[furo[2,3-f][1,3]benzodioxole-7,3'-indol]-2'(1'H)-one;

4'-(2,4-difluorophenyl)-1'-pentylspiro[furo[2,3-f][1,3]benzodioxole-7,3'-indol]-2'(1'H)-one;

4'-(4-morpholin-4-ylphenyl)-1'-pentylspiro[furo[2,3-f][1,3]benzodioxole-7,3'-indol]-2'(1'H)-one;

tert-butyl 5-methoxy-3-(2'-oxo-1'-pentyl-1',2'-dihydrospiro[furo[2,3-f][1,3]benzodioxole-7,3'-indol]-4'-yl)-1H-indole-1-carboxylate;

1'-pentyl-4'-pyrimidin-5-ylspiro[furo[2,3-f][1,3]benzodioxole-7,3'-indol]-2'(1'H)-one;

tert-butyl 4-[2-(2'-oxo-1'-pentyl-1',2'-dihydrospiro[furo[2,3-f][1,3]benzodioxole-7,3'-indol]-4'-yl)phenyl]piperazine-1-carboxylate;

4'-(2-methoxypyridin-3-yl)-1'-pentylspiro[furo[2,3-f][1,3]benzodioxole-7,3'-indol]-2'(1'H)-one;

4'-(5-methoxypyridin-3-yl)-1'-pentylspiro[furo[2,3-f][1,3]benzodioxole-7,3'-indol]-2'(1'H)-one;

4'-(4-butoxy-3-fluorophenyl)-1'-pentylspiro[furo[2,3-f][1,3]benzodioxole-7,3'-indol]-2'(1'H)-one;

1'-pentyl-4'-pyridin-4-ylspiro[furo[2,3-f][1,3]benzodioxole-7,3'-indol]-2'(1'H)-one;

1'-pentyl-4'-phenoxathiin-4-ylspiro[furo[2,3-f][1,3]benzodioxole-7,3'-indol]-2'(1'H)-one;

4'-[(1Z)-3-chloroprop-1-en-1-yl]-1'-pentylspiro[furo[2,3-f][1,3]benzodioxole-7,3'-indol]-2'(1'H)-one;

1'-pentyl-4'-(3-thienyl)spiro[furo[2,3-f][1,3]benzodioxole-7,3'-indol]-2'(1'H)-one;

4'(2,3-dimethoxyphenyl)-1'-pentylspiro[furo[2,3-f][1,3]benzodioxole-7,3'-indol]-2'(1'H)-one;

4'-(4-butylphenyl)-1'-pentylspiro[furo[2,3-f][1,3]benzodioxole-7,3'-indol]-2'(1'H)-one;

4'-(3-fluoro-5-methoxyphenyl)-1-pentylspiro[furo[2,3-f][1,3]benzodioxole-7,3'-indol]-2'(1'H)-one;

4'-[3-fluoro-4-(pentyloxy)phenyl]-1'-pentylspiro[furo[2,3-f][1,3]benzodioxole-7,3'-indol]-2'(1'H)-one;

4'-(2-butoxy-5-fluorophenyl)-1-pentylspiro[furo[2,3-f][1,3]benzodioxole-7,3'-indol]-2'(1'H)-one;

4'-(3-butoxyphenyl)-1-pentylspiro[furo[2,3-f][1,3]benzodioxole-7,3'-indol]-2'(1'H)-one;

4'-(4-butoxyphenyl)-1-pentylspiro[furo[2,3-f][1,3]benzodioxole-7,3'-indol]-2'(1'H)-one;

4'-(4-isobutoxyphenyl)-1'-pentylspiro[furo[2,3-f][1,3]benzodioxole-7,3'-indol]-2'(1'H)-one;

4'-{2-chloro-4-[(3,5-dimethoxybenzyl)oxy]phenyl}-1'-pentylspiro[furo[2,3-f][1,3]benzodioxole-7,3'-indol]-2'(1'H)-one;

4'-[4-(benzyloxy)-3-chlorophenyl]-1'-pentylspiro[furo[2,3-f][1,3]benzodioxole-7,3'-indol]-2'(1'H)-one;
4'-(1-methyl-1H-indol-5-yl)-1'-pentylspiro[furo[2,3-f][1,3]benzodioxole-7,3'-indol]-2'(1'H)-one;
4'-(4-methoxypyridin-3-yl)-1'-pentylspiro[furo[2,3-f][1,3]benzodioxole-7,3'-indol]-2'(1'H)-one;
4'-[(6-methoxypyridin-3-yl)amino]-1-pentylspiro[furo[2,3-f][1,3]benzodioxole-7,3'-indol]-2'(1'H)-one;
4'-(3-furyl)spiro[furo[2,3-f][1,3]benzodioxole-7,3'-indol]-2'(1'H)-one;
4'-dibenzo[b,d]furan-4-ylspiro[furo[2,3-f][1,3]benzodioxole-7,3'-indol]-2'(1'H)-one;
4'-pyrimidin-5-ylspiro[furo[2,3-f][1,3]benzodioxole-7,3'-indol]-2'(1'H)-one;
1-methyl-4'-pyrimidin-5-ylspiro[furo[2,3-f][1,3]benzodioxole-7,3'-indol]-2'(1'H)-one;
4'-(3-furyl)-1-methylspiro[furo[2,3-f][1,3]benzodioxole-7,3'-indol]-2'(1'H)-one;
4'-(6-fluoropyridin-3-yl)-1-methylspiro[furo[2,3-f][1,3]benzodioxole-7,3'-indol]-2'(1'H)-one;
1'-(2-cyclopropylethyl)-4'-quinolin-3-ylspiro[furo[2,3-f][1,3]benzodioxole-7,3'-indol]-2'(1'H)-one;
4'-[(6-methoxypyridin-3-yl)amino]-1-pentylspiro[furo[2,3-f][1,3]benzodioxole-7,3'-indol]-2'(1'H)-one;
4'-[(3,5-difluorophenyl)amino]-1-pentylspiro[furo[2,3-f][1,3]benzodioxole-7,3'-indol]-2'(1'H)-one;
4'-[(4,6-dimethylpyridin-2-yl)amino]-1-pentylspiro[furo[2,3-f][1,3]benzodioxole-7,3'-indol]-2'(1'H)-one;
4'-[(4-methyl-1,3-thiazol-2-yl)amino]-1-pentylspiro[furo[2,3-f][1,3]benzodioxole-7,3'-indol]-2'(1'H)one;
4'-bromo-1'-pentylspiro[furo[2,3-f][1,3]benzodioxole-7,3'-indol]-2'(1'H)-one;
4'-morpholino-t-pentyl-6H-spiro[benzofuro[6,5-d][1,3]dioxole-7,3'-indolin]-2'-one;
4'-(4-methylpiperazin-1-yl)-1'-pentyl-6H-spiro[benzofuro[6,5-d][1,3]dioxole-7,3'-indolin]-2'-one;
1-pentyl-4'-(pyrimidin-4-ylamino)-6H-spiro[benzofuro[6,5-d][1,3]dioxole-7,3'-indolin]-2'-one;
1-pentyl-4'-(pyridin-3-ylamino)-6H-spiro[benzofuro[6,5-d][1,3]dioxole-7,3'-indolin]-2'-one;
4'-(4-chloro-2-(trifluoromethyl)phenylamino)-1'-pentyl-6H-spiro[benzofuro[6,5-d][1,3]dioxole-7,3'-indolin]-2'-one;
1'-pentyl-4'-(pyrimidin-2-ylamino)-6H-spiro[benzofuro[6,5-d][1,3]dioxole-7,3'-indolin]-2'-one;
4'-(benzo[d][1,3]dioxol-5-ylamino)-1'-pentyl-6H-spiro[benzofuro[6,5-d][1,3]dioxole-7,3'-indolin]-2'-one;
4'-(3-fluorophenylamino)-1'-pentyl-6H-spiro[benzofuro[6,5-d][1,3]dioxole-7,3'-indolin]-2'-one;
4'-(naphthalen-2-ylamino)-1-pentyl-6H-spiro[benzofuro[6,5-d][1,3]-dioxole-7,3'-indolin]-2'-one;
4'-(2-methoxyphenylamino)-1'-pentyl-6H-spiro[benzofuro[6,5-d][1,3]dioxole-7,3'-indolin]-2'-one;
4'-(4-methylthiazol-2-ylamino)-1'-pentyl-6H-spiro[benzofuro[6,5-d][1,3]-dioxole-7,3'-indolin]-2'-one;
4'-(4,6-dimethylpyridin-2-ylamino)-1-pentyl-6H-spiro[benzofuro[6,5-d][1,3]-dioxole-7,3'-indolin]-2'-one;
4'-(3,5-difluorophenylamino)-1'-pentyl-6H-spiro[benzofuro[6,5-d][1,3]dioxole-7,3'-indolin]-2'-one;
4'-(6-methoxypyridin-3-ylamino)-1'-pentyl-6H-spiro[benzofuro[6,5-d][1,3]dioxole-7,3'-indolin]-2'-one;
1'-pentyl-7H-spiro[furo[3,4-f][1,3]benzodioxole-5,3'-indol]-2'(1'H)-one;
2'-oxo-1'-pentyl-N-pyridin-2-yl-1',2'-dihydrospiro[furo[2,3-f][1,3]benzodioxole-7,3'-indole]-4'-carboxamide;
N-(3-methoxyphenyl)-2'-oxo-1'-pentyl-1',2'-dihydrospiro[furo[2,3-f][1,3]benzodioxole-7,3'-indole]-4'-carboxamide;
2-(5,6-difluoro-2'-oxo-4'-pyrimidin-5-ylspiro[1-benzofuran-3,3'-indol]-1'(2'H)-yl)-N-(2-fluorophenyl)acetamide;
2-(6,6-dimethyl-2'-oxo-4'-pyrimidin-5-yl-5,6-dihydrospiro[benzo[1,2-b:5,4-b']difuran-3,3'-indol]-1'(2'H)-yl)-N-(2-fluorophenyl)acetamide; and
N-(2-fluorophenyl)-2-(2'-oxo-4'-pyrimidin-5-yl-5,6-dihydrospiro[benzo[1,2-b:5,4-b']difuran-3,3'-indol]-1'(2'H)-yl)acetamide.

Another embodiment of the invention are the compounds of formula (I) as set forth above in the Summary of the invention wherein:

at least one of j and k is 1 and the other is 0 or 1;
Q is —O—;
$R^1$ is aralkyl substituted by —C(O)N($R^6$)$R^7$ where:
  $R^6$ is hydrogen, alkyl, aryl or aralkyl; and
  $R^7$ is hydrogen, alkyl, haloalkyl, —$R^9$—CN, —$R^9$—$OR^5$, —$R^9$—N($R^4$)$R^5$, aryl, aralkyl, cycloalkyl, cycloalkylalkyl, heterocyclyl, heterocyclylalkyl, heteroaryl, heteroarylalkyl;
  or $R^6$ and $R^7$, together with the nitrogen to which they are attached, form a heterocyclyl or heteroaryl;
  and wherein each aryl, aralkyl, cycloalkyl, cycloalkylalkyl, heterocyclyl, heterocyclylalkyl, heteroaryl and heteroaryl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—N($R^4$)$R^5$, —N=C($R^4$)$R^5$, —S(O)$_m$$R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—$OR^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$NO_2$, —$R^8$—$OR^5$, —$R^8$—$N(R^4)R^5$, —N=$C(R^4)R^5$, —$S(O)_mR^4$, —$OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;
Q is —O—;
$R^1$ is aralkyl substituted by —$C(O)N(R^6)R^7$ where:
  $R^6$ is hydrogen, alkyl, aryl or aralkyl; and
  $R^7$ is hydrogen, alkyl, haloalkyl, —$R^9$—CN, —$R^9$—$OR^5$, —$R^9$—$N(R^4)R^5$, aryl, aralkyl, cycloalkyl, cycloalkylalkyl, heterocyclyl, heterocyclylalkyl, heteroaryl, heteroarylalkyl;
  or $R^6$ and $R^7$, together with the nitrogen to which they are attached, form a heterocyclyl or heteroaryl;
  and wherein each aryl, aralkyl, cycloalkyl, cycloalkylalkyl, heterocyclyl, heterocyclylalkyl, heteroaryl and heteroaryl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;
$R^{2a}$, $R^{2b}$, $R^{2c}$ and $R^{2d}$ are each hydrogen;
$R^{3a}$ and $R^{3d}$ are each hydrogen;

$R^{3b}$ and $R^{3c}$, together with the carbon ring atoms to which they are directly attached, form a fused ring selected from cycloalkyl, heterocyclyl, aryl or heteroaryl;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;
Q is —O—;
$R^1$ is aralkyl substituted by —$C(O)N(R^6)R^7$ where:
  $R^6$ is hydrogen, alkyl, aryl or aralkyl; and
  $R^7$ is hydrogen, alkyl, haloalkyl, —$R^9$—CN, —$R^9$—$OR^5$ or —$R^9$—$N(R^4)R^5$;
  or $R^6$ and $R^7$, together with the nitrogen to which they are attached, form a heterocyclyl or heteroaryl;
  wherein each aryl, aralkyl, heterocyclyl and heteroaryl groups for $R^6$ and $R^7$ is optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused dioxolyl ring;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

N-(3-methylbutyl)-2-[(2'-oxospiro[furo[2,3-f][1,3]benzodioxole-7,3'-indol]-1'(2'H)-yl)methyl]benzamide;

N,N-diisopropyl-2-[(2'-oxospiro[furo[2,3-f][1,3]benzodioxole-7,3'-indol]-1'(2'H)-yl)methyl]benzamide;

N-butyl-2-[(2'-oxospiro[furo[2,3-f][1,3]benzodioxole-7,3'-indol]-1'(2'H)-yl)methyl]benzamide;

2-[(2'-oxospiro[furo[2,3-f][1,3]benzodioxole-7,3'-indol]-1'(2'H)-yl)methyl]-N-pentylbenzamide;

N-hexyl-2-[(2'-oxospiro[furo[2,3-f][1,3]benzodioxole-7,3'-indol]-1'(2'H)-yl)methyl]benzamide;

2-[(2'-oxospiro[furo[2,3-f][1,3]benzodioxole-7,3'-indol]-1'(2'H)-yl)methyl]-N-propylbenzamide;

N-isopropyl-2-[(2'-oxospiro[furo[2,3-f][1,3]benzodioxole-7,3'-indol]-1'(2'H)-yl)methyl]benzamide;
N-heptyl-2-[(2'-oxospiro[furo[2,3-f][1,3]benzodioxole-7,3'-indol]-1'(2'H)-yl)methyl]benzamide;
1'-[2-(piperidin-1-ylcarbonyl)benzyl]spiro[furo[2,3-f][1,3]benzodioxole-7,3'-indol]-2'(1'H)-one;
N-isobutyl-2-[(2'-oxospiro[furo[2,3-f][1,3]benzodioxole-7,3'-indol]-1'(2'H)-yl)methyl]benzamide;
N-(3-methoxypropyl)-2-[(2'-oxospiro[furo[2,3-f][1,3]benzodioxole-7,3'-indol]-1'(2'H)-yl)methyl]benzamide;
N-(3-ethoxypropyl)-2-[(2'-oxospiro[furo[2,3-f][1,3]benzodioxole-7,3'-indol]-1'(2'H)-yl)methyl]benzamide;
N-hexyl-N-methyl-2-[(2'-oxospiro[furo[2,3-f][1,3]benzodioxole-7,3'-indol]-1'(2'H)-yl)methyl]benzamide;
N-(3-isopropoxypropyl)-2-[(2'-oxospiro[furo[2,3-f][1,3]benzodioxole-7,3'-indol]-1'(2'H)-yl)methyl]benzamide;
N-(2-ethoxyethyl)-2-[(2'-oxospiro[furo[2,3-f][1,3]benzodioxole-7,3'-indol]-1'(2'H)-yl)methyl]benzamide;
N-methyl-2-[(2'-oxospiro[furo[2,3-f][1,3]benzodioxole-7,3'-indol]-1'(2'H)-yl)methyl]benzamide;
N-ethyl-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(2,2,2-trifluoroethyl)benzamide;
N-[2-(diethylamino)ethyl]-2-[(2'-oxospiro[furo[2,3-f][1,3]benzodioxole-7,3'-indol]-1'(2'H)-yl)methyl]benzamide;
N-(3,3-dimethylbutyl)-2-[(2'-oxospiro[furo[2,3-f][1,3]benzodioxole-7,3'-indol]-1'(2'H)-yl)methyl]benzamide;
N-(2-ethylbutyl)-2-[(2'-oxospiro[furo[2,3-f][1,3]benzodioxole-7,3'-indol]-1'(2'H)-yl)methyl]benzamide;
N-(2-methoxyethyl)-2-[(2'-oxospiro[furo[2,3-f][1,3]benzodioxole-7,3'-indol]-1'(2'H)-yl)methyl]benzamide;
N-(2-cyanoethyl)-2-[(2'-oxospiro[furo[2,3-f][1,3]benzodioxole-7,3'-indol]-1'(2'H)-yl)methyl]benzamide;
1'-{2-[(4-pyrimidin-2-ylpiperazin-1-yl)carbonyl]benzyl}spiro[furo[2,3-f][1,3]benzodioxole-7,3'-indol]-2'(1'H)-one;
1'-(2-{[4-(1,3-benzodioxol-5-ylmethyl)piperazin-1-yl]carbonyl}benzyl)spiro[furo[2,3-f][1,3]benzodioxole-7,3'-indol]-2'(1'H)-one;
1'-[2-(morpholin-4-ylcarbonyl)benzyl]spiro[furo[2,3-f][1,3]benzodioxole-7,3'-indol]-2'(1'H)-one;
N-[3-(dimethylamino)propyl]-N-methyl-2-[(2'-oxospiro[furo[2,3-f][1,3]benzodioxole-7,3'-indol]-1'(2'H)-yl)methyl]benzamide;
N-(3-methylbutyl)-3-[(2'-oxospiro[furo[2,3-f][1,3]benzodioxole-7,3'-indol]-1'(2'H)-yl)methyl]benzamide;
N,N-diisopropyl-3-[(2'-oxospiro[furo[2,3-f][1,3]benzodioxole-7,3'-indol]-1'(2'H)-yl)methyl]benzamide;
N-butyl-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-pentylbenzamide;
3-[(2'-oxospiro[furo[2,3-f][1,3]benzodioxole-7,3'-indol]-1'(2'H)-yl)methyl]-N-propylbenzamide;
N-isopropyl-3-[(2'-oxospiro[furo[2,3-f][1,3]benzodioxole-7,3'-indol]-1'(2'H)-yl)methyl]benzamide;
1'-[3-(piperidin-1-ylcarbonyl)benzyl]spiro[furo[2,3-f][1,3]benzodioxole-7,3'-indol]-2'(1'H)-one;
N-isobutyl-3-[(2'-oxospiro[furo[2,3-f][1,3]benzodioxole-7,3'-indol]-1'(2'H)-yl)methyl]benzamide;
N-hexyl-3-[(2'-oxospiro[furo[2,3-f][1,3]benzodioxole-7,3'-indol]-1'(2'H)-yl)methyl]benzamide;
N-heptyl-3-[(2'-oxospiro[furo[2,3-f][1,3]benzodioxole-7,3'-indol]-1'(2'H)-yl)methyl]benzamide;
N-(3-methoxypropyl)-3-[(2'-oxospiro[furo[2,3-f][1,3]benzodioxole-7,3'-indol]-1'(2'H)-yl)methyl]benzamide;
N-[2-(diethylamino)ethyl]-3-[(2'-oxospiro[furo[2,3-f][1,3]benzodioxole-7,3'-indol]-1'(2'H)-yl)methyl]benzamide;
N-methyl-3-[(2'-oxospiro[furo[2,3-f][1,3]benzodioxole-7,3'-indol]-1'(2'H)-yl)methyl]benzamide;
N-ethyl-3-[(2'-oxospiro[furo[2,3-f][1,3]benzodioxole-7,3'-indol]-1'(2'H)-yl)methyl]benzamide;
N-(3-ethoxypropyl)-3-[(2'-oxospiro[furo[2,3-f][1,3]benzodioxole-7,3'-indol]-1'(2'H)-yl)methyl]benzamide;
N-hexyl-N-methyl-3-[(2'-oxospiro[furo[2,3-f][1,3]benzodioxole-7,3'-indol]-1'(2'H)-yl)methyl]benzamide;
N-(3-isopropoxypropyl)-3-[(2'-oxospiro[furo[2,3-f][1,3]benzodioxole-7,3'-indol]-1'(2'H)-yl)methyl]benzamide;
N-(2-ethoxyethyl)-3-[(2'-oxospiro[furo[2,3-f][1,3]benzodioxole-7,3'-indol]-1'(2'H)-yl)methyl]benzamide;
N-(2-ethylbutyl)-3-[(2'-oxospiro[furo[2,3-f][1,3]benzodioxole-7,3'-indol]-1'(2'H)-yl)methyl]benzamide;
N-(2-methoxyethyl)-3-[(2'-oxospiro[furo[2,3-f][1,3]benzodioxole-7,3'-indol]-1'(2'H)-yl)methyl]benzamide;
1'-[3-(morpholin-4-ylcarbonyl)benzyl]spiro[furo[2,3-f][1,3]benzodioxole-7,3'-indol]-2'(1'H)-one;
1'-{3-[(4-pyrimidin-2-ylpiperazin-1-yl)carbonyl]benzyl}spiro[furo[2,3-f][1,3]benzodioxole-7,3'-indol]-2'(1'H)-one;
1'-{3-[(4-methylpiperazin-1-yl)carbonyl]benzyl}spiro[furo[2,3-f][1,3]benzodioxole-7,3'-indol]-2'(1'H)-one;
N-(3,3-dimethylbutyl)-3-[(2'-oxospiro[furo[2,3-f][1,3]benzodioxole-7,3'-indol]-1'(2'H)-yl)methyl]benzamide;
N-(2-cyanoethyl)-3-[(2'-oxospiro[furo[2,3-f][1,3]benzodioxole-7,3'-indol]-1'(2'H)-yl)methyl]benzamide;
N-butyl-4-[(2'-oxospiro[furo[2,3-f][1,3]benzodioxole-7,3'-indol]-1'(2'H)-yl)methyl]benzamide;
1'-[4-(piperidin-1-ylcarbonyl)benzyl]spiro[furo[2,3-f][1,3]benzodioxole-7,3'-indol]-2'(1'H)-one;
N,N-diisopropyl-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-pentylbenzamide;
4-[(2'-oxospiro[furo[2,3-f][1,3]benzodioxole-7,3'-indol]-1'(2'H)-yl)methyl]-N-propylbenzamide;
N-isopropyl-4-[(2'-oxospiro[furo[2,3-f][1,3]benzodioxole-7,3'-indol]-1'(2'H)-yl)methyl]benzamide;
N-isobutyl-4-[(2'-oxospiro[furo[2,3-f][1,3]benzodioxole-7,3'-indol]-1'(2'H)-yl)methyl]benzamide;
N-hexyl-4-[(2'-oxospiro[furo[2,3-f][1,3]benzodioxole-7,3'-indol]-1'(2'H)-yl)methyl]benzamide;
N-heptyl-4-[(2'-oxospiro[furo[2,3-f][1,3]benzodioxole-7,3'-indol]-1'(2'H)-yl)methyl]benzamide;
N-(3-methoxypropyl)-4-[(2'-oxospiro[furo[2,3-f][1,3]benzodioxole-7,3'-indol]-1'(2'H)-yl)methyl]benzamide;
N-[2-(diethylamino)ethyl]-4-[(2'-oxospiro[furo[2,3-f][1,3]benzodioxole-7,3'-indol]-1'(2'H)-yl)methyl]benzamide;
N-methyl-4-[(2'-oxospiro[furo[2,3-f][1,3]benzodioxole-7,3'-indol]-1'(2'H)-yl)methyl]benzamide;
N-ethyl-4-[(2'-oxospiro[furo[2,3-f][1,3]benzodioxole-7,3'-indol]-1'(2'H)-yl)methyl]benzamide;
N-(3-ethoxypropyl)-4-[(2'-oxospiro[furo[2,3-f][1,3]benzodioxole-7,3'-indol]-1'(2'H)-yl)methyl]benzamide;
N-(4-methylpentyl)-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-(2,2,2-trifluoroethyl)benzamide;
N-hexyl-N-methyl-4-[(2'-oxospiro[furo[2,3-f][1,3]benzodioxole-7,3'-indol]-1'(2'H)-yl)methyl]benzamide;
N-(3-isopropoxypropyl)-4-[(2'-oxospiro[furo[2,3-f][1,3]benzodioxole-7,3'-indol]-1'(2'H)-yl)methyl]benzamide;
N-(2-ethoxyethyl)-4-[(2'-oxospiro[furo[2,3-f][1,3]benzodioxole-7,3'-indol]-1'(2'H)-yl)methyl]benzamide;

N-(2-ethylbutyl)-4-[(2'-oxospiro[furo[2,3-f][1,3]benzodioxole-7,3'-indol]-1'(2'H)-yl)methyl]benzamide;
N-(2-methoxyethyl)-4-[(2'-oxospiro[furo[2,3-f][1,3]benzodioxole-7,3'-indol]-1'(2'H)-yl)methyl]benzamide;
N-(2-cyanoethyl)-4-[(2'-oxospiro[furo[2,3-f][1,3]benzodioxole-7,3'-indol]-1'(2'H)-yl)methyl]benzamide; and
N-[3-(dimethylamino)propyl]-N-methyl-4-[(2'-oxospiro[furo[2,3-f][1,3]benzodioxole-7,3'-indol]-1'(2'H)-yl)methyl]benzamide.

Another embodiment of the invention are the compounds of formula (I) as set forth above in the Summary of the invention wherein:

j is 0 and k is 1;
Q is —O—;
$R^1$ is aralkyl substituted by —C(O)N($R^6$)$R^7$ where:
  $R^6$ is hydrogen, alkyl, aryl or aralkyl; and
  $R^7$ is aryl, aralkyl, cycloalkyl, cycloalkylalkyl, heterocyclyl, heterocyclylalkyl, heteroaryl, heteroarylalkyl;
  and wherein each aryl, aralkyl, cycloalkyl, cycloalkylalkyl, heterocyclyl, heterocyclylalkyl, heteroaryl and heteroaryl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;
$R^{2a}$, $R^{2b}$, $R^{2c}$ and $R^{2d}$ are each hydrogen;
$R^{3a}$ and $R^{2d}$ are each hydrogen;
$R^{3b}$ and $R^{3c}$, together with the carbon ring atoms to which they are directly attached, form a fused dioxolyl ring;
each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl; and
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:
N-[2-(4-chlorophenyl)ethyl]-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-phenylbenzamide;
N-(3-fluorophenyl)-2-[(2'-oxospiro[furo[2,3-f][1,3]benzodioxole-7,3'-indol]-1'(2'H)-yl)methyl]benzamide;
N-(4-chlorobenzyl)-2-[(2'-oxospiro[furo[2,3-f][1,3]benzodioxole-7,3'-indol]-1'(2'H)-yl)methyl]benzamide;
N-cyclohexyl-2-[(2'-oxospiro[furo[2,3-f][1,3]benzodioxole-7,3'-indol]-1'(2'H)-yl)methyl]benzamide;
N-cyclopentyl-2-[(2'-oxospiro[furo[2,3-f][1,3]benzodioxole-7,3'-indol]-1'(2'H)-yl)methyl]benzamide;
N-(4-fluorophenyl)-2-[(2'-oxospiro[furo[2,3-f][1,3]benzodioxole-7,3'-indol]-1'(2'H)-yl)methyl]benzamide;
N-(3-fluorobenzyl)-2-[(2'-oxospiro[furo[2,3-f][1,3]benzodioxole-7,3'-indol]-1'(2'H)-yl)methyl]benzamide;
N-(3-chlorophenyl)-2-[(2'-oxospiro[furo[2,3-f][1,3]benzodioxole-7,3'-indol]-1'(2'H)-yl)methyl]benzamide;
N-(2-fluorophenyl)-2-[(2'-oxospiro[furo[2,3-f][1,3]benzodioxole-7,3'-indol]-1'(1'H)-yl)methyl]benzamide;
N-(2-ethylphenyl)-2-[(2'-oxospiro[furo[2,3-f][1,3]benzodioxole-7,3'-indol]-1'(2'H)-yl)methyl]benzamide;
N-(4-ethylphenyl)-2-[(2'-oxospiro[furo[2,3-f][1,3]benzodioxole-7,3'-indol]-1'(2'H)-yl)methyl]benzamide;
N-(3-methylphenyl)-2-[(2'-oxospiro[furo[2,3-f][1,3]benzodioxole-7,3'-indol]-1'(2'H)-yl)methyl]benzamide;
N-(2,3-dimethylphenyl)-2-[(2'-oxospiro[furo[2,3-f][1,3]benzodioxole-7,3'-indol]-1'(2'H)-yl)methyl]benzamide;
N-(3,5-dimethylphenyl)-2-[(2'-oxospiro[furo[2,3-f][1,3]benzodioxole-7,3'-indol]-1'(2'H)-yl)methyl]benzamide;
N-(2-chlorobenzyl)-2-[(2'-oxospiro[furo[2,3-f][1,3]benzodioxole-7,3'-indol]-1'(2'H)-yl)methyl]benzamide;
N-(2,6-dimethylphenyl)-2-[(2'-oxospiro[furo[2,3-f][1,3]benzodioxole-7,3'-indol]-1'(2'H)-yl)methyl]benzamide;
N-(2-methoxyphenyl)-2-[(2'-oxospiro[furo[2,3-f][1,3]benzodioxole-7,3'-indol]-1'(2'H)-yl)methyl]benzamide;
N-[2-(4-methylphenyl)ethyl]-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(tetrahydrofuran-2-ylmethyl)benzamide;
N,N-dibenzyl-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(3-phenylpropyl)benzamide;
N-[2-(3-chlorophenyl)ethyl]-2-[(2'-oxospiro[furo[2,3-f][1,3]benzodioxole-7,3'-indol]-1'(2'H)-yl)methyl]benzamide;
N-[2-(4-fluorophenyl)ethyl]-2-[(2'-oxospiro[furo[2,3-f][1,3]benzodioxole-7,3'-indol]-1'(2'H)-yl)methyl]benzamide;
N-(4-fluorobenzyl)-2-[(2'-oxospiro[furo[2,3-f][1,3]benzodioxole-7,3'-indol]-1'(2'H)-yl)methyl]benzamide;
N-(4-methoxybenzyl)-2-[(2'-oxospiro[furo[2,3-f][1,3]benzodioxole-7,3'-indol]-1'(2'H)-yl)methyl]benzamide;
N-(cyclopropylmethyl)-2-[(2'-oxospiro[furo[2,3-f][1,3]benzodioxole-7,3'-indol]-1'(2'H)-yl)methyl]benzamide;
N-(cyclohexylmethyl)-2-[(2'-oxospiro[furo[2,3-f][1,3]benzodioxole-7,3'-indol]-1'(2'H)-yl)methyl]benzamide;
N-(2-furylmethyl)-2-[(2'-oxospiro[furo[2,3-f][1,3]benzodioxole-7,3'-indol]-1'(2'H)-yl)methyl]benzamide;
N-(2,4-dimethylphenyl)-2-[(2'-oxospiro[furo[2,3-f][1,3]benzodioxole-7,3'-indol]-1'(2'H)-yl)methyl]benzamide;
N-(4-cyanophenyl)-2-[(2'-oxospiro[furo[2,3-f][1,3]benzodioxole-7,3'-indol]-1'(2'H)-yl)methyl]benzamide;
N-(3,5-dichlorophenyl)-2-[(2'-oxospiro[furo[2,3-f][1,3]benzodioxole-7,3'-indol]-1'(2'H)-yl)methyl]benzamide;
N-(3-fluoro-2-methylphenyl)-2-[(2'-oxospiro[furo[2,3-f][1,3]benzodioxole-7,3'-indol]-1'(2'H)-yl)methyl]benzamide;
N-(4-methoxyphenyl)-2-[(2'-oxospiro[furo[2,3-f][1,3]benzodioxole-7,3'-indol]-1'(2'H)-yl)methyl]benzamide;
N-(5-chloro-2-methylphenyl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-[3-(trifluoromethyl)phenyl]benzamide;
2-[(2'-oxospiro[furo[2,3-f][1,3]benzodioxole-7,3'-indol]-1'(2'H)-yl)methyl]-N-(pyridin-4-ylmethyl)benzamide;
N-cyclobutyl-2-[(2'-oxospiro[furo[2,3-f][1,3]benzodioxole-7,3'-indol]-1'(2'H)-yl)methyl]benzamide;
N-(2,2-diphenylethyl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(2-pyrrolidin-1-ylethyl)benzamide;
N-[(1-ethylpyrrolidin-2-yl)methyl]-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(2-piperidin-1-ylethyl)benzamide;

N-(2-morpholin-4-ylethyl)-2-[(2'-oxospiro[furo[2,3-f][1,3]benzodioxole-7,3'-indol]-1'(2'H)-yl)methyl]benzamide;
N-[(1S)-1-cyclohexylethyl]-2-[(2'-oxospiro[furo[2,3-f][1,3]benzodioxole-7,3'-indol]-1'(2'H)-yl)methyl]benzamide;
N-(2-fluoro-5-methylphenyl)-2-[(2'-oxospiro[furo[2,3-f][1,3]benzodioxole-7,3'-indol]-1'(2'H)-yl)methyl]benzamide;
N-(2,4-difluorophenyl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(4-propylphenyl)benzamide;
N-(3,3-diphenylpropyl)-2-[(2'-oxospiro[furo[2,3-f][1,3]benzodioxole-7,3'-indol]-1'(2'H)-yl)methyl]benzamide;
N-(2,5-difluorobenzyl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(2-thienylmethyl)benzamide;
N-[4-chloro-2-(trifluoromethyl)phenyl]-2-[(2'-oxospiro[furo[2,3-f][1,3]benzodioxole-7,3'-indol]-1'(2'H)-yl)methyl]benzamide;
N-[2-(4-methoxyphenyl)ethyl]-2-[(2'-oxospiro[furo[2,3-f][1,3]benzodioxole-7,3'-indol]-1'(2'H)-yl)methyl]benzamide;
N-(3,5-dichlorobenzyl)-2-[(2'-oxospiro[furo[2,3-f][1,3]benzodioxole-7,3'-indol]-1'(2'H)-yl)methyl]benzamide;
N-(3-chlorobenzyl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-[2-(2-thienyl)ethyl]benzamide;
N-(2,3-dihydro-1H-inden-1-yl)-2-[(7-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-[4-(trifluoromethyl)benzyl]benzamide;
N-[4-fluoro-2-(trifluoromethyl)phenyl]-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-(pyridin-3-ylmethyl)benzamide;
2-[(2'-oxospiro[furo[2,3-f][1,3]benzodioxole-7,3'-indol]-1'(2'H)-yl)methyl]-N-[2-(trifluoromethyl)benzyl]benzamide;
N-(3-methylpyridin-2-yl)-2-[(2'-oxospiro[furo[2,3-f][1,3]benzodioxole-7,3'-indol]-1'(2'H)-yl)methyl]benzamide;
N-(1-benzylpiperidin-4-yl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-[2-(trifluoromethyl)phenyl]benzamide;
N-[(1R)-1-cyclohexylethyl]-2-[(2'-oxospiro[furo[2,3-f][1,3]benzodioxole-7,3'-indol]-1'(2'H)-yl)methyl]benzamide;
N-(6-methoxypyridin-3-yl)-2-[(2'-oxospiro[furo[2,3-f][1,3]benzodioxole-7,3'-indol]-1'(2'H)-yl)methyl]benzamide;
2-[(2'-oxospiro[furo[2,3-f][1,3]benzodioxole-7,3'-indol]-1'(2'H)-yl)methyl]-N-1,3-thiazol-2-ylbenzamide;
2-[(2'-oxospiro[furo[2,3-f][1,3]benzodioxole-7,3'-indol]-1'(2'H)-yl)methyl]-N-1,3,4-thiadiazol-2-ylbenzamide;
N-(4,6-dimethylpyridin-2-yl)-2-[(2'-oxospiro[furo[2,3-f][1,3]benzodioxole-7,3'-indol]-1'(2'H)-yl)methyl]benzamide;
N-(2,3-dihydro-1H-inden-5-yl)-2-[(2'-oxospiro[furo[2,3-f][1,3]benzodioxole-7,3'-indol]-1'(2'H)-yl)methyl]benzamide;
N-2-adamantyl-2-[(2'-oxospiro[furo[2,3-f][1,3]benzodioxole-7,3'-indol]-1'(2'H)-yl)methyl]benzamide;
N-1-adamantyl-2-[(2'-oxospiro[furo[2,3-f][1,3]benzodioxole-7,3'-indol]-1'(2'H)-yl)methyl]benzamide;
N-1-naphthyl-2-[(2'-oxospiro[furo[2,3-f][1,3]benzodioxole-7,3'-indol]-1'(2'H)-yl)methyl]benzamide;
N-(3,5-difluorophenyl)-2-[(2'-oxospiro[furo[2,3-f][1,3]benzodioxole-7,3'-indol]-1'(2'H)-yl)methyl]benzamide;
N-[2-(3-chlorophenyl)ethyl]-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-phenylbenzamide;
N-(3-fluorophenyl)-3-[(2'-oxospiro[furo[2,3-f][1,3]benzodioxole-7,3'-indol]-1'(2'H)-yl)methyl]benzamide;
N-(4-chlorobenzyl)-3-[(2'-oxospiro[furo[2,3-f][1,3]benzodioxole-7,3'-indol]-1'(2'H)-yl)methyl]benzamide;
N-(3-fluorobenzyl)-3-[(2'-oxospiro[furo[2,3-f][1,3]benzodioxole-7,3'-indol]-1'(2'H)-yl)methyl]benzamide;
N-(3-chlorophenyl)-3-[(2'-oxospiro[furo[2,3-f][1,3]benzodioxole-7,3'-indol]-1'(2'H)-yl)methyl]benzamide;
N-(2-fluorophenyl)-3-[(2'-oxospiro[furo[2,3-f][1,3]benzodioxole-7,3'-indol]-1'(2'H)-yl)methyl]benzamide;
N-(2-ethylphenyl)-3-[(2'-oxospiro[furo[2,3-f][1,3]benzodioxole-7,3'-indol]-1'(2'H)-yl)methyl]benzamide;
N-(4-ethylphenyl)-3-[(2'-oxospiro[furo[2,3-f][1,3]benzodioxole-7,3'-indol]-1'(2'H)-yl)methyl]benzamide;
N-(3-methylphenyl)-3-[(2'-oxospiro[furo[2,3-f][1,3]benzodioxole-7,3'-indol]-1'(2'H)-yl)methyl]benzamide;
N-(2,3-dimethylphenyl)-3-[(2'-oxospiro[furo[2,3-f][1,3]benzodioxole-7,3'-indol]-1'(2'H)-yl)methyl]benzamide;
N-(3,5-dimethylphenyl)-3-[(2'-oxospiro[furo[2,3-f][1,3]benzodioxole-7,3'-indol]-1'(2'H)-yl)methyl]benzamide;
N-cyclohexyl-3-[(2'-oxospiro[furo[2,3-f][1,3]benzodioxole-7,3'-indol]-1'(2'H)-yl)methyl]benzamide;
N-cyclopentyl-3-[(2'-oxospiro[furo[2,3-f][1,3]benzodioxole-7,3'-indol]-1'(2'H)-yl)methyl]benzamide;
N-(2-methoxybenzyl)-3-[(2'-oxospiro[furo[2,3-f][1,3]benzodioxole-7,3'-indol]-1'(2'H)-yl)methyl]benzamide;
N-(2-methoxyphenyl)-3-[(2'-oxospiro[furo[2,3-f][1,3]benzodioxole-7,3'-indol]-1'(2'H)-yl)methyl]benzamide;
N-cyclopropyl-3-[(2'-oxospiro[furo[2,3-f][1,3]benzodioxole-7,3'-indol]-1'(2'H)-yl)methyl]benzamide;
N-(2,4-dimethylphenyl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-(tetrahydrofuran-2-ylmethyl)benzamide;
N,N-dibenzyl-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-[3-(trifluoromethyl)phenyl]benzamide;
N-(4-methoxybenzyl)-3-[(2'-oxospiro[furo[2,3-f][1,3]benzodioxole-7,3'-indol]-1'(2'H)-yl)methyl]benzamide;
N-(3,5-dichlorophenyl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-pyridin-3-ylbenzamide;
3-[(2'-oxospiro[furo[2,3-f][1,3]benzodioxole-7,3'-indol]-1'(2'H)-yl)methyl]-N-(pyridin-4-ylmethyl)benzamide;
N-(2-furylmethyl)-3-[(2'-oxospiro[furo[2,3-f][1,3]benzodioxole-7,3'-indol]-1'(2'H)-yl)methyl]benzamide;
N-(3-fluoro-2-methylphenyl)-3-[(2'-oxospiro[furo[2,3-f][1,3]benzodioxole-7,3'-indol]-1'(2'H)-yl)methyl]benzamide;
N-(cyclopropylmethyl)-3-[(2'-oxospiro[furo[2,3-f][1,3]benzodioxole-7,3'-indol]-1'(2'H)-yl)methyl]benzamide;
N-(4-methoxyphenyl)-3-[(2'-oxospiro[furo[2,3-f][1,3]benzodioxole-7,3'-indol]-1'(2'H)-yl)methyl]benzamide;
N-cyclobutyl-3-[(2'-oxospiro[furo[2,3-f][1,3]benzodioxole-7,3'-indol]-1'(2'H)-yl)methyl]benzamide;

N-[2-(4-fluorophenyl)ethyl]-3-[(2'-oxospiro[furo[2,3-f][1,3]benzodioxole-7,3'-indol]-1'(2'H)-yl)methyl]benzamide;
N-(cyclohexylmethyl)-3-[(2'-oxospiro[furo[2,3-f][1,3]benzodioxole-7,3'-indol]-1'(2'H)-yl)methyl]benzamide;
N-[2-(4-methylphenyl)ethyl]-3-[(2'-oxospiro[furo[2,3-f][1,3]benzodioxole-7,3'-indol]-1'(2'H)-yl)methyl]benzamide;
N-benzyl-3-[(2'-oxospiro[furo[2,3-f][1,3]benzodioxole-7,3'-indol]-1'(2'H)-yl)methyl]benzamide;
N-(1-benzylpiperidin-4-yl)-3-[(2'-oxospiro[furo[2,3-f][1,3]benzodioxole-7,3'-indol]-1'(2'H)-yl)methyl]benzamide;
N-[2-(4-methoxyphenyl)ethyl]-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-(2-piperidin-1-ylethyl)benzamide;
N-(1-cyclohexylethyl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-(2-thienylmethyl)benzamide;
3-[(2'-oxospiro[furo[2,3-f][1,3]benzodioxole-7,3'-indol]-1'(2'H)-yl)methyl]-N-(4-propylphenyl)benzamide;
N-(2,4-difluorobenzyl)-3-[(2'-oxospiro[furo[2,3-f][1,3]benzodioxole-7,3'-indol]-1'(2'H)-yl)methyl]benzamide;
N-(3,5-difluorophenyl)-3-[(2'-oxospiro[furo[2,3-f][1,3]benzodioxole-7,3'-indol]-1'(2'H)-yl)methyl]benzamide;
N-(2,3-dihydro-1H-inden-5-yl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-[4-(trifluoromethyl)benzyl]benzamide;
3-[(2'-oxospiro[furo[2,3-f][1,3]benzodioxole-7,3'-indol]-1'(2'H)-yl)methyl]-N-[2-(2-thienyl)ethyl]benzamide;
3-[(2'-oxospiro[furo[2,3-f][1,3]benzodioxole-7,3'-indol]-1'(2'H)-yl)methyl]-N-(pyridin-3-ylmethyl)benzamide;
3-[(2'-oxospiro[furo[2,3-f][1,3]benzodioxole-7,3'-indol]-1'(2'H)-yl)methyl]-N-[2-(trifluoromethyl)benzyl]benzamide;
N-[2-(4-chlorophenyl)ethyl]-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-(2-pyrrolidin-1-ylethyl)benzamide;
N-(3-methylpyridin-2-yl)-3-[(2'-oxospiro[furo[2,3-f][1,3]benzodioxole-7,3'-indol]-1'(2'H)-yl)methyl]benzamide;
N-1,3-benzodioxol-5-yl-3-[(2'-oxospiro[furo[2,3-f][1,3]benzodioxole-7,3'-indol]-1'(2'H)-yl)methyl]benzamide;
N-(2-morpholin-4-ylethyl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-1,3-thiazol-2-ylbenzamide;
N-(6-methoxypyridin-3-yl)-3-[(2'-oxospiro[furo[2,3-f][1,3]benzodioxole-7,3'-indol]-1'(2'H)-yl)methyl]benzamide;
N-(3,5-dichlorobenzyl)-3-[(2'-oxospiro[furo[2,3-f][1,3]benzodioxole-7,3'-indol]-1'(2'H)-yl)methyl]benzamide;
N-1-naphthyl-3-[(2'-oxospiro[furo[2,3-f][1,3]benzodioxole-7,3'-indol]-1'(2'H)-yl)methyl]benzamide;
N-(4,6-dimethylpyridin-2-yl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-pyrimidin-4-ylbenzamide;
N-(5-methyl-1,3-thiazol-2-yl)-3-[(2'-oxospiro[furo[2,3-f][1,3]benzodioxole-7,3'-indol]-1'(2'H)-yl)methyl]benzamide;
N-(4-methylbenzyl)-3-[(2'-oxospiro[furo[2,3-f][1,3]benzodioxole-7,3'-indol]-1'(2'H)-yl)methyl]benzamide;
N-[3-(1H-imidazol-1-yl)propyl]-3-[(2'-oxospiro[furo[2,3-f][1,3]benzodioxole-7,3'-indol]-1'(2'H)-yl)methyl]benzamide;
N-(5-cyclopropyl-1,3,4-thiadiazol-2-yl)-3-[(2'-oxospiro[furo[2,3-f][1,3]benzodioxole-7,3'-indol]-1'(2'H)-yl)methyl]benzamide;
3-[(2'-oxospiro[furo[2,3-f][1,3]benzodioxole-7,3'-indol]-1'(2'H)-yl)methyl]-N-1,3,4-thiadiazol-2-ylbenzamide;
N-(4-morpholin-4-ylphenyl)-3-[(2'-oxospiro[furo[2,3-f][1,3]benzodioxole-7,3'-indol]-1'(2'H)-yl)methyl]benzamide;
N-[(1-ethylpyrrolidin-2-yl)methyl]-3-[(2'-oxospiro[furo[2,3-f][1,3]benzodioxole-7,3'-indol]-1'(2'H)-yl)methyl]benzamide;
N-(2,2-diphenylethyl)-3-[(2'-oxospiro[furo[2,3-f][1,3]benzodioxole-7,3'-indol]-1'(2'H)-yl)methyl]benzamide;
N-(3-fluorophenyl)-4-[(2'-oxospiro[furo[2,3-f][1,3]benzodioxole-7,3'-indol]-1'(2'H)-yl)methyl]benzamide;
N-(3-fluorobenzyl)-4-[(2'-oxospiro[furo[2,3-f][1,3]benzodioxole-7,3'-indol]-1'(2'H)-yl)methyl]benzamide;
N-(4-chlorobenzyl)-4-[(2'-oxospiro[furo[2,3-f][1,3]benzodioxole-7,3'-indol]-1'(2'H)-yl)methyl]benzamide;
N-(3-chlorophenyl)-4-[(2'-oxospiro[furo[2,3-f][1,3]benzodioxole-7,3'-indol]-1'(2'H)-yl)methyl]benzamide;
N-(2-fluorophenyl)-4-[(2'-oxospiro[furo[2,3-f][1,3]benzodioxole-7,3'-indol]-1'(2'H)-yl)methyl]benzamide;
N-(2-ethylphenyl)-4-[(2'-oxospiro[furo[2,3-f][1,3]benzodioxole-7,3'-indol]-1'(2'H)-yl)methyl]benzamide;
N-(4-ethylphenyl)-4-[(2'-oxospiro[furo[2,3-f][1,3]benzodioxole-7,3'-indol]-1'(2'H)-yl)methyl]benzamide;
N-(4-methylphenyl)-4-[(2'-oxospiro[furo[2,3-f][1,3]benzodioxole-7,3'-indol]-1'(2'H)-yl)methyl]benzamide;
N-(3,5-dimethylphenyl)-4-[(2'-oxospiro[furo[2,3-f][1,3]benzodioxole-7,3'-indol]-1'(2'H)-yl)methyl]benzamide;
N-(2,3-dimethylphenyl)-4-[(2'-oxospiro[furo[2,3-f][1,3]benzodioxole-7,3'-indol]-1'(2'H)-yl)methyl]benzamide;
N-cyclohexyl-4-[(2'-oxospiro[furo[2,3-f][1,3]benzodioxole-7,3'-indol]-1'(2'H)-yl)methyl]benzamide;
N-cyclopentyl-4-[(2'-oxospiro[furo[2,3-f][1,3]benzodioxole-7,3'-indol]-1'(2'H)-yl)methyl]benzamide;
N-(2-methoxybenzyl)-4-[(2'-oxospiro[furo[2,3-f][1,3]benzodioxole-7,3'-indol]-1'(2'H)-yl)methyl]benzamide;
N-(2,6-dimethylphenyl)-4-[(2'-oxospiro[furo[2,3-f][1,3]benzodioxole-7,3'-indol]-1'(2'H)-yl)methyl]benzamide;
N-(2-methoxyphenyl)-4-[(2'-oxospiro[furo[2,3-f][1,3]benzodioxole-7,3'-indol]-1'(2'H)-yl)methyl]benzamide;
N-cyclopropyl-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-phenylbenzamide;
N-(2,4-dimethylphenyl)-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-(tetrahydrofuran-2-ylmethyl)benzamide;
N,N-dibenzyl-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-[3-(trifluoromethyl)phenyl]benzamide;
N-(4-methoxybenzyl)-4-[(2'-oxospiro[furo[2,3-f][1,3]benzodioxole-7,3'-indol]-1'(2'H)-yl)methyl]benzamide;
N-(3,5-dichlorophenyl)-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-pyridin-3-ylbenzamide;
N-(4-cyanophenyl)-4-[(2'-oxospiro[furo[2,3-f][1,3]benzodioxole-7,3'-indol]-1'(2'H)-yl)methyl]benzamide;
4-[(2'-oxospiro[furo[2,3-f][1,3]benzodioxole-7,3'-indol]-1'(2'H)-yl)methyl]-N-(pyridin-4-ylmethyl)benzamide;

N-[2-(3-chlorophenyl)ethyl]-4-[(2'-oxospiro[furo[2,3-f][1,3]benzodioxole-7,3'-indol]-1'(2'H)-yl)methyl]benzamide;

N-(2-furylmethyl)-4-[(2'-oxospiro[furo[2,3-f][1,3]benzodioxole-7,3'-indol]-1'(2'H)-yl)methyl]benzamide;

N-(3-fluoro-2-methylphenyl)-4-[(2'-oxospiro[furo[2,3-f][1,3]benzodioxole-7,3'-indol]-1'(2'H)-yl)methyl]benzamide;

N-(cyclopropylmethyl)-4-[(2'-oxospiro[furo[2,3-f][1,3]benzodioxole-7,3'-indol]-1'(2'H)-yl)methyl]benzamide;

N-(4-methoxyphenyl)-4-[(2'-oxospiro[furo[2,3-f][1,3]benzodioxole-7,3'-indol]-1'(2'H)-yl)methyl]benzamide;

N-cyclobutyl-4-[(2'-oxospiro[furo[2,3-f][1,3]benzodioxole-7,3'-indol]-1'(2'H)-yl)methyl]benzamide;

N-(2,2-diphenylethyl)-4-[(2'-oxospiro[furo[2,3-f][1,3]benzodioxole-7,3'-indol]-1'(2'H)-yl)methyl]benzamide;

N-[2-(4-fluorophenyl)ethyl]-4-[(2'-oxospiro[furo[2,3-f][1,3]benzodioxole-7,3'-indol]-1'(2'H)-yl)methyl]benzamide;

N-(cyclohexylmethyl)-4-[(2'-oxospiro[furo[2,3-f][1,3]benzodioxole-7,3'-indol]-1'(2'H)-yl)methyl]benzamide;

N-(2-fluoro-4-methylphenyl)-4-[(2'-oxospiro[furo[2,3-f][1,3]benzodioxole-7,3'-indol]-1'(2'H)-yl)methyl]benzamide;

N-[2-(4-methylphenyl)ethyl]-4-[(2'-oxospiro[furo[2,3-f][1,3]benzodioxole-7,3'-indol]-1'(2'H)-yl)methyl]benzamide;

N-benzyl-4-[(2'-oxospiro[furo[2,3-f][1,3]benzodioxole-7,3'-indol]-1'(2'H)-yl)methyl]benzamide;

N-(2-methoxyethyl)-4-[(2'-oxospiro[furo[2,3-f][1,3]benzodioxole-7,3'-indol]-1'(2'H)-yl)methyl]benzamide;

1'-[4-(morpholin-4-ylcarbonyl)benzyl]spiro[furo[2,3-f][1,3]benzodioxole-7,3'-indol]-2'(1'H)-one;

N-(1-benzylpiperidin-4-yl)-4-[(2'-oxospiro[furo[2,3-f][1,3]benzodioxole-7,3'-indol]-1'(2'H)-yl)methyl]benzamide;

N-[2-(4-methoxyphenyl)ethyl]-4-[(2'-oxospiro[furo[2,3-f][1,3]benzodioxole-7,3'-indol]-1'(2'H)-yl)methyl]benzamide;

4-[(2'-oxospiro[furo[2,3-f][1,3]benzodioxole-7,3'-indol]-1'(2'H)-yl)methyl]-N-[2-(trifluoromethyl)phenyl]benzamide;

N-[4-chloro-2-(trifluoromethyl)phenyl]-4-[(2'-oxospiro[furo[2,3-f][1,3]benzodioxole-7,3'-indol]-1'(2'H)-yl)methyl]benzamide;

N-[4-fluoro-2-(trifluoromethyl)phenyl]-4-[(2'-oxospiro[furo[2,3-f][1,3]benzodioxole-7,3'-indol]-1'(2'H)-yl)methyl]benzamide;

N-[(1S)-1-cyclohexylethyl]-4-[(2'-oxospiro[furo[2,3-f][1,3]benzodioxole-7,3'-indol]-1'(2'H)-yl)methyl]benzamide;

N-[(1R)-1-cyclohexylethyl]-4-[(2'-oxospiro[furo[2,3-f][1,3]benzodioxole-7,3'-indol]-1'(2'H)-yl)methyl]benzamide;

N-(2,4-difluorophenyl)-4-[(2'-oxospiro[furo[2,3-f][1,3]benzodioxole-7,3'-indol]-1'(2'H)-yl)methyl]benzamide;

N-(2,3-dihydro-1H-inden-1-yl)-4-[(2'-oxospiro[furo[2,3-f][1,3]benzodioxole-7,3'-indol]-1'(2'H)-yl)methyl]benzamide;

4-[(2'-oxospiro[furo[2,3-f][1,3]benzodioxole-7,3'-indol]-1'(2'H)-yl)methyl]-N-(2-thienylmethyl)benzamide;

N-[(1-ethyl pyrrolidin-2-yl)methyl]-4-[(2'-oxospiro[furo[2,3-f][1,3]benzodioxole-7,3'-indol]-1'(2'H)-yl)methyl]benzamide;

4-[(2'-oxospiro[furo[2,3-f][1,3]benzodioxole-7,3'-indol]-1'(2'H)-yl)methyl]-N-(4-propylphenyl)benzamide;

N-(2,5-difluorobenzyl)-4-[(2'-oxospiro[furo[2,3-f][1,3]benzodioxole-7,3'-indol]-1'(2'H)-yl)methyl]benzamide;

N-(2,3-dihydro-1H-inden-5-yl)-4-[(2'-oxospiro[furo[2,3-f][1,3]benzodioxole-7,3'-indol]-1'(2'H)-yl)methyl]benzamide;

N-(2,5-difluorophenyl)-4-[(2'-oxospiro[furo[2,3-f][1,3]benzodioxole-7,3'-indol]-1'(2'H)-yl)methyl]benzamide;

4-[(2'-oxospiro[furo[2,3-f][1,3]benzodioxole-7,3'-indol]-1'(2'H)-yl)methyl]-N-[4-(trifluoromethyl)benzyl]benzamide;

4-[(2'-oxospiro[furo[2,3-f][1,3]benzodioxole-7,3'-indol]-1'(2'H)-yl)methyl]-N-[2-(2-thienyl)ethyl]benzamide;

4-[(2'-oxospiro[furo[2,3-f][1,3]benzodioxole-7,3'-indol]-1'(2'H)-yl)methyl]-N-(pyridin-3-ylmethyl)benzamide;

4-[(2'-oxospiro[furo[2,3-f][1,3]benzodioxole-7,3'-indol]-1'(2'H)-yl)methyl]-N-[2-(trifluoromethyl)benzyl]benzamide;

N-[2-(4-chlorophenyl)ethyl]-4-[(2'-oxospiro[furo[2,3-f][1,3]benzodioxole-7,3'-indol]-1'(2'H)-yl)methyl]benzamide;

4-[(2'-oxospiro[furo[2,3-f][1,3]benzodioxole-7,3'-indol]-1'(2'H)-yl)methyl]-N-(2-pyrrolidin-1-ylethyl)benzamide;

N-(3-methylpyridin-2-yl)-4-[(2'-oxospiro[furo[2,3-f][1,3]benzodioxole-7,3'-indol]-1'(2'H)-yl)methyl]benzamide;

N-1,3-benzodioxol-5-yl-4-[(2'-oxospiro[furo[2,3-f][1,3]benzodioxole-7,3'-indol]-1'(2'H)-yl)methyl]benzamide;

N-(2-morpholin-4-ylethyl)-4-[(2'-oxospiro[furo[2,3-f][1,3]benzodioxole-7,3'-indol]-1'(2'H)-yl)methyl]benzamide;

1'-{4-[(4-pyrimidin-2-ylpiperazin-1-yl)carbonyl]benzyl}spiro[furo[2,3-f][1,3]benzodioxole-7,3'-indol]-2'(1'H)-one;

4-[(2'-oxospiro[furo[2,3-f][1,3]benzodioxole-7,3'-indol]-1'(2'H)-yl)methyl]-N-1,3-thiazol-2-ylbenzamide;

N-(6-methoxypyridin-3-yl)-4-[(2'-oxospiro[furo[2,3-f][1,3]benzodioxole-7,3'-indol]-1'(2'H)-yl)methyl]benzamide;

N-(3,5-dichlorobenzyl)-4-[(2'-oxospiro[furo[2,3-f][1,3]benzodioxole-7,3'-indol]-1'(2'H)-yl)methyl]benzamide;

N-1-naphthyl-4-[(2'-oxospiro[furo[2,3-f][1,3]benzodioxole-7,3'-indol]-1'(2'H)-yl)methyl]benzamide;

1'-(4-{[4-(1,3-benzodioxol-5-ylmethyl)piperazin-1-yl]carbonyl}benzyl)spiro[furo[2,3-f][1,3]benzodioxole-7,3'-indol]-2'(1'H)-one;

N-(4,6-dimethylpyridin-2-yl)-4-[(2'-oxospiro[furo[2,3-f][1,3]benzodioxole-7,3'-indol]-1'(2'H)-yl)methyl]benzamide;

4-[(2'-oxospiro[furo[2,3-f][1,3]benzodioxole-7,3'-indol]-1'(2'H)-yl)methyl]-N-pyrimidin-4-ylbenzamide;

N-(5-methyl-1,3-thiazol-2-yl)-4-[(2'-oxospiro[furo[2,3-f][1,3]benzodioxole-7,3'-indol]-1'(2'H)-yl)methyl]benzamide;

N-(2-cyano-6-fluorophenyl)-4-[(2'-oxospiro[furo[2,3-f][1,3]benzodioxole-7,3'-indol]-1'(2'H)-yl)methyl]benzamide;

N-(4-methylbenzyl)-4-[(2'-oxospiro[furo[2,3-f][1,3]benzodioxole-7,3'-indol]-1'(2'H)-yl)methyl]benzamide;

N-[3-(1H-imidazol-1-yl)propyl]-4-[(2'-oxospiro[furo[2,3-f][1,3]benzodioxole-7,3'-indol]-1'(2'H)-yl)methyl]benzamide;

N-(4-morpholin-4-ylphenyl)-4-[(2'-oxospiro[furo[2,3-f][1,3]benzodioxole-7,3'-indol]-1'(2'H)-yl)methyl]benzamide;

1-{4-[(4-methylpiperazin-1-yl)carbonyl]benzyl}spiro[furo[2,3-f][1,3]benzodioxole-7,3'-indol]-2'(1'H)one; and N-(5-cyclopropyl-1,3,4-thiadiazol-2-yl)-4-[(2'-oxospiro[furo[2,3-f][1,3]benzodioxole-7,3'-indol]-1'(2'H)-yl)methyl]benzamide.

Another embodiment of the invention are the compounds of formula (I) as set forth above in the Summary of the invention wherein:

at least one of j and k is 1 and the other is 0 or 1;

Q is —O—;

$R^1$ is aralkyl optionally substituted by one or more substituents selected from the group consisting of —$R^8$—$OR^5$, —C(O)$OR^5$, halo, haloalkyl, alkyl, nitro, cyano, aryl, aralkyl, heterocyclyl and heteroaryl;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_mR^4$, —$S(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C(=NR^5)N(R^4)R^5$, and —$N(R^5)C(=N-CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —$S(O)_mR^4$, —$R^8$—$S(O)_nN(R^4)R^5$, —$R^8$—$C(O)R^4$, —$R^8$—$C(O)OR^4$, —$R^8$—$C(O)N(R^4)R^5$, —$N(R^5)C(O)R^4$, and —$N(R^5)S(O)_nR^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_mR^4$, —$S(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl optionally substituted by one or more substituents selected from the group consisting of —$R^8$—$OR^5$, —$C(O)OR^5$, halo, haloalkyl, alkyl, nitro, cyano, aryl, aralkyl, heterocyclyl and heteroaryl;

$R^{2a}$, $R^{2b}$, $R^{2c}$ and $R^{2d}$ are each independently selected from hydrogen, alkyl or halo;

$R^{3a}$, $R^{3b}$, $R^{2c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, $OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)N(R^4)R^5$, —$N(R^5)C(=NR^5)N(R^4)R^5$, $N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each $R^8$ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl optionally substituted by one or more substituents selected from the group consisting of —$R^8$—$OR^5$, —$C(O)OR^5$, halo, haloalkyl, alkyl, nitro, cyano, aryl, aralkyl, heterocyclyl and heteroaryl;

R$^{2a}$, R$^{2b}$, R$^{2c}$ and R$^{2d}$ are each independently selected from hydrogen, alkyl or halo;

R$^{3a}$, R$^{3b}$, R$^{3c}$ and R$^{3d}$ are each independently selected from the group consisting of hydrogen, halo, and —R$^8$—OR$^5$;

or R$^{3b}$ and R$^{3c}$, together with the carbon ring atoms to which they are directly attached, form a fused ring selected from cycloalkyl, dioxolyl, tetrahydrofuranyl, and heteroaryl, and R$^{3a}$ and R$^{3d}$ are each hydrogen;

each R$^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each R$^8$ is a direct bond or a straight or branched alkylene chain, a straight or branched alkenylene chain or a straight or branched alkynylene chain.

Another embodiment of the invention are the compounds of formula (I) as set forth above in the Summary of the invention, selected from the group consisting of:

methyl 2-[(2'-oxospiro[furo[2,3-f][1,3]benzodioxole-7,3'-indol]-1'(2'H)-yl)methyl]benzoate;
methyl 3-[(2'-oxospiro[furo[2,3-f][1,3]benzodioxole-7,3'-indol]-1'(2'H)-yl)methyl]benzoate;
methyl 4-[(2'-oxospiro[furo[2,3-f][1,3]benzodioxole-7,3'-indol]-1'(2'H)-yl)methyl]benzoate;
1'-(diphenylmethyl)spiro[furo[2,3-f][1,3]benzodioxole-7,3'-indol]-2'(1'H)-one;
1-(diphenylmethyl)-5'-methylspiro[furo[2,3-f][1,3]benzodioxole-7,3'-indol]-2'(1'H)-one;
2-[(2'-oxospiro[furo[2,3-f][1,3]benzodioxole-7,3'-indol]-1'(2'H)-yl)methyl]benzoic acid;
3-[(2'-oxospiro[furo[2,3-f][1,3]benzodioxole-7,3'-indol]-1'(2'H)-yl)methyl]benzoic acid;
1'-(4-fluorobenzyl)spiro[furo[2,3-f][1,3]benzodioxole-7,3'-indol]-2'(1'H)-one;
1'-benzylspiro[furo[2,3-f][1,3]benzodioxole-7,3'-indol]-2'(1'H)-one;
1'-(3,5-difluorobenzyl)spiro[furo[2,3-f][1,3]benzodioxole-7,3'-indol]-2'(1'H)-one;
1-(3-nitrobenzyl)spiro[furo[2,3-f][1,3]benzodioxole-7,3'-indol]-2'(1'H)-one;
1'-(3-fluorobenzyl)spiro[furo[2,3-f][1,3]benzodioxole-7,3'-indol]-2'(1'H)-one;
3-[(2'-oxospiro[furo[2,3-f][1,3]benzodioxole-7,3'-indol]-1'(2'H)-yl)methyl]benzonitrile;
1'-[4-(1H-pyrazol-1-yl)benzyl]spiro[furo[2,3-f][1,3]benzodioxole-7,3'-indol]-2'(1'H)-one;
1'-(biphenyl-4-ylmethyl)spiro[furo[2,3-f][1,3]benzodioxole-7,3'-indol]-2'(1'H)-one;
4'-[(2'-oxospiro[furo[2,3-f][1,3]benzodioxole-7,3'-indol]-1'(2'H)-yl)methyl]biphenyl-2-carbonitrile;
1'-(biphenyl-2-ylmethyl)spiro[furo[2,3-f][1,3]benzodioxole-7,3'-indol]-2'(1'H)-one;
1'-(diphenylmethyl)spiro[furo[2,3-f][1,3]benzodioxole-7,3'-indol]-2'(1'H)-one;
1-(4-fluoro-3-methylbenzyl)spiro[furo[2,3-f][1,3]benzodioxole-7,3'-indol]-2'(1H)-one;
1'-(5-fluoro-2-methylbenzyl)spiro[furo[2,3-f][1,3]benzodioxole-7,3'-indol]-2'(1'H)-one;
1'-(2,5-difluorobenzyl)spiro[furo[2,3-f][1,3]benzodioxole-7,3'-indol]-2'(1'H)-one;
1'-[4-(1H-pyrrol-1-yl)benzyl]spiro[furo[2,3-f][1,3]benzodioxole-7,3'-indol]-2'(1'H)-one;
1'-[3-(1H-pyrrol-1-yl)benzyl]spiro[furo[2,3-f][1,3]benzodioxole-7,3'-indol]-2'(1'H)-one;
1-[(4-chlorophenoxy)methyl]spiro[furo[2,3-f][1,3]benzodioxole-7,3'-indol]-2'(1'H)-one;
1'-[2-fluoro-3-(trifluoromethyl)benzyl]spiro[furo[2,3-f][1,3]benzodioxole-7,3'-indol]-2'(1'H)-one;
1'-[2-fluoro-6-(trifluoromethyl)benzyl]spiro[furo[2,3-f][1,3]benzodioxole-7,3'-indol]-2'(1'H)-one;
1'-[3-fluoro-4-(trifluoromethyl)benzyl]spiro[furo[2,3-f][1,3]benzodioxole-7,3'-indol]-2'(1'H)-one;
1'-[4-fluoro-3-(trifluoromethyl)benzyl]spiro[furo[2,3-f][1,3]benzodioxole-7,3'-indol]-2'(1'H)-one;
1'-[2-fluoro-5-(trifluoromethyl)benzyl]spiro[furo[2,3-f][1,3]benzodioxole-7,3'-indol]-2'(1'H)-one;
1'-[4-fluoro-2-(trifluoromethyl)benzyl]spiro[furo[2,3-f][1,3]benzodioxole-7,3'-indol]-2'(1'H)-one;
1'-[5-fluoro-2-(trifluoromethyl)benzyl]spiro[furo[2,3-f][1,3]benzodioxole-7,3'-indol]-2'(1'H)-one;
1'-[2-fluoro-4-(trifluoromethyl)benzyl]spiro[furo[2,3-f][1,3]benzodioxole-7,3'-indol]-2'(1'H)-one;
1'-(2,3-difluorobenzyl)spiro[furo[2,3-f][1,3]benzodioxole-7,3'-indol]-2'(1'H)-one;
1'-[(1-bromo-2-naphthyl)methyl]spiro[furo[2,3-f][1,3]benzodioxole-7,3'-indol]-2'(1'H)-one;
1-(1-naphthylmethyl)spiro[furo[2,3-f][1,3]benzodioxole-7,3'-indol]-2'(1'H)-one;
1'-[3-fluoro-5-(trifluoromethyl)benzyl]spiro[furo[2,3-f][1,3]benzodioxole-7,3'-indol]-2'(1'H)-one;
1'-(2,4-difluorobenzyl)spiro[furo[2,3-f][1,3]benzodioxole-7,3'-indol]-2'(1'H)-one;
1-(2,6-difluorobenzyl)spiro[furo[2,3-f][1,3]benzodioxole-7,3'-indol]-2'(1'H)-one;
1-(3-methoxybenzyl)spiro[furo[2,3-f][1,3]benzodioxole-7,3'-indol]-2'(1'H)-one;
1'-[4-(1H-1,2,4-triazol-1-yl)benzyl]spiro[furo[2,3-f][1,3]benzodioxole-7,3'-indol]-2'(1'H)-one;
1'-[4,4-bis(4-fluorophenyl)butyl]spiro[furo[2,3-f][1,3]benzodioxole-7,3'-indol]-2'(1'H)-one;
1'-(2-chloro-4-fluorobenzyl)spiro[furo[2,3-f][1,3]benzodioxole-7,3'-indol]-2'(1'H)-one;
1'-[2-(trifluoromethoxy)benzyl]spiro[furo[2,3-f][1,3]benzodioxole-7,3'-indol]-2'(1'H)-one;
1'-[3-(trifluoromethoxy)benzyl]spiro[furo[2,3-f][1,3]benzodioxole-7,3'-indol]-2'(1'H)-one;
1'[4-(trifluoromethoxy)benzyl]spiro[furo[2,3-f][1,3]benzodioxole-7,3'-indol]-2'(1'H)-one;
1'-(2,3-difluorobenzyl)-5,6-dihydrospyro[benzo[1,2-b:5,4-b']difuran-3,3'-indol]2'(1'H)-one;
1'-(4-methoxybenzyl)-5,6-dihydrospiro[benzo[1,2-b:5,4-b']difuran-3,3'-indol]2'(1'H)-one;
4-[(2'-oxospiro[furo[2,3-f][1,3]benzodioxole-7,3'-indol]-1'(2'H)-yl)methyl]benzoic acid;
5-bromo-1-(diphenylmethyl)spiro[1-benzofuran-3,3'-indol]-2'(1'H)-one;
1-(diphenylmethyl)-6-(trifluoromethoxy)spiro[1-benzofuran-3,3'-indol]-2'(1'H)-one;
1'-(4-methoxybenzyl)-6-(trifluoromethoxy)spiro[1-benzofuran-3,3'-indol]-2'(1'H)-one;
1'-(diphenylmethyl)-5-hydroxyspiro[1-benzofuran-3,3'-indol]-2'(1'H)-one;
1-(diphenylmethyl)-5-pyridin-3-ylspiro[1-benzofuran-3,3'-indol]-2'(1'H)-one;
1-(diphenylmethyl)-5,5-dimethyl-5,6-dihydrospiro[benzo[1,2-b:5,4-b']difuran-3,3'-indol]-2'(1'H)-one;
2-methyl-1-pentylspiro[furo[2,3-f][1,3]benzothiazole-7,3'-indol]-2'(1'H)-one;
1'-(diphenylmethyl)-6,7-dihydrospiro[benzo[1,2-b:4,5-b']difuran-3,3'-indol]-2'(1'H)-one; and
1'-(diphenylmethyl)-5,6-dihydrospiro[benzo[1,2-b:5,4-b']difuran-3,3'-indol]-2'(1'H)-one.

Another embodiment of the invention are the compounds of formula (I) as set forth above in the Summary of the invention wherein:

at least one of j and k is 1 and the other is 0 or 1;

Q is —O—;

$R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;

$R^{12}$ is hydrogen, alkyl, aryl, aralkyl or —C(O)$R^5$;

and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —S(O)$_2$CF$_3$, —$R^8$—C(O)$R^4$, —C(S)$R^4$, —C($R^4$)$_2$C(O)$R^5$, —$R^5$—C(O)O$R^4$, —C(S)O$R^4$, —$R^5$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^8$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is —$R^9$—N($R^{19}$)$R^{11}$, —$R^9$—N($R^{12}$)C(O)$R^{11}$ or —$R^9$—N($R^{10}$)C(O)N($R^{10}$)$R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;

$R^{12}$ is hydrogen, alkyl, aryl, aralkyl or —C(O)$R^5$;

and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused ring selected from cycloalkyl, heterocyclyl, aryl or heteroaryl;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is —$R^9$—N($R^{10}$)$R^{11}$ where:
  each $R^{10}$ is hydrogen, alkyl, aryl, aralkyl or heteroaryl;
  each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;
  and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused dioxolyl ring;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

1'-[2-(diethylamino)ethyl]spiro[furo[2,3-f][1,3]benzodioxole-7,3'-indol]-2'(1'H)-one;

1'-[2-(pyridin-2-ylamino)ethyl]spiro[furo[2,3-f][1,3]benzodioxole-7,3'-indol]-2'(1'H)-one;

1'-[2-(dipyridin-2-ylamino)ethyl]spiro[furo[2,3-f][1,3]benzodioxole-7,3'-indol]-2'(1'H)-one;

1'-{3-[(cyclopropylmethyl)amino]propyl}spiro[furo[2,3-f][1,3]benzodioxole-7,3'-indol]-2'(1'H)-one;

1'-{3-[(4-fluorobenzyl)amino]propyl}spiro[furo[2,3-f][1,3]benzodioxole-7,3'-indol]-2'(1'H)-one;

1'-{3-[(4-chlorophenyl)amino]propyl}spiro[furo[2,3-f][1,3]benzodioxole-7,3'-indol]-2'(1'H)-one;

1'-[3-(pentylamino)propyl]spiro[furo[2,3-f][1,3]benzodioxole-7,3'-indol]-2'(1'H)-one;

1'-{3-[(2-ethoxyethyl)amino]propyl}spiro[furo[2,3-f][1,3]benzodioxole-7,3'-indol]-2'(1'H)-one;

1'-{3-[(3-methoxypropyl)amino]propyl}spiro[furo[2,3-f][1,3]benzodioxole-7,3'-indol]-2'(1'H)-one;

1'-{3-[(3-methylbutyl)amino]propyl}spiro[furo[2,3-f][1,3]benzodioxole-7,3'-indol]-2'(1'H)-one;

1'-{3-[(3-ethoxypropyl)amino]propyl}spiro[furo[2,3-f][1,3]benzodioxole-7,3'-indol]-2'(1'H)-one;

1'-{3-[(2,2-dimethylpropyl)amino]propyl}spiro[furo[2,3-f][1,3]benzodioxole-7,3'-indol]-2'(1'H)-one;

3-{[3-(2'-oxospiro[furo[2,3-f][1,3]benzodioxole-7,3'-indol]-1'(2'H)-yl)propyl]amino}propanenitrile;

1'-{3-[(2,2,2-trifluoroethyl)amino]propyl}spiro[furo[2,3-f][1,3]benzodioxole-7,3'-indol]-2'(1'H)-one;

1'-[3-(cyclopropylamino)propyl]spiro[furo[2,3-f][1,3]benzodioxole-7,3'-indol]-2'(1'H)-one;

1'-[3-(cyclobutylamino)propyl]spiro[furo[2,3-f][1,3]benzodioxole-7,3'-indol]-2'(1'H)-one;

1'-{3-[(2-cyclopropylethyl)amino]propyl}spiro[furo[2,3-f][1,3]benzodioxole-7,3'-indol]-2'(1'H)-one;

1'-[3-(isobutylamino)propyl]spiro[furo[2,3-f][1,3]benzodioxole-7,3'-indol]-2'(1'H)-one;

1'-[3-(hexylamino)propyl]spiro[furo[2,3-f][1,3]benzodioxole-7,3'-indol]-2'(1'H)-one;

1'-[3-(heptylamino)propyl]spiro[furo[2,3-f][1,3]benzodioxole-7,3'-indol]-2'(1'H)-one;

1'-[3-(isopropylamino)propyl]spiro[furo[2,3-f][1,3]benzodioxole-7,3'-indol]-2'(1'H)-one;

1'-{3-[(tetrahydrofuran-2-ylmethyl)amino]propyl}spiro[furo[2,3-f][1,3]benzodioxole-7,3'-indol]-2'(1'H)-one;

1'-[3-(benzylamino)propyl]spiro[furo[2,3-f][1,3]benzodioxole-7,3'-indol]-2'(1'H)-one;

1'-{3-[(2-phenylethyl)amino]propyl}spiro[furo[2,3-f][1,3]benzodioxole-7,3'-indol]-2'(1'H)-one;

1'-[3-(dibenzylamino)propyl]spiro[furo[2,3-f][1,3]benzodioxole-7,3'-indol]-2'(1'H)-one;

1'-[3-(propylamino)propyl]spiro[furo[2,3-f][1,3]benzodioxole-7,3'-indol]-2'(1'H)-one;

1'-(3-{[2-(3-fluorophenyl)ethyl]amino}propyl)spiro[furo[2,3-f][1,3]benzodioxole-7,3'-indol]-2'(1'H)-one;

1'-{3-[(3-phenylpropyl)amino]propyl}spiro[furo[2,3-f][1,3]benzodioxole-7,3'-indol]-2'(1'H)-one;

1'-{3-[(2,2-diphenylethyl)amino]propyl}spiro[furo[2,3-f][1,3]benzodioxole-7,3'-indol]-2'(1'H)-one;

1'-(3-{[2-(4-methylphenyl)ethyl]amino}propyl)spiro[furo[2,3-f][1,3]benzodioxole-7,3'-indol]-2'(1'H)-one;

1'-(3-{[2-(3-chlorophenyl)ethyl]amino}propyl)spiro[furo[2,3-f][1,3]benzodioxole-7,3'-indol]-2'(1'H)-one;

1'-{3-[(2-pyridin-4-ylethyl)amino]propyl}spiro[furo[2,3-f][1,3]benzodioxole-7,3'-indol]-2'(1'H)-one;

1'-{3-[(pyridin-4-ylmethyl)amino]propyl}spiro[furo[2,3-f][1,3]benzodioxole-7,3'-indol]-2'(1'H)-one;

1'-(3-{[2-(4-fluorophenyl)ethyl]amino}propyl)spiro[furo[2,3-f][1,3]benzodioxole-7,3'-indol]-2'(1'H)-one;

1'-{3-[(pyridin-2-ylmethyl)amino]propyl}spiro[furo[2,3-f][1,3]benzodioxole-7,3'-indol]-2'(1'H)-one;

1'-(3-{[(1R)-1-cyclohexylethyl]amino}propyl)spiro[furo[2,3-f][1,3]benzodioxole-7,3'-indol]-2'(1'H)-one;

1'-{3-[(2-furylmethyl)amino]propyl}spiro[furo[2,3-f][1,3]benzodioxole-7,3'-indol]-2'(1'H)-one;

1-{3-[(4-chlorobenzyl)amino]propyl}spiro[furo[2,3-f][1,3]benzodioxole-7,3'-indol]-2'(1'H)-one;

1'-{3-[(4-methoxybenzyl)amino]propyl}spiro[furo[2,3-f][1,3]benzodioxole-7,3'-indol]-2'(1'H)-one;

1'-{3-[(3-isopropoxypropyl)amino]propyl}spiro[furo[2,3-f][1,3]benzodioxole-7,3'-indol]2'(1'H)-one;

1'-(3-{[2-(2-fluorophenyl)ethyl]amino}propyl)spiro[furo[2,3-f][1,3]benzodioxole-7,3'-indol]-2'(1'H)-one;

1'-{3-[(3,3-dimethylbutyl)amino]propyl}spiro[furo[2,3-f][1,3]benzodioxole-7,3'-indol]-2'(1'H)-one;
1'-{3-[(cyclohexylmethyl)amino]propyl}spiro[furo[2,3-f][1,3]benzodioxole-7,3'-indol]-2'(1'H)-one;
1'-(3-{[(1S)-1-cyclohexylethyl]amino}propyl)spiro[furo[2,3-f][1,3]benzodioxole-7,3'-indol]-2'(1'H)-one;
1'-{3-[(2-piperidin-1-ylethyl)amino]propyl}spiro[furo[2,3-f][1,3]benzodioxole-7,3'-indol]-2'(1'H)-one;
1'-{3-[(2-pyrrolidin-1-ylethyl)amino]propyl}spiro[furo[2,3-f][1,3]benzodioxole-7,3'-indol]-2'(1'H)-one;
1-{3-[(2-morpholin-4-ylethyl)amino]propyl}spiro[furo[2,3-f][1,3]benzodioxole-7,3'-indol]-2'(1'H)-one;
1'-[3-(cyclohexylamino)propyl]spiro[furo[2,3-f][1,3]benzodioxole-7,3'-indol]-2'(1'H)-one;
1'-[3-(cyclopentylamino)propyl]spiro[furo[2,3-f][1,3]benzodioxole-7,3'-indol]-2'(1'H)-one;
1-{3-[(2-chlorobenzyl)amino]propyl}spiro[furo[2,3-f][1,3]benzodioxole-7,3'-indol]-2'(1'H)-one;
1'-[3-(dibutylamino)propyl]spiro[furo[2,3-f][1,3]benzodioxole-7,3'-indol]-2'(1'H)-one;
1'-[3-(dipropylamino)propyl]spiro[furo[2,3-f][1,3]benzodioxole-7,3'-indol]-2'(1'H)-one;
1'-(3-{[2-(dimethylamino)ethyl]amino}propyl)spiro[furo[2,3-f][1,3]benzodioxole-7,3'-indol]-2'(1'H)-one;
1'-(3-{[2-(diethylamino)ethyl](methyl)amino}propyl)spiro[furo[2,3-f][1,3]benzodioxole-7,3'-indol]-2'(1'H)one;
1'-(3-{[2-(diisopropylamino)ethyl]amino}propyl)spiro[furo[2,3-f][1,3]benzodioxole-7,3'-indol]-2'(1'H)-one;
1-[3-(diisopropylamino)propyl]spiro[furo[2,3-f][1,3]benzodioxole-7,3'-indol]-2'(1'H)-one;
1'-[3-(methylamino)propyl]spiro[furo[2,3-f][1,3]benzodioxole-7,3'-indol]-2'(1'H)-one;
1'-[3-(ethylamino)propyl]spiro[furo[2,3-f][1,3]benzodioxole-7,3'-indol]-2'(1'H)-one;
1'-{3-[bis(2-methoxyethyl)amino]propyl}spiro[furo[2,3-f][1,3]benzodioxole-7,3'-indol]-2'(1'H)-one;
1-{3-[(2-fluorobenzyl)amino]propyl}spiro[furo[2,3-f][1,3]benzodioxole-7,3'-indol]-2'(1'H)-one;
1'-{3-[(3,5-difluorobenzyl)amino]propyl}spiro[furo[2,3-f][1,3]benzodioxole-7,3'-indol]-2'(1'H)-one;
1'-(3-{[3-(dimethylamino)propyl]amino}propyl)spiro[furo[2,3-f][1,3]benzodioxole-7,3'-indol]-2'(1'H)-one;
1'-[3-(diethylamino)propyl]spiro[furo[2,3-f][1,3]benzodioxole-7,3'-indol]-2'(1'H)-one;
1'-[3-(octylamino)propyl]spiro[furo[2,3-f][1,3]benzodioxole-7,3'-indol]-2'(1'H)-one;
1'-{3-[(1-methylbutyl)amino]propyl}spiro[furo[2,3-f][1,3]benzodioxole-7,3'-indol]-2'(1'H)-one;
1'-{3-[butyl(methyl)amino]propyl}spiro[furo[2,3-f][1,3]benzodioxole-7,3'-indol]-2'(1'H)-one;
1'-{3-[(2-isopropoxyethyl)amino]propyl}spiro[furo[2,3-f][1,3]benzodioxole-7,3'-indol]-2'(1'H)-one;
1-{3-[(2,4-difluorobenzyl)amino]propyl}spiro[furo[2,3-f][1,3]benzodioxole-7,3'-indol]-2'(1'H)-one;
1'-{3-[(2-methylbenzyl)amino]propyl}spiro[furo[2,3-f][1,3]-benzodioxole-7,3'-indol]-2'(1'H)-one;
1'-{3-[(3-fluorobenzyl)amino]propyl}spiro[furo[2,3-f][1,3]benzodioxole-7,3'-indol]-2'(1'H)-one;
1'-{3-[(2,6-difluorobenzyl)amino]propyl}spiro[furo[2,3-f][1,3]benzodioxole-7,3'-indol]-2'(1'H)-one;
1-{3-[(1,2-dimethylpropyl)amino]propyl}spiro[furo[2,3-f][1,3]benzodioxole-7,3'-indol]-2'(1'H)-one;
1'-(3-{[2-(1-methylpyrrolidin-2-yl)ethyl]amino}propyl)spiro[furo[2,3-f][1,3]benzodioxole-7,3'-indol]-2'(1'H)-one;
1'-{3-[(2-pyridin-3-ylethyl)amino]propyl}spiro[furo[2,3-f][1,3]benzodioxole-7,3'-indol]-2'(1'H)-one;
1'-{3-[(1-methyl-2-phenylethyl)amino]propyl}spiro[furo[2,3-f][1,3]benzodioxole-7,3'-indol]-2'(1'H)-one;
1'-(3-{[2-(2-chlorophenyl)ethyl]amino}propyl)spiro[furo[2,3-f][1,3]benzodioxole-7,3'-indol]-2'(1'H)-one;
1'-{3-[(2-cyclohexylethyl)amino]propyl}spiro[furo[2,3-f][1,3]benzodioxole-7,3'-indol]-2'(1'H)-one;
1'-{3-[(2-pyridin-2-ylethyl)amino]propyl}spiro[furo[2,3-f][1,3]benzodioxole-7,3'-indol]-2'(1'H)-one;
1'-{3-[(2-biphenyl-4-ylethyl)amino]propyl}spiro[furo[2,3-f][1,3]benzodioxole-7,3'-indol]-2'(1'H)-one;
1'-{3-[(3-morpholin-4-ylpropyl)amino]propyl}spiro[furo[2,3-f][1,3]benzodioxole-7,3'-indol]-2'(1'H)-one;
1'-(3-{[(5-methyl-2-furyl)methyl]amino}propyl)spiro[furo[2,3-f][1,3]benzodioxole-7,3'-indol]-2'(1'H)-one;
1'-{3-[(3-methylbenzyl)amino]propyl}spiro[furo[2,3-f][1,3]benzodioxole-7,3'-indol]-2'(1'H)-one;
1-(3-aminopropyl)spiro[furo[2,3-f][1,3]benzodioxole-7,3'-indol]-2'(1'H)-one; and
1'-(2-aminoethyl)spiro[furo[2,3-f][1,3]benzodioxole-7,3'-indol]-2'(1'H)-one.

Another embodiment of the invention are the compounds of formula (I) as set forth above in the Summary of the invention wherein:
j is 0 and k is 1;
Q is —O—;
$R^1$ is —$R^9$—N($R^{12}$)C(O)$R^{11}$ where:
each $R^{10}$ is hydrogen, alkyl, aryl, aralkyl or heteroaryl;
each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;
$R^{12}$ is hydrogen, alkyl, aryl, aralkyl or —C(O)$R^5$; and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
$R^{2a}$, $R^{2b}$, $R^{2c}$ and $R^{2d}$ are each hydrogen;
$R^{2a}$ and $R^{3d}$ are each hydrogen;
$R^{3b}$ and $R^{3c}$, together with the carbon ring atoms to which they are directly attached, form a fused dioxolyl ring;
each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl; and
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:
1'-(3-aminopropyl)spiro[furo[2,3-f][1,3]benzodioxole-7,3'-indol]-2'(1'H)-one;
3-chloro-N-[3-(2'-oxospiro[furo[2,3-f][1,3]benzodioxole-7,3'-indol]-1'(2'H)-yl)propyl]thiophene-2-carboxamide;
N-[3-(2'-oxospiro[furo[2,3-f][1,3]benzodioxole-7,3'-indol]-1'(2'H)-yl)propyl]cyclopropanecarboxamide;

N-[3-(2'-oxospiro[furo[2,3-f][1,3]benzodioxole-7,3'-indol]-1'(2'H)-yl)propyl]cyclobutanecarboxamide;
2-chloro-N-[3-(2'-oxospiro[furo[2,3-f][1,3]benzodioxole-7,3'-indol]-1'(2'N)-yl)propyl]nicotinamide;
N-[3-(2'-oxospiro[furo[2,3-f][1,3]benzodioxole-7,3'-indol]-1'(2'N)-yl)propyl]cyclopentanecarboxamide;
2,2-dimethyl-N-[3-(2'-oxospiro[furo[2,3-f][1,3]benzodioxole-7,3'-indol]-1'(2'H)-yl)propyl]propanamide;
2-(4-methoxyphenyl)-N-[3-(2'-oxospiro[furo[2,3-f][1,3]benzodioxole-7,3'-indol]-1'(2'H)-yl)propyl]acetamide;
4-tert-butyl-N-[3-(2'-oxospiro[furo[2,3-f][1,3]benzodioxole-7,3'-indol]-1'(2'H)-yl)propyl]benzamide;
3,3-dimethyl-N-[3-(2'-oxospiro[furo[2,3-f][1,3]benzodioxole-7,3'-indol]-1'(2'H)-yl)propyl]butanamide;
N-[3-(2'-oxospiro[furo[2,3-f][1,3]benzodioxole-7,3'-indol]-1'(2'H)-yl)propyl]biphenyl-4-carboxamide;
3-methyl-N-[3-(2'-oxospiro[furo[2,3-f][1,3]benzodioxole-7,3'-indol]-1'(2'H)-yl)propyl]-1-benzofuran-2-carboxamide;
2-(benzyloxy)-N-[3-(2'-oxospiro[furo[2,3-f][1,3]benzodioxole-7,3'-indol]-1'(2'H)-yl)propyl]acetamide;
N-[3-(2'-oxospiro[furo[2,3-f][1,3]benzodioxole-7,3'-indol]-1'(2'H)-yl)propyl]-2-furamide;
N-[3-(2'-oxospiro[furo[2,3-f][1,3]benzodioxole-7,3'-indol]-1'(2'H)-yl)propyl]-1,3-benzodioxole-5-carboxamide;
N-[3-(2'-oxospiro[furo[2,3-f][1,3]benzodioxole-7,3'-indol]-1'(2'H)-yl)propyl]quinoline-2-carboxamide;
N-[3-(2'-oxospiro[furo[2,3-f][1,3]benzodioxole-7,3'-indol]-1'(2'H)-yl)propyl]-2-phenylacetamide;
N-[3-(2'-oxospiro[furo[2,3-f][1,3]benzodioxole-7,3'-indol]-1'(2'H)-yl)propyl]piperidine-1-carboxamide;
2-methoxy-N-[3-(2'-oxospiro[furo[2,3-f][1,3]benzodioxole-7,3'-indol]-1'(2'H)-yl)propyl]acetamide;
4-(dimethylamino)-N-[3-(2'-oxospiro[furo[2,3-f][1,3]benzodioxole-7,3'-indol]-1'(2'H)-yl)propyl]benzamide;
4-ethoxy-N-[3-(2'-oxospiro[furo[2,3-f][1,3]benzodioxole-7,3'-indol]-1'(2'H)-yl)propyl]benzamide;
2-methyl-N-[3-(2'-oxospiro[furo[2,3-f][1,3]benzodioxole-7,3'-indol]-1'(2'H)-yl)propyl]butanamide;
N-[3-(2'-oxospiro[furo[2,3-f][1,3]benzodioxole-7,3'-indol]-1'(2'H)-yl)propyl]-2-phenoxyacetamide;
N-[3-(2'-oxospiro[furo[2,3-f][1,3]benzodioxole-7,3'-indol]-1'(2'H)-yl)propyl]quinoxaline-2-carboxamide;
N-[3-(2'-oxospiro[furo[2,3-f][1,3]benzodioxole-7,3'-indol]-1'(2'H)-yl)propyl]cyclohexanecarboxamide;
4-fluoro-N-[3-(2'-oxospiro[furo[2,3-f][1,3]benzodioxole-7,3'-indol]-1'(2'H)-yl)propyl]benzamide;
2-ethyl-N-[3-(2'-oxospiro[furo[2,3-f][1,3]benzodioxole-7,3'-indol]-1'(2'H)-yl)propyl]butanamide;
2-(4-fluorophenyl)-N-[3-(2'-oxospiro[furo[2,3-f][1,3]benzodioxole-7,3'-indol]-1'(2'H)-yl)propyl]acetamide;
6-chloro-N-[3-(2'-oxospiro[furo[2,3-f][1,3]benzodioxole-7,3'-indol]-1'(2'H)-yl)propyl]nicotinamide;
2-fluoro-N-[3-(2'-oxospiro[furo[2,3-f][1,3]benzodioxole-7,3'-indol]-1'(2'H)-yl)propyl]benzamide;
N-[3-(2'-oxospiro[furo[2,3-f][1,3]benzodioxole-7,3'-indol]-1'(2'H)-yl)propyl]-2-phenylcyclopropanecarboxamide;
4-methyl-N-[3-(2'-oxospiro[furo[2,3-f][1,3]benzodioxole-7,3'-indol]-1'(2'H)-yl)propyl]benzamide;
1-(4-fluorophenyl)-5-methyl-N-[3-(2'-oxospiro[furo[2,3-f][1,3]benzodioxole-7,3'-indol]-1'(2'H)-yl)propyl]-1H-pyrazole-4-carboxamide;
N-[3-(2'-oxospiro[furo[2,3-f][1,3]benzodioxole-7,3'-indol]-1'(2'H)-yl)propyl]-1-benzofuran-5-carboxamide;
N-[3-(2'-oxospiro[furo[2,3-f][1,3]benzodioxole-7,3'-indol]-1'(2'H)-yl)propyl]-2,1,3-benzoxadiazole-5-carboxamide;
2,4-dichloro-N-[3-(2'-oxospiro[furo[2,3-f][1,3]benzodioxole-7,3'-indol]-1'(2'H)-yl)propyl]benzamide;
1-methyl-N-[3-(2'-oxospiro[furo[2,3-f][1,3]benzodioxole-7,3'-indol]-1'(2'H)-yl)propyl]-1H-1,2,3-benzotriazole-5-carboxamide;
5-fluoro-2-methyl-N-[3-(2'-oxospiro[furo[2,3-f][1,3]benzodioxole-7,3'-indol]-1'(2'H)-yl)propyl]benzamide;
2-chloro-N-[3-(2'-oxospiro[furo[2,3-f][1,3]benzodioxole-7,3'-indol]-1'(2'H)-yl)propyl]isonicotinamide;
N-[3-(2'-oxospiro[furo[2,3-f][1,3]benzodioxole-7,3'-indol]-1'(2'H)-yl)propyl]-2,3-dihydro-1,4-benzodioxine-6-carboxamide;
5-methyl-N-[3-(2'-oxospiro[furo[2,3-f][1,3]benzodioxole-7,3'-indol]-1'(2'H)-yl)propyl]isoxazole-3-carboxamide;
N-[3-(2'-oxospiro[furo[2,3-f][1,3]benzodioxole-7,3'-indol]-1'(2'H)-yl)propyl]-1-benzofuran-2-carboxamide;
N-[3-(2'-oxospiro[furo[2,3-f][1,3]benzodioxole-7,3'-indol]-1'(2'H)-yl)propyl]-1-benzothiophene-2-carboxamide;
N-[3-(2'-oxospiro[furo[2,3-f][1,3]benzodioxole-7,3'-indol]-1'(2'H)-yl)propyl]-2,3-dihydro-1,4-benzodioxine-2-carboxamide;
N-[3-(2'-oxospiro[furo[2,3-f][1,3]benzodioxole-7,3'-indol]-1'(2'H)-yl)propyl]-4-(1H-pyrazol-1-yl)benzamide;
1,3-dimethyl-N-[3-(2'-oxospiro[furo[2,3-f][1,3]benzodioxole-7,3'-indol]-1'(2'H)-yl)propyl]-1H-pyrazole-5-carboxamide;
4-methyl-N-[3-(2'-oxospiro[furo[2,3-f][1,3]benzodioxole-7,3'-indol]-1'(2'H)-yl)propyl]-3,4-dihydro-2H-1,4-benzoxazine-7-carboxamide;
N-[3-(2'-oxospiro[furo[2,3-f][1,3]benzodioxole-7,3'-indol]-1'(2'H)-yl)propyl]quinoxaline-6-carboxamide;
N-[3-(2'-oxospiro[furo[2,3-f][1,3]benzodioxole-7,3'-indol]-1'(2'H)-yl)propyl]-2,3-dihydro-1-benzofuran-2-carboxamide;
N-[3-(2'-oxospiro[furo[2,3-f][1,3]benzodioxole-7,3'-indol]-1'(2'H)-yl)propyl]-2,3-dihydro-1-benzothiophene-5-carboxamide;
N-[3-(2'-oxospiro[furo[2,3-f][1,3]benzodioxole-7,3'-indol]-1'(2'H)-yl)propyl]-2-(trifluoromethoxy)benzamide;
N-[3-(2'-oxospiro[furo[2,3-f][1,3]benzodioxole-7,3'-indol]-1'(2'H)-yl)propyl]pentanamide;
N-[3-(2'-oxospiro[furo[2,3-f][1,3]benzodioxole-7,3'-indol]-1'(2'H)-yl)propyl]heptanamide;
3-cyclopentyl-N-[3-(2'-oxospiro[furo[2,3-f][1,3]benzodioxole-7,3'-indol]-1'(2'H)-yl)propyl]propanamide;
9-oxo-N-[3-(2'-oxospiro[furo[2,3-f][1,3]benzodioxole-7,3'-indol]-1'(2'H)-yl)propyl]-9H-fluorene-4-carboxamide;
N-[3-(2'-oxospiro[furo[2,3-f][1,3]benzodioxole-7,3'-indol]-1'(2'H)-yl)propyl]-4-(trifluoromethyl)benzamide;
2,5-difluoro-N-[3-(2'-oxospiro[furo[2,3-f][1,3]benzodioxole-7,3'-indol]-1'(2'H)-yl)propyl]benzamide;
2,5-dimethyl-N-[3-(2'-oxospiro[furo[2,3-f][1,3]benzodioxole-7,3'-indol]-1'(2'H)-yl)propyl]-3-furamide;
N-[3-(2'-oxospiro[furo[2,3-f][1,3]benzodioxole-7,3'-indol]-1'(2'H)-yl)propyl]-4-phenoxybutanamide;
4-fluoro-N-[3-(2'-oxospiro[furo[2,3-f][1,3]benzodioxole-7,3'-indol]-1'(2'H)-yl)propyl]-2-(trifluoromethyl)benzamide;
N-[3-(2'-oxospiro[furo[2,3-f][1,3]benzodioxole-7,3'-indol]-1'(2'H)-yl)propyl]-2-(2-thienyl)acetamide;
2-chloro-5-fluoro-N-[3-(2'-oxospiro[furo[2,3-f][1,3]benzodioxole-7,3'-indol]-1'(2'H)-yl)propyl]benzamide;
N-[3-(2'-oxospiro[furo[2,3-f][1,3]benzodioxole-7,3'-indol]-1'(2'H)-yl)propyl]-2-naphthamide;
2-(4-chlorophenoxy)-N-[3-(2'-oxospiro[furo[2,3-f][1,3]benzodioxole-7,3'-indol]-1'(2'H)-yl)propyl]acetamide;

2,4-dimethoxy-N-[3-(2'-oxospiro[furo[2,3-f][1,3]benzodioxole-7,3'-indol]-1'(2'H)-yl)propyl]benzamide;
2-nitro-N-[3-(2'-oxospiro[furo[2,3-f][1,3]benzodioxole-7,3'-indol]-1'(2'H)-yl)propyl]benzamide;
2-(4-chlorophenyl)-3-methyl-N-[3-(2'-oxospiro[furo[2,3-f][1,3]benzodioxole-7,3'-indol]-1'(2'H)-yl)propyl]butanamide;
4-amino-N-[3-(2'-oxospiro[furo[2,3-f][1,3]benzodioxole-7,3'-indol]-1'(2'H)-yl)propyl]benzamide;
3,4-dimethoxy-N-[3-(2'-oxospiro[furo[2,3-f][1,3]benzodioxole-7,3'-indol]-1'(2'H)-yl)propyl]benzamide;
N-[3-(2'-oxospiro[furo[2,3-f][1,3]benzodioxole-7,3'-indol]-1'(2'H)-yl)propyl]-5H-dibenzo[b,f]azepine-5-carboxamide;
N-[3-(2'-oxospiro[furo[2,3-f][1,3]benzodioxole-7,3'-indol]-1'(2'H)-yl)propyl]adamantane-1-carboxamide;
2-[(2-isopropyl-5-methylcyclohexyl)oxy]-N-[3-(2'-oxospiro[furo[2,3-f][1,3]benzodioxole-7,3'-indol]-1'(2'H)-yl)propyl]acetamide;
N-[3-(2'-oxospiro[furo[2,3-f][1,3]benzodioxole-7,3'-indol]-1'(2'H)-yl)propyl]-3,5-bis(trifluoromethyl)benzamide;
2-(2,5-dimethoxyphenyl)-N-[3-(2'-oxospiro[furo[2,3-f][1,3]benzodioxole-7,3'-indol]-1'(2'H)-yl)propyl]acetamide;
2-chloro-N-[3-(2'-oxospiro[furo[2,3-f][1,3]benzodioxole-7,3'-indol]-1'(2'H)-yl)propyl]benzamide;
3-chloro-N-[3-(2'-oxospiro[furo[2,3-f][1,3]benzodioxole-7,3'-indol]-1'(2'H)-yl)propyl]benzamide;
4-chloro-N-[3-(2'-oxospiro[furo[2,3-f][1,3]benzodioxole-7,3'-indol]-1'(2'H)-yl)propyl]benzamide;
N-[3-(2'-oxospiro[furo[2,3-f][1,3]benzodioxole-7,3'-indol]-1'(2'H)-yl)propyl]hexanamide;
2,6-difluoro-N-[3-(2'-oxospiro[furo[2,3-f][1,3]benzodioxole-7,3'-indol]-1'(2'H)-yl)propyl]benzamide;
2-chloro-N-[3-(2'-oxospiro[furo[2,3-f][1,3]benzodioxole-7,3'-indol]-1'(2'H)-yl)propyl]acetamide;
N-[3-(2'-oxospiro[furo[2,3-f][1,3]benzodioxole-7,3'-indol]-1'(2'H)-yl)propyl]-2,5-bis(trifluoromethyl)benzamide;
N-[3-(2'-oxospiro[furo[2,3-f][1,3]benzodioxole-7,3'-indol]-1'(2'H)-yl)propyl]pyrrolidine-1-carboxamide;
2-bromo-2,2-difluoro-N-[3-(2'-oxospiro[furo[2,3-f][1,3]benzodioxole-7,3'-indol]-1'(2'H)-yl)propyl]acetamide;
2,3,5-trifluoro-N-[3-(2'-oxospiro[furo[2,3-f][1,3]benzodioxole-7,3'-indol]-1'(2'H)-yl)propyl]benzamide;
5-fluoro-N-[3-(2'-oxospiro[furo[2,3-f][1,3]benzodioxole-7,3'-indol]-1'(2'H)-yl)propyl]-2-(trifluoromethyl)benzamide;
5-chloro-N-[3-(2'-oxospiro[furo[2,3-f][1,3]benzodioxole-7,3'-indol]-1'(2'H)-yl)propyl]-2-(trifluoromethyl)benzamide;
N-[3-(2'-oxospiro[furo[2,3-f][1,3]benzodioxole-7,3'-indol]-1'(2'H)-yl)propyl]thiophene-2-carboxamide;
N-[3-(2'-oxospiro[furo[2,3-f][1,3]benzodioxole-7,3'-indol]-1'(2'H)-yl)propyl]morpholine-4-carboxamide;
2-(1-naphthyl)-N-[3-(2'-oxospiro[furo[2,3-f][1,3]benzodioxole-7,3'-indol]-1'(2'H)-yl)propyl]acetamide;
2-methyl-N-[3-(2'-oxospiro[furo[2,3-f][1,3]benzodioxole-7,3'-indol]-1'(2'H)-yl)propyl]propanamide;
N-[3-(2'-oxospiro[furo[2,3-f][1,3]benzodioxole-7,3'-indol]-1'(2'H)-yl)propyl]-N-propionylpropanamide;
N-[3-(2'-oxospiro[furo[2,3-f][1,3]benzodioxole-7,3'-indol]-1'(2'H)-yl)propyl]-4-pentylbenzamide;
4,7,7-trimethyl-3-oxo-N-[3-(2'-oxospiro[furo[2,3-f][1,3]benzodioxole-7,3'-indol]-1'(2'H)-yl)propyl]-2-oxabicyclo[2.2.1]heptane-1-carboxamide;
2-bromo-N-[3-(2'-oxospiro[furo[2,3-f][1,3]benzodioxole-7,3'-indol]-1'(2'H)-yl)propyl]benzamide;
3-cyano-N-[3-(2'-oxospiro[furo[2,3-f][1,3]benzodioxole-7,3'-indol]-1'(2'H)-yl)propyl]benzamide;
4-cyano-N-[3-(2'-oxospiro[furo[2,3-f][1,3]benzodioxole-7,3'-indol]-1'(2'H)-yl)propyl]benzamide; and
N-[2-(2'-oxospiro[furo[2,3-f][1,3]benzodioxole-7,3'-indol]-1'(2'H)-yl)ethyl]-2-(trifluoromethoxy)benzamide.

Another embodiment of the invention are the compounds of formula (I) as set forth above in the Summary of the invention wherein:
j is 0 and k is 1;
Q is —O—;
$R^1$ is —$R^9$—N($R^{10}$)C(O)N($R^{10}$)$R^{11}$ where:
   each $R^{10}$ is hydrogen, alkyl, aryl, aralkyl or heteroaryl;
   each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;
   and wherein each aryl, aralkyl, cycloalkyl, cycloalkylalkyl, heterocyclyl, heterocyclylalkyl, heteroaryl and heteroarylalkyl groups for $R^{19}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused dioxolyl ring;
each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl; and
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:
1-(4-fluorophenyl)-3-[2-(2'-oxospiro[furo[2,3-f][1,3]benzodioxole-7,3'-indol]-1'(2'H)-yl)ethyl]urea;
1-benzyl-3-[2-(2'-oxospiro[furo[2,3-f][1,3]benzodioxole-7,3'-indol]-1'(2'H)-yl)ethyl]urea;
1-[2-(2'-oxospiro[furo[2,3-f][1,3]benzodioxole-7,3'-indol]-1'(2'H)-yl)ethyl]-3-(4-phenoxyphenyl)urea;
1-butyl-3-[2-(2'-oxospiro[furo[2,3-f][1,3]benzodioxole-7,3'-indol]-1'(2'H)-yl)ethyl]urea;
1-cyclohexyl-3-[2-(2'-oxospiro[furo[2,3-f][1,3]benzodioxole-7,3'-indol]-1'(2'H)-yl)ethyl]urea;
1-ethyl-3-[2-(2'-oxospiro[furo[2,3-f][1,3]benzodioxole-7,3'-indol]-1'(2'H)-yl)ethyl]urea;
1-isopropyl-3-[2-(2'-oxospiro[furo[2,3-f][1,3]benzodioxole-7,3'-indol]-1'(2'H)-yl)ethyl]urea;
1-[2-(2'-oxospiro[furo[2,3-f][1,3]benzodioxole-7,3'-indol]-1'(2'H)-yl)ethyl]-3-propylurea;
1-tert-butyl-3-[2-(2'-oxospiro[furo[2,3-f][1,3]benzodioxole-7,3'-indol]-1'(2'H)-yl)ethyl]urea;
1-cyclopentyl-3-[2-(2'-oxospiro[furo[2,3-f][1,3]benzodioxole-7,3'-indol]-1'(2'H)-yl)ethyl]urea;

1'-[2-(2'-oxospiro[furo[2,3-f][1,3]benzodioxole-7,3'-indol]-1'(2'H)-yl)ethyl]-3-pentylurea;
1'-[2-(2'-oxospiro[furo[2,3-f][1,3]benzodioxole-7,3'-indol]-1'(2'H)-yl)ethyl]-3-phenylurea;
1-(2-furylmethyl)-3-[2-(2'-oxospiro[furo[2,3-f][1,3]benzodioxole-7,3'-indol]-1'(2'H)-yl)ethyl]urea;
1-hexyl-3-[2-(2'-oxospiro[furo[2,3-f][1,3]benzodioxole-7,3'-indol]-1'(2'H)-yl)ethyl]urea;
ethyl N-({[2-(2'-oxospiro[furo[2,3-f][1,3]benzodioxole-7,3'-indol]-1'(2'H)-yl)ethyl]amino}carbonyl)glycinate;
1-(3-methylphenyl)-3-[2-(2'-oxospiro[furo[2,3-f][1,3]benzodioxole-7,3'-indol]-1'(2'H)-yl)ethyl]urea;
1-(4-methylphenyl)-3-[2-(2'-oxospiro[furo[2,3-f][1,3]benzodioxole-7,3'-indol]-1'(2'H)-yl)ethyl]urea;
ethyl N-({[2-(2'-oxospiro[furo[2,3-f][1,3]benzodioxole-7,3'-indol]-1'(2'H)-yl)ethyl]amino}carbonyl)-beta-alaninate;
1-(4-cyanophenyl)-3-[2-(2'-oxospiro[furo[2,3-f][1,3]benzodioxole-7,3'-indol]-1'(2'H)-yl)ethyl]urea;
N-({[2-(2'-oxospiro[furo[2,3-f][1,3]benzodioxole-7,3'-indol]-1'(2'H)-yl)ethyl]amino}carbonyl)benzamide;
1'-[2-(2'-oxospiro[furo[2,3-f][1,3]benzodioxole-7,3'-indol]-1'(2'H)-yl)ethyl]-3-(2-phenylethyl)urea;
1-(4-methylbenzyl)-3-[2-(2'-oxospiro[furo[2,3-f][1,3]benzodioxole-7,3'-indol]-1'(2'H)-yl)ethyl]urea;
1-(2-methylbenzyl)-3-[2-(2'-oxospiro[furo[2,3-f][1,3]benzodioxole-7,3'-indol]-1'(2'H)-yl)ethyl]urea;
1-(4-ethylphenyl)-3-[2-(2'-oxospiro[furo[2,3-f][1,3]benzodioxole-7,3'-indol]-1'(2'H)-yl)ethyl]urea;
1-(3-methoxyphenyl)-3-[2-(2'-oxospiro[furo[2,3-f][1,3]benzodioxole-7,3'-indol]-1'(2'H)-yl)ethyl]urea;
1-(2-fluoro-5-methylphenyl)-3-[2-(2'-oxospiro[furo[2,3-f][1,3]benzodioxole-7,3'-indol]-1'(2'H)-yl)ethyl]urea;
1-(3-fluoro-4-methylphenyl)-3-[2-(2'-oxospiro[furo[2,3-f][1,3]benzodioxole-7,3'-indol]-1'(2'H)-yl)ethyl]urea;
1-(4-chlorophenyl)-3-[2-(2'-oxospiro[furo[2,3-f][1,3]benzodioxole-7,3'-indol]-1'(2'H)-yl)ethyl]urea;
2-[({[2-(2'-oxospiro[furo[2,3-f][1,3]benzodioxole-7,3'-indol]-1'(2'H)-yl)ethyl]amino}carbonyl)amino]ethyl 2-methylacrylate;
1'-[2-(2'-oxospiro[furo[2,3-f][1,3]benzodioxole-7,3'-indol]-1'(2'H)-yl)ethyl]-3-(1,1,3,3-tetramethylbutyl)urea;
ethyl 4-[({[2-(2'-oxospiro[furo[2,3-f][1,3]benzodioxole-7,3'-indol]-1'(2'H)-yl)ethyl]amino}carbonyl)amino]butanoate;
1'-[4-(cyanomethyl)phenyl]-3-[2-(2'-oxospiro[furo[2,3-f][1,3]benzodioxole-7,3'-indol]-1'(2'H)-yl)ethyl]urea;
1-(2,3-dihydro-1H-inden-5-yl)-3-[2-(2'-oxospiro[furo[2,3-f][1,3]benzodioxole-7,3'-indol]-1'(2'H)-yl)ethyl]urea;
1-(3-acetylphenyl)-3-[2-(2'-oxospiro[furo[2,3-f][1,3]benzodioxole-7,3'-indol]-1'(2'H)-yl)ethyl]urea;
1-(4-acetylphenyl)-3-[2-(2'-oxospiro[furo[2,3-f][1,3]benzodioxole-7,3'-indol]-1'(2'H)-yl)ethyl]urea;
1-(4-isopropylphenyl)-3-[2-(2'-oxospiro[furo[2,3-f][1,3]benzodioxole-7,3'-indol]-1'(2'H)-yl)ethyl]urea;
1-(2-methoxybenzyl)-3-[2-(2'-oxospiro[furo[2,3-f][1,3]benzodioxole-7,3'-indol]-1'(2'H)-yl)ethyl]urea;
1-(4-methoxybenzyl)-3-[2-(2'-oxospiro[furo[2,3-f][1,3]benzodioxole-7,3'-indol]-1'(2'H)-yl)ethyl]urea;
1-(4-methoxy-2-methylphenyl)-3-[2-(2-oxospiro[furo[2,3-f][1,3]benzodioxole-7,3'-indol]-1'(2'H)-yl)ethyl]urea;
1-(4-chloro-2-methylphenyl)-3-[2-(2'-oxospiro[furo[2,3-f][1,3]benzodioxole-7,3'-indol]-1'(2'H)-yl)ethyl]urea;
1-(3-chloro-4-methylphenyl)-3-[2-(2'-oxospiro[furo[2,3-f][1,3]benzodioxole-7,3'-indol]-1'(2'H)-yl)ethyl]urea;
1-(3-chloro-2-methylphenyl)-3-[2-(2'-oxospiro[furo[2,3-f][1,3]benzodioxole-7,3'-indol]-1'(2'H)-yl)ethyl]urea;
1-(5-chloro-2-methylphenyl)-3-[2-(2'-oxospiro[furo[2,3-f][1,3]benzodioxole-7,3'-indol]-1'(2'H)-yl)ethyl]urea;
1-(2-chlorobenzyl)-3-[2-(2'-oxospiro[furo[2,3-f][1,3]benzodioxole-7,3'-indol]-1'(2'H)-yl)ethyl]urea;
1-(1-naphthyl)-3-[2-(2'-oxospiro[furo[2,3-f][1,3]benzodioxole-7,3'-indol]-1'(2'H)-yl)ethyl]urea;
1-(2-naphthyl)-3-[2-(2'-oxospiro[furo[2,3-f][1,3]benzodioxole-7,3'-indol]-1'(2'H)-yl)ethyl]urea;
1-(3-chloro-2-fluorophenyl)-3-[2-(2'-oxospiro[furo[2,3-f][1,3]benzodioxole-7,3'-indol]-1'(2'H)-yl)ethyl]urea;
1'-[2-(2'-oxospiro[furo[2,3-f][1,3]benzodioxole-7,3'-indol]-1'(2'H)-yl)ethyl]-3-(5,6,7,8-tetrahydronaphthalen-1-yl)urea;
1-(4-tert-butylphenyl)-3-[2-(2'-oxospiro[furo[2,3-f][1,3]benzodioxole-7,3'-indol]-1'(2'H)-yl)ethyl]urea;
1-(4-butylphenyl)-3-[2-(2'-oxospiro[furo[2,3-f][1,3]benzodioxole-7,3'-indol]-1'(2'H)-yl)ethyl]urea;
1-[2-(4-ethylphenyl)ethyl]-3-[2-(2'-oxospiro[furo[2,3-f][1,3]benzodioxole-7,3'-indol]-1'(2'H)-yl)ethyl]urea;
1-(2,3-dihydro-1,4-benzodioxin-6-yl)-3-[2-(2'-oxospiro[furo[2,3-f][1,3]benzodioxole-7,3'-indol]-1'(2'H)-yl)ethyl]urea;
methyl 4-[({[2-(2'-oxospiro[furo[2,3-f][1,3]benzodioxole-7,3'-indol]-1'(2'H)-yl)ethyl]amino}carbonyl)amino]benzoate;
1-(2-ethoxybenzyl)-3-[2-(2'-oxospiro[furo[2,3-f][1,3]benzodioxole-7,3'-indol]-1'(2'H)-yl)ethyl]urea;
1-(3,4-dimethoxyphenyl)-3-[2-(2'-oxospiro[furo[2,3-f][1,3]benzodioxole-7,3'-indol]-1'(2'H)-yl)ethyl]urea;
1-(3,5-dimethoxyphenyl)-3-[2-(2'-oxospiro[furo[2,3-f][1,3]benzodioxole-7,3'-indol]-1'(2'H)-yl)ethyl]urea;
1-(3-chloro-4-methoxyphenyl)-3-[2-(2'-oxospiro[furo[2,3-f][1,3]benzodioxole-7,3'-indol]-1'(2'H)-yl)ethyl]urea;
1-[4-(difluoromethoxy)phenyl]-3-[2-(2'-oxospiro[furo[2,3-f][1,3]benzodioxole-7,3'-indol]-1'(2'H)-yl)ethyl]urea;
1-[2-(difluoromethoxy)phenyl]-3-[2-(2'-oxospiro[furo[2,3-f][1,3]benzodioxole-7,3'-indol]-1'(2'H)-yl)ethyl]urea;
1-[2-(2'-oxospiro[furo[2,3-f][1,3]benzodioxole-7,3'-indol]-1'(2'H)-yl)ethyl]-3-[3-(trifluoromethyl)phenyl]urea;
1-[2-(2'-oxospiro[furo[2,3-f][1,3]benzodioxole-7,3'-indol]-1'(2H)-yl)ethyl]-3-[2-(trifluoromethyl)phenyl]urea;
1-[2-(2'-oxospiro[furo[2,3-f][1,3]benzodioxole-7,3'-indol]-1'(2'H)-yl)ethyl]-3-[4-(trifluoromethyl)phenyl]urea;
1-(3,4-dichlorophenyl)-3-[2-(2'-oxospiro[furo[2,3-f][1,3]benzodioxole-7,3'-indol]-1'(2'H)-yl)ethyl]urea;
1-(2,3-dichlorophenyl)-3-[2-(2'-oxospiro[furo[2,3-f][1,3]benzodioxole-7,3'-indol]-1'(2'H)-yl)ethyl]urea;
1-(3,5-dichlorophenyl)-3-[2-(2'-oxospiro[furo[2,3-f][1,3]benzodioxole-7,3'-indol]-1'(2'H)-yl)ethyl]urea;
ethyl 4-[({[2-(2'-oxospiro[furo[2,3-f][1,3]benzodioxole-7,3'-indol]-1'(2'H)-yl)ethyl]amino}carbonyl)amino]benzoate;
ethyl 2-[({[2-(2'-oxospiro[furo[2,3-f][1,3]benzodioxole-7,3'-indol]-1'(2'H)-yl)ethyl]amino}carbonyl)amino]benzoate;
1-[2-(1,3-benzodioxol-5-yl)ethyl]-3-[2-(2'-oxospiro[furo[2,3-f][1,3]benzodioxole-7,3'-indol]-1'(2'H)-yl)ethyl]urea;
methyl 2-methyl-3-[({[2-(2'-oxospiro[furo[2,3-f][1,3]benzodioxole-7,3'-indol]-1'(2'H)-yl)ethyl]amino}carbonyl)amino]benzoate;
1-(4-butoxyphenyl)-3-[2-(2'-oxospiro[furo[2,3-f][1,3]benzodioxole-7,3'-indol]-1'(2'H)-yl)ethyl]urea;
1-(2-methoxy-4-nitrophenyl)-3-[2-(2'-oxospiro[furo[2,3-f][1,3]benzodioxole-7,3'-indol]1'(2'H)-yl)ethyl]urea;
1-biphenyl-2-yl-3-[2-(2'-oxospiro[furo[2,3-f][1,3]benzodioxole-7,3'-indol]-1'(2'H)-yl)ethyl]urea;

1-[4-methyl-3-(trifluoromethyl)phenyl]-3-[2-(2'-oxospiro [furo[2,3-f][1,3]benzodioxole-7,3'-indol]-1'(2'H)-yl) ethyl]urea;

1-(2,4-dichlorobenzyl)-3-[2-(2'-oxospiro[furo[2,3-f][1,3] benzodioxole-7,3'-indol]1'(2'H)-yl)ethyl]urea;

1-[2-(2'-oxospiro[furo[2,3-f][1,3]benzodioxole-7,3'-indol]-1'(2'H)-yl)ethyl]-3-[2-(trifluoromethoxy)phenyl]urea;

1-[4-fluoro-2-(trifluoromethyl)phenyl]-3-[2-(2'-oxospiro [furo[2,3-f][1,3]benzodioxole-7,3'-indol]-1'(2'H)-yl) ethyl]urea;

1-(5-tert-butyl-2-methoxyphenyl)-3-[2-(2'-oxospiro[furo[2, 3-f][1,3]benzodioxole-7,3'-indol]-1'(2'H)-yl)ethyl]urea;

1-[2-(3,5-dimethoxyphenyl)ethyl]-3-[2-(2'-oxospiro[furo[2, 3-f][1,3]benzodioxole-7,3'-indol]-1'(2'H)-yl)ethyl]urea;

1-(9H-fluoren-2-yl)-3-[2-(2'-oxospiro[furo[2,3-f][1,3]benzodioxole-7,3'-indol]-1'(2'H)-yl)ethyl]urea;

1-(9H-fluoren-9-yl)-3-[2-(2'-oxospiro[furo[2,3-f][1,3]benzodioxole-7,3'-indol]-1'(2'H)-yl)ethyl]urea;

1-[2-(2'-oxospiro[furo[2,3-f][1,3]benzodioxole-7,3'-indol]-1'(2'H)-yl)ethyl]-3-(3,4,5-trimethoxyphenyl)urea;

1-(diphenylmethyl)-3-[2-(2'-oxospiro[furo[2,3-f][1,3]benzodioxole-7,3'-indol]-1'(2'H)-yl)ethyl]urea;

1'-[2-(2'-oxospiro[furo[2,3-f][1,3]benzodioxole-7,3'-indol]-1'(2'H)-yl)ethyl]-3-(2-phenoxyphenyl)urea;

1-(2-biphenyl-4-ylethyl)-3-[2-(2'-oxospiro[furo[2,3-f][1,3] benzodioxole-7,3'-indol]-1'(2'H)-yl)ethyl]urea;

1-[2-(2'-oxospiro[furo[2,3-f][1,3]benzodioxole-7,3'-indol]-1'(2'H)-yl)ethyl]-3-(3,4,5-trimethoxybenzyl)urea;

1-(2-nitrophenyl)-3-[2-(2'-oxospiro[furo[2,3-f][1,3]benzodioxole-7,3'-indol]-1'(2'H)-yl)ethyl]urea;

1-(1,3-benzodioxol-5-yl)-3-[2-(2'-oxospiro[furo[2,3-f][1,3] benzodioxole-7,3'-indol]-1'(2'H)-yl)ethyl]urea;

1-[4-(dimethylamino)phenyl]-3-[2-(2'-oxospiro[furo[2,3-f] [1,3]benzodioxole-7,3'-indol]-1'(2'H)-yl)ethyl]urea;

1-(2-fluorobenzyl)-3-[2-(2'-oxospiro[furo[2,3-f][1,3]benzodioxole-7,3'-indol]-1'(2'H)-yl)ethyl]urea;

1-(4-fluoro-3-methylphenyl)-3-[2-(2'-oxospiro[furo[2,3-f] [1,3]benzodioxole-7,3'-indol]-1'(2'H)-yl)ethyl]urea;

1-(3-fluorobenzyl)-3-[2-(2'-oxospiro[furo[2,3-f][1,3]benzodioxole-7,3'-indol]-1'(2'H)-yl)ethyl]urea;

1-(cyclohexylmethyl)-3-[2-(2'-oxospiro[furo[2,3-f][1,3] benzodioxole-7,3'-indol]-1'(2'H)-yl)ethyl]urea;

1-(2-methylphenyl)-3-[2-(2'-oxospiro[furo[2,3-f][1,3]benzodioxole-7,3'-indol]-1'(2'H)-yl)ethyl]urea; and 1-[4-(6-methyl-1,3-benzothiazol-2-yl)phenyl]-3-[2-(2'-oxospiro[furo[2,3-f][1,3]benzodioxole-7,3'-indol]-1'(2'H)-yl)ethyl]urea.

Another embodiment of the invention are the compounds of formula (I) as set forth above in the Summary of the invention wherein:

at least one of j and k is 1 and the other is 0 or 1;

Q is —O—;

$R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—C(O)$OR^5$, —$R^8$—N($R^4$)$R^5$, —$R^8$—C(O)N($R^4$)$R^5$, —$R^8$—N($R^5$)C(O)$R^4$, —$R^8$—S(O)$_m$$R^4$ (where m is 0, 1 or 2), —$R^8$—CN, or —$R^8$—$NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m$$R^4$, —OS(O)$_2$$CF_3$, —$R^8$—C(O) $R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N ($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$NO_2$, —$R^8$—$OR^5$, —$R^8$—N ($R^4$)$R^5$, —S(O)$_m$$R^4$, —$R^5$—S(O)$_n$N($R^4$)$R^5$, —$R^5$—C (O)$R^4$, —$R^8$—C(O)$OR^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$OR^5$, —$R^8$—N($R^4$)$R^5$, —N=C($R^4$) $R^5$, —S(O)$_m$$R^4$, —S(O)$_2$$CF_3$, —$R^5$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S (O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$) N($R^4$)$R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R⁴ and R⁵ are each attached to the same nitrogen atom, then R⁴ and R⁵, together with the nitrogen atom to which they are attached, may form a heterocyclyl or heteroaryl; and each R⁸ is a direct bond or a straight or branched alkylene chain, a straight or branched alkenylene chain or a straight or branched alkynylene chain; and each R⁹ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

R¹ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R⁸—OR⁵, —R⁸—C(O)OR⁵, —R⁸—N(R⁴)R⁵, —R⁸—C(O)N(R⁴)R⁵, —R⁸—N(R⁵)C(O)R⁴, S(O)ₘR⁴ (where m is 0, 1 or 2), —R⁸—CN, or —R⁸—NO₂;

R²ᵃ, R²ᵇ, R²ᶜ and R²ᵈ are each independently selected from hydrogen, halo, alkyl or —R⁸—OR⁵;

R³ᵃ, R³ᵇ, R³ᶜ and R³ᵈ are each independently selected from hydrogen, halo, alkyl or —R⁸—OR⁵;

or R³ᵇ and R³ᶜ, together with the carbon ring atoms to which they are directly attached, form a fused ring selected from cycloalkyl, heterocyclyl, aryl or heteroaryl, and R³ᵃ and R³ᵈ are each hydrogen;

each R⁵ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each R⁸ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

R¹ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R⁸—OR⁵, —R⁸—C(O)OR⁵, —R⁸—N(R⁴)R⁵, —R⁸—C(O)N(R⁴)R⁵, —R⁸—N(R⁵)C(O)R⁴, —R⁸—S(O)ₘR⁴ (where m is 0, 1 or 2), —R⁸—CN, or —R⁸—NO₂;

R²ᵃ, R²ᵇ, R²ᶜ and R²ᵈ are each independently selected from hydrogen, halo, alkyl or —R⁸—OR⁵;

R³ᵃ, R³ᵇ, R³ᶜ and R³ᵈ are each independently selected from hydrogen, halo, alkyl or —R⁸—OR⁵;

or R³ᵇ and R³ᶜ, together with the carbon ring atoms to which they are directly attached, form a fused ring selected from dioxolyl or tetrahydrofuranyl, and R³ᵃ and R³ᵈ are each hydrogen;

each R⁵ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each R⁸ is a direct bond or a straight or branched alkylene chain, a straight or branched alkenylene chain or a straight or branched alkynylene chain.

Another embodiment of the invention are the compounds of formula (I) as set forth above in the Summary of the invention, selected from the group consisting of:

2-[3-(2'-oxospiro[furo[2,3-f][1,3]benzodioxole-7,3'-indol]-1'(2'H)-yl)propyl]-1H-isoindole-1,3(2H)-dione;

2-[2-(2'-oxospiro[furo[2,3-f][1,3]benzodioxole-7,3'-indol]-1'(2'H)-yl)ethyl]-1H-isoindole-1,3(2H)-dione;

4'-bromo-1'-(pyridin-2-ylmethyl)-5,6-dihydrospiro[benzo[1,2-b:5,4-b']difuran-3,3'-indol]-2'(1'H)-one;

5'-fluoro-1'-{[5-(trifluoromethyl)-2-furyl]methyl}spiro[furo[2,3-f][1,3]benzodioxole-7,3'-indol]-2'(1'H)-one;

5'-methyl-1'-{[5-(trifluoromethyl)-2-furyl]methyl}spiro[furo[2,3-f][1,3]benzodioxole-7,3'-indol]-2'(1'H)-one;

5-bromo-1'-{[5-(trifluoromethyl)-2-furyl]methyl}spiro[1-benzofuran-3,3'-indol]-2'(1'H)-one;

4'-Methoxy-1'-{[5-(trifluoromethyl)-2-furyl]methyl}spiro[furo[2,3-f][1,3]benzodioxole-7,3'-indol]-2'(1'H)-one;

7'-fluoro-1'-{[5-(trifluoromethyl)-2-furyl]methyl}spiro[furo[2,3-f][1,3]benzodioxole-7,3'-indol]-2'(1'H)one;

1'-{[1-(2,6-difluorobenzyl)-1H-1,2,3-triazol-4-yl]methyl}spiro[furo[2,3-f][1,3]benzodioxole-7,3'-indol]-2'(1'H)-one;

1'-{[6-(trifluoromethyl)pyridin-3-yl]methyl}spiro[furo[2,3-f][1,3]benzodioxole-7,3'-indol]-2'(1'H)-one;

1'-[(6-chloropyridin-3-yl)methyl]spiro[furo[2,3-f][1,3]benzodioxole-7,3'-indol]-2'(1'H)-one;

1'-(tetrahydro-2H-pyran-2-ylmethyl)spiro[furo[2,3-f][1,3]benzodioxole-7,3'-indol]-2'(1'H)-one;

1'-(tetrahydrofuran-2-ylmethyl)spiro[furo[2,3-f][1,3]benzodioxole-7,3'-indol]-2'(1'H)-one;

1'-(2,3-dihydro-1,4-benzodioxin-2-ylmethyl)spiro[furo[2,3-f][1,3]benzodioxole-7,3'-indol]-2'(1'H)-one;

1'-[(7-methoxy-2-oxo-2H-1,4-benzoxazin-3-yl)methyl]spiro[furo[2,3-f][1,3]benzodioxole-7,3'-indol]-2'(1'H)-one;

1'-[(5-methyl-2-phenyl-2H-1,2,3-triazol-4-yl)methyl]spiro[furo[2,3-f][1,3]benzodioxole-7,3'-indol]-2'(1'H)-one;

1'-{[5-(trifluoromethyl)-2-furyl]methyl}spiro[furo[2,3-f][1,3]benzodioxole-7,3'-indol]-2'(1'H)-one;

1-(3,4-dihydro-2H-1,5-benzodioxepin-7-ylmethyl)spiro[furo[2,3-f][1,3]benzodioxole-7,3'-indol]-2'(1'H)-one;

1'-(1H-1,2,3-triazol-4-ylmethyl)spiro[furo[2,3-f][1,3]benzodioxole-7,3'-indol]-2'(1'H)-one;

ethyl 1-[2-(2'-oxospiro[furo[2,3-f][1,3]benzodioxole-7,3'-indol]-1'(2'H)-yl)ethyl]-1H-1,2,3-triazole-5-carboxylate;

ethyl 1-[2-(2'-oxospiro[furo[2,3-f][1,3]benzodioxole-7,3'-indol]-1'(2'H)-yl)ethyl]-1H-1,2,3-triazole-4-carboxylate;

1'-(1,3-thiazol-4-ylmethyl)spiro[furo[2,3-f][1,3]benzodioxole-7,3'-indol]-2'(1'H)-one;

1'-[(5-chloro-1-benzothien-3-yl)methyl]spiro[furo[2,3-f][1,3]benzodioxole-7,3'-indol]-2'(1'H)-one;

1'-(pyridin-2-ylmethyl)spiro[furo[2,3-f][1,3]benzodioxole-7,3'-indol]-2'(1'H)-one;

1'-(pyridin-4-ylmethyl)spiro[furo[2,3-f][1,3]benzodioxole-7,3'-indol]-2'(1'H)-one;

1'-(pyridin-3-ylmethyl)spiro[furo[2,3-f][1,3]benzodioxole-7,3'-indol]-2'(1'H)-one;

1'-[2-(1H-pyrrol-1-yl)ethyl]spiro[furo[2,3-f][1,3]benzodioxole-7,3'-indol]-2'(1'H)-one;

1-{[4-chloro-2-(trifluoromethyl)quinolin-6-yl]methyl}spiro[furo[2,3-f][1,3]benzodioxole-7,3'-indol]-2'(1'H)-one;

1'-[(2-methyl-1,3-thiazol-4-yl)methyl]spiro[furo[2,3-f][1,3]benzodioxole-7,3'-indol]-2'(1'H)-one;

1'-(1,3-benzothiazol-2-ylmethyl)spiro[furo[2,3-f][1,3]benzodioxole-7,3'-indol]-2'(1'H)-one;
1'-(2,1,3-benzothiadiazol-4-ylmethyl)spiro[furo[2,3-f][1,3]benzodioxole-7,3'-indol]-2'(1'H)-one;
1'-(2,1,3-benzothiadiazol-5-ylmethyl)spiro[furo[2,3-f][1,3]benzodioxole-7,3'-indol]-2'(1'H)-one;
1'-[(1-methyl-1H-1,2,3-benzotriazol-5-yl)methyl]spiro[furo[2,3-f][1,3]benzodioxole-7,3'-indol]-2'(1'H)-one;
1'-[3-(1H-pyrrol-1-yl)propyl]spiro[furo[2,3-f][1,3]benzodioxole-7,3'-indol]-2'(1'H)-one;
1'-[(3-methyl-5-phenylisoxazol-4-yl)methyl]spiro[furo[2,3-f][1,3]benzodioxole-7,3'-indol]-2'(1'H)-one;
1'-[(7-methoxy-2-oxo-2H-chromen-4-yl)methyl]spiro[furo[2,3-f][1,3]benzodioxole-7,3'-indol]-2'(1'H)-one;
1'-[2-(2,5,5-trimethyl-1,3-dioxan-2-yl)ethyl]spiro[furo[2,3-f][1,3]benzodioxole-7,3'-indol]-2'(1'H)-one;
1'-[(6-fluoro-4H-1,3-benzodioxin-8-yl)methyl]spiro[furo[2,3-f][1,3]benzodioxole-7,3'-indol]-2'(1'H)-one;
1'-[(5-phenyl-1,3-oxazol-4-yl)methyl]spiro[furo[2,3-f][1,3]benzodioxole-7,3'-indol]-2'(1'H)-one;
1-(1,3-benzodioxol-5-ylmethyl)spiro[furo[2,3-f][1,3]benzodioxole-7,3'-indol]-2'(1'H)-one;
1'(piperidin-4-ylmethyl)spiro[furo[2,3-f][1,3]benzodioxole-7,3'-indol]-2'(1'H)-one;
1'[(1-methylpiperidin-4-yl)methyl]spiro[furo[2,3-f][1,3]benzodioxole-7,3'-indol]-2'(1'H)-one hydrochloride;
1'[(1-ethylpiperidin-4-yl)methyl]spiro[furo[2,3-f][1,3]benzodioxole-7,3'-indol]-2'(1'H)-one hydrochloride;
1'[(1-cyclohexylpiperidin-4-yl)methyl]spiro[furo[2,3-f][1,3]benzodioxole-7,3'-indol]-2'(1'H)-one hydrochloride;
1'{(1-cyclopropylmethyl)piperidin-4-yl]methyl}spiro[furo[2,3-f][1,3]benzodioxole-7,3'-indol]-2'(1'H)-one hydrochloride;
1'[(1-cyclopentylpiperidin-4-yl)methyl]spiro[furo[2,3-f][1,3]benzodioxole-7,3'-indol]-2'(1'H)-one hydrochloride;
1'{[1-(pyridine-3-ylmethyl)piperidin-4-yl]methyl}spiro[furo[2,3-f][1,3]benzodioxole-7,3'-indol]-2'(1'H)-one hydrochloride;
1'{[1-(3-methylbutyl)piperidin-4-yl]methyl}spiro[furo[2,3-f][1,3]benzodioxole-7,3'-indol]-2'(1'H)-one hydrochloride;
1'{[1-(1-ethylpropyl)piperidin-4-yl]methyl}spiro[furo[2,3-f][1,3]benzodioxole-7,3'-indol]-2'(1'H)-one hydrochloride;
1'[(1-cyclobutylpiperidin-4-yl)methyl]spiro[furo[2,3-f][1,3]benzodioxole-7,3'-indol]-2'(1'H)-one hydrochloride;
1'[(1-isopropylpiperidin-4-yl)methyl]spiro[furo[2,3-f][1,3]benzodioxole-7,3'-indol]-2'(1'H)-one hydrochloride;
1'{[1-(pyridin-2-ylmethyl)piperidin-4-yl]methyl}spiro[furo[2,3-f][1,3]benzodioxole-7,3'-indol]-2'(1'H)-one hydrochloride;
1'{[1-(2-thienylmethyl)piperidin-4-yl]methyl}spiro[furo[2,3-f][1,3]benzodioxole-7,3'-indol]-2'(1'H)-one hydrochloride;
1'-({1-[3-(methylthio)propyl]piperidin-4-yl}methyl)spiro[furo[2,3-f][1,3]benzodioxole-7,3'-indol]-2'(1'H)-one hydrochloride;
1'{[1-(tetrahydro-2H-pyran-4-yl)piperidin-4-yl]methyl}spiro[furo[2,3-f][1,3]benzodioxole-7,3'-indol]-2'(1'H)-one hydrochloride;
1'-{[1-(3,3-dimethylbutyl)piperidin-4-yl]methyl}spiro[furo[2,3-f][1,3]benzodioxole-7,3'-indol]-2'(1'H)-one hydrochloride;
7'-fluoro-1-[(1-isopropylpiperidin-4-yl)methyl]spiro[furo[2,3-f][1,3]benzodioxole-7,3'-indol]-2(1H)-one hydrochloride;
1'-[(6-methylpyridin-3-yl)methyl]spiro[furo[2,3-f][1,3]benzodioxole-7,3'-indol]-2'(1H)-one hydrochloride;
1'-[(6-methoxypyridin-3-yl)methyl]spiro[furo[2,3-f][1,3]benzodioxole-7,3'-indol]-2'(1'H)-one;
1-[(6-chloropyridin-3-yl)methyl]spiro[furo[2,3-f][1,3]benzodioxole-7,3'-indol]-2'(1'H)-one;
1'-{[6-(dimethylamino)pyridin-3-yl]methyl}spiro[furo[2,3-f][1,3]benzodioxole-7,3'-indol]-2'(1'H)-one hydrochloride;
1'-[(6-morpholin-4-ylpyridin-3-yl)methyl]spiro[furo[2,3-f][1,3]benzodioxole-7,3'-indol]-2'(1'H)-one hydrochloride;
1'-[(6-pyrrolidin-1-ylpyridin-3-yl)methyl]spiro[furo[2,3-f][1,3]benzodioxole-7,3'-indol]-2'(1'H)-one hydrochloride;
1'-[(5-methylisoxazol-4-yl)methyl]spiro[furo[2,3-f][1,3]benzodioxole-7,3'-indol]-2'(1'H)-one;
1'-(tetrahydro-2H-pyran-4-ylmethyl)spiro[furo[2,3-f][1,3]benzodioxole-7,3'-indol]-2'(1'H)-one;
1'(2,1,3-benzoxadiazol-5-ylmethyl)spiro[furo[2,3-f][1,3]benzodioxole-7,3'-indol]-2'(1'H)-one;
1'[(1-methyl-1H-benzotriazol-6-yl)methyl]spiro[furo[2,3-f][1,3]benzodioxole-7,3'-indol]-2'(1'H)-one;
tent-butyl 4-[(2'-oxo-5,6-dihydrospiro[benzo[1,2-b:5,4-b']difuran-3,3'-indol]-1'(2'H)-yl)methyl]piperidine 1-carboxylate;
1'-(pyridin-2-ylmethyl)-5,6-dihydrospiro[benzo[1,2-b:5,4-b']difuran-3,3'-indol]2'(1'H)-one hydrochloride;
4'-bromo-1'-{[5-(trifluoromethyl)-2-furyl]methyl}spiro[furo[2,3-f][1,3]benzodioxole-7,3'-indol]-2'(1'H)-one;
4'-bromo-1'-{[5-(trifluoromethyl)-2-furyl]methyl}-5,6-dihydrospiro[benzo[1,2-b:5,4-b']difuran-3,3'-indol]-2'(1'H)-one;
1'-[(3,5-dimethylisoxazol-4-yl)methyl]spiro[furo[2,3-f][1,3]benzodioxole-7,3'-indol]-2'(1'H)-one;
1'-(2-furylmethyl)spiro[furo[2,3-f][1,3]benzodioxole-7,3'-indol]-2'(1'H)-one;
1'-(1,2,4-oxadiazol-3-ylmethyl)spiro[furo[2,3-f][1,3]benzodioxole-7,3'-indol]-2'(1'H)-one;
1-{[5-(3-chlorophenyl)-2-furyl]methyl}spiro[furo[2,3-f][1,3]benzodioxole-7,3'-indol]-2'(1'H)-one;
1'-[(2-isopropyl-1,3-oxazol-4-yl)methyl]spiro[furo[2,3-f][1,3]benzodioxole-7,3'-indol]-2'(1'H)-one;
1-[(1-methyl-1H-benzimidazol-2-yl)methyl]spiro[furo[2,3-f][1,3]benzodioxole-7,3'-indol]-2'(1'H)-one;
1'-[(2-oxo-1,3-benzothiazol-3(2H)-yl)methyl]spiro[furo[2,3-f][1,3]benzodioxole-7,3'-indol]-2'(1'H)-one;
1-[(5-chloro-2-thienyl)methyl]-5'-fluorospiro[furo[2,3-f][1,3]benzodioxole-7,3'-indol]-2'(1'H)-one;
1'-[(5-chloro-2-furyl)methyl]spiro[furo[2,3-f][1,3]benzodioxole-7,3'-indol]-2'(1'H)-one;
1'-[(4-hydroxy-1,2,2,6,6-pentamethylpiperidin-4-yl)methyl]spiro[furo[2,3-f][1,3]benzodioxole-7,3'-indol]-2'(1'H)-one;
1'-{[5-(2-chlorophenyl)-2-furyl]methyl}spiro[furo[2,3-f][1,3]benzodioxole-7,3'-indol]-2'(1'H)-one;
1-[(5-methyl-2-furyl)methyl]spiro[furo[2,3-f][1,3]benzodioxole-7,3'-indol]-2'(1'H)-one;
1-[(5-bromo-2-furyl)methyl]spiro[furo[2,3-f][1,3]benzodioxole-7,3'-indol]-2'(1'H)-one;
1'-[(5-chloro-2-thienyl)methyl]spiro[furo[2,3-f][1,3]benzodioxole-7,3'-indol]-2'(1'H)-one;
1'-{[3-hydroxy-5-(trifluoromethyl)-2-thienyl]methyl}spiro[furo[2,3-f][1,3]benzodioxole-7,3'-indol]-2'(1'H)-one;
1'-{[5-(2-trifluoromethylphenyl)-2-furyl]methyl}-4H-spiro[furo[2,3-g][1,3]benzodioxine-8,3'-indol]-2'(1'H)one;
1'[(2-chloro-1,3-thiazol-5-yl)methyl]spiro[furo[2,3-f][1,3]benzodioxole-7,3'-indol]-2'(1'H)-one;

1'-{[5-(trifluoromethyl)-2-thienyl]methyl}spiro[furo[2,3-f][1,3]benzodioxole-7,3'-indol]-2'(1'H)-one;

1'-{[3-methoxy-5-(trifluoromethyl)-2-thienyl]methyl}spiro[furo[2,3-f][1,3]benzodioxole-7,3'-indol]-2'(1'H)-one;

4'-methyl-1'-{[5-(trifluoromethyl)-2-furyl]methyl}spiro[furo[2,3-f][1,3]benzodioxole-7,3'-indol]-2'(1'H)-one;

5'-methyl-1'-{[5-(trifluoromethyl)-2-furyl]methyl}spiro[furo[2,3-f][1,3]benzodioxole-7,3'-indol]-2'(1'H)-one;

1'-({5-[4-(trifluoromethyl)phenyl]-1,2,4-oxadiazol-3-yl}methyl)spiro[furo[2,3-f][1,3]benzodioxole-7,3'-indol]-2'(1'H)-one;

1'-(2-thienylmethyl)spiro[furo[2,3-f][1,3]benzodioxole-7,3'-indol]-2'(1'H)-one;

5-[(2'-oxospiro[furo[2,3-f][1,3]benzodioxole-7,3'-indol]-1'(2'H)-yl)methyl]thiophene-2-carbonitrile;

5-[(2'-oxospiro[furo[2,3-f][1,3]benzodioxole-7,3'-indol]-1'(2'H)-yl)methyl]-2-furonitrile;

1'-{[5-(methylsulfonyl)-2-furyl]methyl}spiro[furo[2,3-f][1,3]benzodioxole-7,3'-indol]-2'(1'H)-one;

1'-[(6-oxo-1,6-dihydropyridin-3-yl)methyl]spiro[furo[2,3-f][1,3]benzodioxole-7,3'-indol]-2'(1'H)-one;

1'-[(1-methyl-6-oxo-1,6-dihydropyridin-3-yl)methyl]spiro[furo[2,3-f][1,3]benzodioxole-7,3'-indol]-2'(1'H)-one;

1'-[(5-chloro-1,3,4-thiadiazol-2-yl)methyl]spiro[furo[2,3-f][1,3]benzodioxole-7,3'-indol]-2'(1'H)-one;

1'-[(1-pyridin-2-ylpiperidin-4-yl)methyl]spiro[furo[2,3-f][1,3]benzodioxole-7,3'-indol]-2'(1'H)-one;

1'-[(1-phenyl-2-ylpiperidin-4-yl)methyl]spiro[furo[2,3-f][1,3]benzodioxole-7,3'-indol]-2'(1'H)-one;

1'-(pyridin-2-ylmethyl)-6-(trifluoromethoxy)spiro[1-benzofuran-3,3'-indol]-2'(1'H)-one hydrochloride;

1'-(2-piperidin-1-ylethyl)spiro[furo[2,3-f][1,3]benzodioxole-7,3'-indol]-2'(1'H)-one hydrochloride;

tert-butyl 4-[2-(2'-oxospiro[furo[2,3-f][1,3]benzodioxole-7,3'-indol]-1'(2'H)-yl)ethyl]piperidine-1-carboxylate;

1'-(2-piperidin-4-ylethyl)spiro[furo[2,3-f][1,3]benzodioxole-7,3'-indol]-2'(1'H)-one hydrochloride;

1'-[2-(1-cyclopentylpiperidin-4-yl)ethyl]spiro[furo[2,3-f][1,3]benzodioxole-7,3'-indol]-2'(1'H)-one hydrochloride;

1-[2-(1-isopropylpiperidin-4-yl)ethyl]spiro[furo[2,3-f][1,3]benzodioxole-7,3'-indol]-2'(1'H)-one hydrochloride;

1'-[2-(1-cyclobutylpiperidin-4-yl)ethyl]spiro[furo[2,3-f][1,3]benzodioxole-7,3'-indol]-2'(1'H)-one hydrochloride;

1'-{2-[1-(tetrahydro-2H-pyran-4-yl)piperidin-4-yl]ethyl}spiro[furo[2,3-f][1,3]benzodioxole-7,3'-indol]-2'(1'H)one hydrochloride;

1'-(3-pyrrolidin-1-ylpropyl)spiro[furo[2,3-f][1,3]benzodioxole-7,3'-indol]-2'(1'H)-one;

1-(3-piperidin-1-ylpropyl)spiro[furo[2,3-f][1,3]benzodioxole-7,3'-indol]-2'(1'H)-one; and 1'-[(5-fluoro-1H-benzimidazol-2-yl)methyl]spiro[furo[2,3-f][1,3]benzodioxole-7,3'-indol]-2'(1'H)-one.

Another embodiment of the invention are the compounds of formula (I) as set forth above in the Summary of the invention wherein:

at least one of j and k is 1 and the other is 0 or 1;

Q is —O—;

$R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—C(O)$OR^5$, —$R^8$—N($R^4$)$R^5$, —$R^8$—C(O)N($R^4$)$R^5$, —$R^8$—N($R^5$)C(O)$R^4$, —$R^8$—S(O)$_m$$R^4$ (where m is 0, 1 or 2), —$R^8$—CN, or —$R^8$—$NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m$$R^4$, —S(O)$_2$$CF_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)$OR^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

$R^{3a}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$NO_2$, —$R^8$—$OR^5$, —$R^8$—N($R^4$)$R^5$, —N=C($R^4$)$R^5$, —S(O)$_m$$R^4$, —S(O)$_2$$CF_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3b}$ and $R^{3c}$, together with the carbon ring atoms to which they are directly attached, may form a fused ring selected from dioxolyl or tetrahydrofuranyl, and $R^{3a}$ and $R^{3d}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

4'-(6-methoxypyridin-3-yl)-1'-{[5-(trifluoromethyl)-2-furyl]methyl}spiro[furo[2,3-f][1,3]benzodioxole-7,3'-indol]-2'(1'H)one;

4'-[6-(dimethylamino)pyridin-3-yl]-1'-{[5-(trifluoromethyl)-2-furyl]methyl}spiro[furo[2,3-f][1,3]benzodioxole-7,3'-indol]-2'(1'H)-one;

4'-(3-furyl)-1'-(pyridin-2-ylmethyl)-5,6-dihydrospiro[benzo[1,2-b:5,4-b']difuran-3,3'-indol]-2'(1'H)one;

1-(pyridin-2-ylmethyl)-4'-pyrimidin-5-yl-5,6-dihydrospiro[benzo[1,2-b:5,4-b']difuran-3,3'-indol]-2'(1'H)-one;

4'-pyridin-3-yl-1'-(pyridin-2-ylmethyl)-5,6-dihydrospiro[benzo[1,2-b:5,4-b']difuran-3,3'-indol]-2'(1'H)-one;

4'-(3-furyl)-1'-{[5-(trifluoromethyl)-2-furyl]methyl}-5,6-dihydrospiro[benzo[1,2-b:5,4-b']difuran-3,3'-indol]-2'(1'H)-one;

4'-quinolin-3-yl-1'-{[5-(trifluoromethyl)-2-furyl]methyl}spiro[furo[2,3-f][1,3]benzodioxole-7,3'-indol]-2'(1'H)-one;

4'-pyrimidin-5-yl-1'-{[5-(trifluoromethyl)-2-furyl]methyl}-5,6-dihydrospiro[benzo[1,2-b:5,4-b']difuran-3,3'-indol]-2'(1'H)-one;

tert-butyl 4-[(2'-oxo-4'-pyrimidin-5-ylspiro[furo[2,3-f][1,3]benzodioxole-7,3'-indol]-1'(2'H)-yl)methyl]piperidine-1-carboxylate;

tert-butyl 4-[(5,5-dimethyl-2'-oxo-5,6-dihydrospiro[benzo[1,2-b:5,4-b']difuran-3,3'-indol]-1'(2'H)-yl)methyl]piperidine-1-carboxylate;

5,5-dimethyl-1'-(piperidin-4-ylmethyl)-5,6-dihydrospiro[benzo[1,2-b:5,4-b']difuran-3,3'-indol]-2'(1'H)-one hydrochloride;

5,5-dimethyl-1-{[5-(trifluoromethyl)-2-furyl]methyl}-5,6-dihydrospiro[benzo[1,2-b:5,4-b']difuran-3,3'-indol]-2'(1'H)-one;

5,5-dimethyl-1'-(pyridin-3-ylmethyl)-5,6-dihydrospiro[benzo[1,2-b:5,4-b']difuran-3,3'-indol]-2'(1'H)one hydrochloride;

5,5-dimethyl-1'-(pyridin-2-ylmethyl)-5,6-dihydrospiro[benzo[1,2-b:5,4-b']difuran-3,3'-indol]-2'(1'H)-one hydrochloride;

1'-[(6-methylpyridin-3-yl)methyl]spiro[furo[2,3-f][1,3]benzodioxole-7,3'-indol]-2'(1'H)-one hydrochloride; and 1'-[(6-methoxypyridin-3-yl)methyl]spiro[furo[2,3-f][1,3]benzodioxole-7,3'-indol]-2'(1'H)-one.

Another embodiment of the invention are the compounds of formula (I) as set forth above in the Summary of the invention wherein:

at least one of j and k is 1 and the other is 0 or 1;

Q is —O—;

$R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, $—R^8—OR^5$, $—R^8—C(O)OR^5$, $—R^8—N(R^4)R^5$, $—R^8—C(O)N(R^4)R^5$, $—R^8—N(R^5)C(O)R^4$, $—R^8—S(O)_mR^4$ (where m is 0, 1 or 2), $—R^8—CN$, or $—R^8—NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $—R^8—CN$, $—R^8—NO_2$, $—R^8—OR^5$, $—R^8—N(R^4)R^5$, $—N=C(R^4)R^5$, $—S(O)_mR^4$, $—S(O)_2CF_3$, $—R^8—C(O)R^4$, $—C(S)R^4$, $—C(R^4)_2C(O)R^5$, $—R^8—C(O)OR^4$, $—C(S)OR^4$, $—R^8—C(O)N(R^4)R^5$, $—C(S)N(R^4)R^5$, $—N(R^5)C(O)R^4$, $—N(R^5)C(S)R^4$, $—N(R^5)C(O)OR^4$, $—N(R^5)C(S)OR^4$, $—N(R^5)C(O)N(R^4)R^5$, $—N(R^5)C(S)N(R^4)R^5$, $—N(R^5)S(O)_nR^4$, $—N(R^5)S(O)_nN(R^4)R^5$, $—R^8—S(O)_nN(R^4)R^5$, $—N(R^5)C(=NR^5)N(R^4)R^5$, and $—N(R^5)C(=N—CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $—R^8—CN$, $—R^8—NO_2$, $—R^8—OR^5$, $—R^8—N(R^4)R^5$, $—S(O)_mR^4$, $—R^8—S(O)_nN(R^4)R^5$, $—R^8—C(O)R^4$, $—R^8—C(O)OR^4$, $—R^8—C(O)N(R^4)R^5$, $—N(R^5)C(O)R^4$, and $—N(R^5)S(O)_nR^4$, wherein each m is independently 0, 1, or 2 and each n is independently 1 or 2;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $—R^8—NO_2$, $—R^8—OR^5$, $—R^8—N(R^4)R^5$, $—N=C(R^4)R^5$, $—S(O)_mR^4$, $—S(O)_2CF_3$, $—R^8—C(O)R^4$, $—C(S)R^4$, $—C(R^4)_2C(O)R^5$, $—R^8—C(O)OR^4$, $—C(S)OR^4$, $—R^8—C(O)N(R^4)R^5$, $—C(S)N(R^4)R^5$, $—N(R^5)C(O)R^4$, $—N(R^5)C(S)R^4$, $—N(R^5)C(O)OR^4$, $—N(R^5)C(S)OR^4$, $—N(R^5)C(O)N(R^4)R^5$, $—N(R^5)C(S)N(R^4)R^5$, $—N(R^5)S(O)_nR^4$, $—N(R^5)S(O)_nN(R^4)R^5$, $—R^8—S(O)_nN(R^4)R^5$, $—N(R^5)C(=NR^5)N(R^4)R^5$, and $—N(R^5)C(N=C(R^4)R^5)N(R^4)R^5$, wherein each m is independently 0, 1, or 2 and each n is independently 1 or 2;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention, selected from the group consisting of:

5-bromo-1-[(5-chloro-2-thienyl)methyl]spiro[1-benzofuran-3,3'-indol]-2'(1'H)-one;

1'-(pyridin-3-ylmethyl)-6-(trifluoromethoxy)spiro[1-benzofuran-3,3'-indol]-2'(1'H)-one hydrochloride;

6-(trifluoromethoxy)-1'-{[5-(trifluoromethyl)-2-furyl]methyl}spiro[1-benzofuran-3,3'-indol]-2'(1'H)-one;

2'-oxo-1-{[5-(trifluoromethyl)-2-furyl]methyl}-1,2'-dihydrospiro[1-benzofuran-3,3'-indol]-5-yl trifluoromethanesulfonate;

5-pyridin-3-yl-1'-{[5-(trifluoromethyl)-2-furyl]methyl}spiro[1-benzofuran-3,3'-indol]-2'(1'H)-one hydrochloride;

tert-butyl 3-(2'-oxo-1'-{[5-(trifluoromethyl)-2-furyl]methyl}-1',2'-dihydrospiro[1-benzofuran-3,3'-indol]-5-yl)piperidine-1-carboxylate; and 5-pyridin-4-yl-1'-{[5-(trifluoromethyl)-2-furyl]
methyl}spiro[1-benzofuran-3,3'-indol]-2'(1'H)-one
hydrochloride.

Another embodiment of the invention are the compounds of formula (I) as set forth above in the Summary of the invention wherein:

j is 0 and k is 1 or 2;

Q is —O—;

$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^8$, —$R^8$—C(O)N($R^4$)$R^8$, —S(O)$_2$—$R^5$, —$R^9$—S(O)$_m$—$R^8$ (where m is 0, 1 or 2), —$R^8$—O$R^5$, —$R^8$—CN, —$R^9$—P(O)(O$R^5$)$_2$, or —$R^9$—O—$R^9$—O$R^5$;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused ring selected from cycloalkyl, heterocyclyl, aryl or heteroaryl;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C($R^{1a}$)H—, —C(O)—, —CF$_2$—, —C(O)O— or —N($R^5$)C(O)—;

$R^{1a}$ is hydrogen or —O$R^5$;

$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;

or $R^1$ is aralkyl substituted by —C(O)N($R^6$)$R^7$ where:

$R^6$ is hydrogen, alkyl, aryl or aralkyl; and $R^7$ is hydrogen, alkyl, haloalkyl, —$R^9$—CN, —$R^9$—O$R^5$, —$R^9$—N($R^4$)$R^5$, aryl, aralkyl, cycloalkyl, cycloalkylalkyl, heterocyclyl, heterocyclylalkyl, heteroaryl, heteroarylalkyl;

or $R^6$ and $R^7$, together with the nitrogen to which they are attached, form a heterocyclyl or heteroaryl;

and wherein each aryl, aralkyl, cycloalkyl, cycloalkylalkyl, heterocyclyl, heterocyclylalkyl, heteroaryl and heteroaryl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—O$R^5$, heterocyclyl and heteroaryl;

or $R^1$ is aralkyl optionally substituted by one or more substituents selected from the group consisting of —$R^8$—O$R^5$, —C(O)O$R^5$, halo, haloalkyl, alkyl, nitro, cyano, aryl, aralkyl, heterocyclyl and heteroaryl;

or $R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;

$R^{12}$ is hydrogen, alkyl, aryl, aralkyl or —C(O)$R^5$;

and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;

or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—O$R^5$, —$R^8$—C(O)O$R^5$, —$R^8$—N($R^4$)$R^5$, —$R^8$—C(O)N($R^4$)$R^5$, —$R^8$—N($R^5$)C(O)$R^4$, —$R^8$—S(O)$_m$$R^4$ (where m is 0, 1 or 2), —$R^8$—CN, or —$R^8$—NO$_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —S(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_m R^4$, —$S(O)_2 CF_3$, —$R^8$—C(O)$R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;
Q is —$C(R^{1a})H$—;
$R^{1a}$ is hydrogen or —$OR^5$;
$R^1$ is hydrogen, alkyl, alkenyl, alkynyl, haloalkyl, aryl, cycloalkyl, cycloalkylalkyl, heteroaryl, heterocyclyl, —$R^8$—$C(O)R^5$, —$R^8$—$C(O)OR^5$, —$R^8$—$C(O)N(R^4)R^5$, —$S(O)_2$—$R^5$, —$R^9$—$S(O)_m$—$R^5$ (where m is 0, 1 or 2), —$R^8$—$OR^5$, —$R^8$—CN, —$R^9$—$P(O)(OR^5)_2$, or —$R^9$—O—$R^9$—$OR^5$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_m R^4$, —$S(O)_2 CF_3$, —$R^8$—C(O)$R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(=N-CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —$S(O)_m R^4$, —$R^8$—$S(O)_n N(R^4)R^5$, —$R^8$—$C(O)R^4$, —$R^8$—$C(O)OR^4$, —$R^5$—$C(O)N(R^4)R^5$, —$N(R^5)C(O)R^4$, and —$N(R^5)S(O)_n R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^5$—CN—$R^5$—$NO_2$, —$R^5$—$OR^5$, —$R^5$—$N(R^4)R^5$, —N=$C(R^4)R^5$, —$S(O)_m R^4$, —$S(O)_2 CF_3$, —$R^5$—C(O)$R^4$, —$C(S)R^4$, —$C(R^4)_2 C(O)R^5$, —$R^5$—$C(O)OR^4$, —$C(S)OR^4$, —$R^5$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^5$—$S(O)_n N(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3a}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;
Q is —C($R^{1a}$)H—;
$R^{1a}$ is hydrogen or —$OR^5$;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—$OR^5$, —$R^8$—CN, —$R^9$—P(O)(O$R^5$)$_2$, or —$R^9$—O—$R^9$—$OR^5$;
$R^{2a}$, $R^{2b}$, $R^{2c}$ and $R^{2d}$ are each hydrogen;
$R^{2a}$, $R^{2b}$, $R^{2c}$ and $R^{2b}$ are each hydrogen;
$R^{3a}$ and $R^{3d}$ are each hydrogen;
$R^{3b}$ and $R^{3c}$, together with the carbon ring atoms to which they are directly attached, form a fused ring selected from cycloalkyl, heterocyclyl, aryl or heteroaryl;
each $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl;
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention wherein:
j is 0 and k is 1 or 2;
Q is —C($R^{1a}$)H—;
$R^{1a}$ is hydrogen or —$OR^5$;
$R^1$ is pentyl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused dioxolyl ring; and
each $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl.

Another embodiment of the invention are the compounds of formula (I) as set forth above in the Summary of the invention, selected from the group consisting of:
1-pentyl-6,7-dihydrospiro[indeno[5,6-d][1,3]dioxole-5,3'-indol]-2'(1'H)-one;
1-pentyl-7',8'-dihydro-6'H-spiro[indole-3,5'-naphtho[2,3-f][1,3]dioxol]-2(1H)-one; and
7-methoxy-1'-pentyl-6,7-dihydrospiro[indeno[5,6-f][1,3]dioxole-5,3'-indol]-2'(1'H)-one.

Another embodiment of the invention are the compounds of formula (I) as set forth above in the Summary of the invention wherein:
j is 0 and k is 1 or 2;
Q is —C(O)—, —CF$_2$—, —C(O)O— or —N($R^5$)C(O)—;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—$OR^5$, —$R^8$—CN, —$R^9$—P(O)(O$R^5$)$_2$, or —$R^9$—O—$R^9$—$OR^5$;
or $R^1$ is aralkyl substituted by —C(O)N($R^6$)$R^7$ where:
$R^6$ is hydrogen, alkyl, aryl or aralkyl; and
$R^7$ is hydrogen, alkyl, haloalkyl, —$R^9$—$OR^5$, —$R^9$—N($R^4$)$R^5$, aryl, aralkyl, cycloalkyl, cycloalkylalkyl, heterocyclyl, heterocyclylalkyl, heteroaryl, heteroarylalkyl;
or $R^6$ and $R^7$, together with the nitrogen to which they are attached, form a heterocyclyl or heteroaryl;
and wherein each aryl, aralkyl, cycloalkyl, cycloalkylalkyl, heterocyclyl, heterocyclylalkyl, heteroaryl and heteroaryl groups for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;
or $R^1$ is aralkyl optionally substituted by one or more substituents selected from the group consisting of —$R^8$—$OR^5$, —C(O)O$R^6$, halo, haloalkyl, alkyl, nitro, cyano, aryl, aralkyl, heterocyclyl and heteroaryl;
or $R^1$ is —$R^6$—N($R^{10}$)$R^{11}$, —$R^9$—N($R^{12}$)C(O)$R^{11}$ or —$R^6$—N($R^{10}$)C(O)N($R^{16}$)$R^{11}$ where:
each $R^{10}$ is hydrogen, alkyl, aryl, aralkyl or heteroaryl;
each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—$OR^5$, or —$R^9$—CN;
$R^{12}$ is hydrogen, alkyl, aryl, aralkyl or —C(O)$R^5$;
and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—$OR^5$, —$R^8$—C(O)$R^5$, heterocyclyl and heteroaryl;
or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—C(O)O$R^5$, —$R^8$—N($R^4$)$R^5$, —$R^8$—C(O)N($R^4$)$R^5$, —$R^8$—N($R^5$)C(O)$R^4$, —$R^8$—S(O)$_m$$R^4$ (where m is 0, 1 or 2), —$R^8$—CN, or —$R^8$—NO$_2$;
$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$OR^5$, —$R^8$—N($R^4$)$R^5$, —N═C($R^4$)$R^5$, —S(O)$_m$$R^4$, —S(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(═N$R^5$)N($R^4$)$R^5$, and —N($R^5$)C(═N—CN)N($R^4$)$R^5$, wherein each m is independently 0, 1, or 2 and each n is independently 1 or 2;
and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—$OR^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —$S(O)_mR^4$, —$S(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^5$—$S(O)_nN(R^4)R^5$, —$N(R^5)C(=NR^5)N(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;
Q is —C(O)—, —$CF_2$—, —C(O)O— or —$N(R^5)C(O)$—;
$R^1$ is hydrogen, alkyl, alkenyl, alkynyl, haloalkyl, aryl, cycloalkyl, cycloalkylalkyl, heteroaryl, heterocyclyl, —$R^8$—$C(O)R^5$, —$R^8$—$C(O)OR^5$, —$R^8$—$C(O)N(R^4)R^5$, —$S(O)_2$—$R^5$, —$R^9$—$S(O)_mR^5$ (where m is 0, 1 or 2), —$R^8$—$OR^5$, —$R^9$—$P(O)(OR^5)_2$, or —$R^9$—O—$R^9$—$OR^5$;

$R^{2a}$, $R^{2b}$, $R^{2c}$ and $R^{2d}$ are each hydrogen;
$R^{2a}$, $R^{2b}$, $R^{2c}$ and $R^{2d}$ are each hydrogen;
$R^{3a}$ and $R^{3d}$ are each hydrogen;

$R^{3b}$ and $R^{3c}$, together with the carbon ring atoms to which they are directly attached, form a fused ring selected from cycloalkyl, heterocyclyl, aryl or heteroaryl;

each $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;
Q is —C(O)—, —$CF_2$—, —C(O)O— or —$N(R^5)C(O)$—;
$R^1$ is pentyl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused dioxolyl ring; and each $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl and heteroaryl.

Another embodiment of the invention are the compounds of formula (I) as set forth above in the Summary of the invention, selected from the group consisting of:

1'-pentylspiro[indeno[5,6-d][1,3]dioxole-5,3'-indole]-2',7(1'H,6H)-dione;

1-pentyl-6'H-spiro[indole-3,5'-naphtho[2,3-d][1,3]dioxole]-2,8'(1'H,7'H)-dione;

8',8'-difluoro-1-pentyl-7',8'-dihydro-6'H-spiro[indole-3,5'-naphtho[2,3-d][1,3]dioxol]-2(1H)-one;

1'-pentyl-6,7-dihydro-5H-spiro[1,3-dioxolo[4,5-g]isoquinoline-8,3'-indole]-2',5(1H)-dione; and 1'-hexylspiro[1,3-dioxolo[4,5-g]chromene-8,3'-indole]-2',6(1'H,7H)-dione.

One embodiment of the invention is the method of treating or preventing hypercholesterolemia in a mammal, wherein the method comprises administering to the mammal in need thereof a therapeutically effective amount of a compound of formula (I) as set forth above for the embodiments of the compounds of formula (I).

Another embodiment of the invention is the method of treating or preventing benign prostatic hyperplasia in a mammal, wherein the method comprises administering to the mammal in need thereof a therapeutically effective amount of a compound of formula (I) as set forth above for the embodiments of the compounds of formula (I).

Another embodiment of the invention is the method of treating or preventing pruritis in a mammal, wherein the method comprises administering to the mammal in need thereof a therapeutically effective amount of a compound of formula (I) as set forth above for the embodiments of the compounds of formula (I).

Another embodiment of the invention is the method of treating or preventing cancer in a mammal, wherein the method comprises administering to the mammal in need thereof a therapeutically effective amount of a compound of formula (I) as set forth above for the embodiments of the compounds of formula (I).

Specific embodiments of the compounds of formula (I) are described in more detail below in the Preparation of the Compounds of the Invention.

Utility and Testing of the Compounds of the Invention

The compounds of the invention modulate, preferably inhibit, ion flux through a voltage-dependent sodium channel in a mammal, especially in a human. Any such modulation, whether it be partial or complete inhibition or prevention of ion flux, is sometimes referred to herein as "blocking" and corresponding compounds as "blockers". In general, the compounds of the invention modulates the activity of a sodium channel downwards, inhibits the voltage-dependent activity of the sodium channel, and/or reduces or prevents sodium ion flux across a cell membrane by preventing sodium channel activity such as ion flux.

The compounds of the invention inhibit the ion flux through a voltage-dependent sodium channel. Preferably, the compounds are state or frequency dependent modifers of the sodium channels, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, while not wishing to be bound to any particular mechanism of action, the compounds and pharmaceutical compositions of the invention are useful in the treatment and/or prevention of benign prostatic hyperplasia (BPH), hypercholesterolemia, cancer and/or pruritus (itch) in a mammal, preferably a human.

Benign prostatic hyperplasia (BPH), also known as benign prostatic hypertrophy, is one of the most common diseases affecting aging men. BPH is a progressive condition which is characterized by a nodular enlargement of prostatic tissue resulting in obstruction of the urethra. Consequences of BPH can include hypertrophy of bladder smooth muscle, a decompensated bladder, acute urinary retention and an increased incidence of urinary tract infection.

BPH has a high public health impact and is one of the most common reasons for surgical intervention among elderly men. Attempts have been made to clarify the etiology and pathogenesis and, to that end, experimental models have been developed. Spontaneous animal models are limited to the chimpanzee and the dog. BPH in man and the dog share many common features. In both species, the development of BPH occurs spontaneously with advanced age and can be prevented by early/prepubertal castration. A medical alternative to surgery is very desirable for treating BHP and the consequences.

The prostatic epithelial hyperplasia in both man and the dog is androgen sensitive, undergoing involution with androgen deprivation and resuming epithelial hyperplasia when androgen is replaced. Cells originating from the prostate gland have been shown to express high levels of voltage gated sodium channels. Immunostaining studies clearly demonstrated evidence for voltage gated sodium channels in prostatic tissues (*Prostate Cancer Prostatic Dis.* 2005; 8(3):266-73).

Hypercholesterolemia, i.e., elevated blood cholesterol, is an established risk factor in the development of, e.g., atherosclerosis, coronary artery disease, hyperlipidemia, stroke, hyperinsulinemias, hypertension, obesity, diabetes, cardiovascular diseases (CVD), myocardial ischemia, and heart attack. Thus, lowering the levels of total serum cholesterol in individuals with high levels of cholesterol has been known to reduce the risk of these diseases. The lowering of low density lipoprotein cholesterol in particular is an essential step in the prevention of CVD. Although there are a variety of hypercholesterolemia therapies, there is a continuing need and a continuing search in this field of art for alternative therapies.

The invention provides compounds which are useful as antihypercholesterolemia agents and their related conditions. The present compounds may act in a variety of ways. While not wishing to be bound to any particular mechanism of action, the compounds may be direct or indirect inhibitors of the enzyme acyl CoA: cholesterol acyl transferase (ACAT) that results in inhibition of the esterification and transport of cholesterol across the intestinal wall. Another possibility may be that the compounds of the invention may be direct or indirect inhibitors of cholesterol biosynthesis in the liver. It is possible that some compounds of the invention may act as both direct or indirect inhibitors of ACAT and cholesterol biosynthesis.

Pruritus, commonly known as itch, is a common dermatological condition. While the exact causes of pruritis are complex and poorly understood, there has long been acknowledged to have interactions with pain. In particular, it is believed that sodium channels likely communicate or propagate along the nerve axon the itch signals along the skin. Transmission of the itch impulses results in the unpleasant sensation that elicits the desire or reflex to scratch.

From a neurobiology level, it is believed that there is a shared complexity of specific mediators, related neuronal pathways and the central processes of itch and pain and recent data suggest that there is a broad overlap between pain- and itch-related peripheral mediators and/or receptors (Ikoma et al., *Nature Reviews Neuroscience,* 7:535-547, 2006). Remarkably, pain and itch have similar mechanisms of neuronal sensitization in the peripheral nervous system and the central nervous system but exhibits intriguing differences as well.

For example, the mildly painful stimuli from scratching are effective in abolishing the itch sensation. In contrast, analgesics such as opioids can generate severe pruritus. The antagonistic interaction between pain and itch can be exploited in pruritus therapy, and current research concentrates on the identification of common targets for future analgesic and antipruritic therapy.

Compounds of the present invention have been shown to have analgesic effects in a number of animal models at oral doses ranging from 1 mg/kg to 100 mg/kg. The compounds of the invention can also be useful for treating pruritus.

The types of itch or skin irritation, include, but are not limited to:

a) psoriatic pruritis, itch due to hemodyalisis, aguagenic pruritus, and itching caused by skin disorders (e.g., contact dermatitis), systemic disorders, neuropathy, psychogenic factors or a mixture thereof;

b) itch caused by allergic reactions, insect bites, hypersensitivity (e.g., dry skin, acne, eczema, psoriasis), inflammatory conditions or injury;

c) itch associated with vulvar vestibulitis; and d) skin irritation or inflammatory effect from administration of another therapeutic such as, for example, antibiotics, antivirals and antihistamines.

The compounds of the invention are also useful in treating or preventing certain hormone sensitive cancers, such as prostate cancer (adenocarcinoma), breast cancer, ovarian cancer, testicular cancer, thyroid neoplasia. The voltage gated sodium channels have been demonstrated to be expressed in prostate and breast cancer cells. Up-regulation of neonatal Na(v)1.5 occurs as an integral part of the metastatic process in human breast cancer and could serve both as a novel marker of the metastatic phenotype and a therapeutic target (*Clin. Cancer Res.* 2005, Aug. 1; 11(15): 5381-9). Functional expression of voltage-gated sodium channel alpha-subunits, specifically $Na_v1.7$, is associated with strong metastatic potential in prostate cancer (CaP) in vitro. Voltage-gated sodium channel alpha-subunits immunostaining, using antibodies specific to the sodium channel alpha subunit was evident in prostatic tissues and markedly stronger in CaP vs non-CaP patients (Prostate Cancer Prostatic Dis. 2005; 8(3): 266-73)

The compounds of the invention are also useful in treating or preventing symptoms associated with BPH such as, but not limited to, acute urinary retention and urinary tract infection.

The compounds of the invention are also useful in treating or preventing certain endocrine imbalances or endocrinopathies such as congenital adrenal hyperplasia, hyperthyroidism, hypothyroidism, osteoporosis, osteomalacia, rickets, Cushing's Syndrome, Conn's syndrome, hyperaldosteronism, hypogonadism, hypergonadism, infertility, fertility and diabetes.

The present invention readily affords many different means for identification of therapeutic agents, especially as sodium channel modulating agents. Identification of the therapeutic agents can be assessed using a variety of in vitro and in vivo assays, e.g., measuring current, measuring membrane potential, measuring ion flux, (e.g. sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

A competitive binding assay with known sodium channel toxins such as tetrodotoxin, alpha-scorpion toxins, aconitine, BTX and the like, may be suitable for identifying potential therapeutic agents with high selectivity for a particular sodium channel. The use of BTX in such a binding assay is well known and is described in McNeal, E. T., et al., *J. Med. Chem.* (1985), 28(3):381-8; and Creveling, C. R., et al., *Methods in Neuroscience, Vol.* 8: *Neurotoxins* (Conn P M Ed) (1992), pp. 25-37, Academic Press, New York.

These assays can be carried out in cells, or cell or tissue extracts expressing the channel of interest in a natural endogenous setting or in a recombinant setting. The assays that can be used include plate assays which measure Na+ influx through surrogate markers such as $^{14}C$-guanidine influx or determine cell depolarization using fluorescent dyes such as the FRET based and other fluorescent assays or a radiolabelled binding assay employing radiolabelled aconitine, BTX, TTX or STX. More direct measurements can be made with manual or automated electrophysiology systems. The guanidine influx assay is explained in more detail below in the Biological Assays section.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the sodium channel, such as the open state, closed state or the resting state, or which block transition from open to closed, closed to resting or resting to open. Those skilled in the art are generally familiar with such assays.

Binding assays are also available, however these are of only limited functional value and information content. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures subsecond responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they alleviate the diseases or conditions, especially benign prostatic hyperplasia (BPH), hypercholesterolemia, cancer and pruritis (itch), with minimal adverse events. The assays described below in the Biological Assays Section are useful in assessing the biological activity of the instant compounds.

Typically, a successful therapeutic agent of the present invention will meet some or all of the following criteria. Oral availability should be at or above 20%. Animal model efficacy is less than about 0.1 μg to about 100 mg/Kg body weight and the target human dose is between 0.1 μg to about 100 mg/Kg body weight, although doses outside of this range may be acceptable ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 μM, preferably below 1 μM and most preferably below 50 nM. The $IC_{50}$ ("Inhibitory Concentration—50%") is a measure of the amount of compound required to achieve 50% inhibition of ion flux through a sodium channel, over a specific time period, in an assay of the invention. Compounds of the present invention in the guanidine influx assay have demonstrated $IC_{50}$'s ranging from less than a nanomolar to less than 10 micromolar.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

A compound of the invention, as set forth above in the Summary of the Invention, as a stereoisomer, enantiomer or tautomer or mixtures thereof, or a pharmaceutically acceptable salt, solvate or prodrug thereof, and/or a pharmaceutical composition of the invention, comprising a pharmaceutically acceptable excipient and one or more compounds of the invention, as set forth above in the Summary of the Invention, as a stereoisomer, enantiomer or tautomer or mixtures thereof, or a pharmaceutically acceptable salt, solvate or prodrug thereof, can also be used in the preparation of a medicament for the treatment and/or prevention of hypercholesterolemia, benign prostatic hyperplasia, pruritis, and/or cancer in a mammal.

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., The Merck Manual, 16$^{th}$ edition, Merck and Co., Rahway, N.J., 1992; Goodmanetna., eds., Goodman and Cilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. Effective amounts of a diagnostic pharmaceutical compound or composition of the invention are from about 0.1 µg to about 100 mg/Kg body weight, administered at intervals of 4-72 hours, for a period of 2 hours to 1 year, and/or any range or value therein, such as 0.0001-0.001, 0.001-0.01, 0.01-0.1, 0.1-1.0, 1, 0-10, 5-10, 10-20, 20-50 and 50-100 mg/Kg, at intervals of 1-4, 4-10, 10-16, 16-24, 24-36, 24-36, 36-48, 48-72 hours, for a period of 1-14, 14-28, or 30-44 days, or 1-24 weeks, or any range or value therein. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Patent No. WO 98/50016.

Current methods for ocular delivery include topical administration (eye drops), subconjunctival injections, periocular injections, intravitreal injections, surgical implants and iontophoresis (uses a small electrical current to transportionized drugs into and through body tissues). Those skilled in the art would combine the best suited excipients with the compound for safe and effective intra-occular administration.

The most suitable route will depend on the nature and severity of the condition being treated. Those skilled in the art are also familiar with determining administration methods (oral, intravenous, inhalation, sub-cutaneous, rectal etc.), dosage forms, suitable pharmaceutical excipients and other matters relevant to the delivery of the compounds to a subject in need thereof.

Kits-of-Parts

The present invention also provides kits that contain a pharmaceutical composition which includes one or more compounds of the above formulae. The kit also includes instructions for the use of the pharmaceutical composition for modulating the activity of ion channels, for the treatment of benign prostatic hyperplasia (BPH), hypercholesterolemia, cancer and pruritus (itch), as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of this invention, i.e., compounds of formula (I):

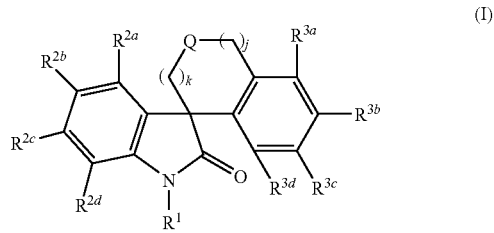

wherein k, j, Q, $R^1$, $R^{2a}$, $R^{2b}$, $R^{2c}$, $R^{2d}$, $R^{3a}$, $R^{3b}$, $R^{3c}$, and $R^{3d}$ are as defined herein, as a stereoisomer, enantiomer, tautomer thereof or mixtures thereof; or a pharmaceutically acceptable salt, solvate or prodrug thereof.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one skilled in the art would be able to make these compounds by similar methods or by methods known to one skilled in the art. It is also understood that one skilled in the art would be able to make in a similar manner as described below other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry: Reactions, Mechanisms, and Structure*, 5th edition (Wiley, December 2000)) or prepared as described herein.

In the following Reaction Schemes, $R^1$, $R^{2a}$, $R^{2b}$, $R^{2c}$, $R^{2d}$, $R^{3a}$, $R^{3b}$, $R^{3c}$ and $R^{3d}$ are defined as in the Specification unless specifically defined otherwise. X is Cl or Br. $R^{11}$ is an alkyl group.

In general, the compounds of formula (I) of the invention where Q is —O—, j is 0 and k is 1 can be synthesized following the general procedure as described below in REACTION SCHEME 1. As set forth below, an isatin compound of formula (101) is alkylated with the chloro or bromo compound of formula (102) to afford the product of formula (103). The phenol compound of formula (104) is treated with a Grignard reagent of formula (105) at low temperature (0° C.) to form the phenoxymagnesium halide intermediate which reacts with the keto-carbonyl group of the isatin compound of formula (103) in a solvent, such as, but not limited to, methylene chloride or toluene, to afford the oxindole of formula (106). The compound of formula (107) is obtained after the removal of the hydroxyl group at C-3 position of the oxindole by treating the compound of formula (106) with silane such as triethylsilane. The compound of formula (107) can also be achieved by treating the compound of formula (106) with $SOCl_2/NEt_3$ then reduction with Zn dust. Compound of formula (107) is treated with a silyl compound, such as, but not limited to, trimethylsilyl chloride, to generate the silyl ether intermediate which is treated with ytterbium (III) trifluoromethanesulfonate and formaldehyde to afford the compound of formula (108). Alternatively, compound of formula (108) can be obtained by treating the compound of formula (107) with a base, such as, but not limited to, LiOH, $iPr_2NH$, LDA, and subsequently reacting with formaldehyde. Intramolecular cyclization via Mitsunobu reaction affords the compound of formula (I) of the invention where Q is —O—, j is 0 and k is 1.

REACTION SCHEME 1

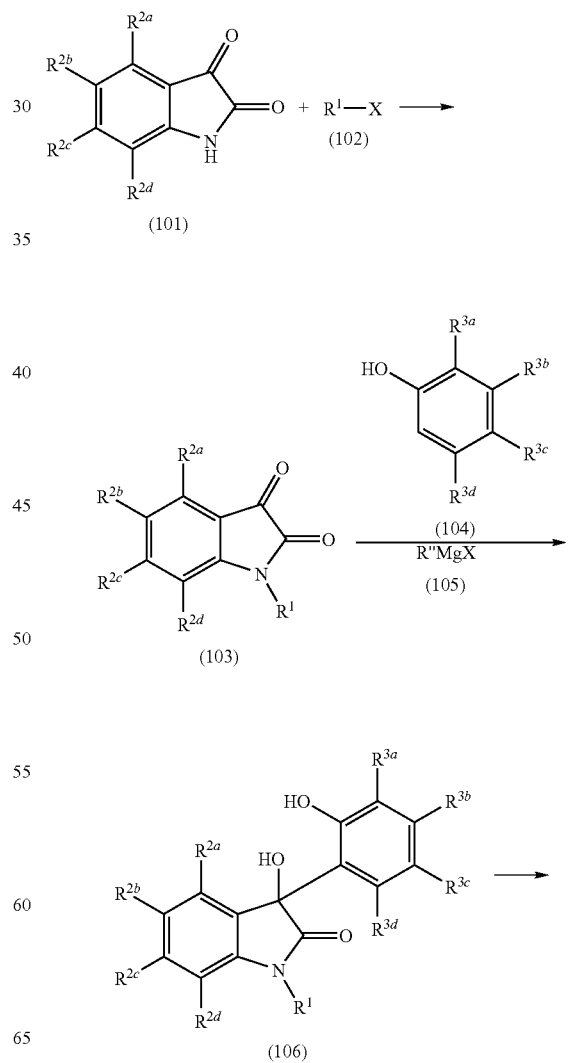

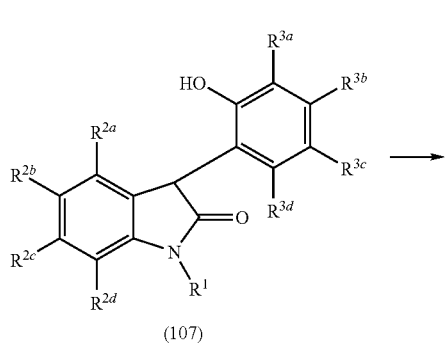

(107)

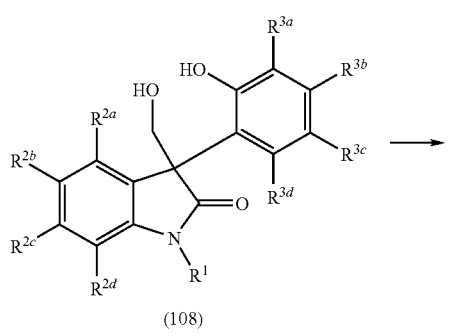

(108)

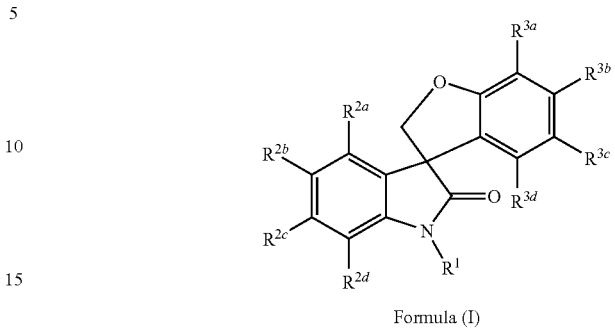

Formula (I)

REACTION SCHEME 1.1 below illustrates a schematic synthesis of amide and heterocyclic compounds as compounds of formula (I). When $R^1$ consists of an ester group, a compound such as a compound of formula (109) (in which A is alkyl or aralkyl) can be converted to the corresponding carboxylic acid compound of formula (110) by treatment of a compound of formula (109) with a base such as, but not limited to, lithium hydroxide, sodium hydroxide or potassium hydroxide, in a mixed solvent such as, but not limited to, tetrahydrofuran or methanol with water. The acid compound of formula (110) can be converted to a mixed anhydride, by treatment with iso-butyl chloroformate in the presence of a base such as, but not limited to, N-methylmorpholine, or to the corresponding acid chloride, by treatment with oxalyl chloride in the presence of catalytic amount of N,N-dimethylformamide in a solvent such as, but not limited to, toluene, dichloromethane or chloroform. The mixed anhydride can react directly with, or the acid chloride can react with, in the presence of a base such as, but not limited to, triethylamine or diisopropyl ethylamine, a primary or secondary amine to form the amide compound of formula (111) as a compound of formula (I). The acid compound of formula (110) can react with an aromatic diamine compound in a solvent such as, but not limited to, toluene to form the benzimidazole compound of formula (111.1) as a compound of formula (I).

REACTION SCHEME 1.1

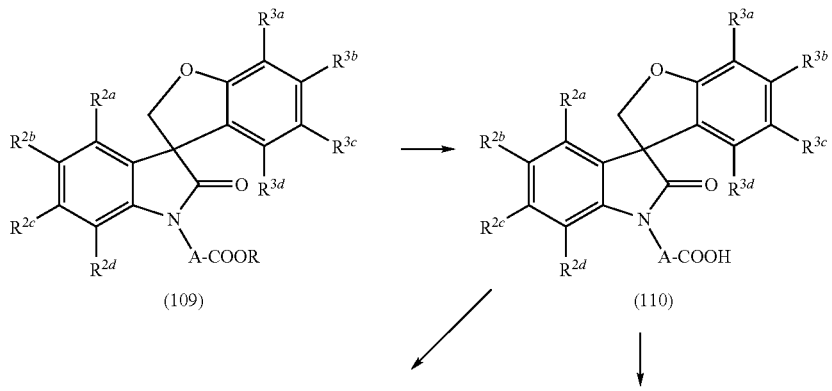

(109)            (110)

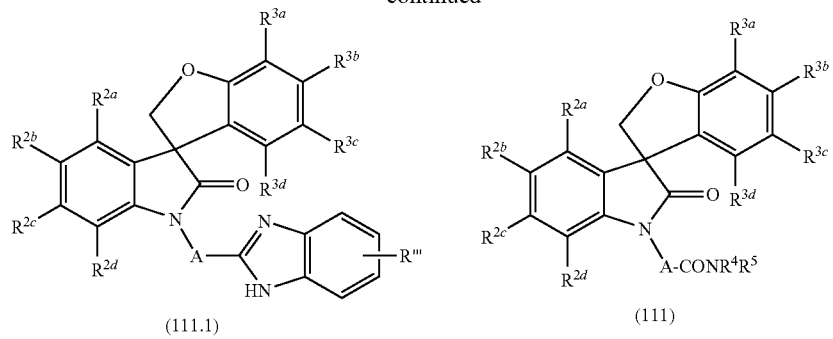

(111.1) (111)

REACTION SCHEME 1.2 below illustrates a schematic synthesis of amine compounds as compounds of formula (I). From compound (112), after removal of the protecting group (PG) such as, but not limited to, phthalimido or tert-butyloxycarbonyl, either the primary or secondary amino compound of formula (113) can be formed. Reaction of the amino compound of formula (113) with an acyl chloride in the presence of a base such as, but not limited to, triethylamine or diisopropyl ethylamine, in a solvent such as, but not limited to, toluene, dichloromethane or chloroform provides the amide compound of formula (114) as a compound of formula (I). Treatment of amino compound of formula (113) with an isocyanate in the presence of a base such as, but not limited to, triethylamine or diisopropyl ethylamine, in a solvent such as, but not limited to, dichloromethane or chloroform leads to the formation of the urea compound of formula (115) as a compound of formula (I). When the primary or secondary amino compound of formula (113) is treated with an aldehyde or a ketone in the presence of a reducing agent such as, but not limited to, sodium cyanoborohydride or sodium triacetoxyborohydride, in a solvent such as, but not limited to, dichloromethane, a high order functionalized amine (116) is produced as a compound of formula (I).

REACTION SCHEME 1.2

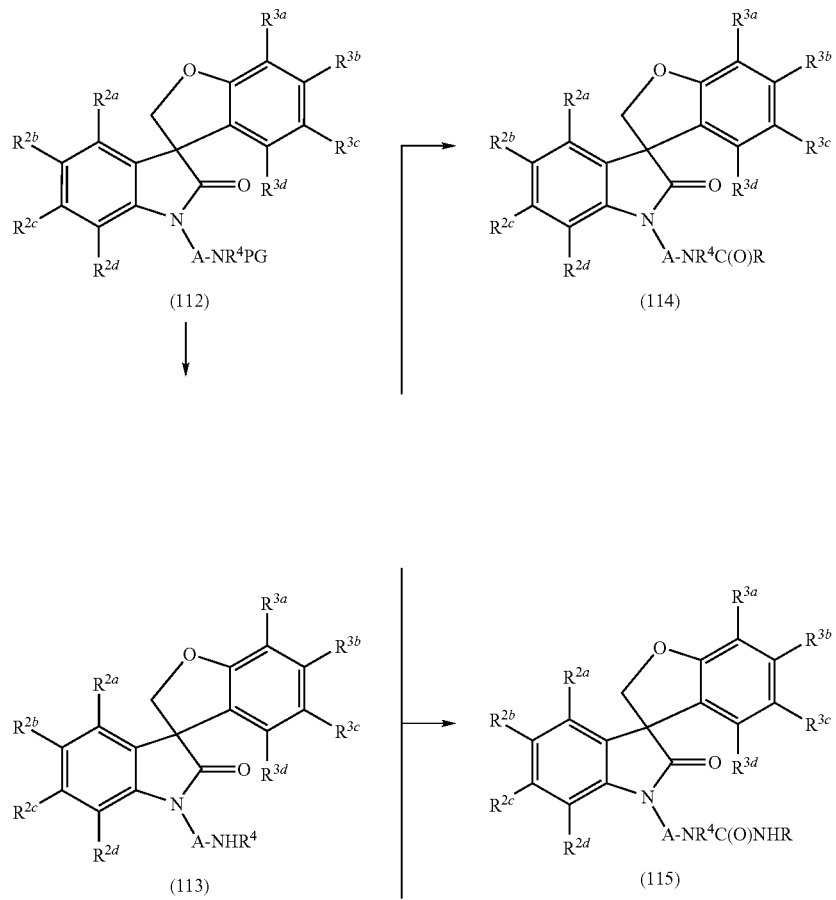

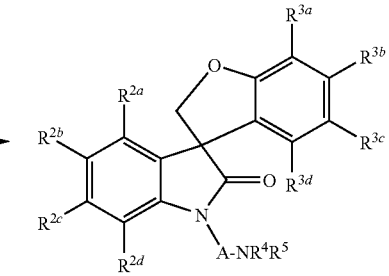

(116)

REACTION SCHEME 1.3 below illustrates a schematic synthesis of amine compounds as compounds of formula (I). The alcohol compound of formula (118), upon removal of the protecting group in compound of formula (117), can be oxidized to the aldehyde compound of (119) by using an oxidant such as, but not limited to, pyridinium dichromate or Dess-Martin's reagent. Similarly to the transformation of the compound of formula (113) to the compound of formula (116) as illustrated in REACTION SCHEME 1.2, the amine compound of formula (120) can be obtained as a compound of formula (I) through the reductive amination of the aldehyde compound of formula (119) with a primary or secondary amine.

be removed under a high pressure of hydrogen such as 60 psi to form the oxindole compound of formula (122). The formation of a compound of formula (I) can be achieved by alkylation of the compound of formula (122) with a halide reagent $XR^1$ (where X is chloro, bromo or iodo) in the presence of a base such as, but not limited to, sodium hydride, sodium bis(trimethylsilyl)amide, and lithium hydroxide, in a solvent such as, but not limited to, N,N-dimethylformamide, tetrahydrofuran, acetone or acetonitrile. Alternatively, reaction of compound of formula (122) with an alcohol under Mitsunobu reaction conditions in the presence of a phosphine reagent such as, but not limited to, triphenylphosphine, tributylphosphine or trimethyl phosphine, and azadicarboxylate of

REACTION SCHEME 1.3

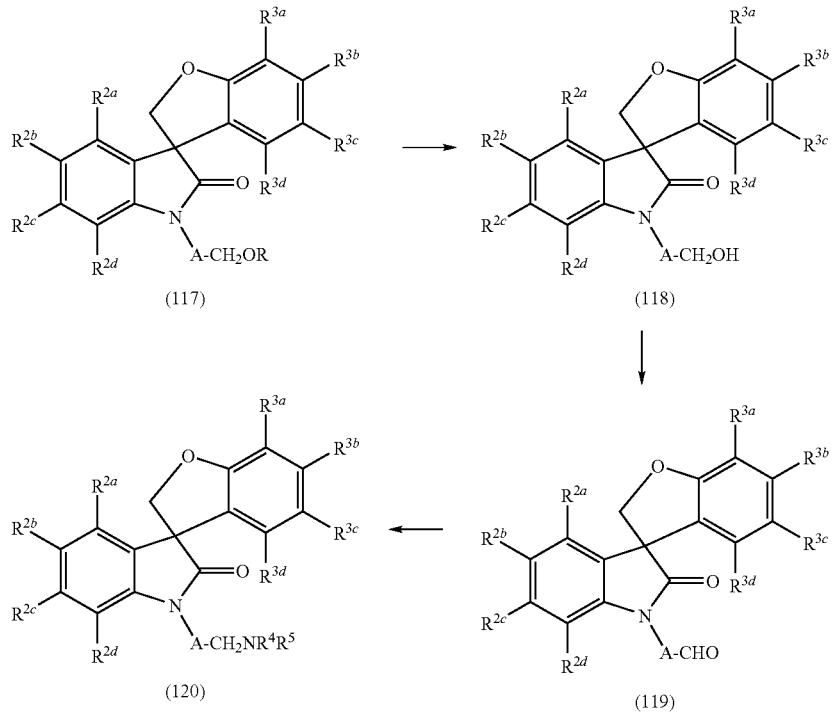

REACTION SCHEME 1.4 below illustrates an alternative synthesis of compounds of formula (I) with the introduction of a variety of $R^1$ groups. Compound of formula (121) where PG is a protecting group such as, but not limited to, diphenylmethyl, can be synthesized through the sequence as shown in REACTION SCHEME 1 above. The protecting group can diethyl, diisopropyl or di-tert-butyl in a solvent such as, but not limited to, tetrahydrofuran, ethyl acetate or dichloromethane, provides the compound of formula (I). Alternatively, treatment of compound of formula (122) with a base such as, but not limited to, sodium hydride or lithium hydroxide, followed by reacting with an acyl chloride or anhydride, or with a sulfonyl chloride reagent, provides the corresponding acyl or sulfonyl ($R^1$) compound of formula (I) respectively.

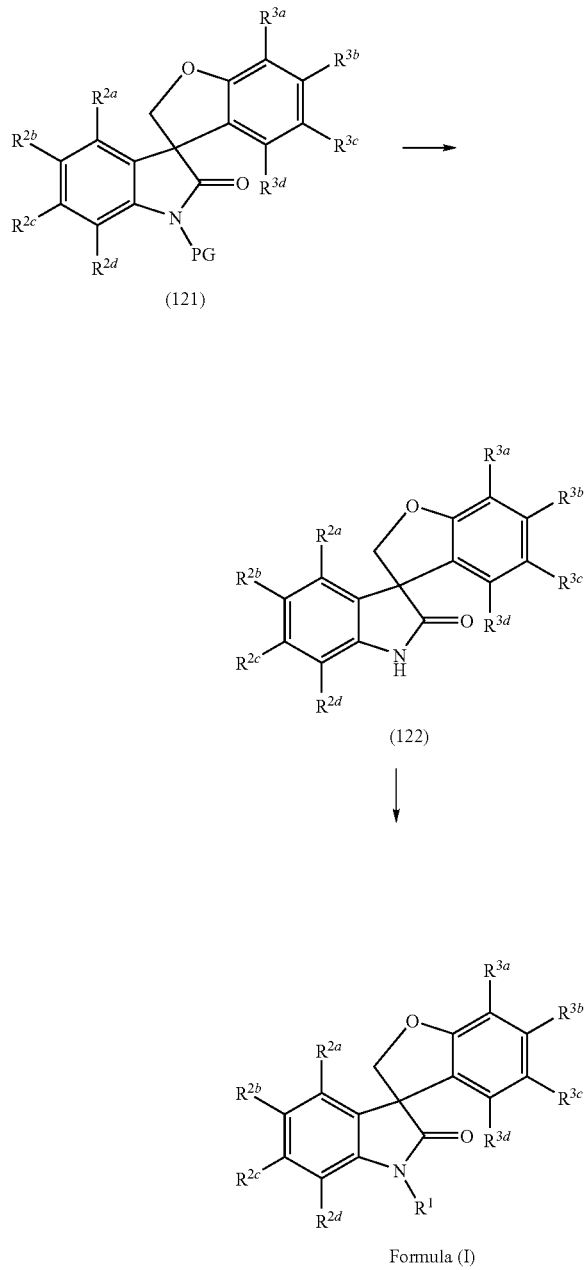

REACTION SCHEME 1.4

(121)

(122)

Formula (I)

When $R^{2a}$, $R^{2b}$, $R^{2c}$, $R^{2d}$, $R^{3a}$, $R^{3b}$, $R^{3c}$ or $R^{3d}$ of the compound of formula (I) is a bromo or trifluoromethylsulfonyloxy group, further derivatives can be synthesized as shown in REACTION SCHEME 1.5 and REACTION SCHEME 1.6 below. The triflate compound can be obtained by treating the bromo compound with diborane in the presence of a palladium catalyst followed by sequential oxidation with hydrogen peroxide/sodium hydroxide and reaction with trifluoromethanesulfonyl anhydride. Compounds of formula (123) or (129) (with either a bromo or a trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with zinc cyanide or tributyltin cyanide and potassium cyanide in the presence of a palladium catalyst such as, but not limited to, palladium acetate or tris(dibenzylideneacetone)dipalladium(0), and a ligand such as, but not limited to, tri(o-tolyl)phosphine, 1,1'-bis(diphenylphosphino)ferrocene or 2-(di-tert-butylphosphino)biphenyl in a solvent such as, but not limited to, N,N-dimethylformamide or acetonitrile to provide the cyano compounds of formula (124) or formula (130) as compounds of formula (I) (see Marcantonio, K. M., et al, *Org. Lett.* (2004), 6:3723-5 and Yang, C., et al, *Org. Lett.* (2004), 6:2837-40). Reaction of compounds of formula (123) or formula (129) (with either a bromo or a trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) with a primary or secondary amine in the presence of a palladium catalyst such as, but not limited to, palladium acetate, tetrakis(triphenylphosphine)palladium(0), or tris(dibenzylideneacetone)dipalladium(0), under a pressure of carbon monoxide in a solvent such as, but not limited to, N,N-dimethylformamide or acetonitrile leads to the formation of the amide compound of formula (125) or formula (131) as compounds of formula (I) (See Takahashi, T., et al, *Tetrahedron Lett.* (1999), 40:7843-6 and Schnyder, A., et al, *J. Org. Chem.* (2001), 66:4311-5). Under a typical Ullmann coupling reaction conditions, compounds of formula (123) or formula (129) (with either bromo or trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with a phenol compound in the presence of a copper reagent such as, but not limited to, copper iodide or copper bromide, a base such as, but not limited to, cesium carbonate or potassium carbonate, an amino acid such as, but not limited to, N,N-dimethylglycine, in a solvent such as, but not limited to, dimethyl sulfoxide, dioxane or acetonitrile, to form the diaryl ether compounds of formula (126) or formula (132) as compounds of formula (I) (see Sawyer, J. S. *Tetrahedron* (2000), 56:5045-65 and Ma, D., et al, *Org. Lett.* (2003), 5(21):3799-802). Compounds of formula (123) or formula (129) (with either bromo or trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with an arylboronic acid in the presence of a palladium catalyst such as, but not limited to, palladium acetate, tetrakis(triphenylphosphine)palladium(0), or tris(dibenzylideneacetone)dipalladium(0), with or without a ligand such as, but not limited to, triphenylphosphine, tri(o-tolyl)phosphine, 1,1'-bis(diphenylphosphino)ferrocene or 2-(di-tert-butylphosphino)biphenyl, a base such as, but not limited to, sodium carbonate, cesium carbonate, or sodium bicarbonate, in a solvent such as, but not limited to, dimethoxyethane, dioxane, or tetrahydrofuran to provide the coupled product of formula (127) or formula (133) as compounds of formula (I) (see Kotha, S., et al, *Tetrahedron* (2002), 58:9633 and Miyaura, N., et al, *Chem. Rev.* (1995), 95:2457). Compound of formula (123) or formula (129) (with either a bromo or a trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with a primary or secondary amine in the presence of a palladium catalyst such as, but not limited to, tetrakis(triphenylphosphine)palladium(0) or tris(dibenzylideneacetone)dipalladium(0), with or without a ligand such as, but not limited to, triphenylphosphine, tri(o-tolyl)phosphine, 1,1'-bis(diphenylphosphino)ferrocene or 2-(di-tert-butylphosphino)biphenyl, a base such as, but not limited to, sodium carbonate, cesium carbonate or sodium tert-butoxide, in a solvent such as, but not limited to, dioxane or tetrahydrofuran, to provide the amino compound of formula (128) or formula (134) as compounds of formula (I) (see Muci, A. R., et al, *Topics in Current Chemistry* (2002), 219: 131).

REACTION SCHEME 1.5
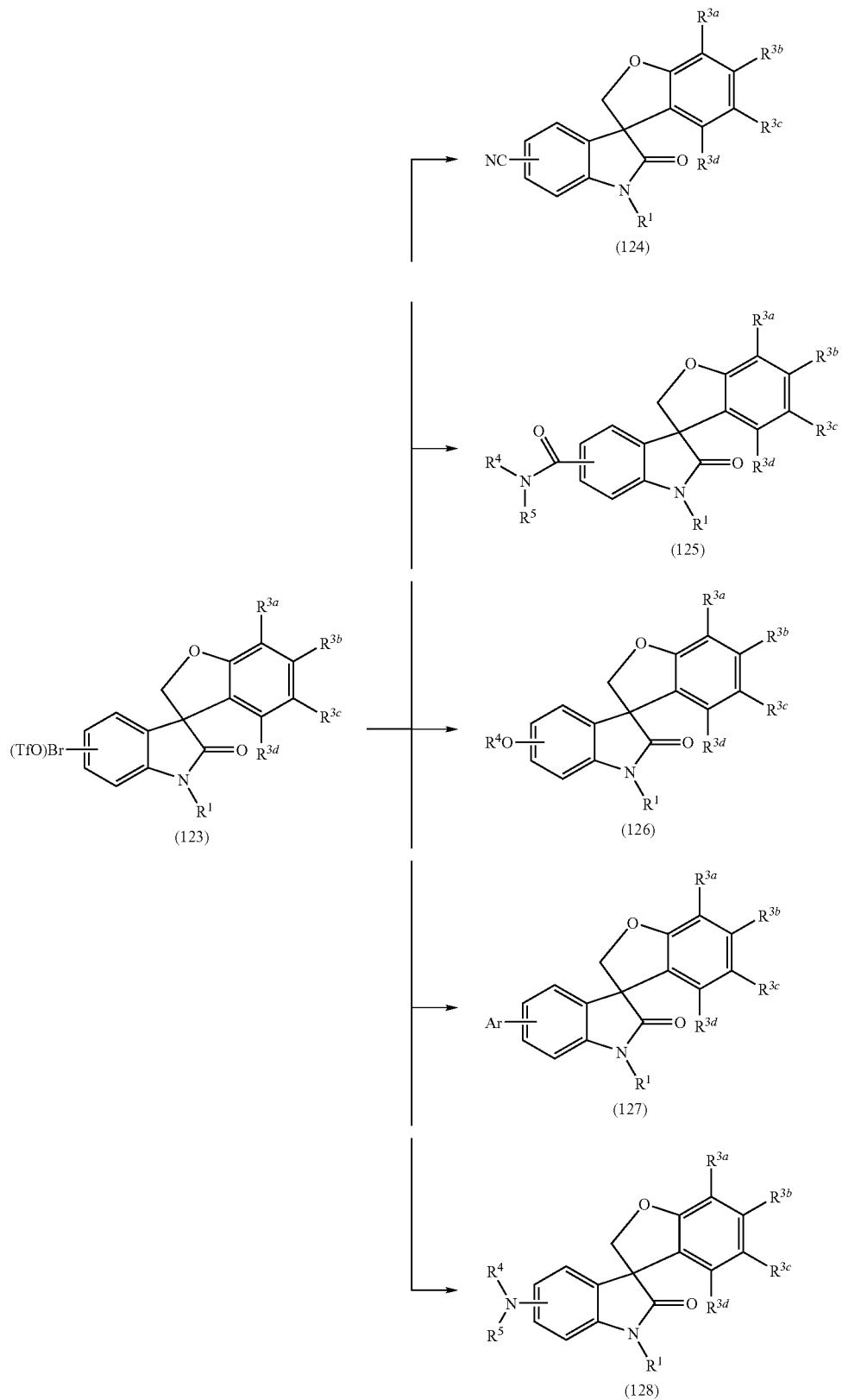

REACTION SCHEME 1.6

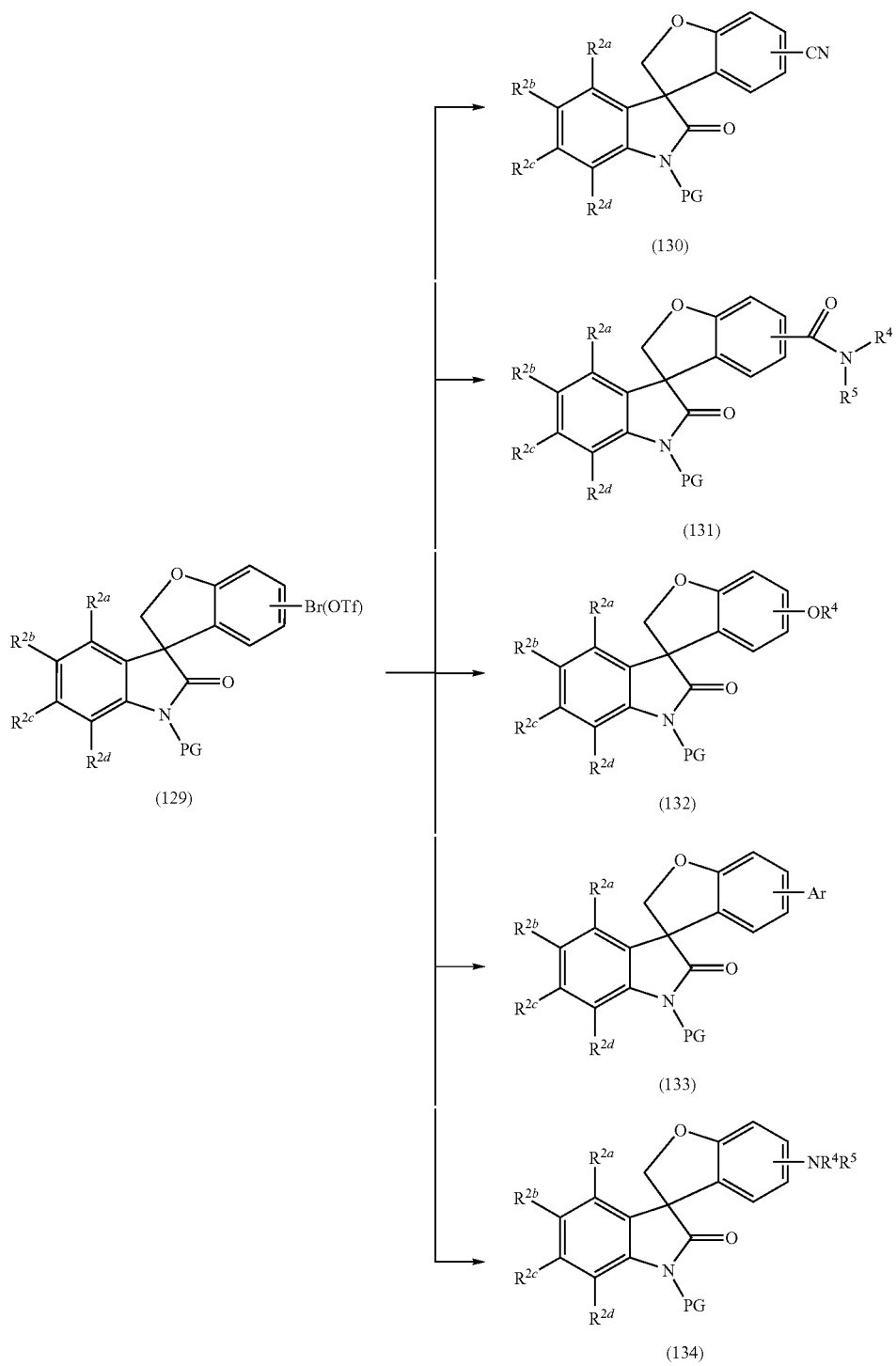

Alternatively, the compound of formula (I) of the invention where Q is —O— and k is 1 can be synthesized following the general procedure as described below in REACTION SCHEME 2. As set forth below, a compound of formula (201) is treated with a lithium reagent of formula (202), such as, but not limited to, n-BuLi at low temperature followed by the reaction with keto-carbonyl group of the isatin compound of formula (103) in a solvent, such as, but not limited to, THF to afford the oxindole of formula (203). The compound of formula (204) is obtained after the removal of the hydroxyl group at C-3 position of the oxindole by treating the compound of formula (203) with silane such as triethylsilane. The compound of formula (204) can also be achieved by treating the compound of formula (203) with $SOCl_2/NEt_3$ then reduction with Zn dust. Compound of formula (204) is treated with a silyl compound, such as, but not limited to, trimethylsilyl chloride to generate the silyl ether intermediate which is treated with ytterbium (III) trifluoromethanesulfonate and formaldehyde to afford the compound of formula (205). Alternatively, a compound of formula (205) can be obtained by treating the compound of formula (204) with a base, such as, but not limited to, LiOH, iPr$_2$NH, or LDA, and subsequently reacting with formaldehyde. Intramolecular cyclization via Mitsunobu reaction affords the compound of formula (I) of the invention where Q is —O— and k is 1.

REACTION SCHEME 2

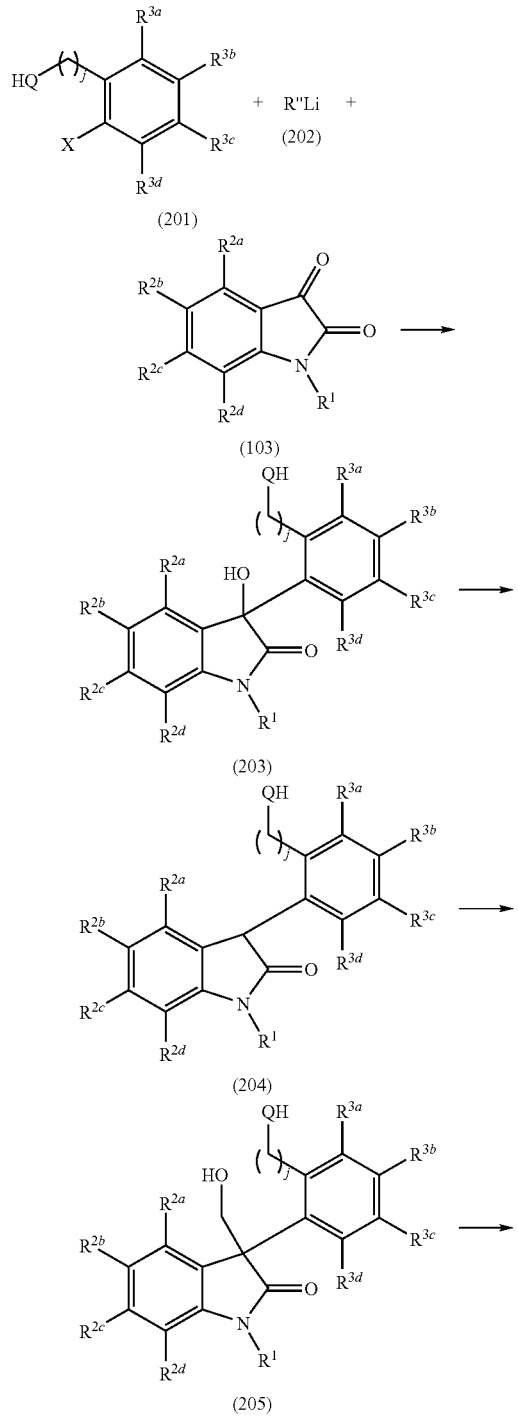

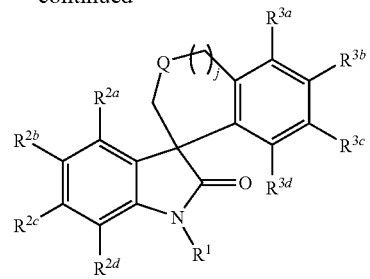

Formula (I)

Alternatively, the compound of formula (I) of the invention where Q is —O— or —S— and k is 0 can be synthesized following the general procedure as described below in REACTION SCHEME 3 wherein intramolecular cyclization of the compound of formula (203) via Mitsunobu reaction affords the compound of formula (I) of the invention where Q is —O— or —S— and k is 0.

REACTION SCHEME 3

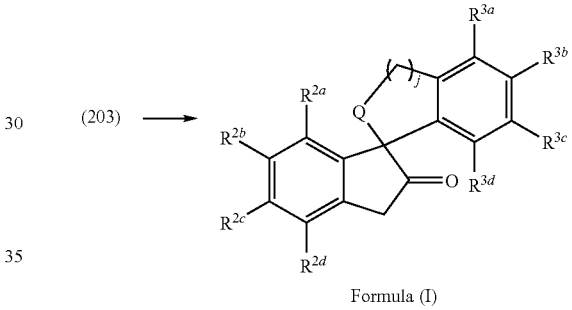

Formula (I)

Alternatively, the compound of formula (I) of the invention where Q is —C(O)—, —(CH$_2$)— or —(CF$_2$)— and j is 0 can be synthesized following the general procedure as described in REACTION SCHEME 4. As set forth below, the Grignard reagent of formula (401) reacts with keto-carbonyl group of the isatin compound of formula (103) in a solvent, such as, but not limited to, methylene chloride or toluene to afford the oxindole of formula (402). The compound of formula (403) is obtained after the removal of the hydroxyl group at C-3 position of the oxindole by treating the compound of formula (402) with silane such as triethylsilane. The compound of formula (403) can also be achieved by treating the compound of formula (402) with SOCl$_2$/NEt$_3$, followed by reduction with Zn dust. Compound of formula (403) is alkylated at C-3 position of oxindole ring with a compound of formula (404) to afford the compound of formula (405) which is subjected to saponification to generate the carboxylic acid of formula (406). This carboxylic acid is then converted to an acid chloride of formula (407) following procedures known to one skilled in the art. Intramolecular cyclization in the presence of an Lewis acid, such as, but not limited to, tin(IV) chloride, yields the compound of formula (I) of the invention where Q is —C(O)— and j is 0. The removal of the carbonyl group of the compound of formula (I) using a silane, such as triethylsilane, or other reagents known to the one skilled in the art, yields the compound of formula (I) of the invention where Q is —CH$_2$— and j is 0. Reaction of the carbonyl group of the compound (408) of formula (I) with a fluorinating reagent such as, but not limited to, bis(2-methoxyethyl)aminosulfur trifluoride leads to the formation of di-fluoro compound of formula (I) of the invention where Q is —CF$_2$— and j is 0. Reduction of the carbonyl group of the compound (408) of formula (I) with a reducing agent such as, but not limited to, sodium borohydride provides the hydroxy compound of formula (I) of the invention where Q is —CH(OH)— and j is 0. Further alkylation of the hydroxy compound of formula (I) by the method known to one skilled in the art gives the alkylated compound of formula (I) of the invention where Q is —CH(OR$^5$)— and j is 0.

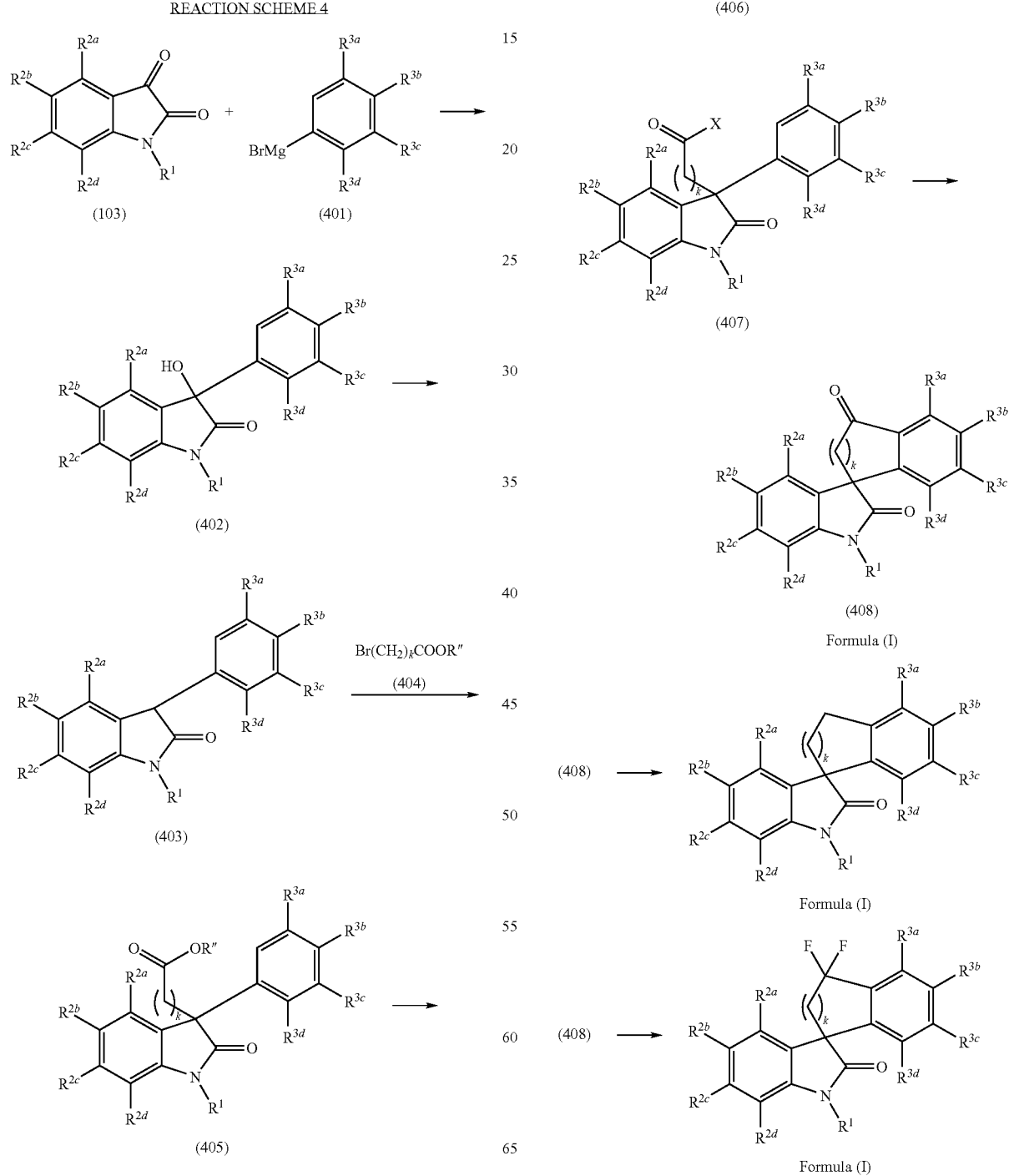

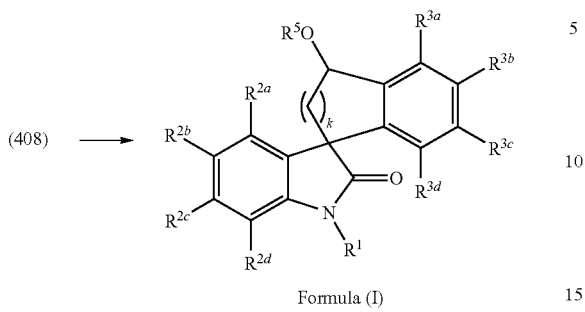

Formula (I)

Alternatively, the compound of formula (I) of the invention where Q is —O—, j is 0 and k is 1 can be synthesized following the general procedure as described below in REACTION SCHEME 5. As set forth below, the phenol compound of formula (104) is treated with a Grignard reagent of formula (105) at low temperature (0° C.) to form the phenoxymagnesium halide intermediate which reacts with the keto-carbonyl group of the isatin compound of formula (101) in a solvent, such as, but not limited to, tetrahydrofuran, methylene chloride or toluene, to afford the heterocyclic compound of formula (501). The compound of formula (502) can be obtained after the removal of the hydroxyl group of the heterocyclic compound by treating the compound of formula (501) with a silane such as triethylsilane. The compound of formula (502) can also be achieved by treating the compound of formula (501) with $SOCl_2/NEt_3$ followed by reduction with Zn dust. Compound of formula (502) is treated with a silyl compound such as, but not limited to, trimethylsilyl chloride, to generate the silyl ether intermediate which is treated with ytterbium (III) trifluoromethanesulfonate and formaldehyde to afford the compound of formula (503). Alternatively, compound of formula (503) can be obtained by treating the compound of formula (502) with a base such as, but not limited to, LiOH, $iPr_2NH$, or LDA, and by subsequently reacting with formaldehyde. Intramolecular cyclization via Mitsunobu reaction affords the compound of formula (504) which can be alkylated with a chloro or bromo compound of formula (102) to afford the compound of formula (I) of the invention where Q is —O—, j is 0 and k is 1.

REACTION SCHEME 5

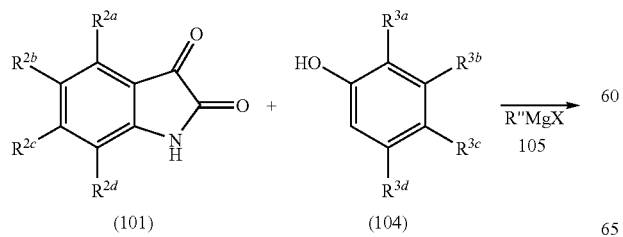

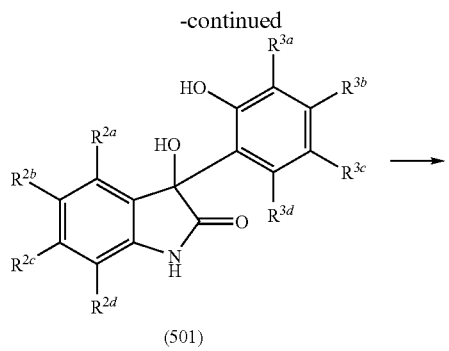

(501)

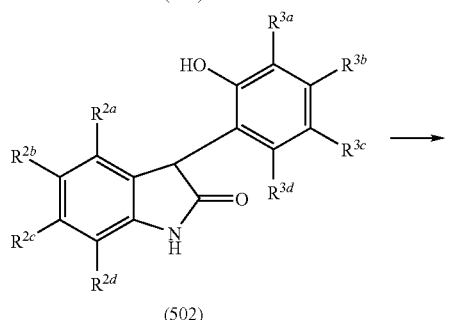

(502)

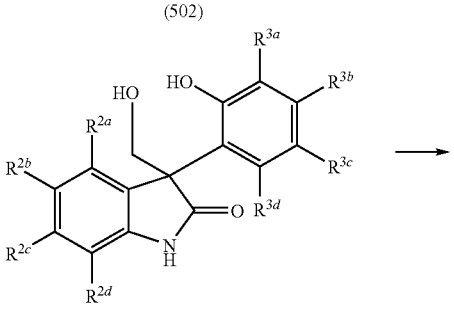

(503)

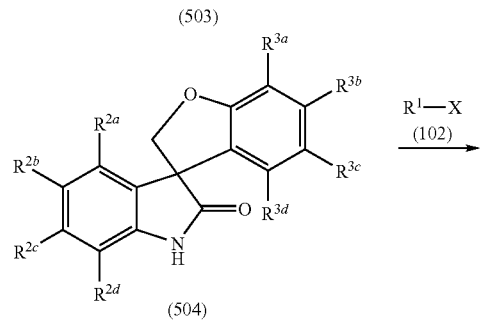

(504)

Formula (I)

Alternatively, the compound of formula (I) of the invention where Q is —NHC(O)—, j is 0 can be synthesized following the general procedure as described below in REACTION SCHEME 6. As set forth below, treatment of the ketone compound (408) with an azide such as, but not limited to, sodium azide in an acid such as, but not limited to, trifluoroacetic acid provides the Schmidt reaction product of formula (I) of the invention where Q is —NHC(O)—, j is 0.

REACTION SCHEME 6

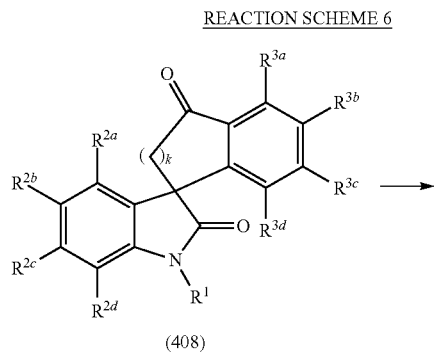

(408)

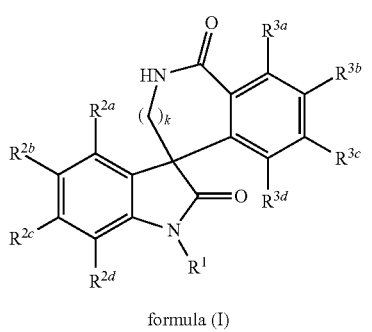

formula (I)

Alternatively, the compound of formula (I) of the invention where Q is —C(O)O—, j is 0 can be synthesized following the general procedure as described below in REACTION SCHEME 7. As set forth below, treatment of the compound of formula (701), which can be obtained following a similar procedure as for the synthesis of compound of formula (405) as described in REACTION SCHEME 4, with a base such as, but not limited to, lithium hydroxide, sodium hydroxide or potassium hydroxide, in a mixed solvent such as, but not limited to, tetrahydrofuran or methanol with water, leads to the formation of the lactone product of formula (I) of the invention where Q is —C(O)O—, j is 0.

REACTION SCHEME 7

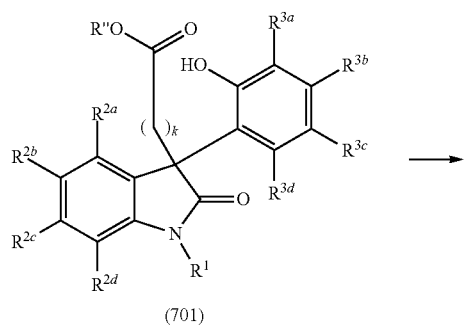

(701)

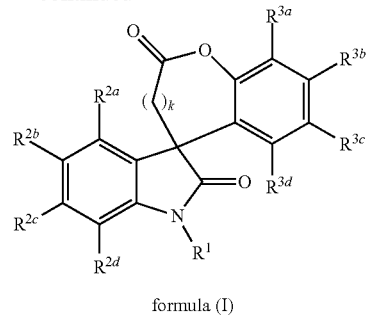

formula (I)

In the following Preparations, which are directed to intermediates used in the preparation of the compounds of formula (I), and in the following Examples, which are directed to compounds of formula (I), the compound numbers presented therein do not correspond to the compound numbers in the above REACTION SCHEMES.

Preparation 1

Synthesis of 4-bromo-3-(6-hydroxy-1,3-benzodioxol-5-yl)-3-(hydroxymethyl)-1-pentyl-1,3-dihydro-2H-indol-2-one A. Synthesis of 4-bromo-1-pentyl-1H-indole To a mixture of sodium hydride (2.54 g, 66.3 mmol, 60% dispersion in mineral oil) in anhydrous N,N-dimethylformamide (50.0 mL) was added 4-bromoindole (10.0 g, 51.0 mmol) at 0° C. The reaction mixture was stirred for 0.5 h followed by the addition of 1-bromopentane (9.25 g, 61.2 mmol) at 0° C. The reaction mixture was stirred at ambient temperature for 6 h and quenched with brine solution (20.0 mL). The reaction mixture was diluted with water (100 mL) and extracted with ether (3×200 mL). The combined organic layers was washed with brine (100 mL), dried over anhydrous sodium sulfate and filtered. The filtrate was concentrated in vacuo to dryness. The residue was subjected to column chromatography eluting with hexane (100%) to give the title compound (13.3 g, 98%) as a yellow oil: $^1$H NMR (300 MHz, CDCl$_3$) δ 7.30-7.27 (m, 2H), 7.14 (t, 1H), 6.88 (t, 1H), 6.55 (d, 1H), 4.08 (t, 2H), 1.87-1.77 (m, 2H), 1.39-1.22 (m, 4H), 0.89 (t, 3H); $^{13}$C NMR (75 MHz, CDCl$_3$) δ 136.3, 129.2, 128.4, 122.2, 122.1, 114.9, 108.7, 101.3, 46.8, 29.9, 29.1, 22.3, 13.9.

B. Synthesis of 4-bromo-1-pentyl-1H-indole-2,3-dione

To a solution of 4-bromo-1-pentyl-1H-indole (25.0 g, 93.9 mmol) in anhydrous dimethylsulfoxide (350 mL) was added N-bromosuccinimide (50.2 g, 282 mmol) in portions over 30 min. The reaction mixture was heated at 60° C. for 3 h, upon which time the internal temperature increased to 120° C. After cooling down to ambient temperature, the reaction mixture was poured onto ethyl acetate/water (1/1, 600 mL). The organic layer was separated and the aqueous layer was extracted with ethyl acetate (3×500 mL). The combined organic layers was washed with water (3×500 mL), dried over anhydrous sodium sulfate and filtered. The filtrate was concentrated in vacuo to dryness to yield the title compound (25.7 g, 92%) as a yellow solid: $^1$H NMR (300 MHz, CDCl$_3$) δ 7.38 (t, 1H), 7.21 (t, 1H), 6.82 (d, 1H), 3.68 (t, 2H), 1.72-1.59 (m, 2H), 1.39-1.25 (m, 4H), 0.86 (t, 3H); $^{13}$C NMR (75 MHz, CDCl$_3$) δ 180.9, 157.2, 152.6, 138.4, 128.3, 121.7, 116.3, 108.9, 40.4, 28.9, 26.9, 22.3, 13.9.

C. Synthesis of 4-bromo-3-hydroxy-3-(6-hydroxy-1,3-benzodioxol-5-yl)-1-pentyl-1,3-dihydro-2H-indol-2-one To a solution of 1,3-benzodioxol-5-ol (12.8 g, 92.9 mmol) in tetrahydrofuran (200 mL) was added isopropylmagnesium chloride solution (50.7 mL, 101 mmol, 2.0 M in ether) at 0° C. The reaction mixture was stirred at 0° C. for 0.5 h, upon which time the colorless precipitate was formed. After the solvent was removed under reduced pressure, the residue was dissolved in methylene chloride (100 mL) and added to a solution of 4-bromo-1-pentyl-1H-indole-2,3-dione (25.0 g, 84.5 mmol) in dichloromethane (100 mL) via a canula over 10 min at 0° C. The reaction mixture was stirred at ambient temperature for 16 h, quenched with saturated ammonium chloride solution (100 mL) and the organic layer was separated. The aqueous layer was extracted with dichloromethane (100 mL). The combined organic layers was washed with brine, dried over anhydrous sodium sulfate and filtered. The filtrate was concentrated in vacuo to dryness. The residue was subjected to column chromatography eluting with ethyl acetate-hexane to give the title compound (34.9 g, 97%) as a brown gummy material: $^1$H NMR (300 MHz, DMSO-d$_6$) δ 8.95 (s, 1H), 7.29-7.21 (m, 2H), 6.88-6.81 (m, 1H), 6.55, (s, 1H), 6.14 (s, 1H), 5.86 (dd, 2H), 4.24 (s, 1H), 3.70-3.52 (m, 2H), 1.69-1.55 (m, 2H), 1.31-1.24 (m, 4H), 0.83 (t, 3H); $^{13}$C NMR (75 MHz, DMSO-d$_6$) δ 177.6, 152.6, 149.1, 144.8, 141.2, 131.7, 127.7, 127.6, 121.0, 113.8, 108.3, 106.7, 101.7, 101.4, 80.5 40.5, 28.8, 26.7 22.2, 13.9.

D. Synthesis of 4-bromo-3-(6-hydroxy-1,3-benzodioxol-5-yl)-1-pentyl-1,3-dihydro-2H-indol-2-one To a solution of 4-bromo-3-hydroxy-3-(6-hydroxy-1,3-benzodioxol-5-yl)-1-pentyl-1,3-dihydro-2H-indol-2-one (34.9 g, 80.4 mmol) in dichloromethane (100 mL) was added trifluoroacetic acid (18.7 g, 161 mmol) and triethylsilane (18.3 g, 161 mmol). The brown solution was stirred at ambient temperature for 3 h and concentrated in vacuo to dryness. The residue was diluted with dichloromethane (200 mL), washed with saturated ammonium chloride solution (50.0 mL), brine (3×50.0 mL), dried over anhydrous sodium sulfate and filtered. The filtrate was concentrated in vacuo to dryness. The residue was crystallized from ether to give the title compound (16.5 g, 49%) as a brown solid: $^1$H NMR (300 MHz, CDCl$_3$) δ 7.29-7.21 (m, 2H), 7.14 (dd, 1H), 6.58 (s, 1H), 6.10 (s, 1H), 5.85 (dd, 2H), 5.01 (s, 1H), 3.75-3.55 (m, 2H), 1.69-1.56 (m, 2H), 1.35-1.21 (m, 4H), 0.86 (t, 3H); $^{13}$C NMR (75 MHz, CDCl$_3$) δ 177.9, 150.9, 147.6, 145.4, 141.6, 130.3 127.1 126.8, 120.8, 113.3 108.0, 106.7, 101.5, 101.2, 59.9, 48.6, 40.7, 28.9, 26.9, 22.3 13.9; MS (ES+) m/z 418.3 (M+1), 420.3 (M+1).

E. Synthesis of 4-bromo-3-(6-hydroxy-1,3-benzodioxol-5-yl)-3-hydroxymethyl-1-pentyl-1,3-dihydro-2H-indol-2-one To a solution of 4-bromo-3-(6-hydroxy-1,3-benzodioxol-5-yl)-1-pentyl-1,3-dihydro-2H-indol-2-one (7.50 g, 17.9 mmol) in dry dichloromethane (150 mL) was added triethylamine (10.9 g, 108 mmol) and chlorotrimethylsilane (7.80 g, 71.8 mmol) at 0° C. The reaction mixture was stirred at 0° C. for 2 h and diluted with dichloromethane (100 mL). The mixture was washed with water (3×50.0 mL), dried over anhydrous magnesium sulfate and filtered. The filtrate was concentrated in vacuo to dryness. The residue was dissolved in THF (150 mL) followed by the additions of formaldehyde solution (4.90 mL, 179 mmol, 37 wt % in water) and ytterbium (III) trifluoromethanesulfonate (1.11 g, 1.79 mmol). The resulting mixture was stirred at ambient temperature for 36 h. After the solvent was removed under reduced pressure, the residue was diluted with dichloromethane (200 mL), washed with saturated sodium bicarbonate (50.0 mL), saturated ammonium chloride (50.0 mL) and water (100 mL). The organic layer was dried over anhydrous sodium sulfate and filtered. The filtrate was concentrated in vacuo to dryness to yield the title compound (6.32 g, 79%) as a fluffy solid: $^1$H NMR (300 MHz, CDCl$_3$) δ 8.28 (s, 1H), 7.10 (t, 1H), 7.00 (dd, 1H), 6.89 (dd, 1H), 6.83 (s, 1H), 6.27 (s, 1H), 6.85 (dd, 2H), 4.52-4.41 (m, 2H), 3.90 (dd, 1H), 3.70-3.65 (m, 2H), 1.68-1.57 (m, 2H), 1.36-1.29 (m, 4H), 0.83 (t, 3H); $^{13}$C NMR (75 MHz, CDCl$_3$) δ 178.1, 150.3, 147.2, 147.2, 140.5, 129.6, 129.2, 125.6, 118.4, 114.8, 109.2, 106.9, 101.0, 98.2, 62.6, 57.6, 39.9, 28.9, 26.7, 22.2, 13.5.

Preparation 2

Synthesis of 1-(2-cyclopropylethyl)-3-(6-hydroxy-1,3-benzodioxol-5-yl)-3-(hydroxymethyl)-1,3-dihydro-2H-indol-2-one A. Synthesis of 1-(2-cyclopropylethyl)-1H-indole-2,3-dione To a suspension of sodium hydride (1.61 g, 41.9 mmol, 60% dispersion in mineral oil) in anhydrous N,N-dimethylformamide (25.0 mL) was added isatin (6.17 g, 41.9 mmol) at 0° C. The reaction mixture was stirred for 0.5 h followed by the addition of (2-bromoethyl)cyclopropane (Maercker, A., et al, Justus Liebigs Ann. Chem. (1972), 759:132-157) (9.25 g, 61.2 mmol). The resulting mixture was stirred at ambient temperature for 16 h and quenched with water (50.0 mL). The mixture was extracted with ethyl acetate (3×100 mL). The combined organic layers was washed with water (3×50.0 mL), dried over anhydrous sodium sulfate and filtered. The filtrate was concentrated in vacuo to dryness to yield the title compound (6.50 g, 90%) as a viscous gum: $^1$H NMR (300 MHz, CDCl$_3$) δ 7.57-7.51 (m, 2H), 7.05 (t, 1H), 6.88 (d, 1H), 3.79-3.74 (m, 2H), 1.59-1.52 (m, 2H), 0.70-0.61 (m, 1H), 0.44-0.38 (m, 2H), 0.05-0.02 (m, 2H); $^{13}$C NMR (75 MHz, CDCl$_3$) δ 183.7, 158.2, 151.2, 138.4, 125.4, 123.6, 117.5, 110.3, 40.3, 32.2, 8.6, 4.3.

B. Synthesis of 1-(2-cyclopropylethyl)-3-hydroxy-3-(6-hydroxy-1,3-benzodioxol-5-yl)-1,3-dihydro-2H-indol-2-one To a solution of 1,3-benzodioxol-5-ol (1.25 g, 9.06 mmol) in THF (20.0 mL) was added dropwise a solution of isopropylmagnesium chloride solution (4.53 mL, 9.06 mmol, 2.0 M in THF) at 0° C. over 5 min. The reaction mixture was stirred for 0.5 h upon which time colorless precipitate was formed. After the solvent was removed under reduced pressure, the residue was dissolved in dichloromethane (20.0 mL) and cooled to 0° C. A solution of 1-(2-cyclopropylethyl)-1H-indole-2,3-dione (1.77 g, 8.23 mmol) in dichloromethane (20.0 mL) was added to the above solution at 0° C. The resulting mixture was stirred at ambient temperature for 16 h and quenched with saturated ammonium chloride solution (30.0 mL). The organic layer was separated and washed with water (3×25.0 mL), dried over anhydrous sodium sulfate and filtered. The filtrate was concentrated in vacuo to dryness. The residue was crystallized from ethyl acetate and ether to give the title compound (2.22 g, 76%) as a colorless solid: $^1$H NMR (300 MHz, CDCl$_3$) δ 9.52 (s, 1H), 7.46 (d, 1H), 7.37 (dt, 1H), 7.18 (dt, 1H), 6.90 (d, 1H), 6.56 (s, 1H), 6.23 (s, 1H), 5.84 (dd, 2H), 4.55 (s, 1H), 3.87-3.63 (m, 2H), 1.64-1.44 (m, 2H), 0.68-0.55 (m, 1H), 0.41-0.27 (m, 2H), −0.02- (−0.07) (m, 2H); $^{13}$C NMR (75 MHz, CDCl$_3$) δ 179.1, 152.4, 148.8, 142.7, 141.3, 130.3, 129.1, 126.3, 123.7, 117.3, 109.5, 106.9, 101.9, 101.4, 79.3, 40.6, 32.2, 8.6, 4.3, 4.2; MS (ES+) m/z 337.6 (M−17).

C. Synthesis of 1-(2-cyclopropylethyl)-3-(6-hydroxy-1,3-benzodioxol-5-yl)-1,3-dihydro-2H-indol-2-one To a solution of 1-(2-cyclopropylethyl)-3-hydroxy-3-(6-hydroxy-1,3-benzodioxol-5-yl)-1,3-dihydro-2H-indol-2-one (2.22 g, 6.27 mmol) in dichloromethane (30.0 mL) was added trifluoroacetic acid (2.12 g, 18.8 mmol) and triethylsilane (2.14 g, 18.8 mmol). The brown solution was stirred at ambient temperature for 0.5 h and concentrated in vacuo to dryness. The residue was diluted with dichloromethane (100 mL), washed with water (3×50.0 mL), dried over anhydrous sodium sulfate and filtered. The filtrate was concentrated in vacuo to dryness. The residue was subjected to column chromatography eluting with ethyl acetate/hexane (20/80) to give the title compound (1.69 g, 80%) as a brown solid: $^1$H NMR (300 MHz, CDCl$_3$) δ 9.21-9.10 (br, 1H), 7.38-7.30 (m, 2H), 7.16 (t, 1H), 6.96 (d, 1H), 6.63 (s, 1H), 6.33 (s, 1H), 5.84 (dd, 2H), 5.01 (s, 1H), 3.87-3.72 (m, 2H), 1.66-1.46 (m, 2H), 0.69-0.59 (m, 1H), 0.43-0.30 (m, 2H), 0.09-0.06 (m, 2H); $^{13}$C NMR (75 MHz, CDCl$_3$) δ 178.8, 151.3, 147.6, 144.1, 141.5, 128.7, 126.2, 123.1, 115.2, 109.5, 109.4, 106.5, 101.5, 101.2, 47.4, 40.5, 32.2, 8.6, 4.3, 4.2; MS (ES+) m/z 338.3 (M+1).

D. Synthesis of 1-(2-cyclopropylethyl)-3-(6-hydroxy-1,3-benzodioxol-5-yl)-3-(hydroxymethyl)-1,3-dihydro-2H-indol-2-one Following the procedure as described in PREPARATION 1E, making variations to replace 4-bromo-3-(6-hydroxy-1,3-benzodioxol-5-yl)-1-pentyl-1,3-dihydro-2H-indol-2-one with 1-(2-cyclopropylethyl)-3-(6-hydroxy-1,3-benzodioxol-5-yl)-1,3-dihydro-2H-indol-2-one, the title compound was obtained (53%): R$_f$=0.28 (EtOAc/Hexanes, 1/1).

Preparation 3

Synthesis of ethyl [3-(6-hydroxy-1,3-benzodioxol-5-yl)-3-(hydroxymethyl)-2-oxo-2,3-dihydro-1H-indol-1-yl]acetate A. Synthesis of ethyl (2,3-dioxo-2,3-dihydro-1H-indol-1-yl)acetate Following the procedure as described in PREPARATION 2A, and making non-critical variations to replace (2-bromoethyl)cyclopropane with ethyl bromoacetate, the title compound was obtained (79%) as a light yellow powder: $^1$H NMR (300 MHz, CDCl$_3$) δ 7.64-7.54 (m, 2H), 7.16-7.11 (m, 1H), 6.77 (d, 1H), 4.47 (s, 2H), 4.22 (q, 2H), 1.26 (t, 3H); MS (ES+) m/z 256.2 (M+23).

B. Synthesis of ethyl [3-hydroxy-3-(6-hydroxy-1,3-benzodioxol-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (2,3-dioxo-2,3-dihydro-1H-indol-1-yl)acetate, the title compound was obtained (95%): $^1$H NMR (300 MHz, DMSO-d$_6$) δ 9.08 (s, 1H), 7.21-7.13 (m, 2H), 6.93-6.86 (m, 3H), 6.57 (s, 1H), 6.19 (s, 1H), 5.88 (m, 2H), 4.47 (m, 2H), 4.13 (q, 2H), 1.19 (t, 3H); MS (ES−) m/z 370.2 (M−1).

C. Synthesis of ethyl [3-(6-hydroxy-1,3-benzodioxol-5-yl)-2-oxo-2,3-dihydro-1H-indol-1-yl]acetate Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with ethyl [3-hydroxy-3-(6-hydroxy-1,3-benzodioxol-5-yl)-2-oxo-2,3-dihydro-1H-indol-1-yl]acetate, the title compound was obtained (84%) as a white powder: $^1$H NMR (300 MHz, DMSO-d$_6$) δ 9.37 (s, 1H), 7.19 (m, 1H), 7.01-6.90 (m, 3H), 6.43 (s, 2H), 5.84 (m, 2H), 4.86 (s, 1H), 4.56 (s, 2H), 4.13 (q, 2H), 1.18 (t, 3H); MS (ES+) m/z 378.2 (M+23).

D. Synthesis of ethyl [3-(6-hydroxy-1,3-benzodioxol-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [3-(6-hydroxy-1,3-benzodioxol-5-yl)-2-oxo-2,3-dihydro-1H-indol-1-yl]acetate, the title compound was obtained as a white powder: $^1$H NMR (300 MHz, DMSO-d$_6$) δ 9.03 (s, 1H), 7.17-6.85 (m, 5H), 6.22 (s, 1H), 5.83 (s, 2H), 5.04 (t, 1H), 4.56-4.08 (m, 5H), 3.69 (m, 1H), 1.18 (t, 3H); MS (ES+) m/z 408.1 (M+23).

Preparation 4

Synthesis of methyl 3-{[3-(6-hydroxy-1,3-benzodioxol-5-yl)-3-(hydroxymethyl)-2-oxo-2,3-dihydro-1H-indol-1-yl]methyl}benzoate A. Synthesis of methyl 3-[(2,3-dioxo-2,3-dihydro-1H-indol-1-yl)methyl]benzoate Following the procedure as described in PREPARATION 2A, and making non-critical variations to replace (2-bromoethyl)cyclopropane with methyl 3-(bromomethyl)benzoate, the title compound was obtained (84%) as a orange solid: $^1$H NMR (300 MHz, CDCl$_3$) δ 7.99-7.95 (m, 2H), 7.60 (d, 1H), 7.53-7.47 (m, 2H), 7.43 (d, 1H), 7.09 (t, 1H), 6.43 (d, 1H), 4.95 (s, 2H), 3.89 (s, 3H).

B. Synthesis of methyl 3-{[3-hydroxy-3-(6-hydroxy-1,3-benzodioxol-5-yl)-2-oxo-2,3-dihydro-1H-indol-1-yl]methyl}benzoate Following the procedure as described in PREPARATION 2B, and making non-critical variations to replace 1-(2-cyclopropylethyl)-1H-indole-2,3-dione with methyl 3-[(2,3-dioxo-2,3-dihydro-1H-indol-1-yl)methyl]benzoate, the title compound was obtained (96%): $^1$H NMR (300 MHz, CDCl$_3$) δ 8.65 (s, 1H), 7.92 (s, 1H), 7.85 (d, 1H), 7.41-7.38 (m, 1H), 7.32-7.24 (m, 2H), 7.19-7.13 (m, 1H), 7.04-6.9 (m, 1H), 6.63 (d, 1H), 6.44 (s, 1H), 6.39 (s, 1H), 5.79 (s, 2H), 5.05 (s, 1H), 4.83 (dd, 2H), 3.80 (s, 3H); $^{13}$C NMR (75 MHz, CDCl$_3$) δ 178.7, 167.0, 151.0, 148.5, 142.1, 141.1, 135.7, 131.6, 130.5, 130.1, 129.1, 129.0, 128.4, 125.5, 123.9, 116.7, 109.7, 106.5, 101.3, 100.5, 78.6, 60.6, 52.4, 43.6; MS (ES+) m/z 456.1 (M+23).

C. Synthesis of methyl 3-{[3-(6-hydroxy-1,3-benzo-dioxol-5-yl)-2-oxo-2,3-dihydro-1H-indol-1-yl]methyl}benzoate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with methyl 3-{[3-hydroxy-3-(6-hydroxy-1,3-benzodioxol-5-yl)-2-oxo-2,3-dihydro-1H-indol-1-yl]methyl}benzoate, the title compound was obtained (98%): MS (ES+) m/z 418.2 (M+1).

D. Synthesis of methyl 3-{[3-(6-hydroxy-1,3-benzo-dioxol-5-yl)-3-(hydroxymethyl)-2-oxo-2,3-dihydro-1H-indol-1-yl]methyl}benzoate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl 3-{[3-(6-hydroxy-1,3-benzodioxol-5-yl)-2-oxo-2,3-dihydro-1H-indol-1-yl]methyl}benzoate, the title compound was obtained (81%) as a white powder: MS (ES+) m/z 470.3 (M+23), 448.3 (M+1).

Preparation 5

Synthesis of methyl 4-{[3-(6-hydroxy-1,3-benzo-dioxol-5-yl)-3-(hydroxymethyl)-2-oxo-2,3-dihydro-1H-indol-1-yl]methyl}benzoate A. Synthesis of methyl 4-[(2,3-dioxo-2,3-dihydro-1H-indol-1-yl)methyl]benzoate Following the procedure as described in PREPARATION 2A, and making non-critical variations to replace (2-bromoethyl)cyclopropane with methyl 4-(bromomethyl)benzoate, the title compound was obtained (84%) as an orange solid: $^1$H-NMR (300 MHz, CDCl$_3$) δ 8.00 (d, 2H), 7.61 (d, 1H), 7.46 (t, 1H), 7.38 (d, 2H), 7.09 (t, 1H), 6.69 (d, 1H), 4.96 (s, 2H), 3.88 (s, 3H); MS (ES+) m/z 296.1 (M+1).

B. Synthesis of methyl 4-{[3-hydroxy-3-(6-hydroxy-1,3-benzodioxol-5-yl)-2-oxo-2,3-dihydro-1H-indol-1-yl]methyl}benzoate Following the procedure as described in PREPARATION 2B, and making non-critical variations to replace 1-(2-cyclopropylethyl)-1H-indole-2,3-dione with methyl 4-[(2,3-dioxo-2,3-dihydro-1H-indol-1-yl)methyl]benzoate, the title compound was obtained (79%): MS (ES+) m/z 416.1 (M−17).

C. Synthesis of methyl 4-{[3-(6-hydroxy-1,3-benzo-dioxol-5-yl)-2-oxo-2,3-dihydro-1H-indol-1-yl]methyl}benzoate Following the procedure as described in PREPARATION 2C, and making the variations to replace 1-(2-cyclopropyl-ethyl)-3-hydroxy-3-(6-hydroxy-1,3-benzodioxol-5-yl)-1,3-dihydro-2H-indol-2-one with methyl 4-{[3-hydroxy-3-(6-hydroxy-1,3-benzodioxol-5-yl)-2-oxo-2,3-dihydro-1H-indol-1-yl]methyl}benzoate, the title compound was obtained (98%) as a solid: MS (ES+) m/z 418.1 (M+1).

D. Synthesis of methyl 4-{[3-(6-hydroxy-1,3-benzo-dioxol-5-yl)-3-(hydroxymethyl)-2-oxo-2,3-dihydro-1H-indol-1-yl]methyl}benzoate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl 4-{[3-(6-hydroxy-1,3-benzodioxol-5-yl)-2-oxo-2,3-dihydro-1H-indol-1-yl]methyl}benzoate, the title compound was obtained (81%): MS (ES+) m/z 448.1 (M+1).

Preparation 6

Synthesis of 2-{3-[3-(6-hydroxy-1,3-benzodioxol-5-yl)-3-(hydroxymethyl)-2-oxo-2,3-dihydro-1H-indol-1-yl]propyl}-1H-isoindole-1,3(2H)-dione A. Synthesis of 1-[3-(1,3-dioxo-1,3-dihydro-isoindol-2-yl)-propyl]-1H-indole-2,3-dione Following the procedure as described in PREPARATION 2A, and making non-critical variations to replace (2-bromoethyl)cyclopropane with 2-(3-bromopropyl)-1H-isoindole-1,3(2H)-dione, the title compound was obtained (92%): $^1$H NMR (300 MHz, CDCl$_3$) δ 7.80-7.79 (m, 4H), 7.61-7.56 (m, 1H), 7.49-7.46 (m, 1H), 7.18-7.16 (m, 1H), 7.07-7.05 (m, 1H), 3.72-3.60 (m, 4H), 1.97-1.92 (m, 2H).

B. Synthesis of 2-{3-[3-hydroxy-3-(6-hydroxy-1,3-benzodioxol-5-yl)-2-oxo-2,3-dihydro-1H-indol-1-yl]propyl}-1H-isoindole-1,3(2H)-dione Following the procedure as described in PREPARATION 2B, and making non-critical variations to replace 1-(2-cyclopropylethyl)-1H-indole-2,3-dione with 1-[3-(1,3-dioxo-1,3-dihydro-isoindol-2-yl)-propyl]-1H-indole-2,3-dione, the title compound was obtained (96%): $^1$H NMR (300 MHz, CDCl$_3$) δ 7.86-7.78 (m, 4H), 7.21-7.13 (m, 2H), 7.00-6.97 (m, 1H), 6.87-6.85 (m, 2H), 6.15 (s, 1H), 5.86-5.84 (m, 2H), 3.69-3.65 (m, 4H), 2.46-2.45 (m, 1H), 1.94-1.87 (m, 2H); MS (ES+) m/z 473.4 (M−17).

C. Synthesis of 2-{3-[3-(6-hydroxy-1,3-benzodioxol-5-yl)-2-oxo-2,3-dihydro-1H indol-1-yl]propyl}-1H-isoindole-1,3(2H)-dione Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 2-{3-[3-hydroxy-3-(6-hydroxy-1,3-benzodioxol-5-yl)-2-oxo-2,3-dihydro-1H-indol-1-yl]propyl}-1H-isoindole-1,3(2H)-dione, the title compound was obtained (94%): $^1$H NMR (300 MHz, CDCl$_3$,) δ 7.81-7.78 (m, 2H), 7.70-7.67 (m, 2H), 7.32-7.27 (m, 2H), 7.12-7.07 (m, 1H), 6.90-6.87 (m, 1H), 6.54 (s, 1H), 6.45 (s, 1H), 5.86 (dd, 2H), 4.82 (s, 1H), 3.96-3.66 (m, 4H), 2.17-2.04 (m, 2H); MS (ES+) m/z 457.0 (M+1).

D. Synthesis of 2-{3-[3-(6-hydroxy-1,3-benzodioxol-5-yl)-3-(hydroxymethyl)-2-oxo-2,3-dihydro-1H-indol-1-yl]propyl}-1H-isoindole-1,3(2H)-dione Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 2-{3-[3-(6-hydroxy-1,3-benzodioxol-5-yl)-2-oxo-2,3-dihydro-1H-indol-1-yl]propyl}-1H-isoindole-1,3(2H)-dione, the title compound was obtained (94%) as a foam solid: $^1$H NMR (300 MHz, CDCl$_3$) δ 9.20 (s, 1H), 7.81-7.79 (m, 2H), 7.68-7.61 (m, 2H), 7.35-7.25 (m, 2H), 7.16-7.14 (m, 1H), 6.90 (d, 1H), 6.80 (s, 1H), 6.48 (s, 1H), 5.86 (dd, 2H), 4.64 (d, 1H), 3.67-4.13 (m, 5H), 2.18-2.05- (m, 2H); $^{13}$C NMR (75 MHz, CDCl$_3$) δ 180.6, 168.6, 151.2, 147.8, 143.2, 141.2, 134.2, 134.2, 131.9, 130.0, 128.7, 125.1, 123.2, 113.9, 108.7, 108.3, 101.3, 100.6, 64.9, 58.0, 37.6, 36.1, 26.5; MS (ES+) m/z 487.3 (M+1).

Preparation 7

Synthesis of 2-{2-[3-(6-hydroxy-1,3-benzodioxol-5-yl)-3-(hydroxymethyl)-2-oxo-2,3-dihydro-1H-indol-1-yl]ethyl}-1H-isoindole-1,3(2H)-dione

A. Synthesis of 1'-[2-(1,3-dioxo-1,3-dihydro-isoindol-2-yl)-ethyl]-1H-indole-2,3-dione Following the procedure as described in PREPARATION 2A, and making non-critical variations to replace (2-bromoethyl)cyclopropane with 2-(2-bromoethyl)-1H-isoindole-1,3(2H)-dione, the title compound was obtained (75%): $^1$H NMR (300 MHz, CDCl$_3$) δ 7.85-7.78 (m, 4H), 7.65 (td, 1H), 7.55 (dd, 1H), 7.25 (d, 1H), 7.12 (t, 1H), 4.00-3.80 (m, 4H); MS (ES+) m/z 321 (M+1), 343 (M+23).

B. Synthesis of 2-{2-[3-hydroxy-3-(6-hydroxy-1,3-benzodioxol-5-yl)-2-oxo-2,3-dihydro-1H-indol-1-yl]ethyl}-1H-isoindole-1,3(2H)-dione Following the procedure as described in PREPARATION 2B, and making non-critical variations to replace 1-(2-cyclopropylethyl)-1H-indole-2,3-dione with 1-[2-(1,3-dioxo-1,3-dihydro-isoindol-2-yl)-ethyl]H-indole-2,3-dione, the title compound was obtained (99%): $^1$H NMR (300 MHz, CD$_3$OD) δ 7.85-7.68 (m, 4H), 7.29 (td, 1H), 7.18-6.96 (m, 3H), 6.88 (s, 1H), 6.16 (s, 1H), 5.85 (s, 1H), 5.82 (s, 1H), 3.81-4.01 (m, 4H); MS (ES+) m/z 441 (M−17), 458 (M+23).

C. Synthesis of 2-{2-[3-(6-hydroxy-1,3-benzodioxol-5-yl)-2-oxo-2,3-dihydro-1H-indol-1-yl]ethyl}-1H-isoindole-1,3(2H)-dione Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 2-{2-[3-hydroxy-3-(6-hydroxy-1,3-benzodioxol-5-yl)-2-oxo-2,3-dihydro-1H-indol-1-yl]ethyl}-1H-isoindole-1,3(2H)-dione, the title compound was obtained (90%) as a white solid: $^1$H NMR (300 MHz, CD$_3$OD) δ 10.15-10.05 (br, 1H), 8.66-8.58 (m, 4H), 8.07-7.70 (m, 4H), 7.12 (s, 1H), 7.18 (s, 1H), 6.70 (s, 1H), 6.69 (s, 1H), 5.50 (s, 1H), 4.91-4.56 (m, 4H); MS (ES+) m/z 443 (M+1).

D. Synthesis of 2-{2-[3-(6-hydroxy-1,3-benzodioxol-5-yl)-3-(hydroxymethyl)-2-oxo-2,3-dihydro-1H-indol-1-yl]ethyl}-1H-isoindole-1,3(2H)-dione Following the procedure as described in PREPARATION 1E, making variation to replace 4-bromo-3-(6-hydroxy-1,3-benzodioxol-5-yl)-1-pentyl-1,3-dihydro-2H-indol-2-one with 2-{2-[3-(6-hydroxy-1,3-benzodioxol-5-yl)-2-oxo-2,3-dihydro-1H-indol-1-yl]ethyl}-1H-isoindole-1,3(2H)-dione, the title compound was obtained (56%): $^1$H NMR (300 MHz, CD$_3$OD) δ 9.97 (s, 1H), 8.72-8.62 (m, 4H), 8.07-7.67 (m, 5H), 7.01 (s, 1H), 6.71 (s, 1H), 6.70 (s, 1H), 5.79 (t, 1H), 4.88-4.50 (m, 6H); MS (ES+) m/z 455 (M−17), 473 (M+1), 495 (M+23).

Preparation 8

Synthesis of 1-(diphenylmethyl)-3-(6-hydroxy-1,3-benzodioxol-5-yl)-3-(hydroxymethyl)-1,3-dihydro-2H-indol-2-one

A. Synthesis of 1-(diphenylmethyl)-1H-indole-2,3-dione

Following the procedure as described in PREPARATION 2A, and making non-critical variations to replace (2-bromoethyl)cyclopropane with 1,1'-(bromomethylene)dibenzene, the title compound was obtained (68%) as an orange solid: MS (ES+) m/z 336.4 (M+23).

B. Synthesis of 1-(diphenylmethyl)-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, the title compound was obtained (99%) as an off-white powder: MS (ES+) m/z 474.5 (M+23).

C. Synthesis of 1-(diphenylmethyl)-3-(6-hydroxy-1,3-benzodioxol-5-yl)-1,3-dihydro-2H-indol-2-one Following the procedure as described in PREPARATION 2C, and making the variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-1,3-benzodioxol-5-yl)-1,3-dihydro-2H-indol-2-one, the title compound was obtained (84%) as an off-white solid: MS (ES+) m/z 458.4 (M+23).

D. Synthesis of 1-(diphenylmethyl)-3-(6-hydroxy-1,3-benzodioxol-5-yl)-3-(hydroxymethyl)-1,3-dihydro-2H-indol-2-one Following the procedure as described in PREPARATION 1E, and making non-critical variations using 1-(diphenylmethyl)-3-(6-hydroxy-1,3-benzodioxol-5-yl)-1,3-dihydro-2H-indol-2-one to replace 4-bromo-3-(6-hydroxy-1,3-benzodioxol-5-yl)-1-pentyl-1,3-dihydro-2H-indol-2-one, the title compound was obtained (56%): MS (ES+) m/z 488.3 (M+23).

Preparation 9

Synthesis of 1-[3-(benzyloxy)propyl]-3-(6-hydroxy-1,3-benzodioxol-5-yl)-3-(hydroxymethyl)-1,3-dihydro-2H-indol-2-one A. Synthesis of
1-[3-(benzyloxy)propyl]-1H-indole-2,3-dione Following the procedure as described in PREPARATION 1A, and making non-critical variations to replace 4-bromoindole with isatin, and 1-bromopentane with benzyl 3-bromopropyl ether, the title compound was obtained (95%) as a pale yellow syrup: $^1$H NMR (300 MHz, CDCl$_3$) δ 7.57-6.92 (m, 9H), 4.50 (s, 2H), 3.84 (t, 2H), 3.54 (t, 2H), 2.03-1.94 (m, 2H); MS (ES$^+$) m/z 296.3 (M+1), 318.3 (M+23).

B. Synthesis of 1-[3-(benzyloxy)propyl]-3-hydroxy-3-(6-hydroxy-1,3-benzodioxol-5-yl)-1,3-dihydro-2H-indol-2-one Following the procedure as described in PREPARATION 1C, and making non-critical variations to replace 4-bromo-1-pentyl-1H-indole-2,3-dione with 1-[3-(benzyloxy)propyl]-1H-indole-2,3-dione, the title compound was obtained (70%): $^1$H NMR (300 MHz, CDCl$_3$) δ 9.42 (s, 1H), 7.32-7.16 (m, 8H), 6.96 (d,), 6.61 (s, 1H), 6.23 (s, 1H), 5.86-5.83 (m, 2H), 4.44 (s, 2H), 3.88-3.73 (m, 2H), 3.46 (t, 2H), 2.06-1.85 (m, 2H); MS (ES+) m/z 416.3 (M−17), 456.3 (M+23).

C. Synthesis of 1-[2-(benzyloxy)propyl]-3-(6-hydroxy-1,3-benzodioxol-5-yl)-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 1-[3-(benzyloxy)propyl]-3-hydroxy-3-(6-hydroxy-1,3-benzodioxol-5-yl)-1,3-dihydro-2H-indol-2-one, the title compound was obtained (92%): $^1$H NMR (300 MHz, CDCl$_3$) δ7.42-6.95 (m, 9H), 6.56 (s, 1H), 6.24 (s, 1H), 5.86 (ABq, 1H), 5.81 (ABq, 1H), 4.99 (s, 1H), 4.42 (s, 2H), 3.91-3.76 (m, 2H), 3.46 (t, 2H), 2.03-1.93 (m, 2H); MS (ES+) m/z 418.3 (M+1).

D. Synthesis of 1-[3-(benzyloxy)propyl]-3-(6-hydroxy-1,3-benzodioxol-5-yl)-3-(hydroxymethyl)-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 1-[3-(benzyloxy)propyl]-3-(6-hydroxy-1,3-benzodioxol-5-yl)-1,3-dihydro-2H-indol-2-one, the title compound was obtained (93%): MS (ES+) m/z 448.2 (M+1).

Preparation 10

Synthesis of methyl 2-{[3-(6-hydroxy-1,3-benzodioxol-5-yl)-3-(hydroxymethyl)-2-oxo-2,3-dihydro-1H-indol-1-yl]methyl}benzoate A. Synthesis of methyl 2-[(2,3-dioxo-2,3-dihydro-1H-indol-1-yl)methyl]benzoate Following the procedure as described in PREPARATION 2A, and making non-critical variations to replace (2-bromoethyl)cyclopropane with methyl 2-(bromomethyl)benzoate, the title compound was obtained (68%) as a yellow solid: $^1$H NMR (300 MHz, CDCl$_3$) δ 8.05 (dd, 1H), 7.64 (dd, 1H), 7.50-7.31 (m, 3H), 7.22 (d, 1H), 7.10 (t, 1H), 6.72 (d, 1H), 5.41 (s, 2H), 3.95 (s, 3H).

B. Synthesis of methyl 2-{[3-hydroxy-3-(6-hydroxy-1,3-benzodioxol-5-yl)-2-oxo-2,3-dihydro-1H-indol-1-yl]methyl}benzoate Following the procedure as described in PREPARATION 2B, and making non-critical variations to replace 1-(2-cyclopropylethyl)-1H-indole-2,3-dione with methyl 2-[(2,3-dioxo-2,3-dihydro-1H-indol-1-yl)methyl]benzoate, the title compound was obtained (97%) as a colorless solid: $^1$H NMR (300 MHz, DMSO-d$_6$) δ 9.29 (s, 1H), 7.97 (dd, 1H), 7.53-7.36 (m, 3H), 7.28 (s, 1H), 7.10 (td, 1H), 6.96-6.83 (m, 2H), 6.59 (d, 2H), 6.25 (s, 1H), 5.95-5.86 (m, 2H), 5.31-5.07 (m, 2H), 3.88 (s, 3H); MS (ES+) m/z 456.1 (M+23).

C. Synthesis of methyl 2-{[3-(6-hydroxy-1,3-benzodioxol-5-yl)-2-oxo-2,3-dihydro-1H-indol-1-yl]methyl}benzoate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with methyl 2-{[3-hydroxy-3-(6-hydroxy-1,3-benzodioxol-5-yl)-2-oxo-2,3-dihydro-1H-indol-1-yl]methyl}benzoate, the title compound was obtained (100%) as a white solid: $^1$H NMR (300 MHz, DMSO-d$_6$) δ 9.32 (s, 1H), 7.94 (dd, 1H), 7.50-7.34 (m, 2H), 7.26 (d, 1H), 7.08 (t, 1H), 7.00-6.86 (m, 2H), 6.76 (s, 1H), 6.64 (d, 1H), 6.38 (s, 1H), 5.93-5.86 (m, 2H), 5.34-5.12 (m, 2H), 4.83 (s, 1H), 3.87 (s, 3H); MS (ES+) m/z 418.2 (M+1).

D. Synthesis of methyl 2-{[3-(6-hydroxy-1,3-benzodioxol-5-yl)-3-(hydroxymethyl)-2-oxo-2,3-dihydro-1H-indol-1-yl]methyl}benzoate A solution of methyl 2-{[3-(6-hydroxy-1,3-benzodioxol-5-yl)-2-oxo-2,3-dihydro-1H-indol-1-yl]methyl}benzoate (17.1 g, 40.0 mmol) and paraformaldehyde (10.3 g, 330 mmol) in THF (500 mL) was degassed by bubbling through argon for 2 hours. To this solution was added lithium diisopropylamide solution (45.1 mL, 2 M solution, 90.0 mmol) slowly at −78° C. The mixture was stirred at ambient temperature overnight and quenched with saturated ammonium chloride solution. The mixture was concentrated in vacuo to remove THF followed by the addition of ethyl acetate (500 mL). The organic layer was washed with water, dried over sodium sulfate and filtered. The filtrate was concentrated in vacuo to dryness. The residue was recrystallized from ethyl acetate/hexanes to give the title compound (13.7 g, 75%): $^1$H NMR (300 MHz, DMSO-d$_6$) δ 9.20 (s, 1H), 7.95 (dd, 1H), 7.53-7.33 (m, 3H), 7.08-6.82 (m, 4H), 6.53 (d, 1H), 6.25 (s, 1H), 5.93-5.86 (m, 2H), 5.31-5.07 (m, 3H), 4.26-4.17 (m, 1H), 4.00-3.92 (m, 1H), 3.88 (s, 3H); MS (ES+) m/z 448.3 (M+1).

Preparation 11

Synthesis of [3-(1,3-benzodioxol-5-yl)-2-oxo-1-pentyl-2,3-dihydro-1H-indol-3-yl]acetic acid A. Synthesis of 1-pentyl-1H-indole-2,3-dione Following the procedure as described in PREPARATION 2A, and making non-critical variations to replace (2-bromoethyl)cyclopropane with 1-bromopentane, the title compound was obtained (85%) as an orange solid: $^1$H NMR (300 MHz, CDCl$_3$) δ 7.60-7.52 (m, 2H), 7.08 (td, 1H), 6.87 (d, 1H), 3.69 (t, 2H), 1.74-1.61 (m, 2H), 1.40-1.28 (m, 4H), 0.88 (t, 3H).

B. Synthesis of 3-(1,3-benzodioxol-5-yl)-3-hydroxy-1-pentyl-1,3-dihydro-2H-indol-2-one To a solution of 1-pentyl-1H-indole-2,3-dione (2.80 g, 12.8 mmol) in THF (50.0 mL) was added 3,4-(methylenedioxy)phenylmagnesium bromide (14.0 mL, 1 M THF solution, 14.0 mmol) slowly at −78° C. The mixture was stirred at 0° C. for 1 h and quenched with ammonium chloride solution. The mixture was poured into water (150 mL) and extracted with ethyl acetate (200 mL). The organic layer was washed with water, dried over sodium sulfate and filtered. The filtrate was concentrated in vacuo to dryness. The residue was subjected to flash column chromatography to afford the title compound (3.10 g, 71%) as an orange oil: $^1$H NMR (300 MHz, CDCl$_3$) δ 7.34-7.23 (m, 2H), 7.05 (t, 1H), 6.91-6.85 (m, 2H), 6.83-6.78 (m, 1H), 6.71 (d, 1H), 5.92-5.89 (m, 2H), 3.82-3.55 (m, 2H), 3.40 (br, 1H), 1.76-1.61 (m, 2H), 1.39-1.28 (m, 4H), 0.87 (t, 3H).

C. Synthesis of 3-(1,3-benzodioxol-5-yl)-1-pentyl-1,3-dihydro-2H-indol-2-one

Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-(1,3-benzodioxol-5-yl)-3-hydroxy-1-pentyl-1,3-dihydro-2H-indol-2-one, the title compound was obtained (90%) as an oil: $^1$H NMR (300 MHz, CDCl$_3$) δ 7.30 (td, 1H), 7.14 (d, 1H), 7.03 (td, 1H), 6.89 (d, 1H), 6.75 (d, 1H), 6.67 (dd, 1H), 6.57 (d, 1H), 5.90 (s, 2H), 4.50 (s, 1H), 3.81-3.62 (m, 2H), 1.76-1.62 (m, 2H), 1.41-1.28 (m, 4H), 0.88 (t, 3H); $^{13}$C NMR (75 MHz, CDCl$_3$) δ 176.8, 148.1, 147.2, 143.5, 130.0, 129.4, 128.4, 125.1, 122.9, 122.0, 108.7, 108.6, 101.1, 51.9, 40.4, 29.0, 27.1, 22.3, 14.0.

D. Synthesis of methyl [3-(1,3-benzodioxol-5-yl)-2-oxo-1-pentyl-2,3-dihydro-1H-indol-3-yl]acetate A solution of 3-(1,3-benzodioxol-5-yl)-1-pentyl-1,3-dihydro-2H-indol-2-one (1.00 g, 3.10 mmol) and methyl bromoacetate (0.44 mL, 4.60 mmol) in THF (20.0 mL) was degassed by bubbling through argon for one hour. Sodium hydride (0.19 g, 4.60 mmol) was added at 0° C. The mixture was stirred at 0° C. for 1 h and quenched with ammonium chloride solution. The mixture was poured into water (150 mL), and extracted with ethyl acetate (200 mL). The organic layer was washed with water, dried over sodium sulfate and filtered. The filtrate was concentrated in vacuo to dryness. The residue was subjected to flash column chromatography to afford the title compound (0.94 g, 76%) as a colorless oil: $^1$H NMR (300 MHz, CDCl$_3$) δ 7.30 (td, 1H), 7.25 (dd, 1H), 7.06 (td, 1H), 6.89 (d, 1H), 6.81 (d, 1H), 6.74-6.65 (m, 2H), 5.90-5.87 (m, 2H), 3.71-3.64 (m, 2H), 3.45 (d, 1H), 3.41 (s, 3H), 3.18 (d, 1H), 1.74-1.60 (m, 2H), 1.39-1.22 (m, 4H), 0.85 (t, 3H); $^{13}$C NMR (75 MHz, CDCl$_3$,) δ 177.8, 170.0, 147.9, 147.0, 143.9, 133.1, 131.3, 128.6, 124.6, 122.3, 119.9, 108.7, 108.1, 107.4, 101.2, 52.8, 51.6, 41.8, 40.4, 29.0, 26.8, 22.3, 14.0; MS (ES+) m/z 418.1 (M+23), 396.1 (M+1).

E. Synthesis of [3-(1,3-benzodioxol-5-yl)-2-oxo-1-pentyl-2,3-dihydro-1H-indol-3-yl]acetic acid To a solution of methyl [3-(1,3-benzodioxol-5-yl)-2-oxo-1-pentyl-2,3-dihydro-1H-indol-3-yl]acetate (5.90 g, 15.0 mmol) in THF/water (2/1 v/v, 120 mL) was added lithium hydroxide monohydrate (1.26 g, 28.0 mmol). The mixture was stirred at ambient temperature overnight. Most THF was removed under vacuum and water (150 mL) was added. The solution was extracted with ethyl acetate/hexanes (1/3 v/v, 50.0 mL). The water layer was acidified with 1 N HCl solution until the pH value reached 2 and extracted with ethyl acetate (200 mL). The organic layer was washed with water, dried over sodium sulfate and filtered. The filtrate was concentrated in vacuo to dryness to afford the title compound (5.00 g, 88%) as a white solid: $^1$H NMR (300 MHz, CDCl$_3$) δ 7.29 (td, 1H), 7.21 (dd, 1H), 7.05 (td, 1H), 6.87 (d, 1H), 6.76 (d, 1H), 6.72-6.64 (m, 2H), 5.90-5.86 (m, 2H), 3.65 (t, 2H), 3.43 (d, 1H), 3.11 (d, 1H), 1.70-1.55 (m, 2H), 1.36-1.22 (m, 4H), 0.85 (t, 3H); $^{13}$C NMR (75 MHz, CDCl$_3$) δ 178.2, 174.0, 148.0, 147.1, 143.4, 132.6, 131.4, 128.7, 124.4, 122.7, 119.8, 108.9, 108.2, 107.2, 101.2, 52.6, 41.5, 40.4, 29.0, 26.6, 22.3, 14.0; MS (ES+) m/z 404.0 (M+23), 382.0 (M+1).

Preparation 12

Synthesis of 3-[3-(1,3-benzodioxol-5-yl)-2-oxo-1-pentyl-2,3-dihydro-1H-indol-3-yl]propanoic acid A. Synthesis of methyl 3-[3-(1,3-benzodioxol-5-yl)-2-oxo-1-pentyl-2,3-dihydro-1H-indol-3-yl]propanoate Following the procedure as described in PREPARATION 11D, and making non-critical variations to replace methyl bromoacetate with methyl 3-bromopropionate, the title compound was obtained (76%) as a colorless oil: $^1$H NMR (300 MHz, CDCl$_3$) δ 7.28 (td, 1H), 7.17 (dd, 1H), 7.06 (td, 1H), 6.89 (d, 1H), 6.84 (d, 1H), 6.77 (dd, 1H), 6.68 (d, 1H), 5.89-5.84 (m, 2H), 3.67 (t, 2H), 3.53 (s, 3H), 2.69-2.56 (m, 1H), 2.54-2.41 (m, 1H), 2.21-2.08 (m, 1H), 1.99-1.86 (m, 1H), 1.72-1.59 (m, 2H), 1.38-1.24 (m, 4H), 0.85 (t, 3H); $^{13}$C NMR (75 MHz, CDCl$_3$) δ 177.8, 173.1, 147.9, 146.9, 143.2, 133.5, 131.6, 128.5, 124.9, 122.6, 120.1, 108.7, 108.1, 107.6, 101.1, 55.2, 51.6, 40.2, 32.4, 29.5, 29.1, 27.1, 22.3, 14.0; MS (ES+) m/z 410.1 (M+1), 432.0 (M+23).

B. Synthesis of 3-[3-(1,3-benzodioxol-5-yl)-2-oxo-1-pentyl-2,3-dihydro-1H-indol-3-yl]propanoic acid Following the procedure as described in PREPARATION 11E, and making non-critical variations to replace methyl [3-(1,3-benzodioxol-5-yl)-2-oxo-1-pentyl-2,3-dihydro-1H-indol-3-yl]acetate with methyl 3-[3-(1,3-benzodioxol-5-yl)-2-oxo-1-pentyl-2,3-dihydro-1H-indol-3-yl]propanoate, the title compound was obtained (92%) as a colorless solid: MS (ES−) m/z 394.2 (M−1).

Preparation 13

Synthesis of 3-(4,5-difluoro-2-hydroxyphenyl)-3-(hydroxymethyl)-1-pentyl-1,3-dihydro-2H-indol-2-one A. Synthesis of 3-(4,5-difluoro-2-hydroxyphenyl)-3-hydroxy-1-pentyl-1,3-dihydro-2H-indol-2-one Following the procedure as described in PREPARATION 2B, and making non-critical variations to replace 1-(2-cyclopropylethyl)-1H-indole-2,3-dione with 1-pentyl-1H-indole-2,3-dione, and 1,3-benzodioxol-5-ol with 3,4-difluorophenol, the title compound was obtained (31%): $^1$H NMR (300

MHz, CDCl$_3$) δ 9.69-9.65 (br, 1H), 7.51-7.41 (m, 2H), 7.26-7.21 (m, 1H), 6.99-6.57 (m, 3H), 4.18-4.14 (br, 1H), 3.78-3.58 (m, 2H), 1.76-1.62 (m, 2H), 1.40-1.28 (m, 4H), 0.87 (t, 3H); MS (ES+) m/z 330 (M−17), 370 (M+23).

B. Synthesis of 3-(4,5-difluoro-2-hydroxyphenyl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-(4,5-difluoro-2-hydroxyphenyl)-3-hydroxy-1-pentyl-1,3-dihydro-2H-indol-2-one, the title compound was obtained (98%): $^1$H NMR (300 MHz, CDCl$_3$) δ 7.46-7.19 (m, 3H), 7.03-6.68 (m, 3H), 5.03 (s, 1H), 3.76-3.67 (m, 2H), 1.76-1.62 (m, 2H), 1.40-1.28 (m, 4H), 0.87 (t, 3H); MS (ES+) m/z 332 (M+1).

C. Synthesis of 3-(4,5-difluoro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4,5-difluoro-2-hydroxyphenyl)-1-pentyl-1,3-dihydro-2H-indol-2-one, the title compound was obtained (96%): MS (ES+) m/z 344 (M−17), 384 (M+23).

Preparation 14

Synthesis of 3-(5-fluoro-2-hydroxyphenyl)-3-(hydroxymethyl)-1-pentyl-1,3-dihydro-2H-indol-2-one A. Synthesis of 3-(5-fluoro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 4-fluorophenol, the title compound was obtained (53%): $^1$H NMR (300 MHz, CDCl$_3$) δ 9.42-9.14 (br, 1H), 7.53-6.86 (m, 6H), 6.56-6.48 (m, 1H), 4.58-4.28 (br, 1H), 3.79-3.58 (m, 2H), 1.77-1.61 (m, 2H), 1.41-1.24 (m, 4H), 0.87 (t, 3H); MS (ES+) m/z 312 (M−17), 352 (M+23).

B. Synthesis of 3-(5-fluoro-2-hydroxyphenyl)-1-pentyl-1,3-dihydro-2H-indol-2-one To a solution of 3-(5-fluoro-2-hydroxyphenyl)-3-hydroxy-1-pentyl-1,3-dihydro-2H-indol-2-one (2.42 g, 7.35 mmol) in dichloromethane (10.0 mL) were added trifluoroacetic acid (1.00 mL) and triethylsilane (1.00 mL) at ambient temperature. The reaction mixture was stirred at 40° C. for 15 hrs and concentrated in vacuo to dryness. The residue was triturated with ether to give the title compound (2.10 g, 91%) as a solid: MS (ES+) m/z 314 (M+1).

C. Synthesis of 3-(5-fluoro-2-hydroxyphenyl)-3-(hydroxymethyl)-1-pentyl-1,3-dihydro-2H-indol-2-one To a solution of 3-(5-fluoro-2-hydroxyphenyl)-1-pentyl-1,3-dihydro-2H-indol-2-one (2.10 g, 6.70 mmol) in THF (20.0 mL) were added paraformaldehyde (1.76 g, 58.8 mmol) and lithium diisopropylamide (7.35 mL, 2.0 M in THF, 14.7 mmol) at 0° C. The reaction mixture was stirred at 0° C. for 2 hrs followed by the addition of ammonium chloride solution (10.0 mL) and ethyl acetate (100 mL). The organic layer was washed with water and brine, dried over Na$_2$SO$_4$ and filtered. The filtrate was concentrated in vacuo to dryness to give the title compound: $^1$H NMR (300 MHz, CDCl$_3$) δ 9.55-9.10 (br, 1H), 7.53-6.86 (m, 6H), 6.57-6.49 (m, 1H), 4.74-4.30 (br, 1H), 4.18-4.07 (m, 2H), 3.79-3.60 (m, 2H), 1.77-1.61 (m, 2H), 1.41-1.24 (m, 4H), 0.87 (t, 3H); MS (ES+) m/z 326 (M−17), 366 (M+23).

Preparation 15

Synthesis of 3-(5-bromo-2-hydroxyphenyl)-3-(hydroxymethyl)-1-pentyl-1,3-dihydro-2H-indol-2-one A. Synthesis of 3-(5-bromo-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 4-bromophenol, the title compound was obtained (41%): $^1$H NMR (300 MHz, CDCl$_3$) δ 9.46-9.25 (br, 1H), 7.51-6.80 (m, 7H), 4.73-4.51 (br, 1H), 3.79-3.56 (m, 2H), 1.76-1.60 (m, 2H), 1.41-1.22 (m, 4H), 0.87 (t, 3H); MS (ES+) m/z 377 (M−17), 379 (M−17), 412 (M+23), 414 (M+23).

B. Synthesis of 3-(5-bromo-2-hydroxyphenyl)-1-pentyl-1,3-dihydro-2H-indol-2-one

To a solution of 3-(5-bromo-2-hydroxyphenyl)-3-hydroxy-1-pentyl-1,3-dihydro-2H-indol-2-one (2.22 g, 5.64 mmol) in dichloromethane (10.0 mL) were added trifluoroacetic acid (1.00 mL) and triethylsilane (1.00 mL) at ambient temperature. The reaction mixture was stirred at 50° C. for 15 hrs and concentrated in vacuo to dryness to give the title compound: MS (ES+) m/z 374 (M+1), 376 (M+1).

C. Synthesis of 3-(5-bromo-2-hydroxyphenyl)-3-(hydroxymethyl)-1-pentyl-1,3-dihydro-2H-indol-2-one Following the procedure as described in PREPARATION 14C, and making non-critical variations to replace 3-(5-fluoro-2-hydroxyphenyl)-1-pentyl-1,3-dihydro-2H-indol-2-one with 3-(5-bromo-2-hydroxyphenyl)-1-pentyl-1,3-dihydro-2H-indol-2-one, the title compound was obtained: MS (ES+) m/z 386 (M−17), 388 (M−17), 426 (M+23), 428 (M+23).

Preparation 16

Synthesis of 3-(5-chloro-4-fluoro-2-hydroxyphenyl)-3-(hydroxymethyl)-1-pentyl-1,3-dihydro-2H-indol-2-one A. Synthesis of 3-(5-chloro-4-fluoro-2-hydroxyphenyl)-3-hydroxy-1-pentyl-1,3-dihydro-2H-indol-2-one Following the procedure as described in PREPARATION 10, and making non-critical variations to replace 4-bromo-1-pentyl-1H-indole-2,3-dione with 1-pentyl-1H-indole-2,3-dione, and 1,3-benzodioxol-5-ol with 4-chloro-3-fluorophenol, the title compound was obtained (33%): $^1$H NMR (300 MHz, CDCl$_3$) δ 9.80 (s, 1H), 7.52-7.41 (m, 2H), 7.23 (t, 1H), 6.96

(d, 1H), 6.84 (d, 1H), 6.80 (d, 1H), 4.15 (s, 1H), 3.79-3.58 (m, 2H), 1.76-1.62 (m, 2H), 1.40-1.28 (m, 4H), 0.87 (t, 3H); MS (ES+) m/z 346 (M−17), 386 (M+23).

B. Synthesis of 3-(5-chloro-4-fluoro-2-hydroxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(5-chloro-4-fluoro-2-hydroxyphenyl)-3-hydroxy-1-pentyl-1,3-dihydro-2H-indol-2-one, the title compound was obtained (99%): $^1$H NMR (300 MHz, CDCl$_3$) δ 10.0-9.70 (br, 1H), 7.45-7.18 (m, 3H), 6.98 (d, 1H), 6.90-6.82 (m, 2H), 5.01 (s, 1H), 3.75-3.66 (m, 2H), 1.76-1.62 (m, 2H), 1.40-1.28 (m, 4H), 0.87 (t, 3H); MS (ES+) m/z 348 (M+1).

C. Synthesis of 3-(5-chloro-4-fluoro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(5-chloro-4-fluoro-2-hydroxyphenyl)-1-pentyl-1,3-dihydro-2H-indol-2-one, the title compound was obtained (46%): MS (ES+) m/z 360 (M−17), 400 (M+23).

Preparation 17

Synthesis of 3-(4-chloro-5-fluoro-2-hydroxyphenyl)-3-(hydroxymethyl)-1-pentyl-1,3-dihydro-2H-indol-2-one A. Synthesis of 3-(4-chloro-5-fluoro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 3-chloro-4-fluorophenol, the title compound was obtained (14%): MS (ES+) m/z 346 (M−17), 386 (M+23).

B. Synthesis 3-(4-chloro-5-fluoro-2-hydroxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(4-chloro-5-fluoro-2-hydroxyphenyl)-3-hydroxy-1-pentyl-1,3-dihydro-2H-indol-2-one, the title compound was obtained: MS (ES+) m/z 348 (M+1).

C. Synthesis of 3-(4-chloro-5-fluoro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4-chloro-5-fluoro-2-hydroxyphenyl)-1-pentyl-1,3-dihydro-2H-indol-2-one, the title compound was obtained (50% for two steps): MS (ES+) m/z 360 (M−17), 400 (M+23).

Preparation 18

Synthesis of 3-(4,5-dichloro-2-hydroxyphenyl)-3-(hydroxymethyl)-1-pentyl-1,3-dihydro-2H-indol-2-one A. Synthesis of 3-(4,5-dichloro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 3,4-dichlorophenol, the title compound was obtained (26%): $^1$H NMR (300 MHz, CDCl$_3$) δ 9.60 (s, 1H), 7.50-7.40 (m, 2H), 7.22 (td, 1H), 7.11 (s, 1H), 6.95 (d, 1H), 6.86 (s, 1H), 4.31-4.12 (br, 1H), 3.79-3.59 (m, 2H), 1.76-1.62 (m, 2H), 1.40-1.27 (m, 4H), 0.88 (t, 3H); MS (ES+) m/z 363 (M−17), 403 (M+23).

B. Synthesis of 3-(4,5-dichloro-2-hydroxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(4,5-dichloro-2-hydroxyphenyl)-3-hydroxy-1-pentyl-1,3-dihydro-2H-indol-2-one, the title compound was obtained (86%): $^1$H NMR (300 MHz, CDCl$_3$) δ 10.0-9.50 (br, 1H), 7.42 (t, 1H), 7.32 (d, 1H), 7.22 (td, 1H), 7.09 (s, 1H), 6.95 (d, 1H), 6.93 (s, 1H), 5.04 (s, 1H), 3.77-3.68 (m, 2H), 1.77-1.62 (m, 2H), 1.40-1.27 (m, 4H), 0.88 (t, 3H); MS (ES+) m/z 348 (M+1).

C. Synthesis of 3-(4,5-dichloro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4,5-dichloro-2-hydroxyphenyl)-1-pentyl-1,3-dihydro-2H-indol-2-one, the title compound was obtained: MS (ES+) m/z 376 (M−17), 416 (M+23).

Preparation 19

Synthesis of 3-(hydroxymethyl)-3-[2-hydroxy-5-(trifluoromethyl)phenyl]-1-pentyl-1,3-dihydro-2H-indol-2-one A. Synthesis of 3-hydroxy-3-[2-hydroxy-5-(trifluoromethyl)phenyl]-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with α,α,α-trifluorocresol, the title compound was obtained (46%): $^1$H NMR (300 MHz, CDCl$_3$) δ 9.75 (s, 1H), 7.50-7.39 (m, 3H), 7.21 (td, 1H), 7.10-7.02 (m, 2H), 6.96 (d, 1H), 4.26 (s, 1H), 3.82-3.59 (m, 2H), 1.77-1.63 (m, 2H), 1.40-1.27 (m, 4H), 0.88 (t, 3H); MS (ES+) m/z 362 (M−17), 402 (M+23).

B. Synthesis of 3-[2-hydroxy-5-(trifluoromethyl)phenyl]-1-pentyl-1,3-dihydro-2H-indol-2-one Following the procedure as described in PREPARATION 15B, and making non-critical variations to replace 3-(5- bromo-2-hydroxyphenyl)-3-hydroxy-1-pentyl-1,3-dihydro-2H-indol-2-one with 3-hydroxy-3-[2-hydroxy-5-(trifluoromethyl)phenyl]-1-pentyl-1,3-dihydro-2H-indol-2-one, the title compound was obtained (78%): $^1$H NMR (300 MHz, CDCl$_3$) δ 8.20-8.00 (br, 1H), 7.43-7.14 (m, 5H), 7.02 (d, 1H), 6.95 (d, 1H), 5.11 (s, 1H), 3.82-3.72 (m, 2H), 1.79-1.66 (m, 2H), 1.40-1.27 (m, 4H), 0.88 (t, 3H); MS (ES+) m/z 364 (M+1).

C. Synthesis of 3-(hydroxymethyl)-3-[2-hydroxy-5-(trifluoromethyl)phenyl]-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-[2-hydroxy-5-(trifluoromethyl)phenyl]-1-pentyl-1,3-dihydro-2H-indol-2-one, the title compound was obtained: MS (ES+) m/z 376 (M–17), 416 (M+23).

Preparation 20

Synthesis of 3-(2-hydroxy-4-methoxyphenyl)-3-(hydroxymethyl)-1-pentyl-1,3-dihydro-2H-indol-2-one A. Synthesis of 3-(5-bromo-2-hydroxy-4-methoxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 4-bromo-3-methoxyphenol, the title compound was obtained (48%): $^1$H NMR (300 MHz, CDCl$_3$) δ 9.85 (s, 1H), 7.52-7.38 (m, 2H), 7.22 (td, 1H), 6.94 (d, 1H), 6.89 (s, 1H), 6.63 (s, 1H), 4.13-4.03 (br, 1H), 3.86 (s, 3H), 3.80-3.57 (m, 2H), 1.75-1.63 (m, 2H), 1.40-1.25 (m, 4H), 0.88 (t, 3H); MS (ES+) m/z 402 (M–17), 404 (M–17), 442 (M+23), 444 (M+23).

B. Synthesis of 3-(2-hydroxy-4-methoxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(5-bromo-2-hydroxy-4-methoxyphenyl)-3-hydroxy-1-pentyl-1,3-dihydro-2H-indol-2-one, the title compound was obtained (83%): $^1$H NMR (300 MHz, CDCl$_3$) δ 9.78-9.20 (br, 1H), 7.43-7.31 (m, 2H), 7.19 (t, 1H), 6.97 (d, 1H), 6.79 (d, 1H), 6.70-6.64 (m, 1H), 6.38 (dd, 1H), 5.02 (s, 1H), 3.77 (s, 3H), 3.70 (t, 2H), 1.75-1.63 (m, 2H), 1.40-1.25 (m, 4H), 0.87 (t, 3H); MS (ES+) m/z 326 (M+1).

C. Synthesis of 3-(2-hydroxy-4-methoxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(2-hydroxy-4-methoxyphenyl)-1-pentyl-1,3-dihydro-2H-indol-2-one, the title compound was obtained (41%): $^1$H NMR (300 MHz, CDCl$_3$) δ 10.79 (s, 1H), 7.51-7.37 (m, 2H), 7.26 (td, 1H), 6.99 (d, 1H), 6.95 (d, 1H), 6.59 (d, 1H), 6.34 (dd, 1H), 4.67 (d, 1H), 4.14 (d, 1H), 3.76 (s, 3H), 3.78-3.69 (m, 2H), 1.75-1.63 (m, 2H), 1.40-1.25 (m, 4H), 0.87 (t, 3H); MS (ES+) m/z 338 (M–17), 378 (M+23).

Preparation 21

Synthesis of ethyl [3-(6-hydroxy-2,3-dihydro-1H-inden-5-yl)-3-(hydroxymethyl)-2-oxo-2,3-dihydro-1H-indol-1-yl]acetate A. Synthesis of ethyl [3-hydroxy-3-(6-hydroxy-2,3-dihydro-1H-inden-5-yl)-2-oxo-2,3-dihydro-1H-indol-1-yl]acetate Following the procedure as described in PREPARATION 10, and making non-critical variations to replace 4-bromo-1-pentyl-1H-indole-2,3-dione with ethyl (2,3-dioxo-2,3-dihydro-1H-indol-1-yl)acetate, and 1,3-benzodioxol-5-ol with 5-indanol, the title compound was obtained (84%): $^1$H NMR (300 MHz, CDCl$_3$) δ 8.76 (s, 1H), 7.55 (d, 1H), 7.38 (td, 1H), 7.20 (t, 1H), 6.9 (s, 1H), 6.80 (d, 1H), 6.65 (s, 1H), 4.45 (ABq, 2H), 4.32-4.25 (br, 1H), 4.20 (q, 2H), 2.83 (t, 2H), 2.74-2.65 (m, 2H), 2.06-1.94 (m, 2H), 1.27 (t, 3H); MS (ES+) m/z 350 (M–17), 390 (M+23).

B. Synthesis of ethyl [3-(6-hydroxy-2,3-dihydro-1H-inden-5-yl)-2-oxo-2,3-dihydro-1H-indol-1-yl]acetate Following the procedure as described in PREPARATION 15B, and making non-critical variations to replace 3-(5-bromo-2-hydroxyphenyl)-3-hydroxy-1-pentyl-1,3-dihydro-2H-indol-2-one with ethyl [3-hydroxy-3-(6-hydroxy-2,3-dihydro-1H-inden-5-yl)-2-oxo-2,3-dihydro-1H-indol-1-yl]acetate, the title compound was obtained: $^1$H NMR (300 MHz, CDCl$_3$) δ 8.50-7.90 (br, 1H), 7.40-7.32 (m, 2H), 7.38 (td, 1H), 6.94 (s, 1H), 6.84 (d, 1H), 6.75 (s, 1H), 5.16 (s, 1H), 4.48 (ABq, 2H), 4.21 (q, 2H), 2.85 (t, 2H), 2.81-2.61 (m, 2H), 2.09-1.92 (m, 2H), 1.25 (t, 3H); MS (ES+) m/z 352 (M+1).

C. Synthesis of ethyl [3-(6-hydroxy-2,3-dihydro-1H-inden-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [3-(6-hydroxy-2,3-dihydro-1H-inden-5-yl)-2-oxo-2,3-dihydro-1H-indol-1-yl]acetate, the title compound was obtained: MS (ES+) m/z 364 (M–17), 404 (M+23).

Preparation 22

Synthesis of ethyl [3-(hydroxymethyl)-3-(3-hydroxy-5,6,7,8-tetrahydronaphthalen-2-yl)-2-oxo-2,3-dihydro-1H-indol-1-yl]acetate A. Synthesis of ethyl [3-hydroxy-3-(3-hydroxy-5,6,7,8-tetrahydronaphthalen-2-yl)-2-oxo-2,3-dihydro-1H-indol-1-yl]acetate Following the procedure as described in PREPARATION 1C, and making non-critical variations to replace 4-bromo-1-pentyl-1H-indole-2,3-dione with ethyl (2,3-dioxo-2,3-dihydro-1H-indol-1-yl)acetate, and 1,3-benzodioxol-5-ol with 5,6,7,8-tetrahydronapthalen-2-ol, the title compound was obtained (81%): $^1$H NMR (300 MHz, CDCl$_3$) δ 8.61 (s, 1H), 7.54 (dd, 1H), 7.38 (td, 1H), 7.20 (t, 1H), 6.80 (d, 1H), 6.76 (s, 1H), 6.50 (s, 1H), 4.45 (ABq, 2H), 4.21 (q, 2H), 4.18-4.14 (br, 1H), 2.73-2.47 (m, 4H), 1.77-1.63 (m, 4H), 1.24 (t, 3H); MS (ES+) m/z 364 (M−17), 404 (M+23)

B. Synthesis of ethyl [3-(3-hydroxy-5,6,7,8-tetrahydronaphthalen-2-yl)-2-oxo-2,3-dihydro-1H-indol-1-yl]acetate Following the procedure as described in PREPARATION 15B, and making non-critical variations to replace 3-(5-bromo-2-hydroxyphenyl)-3-hydroxy-1-pentyl-1,3-dihydro-2H-indol-2-one with ethyl [3-hydroxy-3-(3-hydroxy-5,6,7,8-tetrahydronaphthalen-2-yl)-2-oxo-2,3-dihydro-1H-indol-1-yl]acetate, the title compound was obtained: $^1$H NMR (300 MHz, CDCl$_3$) δ 7.42-7.32 (m, 2H), 7.20 (t, 1H), 6.84 (d, 1H), 6.78 (s, 1H), 6.61 (s, 1H), 5.12 (s, 1H), 4.47 (ABq, 2H), 4.21 (q, 2H), 2.76-2.44 (m, 4H), 1.78-1.64 (m, 4H), 1.24 (t, 3H); MS (ES+) m/z 366 (M+1).

C. Synthesis of ethyl [3-(hydroxymethyl)-3-(3-hydroxy-5,6,7,8-tetrahydronaphthalen-2-yl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [3-(3-hydroxy-5,6,7,8-tetrahydronaphthalen-2-yl)-2-oxo-2,3-dihydro-1H-indol-1-yl]acetate, the title compound was obtained: MS (ES+) m/z 378 (M−17), 418 (M+23).

Preparation 23

Synthesis of ethyl [4-bromo-3-(4,5-difluoro-2-hydroxyphenyl)-3-(hydroxymethyl)-2-oxo-2,3-dihydro-1H-indol-1-yl]acetate A. Synthesis of ethyl (4-bromo-2,3-dioxo-2,3-dihydro-1H-indol-1-yl)acetate Following the procedure as described in PREPARATION 2A, and making non-critical variations to replace isatin with 4-bromoisatin and (2-bromoethyl)cyclopropane with ethyl bromoacetate, the title compound was obtained as a yellow solid (68%): $^1$H NMR (300 MHz, CDCl$_3$) δ 7.39 (t, 1H), 7.27 (dd, 1H), 6.71 (dd, 1H), 4.47 (s, 2H), 4.23 (q, 2H), 1.27 (t, 3H); MS (ES+) m/z 312 (M+1), 314 (M+1), 334 (M+23), 336 (M+23).

B. Synthesis of ethyl [4-bromo-3-(4,5-difluoro-2-hydroxyphenyl)-3-hydroxy-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-bromo-2,3-dioxo-2,3-dihydro-1H-indol-1-yl)acetate and 1,3-benzodioxol-5-ol with 3,4-difluorophenol, the title compound was obtained as a white solid (42%); MS (ES+) m/z 424 (M−17), 426 (M−17), 464 (M+23), 466 (M+23).

C. Synthesis of ethyl [4-bromo-3-(4,5-difluoro-2-hydroxyphenyl)-2-oxo-2,3-dihydro-1H-indol-1-yl]acetate A mixture of ethyl [4-bromo-3-(4,5-difluoro-2-hydroxyphenyl)-3-hydroxy-2-oxo-2,3-dihydro-1H-indol-1-yl]acetate (0.90 g, 2.00 mmol), triethylsilane (2.00 mL, 12.2 mmol) and trifluoroacetic acid (0.94 mL, 12.2 mmol) was heated at 90° C. for two days. After cooling down to ambient temperature, the mixture was diluted with ethyl acetate (200 mL), washed with water, dried over anhydrous sodium sulfate and filtered. The filtrate was concentrated in vacuo to dryness. The residue was subjected to column chromatography (ethyl acetate/hexanes, 1/3) to give the title compound (0.37 g, 43%): $^1$H NMR (300 MHz, CDCl$_3$) δ 7.35-7.22 (m, 3H), 6.82-6.71 (m, 2H), 6.52 (t, 1H), 5.10 (s, 1H), 4.45 (s, 2H), 4.21 (q, 2H), 1.23 (t, 3H); MS (ES+) m/z 426.4 (M+1), 428.4 (M+1).

D. Synthesis of ethyl [4-bromo-3-(4,5-difluoro-2-hydroxyphenyl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-bromo-3-(4,5-difluoro-2-hydroxyphenyl)-2-oxo-2,3-dihydro-1H-indol-1-yl]acetate, the title compound was obtained (83%): MS (ES+) m/z 456.3 (M+1), 458.3 (M+1).

Preparation 24

Synthesis of ethyl [4-bromo-3-(6-hydroxy-2,2-dimethyl-2,3-dihydro-1-benzofuran-5-yl)-3-(hydroxymethyl)-2-oxo-2,3-dihydro-1H-indol-1-yl]acetate A. Synthesis of 6-(benzyloxy)-2,2-dimethylbenzofuran-3(2H)-one To a solution of 6-(benzyloxy)benzofuran-3(2H)-one (Adams, J. L., et al., *J. Med. Chem.* (1996), 39(26):5035-46) (1.60 g, 6.67 mmol) in DMF (50.0 mL) were added sodium hydride (0.59 g, 14.7 mmol) and iodomethane (1.46 mL, 23.3 mmol) at 0° C. The reaction mixture was stirred at ambient temperature for 16 h and quenched with saturated ammonium chloride (50.0 mL). The aqueous mixture was extracted with ethyl acetate (3×50.0 mL). The combined organic layers was dried over anhydrous sodium sulfate and filtered. The filtrate was concentrated in vacuo to dryness. The residue was subjected to column chromatography (ethyl acetate/hexane, 1/10) to give the title compound (0.85 g, 47%): $^1$H NMR (300 MHz, CDCl$_3$) δ 7.55 (d, 1H), 7.44-7.30 (m, 5H), 6.69 (dd, 1H), 6.54 (d, 1H), 5.10 (s, 2H), 1.43 (s, 6H); MS (ES+) m/z 269.5 (M+1).

B. Synthesis of 2,2-dimethyl-2,3-dihydrobenzofuran-6-ol

To a solution of 6-(benzyloxy)-2,2-dimethylbenzofuran-3(2H)-one (0.85 g, 3.20 mmol) in methanol (100 mL) was added palladium hydroxide (0.22 g, 20 wt. % loading, 0.32 mmol). The resulting mixture was hydrogenated for 16 hours under 60 psi of hydrogen. The reaction mixture was filtered through celite, washed with methanol. The filtrate was concentrated in vacuo to dryness. The residue was subjected to column chromatography (ethyl acetate/hexane, 1/5) to give the title compound (0.46 g, 88%): $^1$H NMR (300 MHz, CDCl$_3$) δ 6.92 (d, 1H), 6.30-6.21 (m, 2H), 4.77 (s, 1H), 2.90 (s, 2H), 1.44 (s, 6H).

C. Synthesis of ethyl [4-bromo-3-hydroxy-3-(6-hydroxy-2,2-dimethyl-2,3-dihydro-1-benzofuran-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-bromo-2,3-dioxo-2,3-dihydro-1H-indol-1-yl)acetate and 1,3-benzodioxol-5-ol with 2,2-dimethyl-2,3-dihydrobenzofuran-6-ol, the title compound was obtained: MS (ES+) m/z 498.5 (M+23), 500.5 (M+23).

D. Synthesis of ethyl [4-bromo-3-(6-hydroxy-2,2-dimethyl-2,3-dihydro-1-benzofuran-5-yl)-2-oxo-2,3-dihydro-1H-indol-1-yl]acetate A mixture of ethyl [4-bromo-3-hydroxy-3-(6-hydroxy-2,2-dimethyl-2,3-dihydro-1-benzofuran-5-yl)-2-oxo-2,3-dihydro-1H-indol-1-yl]acetate (1.32 g, 2.80 mmol), triethylsilane (2.00 mL, 12.2 mmol) and trifluoroacetic acid (0.94 mL, 12.2 mmol) in dichloromethane (50.0 mL) was stirred at 35° C. for 3 hours. The mixture was diluted with dichloromethane (100 mL), washed with water, dried over anhydrous sodium sulfate and filtered. The filtrate was concentrated in vacuo to dryness. The residue was subjected to column chromatography (ethyl acetate/hexane, 1/3) to give the title compound (1.04 g, 81%): $^1$H NMR (300 MHz, CDCl$_3$) δ 7.32-7.15 (m, 2H), 6.74 (d, 1H), 6.50-6.36 (br, 2H), 5.04 (s, 1H), 4.51-4.34 (m, 2H), 4.25-4.14 (m, 2H), 2.92-2.69 (m, 2H), 1.43 (s, 3H), 1.37 (s, 3H), 1.23 (t, 3H); MS (ES+) m/z 460.5 (M+1), 462.5 (M+1).

E. Synthesis of ethyl [4-bromo-3-(6-hydroxy-2,2-dimethyl-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-bromo-3-(6-hydroxy-2,2-dimethyl-2,3-dihydro-1-benzofuran-5-yl)-2-oxo-2,3-dihydro-1H-indol-1-yl]acetate, the title compound was obtained (25%): MS (ES+) m/z 490.5 (M+1), 492.5 (M+1).

Preparation 25

Synthesis of 3,3-dimethyl-2,3-dihydro-1-benzofuran-6-ol

A. Synthesis of 4-(benzyloxy)-1-bromo-2-(2-methylallyloxy)benzene

To a solution of 5-(benzyloxy)-2-bromophenol (Simas, A. B. C., et al, *Synthesis*, (1999):1017-21) (8.15 g, 29.3 m mol) in DMF (150 mL) was added potassium carbonate (4.46 g, 32.2 mmol) slowly at 0° C. The mixture was stirred at ambient temperature for half an hour, followed by the addition of 3-bromo-2-methylpropene (3.35 mL, 32.2 mmol) during half an hour at 0° C. The mixture was stirred at ambient temperature overnight and quenched with saturated ammonium chloride (50 mL). The aqueous mixture was extracted with ethyl acetate (3×200 mL). The combined organic layers was dried over anhydrous sodium sulfate and filtered. The filtrate was concentrated in vacuo. The residue was subjected to column chromatography (ethyl acetate/hexane, 1/20) to give the title compound (10.0 g, 94%): $^1$H NMR (300 MHz, CDCl$_3$) δ 7.43-7.29 (m, 5H), 6.53 (d, 1H), 6.45 (dd, 1H), 5.15-4.94 (m, 4H), 4.43 (s, 2H), 1.82 (s, 3H); $^{13}$C NMR (75 MHz, CDCl$_3$) δ 159.1, 155.6, 140.1, 136.5, 133.1, 128.6, 128.1, 127.5, 112.9, 107.2, 103.3, 102.0, 72.4, 70.3, 19.3.

B. Synthesis of 6-(benzyloxy)-3,3-dimethyl-2,3-dihydrobenzofuran

To a solution of 4-(benzyloxy)-1-bromo-2-(2-methylallyloxy)benzene (5.00 g, 15.1 mmol) in benzene (400 mL) was added tributyltin hydride (7.42 mL, 27.2 mmol) and benzoyl peroxide (0.70 g, 2.90 mmol) at 0° C. The resulting mixture was refluxed at 100° C. overnight. After cooling down to ambient temperature, the mixture was washed with water, dried over anhydrous sodium sulfate and filtered. The filtrate was concentrated in vacuo to dryness. The residue was subjected to column chromatography (ethyl acetate/hexane, 1/20) to give the title compound (3.48 g, 91%): MS (ES+) m/z 255.6 (M+1).

C. Synthesis of 3,3-dimethyl-2,3-dihydro-1-benzofuran-6-ol

To a solution of 6-(benzyloxy)-3,3-dimethyl-2,3-dihydrobenzofuran (3.48 g, 13.7 mmol) in methanol (200 mL) was added Pd/C (1.45 g) and the mixture was hydrogenated under 40 psi of hydrogen overnight. The reaction mixture was filtered through celite, washed with methanol. The filtrate was concentrated in vacuo to dryness. The residue was subjected to column chromatography (ethyl acetate/hexane, 1/7) to give the title compound (1.66 g, 74%): MS (ES+) m/z 165.4 (M+1).

Preparation 26

Synthesis of 1-(diphenylmethyl)-3-(5-hydroxy-2,3-dihydro-1-benzofuran-6-yl)-3-(hydroxymethyl)-1,3-dihydro-2H-indol-2-one

A. Synthesis of 1-(diphenylmethyl)-3-hydroxy-3-(5-hydroxy-2,3-dihydro-1-benzofuran-6-yl)-1,3-dihydro-2H-indol-2-one Following the procedure as described in PREPARATION 2B, and making non-critical variations to replace 1,3-benzodioxol-5-ol with 2,3-dihydrobenzofuran-5-ol, (Alabaster, R. J., et al.; *Synthesis* (1988), 12:950-2) and 1-(2-cyclopropylethyl)-1H-indole-2,3-dione with 1-(diphenylmethyl)-1H-indole-2,3-dione, the title compound was obtained: MS (ES+) m/z 472.2 (M+23).

B. Synthesis of 1-(diphenylmethyl)-3-(5-hydroxy-2,3-dihydro-1-benzofuran-6-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(5-hydroxy-2,3-dihydro-1-benzofuran-6-yl)-1,3-dihydro-2H-indol-2-one, the title compound was obtained: MS (ES+) m/z 434.4 (M+1).

C. Synthesis of 1-(diphenylmethyl)-3-(5-hydroxy-2,3-dihydro-1-benzofuran-6-yl)-3-(hydroxymethyl)-1,3-dihydro-2H-indol-2-one To a solution of 1-(diphenylmethyl)-3-(5-hydroxy-2,3-dihydro-1-benzofuran-6-yl)-1,3-dihydro-2H-indol-2-one (1.01 g, 2.30 mmol) in THF (50.0 mL) was added paraformaldehyde (1.00 g, 30.0 mmol). Argon was bubbled through the reaction mixture for one hour followed by the addition of diisopropylamine (1.00 g, 10.0 mmol) at 0° C. The reaction mixture was stirred at ambient temperature for 20 hours and diluted with ethyl acetate (100 mL). The resulting mixture was washed with water (2×50.0 mL), dried over sodium sulfate and filtered. The filtrate was concentrated in vacuo to dryness to give 0.67 g (65%) of the title compound: MS (ES+) m/z 486.4 (M+23).

Preparation 27

Synthesis of 3-(6-hydroxy-1,3-benzodioxol-5-yl)-3-(hydroxymethyl)-4-methoxy-1-{[5-(trifluoromethyl)-2-furyl]methyl}-1,3-dihydro-2H-indol-2-one A. Synthesis of ethyl 2-(2-(tert-butoxycarbonylamino)-6-methoxyphenyl)-2-oxoacetate To a solution of tert-butyl 3-methoxyphenylcarbamate (25.6 g, 0.11 mol) in THF (300 mL) was added n-BuLi (0.25 mol, 1.6 M solution in pentane) at −78° C. The resulted solution was stirred at 0° C. for 3 hours and re-cooled to −78° C. followed by the addition of diethyl oxalate (20.1 g, 0.14 mol). The mixture was stirred at −78° C. for 45 min and at ambient temperature for one hour, and quenched with 1 N HCl. The mixture was extracted with ether. The organic solution was dried over sodium sulfate and filtered. The filtrate was concentrated in vacuo to dryness. The residue was subjected to column chromatography to give 3.70 g (27% based on recovered starting material) of the title compound: MS (ES+) m/z 324.3 (M+1).

B. Synthesis of 4-methoxy-1H-indole-2,3-dione

A mixture of ethyl 2-(2-(tert-butoxycarbonylamino)-6-methoxyphenyl)-2-oxoacetate (3.70 g, 110 mmol) and 10% H₂SO₄ (100 mL) was heated at 100° C. for 10 hours. After cooling down to ambient temperature, the reaction mixture was extracted with ether (3×100 mL). The combined ether solution was washed with water (2×50.0 mL), dried over sodium sulfate and filtered. The filtrate was concentrated in vacuo to dryness. The residue was subjected to column chromatography to give 0.37 g (19%) of the title compound: MS (ES+) m/z 200.1 (M+23).

C. Synthesis of 4-methoxy-1-{[5-(trifluoromethyl)-2-furyl]methyl}-1H-indole-2,3-dione Following the procedure as described in PREPARATION 1A, and making non-critical variations to replace 4-bromoindole with 4-methoxy-1H-indole-2,3-dione, and 1-bromopentane with 2-(bromomethyl)-5-(trifluoromethyl)furan, the title compound was obtained (26%): MS (ES+) m/z 348.2 (M+23).

D. Synthesis of 3-hydroxy-3-(6-hydroxy-1,3-benzodioxol-5-yl)-4-methoxy-1-{[5-(trifluoromethyl)-2-furil]methyl}-1,3-dihydro-2H-indol-2-one Following the procedure as described in PREPARATION 2B, and making non-critical variations to replace 1-(2-cyclopropylethyl)-1H-indole-2,3-dione with 4-methoxy-1-{[5-(trifluoromethyl)-2-furyl]methyl}-1H-indole-2,3-dione, the title compound was obtained (56%): MS (ES+) m/z 486.4 (M+23).

E. Synthesis of 3-(6-hydroxy-1,3-benzodioxol-5-yl)-4-methoxy-1-{[5-(trifluoromethyl)-2-furyl]methyl}-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-hydroxy-3-(6-hydroxy-1,3-benzodioxol-5-yl)-4-methoxy-1-{[5-(trifluoromethyl)-2-furil]methyl}-1,3-dihydro-2H-indol-2-one, the title compound was obtained (86%): MS (ES+) m/z 448.4 (M+1).

F. Synthesis of 3-(6-hydroxy-1,3-benzodioxol-5-yl)-3-(hydroxymethyl)-4-methoxy-1-{[5-(trifluoromethyl)-2-furyl]methyl}-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 3-(6-hydroxy-1,3-benzodioxol-5-yl)-4-methoxy-1-{[5-(trifluoromethyl)-2-furyl]methyl}-1,3-dihydro-2H-indol-2-one, the title compound was obtained (64%): MS (ES+) m/z 500.4 (M+23).

Preparation 28

Synthesis of 4,7-dichloro-3-(6-hydroxy-1,3-benzodioxol-5-yl)-3-(hydroxymethyl)-1-pentyl-1,3-dihydro-2H-indol-2-one A. Synthesis of 4,7-dichloro-1-pentyl-1H-indole-2,3-dione To a mixture of sodium hydride (0.17 g, 6.94 mmol, 60% dispersion in mineral oil) in anhydrous N,N-dimethylformamide (5.00 mL) was added a solution of 4,7-dichloro-1H-indole-2,3-dione (1.00 g, 4.60 mmol) in N,N-dimethylformamide (5.00 mL) at 0° C. The brown reaction mixture was stirred for 0.5 h followed by the addition of a solution of 1-bromopentane (0.84 g, 5.55 mmol) in anhydrous N,N-dimethylformamide (5.00 mL). The reaction mixture was stirred at ambient temperature for 16 h and poured into wet ethyl ether (30.0 mL). After the organic layer was separated, it was washed with water (2×20.0 mL), dried over anhydrous sodium sulfate and filtered. The filtrate was concentrated in vacuo to dryness. The gummy residue was dried under vacuum and the solid was triturated with ether to give the title compound (0.98 g, 98%): MS (ES+) m/z 286.2 (M+1).

B. Synthesis of 4,7-dichloro-3-hydroxy-3-(6-hydroxy-1,3-benzodioxol-5-yl)-1-pentyl-1,3-dihydro-2H-indol-2-one Following the procedure as described in PREPARATION 2B, and making non-critical variations to replace 1-(2-cyclopropylethyl)-1H-indole-2,3-dione with 4,7-dichloro-1-pentyl-1H-indole-2,3-dione, the title compound was obtained (68%) as a white solid: ¹H NMR (300 MHz, CDCl₃) δ 8.61 (s, br, 1H), 7.26 (t, 1H), 7.03 (d, 1H), 6.52 (s, 1H), 6.12 (s, 1H), 5.86 (dd, 2H), 4.21 (s, br, 1H), 4.01-3.96 (m, 2H), 1.73-1.58 (m, 2H), 1.34-1.21 (m, 4H), 0.84 (t, 3H); MS (ES+) m/z 408.2 (M−17).

C. Synthesis of 4,7-dichloro-3-(6-hydroxy-1,3-benzodioxol-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 4,7-dichloro-3-hydroxy-3-(6-hydroxy-1,3-benzodioxol-5-yl)-1-pentyl-1,3-dihydro-2H-indol-2-one, the title compound was obtained (72%) as a white solid: $^1$H NMR (300 MHz, CDCl$_3$) δ 7.27-7.23 (m, 1H), 7.03 (d, 1H), 6.55 (s, 1H), 6.04 (s, 1H), 5.84 (dd, 2H), 5.03 (s, 1H), 4.09-3.99 (m, 2H), 1.72-1.62 (m, 2H), 1.33-1.24 (m, 4H), 0.86 (t, 3H); MS (ES+) m/z 409.2 (M+1).

D. Synthesis of 4,7-dichloro-3-(6-hydroxy-1,3-benzodioxol-5-yl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 4,7-dichloro-3-(6-hydroxy-1,3-benzodioxol-5-yl)-1-pentyl-1,3-dihydro-2H-indol-2-one, the title compound was obtained (94%) as a gummy solid: MS (ES+) m/z 439.3 (M+1).

Preparation 29

Synthesis of ethyl 2-(4-chloro-3-(6-hydroxy-2,3-dihydrobenzofuran-5-yl)-3-(hydroxymethyl)-2-oxoindolin-1-yl)acetate A. Synthesis of ethyl (4-chloro-2,3-dioxo-2,3-dihydro-1H-indol-1-yl)acetate Following the procedure as described in PREPARATION 2A, and making non-critical variations to replace isatin with 4-chloro-1H-indole-2,3-dione, and (2-bromoethyl)cyclopropane with ethyl bromoacetate, the title compound was obtained (95%) as a colorless solid: $^1$H NMR (300 MHz, CDCl$_3$) δ 7.48 (t, 1H), 7.08 (d, 1H), 6.67 (d, 1H), 4.47 (s, 2H), 4.23 (q, 2H), 1.27 (t, 3H); MS (ES+) m/z 268.6 (M+1).

B. Synthesis of ethyl [4-chloro-3-hydroxy-3-(6-hydroxy-2,3-dihydro-1-benzofuran-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-chloro-2,3-dioxo-2,3-dihydro-1H-indol-1-yl)acetate, the title compound was obtained (75%) as a white solid: $^1$H NMR (300 MHz, CDCl$_3$) δ 8.70 (br, 1H), 7.31 (t, 1H), 7.12 (d, 1H), 6.68 (d, 1H), 6.46 (d, 2H), 4.53-4.46 (m, 2H), 4.18 (q, 2H), 3.08-2.88 (m, 2H), 1.23 (t, 3H); MS (ES+) m/z 387.8 (M−17).

C. Synthesis ethyl [4-chloro-3-(6-hydroxy-2,3-dihydro-1-benzofuran-5-yl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with ethyl [4-chloro-3-hydroxy-3-(6-hydroxy-2,3-dihydro-1-benzofuran-5-yl)-2-oxo-2,3-dihydro-1H-indol-1-yl]acetate, the title compound was obtained (75%) as a white solid: $^1$H NMR (300 MHz, CDCl$_3$) δ 7.33-7.27 (m, 2H), 7.12 (d, 1H), 6.71 (d, 1H), 6.50-6.48 (m, 1H), 5.10 (s, 1H), 4.54-4.42 (m, 4H), 4.19 (q, 2H), 3.11-2.90 (m, 2H), 1.23 (t, 3H); MS (ES+) m/z 388.8 (M+1).

D. Synthesis of ethyl [4-chloro-3-(6-hydroxy-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-chloro-3-(6-hydroxy-2,3-dihydro-1-benzofuran-5-yl)-2-oxo-2,3-dihydro-1H-indol-1-yl] acetate, the title compound was obtained (99%) as a gummy solid: MS (ES+) m/z 418.7 (M+1).

Preparation 30

Synthesis of 3-hydroxy-3-[6-(hydroxymethyl)-1,3-benzodioxol-5-yl]-1-pentyl-1,3-dihydro-2H-indol-2-one To a solution of (6-bromo-1,3-benzodioxol-5-yl)methanol (Mann, J., et al, *J. Chem. Soc. Perkin Trans.* 1 (1984):2081-8) (1.27 g, 5.50 mmol) in THF (45.0 mL) was added n-BuLi (5.00 mL, 2.0 M, 10.0 mmol) dropwise at −75° C. The reaction mixture was stirred at −75° C. for 45 min followed by the addition of a solution of 1-pentyl-1H-indole-2,3-dione (1.00 g, 4.60 mmol) in THF (20.0 mL) at −75° C. The resulting mixture was stirred at ambient temperature for 12 hrs and quenched with ammonium chloride solution (5.00 mL). More ethyl acetate and water were added and separated. The organic layer was concentrated in vacuo to dryness. The residue was subjected to column chromatography eluting with 50% EtOAc:Hexanes to yield the title compound (0.29 g, 25%) as a solid: $^1$H NMR (300 MHz, CDCl$_3$) δ 7.38-7.24 (m, 2H), 7.11 (t, 1H), 6.91 (d, 1H), 6.81 (s, 1H), 6.43 (s, 1H), 5.90-5.87 (m, 2H), 4.77 (dd, 2H), 3.75-3.56 (m, 2H), 1.75-1.58 (m, 2H), 1.26-1.35 (m, 2H), 0.89-0.83 (m, 3H); $^{13}$C NMR (75 MHz, CDCl$_3$) δ 177.8, 147.4, 147.2, 142.8, 133.5, 132.2, 131.1, 130.1, 125.3, 123.8, 111.4, 109.2, 108.1, 101.5, 79.5, 64.7, 40.4, 29.0, 26.8, 22.3, 13.9; MS (ES+) m/z 352.1 (M−17).

Preparation 31

Synthesis of ethyl [1-hexyl-3-(6-hydroxy-1,3-benzodioxol-5-yl)-2-oxo-2,3-dihydro-1H-indol-3-yl]acetate A. Synthesis of 1-hexyl-1H-indole-2,3-dione Following the procedure as described in PREPARATION 2A, and making non-critical variations to replace (2-bromoethyl)cyclopropane with n-bromohexane, the title compound was obtained (90%) as a viscous gum: $^1$H NMR (300 MHz, CDCl$_3$) δ 7.58-7.51 (m, 2H), 7.08 (t, 1H), 6.87 (d, 1H), 3.68 (t, 2H), 1.71-1.62 (m, 2H), 1.41-1.22 (m, 6H), 0.85 (t, 3H).

B. Synthesis of 1-hexyl-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 1-hexyl-1H-indole-2,3-dione, the title compound was obtained (53%) as a colorless solid: $^1$H NMR (300 MHz, CDCl$_3$) δ 9.44 (br, 1H), 7.47-7.44 (m, 1H), 7.40-7.34 (m, 1H), 7.17 (t, 1H), 6.89 (d, 1H), 6.55 (s, 1H), 6.21 (s, 1H), 5.84-5.82 (m, 2H), 4.58 (br, 1H), 3.71-3.56 (m, 2H), 1.67-1.62 (m, 2H), 1.32-1.21 (m, 6H), 0.84-0.80 (m, 3H); $^{13}$C NMR (75 MHz, CDCl$_3$) δ 179.0, 152.3, 148.8, 142.5, 141.3, 130.3, 129.2, 126.1, 123.7, 117.2, 109.5, 106.8, 101.9, 101.4, 79.2, 40.4, 31.3, 27.1, 26.4, 22.4, 13.9; MS (ES+) m/z 352.5 (M−17).

C. Synthesis of 1-hexyl-3-(6-hydroxy-1,3-benzodioxol-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-hexyl-3-hydroxy-3-(6-hydroxy-1,3-benzodioxol-5-yl)-1,3-dihydro-2H-indol-2-one, the title compound was obtained (98%) as a white solid: $^1$H NMR (300 MHz, CDCl$_3$) δ 7.38-7.13 (m, 3H), 6.94 (d, 1H), 6.60 (s, 1H), 6.32 (s, 1H), 5.84 (dd, 2H), 5.02 (s, 1H), 3.74-3.63 (m, 2H), 1.70-1.61 (m, 2H), 1.37-1.19 (m, 6H), 0.83 (t, 3H); MS (ES+) m/z 354.2 (M+1).

D. Synthesis of ethyl [1-hexyl-3-(6-hydroxy-1,3-benzodioxol-5-yl)-2-oxo-2,3-dihydro-1H-indol-3-yl] acetate To a solution of diisopropylamine (1.14 g, 11.0 mmol) in THF (10.0 mL) was added n-butyl lithium (7.00 mL, 11.0 mmol, 1.6 M solution in hexane) at −75° C. The resulting mixture was stirred at −75° C. for half an hour and added slowly to a solution of 1-hexyl-3-(6-hydroxy-1,3-benzodioxol-5-yl)-1,3-dihydro-2H-indol-2-one in THF (20.0 mL) at −75° C. After stirring at −75° C. for another half an hour, ethyl bromoacetate was added. The mixture was stirred at ambient temperature for 18 hrs and quenched with saturated ammonium chloride solution. The organic solvent was removed in vacuo and the aqueous residue was diluted with ethyl acetate (100 mL). The organic layer was washed with saturated ammonium chloride (25.0 mL), brine (50.0 mL), dried over anhydrous sodium sulfate and filtered. The filtrate was concentrated in vacuo to dryness. The residue was subjected to column chromatography eluting with 40% EtOAc/Hexanes to yield the title compound (0.19 g, 8%) as an oil: MS (ES+) m/z 440.5 (M+1).

Preparation 32

Synthesis of 4-bromo-3-(6-hydroxy-1,3-benzodioxol-5-yl)-3-(hydroxymethyl)-1,3-dihydro-2H-indol-2-one

A. Synthesis of 4-bromo-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 4-bromoisatin, the title compound was obtained (95%) as a beige solid: $^1$H NMR (300 MHz, DMSO-d$_6$) δ 10.40 (s, 1H), 9.09 (s, 1H), 7.22 (s, 1H), 7.04 (t, 1H), 6.90 (d, 1H), 6.75 (d, 1H), 6.43 (br, 1H), 6.21 (s, 1H), 5.88 (d, 2H); $^{13}$C NMR (75 MHz, DMSO-d$_6$) δ 178.0, 148.7, 147.0, 145.8, 139.5, 131.3, 130.8, 125.4, 118.8, 118.4, 109.4, 108.9, 101.0, 97.4, 76.6; MS (ES+) m/z 366.4 (M+1), 364.5 (M+1).

B. Synthesis of 4-bromo-3-(6-hydroxy-1,3-benzodioxol-5-yl)-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 4-bromo-3hydroxy-3-(6-hydroxy-1,3-benzodioxol-5-yl)-1,3-dihydro-2H-indol-2-one, the title compound was obtained (95%) as a cream solid: MS (ES+) m/z 348.5 (M+1), 346.3 (M+1).

C. Synthesis of 4-bromo-3-(6-hydroxy-1,3-benzodioxol-5-yl)-3-(hydroxymethyl)-1,3-dihydro-2H-indol-2-one Following the procedure as described in PREPARATION 31D, and making non-critical variations to replace 1-hexyl-3-(6-hydroxy-1,3-benzodioxol-5-yl)-1,3-dihydro-2H-indol-2-one with 4-bromo-3-(6-hydroxy-1,3-benzodioxol-5-yl)-1,3-dihydro-2H-indol-2-one, and ethyl bromoacetate with para-formaldehyde, the title compound was obtained (70%) as a colorless solid: $^1$H NMR (300 MHz, DMSO-d$_6$) δ 9.00 (br, 1H), 7.13-6.95 (m, 3H), 6.84 (d, 1H), 6.16 (d, 1H), 5.90-5.84 (m, 2H), 5.16-4.83 (m, 2H); $^{13}$C NMR (75 MHz, DMSO-d$_6$) δ 177.8, 150.4, 147.1, 146.8, 139.8, 130.2, 129.3, 125.8, 117.7, 115.8, 109.3, 107.9, 101.2, 97.6, 63.5, 57.4.

Preparation 33

Synthesis of 4-bromo-3-(6-hydroxy-2,3-dihydro-1-benzofuran-5-yl)-3-(hydroxymethyl)-1,3-dihydro-2H-indol-2-one

A. Synthesis of 4-bromo-3-hydroxy-3-(6-hydroxy-2,3-dihydro-1-benzofuran-5-yl)-1,3-dihydro-2H-indol-2-one Following the procedure as described in PREPARATION 2B, and making non-critical variations to replace 1-(2-cyclopropylethyl)-1H-indole-2,3-dione with 4-bromoisatin, and 1,3-benzodioxol-5-ol with 2,3-dihydrobenzofuran-6-ol, the title compound was obtained (78%) as a colorless solid: $^1$H NMR (300 MHz, DMSO-d$_6$) δ 10.36 (s, 1H), 9.15 (s, 1H), 7.49 (1H), 7.04 (t, 1H), 6.89 (d, 1H), 6.74 (d, 1H), 6.35 (br, 1H), 5.90 (s, 1H), 4.45 (t, 2H), 3.05 (t, 2H); $^{13}$C NMR (75 MHz, DMSO-d$_6$) δ 178.4, 160.2, 154.0, 145.7, 131.6, 130.7, 125.5, 125.4, 118.9, 117.7, 116.1, 108.8, 96.8, 76.9, 71.8, 29.1; MS (ES−) m/z 344.4 (M−17), 360.4 (M−1).

B. Synthesis of 4-bromo-3-(6-hydroxy-2,3-dihydro-1-benzofuran-5-yl)-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 4-bromo-3-hydroxy-3-(6-hydroxy-2,3-dihydro-1-benzofuran-5-yl)-1,3-dihydro-2H-indol-2-one, the title compound was obtained (62%) as a solid: MS (ES+) m/z 346.5 (M+1), 348.5 (M+1).

C. Synthesis of 4-bromo-3-(6-hydroxy-2,3-dihydro-1-benzofuran-5-yl)-3-(hydroxymethyl)-1,3-dihydro-2H-indol-2-one Following the procedure as described in PREPARATION 31D, and making non-critical variations to replace 1-hexyl-3-(6-hydroxy-1,3-benzodioxol-5-yl)-1,3-dihydro-2H-indol-2-one with 4-bromo-3-(6-hydroxy-2,3-dihydro-1-benzofuran-5-yl)-1,3-dihydro-2H-indol-2-one, and ethyl bromoacetate with para-formaldehyde, the title compound was obtained that was used directly for further reaction.

Preparation 34

Synthesis of 4-bromo-3-(6-hydroxy-2,3-dihydro-1-benzofuran-5-yl)-3-(hydroxymethyl)-1-(pyridin-2-ylmethyl)-1,3-dihydro-2H-indol-2-one

A. Synthesis of 4-bromo-1-(pyridin-2-ylmethyl)-1H-indole-2,3-dione

To a solution of 4-bromoisatin (8.94 g, 39.5 mmol) in anhydrous N,N-dimethylformamide (100 mL) was added sodium hydride (3.34 g, 86.9 mmol, 60% dispersion in mineral oil) in portions at 0° C. The brown reaction mixture was stirred for 30 min followed by the addition of a solution of 2-(bromomethyl)pyridine hydrobromide (10.0 g, 39.5 mmol) neutralized with sodium hydride (1.52 g, 39.5 mmol, 60% dispersion in mineral oil) in N,N-dimethylformamide at 0° C. The reaction mixture was stirred for 16 h and quenched with water (100 mL). The reaction mixture was extracted with diethyl ether (3×100 mL) and the aqueous layer was extracted with ethyl acetate (3×100 mL). The combined organic layers was washed with water (5×200 mL), dried over anhydrous sodium sulfate and filtered. The filtrate was concentrated in vacuo to dryness. The residue was triturated with ether to afford the title compound (10.6 g, 85%) as a brown solid: $^1$H NMR (300 MHz, DMSO-$d_6$) δ 8.53 (d, 1H), 7.67 (t, 1H), 7.30 (t, 2H), 7.25-7.19 (m, 2H), 6.94 (d, 1H), 5.04 (s, 2H); $^{13}$C NMR (75 MHz, DMSO-$d_6$) δ 180.5, 157.3, 154.2, 152.3, 149.5, 138.4, 137.5, 128.6, 123.3, 122.3, 121.5, 116.4, 110.3, 45.8.

B. Synthesis of 4-bromo-3-hydroxy-3-(6-hydroxy-2,3-dihydro-1-benzofuran-5-yl)-1-(pyridin-2-ylmethyl)-1,3-dihydro-2H-indol-2-one Following the procedure as described in PREPARATION 2B, and making non-critical variations to replace 1-(2-cyclopropylethyl)-1H-indole-2,3-dione with 4-bromo-1-(pyridin-2-ylmethyl)-1H-indole-2,3-dione, and 1,3-benzodioxol-5-ol with 2,3-dihydrobenzofuran-6-ol, the title compound was obtained (91%) as a colorless solid: mp >225° C.; $^1$H NMR (300 MHz, DMSO-$d_6$) δ 9.29 (s, 1H), 8.54 (d, 1H), 7.70 (dt, 1H), 7.61 (br, 1H), 7.32-7.26 (m, 2H), 7.07 (d, 1H), 7.00 (d, 1H), 6.72 (d, 1H), 6.60 (br, 1H), 6.02 (s, 1H), 4.91 (ABq, 2H), 4.47 (t, 2H), 3.06 (d, 2H); $^{13}$C NMR (75 MHz, DMSO-$d_6$) δ 176.9, 160.4, 156.3, 153.8, 149.6, 146.1, 137.5, 130.9, 130.8, 126.5, 125.8, 123.1, 121.5, 118.8, 117.3, 116.4, 108.3, 96.7, 76.6, 71.9, 45.7, 29.1; MS (ES+) m/z 455.4 (M+1), 437.4 (M−17).

C. Synthesis of 4-bromo-3-(6-hydroxy-2,3-dihydro-1-benzofuran-5-yl)-1-(pyridin-2-ylmethyl)-1,3-dihydro-2H-indol-2-one To a solution of 4-bromo-3-hydroxy-3-(6-hydroxy-2,3-dihydro-1-benzofuran-5-yl)-1-(pyridin-2-ylmethyl)-1,3-dihydro-2H-indol-2-one (1.12 g, 2.48 mmol) in anhydrous dichloromethane (25.0 mL) was added triethylamine (1.40 mL, 9.91 mmol) and SOCl$_2$ (0.40 mL, 4.96 mmol) at 0° C. The reaction mixture was stirred at 0° C. for 2 h and quenched with water (30.0 mL). The organic layer was separated, washed with water (3×30.0 mL), dried over anhydrous sodium sulfate and filtered. The filtrate was concentrated in vacuo to dryness to give a gummy material. The residue was dissolved in acetic acid/tetrahydrofuran (3.00 mL/22.0 mL) followed by the addition of zinc dust (0.81 g, 12.4 mmol) in one portion. The reaction mixture was stirred at ambient temperature for 16 h. After the solid was filtered, the solvent was removed in vacuo. The residue was dissolved in ethyl acetate (100 mL), washed with water (3×30.0 mL), dried over anhydrous sodium sulfate and filtered. The filtrate was concentrated in vacuo to dryness to give the title compound (1.50 g, 77%) as a gummy material: MS (ES+) m/z 437.3 (M+1).

D. Synthesis of 4-bromo-3-(6-hydroxy-2,3-dihydro-1-benzofuran-5-yl)-3-(hydroxymethyl)-1-(pyridin-2-ylmethyl)-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 4-bromo-3-(6-hydroxy-2,3-dihydro-1-benzofuran-5-yl)-1-(pyridin-2-ylmethyl)-1,3-dihydro-2H-indol-2-one, the title compound was obtained (34%): MS (ES+) m/z 468.4 (M+1).

Preparation 35

Synthesis of 5-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one

A. Synthesis of 5-fluoro-1-{[5-(trifluoromethyl)-2-furyl]methyl}-1H-indole-2,3-dione Following the procedure as described in PREPARATION 2A, and making non-critical variations to replace isatin with 5-fluoroisatin, and (2-bromoethyl)cyclopropane with 2-(bromomethyl)-5-(trifluoromethyl)furan, the title compound was obtained (59%) as a red solid: $^1$H NMR (300 MHz, DMSO-$d_6$) δ 7.54-7.50 (m, 1H), 7.47-7.44 (m, 1H), 7.20 (dd, 1H), 7.14-7.13 (m, 1H), 6.75 (d, 1H), 4.99 (s, 2H); $^{13}$C NMR (75 MHz, DMSO-$d_6$) δ 182.4 (d), 160.7, 158.5 (d), 157.5, 153.0 (d), 146.5 (d), 139.9 (q), 124.3, 119.3 (d), 114.5 (d), 112.7 (d), 112.0 (d), 110.5, 36.8.

B. Synthesis of 5-fluoro-3-hydroxy-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 2B, and making non-critical variations to replace 1-(2-cyclopropylethyl)-1H-indole-2,3-dione with 5-fluoro-1-{[5-(trifluoromethyl)-2-furyl]methyl}-1H-indole-2,3-dione, the title compound was obtained (66%) as a pale yellow solid: $^1$H NMR (300 MHz, DMSO-$d_6$) δ 9.15 (s, 1H), 7.21 (s, 1H), 7.15 (dd, 1H), 7.08-6.95 (m, 2H), 6.74 (s, 1H), 6.54 (s, 1H), 6.22 (d, 1H), 5.90 (d, 2H), 4.96 (s, 2H); $^{13}$C NMR (75 MHz, DMSO-$d_6$) δ 176.7, 160.57, 157.4, 154.0, 148.6, 147.4, 140.1 (m), 139.6 (m), 134.7 (d, $^2J_{CF}$=29.4 Hz), 121.3, 119.5, 117.7, 115.1 (d, $^1J_{CF}$=92.1 Hz), 114.5, 111.8 (d, $^1J_{CF}$=97.5 Hz), 109.7, 109.6, 107.2, 101.3, 97.8, 75.1, 36.9; MS (ES+) m/z 450.3 (M+1)

C. Synthesis of 5-fluoro-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 5-fluoro-3-hydroxy-3-(6-hydroxy-1,3-benzodioxol-5-yl)-1-{[5-(trifluoromethyl)-2-furyl]methyl}-1,3-dihydro-2H-indol-2-one, the title compound was obtained (72%) as a pale yellow solid: $^1$H NMR (300 MHz, DMSO-d$_6$) δ 9.31 (s, 1H), 7.13 (dd, 1H), 7.02 (dd, 2H), 6.82 (d, 1H), 6.59 (d, 2H), 6.39 (s, 1H), 5.87 (d, 2H), 5.07-4.96 (m, 2H), 4.84 (s, 1H); $^{13}$C NMR (75 MHz, DMSO-d$_6$) δ 176.1, 160.5, 157.4, 153.9, 150.5, 147.5, 140.2, 139.6, 139.1, 132.3 (d, $^2J_{CF}$=33.3 Hz), 115.3, 114.5 (m), 114.2, 113.9, 111.9 (d, $^1J_{CF}$=98.7 Hz), 109.9, 109.7 (d, $^2J_{CF}$=32.7 Hz), 101.3, 98.3, 48.5, 36.8; MS (ES+) m/z 436.2 (M+1).

D. Synthesis of 5-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one A mixture of 5-fluoro-3-(6-hydroxy-1,3-benzodioxol-5-yl)-1-{[5-(trifluoromethyl)-2-furyl]methyl}-1,3-dihydro-2H-indol-2-one (3.64 g, 8.41 mmol), para-formaldehyde (2.52 g, 84.1 mmol) and lithium hydroxide monohydrate (1.06 g, 25.2 mmol) in tetrahydrofuran (84.0 mL) and water (10.0 mL) was stirred at 0° C. for 4 h. After the solvent was removed in vacuo, the residue was dissolved in ethyl acetate (100 mL), washed with 10% aqueous HCl (3×25.0 mL), dried over anhydrous sodium sulfate and filtered. The filtrate was concentrated in vacuo to dryness. The residue was subjected to column chromatography eluting with ethyl acetate/hexanes (50%) to give the title compound (0.65 g, 59%) as a colorless solid: $^1$H NMR (300 MHz, DMSO-d$_6$) δ 9.11 (s, 1H), 7.12 (d, 1H), 6.99-6.87 (m, 3H), 6.80 (dd, 1H), 6.48 (d, 1H), 6.23 (s, 1H), 5.89 (d, 2H), 5.09 (br, 1H), 4.97 (ABq, 2H), 4.01 (ABq, 2H); $^{13}$C NMR (75 MHz, DMSO-d$_6$) δ 176.1, 160.5; MS (ES+) m/z 466.2 (M+1), 448.2 (M−17).

Preparation 36

Synthesis of tert-butyl-(2-chloromethyl-5-trifluoromethylthiophen-3-yloxy)dimethylsilane A. Synthesis of methyl 3-tert-butyl dimethylsilanyloxy-5-trifluoromethyl-2-thiophenecarboxylate To a solution of methyl 3-hydroxy-5-trifluoromethyl-2-thiophenecarboxylate (Karp, G. M., et al, *Synthesis* (2000), 8:1078-1080) (19.4 g, 85.8 mmol) in N,N-dimethylformamide (50.0 mL) was added imidazole (8.77 g, 129 mmol) followed by tert-butyl dimethylsilyl chloride (19.4 g, 129 mmol) at 0° C. The reaction mixture was stirred at ambient temperature overnight. More imidazole (7.50 g) and tert-butyl dimethylsilyl chloride (10.5 g) were added. The reaction mixture was stirred for another 4 h and quenched with water (100 mL). The reaction mixture was extracted with ether (3×500 mL). The combined organic layers was washed with water (3×500 mL), dried over anhydrous sodium sulfate and filtered. The filtrate was concentrated in vacuo to dryness. The residue was subjected to column chromatography eluting with ethyl acetate/hexanes (1/9) to give the title compound (26.5 g, 90%) as a yellow oil: $^1$H NMR (300 MHz, CDCl$_3$) δ 6.91 (s, 1H), 3.82 (s, 3H), 0.21 (s, 6H), 0.06 (s, 9H); $^{13}$C NMR (75 MHz, CDCl$_3$) δ 161.5, 155.5, 133.7, 133.2, 123.6 (q, $^1J_{CF}$=14.4 Hz), 119.8, 51.9, 25.4, 18.2, −4.6.

B. Synthesis of [3-(tert-butyldimethylsilanyloxy)-5-trifluoromethylthiophen-2-yl]methanol To a mixture of lithium aluminum hydride (1.67 g, 43.9 mmol) in anhydrous ether (75.0 mL) was added a solution of methyl 3-tert-butyl dimethylsilanyloxy-5-trifluoromethyl-2-thiophenecarboxylate (10.0 g, 29.3 mmol) in anhydrous ether (25.0 mL) at 0° C. The reaction mixture was stirred at 0° C. for 30 min and quenched by the slow addition of water (50.0 mL). After the aqueous layer was separated, the organic layer was washed with saturated ammonium chloride (3×20.0 mL), dried over anhydrous sodium sulfate and filtered. The filtrate was concentrated in vacuo to dryness. The residue was subjected to column chromatography eluting with ethyl acetate/hexanes (1/9) to give the title compound (6.95 g, 76%) as a yellow oil: $^1$H NMR (300 MHz, CDCl$_3$) δ 6.89 (s, 1H), 4.68 (s, 2H), 2.11 (br, 1H), 0.96 (s, 9H), 0.88 (s, 6H); $^{13}$C NMR (75 MHz, CDCl$_3$) δ 148.0, 127.0, 124.0, 122.4 (q, $^1J_{CF}$=14.7 Hz), 120.5, 56.1, 25.5, 18.1, −4.6.

C. Synthesis of tert-butyl-(2-chloromethyl-5-trifluoromethylthiophen-3-yloxy)dimethylsilane To a solution of [3-(tert-butyldimethylsilanyloxy)-5-trifluoromethylthiophen-2-yl]methanol in anhydrous dichloromethane (100 mL) was added triethylamine (4.05 g, 40.0 mmol) followed by thionyl chloride (2.38 g, 20.0 mmol) at 0° C. The reaction mixture was stirred for 30 min and quenched with water (50.0 mL). After separation, the organic layer was washed with water (3×50.0 mL), dried over anhydrous sodium sulfate and filtered. The filtrate was concentrated in vacuo to dryness. The residue was subjected to column chromatography eluting with hexane to afford the title compound (2.31 g, 70%) as a yellow oil, which was directly used.

Preparation 37

Synthesis of 1-(diphenylmethyl)-3-(6-hydroxy-1,3-benzodioxol-5-yl)-3-(hydroxymethyl)-5-methyl-1,3-dihydro-2H-indol-2-one A. Synthesis of 1-(diphenylmethyl)-5-methyl-1H-indole-2,3-dione Following the procedure as described in PREPARATION 2A, and making non-critical variations to replace isatin with 5-methylisatin, and (2-bromoethyl)cyclopropane with 1,1'-(bromomethylene)dibenzene, the title compound was obtained (74%) as a bright orange solid: $^1$H NMR (300 MHz, CDCl$_3$) δ 7.42-7.26 (m, 11H), 7.09 (d, 1H), 6.95 (s, 1H), 6.37 (d, 1H), 2.24 (s, 3H).

B. Synthesis of 1-(diphenylmethyl)-3-hydroxy-3-(6-hydroxy-1,3-benzodioxol-5-yl)-5-methyl-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-5-methyl-1H-indole-2,3-dione, the title compound was obtained (92%) as a colorless solid: $^1$H NMR (300 MHz, CDCl$_3$) δ 9.23 (br, 1H), 7.40-7.15 (m, 11H), 6.90-6.85 (m, 2H), 6.57 (s, 1H), 6.33 (d, 1H), 6.31 (s, 1H), 5.87 (s, 2H), 4.46 (br s, 1H), 2.28 (s, 3H); MS (ES+) m/z 448.4 (M−17).

C. Synthesis of 1-(diphenylmethyl)-3-(6-hydroxy-1,3-benzodioxol-5-yl)-5-methyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-1,3-benzodioxol-5-yl)-5-methyl-1,3- dihydro-2H-indol-2-one, the title compound was obtained (84%) as a colorless solid: $^1$H NMR (300 MHz, CDCl$_3$) δ 7.37-7.25 (m, 9H), 7.22-7.17 (m, 2H), 7.10 (s, 1H), 6.91 (s, 1H), 6.86 (d, 1H), 6.63 (s, 1H), 6.40 (s, 1H), 6.38 (d, 1H), 5.88 (ABq, 2H), 5.07 (s, 1H), 2.23 (s, 3H); MS (ES+) m/z 450.3 (M+1).

D. Synthesis of 1-(diphenylmethyl)-3-(6-hydroxy-1,3-benzodioxol-5-yl)-3-(hydroxymethyl)-5-methyl-1,3-dihydro-2H-indol-2-one To a solution of 1-(diphenylmethyl)-3-(6-hydroxy-1,3-benzodioxol-5-yl)-5-methyl-1,3-dihydro-2H-indol-2-one (1.61 g, 3.60 mmol) and para-formaldehyde (0.43 g, 14.6 mmol) in dichloromethane (60.0 mL) was added diisopropylamine (7.20 mmol). After stirring at ambient temperature for 3 h, the reaction was quenched with saturated aqueous ammonium chloride (60.0 mL). The organic layer was separated and washed with water (3×100 mL), dried over sodium sulfate and filtered. The filtrate was concentrated in vacuo to dryness. The residue was subjected to column chromatography eluting with ethyl acetate/hexanes (20-60%) to afford the title compound (1.07 g, 63%) as a colorless solid: $^1$H NMR (300 MHz, CDCl$_3$) δ 10.09 (br, 1H), 7.37-7.16 (m, 12H), 6.99 (s, 1H), 6.87 (d, 1H), 6.62 (s, 1H) 6.54 (s, 1H), 6.37 (d, 1H), 5.87 (d, 2H), 4.45 (ABq, 2H), 2.33 (s, 3H); MS (ES+) m/z 480.4 (M+1).

Preparation 38

Synthesis of 3-(hydroxymethyl)-3-(5-hydroxy-2-methyl-1,3-benzothiazol-6-yl)-1-pentyl-1,3-dihydro-2H-indol-2-one A. Synthesis of 3-hydroxy-3-(5-hydroxy-2-methyl-1,3-benzothiazol-6-yl)-1-pentyl-1,3-dihydro-2H-indol-2-one Following the procedure as described in PREPARATION 2B, and making non-critical variations to replace 1-(2-cyclopropylethyl)-1H-indole-2,3-dione with 1-pentyl-1H-indole-2,3-dione, and 1,3-benzodioxol-5-ol with 2-methyl-1,3-benzothiazol-5-ol, the title compound was obtained (81%) as a colorless solid: $^1$H NMR (300 MHz, DMSO-d$_6$) δ 9.90 (br, 1H), 9.05 (br, 1H), 7.78 (d, 1H), 7.25 (dd, 1H), 7.10-6.95 (m, 2H), 6.90-6.80 (m, 2H), 3.81-3.58 (m, 2H), 2.75 (br, 3H), 1.80-1.60 (m, 2H), 1.50-1.31 (m, 4H), 0.90 (t, 3H); MS (ES+) m/z 383.4 (M+1).

B. Synthesis of 3-(5-hydroxy-2-methyl-1,3-benzothiazol-6-yl)-1-pentyl-1,3-dihydro-2H-indol-2-one A suspension of 3-hydroxy-3-(5-hydroxy-2-methyl-1,3-benzothiazol-6-yl)-1-pentyl-1,3-dihydro-2H-indol-2-one (0.50 g, 1.31 mmol) in hydroiodic acid (10.0 mL) was refluxed for 1.5 days. The reaction mixture was concentrated in vacuo to dryness. The residue was used directly in next step.

C. Synthesis of 3-(hydroxymethyl)-3,5-hydroxy-2-methyl-1,3-benzothiazol-6-yl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(5-hydroxy-2-methyl-1,3-benzothiazol-6-yl)-1-pentyl-1,3-dihydro-2H-indol-2-one, the title compound was obtained: MS (ES+) m/z 367.5 (M+1).

Preparation 39

Synthesis of (5-chloro-1,3,4-thiadiazol-2-yl)methanol

To a solution of ethyl 5-chloro-1,3,4-thiadiazole-2-carboxylate (0.51 g, 2.60 mmol) in anhydrous methanol (5.00 mL) was added sodium borohydride (0.30 g, 7.99 mmol) at 0° C. The reaction mixture was stirred at ambient temperature for 16 h, diluted with acetic acid (3.00 mL) and extracted with ethyl acetate (2×150 mL). The combined organics was washed with aqueous saturated sodium bicarbonate (3×25.0 mL) and aqueous saturated sodium chloride (2×25.0 mL). The organic layer was dried over anhydrous sodium sulfate and filtered. The filtrate was concentrated in vacuo to dryness to give the title compound (0.30 g, 75%) as a light yellow semi-solid: $^1$H NMR (300 MHz, CDCl$_3$) δ 5.04 (s, 2H), 2.80 (br, 1H); MS (ES+) 151.1 (M+1), 153.1 (M+1).

Preparation 40

Synthesis of 1-(diphenylmethyl)-3-(6-hydroxy-3,3-dimethyl-2,3-dihydro-1-benzofuran-5-yl)-3-(hydroxymethyl)-1,3-dihydro-2H-indol-2-one A. Synthesis of 1-(diphenylmethyl)-3-hydroxy-3-(6-hydroxy-3,3-dimethyl-2,3-dihydro-1-benzofuran-5-yl)-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, and 1,3-benzodioxol-5-ol with 3,3-dimethyl-2,3-dihydro-1-benzofuran-6-ol, the title compound was obtained: MS (ES+) m/z 478.5 (M+1).

B. Synthesis of 1-(diphenylmethyl)-3-(6-hydroxy-3,3-dimethyl-2,3-dihydro-1-benzofuran-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-3,3-dimethyl-2,3-dihydro-1-benzofuran-5-yl)-1,3-dihydro-2H-indol-2-one, the title compound was obtained (73% for two steps): $^1$H NMR (300 MHz, CDCl$_3$) δ 7.38-7.20 (m, 12H), 7.11-7.04 (m, 2H), 6.97 (s, 1H), 6.58 (s, 1H), 6.57-6.51 (m, 1H), 6.50 (s, 1H), 5.08 (s, 1H), 4.19 (s, 2H), 1.25 (s, 3H), 1.18 (s, 3H); MS (ES+) m/z 426.6 (M+1).

C. Synthesis of 1-(diphenylmethyl)-3-(6-hydroxy-3,3-dimethyl-2,3-dihydro-1-benzofuran-5-yl)-3-(hydroxymethyl)-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 1-(diphenylmethyl)-3-(6-hydroxy-3,3-dimethyl-2,3-dihydro-1-benzofuran-5-yl)-1,3-dihydro-2H-indol-2-one, the title compound was obtained: MS (ES+) m/z 492.5 (M+1)

Preparation 41

Synthesis of 7-fluoro-3-(6-hydroxy-1,3-benzodioxol-5-yl)-1,3-dihydro-2H-indol-2-one

A. Synthesis of 7-fluoro-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 7-fluoro-1H-indole-2,3-dione, the title compound was obtained (80%): $^1$H NMR (300 MHz, DMSO-$d_6$) δ 10.66 (s, 1H), 9.11 (s, 1H), 7.18 (s, 1H), 7.07-6.98 (m, 1H), 6.83-6.74 (m, 1H), 6.66 (d, 1H), 6.48 (s, 1H), 6.18 (s, 1H), 5.92-5.85 (m, 2H); MS (ES+) m/z 304.5 (M+1).

B. Synthesis of 7-fluoro-3-(6-hydroxy-1,3-benzodioxol-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 7-fluoro-3-hydroxy-3-(6-hydroxy-1,3-benzodioxol-5-yl)-1,3-dihydro-2H-indol-2-one, the title compound was obtained (100%): $^1$H NMR (300 MHz, DMSO-$d_6$) δ 10.84 (s, 1H), 9.22 (s, 1H), 7.01 (t, 1H), 6.87-6.78 (m, 1H), 6.71 (d, 1H), 6.62 (s, 1H), 6.35 (s, 1H), 5.90-5.85 (m, 2H), 4.67 (s, 1H); MS (ES+) m/z 288.5 (M+1).

Preparation 42

Synthesis of ethyl [4-bromo-3-(6-hydroxy-2,3-dihydro-1-benzofuran-5-yl)-3-(hydroxymethyl)-2-oxo-2,3-dihydro-1H-indol-1-yl]acetate

A. Synthesis of ethyl [4-bromo-3-hydroxy-3-(6-hydroxy-2,3-dihydro-1-benzofuran-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-bromo-2,3-dioxo-2,3-dihydro-1H-indol-1-yl)acetate, and 1,3-benzodioxol-5-ol with 2,3-dihydrobenzofuran-6-ol, the title compound was obtained (68%) as a white solid: $^1$H NMR (300 MHz, CDCl$_3$). δ 8.66 (br, 1H), 7.31-7.19 (m, 3H), 6.73 (dd, 1H), 6.49-6.45 (m, 1H), 5.09-4.36 (m, 4H), 4.20 (q, 2H), 3.14-2.90 (m, 2H), 1.23 (t, 3H); MS (ES+) m/z 432.2 (M−17).

B. Synthesis of ethyl [4-bromo-3-(6-hydroxy-2,3-dihydro-1-benzofuran-5-yl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with ethyl [4-bromo-3-hydroxy-3-(6-hydroxy-2,3-dihydro-1-benzofuran-5-yl)-2-oxo-2,3-dihydro-1H-indol-1-yl]acetate, the title compound was obtained (81%) as a white solid: $^1$H NMR (CDCl$_3$, 300 MHz) δ 7.31-7.19 (m, 3H), 6.75 (d, 1H), 6.50-6.45 (m, 1H), 5.08 (s, 1H), 5.09-4.36 (m, 4H), 4.20 (q, 2H), 3.14-2.90 (m, 2H), 1.23 (t, 3H); MS (ES+) m/z 433.3 (M+1).

C. Synthesis of ethyl [4-bromo-3-(6-hydroxy-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-bromo-3-(6-hydroxy-2,3-dihydro-1-benzofuran-5-yl)-2-oxo-2,3-dihydro-1H-indol-1-yl]acetate, the title compound was obtained (99%): MS (ES+) m/z 463.2 (M+1).

Preparation 43

Synthesis of ethyl [5-chloro-3-(6-hydroxy-2,3-dihydro-1-benzofuran-5-yl)-3-(hydroxymethyl)-2-oxo-2,3-dihydro-1H-indol-1-yl]acetate

A. Synthesis of ethyl (5-chloro-2,3-dioxo-2,3-dihydro-1H-indol-1-yl)acetate Following the procedure as described in PREPARATION 2A, and making non-critical variations to replace isatin with 5-chloro-1H-indole-2,3-dione, and (2-bromoethyl)cyclopropane with ethyl 2-bromoacetate, the title compound was obtained (98%) as solid: $^1$H NMR (300 MHz, CDCl$_3$) δ 7.60 (d, 1H), 7.54 (dd, 1H), 6.74 (d, 1H), 4.46 (s, 2H), 4.23 (q, 2H), 1.27 (t, 3H); MS (ES+) m/z 268.6 (M+1).

B. Synthesis of ethyl [5-chloro-3-hydroxy-3-(6-hydroxy-2,3-dihydro-1-benzofuran-5-1/1)-2-oxo-2,3-dihydro-1H-indol-1-yl]acetate Following the procedure as described in PREPARATION 1C, and making non-critical variations to replace 4-bromo-1-pentyl-1H-indole-2,3-dione with ethyl (5-chloro-2,3-dioxo-2,3-dihydro-1H-indol-1-yl)acetate, and 1,3-benzodioxol-5-ol with 2,3-dihydrobenzofuran-6-ol, the title compound was obtained (85%) as a white solid: $^1$H NMR (300 MHz, CDCl$_3$) δ 8.70 (br, 1H), 7.31-7.24 (m, 2H), 6.92 (d, 1H), 6.68 (s, 1H), 6.46 (s, 1H), 4.53-4.46 (m, 2H), 5.09-4.40 (d, 2H), 4.18 (q, 2H), 3.08-2.88 (m, 2H), 1.23 (t, 3H); MS (ES+) m/z 387.8 (M−17).

C. Synthesis of ethyl [5-chloro-3-(6-hydroxy-2,3-dihydro-1-benzofuran-5-yl)-2-oxo-2,3-dihydro-1H-indol-1-yl]acetate Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with ethyl [5-chloro-3-hydroxy-3-(6-hydroxy-2,3-dihydro-1-benzofuran-5-yl)-2-oxo-2,3-dihydro-1H-indol-1-yl]acetate, the title compound was obtained (94%) as a white solid: $^1$H NMR (300 MHz, CDCl$_3$) δ 7.30-7.24 (m, 2H), 6.72 (d, 1H), 6.66 (s, 1H), 6.39 (s, 1H), 5.05 (s, 1H), 4.53-4.46 (m, 4H), 4.21 (q, 2H), 3.14-2.94 (m, 2H), 1.25 (t, 3H); MS (ES+) m/z 388.8 (M+1).

D. Synthesis of ethyl [5-chloro-3-(6-hydroxy-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-

(6-hydroxy-1,3-benzodioxol-5-yl)-1-pentyl-1,3-dihydro-2H-indol-2-one with ethyl [5-chloro-3-(6-hydroxy-2,3-dihydro-1-benzofuran-5-yl)-2-oxo-2,3-dihydro-1H-indol-1-yl]acetate, the title compound was obtained (99%): MS (ES+) m/z 418.7 (M+1).

Preparation 44

Synthesis of methyl [3-(4-chloro-2-hydroxyphenyl)-3-(hydroxymethyl)-2-oxo-2,3-dihydro-1H-indol-1-yl]acetate A. Synthesis of methyl (2,3-dioxo-2,3-dihydro-1H-indol-1-yl)acetate Following the procedure as described in PREPARATION 2A, and making non-critical variations to replace (2-bromoethyl)cyclopropane with methyl bromoacetate, the title compound was obtained (72%): $^1$H NMR (300 MHz, CDCl$_3$) δ 7.64-7.53 (m, 2H), 7.14 (t, 1H), 6.77 (d, 1H), 4.48 (s, 2H), 3.76 (s, 3H); MS (ES+) m/z 220.4 (M+1).

B. Synthesis of methyl [3-(4-chloro-2-hydroxyphenyl)-3-hydroxy-2-oxo-2,3-dihydro-1H-indol-1-yl]acetate Following the procedure as described in PREPARATION 1C, and making non-critical variations to replace 4-bromo-1-pentyl-1H-indole-2,3-dione with methyl (2,3-dioxo-2,3-dihydro-1H-indol-1-yl)acetate, and 1,3-benzodioxol-5-ol with 3-chlorophenol, the title compound was obtained (29%) as a yellow solid: $^1$H NMR (300 MHz, CDCl$_3$) δ 9.10 (s, 1H), 7.48 (d, 1H), 7.38 (t, 1H), 7.19 (t, 1H), 7.01 (br, 1H), 6.80-6.64 (m, 3H), 5.28 (br s, 1H), 4.51 (d, 1H), 4.44 (d, 1H), 3.75 (s, 3H); MS (ES+) m/z 370.5 (M+23), 372.4 (M+23).

C. Synthesis of methyl [3-(4-chloro-2-hydroxyphenyl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with methyl [3-(4-chloro-2-hydroxyphenyl)-3-hydroxy-2-oxo-2,3-dihydro-1H-indol-1-yl]acetate, the title compound was obtained (83%) as a semi-solid; $^1$H NMR (300 MHz, CDCl$_3$) δ 7.36 (t, 1H), 7.29 (bd, 1H), 7.18 (t, 1H), 6.95 (br, 1H), 6.86-6.78 (m, 3H), 5.13 (br, 1H), 4.55 (d, 1H), 4.45 (d, 1H), 3.75 (s, 3H); MS (ES+) m/z 332.5 (M+1), 334.5 (M+1).

D. Synthesis of methyl [3-(4-chloro-2-hydroxyphenyl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl [3-(4-chloro-2-hydroxyphenyl)-2-oxo-2,3-dihydro-1H-indol-1-yl]acetate, the title compound was obtained: MS (ES+) m/z 362.5 (M+1) 364.5 (M+1).

Preparation 45

Synthesis of ethyl [3-(4,5-difluoro-2-hydroxyphenyl)-3-(hydroxymethyl)-2-oxo-2,3-dihydro-1H-indol-1-yl]acetate A. Synthesis of ethyl [3-(4,5-difluoro-2-hydroxyphenyl)-3-hydroxy-2-oxo-2,3-dihydro-1H-indol-1-yl]acetate Following the procedure as described in PREPARATION 2B, and non-critical variations to replace 1-(2-cyclopropylethyl)-1H-indole-2,3-dione with ethyl (2,3-dioxo-2,3-dihydro-1H-indol-1-yl)acetate, the title compound was obtained as a brown oil: MS (ES+) m/z 364.3 (M+1), 348.5 (M−17).

B. Synthesis of ethyl [3-(4,5-difluoro-2-hydroxyphenyl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with ethyl [3-(4,5-difluoro-2-hydroxyphenyl)-3-hydroxy-2-oxo-2,3-dihydro-1H-indol-1-yl]acetate, the title compound was obtained (83%) as a light yellow oil: $^1$H NMR (300 MHz, CDCl$_3$) δ 7.39 (t, 1H), 7.34 (d, 1H), 7.26-7.22 (m, 1H), 6.92-6.82 (m, 2H), 6.73 (dd, 1H), 5.11 (br, 1H), 4.50 (d, 1H), 4.43 (d, 1H), 4.21 (q, 2H), 1.23 (t, 3H); MS (ES+) m/z 448.5 (M+1).

C. Synthesis of ethyl [3-(4,5-difluoro-2-hydroxyphenyl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl [3-(4-chloro-2-hydroxyphenyl)-2-oxo-2,3-dihydro-1H-indol-1-yl]acetate, the title compound was obtained: MS (ES+) m/z 378.3 (M+1), 361.3 (M−17).

Preparation 46

Synthesis of 3-(4-bromo-2-hydroxyphenyl)-3-(hydroxymethyl)-1-pentyl-1,3-dihydro-2H-indol-2-one A. Synthesis of 3-(4-bromo-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 3-bromophenol, the title compound was obtained (48%) as a white solid: $^1$H NMR (300 MHz, CDCl$_3$) δ 9.66 (br, 1H), 7.50-7.38 (m, 2H), 7.24-7.16 (m, 2H), 6.98-6.86 (m, 2H), 6.64 (d, 1H), 4.15 (br, 1H), 3.80-3.55 (m, 2H), 1.75-1.62 (m, 2H), 1.40-1.34 (m, 4H), 0.89 (t, 3H); MS (ES+) m/z 391.4 (M+1), 393.4 (M+1).

B. Synthesis of 3-(4-bromo-2-hydroxyphenyl)-1-pentyl-1,3-dihydro-2H-indol-2-one

Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 3-(4-bromo-2-hydroxyphenyl)-3-hydroxy-1-pentyl-1,3-dihydro-2H-indol-2-one, the title compound was obtained (91%) as a white powder: $^1$H NMR (300 MHz, CDCl$_3$) δ 7.40 (t, 1H), 7.31 (d, 1H) 7.24-7.23 (m, 2H), 7.01-6.91 (m, 2H), 6.74 (d, 1H), 5.05 (br, 1H), 3.80-3.65 (m, 2H), 1.75-1.63 (m, 2H), 1.38-1.29 (m, 4H), 0.88 (t, 3H); MS (ES+) m/z 374.4 (M+1), 376.4 (M+1).

C. Synthesis of 3-(4-bromo-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4-bromo-2-hydroxyphenyl)-1-pentyl-1,3-dihydro-2H-indol-2-one, the title compound was obtained: R$_f$=0.5 (EtOAc/Hexanes, %).

Preparation 47

Synthesis of 3-(5-bromo-2-hydroxyphenyl)-3-(hydroxymethyl)-1,3-dihydro-2H-indol-2-one A. Synthesis of 3-(5-bromo-2-hydroxyphenyl)-3-hydroxy-1,3-dihydro-2H-indol-2-one Following the procedure as described in PREPARATION 2B, and making non-critical variations to replace 1-(2-cyclopropylethyl)-1H-indole-2,3-dione with isatin, 1,3-benzodioxol-5-ol with 4-bromophenol, the title compound was obtained (71%) as a yellowish solid: MS (ES+) m/z 319.4 (M+1), 321.4 (M+1).

B. Synthesis of 3-(5-bromo-2-hydroxyphenyl)-1,3-dihydro-2H-indol-2-one

Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 3-(5-bromo-2-hydroxyphenyl)-3-hydroxy-1,3-dihydro-2H-indol-2-one, the title compound was obtained (98%) as a white powder: MS (ES+) m/z 306.2 (M+1), 304.2 (M+1).

C. Synthesis of 3-(5-bromo-2-hydroxyphenyl)-3-(hydroxymethyl)-1,3-dihydro-2H-indol-2-one Following the procedure as described in PREPARATION 35D, and making non-critical variations to replace 5-fluoro-3-(6-hydroxy-1,3-benzodioxol-5-yl)-1-{[5-(trifluoromethyl)-2-furyl]methyl}-1,3-dihydro-2H-indol-2-one with 3-(5-bromo-2-hydroxyphenyl)-1,3-dihydro-2H-indol-2-one, the title compound was obtained: MS (ES+) m/z 334.2 (M+1), 336.2 (M+1).

Preparation 48

Synthesis of 1-(diphenylmethyl)-3-(hydroxymethyl)-3-[2-hydroxy-4-(trifluoromethoxy)phenyl]-1,3-dihydro-2H-indol-2-one A. Synthesis of 1-(diphenylmethyl)-3-hydroxy-3-[2-hydroxy-4-(trifluoromethoxy)phenyl]-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, and 1,3-benzodioxol-5-ol with 3-(trifluoromethoxy)phenol, the title compound was obtained (75%): MS (ES+) m/z 514.5 (M+23).

B. Synthesis of 1-(diphenylmethyl)-3-[2-hydroxy-4-(trifluoromethoxy)phenyl]-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-[2-hydroxy-4-(trifluoromethoxy)phenyl]-1,3-dihydro-2H-indol-2-one, the title compound was obtained (82%): MS (ES+) m/z 498.4 (M+23).

C. Synthesis of 1-(diphenylmethyl)-3-(hydroxymethyl)-3-[2-hydroxy-4-(trifluoromethoxy)phenyl]-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 1-(diphenylmethyl)-3-[2-hydroxy-4-(trifluoromethoxy)phenyl]-1,3-dihydro-2H-indol-2-one, the title compound was obtained: MS (ES+) m/z 488 (M−17), 528 (M+23).

Preparation 49

Synthesis of 1-(diphenylmethyl)-3-(6-hydroxy-2,3-dihydro-1-benzofuran-5-yl)-3-(hydroxymethyl)-1,3-dihydro-2H-indol-2-one A. Synthesis of 1-(diphenylmethyl)-3-hydroxy-3-(6-hydroxy-2,3-dihydro-1-benzofuran-5-yl)-1,3-dihydro-2H-indol-2-one Following the procedure as described in PREPARATION 2B, and making non-critical variations to replace 1,3-benzodioxol-5-ol with 2,3-dihydrobenzofuran-6-ol (Foster et al., *J. Chem. Soc.* 1948:2254-2258) and 1-(2-cyclopropylethyl)-1H-indole-2,3-dione with 1-(diphenylmethyl)-1H-indole-2,3-dione, the title compound was obtained (68%) as a white solid: MS (ES+) m/z 450.4 (M+1).

B. Synthesis of 1-(diphenylmethyl)-3-(6-hydroxy-2,3-dihydro-1-benzofuran-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-2,3-dihydro-1-benzofuran-5-yl)-1,3-dihydro-2H-indol-2-one, the title compound was obtained (67%) as a white solid: MS (ES+) m/z 434.3 (M+1).

C. Synthesis of 1-(diphenylmethyl)-3-(6-hydroxy-2,3-dihydro-1-benzofuran-5-yl)-(3-hydroxymethyl)-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 1-(diphenylmethyl)-3-(6- hydroxy-2,3-dihydro-1-benzofuran-5-yl)-1,3-dihydro-2H-indol-2-one, the title compound was obtained (45%) as a white solid: MS (ES+) m/z 464.5 (M+1).

Preparation 50

Synthesis of 4-bromo-3-(6-hydroxy-2,3-dihydro-1-benzofuran-5-yl)-3-(hydroxymethyl)-1,3-dihydro-2H-indol-2-one A. Synthesis of 4-bromo-3-hydroxy-3-(6-hydroxy-2,3-dihydro-1-benzofuran-5-yl)-1,3-dihydro-2H-indol-2-one Following the procedure as described in PREPARATION 2B, and making non-critical variations to replace 1,3-benzodioxol-5-ol with 2,3-dihydrobenzofuran-6-ol and 1-(2-cyclopropylethyl)-1H-indole-2,3-dione with 4-bromo-1H-indole-2,3-dione, the title compound was obtained (78%) as a white solid: $^1$H NMR (300 MHz, DMSO-d$_6$) δ 10.36 (s, 1H), 9.15 (s, 1H), 7.49 (1H), 7.04 (t, 1H), 6.89 (d, 1H), 6.74 (d, 1H), 6.35 (br, 1H), 5.90 (s, 1H), 4.45 (t, 2H), 3.05 (t, 2H); $^{13}$C NMR (75 MHz, DMSO-d$_6$) δ 178.4, 160.2, 154.0, 145.7, 131.6, 130.7, 125.5, 125.4, 118.9, 117.7, 116.1, 108.8, 96.8, 76.9, 71.8, 29.1; MS (ES−) m/z 344.4 (M−17), 360.4 (M−1).

B. Synthesis of 4-bromo-3-(6-hydroxy-2,3-dihydro-1-benzofuran-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 4-bromo-3-hydroxy-3-(6-hydroxy-2,3-dihydro-1-benzofuran-5-yl)-1,3-dihydro-2H-indol-2-one, the title compound was obtained (62%) as a white solid: MS (ES+) m/z 346.5 (M+1), 348.5 (M+1).

C. Synthesis of 4-bromo-3-(6-hydroxy-2,3-dihydro-1-benzofuran-5-yl)-3-(hydroxymethyl)-1,3-dihydro-2H-indol-2-one Following the procedure as described in PREPARATION 14C, and making non-critical variations to replace 3-(5-fluoro-2-hydroxyphenyl)-1-pentyl-1,3-dihydro-2H-indol-2-one with 4-bromo-3-(6-hydroxy-2,3-dihydro-1-benzofuran-5-yl)-1,3-dihydro-2H-indol-2-one, the title compound was obtained (16%): R$_f$=0.21 (EtOAc/Hexanes, 7/3).

Preparation 51

Synthesis of 7-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one A. Synthesis of 7-fluoro-{[5-(trifluoromethyl)-2-furyl]methyl}-1H-indole-2,3-dione Following the procedure as described in PREPARATION 1A, and making non-critical variations to replace 4-bromoindole with 7-fluoroisatin, and 1-bromopentane with 2-(bromomethyl)-5-(trifluoromethyl)furan, the title compound was obtained (34%): MS (ES+) m/z 336.2 (M+23).

B. Synthesis of 7-fluoro-3-hydroxy-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 2B, and making non-critical variations to replace 1-(2-cyclopropylethyl)-1H-indole-2,3-dione with 7-fluoro-1-{[5-(trifluoromethyl)-2-furyl]methyl}-1H-indole-2,3-dione, the title compound was obtained (75%): MS (ES+) m/z 474.3 (M+23).

C. Synthesis of 7-fluoro-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 7-fluoro-3-hydroxy-3-(6-hydroxy-1,3-benzodioxol-5-yl)-1-{[5-(trifluoromethyl)-2-furyl]methyl}-1,3-dihydro-2H-indol-2-one, the title compound was obtained (65%): MS (ES+) m/z 436.4 (M+1).

D. Synthesis of 7-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 7-fluoro-3-(6-hydroxy-1,3-benzodioxol-5-yl)-1-{[5-(trifluoromethyl)-2-furyl]methyl}-1,3-dihydro-2H-indol-2-one, the title compound was obtained (67%): MS (ES+) m/z 488.4 (M+23).

Preparation 52

Synthesis of 3-(6-hydroxy-2,3-dihydro-1-benzofuran-5-yl)-3-(hydroxymethyl)-1-pentyl-1,3-dihydro-2H-indol-2-one A. Synthesis of 3-hydroxy-3-(6-hydroxy-2,3-dihydro-1-benzofuran-5-yl)-1-pentyl-1,3-dihydro-2H-indol-2-one Following the procedure as described in PREPARATION 2B, and making non-critical variations to replace 1-(2-cyclopropylethyl)-1H-indole-2,3-dione with 1-pentyl-1H-indole-2,3-dione, and 1,3-benzodioxol-5-ol with 2,3-dihydrobenzofuran-6-ol, the title compound was obtained (90%) as a white powder: MS (ES+) m/z 376.3 (M+23).

B. Synthesis of 3-(6-hydroxy-2,3-dihydro-1-benzofuran-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-hydroxy-3-(6-hydroxy-2,3-dihydro-1-benzofuran-5-yl)-1-pentyl-1,3-dihydro-2H-indol-2-one, the title compound was obtained (76%): MS (ES+) m/z 338.3 (M+1).

C. Synthesis of 3-(6-hydroxy-2,3-dihydro-1-benzofuran-5-yl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(6-hydroxy-2,3-dihydro-1-benzofuran-5-yl)-1-pentyl-1,3-dihydro-2H-indol-2-one, the title compound was obtained (46%): MS (ES+) m/z 368.3 (M+1), 380.4 (M+23).

Preparation 53

Synthesis of 3-(5-bromo-2-hydroxyphenyl)-1-(diphenylmethyl)-3-(hydroxymethyl)-1,3-dihydro-2H-indol-2-one A. Synthesis of 3-(5-bromo-2-hydroxyphenyl)-1-(diphenylmethyl)-3-hydroxy-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, and 1,3-benzodioxol-5-ol with 4-bromophenol, the title compound was obtained (90%) as an orange solid: MS (ES+) m/z 486.2 (M+1), 488.2 (M+1).

B. Synthesis of 3-(5-bromo-2-hydroxyphenyl)-1-(diphenylmethyl)-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(5-bromo-2-hydroxyphenyl)-1-(diphenylmethyl)-3-hydroxy-1,3-dihydro-2H-indol-2-one, the title compound was obtained (99%) as a white powder: $^1$H NMR (300 MHz, CDCl$_3$) δ 7.39-7.20 (m, 11H), 7.11-7.06 (m, 4H), 6.82 (d, 1H), 6.57-6.51 (m, 1H), 5.04 (s, 1H); MS (ES+) m/z 471.2 (M+1), 473.2 (M+1).

C. Synthesis of 3-(5-bromo-2-hydroxyphenyl)-1-(diphenylmethyl)-3-(hydroxymethyl)-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 3-(5-bromo-2-hydroxyphenyl)-1-(diphenylmethyl)-1,3-dihydro-2H-indol-2-one, the title compound was obtained: MS (ES+) m/z 500.4 (M+1), 502.4 (M+1).

Preparation 54

Synthesis of 3-(6-hydroxy-1,3-benzodioxol-5-yl)-3-(hydroxymethyl)-1-pentyl-1,3-dihydro-2H-indol-2-one A. Synthesis of 1-pentyl-1H-indole-2,3-dione Following the procedure as described in PREPARATION 2A, and making non-critical variations to replace (2-bromoethyl)cyclopropane with 1-bromopentane, the title compound was obtained (72%) as a red solid: $^1$H NMR (300 MHz, CDCl$_3$) δ 7.90 (d, 1H), 7.53-7.45 (m, 1H), 7.03-6.97 (m, 1H), 6.82 (d, 1H), 3.64-3.57 (m, 2H), 1.68-1.52 (m, 2H), 1.34-1.21 (m, 4H), 0.79 (t, 3H); $^{13}$C NMR (75 MHz, CDCl$_3$) δ 183.6, 158.1, 151.0, 138.4, 125.3, 123.5, 117.5, 110.2, 40.2, 28.9, 26.9, 22.2, 13.9.

B. Synthesis of 3-hydroxy-3-(6-hydroxy-1,3-benzodioxol-5-yl)-1-pentyl-1,3-dihydro-2H-indol-2-one Following the procedure as described in PREPARATION 2B, and making non-critical variations to replace 1-(2-cyclopropylethyl)-1H-indole-2,3-dione with 1-pentyl-1H-indole-2,3-dione, the title compound was obtained (47%) as a colorless solid: $^1$H NMR (300 MHz, CDCl$_3$) δ 9.41 (s, 1H), 7.46 (dd, 1H), 7.37 (dt, 1H), 7.16 (dt, 1H), 6.89 (d, 1H), 6.53 (s, 1H), 6.22 (s, 1H), 5.83 (dd, 2H), 4.70 (br, 1H), 3.73-3.54 (m, 2H), 1.69-1.60 (m, 2H), 1.34-1.26 (m, 4H), 0.85 (t, 3H); $^{13}$C NMR (75 MHz, CDCl$_3$) δ 178.9, 152.2, 148.8, 142.5, 141.3, 130.3, 129.3, 126.1, 123.8, 117.1, 109.5, 106.8, 101.8, 101.4, 79.3, 40.4, 28.9, 26.8, 22.3, 13.9; MS (ES+1) m/z 355.5 (M+1).

C. Synthesis of 3-(6-hydroxy-1,3-benzodioxol-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-hydroxy-3-(6-hydroxy-1,3-benzodioxol-5-yl)-1-pentyl-1,3-dihydro-2H-indol-2-one, the title compound was obtained (81%) as a colorless solid: $^1$H NMR (300 MHz, CDCl$_3$) δ 9.67 (br, 1H), 7.39-7.29 (m, 2H), 7.18-7.13 (m, 1H), 6.94 (d, 1H), 6.62 (s, 1H), 6.32 (s, 1H), 5.84 (dd, 2H), 5.01 (s, 1H), 3.71-3.63 (m, 2H), 1.71-1.61 (m, 2H), 1.35-1.27 (m, 4H), 0.86 (t, 3H); $^{13}$C NMR (75 MHz, CDCl$_3$) δ 178.8, 151.3, 147.6, 143.9, 141.53, 128.7, 126.4, 126.2, 123.1, 115.3, 109.4, 106.5, 101.5, 101.2, 47.4, 40.5, 28.9, 26.9, 22.3, 13.9; MS (ES+) m/z 340 (M+1).

D. Synthesis of 3-(6-hydroxy-1,3-benzodioxol-5-yl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(6-hydroxy-1,3-benzodioxol-5-yl)-1-pentyl-1,3-dihydro-2H-indol-2-one, the title compound was obtained (67%): $^1$H NMR (300 MHz, CDCl$_3$) δ 10.85-10.63 (br, 1H), 7.48-7.35 (m, 2H), 7.28-7.19 (m, 1H), 6.96 (d, 1H), 6.52 (d, 2H), 5.82 (dd, 2H), 4.63 (d, 1H), 4.11 (d, 1H), 3.70 (d, 2H), 2.04-1.74 (br, 1H), 1.65-162 (m, 2H), 1.31-1.24 (m, 4H), 0.84 (t, 3H); $^{13}$C NMR (75 MHz, CDCl$_3$) δ 180.3, 152.6, 148.1, 143.2, 141.3, 129.2, 129.1, 126.2, 123.3, 112.4, 109.6, 108.2, 101.9, 101.3, 64.6, 59.8, 40.6, 28.9, 26.9, 22.2, 13.9; MS (ES+) m/z 370.1 (M+1).

Example 1

Synthesis of 1'-(2-cyclopropylethyl)spiro[furo[2,3-f][1,3]benzodioxole-7,3'-indol]-2'(1'H)-one To a solution of 1-(2-cyclopropylethyl)-3-(6-hydroxy-1,3-benzodioxol-5-yl)-3-(hydroxymethyl)-1,3-dihydro-2H-indol-2-one (0.92 g, 2.51 mmol) in anhydrous THF (20.0 mL) was added triphenylphosphine (0.82 g, 3.13 mmol) and diethyl azodicarboxylate (0.55, 3.13 mmol) at −78° C. The brown reaction solution was stirred at ambient temperature for 16 h, and quenched with saturated ammonium chloride (50.0 mL). The organic solvent was removed under reduced pressure and the aqueous mixture was extracted with ethyl acetate (3×50.0 mL). The combined organic layers were dried over anhydrous sodium sulfate and filtered. The filtrate was concentrated in vacuo to dryness. The brown residue was subjected to column chromatography eluting with ethyl acetate/hexane (5% to 20%, gradient) to give the title compound (0.63 g, 72%) which was crystallized from ether to afford a colorless solid: mp 125-127° C.; $^1$H NMR (300 MHz, CDCl₃) δ 7.30-7.25 (m, 1H), 7.14 (d, 1H), 7.02 (t, 1H), 6.89 (d, 1H), 6.49 (s, 1H), 6.11 (s, 1H), 5.84 (m, 2H), 4.76 (m, 2H), 3.93-3.74 (m, 2H), 1.65-1.57 (m, 2H), 0.76-0.56 (m, 1H), 0.48-0.41 (m, 2H), 0.08-0.03 (m, 2H); $^{13}$C NMR (75 MHz, CDCl₃) δ 177.4, 155.9, 148.8, 142.6, 142.3, 132.4, 128.8, 124.0, 123.1, 119.5, 108.6, 103.1, 101.5, 93.6, 80.6, 58.2, 40.5, 32.5, 30.8, 8.7, 4.4; MS (ES+) m/z 350.3 (M+1).

Example 1.1

Synthesis of 1'-pentylspiro[furo[2,3-f][1,3]benzodioxole-7,3'-indol]-2'(1'H)-one Following the procedure as described in Example 1, and making non-critical variations using 3-(6-hydroxy-1,3-benzodioxol-5-yl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (80%) as a white solid: mp 85-87° C.; $^1$H NMR (300 MHz, CDCl₃) δ 7.28 (t, 1H), 7.15 (d, 1H), 7.02 (t, 1H), 6.89 (d, 1H), 6.49 (s, 1H), 6.11 (s, 1H), 5.84 (dd, 2H), 4.77 (ABq, 2H), 3.85-3.62 (m, 2H), 1.76-1.66 (m, 2H), 1.40-1.33 (m, 4H), 0.89 (t, 3H); $^{13}$C NMR (75 MHz, CDCl₃) δ 177.3, 155.9, 148.8, 142.4, 142.3, 132.5, 128.9, 123.9, 119.6, 108.6, 103.0, 101.5, 93.6, 80.5, 58.2, 40.4, 29.0, 27.1, 22.3, 14.0; MS (ES+) m/z 352 (M+1).

Example 1.2

Synthesis of 4'-bromo-1'-pentylspiro[furo[2,3-f][1,3]benzodioxole-7,3'-indol]-2'(1'H)-one Following the procedure as described in EXAMPLE 1, and making non-critical variations using 4-bromo-3-(6-hydroxy-1,3-benzodioxol-5-yl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a colorless solid: $^1$H NMR (300 MHz, CDCl₃) δ 7.16 (d, 1H), 7.15 (s, 1H), 6.84 (dd, 1H), 6.45 (s, 1H), 6.06 (s, 1H), 5.86 (dd, 2H), 4.90 (ABq, 2H), 3.83-3.60 (m, 2H), 1.74-1.64 (m, 2H), 1.39-1.28 (m, 4H), 0.89 (t, 3H); $^{13}$C NMR (75 MHz, CDCl₃) δ 177.1, 157.2, 149.1, 144.6, 142.0, 130.3, 130.1, 127.0, 120.0, 116.5, 107.6, 102.5, 101.5, 93.3, 77.3, 59.6, 40.6, 29.0, 27.0, 22.3, 14.0; MS (ES+) m/z 430 (M+1).

Example 1.3

Synthesis of ethyl (2'-oxospiro[furo[2,3-f][1,3]benzodioxole-7,3'-indol]-1'(2'H)-yl)acetate Following the procedure as described in EXAMPLE 1, and making non-critical variations using ethyl [3-(6-hydroxy-1,3-benzodioxol-5-yl)-3-(hydroxymethyl)-2-oxo-2,3-dihydro-1H-indol-1-yl]acetate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 90% yield: $^1$H NMR (300 MHz, DMSO-d₆) δ 7.31-7.26 (m, 1H), 7.17-7.00 (m, 3H), 6.67 (s, 1H), 6.18 (s, 1H), 5.90-5.89 (m, 2H), 4.76-4.66 (m, 2H), 4.59 (s, 2H), 4.13 (q, 2H), 1.17 (t, 3H); $^{13}$C NMR (75 MHz, DMSO-d₆) δ 177.3, 168.3, 155.6, 148.8, 142.4, 142.1, 132.0, 129.3, 124.1, 123.7, 120.4, 109.6, 103.3, 101.9, 93.8, 79.8, 61.8, 57.8, 41.8, 14.5; MS (ES+) m/z 390.2 (M+23).

Example 1.4

Synthesis of methyl 2-[(2'-oxospiro[furo[2,3-f][1,3]benzodioxole-7,3'-indol]-1'(2'H)-yl)methyl]benzoate Following the procedure as described in EXAMPLE 1, and making non-critical variations using methyl 2-{[3-(6-hydroxy-1,3-benzodioxol-5-yl)-3-(hydroxymethyl)-2-oxo-2,3-dihydro-1H-indol-1-yl]methyl}benzoate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 74% yield: mp 166-167° C.; $^1$H NMR (300 MHz, CDCl₃) δ 8.05 (m, 1H), 7.44 (m, 1H), 7.34 (t, 1H), 7.22-7.10 (m, 3H), 7.03 (m, 1H), 6.70 (d, 1H), 6.52 (s, 1H), 6.21 (s, 1H), 5.90-5.84 (m, 2H), 5.52-5.33 (m, 2H), 4.99 (d, 1H), 4.72 (d, 1H), 3.95 (s, 3H); $^{13}$C NMR (75 MHz, CDCl₃) δ 177.8, 167.5, 156.0, 148.9, 142.4, 142.3, 137.4, 132.8, 132.1, 131.4, 129.0, 128.6, 127.4, 126.5, 123.9, 123.6, 119.4, 109.5, 103.1, 101.5, 93.7, 80.7, 58.4, 52.3, 42.4; MS (ES+) m/z 430.3 (M+1), 452.3 (M+23).

Example 1.5

Synthesis of methyl 3-[(2'-oxospiro[furo[2,3-f][1,3]benzodioxole-7,3'-indol]-1'(2'H)-yl)methyl]benzoate Following the procedure as described in EXAMPLE 1, and making non-critical variations using methyl 3-{[3-(6-hydroxy-1,3-benzodioxol-5-yl)-3-(hydroxymethyl)-2-oxo-2,3-dihydro-1H-indol-1-yl]methyl}benzoate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 73% yield; $^1$H NMR (300 MHz, CDCl₃) δ 7.97-7.95 (m, 2H), 7.53-7.50 (m, 1H), 7.45-7.40 (m, 1H), 7.21-7.15 (m, 2H), 7.04-6.99 (m, 1H), 6.73-6.71 (m, 1H), 6.52 (s, 1H), 6.20 (s, 1H), 5.86 (s, 1H), 5.18 (d, 1H), 4.72 (d, 1H), 4.80 (d, 1H), 4.69 (d, 1H), 3.89 (s, 1H); $^{13}$C NMR (75 MHz, CDCl₃) δ 177.7, 166.6, 156.0, 149.0, 142.4, 141.7, 136.1, 132.2, 131.7, 130.9, 129.2, 128.1, 124.0, 123.7, 119.4, 109.2, 103.1, 101.6, 93.7, 80.5, 64.3, 58.3, 52.3, 43.7; MS (ES+) m/z 430 (M+1).

Example 1.6

Synthesis of methyl 4-[(2'-oxospiro[furo[2,3-f][1,3]benzodioxole-7,3'-indol]-1'(2'H)-yl)methyl]benzoate Following the procedure as described in EXAMPLE 1, and making non-critical variations using methyl 4-{[3-(6-hydroxy-1,3-benzodioxol-5-yl)-3-(hydroxymethyl)-2-oxo-2,3-dihydro-1H-indol-1-yl]methyl}benzoate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 87% yield: $^1$H NMR (300 MHz, CDCl₃) δ 8.01 (d, 2H), 7.38 (d, 2H), 7.18 (t, 2H), 7.02 (t, 1H), 6.72 (d, 1H), 6.52 (s, 1H), 6.12 (s, 1H), 5.86 (m, 2H), 5.11 (d, 1H), 4.96 (d, 1H), 4.86 (d, 1H), 4.69 (d, 1H), 3.89 (s, 1H); $^{13}$C NMR (75 MHz, CDCl₃) δ 177.7, 166.6, 156.0, 149.0, 142.4, 141.8, 140.8, 132.1, 130.3, 129.8, 129.0, 127.3, 124.1, 123.7, 119.3, 109.2, 103.0, 102.0, 93.7, 80.5, 58.3, 52.2, 43.9; MS (ES+) m/z 430.1 (M+1).

Example 1.7

Synthesis of 1-(diphenylmethyl)spiro[furo[2,3-f][1,3]benzodioxole-7,3'-indol]-2'(1'H)-one Following the procedure as described in EXAMPLE 1, and making non-critical variations using 1-(diphenylmethyl)-3-

(6-hydroxy-1,3-benzodioxol-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 26% yield: MS (ES+) m/z 462.3 (M+1).

Example 1.8

Synthesis of spiro[furo[2,3-f][1,3]benzodioxole-7,3'-indol]-2'(1'H)-one

To a solution of 1-(diphenylmethyl)spiro[furo[2,3-f][1,3]benzodioxole-7,3'-indol]-2'(1'H)-one (2.10 g, 4.70 mmol) in EtOAc (100 mL) and acetic acid (0.10 mL) was added palladium on carbon (1.00 g). The reaction mixture was hydrogenated under 60 psi of hydrogen at ambient temperature for 5 days and filtered. The filtrate was concentrated in vacuo to dryness. The residue was subjected to column chromatography to yield the title compound (0.87 g, 66%) as a white powder: mp 252° C. (dec.); $^1$H NMR (300 MHz, CDCl$_3$) δ 10.55 (s, 1H), 7.25-6.84 (m, 4H), 6.64 (s, 1H), 6.22 (s, 1H), 5.88 (s, 2H), 4.76-4.57 (dd, 2H); MS (ES+) m/z 282.2 (M+1).

Example 1.9

Synthesis of 2-[3-(2'-oxospiro[furo[2,3-f][1,3]benzodioxole-7,3'-indol]-1'(2'H)-yl)propyl]-1H-isoindole-1,3(2H)-dione Following the procedure as described in EXAMPLE 1, and making non-critical variations using 2-{3-[3-(6-hydroxy-1,3-benzodioxol-5-yl)-3-(hydroxymethyl)-2-oxo-2,3-dihydro-1H-indol-1-yl]propyl}-1H-isoindole-1,3(2H)-dione to replace 142-cyclopropylethyl)-3-(6-hydroxy-1,3-benzodioxol-5-yl)-3-(hydroxymethyl)-1,3-dihydro-2H-indol-2-one, the title compound was obtained in 45% yield: $^1$H NMR (300 MHz, CDCl$_3$) δ 7.83-7.80 (m, 2H), 7.70-7.68 (m, 2H), 7.28-7.26 (m, 1H), 7.15 (d, 1H), 7.05-7.00 (m, 1H), 6.86 (d, 1H), 6.48 (s, 1H), 6.23 (s, 1H), 5.85-5.83 (m, 2H), 4.91 (d, 1H), 4.65 (d, 1H), 3.94-3.68- (m, 4H), 2.15-2.10- (m, 2H); $^{13}$C NMR (75 MHz, CDCl$_3$) δ 177.4, 168.2, 155.9, 148.8, 142.4, 141.9, 134.0, 132.5, 132.0, 128.9, 124.1, 123.4, 123.3, 119.4, 108.4, 103.2, 101.5, 93.6, 80.4, 58.2, 38.0, 35.6, 26.8; MS (ES+) m/z 469.3 (M+1), 491.3 (M+23).

Example 1.10

Synthesis of 2-[2-(2'-oxospiro[furo[2,3-f][1,3]benzodioxole-7,3'-indol]-1'(2'H)-yl)ethyl]-1H-isoindole-1,3(2H)-dione Following the procedure as described in EXAMPLE 1, and making non-critical variations using 2-{2-[3-(6-hydroxy-1,3-benzodioxol-5-yl)-3-(hydroxymethyl)-2-oxo-2,3-dihydro-1H-indol-1-yl]ethyl}-1H-isoindole-1,3(2H)-dione to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 61% yield: $^1$H NMR (300 MHz, CDCl$_3$) δ 7.81-7.73 (m, 2H), 7.71-7.62 (m, 2H), 7.18-7.08 (m, 2H), 6.98 (t, 1H), 6.87 (d, 1H), 6.43 (s, 1H), 6.29 (s, 1H), 5.91-5.81 (ABq, 2H), 4.79 (d, 1H), 4.58 (d, 1H), 4.18-3.92 (m, 4H), 3.06 (t, 2H), 1.59-1.35 (br, 2H); $^{13}$C NMR (75 MHz, CDCl$_3$) δ 178, 168.2, 156.1, 148.7, 142.2, 141.9, 134.1, 132.4, 131.8, 128.7, 124.1, 123.4, 123.3, 119.0, 107.8, 103.7, 101.4, 93.4, 80.9, 58.1, 39.0, 35.6; MS (ES+) m/z 455 (M+1), 477 (M+23).

Example 1.11

Synthesis of 1'-[3-(Benzyloxy)propyl]spiro[furo[2,3-f][1,3]benzodioxole-7,3'-indol]-2'(1'H)-one Following the procedure as described in EXAMPLE 1, and making non-critical variations using 1-[3-(benzyloxy)propyl]-3-(6-hydroxy-1,3-benzodioxol-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 98% yield as a pale yellow syrup: $^1$H NMR (300 MHz, CDCl$_3$) δ 7.38-6.95 (m, 9H), 6.49 (s, 1H), 6.08 (s, 1H), 5.83 (dd, 2H), 5.86 (ABq, 1H), 4.58 (ABq, 1H), 3.96-3.79 (m, 2H), 3.53 (t, 2H), 2.06-2.00 (m, 2H); $^{13}$C NMR (75 MHz, CDCl$_3$) δ 177.4, 155.9, 148.8, 142.5, 142.2, 138.1, 132.3, 128.9, 127.9, 127.6, 123.9, 123.1, 119.5, 108.7, 103.0, 101.4, 93.6, 80.4, 73.1, 67.4, 58.1, 37.7, 27.9; MS (ES+) m/z 430.3 (M+1).

Example 1.12

Synthesis of 5,6-difluoro-1'-pentylspiro[1-benzofuran-3,3'-indol]-2'(1'H)-one

Following the procedure as described in EXAMPLE 1, and making non-critical variations using 3-(4,5-difluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 71% yield: mp 48-50° C.; $^1$H NMR (300 MHz, CDCl$_3$) δ 7.33 (td, 1H), 7.18-7.12 (m, 2H), 6.93 (d, 1H), 6.77 (dd, 1H), 6.51 (dd, 1H), 4.96 (d, 1H), 4.71 (d, 1H), 3.87-3.64 (m, 2H), 1.82-1.65 (m, 2H), 1.46-1.28 (m, 4H), 0.92 (t, 3H); $^{13}$C NMR (75 MHz, CDCl$_3$) δ 176.6, 156.8, 152.9, 149.8, 144.2, 142.6, 131.8, 129.4, 124.1, 123.5, 111.7, 109.0, 100.2, 80.9, 57.9, 40.6, 29.1, 27.2, 22.5, 14.1; MS (ES+) m/z 344 (M+1).

Example 1.13

Synthesis of 5-fluoro-1'-pentylspiro[1-benzofuran-3,3'-indol]-2'(1'H)-one

Following the procedure as described in EXAMPLE 1, and making non-critical variations using 3-(5-fluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 3% yield: $^1$H NMR (300 MHz, CDCl$_3$) δ 7.37-7.28 (m, 1H), 7.18-7.11 (m, 1H), 7.09-7.01 (m, 1H), 6.98-6.82 (m, 3H), 6.45-6.37 (m, 1H), 4.95 (d, 1H), 4.69 (d, 1H), 3.89-3.63 (m, 2H), 1.81-1.65 (m, 2H), 1.48-1.28 (m, 4H), 0.92 (t, 3H); $^{13}$C NMR (75 MHz, CDCl$_3$) δ 176.7, 159.4, 156.6, 132.2, 130.1, 129.3, 124.1, 123.4, 116.3, 110.8, 110.5, 108.9, 80.4, 58.4, 40.6, 29.2, 27.3, 22.5, 14.1; MS (ES+) m/z 326 (M+1).

Example 1.14

Synthesis of 5-bromo-1'-pentylspiro[1-benzofuran-3,3'-indol]-2'(1'H)-one

Following the procedure as described in EXAMPLE 1, and making non-critical variations using 3-(5-bromo-2-hydroxyphenyl)-3-(hydroxymethyl)-1-pentyl-1,3-dihydro-2H-indol-2-one to replace 1-(2-cyclopropylethyl)-3-(6-hydroxy-1, 3-benzodioxol-5-yl)-3-(hydroxymethyl)-1,3-dihydro-2H-indol-2-one, the title compound was obtained in 4% yield: $^1$H NMR (300 MHz, CDCl$_3$) δ 7.38-7.23 (m, 2H), 7.17-7.01 (m, 2H), 6.93 (d, 1H), 6.84 (d, 1H), 6.79 (d, 1H), 4.95 (d, 1H), 4.69 (d, 1H), 3.89-3.64 (m, 2H), 1.81-1.65 (m, 2H), 1.48-1.28 (m, 4H), 0.92 (t, 3H); $^{13}$C NMR (75 MHz, CDCl$_3$) δ 176.7, 160.1, 142.6, 132.7, 132.1, 131.4, 129.3, 126.5, 124.1, 123.5, 113.1, 112.2, 108.9, 80.3, 58.0, 40.6, 29.2, 27.3, 22.5, 14.2; MS (ES+) m/z 386 (M+1), 388 (M+23).

Example 1.15

Synthesis of 5-chloro-6-fluoro-1'-pentylspiro[1-benzofuran-3,3'-indol]-2'(1'H)-one Following the procedure as described in EXAMPLE 1, and making non-critical variations using 3-(5-chloro-4-fluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 80% yield; mp 74-76° C.; $^1$H NMR (300 MHz, CDCl$_3$) δ 7.38-7.27 (m, 1H), 7.18-7.02 (m, 2H), 6.94 (d, 1H), 6.77 (d, 1H), 6.69 (d, 1H), 4.98 (d, 1H), 4.72 (d, 1H), 3.87-3.64 (m, 2H), 1.82-1.65 (m, 2H), 1.47-1.28 (m, 4H), 0.92 (t, 3H); $^{13}$C NMR (75 MHz, CDCl$_3$) δ 176.5, 160.6, 157.4, 142.6, 133.9, 131.8, 129.5, 124.6, 124.1, 123.5, 113.1, 109.0, 100.0, 81.2, 57.5, 40.6, 29.2, 27.2, 22.5, 14.1; MS (ES+) m/z 360 (M+1).

Example 1.16

Synthesis of 6-methoxy-1'-pentylspiro[1-benzofuran-3,3'-indol]-2'(1H)-one

Following the procedure as described in EXAMPLE 1, and making non-critical variations using 3-(2-hydroxy-4-methoxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 99% yield: $^1$H NMR (300 MHz, CDCl$_3$) δ 7.30 (td, 1H), 7.14 (dd, 1H), 7.03 (t, 1H), 6.91 (d, 1H), 6.58 (d, 1H), 6.52 (d, 1H), 6.36 (dd, 1H), 4.93 (d, 1H), 4.69 (d, 1H), 3.91-3.63 (m, 2H), 3.77 (s, 3H), 1.81-1.65 (m, 2H), 1.46-1.29 (m, 4H), 0.91 (t, 3H); $^{13}$C NMR (75 MHz, CDCl$_3$) δ 177.4, 162.1, 161.5, 142.5, 132.9, 128.8, 123.9, 123.5, 123.1, 121.0, 108.5, 107.5, 96.6, 80.5, 57.6, 55.6, 40.3, 29.0, 27.1, 22.3, 14.0; MS (ES+) m/z 338 (M+1).

Example 1.17

Synthesis of 6-chloro-5-fluoro-1-pentylspiro[1-benzofuran-3,3'-indol]-2'(1'H)-one Following the procedure as described in EXAMPLE 1, and making non-critical variations using 3-(4-chloro-5-fluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 44% yield: $^1$H NMR (300 MHz, CDCl$_3$) δ 7.34 (td, 1H), 7.14 (dd, 1H), 7.06 (td, 1H), 6.98 (d, 1H), 6.93 (d, 1H), 6.50 (d, 1H), 4.96 (d, 1H), 4.70 (d, 1H), 3.87-3.63 (m, 2H), 1.81-1.65 (m, 2H), 1.47-1.29 (m, 4H), 0.91 (t, 3H); $^{13}$C NMR (75 MHz, CDCl$_3$) δ 176.2, 156.9, 154.8, 151.6, 142.5, 131.5, 129.4, 128.6, 123.7, 121.7, 121.9, 111.2, 108.9, 80.6, 57.9, 40.5, 29.0, 27.1, 22.3, 14.0; MS (ES+) m/z 360 (M+1).

Example 1.18

Synthesis of 1'-pentyl-5-(trifluoromethyl)spiro[1-benzofuran-3,3'-indol]-2'(1'H)-one Following the procedure as described in EXAMPLE 1, and making non-critical variations using 3-(hydroxymethyl)-3-[2-hydroxy-5-(trifluoromethyl)phenyl]-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 27% yield: $^1$H NMR (300 MHz, CDCl$_3$) δ 7.48 (dd, 1H), 7.35 (td, 1H), 7.16-6.90 (m, 5H), 5.02 (d, 1H), 4.76 (d, 1H), 3.91-3.65 (m, 2H), 1.82-1.67 (m, 2H), 1.47-1.29 (m, 4H), 0.91 (t, 3H); $^{13}$C NMR (75 MHz, CDCl$_3$) δ 176.5, 163.3, 142.6, 131.8, 129.8, 129.3, 127.7, 124.1, 124.0, 123.9, 123.6, 121.0, 110.6, 108.9, 80.5, 57.6, 40.5, 29.0, 27.1, 22.3, 13.9; MS (ES+) m/z 376 (M+1).

Example 1.19

Synthesis of 5,6-dichloro-1'-pentylspiro[1-benzofuran-3,3'-indol]-2'(1'H)-one

Following the procedure as described in EXAMPLE 1, and making non-critical variations using 3-(4,5-dichloro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 43% yield. $^1$H NMR (300 MHz, CDCl$_3$) δ 7.35 (td, 1H), 7.17-7.03 (m, 3H), 6.94 (d, 1H), 6.76 (s, 1H), 4.98 (d, 1H), 4.72 (d, 1H), 3.88-3.65 (m, 2H), 1.82-1.67 (m, 2H), 1.47-1.29 (m, 4H), 0.92 (t, 3H). $^{13}$C NMR (75 MHz, CDCl$_3$) δ 176.2, 159.9, 142.5, 133.3, 131.5, 129.4, 124.6, 124.5, 123.9, 123.4, 112.4, 108.9, 80.8, 57.5, 40.5, 29.0, 27.1, 22.3, 14.0; MS (ES+) m/z 376 (M+1), 378 (M+1).

Example 1.20

Synthesis of 1'-(diphenylmethyl)-5,5-dimethyl-5,6-dihydrospiro[benzo[1,2-b:5,4-b']difuran-3,3'-indol]-2'(1'H)-one Following the procedure as described in EXAMPLE 1, and making non-critical variations using 1-(diphenylmethyl)-3-(6-hydroxy-3,3-dimethyl-2,3-dihydro-1-benzofuran-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained: mp 190-192° C.; $^1$H NMR (300 MHz, CDCl$_3$) δ 7.40-7.26 (m, 10H), 7.19-7.15 (m, 1H), 7.07-6.93 (m, 3H), 6.55-6.51 (m, 1H), 6.38 (s, 1H), 6.20 (s, 1H), 4.98 (d, 1H), 4.71 (d, 1H), 4.17 (s, 2H), 1.17 (s, 3H), 1.14 (s, 3H); $^{13}$C NMR (75 MHz, CDCl$_3$) δ 178.1, 161.1, 161.0, 141.8, 137.9, 137.2, 132.8, 130.0, 128.6, 128.5, 128.4, 128.2, 128.0, 127.8, 123.9, 123.1, 120.8, 116.1, 112.1, 93.4, 85.4, 80.4, 58.7, 57.4, 41.3, 27.7, 27.6; MS (ES+) m/z 474.5 (M+1).

Example 1.21

Synthesis of 5,5-dimethyl-5,6-dihydrospiro[benzo[1,2-b:5,4-b']difuran-3,3'-indol]-2'(1'H)-one To a solution of 1-(diphenylmethyl)-5,5-dimethyl-5,6-dihydrospiro[benzo[1,2-b:5,4-b']difuran-3,3'-indol]-2'(1'H)

one (0.23 g, 0.49 mmol) in methanol (50.0 mL) was added palladium on carbon (0.10 g). The mixture was hydrogenated under 120 psi of hydrogen at ambient temperature overnight. The reaction mixture was filtered through celite, washed with methanol. The filtrate was concentrated in vacuo to dryness. The residue was subjected to column chromatography (ethyl acetate/hexane, 1/2) to give the title compound (0.10 g, 68%): mp 95-100° C.; $^1$H NMR (300 MHz, CDCl$_3$) δ 8.74 (s, 1H), 7.28-7.20 (m, 1H), 7.15 (d, 1H), 7.03 (t, 1H), 6.95 (d, 1H), 6.43 (s, 1H), 6.40 (s, 1H), 4.94 (d, 1H), 4.66 (d, 1H), 4.19 (s, 2H), 1.20 (s, 3H), 1.16 (3H); $^{13}$C NMR (75 MHz, CDCl$_3$) δ 180.4, 161.3, 161.0, 140.3, 133.0, 130.1, 128.8, 124.2, 123.4, 120.0, 116.6, 110.1, 93.4, 85.5, 80.6, 58.3, 41.4, 27.7, 27.6; MS (ES+) m/z 308.6 (M+1).

Example 1.22

Synthesis of 4',7'-dichloro-1'-pentylspiro[furo[2,3-f] [1,3]benzodioxole-7,3'-indol]-2'(1'H)-one To a solution of 4,7-dichloro-3-(6-hydroxy-1,3-benzodioxol-5-yl)-3-(hydroxymethyl)-1-pentyl-1,3-dihydro-2H-indol-2-one (0.69 g, 1.57 mmol) in anhydrous tetrahydrofuran (15.0 mL) was added triphenylphosphine (0.54 g, 2.04 mmol) followed by slow addition of diisopropyl azodicarboxylate (0.41 g, 2.04 mmol) at 0° C. The brown reaction mixture was stirred at ambient temperature for 16 h and quenched with ammonium chloride solution (2.00 mL). The organic solvent was removed in vacuo. The residue was dissolved in ethyl acetate (20.0 mL), washed with 10% aqueous HCl solution (10.0 mL), dried over anhydrous sodium sulfate and filtered. The filtrate was concentrated in vacuo to dryness. The residue was subjected to column chromatography eluting with ethyl acetate/hexane (35%) to give a solid, which was crystallized from ethyl acetate/ether to give the title compound (0.13 g, 20%) as a colorless solid: mp 106-108° C.; $^1$H NMR (300 MHz, CDCl$_3$) δ 7.24-7.16 (m, 1H), 6.81 (d, 1H), 6.44 (s, 1H), 6.07 (s, 1H), 5.86 (dd, 2H), 4.87 (dd, 2H), 4.12-4.07 (m, 2H), 1.76-1.66 (m, 2H) 1.36-1.31 (m, 4H), 0.89 (t, 3H); $^{13}$C NMR (75 MHz, CDCl$_3$) δ 177.5, 157.0, 149.2, 142.1, 140.0, 132.3, 131.0, 130.2, 124.6, 116.0, 113.8, 102.3, 101.5, 93.3, 77.2, 58.5, 42.1, 29.5, 28.7, 22.3, 14.0; MS (ES+) m/z 420.4 (M+1).

Example 1.23

Synthesis of 4'-bromospiro[furo[2,3-f][1,3]benzodioxole-7,3'-indol]-2'(1'H)-one

Following the procedure as described in EXAMPLE 1.22, and making non-critical variations using 4-bromo-3-(6-hydroxy-1,3-benzodioxol-5-yl)-3-(hydroxymethyl)-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 71% yield as a colorless solid: $^1$H NMR (300 MHz, DMSO-d$_6$) δ 10.79 (s, 1H), 7.19-7.08 (m, 2H), 6.90 (dd, 1H), 6.58 (s, 1H), 6.25 (s, 1H), 5.90 (d, 2H), 4.74 (ABq, 2H); $^{13}$C NMR (75 MHz, DMSO-d$_6$) δ 178.5, 157.0, 148.8, 144.5, 141.9, 131.2, 130.6, 126.1, 119.2, 117.5, 109.8, 103.3, 101.8, 93.3, 77.6, 59.7; MS (ES−) m/z 360.4 (M−1), 358.4 (M−1).

Example 1.24

Synthesis of 4'-bromo-5,6-dihydrospiro[benzo[1,2-b: 5,4-b']difuran-3,3'-indol]-2'(1'H)-one To a solution of 4-bromo-3-(6-hydroxy-2,3-dihydro-1-benzofuran-5-yl)-3-(hydroxymethyl)-1,3-dihydro-2H-indol-2-one (1.80 g, 4.80 mmol) in anhydrous ethyl acetate (50 mL) was added tributylphosphine (1.26 g, 1.54 mL, 6.24 mmol) at 0° C. under nitrogen. A solution of di-tert-butyl azodicarboxylate (1.44 g, 6.24 mmol) in anhydrous ethyl acetate (15.0 mL) was added over 10 min. The reaction solution was stirred for 2 h, and then quenched with saturated ammonium chloride solution (30.0 mL). After the aqueous layer was separated, the organic layer was washed with 10% aqueous HCl solution (2×25.0 mL), dried over anhydrous sodium sulfate and filtered. The filtrate was concentrated in vacuo to dryness. The residue was subjected to column chromatography eluting with ethyl acetate-hexane (70%) to obtain a solid which was triturated with diethyl ether to give the title compound (0.64 g, 37%) as a colorless solid: $^1$H NMR (300 MHz, DMSO-d$_6$) δ 10.77 (s, 1H), 7.18-7.13 (m, 1H), 7.08 (d, 1H), 6.90 (d, 1H), 6.47 (s, 1H), 6.30 (s, 1H), 4.80 (ABq, 2H), 4.46 (t, 2H), 2.92 (t, 2H); $^{13}$C NMR (75 MHz, DMSO-d$_6$) δ 178.7, 162.2, 161.7, 144.5, 131.1, 131.0, 126.1, 119.8, 119.2, 119.1, 118.3, 109.7, 92.4, 77.6, 72.5, 59.2, 28.8; MS (ES−) m/z 358.4 (M−1), 356.3 (M−1).

Example 1.25

Synthesis of 4'-bromo-1'-(pyridin-2-ylmethyl)-5,6-dihydrospiro[benzo[1,2-b:5,4-b']difuran-3,3'-indol]-2'(1'H)-one A mixture of 4-bromo-3-(6-hydroxy-2,3-dihydro-1-benzofuran-5-yl)-3-(hydroxymethyl)-1-(pyridin-2-ylmethyl)-1, 3-dihydro-2H-indol-2-one (1.81 g, 3.88 mmol), triphenylphosphine (2.04 g, 7.77 mmol) and diisopropyl azodicarboxylate (1.57 g, 7.77 mmol) in anhydrous dioxane (60 mL) was heated at reflux for 16 h. After cooling down to ambient temperature, the solvent was removed in vacuo. The gummy residue was diluted with ethyl acetate (50.0 mL), washed with water (3×25.0 mL), brine (3×25.0 mL), dried over anhydrous sodium sulfate and filtered. The filtrate was concentrated in vacuo to dryness. The residue was subjected to column chromatography eluting with ethyl acetate/hexane (80%) to give the title compound (0.64 g, 37%) as colorless solid: mp >200° C.; $^1$H NMR (300 MHz, DMSO-d$_6$) δ 8.47 (d, 1H), 7.77 (dt, 1H), 7.37 (d, 1H), 7.27 (dt, 1H), 7.19-7.13 (m, 2H), 6.94 (dd, 1H), 6.61 (s, 1H), 6.33 (s, 1H), 5.08 (d, 1H), 5.03 (d, 1H), 4.93 (d, 1H), 4.74 (d, 1H), 4.48 (t, J=8.6 Hz, 2H), 2.96 (t, 2H); $^{13}$C NMR (75 MHz, DMSO-d$_6$) δ 177.4, 162.2, 161.8, 155.3, 149.8, 145.3, 137.6, 131.0, 130.5, 126.8, 123.3, 122.2, 119.9, 119.5, 119.0, 118.1, 109.3, 92.4, 77.5, 72.5, 58.8, 45.3, 28.8; MS (ES+) m/z 451.3 (M+1).

Example 1.26

Synthesis of 5'-fluoro-1'-{[5-(trifluoromethyl)-2-furyl]methyl}spiro[furo[2,3-f][1,3]benzodioxole-7, 3'-indol]-2'(1'H)-one To a solution of 5-fluoro-3-(6-hydroxy-1,3-benzodioxol-5-yl)-3-(hydroxymethyl)-1-{[5-(trifluoromethyl)-2-furyl] methyl}-1,3-dihydro-2H-indol-2-one (3.34 g, 7.18 mmol) in anhydrous tetrahydrofuran (80.0 mL) was added tributylphosphine (2.18 g, 2.70 mL, 10.8 mmol) under nitrogen. A solution of di-tert-butyl azodicarboxylate (2.49 g, 10.8 mmol) in anhydrous tetrahydrofuran (25.0 mL) was added over 10 min. The reaction solution was stirred for 1 h, and quenched with saturated ammonium chloride (30.0 mL). After the solvent was removed under reduced pressure, the gummy material was extracted with ethyl acetate (3×75.0 mL). The organic layer was washed with 10% aqueous HCl solution (2×25.0 mL), saturated aqueous sodium hydrogen carbonate (3×25.0 mL), brine (3×25.0 mL), dried over anhydrous sodium sulfate and filtered. The filtrate was concentrated in vacuo to dryness. The residue was subjected to column chromatography eluting with ethyl acetate/hexane (30%) to afforded the title compound (1.10 g, 34%) as a colorless solid: mp 139-141° C.; $^1$H NMR (300 MHz, CDCl$_3$) δ 7.02-6.96 (m, 1H), 6.93-6.89 (m, 2H), 6.74-6.73 (m, 1H), 6.50 (s, 1H), 6.38 (d, 1H), 6.09 (s, 1H), 5.87 (dd, 2H), 4.95 (ABq, 2H), 4.78 (Abq, 2H); $^{13}$C NMR (75 MHz, CDCl$_3$) δ 176.9, 161.5, 158.3, 155.9, 151.7, 149.2, 142.6, 137.1, 137.1, 133.7, 118.6, 115.6, 115.3, 112.7, 112.4, 112.0, 109.7, 109.6, 109.4, 102.8, 101.7, 93.8, 80.1, 58.6, 37.1; MS (ES+) m/z 448.2 (M+1).

Example 1.27

Synthesis of 1-(diphenylmethyl)-5'-methylspiro[furo [2,3-f][1,3]benzodioxole-7,3'-indol]-2'(1'H)-one To a solution of 1-(diphenylmethyl)-3-(6-hydroxy-1,3-benzodioxol-5-yl)-3-(hydroxymethyl)-5-methyl-1,3-dihydro-2H-indol-2-one (1.31 g, 2.72 mmol) in ethyl acetate (50.0 mL) was added tributylphosphine (0.82 g, 4.07 mmol). A solution of di-tert-butyl azodicarboxylate (0.94 g, 4.07 mmol) in ethyl acetate (45.0 mL) was added to the above reaction mixture over a period of 5 minutes. After stirring for 10 minutes under N$_2$, the reaction was quenched with saturated aqueous ammonium chloride (60.0 mL). The organic layer was separated and washed with 1.0 N hydrochloric acid solution (3×100 mL), dried over sodium sulfate and filtered. The filtrate was concentrated in vacuo to dryness. The residue was subjected to column chromatography eluting with ethyl acetate/hexane (10-50%) to afford the title compound (0.98 g, 78% yield): $^1$H NMR (300 MHz, CDCl$_3$) δ 7.40-7.25 (m, 10H), 7.02, (s, 1H), 6.96 (s, 1H), 6.79 (d, 1H), 6.50 (s, 1H), 6.36 (d, 1H), 6.08 (s, 1H), 5.86 (d, 2H), 4.82 (ABq, 2H), 2.20 (s, 3H).

Example 1.28

Synthesis of 5'-methylspiro[furo[2,3-f][1,3]benzodioxole-7,3'-indol]-2'(1'H)-one A stainless steel hydrogenating vessel was successively charged with (diphenylmethyl)-5'-methylspiro[furo[2,3-f][1,3]benzodioxole-7,3'-indol]-2'(1'H)-one (0.90 g, 1.95 mmol), glacial acetic acid (50.0 mL) and palladium hydroxide (0.10 g, 1.35 mmol, 20 wt % on carbon). The vessel was flushed with nitrogen, sealed then heated to 60° C. and placed under 120 Psi of H$_2$. After 4 days of stirring, the reaction mixture was diluted with ethyl acetate and passed through a bed of celite. The filtrate was washed with water (6×100 mL), dried over sodium sulfate and filtered. The filtrate was concentrated in vacuo to dryness. The residue was subjected to column chromatography eluting with ethyl acetate/hexane (40-50%) to afford the title compound (0.25 g, 43%): mp 269-271° C.; $^1$H NMR (300 MHz, DMSO-d$_6$) δ 10.45 (s, 1H), 7.00 (d, 1H), 6.87 (s, 1H), 6.76 (d, 1H), 6.63 (s, 1H), 6.21 (s, 1H), 5.87 (d, 2H), 4.64 (ABq, 2H), 2.17 (s, 3H); MS (ES+) m/z 296.28 (M+1).

Example 1.29

Synthesis of 5'-methyl-1'-{[5-(trifluoromethyl)-2-furyl]methyl}spiro[furo[2,3-f][1,3]benzodioxole-7, 3'-indol]-2'(1'H)-one To a suspension of sodium hydride (0.03 g, 0.63 mmol, 60% dispersion in mineral oil) in N,N-dimethylformamide (5.00 mL) was slowly added a solution of 5'-methylspiro[furo [2,3-f][1,3]benzodioxole-7,3'-indol]-2'(1'H)-one (0.10 g, 0.33 mmol) in N,N-dimethylformamide (5.00 mL) at 0° C. After stirring for 15 minutes at 0° C., a solution of 2-(bromomethyl)-5-(trifluoromethyl)furan (0.11 g, 0.49 mmol) in N,N-dimethylformamide (40.0 mL) was added. The resulting mixture was stirred at ambient temperature for 4 h and quenched with water (20.0 mL). The mixture was extracted with ethyl acetate (3×25.0 mL). The combined organic layers was washed with water (50.0 mL) and brine (2×25.0 mL), dried over sodium sulfate and filtered. The filtrate was concentrated in vacuo. The residue was subjected to column chromatography eluting with ethyl acetate/hexane (15-50%) to afford the title compound (0.11 g, 77% yield): mp 96-98° C.; $^1$H NMR (300 MHz, CDCl$_3$) δ 7.09 (d, 1H), 7.00 (s, 1H), 6.87 (d, 1H), 6.74 (d, 1H), 6.52 (s, 1H), 6.38 (d, 1H), 6.11 (s, 1H), 5.88 (d, 2H), 4.96 (ABq, 2H), 4.80 (ABq, 2H), 2.29 (s, 3H); MS (ES+) m/z 444.2 (M+1).

Example 1.30

Synthesis of 6-bromo-1'-pentylspiro[1-benzofuran-3, 3'-indol]-2'(1'H)-one

Following the procedure as described in EXAMPLE 1.22, and making non-critical variations using 3-(4-bromo-2-hydroxyphenyl)-3-(hydroxymethyl)-1-pentyl-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 82% yield as a colorless solid: $^1$H NMR (300 MHz, CDCl$_3$) δ 7.33 (td, 1H), 7.15-7.14 (m, 2H), 7.04 (dd, 1H), 6.96-6.90 (m, 2H), 6.56 (d, 1H), 4.95 (d, 1H), 4.69 (d, 1H), 3.89-3.64 (m, 2H), 1.80-1.68 (m, 2H), 1.43-1.34 (m, 4H), 0.92 (t, 3H); $^{13}$C NMR (75 MHz, CDCl$_3$) δ 176.6, 161.6, 142.5, 132.1, 129.1, 128.4, 124.4, 123.9, 123.3, 122.8, 114.1, 108.8, 80.4, 57.6, 40.4, 29.0, 27.1, 22.3, 14.0; MS (ES+) m/z 386.3 (M+1), 388.3 (M+1).

Example 1.31

Synthesis of 5-bromo-1-(diphenylmethyl)spiro[1-benzofuran-3,3'-indol]-2'(1'H)-one Following the procedure as described in Example 1, and making non-critical variations using 3-(5-bromo-2-hydroxyphenyl)-1-(diphenylmethyl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (72%) as a white solid: $^1$H NMR (300 MHz, CDCl$_3$) δ 7.43-7.25 (m, 11H), 7.14-6.93 (m, 4H), 6.83 (d, 1H), 6.71 (d, 1H), 6.52 (d, 1H), 5.0 (d, 1H), 4.73 (d, 1H); MS (ES+) m/z 484.4 (M+1), 482.4 (M+1).

Example 1.32

Synthesis of 2-methyl-1'-pentylspiro[furo[2,3-f][1,3] benzothiazole-7,3'-indol]-2'(1'H)-one Following the procedure as described in EXAMPLE 1.22, and making non-critical variations using 3-(hydroxymethyl)-3-(5-hydroxy-2-methyl-1,3-benzothiazol-6-yl)-1-pentyl-1, 3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained (50%) as a white solid: mp 105-107° C.; $^1$H NMR (300 MHz, CDCl$_3$) δ 7.59 (d, 1H), 7.28 (dt, 1H), 7.02-6.92

(m, 2H), 5.02 (d, 1H), 4.77 (d, 1H), 4.01 (m, 1H), 3.64 (m, 1H), 2.54 (s, 3H), 1.92-1.71 (m, 2H), 1.54-1.34 (m, 4H), 0.92 (t, 3H); $^{13}$C NMR (75 MHz, CDCl$_3$) δ 176.7, 169.2, 160.2, 149.2, 142.7, 138.3, 132.7, 129.0, 128.6, 123.5, 122.7, 122.1, 120.2, 108.6, 108.3, 80.1, 58.1, 40.7, 29.1, 27.0, 22.5, 20.2, 14.1; MS (ES+) m/z 379.5 (M+1).

Example 1.33

Synthesis of 5-bromo-1'-{[5-(trifluoromethyl)-2-furyl]methyl}spiro[1-benzofuran-3,3'-indol]-2'(1'H)-one Following the procedure as described in EXAMPLE 1.22, and making non-critical variations using 3-(hydroxymethyl)-3-(5-hydroxy-2-methyl-1,3-benzothiazol-6-yl)-1-pentyl-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained (30%) as a white solid: mp 143-145° C.; $^1$H NMR (300 MHz, CDCl$_3$) δ 7.35-7.27 (m, 2H), 7.17-6.98 (m, 3H), 6.84 (d, 1H), 6.78-6.73 (m, 2H), 6.40 (d, 1H), 5.07-4.87 (m, 3H), 4.69 (d, 1H); MS (ES+) m/z 464.2 (M+1), 466.2 (M+1).

Example 1.34

Synthesis of 5-bromospiro[1-benzofuran-3,3'-indol]-2'(1'H)-one

Following the procedure as described in EXAMPLE 1, and making non-critical variations using 3-(5-bromo-2-hydroxyphenyl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (25%) as a white solid: mp 225-228° C.; $^1$H NMR (300 MHz, CDCl$_3$) δ 10.65 (s, 1H), 7.35 (dd, 1H), 7.24 (dt, 1H), 7.11 (d, 1H), 6.99-6.88 (m, 3H), 6.83 (d, 1H), 4.81 (d, 1H), 4.69 (d, 1H); MS (ES+) m/z 316.1 (M+1), 318.1 (M+1).

Example 1.35

Synthesis of 1'-(diphenylmethyl)-6-(trifluoromethoxy)spiro[1-benzofuran-3,3'-indol]-2'(1'H)-one To a solution of 1-(diphenylmethyl)-3-(hydroxymethyl)-3-[2-hydroxy-4-(trifluoromethoxy)phenyl]-1,3-dihydro-2H-indol-2-one (17.3 mmol) in anhydrous THF (200 mL) was added triphenylphosphine (6.34 g, 24.2 mmol) followed by diethyl azodicarboxylate (4.39 mL, 24.2 mmol) at 0° C. The reaction mixture was stirred at ambient temperature for 16 h, quenched with saturated ammonium chloride (40.0 mL). The aqueous mixture was extracted with ethyl acetate (3×150 mL). The combined organic layers was dried over anhydrous sodium sulfate and filtered. The filtrate was concentrated in vacuo. The residue was subjected to column chromatography (ethyl acetate/hexane, 1/4) to give the title compound (6.00 g, 71%): $^1$H NMR (300 MHz, CDCl$_3$) δ 7.45-6.51 (m, 18H), 5.08 (d, 1H), 4.81 (d, 1H); MS (ES+) m/z 488 (M+1).

Example 1.36

Synthesis of 6-(trifluoromethoxy)spiro[1-benzofuran-3,3'-indol]-2'(1'H)one

To a suspension of 1-(diphenylmethyl)-6-(trifluoromethoxy)spiro[1-benzofuran-3,3'-indol]-2'(1'H)-one (6.00 g, 12.3 mmol) in methanol (100 mL) and acetic acid (1.00 mL) was added 10% palladium on carbon (0.65 g, 0.62 mmol), and the mixture was hydrogenated at ambient temperature under 130 psi of hydrogen for 5 days. The reaction mixture was filtered over celite and the filtrate was concentrated in vacuo to dryness. The residue was subjected to flash chromatography eluting with 30% ethyl acetate in hexane to give the title compound (2.95 g, 75%) as a white solid: mp 180-182° C.; $^1$H NMR (300 MHz, CDCl$_3$) δ 9.19 (s, 1H), 7.29-6.92 (m., 4H), 6.86-6.64 (m, 3H), 5.03 (d, 1H), 4.75 (d, 1H); $^{13}$C NMR (75 MHz, CDCl$_3$) δ 179.9, 161.9, 150.6, 132.3, 129.4, 127.4, 125.6, 124.3, 124.2, 123.8, 120.5, 114.1, 110.7, 104.3, 80.8, 58.2; MS (ES+) m/z 322 (M+1).

Example 1.37

Synthesis of ethyl (4'-bromo-2'-oxo-5,6-dihydrospiro[benzo[1,2-b:5,4-b']difuran-3,3'-indol]-1'(2'H)-yl)acetate Following the procedure as described in EXAMPLE 1.22, and making non-critical variations using ethyl [4-bromo-3-(6-hydroxy-2,3-dihydro-1-benzofuran-5-yl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained (41%) as a colorless solid: MS (ES+) m/z 445.5 (M+1).

Example 1.38

Synthesis of ethyl (4'-chloro-2'-oxo-5,6-dihydrospiro[benzo[1,2-b:5,4-b']difuran-3,3'-indol]-1'(2'H)-yl)acetate Following the procedure as described in EXAMPLE 1.22, and making non-critical variations using ethyl [4-chloro-3-(6-hydroxy-2,3-dihydro-1-benzofuran-5-yl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 63% yield as a colorless solid: MS (ES+) m/z 400.8 (M+1).

Example 1.39

Synthesis of ethyl (4'-bromo-6,6-dimethyl-2'-oxo-5,6-dihydrospiro[benzo[1,2-b:5,4-b']difuran-3,3'-indol]-1'(2'H)-yl)acetate Following the procedure as described in EXAMPLE 1, and making non-critical variations using ethyl [4-bromo-3-(6-hydroxy-2,2-dimethyl-2,3-dihydro-1-benzofuran-5-yl)-3-(hydroxymethyl)-2-oxo-2,3-dihydro-1H-indol-1-yl]acetate to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 52% yield: $^1$H NMR (300 MHz, CDCl$_3$) δ 7.22-7.10 (m, 2H), 6.70 (d, 1H), 6.48 (s, 1H), 6.30 (s, 1H), 5.0 (d, 1H); 4.86 (d, 1H), 4.63 (d, 1H), 4.35 (d, 1H), 4.28-4.18 (m, 2H), 2.79 (s, 2H), 1.43 (s, 3H), 1.39 (s, 3H), 1.28 (t, 3H); MS (ES+) m/z 472.5 (M+1), 474.5 (M+1).

Example 1.40

Synthesis of ethyl (4'-bromo-5,6-difluoro-2'-oxospiro[1-benzofuran-3,3'-indol]-1'(2'H)-yl)acetate Following the procedure as described in EXAMPLE 1, and making non-critical variations using ethyl [4-bromo-3-(4,5- difluoro-2-hydroxyphenyl)-3-(hydroxymethyl)-2-oxo-2,3-dihydro-1H-indol-1-yl]acetate to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 81% yield: MS (ES+) m/z 438.4 (M+1), 440.4 (M+1).

Example 1.41

Synthesis of ethyl (5'-chloro-2'-oxo-5,6-dihydrospiro[benzo[1,2-b:5,4-b']difuran-3,3'-indol]-1'(2'H)-yl)acetate Following the procedure as described in EXAMPLE 1.22, and making non-critical variations using ethyl [5-chloro-3-(6-hydroxy-2,3-dihydro-1-benzofuran-5-yl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 90% yield as a colorless solid: MS (ES+) m/z 400.8 (M+1).

Example 1.42

Synthesis of 7'-fluorospiro[furo[2,3-f][1,3]benzodioxole-7,3'-indol]-2'(1'H)-one A solution of 7-fluoro-3-(6-hydroxy-1,3-benzodioxol-5-yl)-1,3-dihydro-2H-indol-2-one (2.00 g, 7.00 mmol) and paraformaldehyde (2.10 g, 61.0 mmol) in THF (50 mL) was degassed by bubbling through argon for one hour, followed by the slow addition of lithium diisopropylamide (48.8 mL, freshly made 0.50 M solution, 25 mmol) at −78° C. The mixture was stirred at ambient temperature overnight and quenched with saturated ammonium chloride (50.0 mL). The mixture was extracted with ethyl acetate (3×100 mL). The combined organic layers was dried over anhydrous sodium sulfate and filtered. The filtrate was concentrated in vacuo to dryness. The residue was dissolved in anhydrous ethyl acetate (50 mL) followed by the addition of tributylphosphine (2.10 mL, 8.00 mmol) and di-tert-butyl azodicarboxylate (1.90 g, 8.00 mmol) at 0° C. The reaction mixture was stirred at ambient temperature for 16 h and quenched with saturated ammonium chloride (30.0 mL). The organic layer was separated, dried over anhydrous sodium sulfate and filtered. The filtrate was concentrated in vacuo to dryness. The residue was dissolved in methanol (70.0 mL) followed by the addition of saturated sodium bicarbonate solution (30.0 mL). The resulted mixture was refluxed at 100° C. for one hour. After cooling down to ambient temperature, the mixture was extracted with ethyl acetate (3×50.0 mL). The combined organic layers was dried over anhydrous sodium sulfate and filtered. The filtrate was concentrated in vacuo to dryness. The residue was subjected to column chromatography (ethyl acetate/hexane, 1/5) to give the title compound (0.27 g, 17%): $^1$H NMR (300 MHz, DMSO-$d_6$) δ 11.06 (s, 1H), 7.17-7.08 (m, 1H), 7.00-6.88 (m, 2H), 6.64 (s, 1H), 6.33 (s, 1H), 5.92-5.85 (m, 2H), 4.74 (d, 1H), 4.62 (d, 1H).

Example 1.43

Synthesis of methyl (6-chloro-2'-oxospiro[1-benzofuran-3,3'-indol]-1'(2'H)-yl)acetate Following the procedure as described in EXAMPLE 1.22, and making non-critical variations using methyl [3-(4-chloro-2-hydroxyphenyl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 74% yield as a colorless solid: $^1$H NMR (300 MHz, CDCl$_3$) δ 7.29 (dt, 1H), 7.14 (dd, 1H), 7.06 (t, 1H), 6.95 (d, 1H), 6.81-6.74 (m, 3H), 5.03 (d, 1H), 4.74 (d, 1H), 4.65 (d, 1H), 4.44 (d, 1H), 3.75 (s, 3H); MS (ES+) m/z 344.5 (M+1), 346.5 (M+1).

Example 1.44

Synthesis of ethyl (5,6-difluoro-2'-oxospiro[1-benzofuran-3,3'-indol]-1'(2'H)-yl)acetate Following the procedure as described in EXAMPLE 1.22, and making non-critical variations using ethyl [3-(4,5-difluoro-2-hydroxyphenyl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 46% yield as a light yellow oil: $^1$H NMR (300 MHz, CDCl$_3$) δ 7.31 (dt, 1H), 7.16 (dd, 1H), 7.08 (dt, 1H), 6.81-6.71 (m, 2H), 6.67 (dd, 1H), 4.98 (d, 1H), 4.74 (d, 1H), 4.64 (d, 1H), 4.37 (d, 4.24 (q, 7.1 Hz), 1.28 (t, 3H); MS (ES+) m/z 360.5 (M+1).

Example 1.45

Synthesis of ethyl (2'-oxo-6,7-dihydro-5H-spiro[indeno[5,6-b']furan-3,3'-indol]-1'(2'H)-yl)acetate To a solution of ethyl [3-(6-hydroxy-2,3-dihydro-1H-inden-5-yl)-3-(hydroxymethyl)-2-oxo-2,3-dihydro-1H-indol-1-yl]acetate (4.20 mmol) in anhydrous THF (60.0 mL) was added triphenylphosphine (1.43 g, 5.46 mmol) and diethyl azodicarboxylate (0.95 g, 5.46 mmol) at 0° C. The reaction mixture was stirred at ambient temperature for 16 h and quenched with saturated ammonium chloride (20.0 mL). The mixture was extracted with ethyl acetate (3×50.0 mL). The combined organic layers was dried over anhydrous sodium sulfate and filtered. The filtrate was concentrated in vacuo to dryness. The residue was subjected to column chromatography (ethyl acetate/hexane, 1/4) to give the title compound (0.25 g, 16% in three steps): $^1$H NMR (300 MHz, CDCl$_3$) δ 7.29 (td, 1H), 7.22-7.17 (m, 1H), 7.07 (t, 1H), 6.81 (s, 1H), 6.78 (d, 1H), 6.65 (s, 1H), 4.95 (d, 1H), 4.71 (d, 1H), 4.64 (d, 1H), 4.42 (d, 1H), 4.24 (q, 2H), 2.84 (t, 2H), 2.73-2.65 (m, 2H), 2.10-1.95 (m, 2H), 1.29 (t, 3H); MS (ES+) m/z 364 (M+1).

Example 1.46

Synthesis of ethyl (2-oxo-5',6',7',8'-tetrahydrospiro[indole-3,3'-naphtho[2,3-b']furan]-1(2H)-yl)acetate Following the procedure as described in EXAMPLE 1.45, and making non-critical variations using ethyl [3-(hydroxymethyl)-3-(3-hydroxy-5,6,7,8-tetrahydronaphthalen-2-yl)-2-oxo-2,3-dihydro-1H-indol-1-yl]acetate to replace ethyl [3-(6-hydroxy-2,3-dihydro-1H-inden-5-yl)-3-(hydroxymethyl)-2-oxo-2,3-dihydro-1H-indol-1-yl]acetate, the title compound was obtained (24% in three steps): $^1$H NMR (300 MHz, CDCl$_3$) δ 7.29 (td, 1H), 7.19 (d, 1H), 7.07 (t, 1H), 6.79 (d, 1H), 6.66 (s, 1H), 6.51 (s, 1H),), 4.91 (d, 1H), 4.67 (d, 1H), 4.52 (ABq, 2H), 4.24 (q, 2H), 2.77-2.51 (m, 4H), 1.77-1.64 (m, 4H), 1.29 (t, 3H); MS (ES+) m/z 378 (M+1).

Example 1.47

Synthesis of ethyl (4'-bromo-5,6-difluoro-2'-oxospiro[1-benzofuran-3,3'-indol]-1'(2'H)-yl)acetate Following the procedure as described in EXAMPLE 1.45, and making non-critical variations using ethyl [4-bromo-3-(4,5-difluoro-2-hydroxyphenyl)-3-(hydroxymethyl)-2-oxo-2,3-dihydro-1H-indol-1-yl]acetate to replace ethyl [3-(6-hydroxy-2,3-dihydro-1H-inden-5-yl)-3-(hydroxymethyl)-2-oxo-2,3-dihydro-1H-indol-1-yl]acetate, the title compound was obtained (41%): mp 133-134° C.; $^1$H NMR (300 MHz, CDCl$_3$) δ 7.26-7.15 (m, 3H), 6.78-6.58 (m, 2H), 5.08 (d, 1H), 4.91 (d, 1H), 4.63 (d, 1H), 4.35 (d, 1H), 4.24 (q, 2H), 1.29 (t, 3H); $^{13}$C NMR (75 MHz, CDCl$_3$) δ 176.5, 166.8, 157.1, 143.7, 130.7, 129.0, 127.8, 120.0, 111.8, 111.6, 107.5, 99.8, 99.5, 62.2, 59.1, 41.7, 14.1; MS (ES+) m/z 438 (M+1), 440 (M+1), 460 (M+23), 462 (M+23).

Example 1.48

Synthesis of 1-(diphenylmethyl)-6,7-dihydrospiro [benzo[1,2-b:4,5-b']difuran-3,3'-indol]-2'(1'H)-one Following the procedure described in EXAMPLE 1, and making non-critical variations using 1-(diphenylmethyl)-3-(5-hydroxy-2,3-dihydro-1-benzofuran-6-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (43%): MS (ES+) m/z 446.4 (M+1).

Example 1.49

Synthesis of 6,7-dihydrospiro[benzo[1,2-b:4,5-b']difuran-3,3'-indol]-2'(1'H)-one A mixture of 1-(diphenylmethyl)-6,7-dihydrospiro[benzo[1,2-b:4,5-b']difuran-3,3'-indol]-2'(1'H)-one (0.29 g, 0.65 mmol) and palladium hydroxide (0.10 g, 20% on activated carbon) in acetic acid (20.0 mL) was hydrogenated at 60° C. under normal pressure of hydrogen for 20 hours. The reaction mixture was filtered through celite and washed with acetone (50.0 mL). The filtrate was concentrated in vacuo to dryness to give the title compound (0.13 g, 69%): MS (ES+) m/z 280.2 (M+1).

Example 1.50

Synthesis of 1'-(diphenylmethyl)-5,6-dihydrospiro [benzo[1,2-b:5,4-b']difuran-3,3'-indol]-2'(1'H)-one Following the procedure described in EXAMPLE 1, and making non-critical variations using 1-(diphenylmethyl)-3-(6-hydroxy-2,3-dihydro-1-benzofuran-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (51%) as a white solid: MS (ES+) m/z 446.3 (M+1).

Example 1.51

Synthesis of 5,6-dihydrospiro[benzo[1,2-b:5,4-b']difuran-3,3'-indol]-2'(1'H)-one Following the procedure as described in EXAMPLE 1.49, and making non-critical variations using 1'-(diphenylmethyl)-5,6-dihydrospiro[benzo[1,2-b:5,4-b']difuran-3,3'-indol]-2'(1'H)-one to replace 1'-(diphenylmethyl)-6,7-dihydrospiro[benzo[1,2-b:4,5-b']difuran-3,3'-indol]-2'(1'H)-one, the title compound was obtained (68%): mp 208-210° C.; $^1$H NMR (300 MHz, DMSO-d$_6$) δ 10.53 (s, 1H), 7.39-6.76 (m, 4H), 6.45 (s, 1H), 6.35 (s, 1H), 4.68 (ABq, 2H), 4.45 (t, 2H), 2.92 (t, 2H); MS (ES+) m/z 280.2 (M+1).

Example 1.52

Synthesis of ethyl (2'-oxo-5,6-dihydrospiro[benzo[1,2-b:5,4-b']difuran-3,3'-indol]-1'(2'H)-yl)acetate A mixture of 5,6-dihydrospiro[benzo[1,2-b:5,4-b']difuran-3,3'-indol]2'(1'H)-one (0.28 g, 1.00 mmol), ethyl 2-bromoacetate (0.17 g, 1.00 mmol) and cesium carbonate (0.98 g, 3.00 mmol) in acetone (20.0 mL) was stirred at reflux for 5 hours. After cooling down to ambient temperature, the mixture was filtered. The filtrate was evaporated under reduced pressure and the residue was subjected to column chromatography to give the title compound (0.23 g, 63%) as a white solid: MS (ES+) m/z 366.4 (M+1).

Example 1.53

Synthesis of 4'-methoxy-1'{[5-(trifluoromethyl)-2-furyl]methyl}spiro[furo[2,3-f][1,3]benzodioxole-7,3'-indol]-2'(1'H)-one Following the procedure described in EXAMPLE 1, and making non-critical variations using 3-(6-hydroxy-1,3-benzodioxol-5-yl)-3-(hydroxymethyl)-4-methoxy-1-{[5-(trifluoromethyl)-2-furyl]methyl}-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (33%) as a white solid: mp 149-153° C.; $^1$H NMR (300 MHz, DMSO-d$_6$) δ 7.32-7.24 (m, 1H), 6.82-6.62 (m, 3H), 6.46 (s, 1H), 6.40 (d, 1H), 6.08 (s, 1H), 5.87 (ABq, 2H), 4.92 (ABq, 2H), 4.82 (ABq, 2H), 3.70 (s, 3H); MS (ES+) m/z 460.3 (M+1).

Example 1.54

Synthesis of 7'-fluoro-1-{[5-(trifluoromethyl)-2-furyl]methyl}spiro[furo[2,3-f][1,3]benzodioxole-7,3'-indol]-2'(1'H)-one Following the procedure described in EXAMPLE 1, and making non-critical variations using 7-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (32%) as a white solid: mp 116-118° C.; $^1$H NMR (300 MHz, DMSO-d$_6$) δ 7.36-6.88 (m, 4H), 6.67 (s, 1H), 6.62 (d, 1H), 6.19 (s, 1H), 5.90 (d, 2H), 5.07 (q, 2H), 4.75 (dd, 2H); $^{13}$C NMR (75 MHz, DMSO-d$_6$) δ176.9, 155.8, 154.1, 149.1, 148.8, 145.6, 142.4, 140.9, 140.3, 139.2, 139.2, 135.2, 135.2, 128.5, 128.4, 124.9, 128.4, 124.9, 124.8, 124.7, 121.2, 120.4, 120.4, 119.8, 117.6, 117.2, 117.0, 114.5, 114.5, 109.5, 103.2, 102.0, 93.8, 80.1, 58.3, 58.2, 39.0, 38.9; MS (ES+) m/z 448.3 (M+1).

Example 2

Synthesis of (2'-oxospiro[furo[2,3-f][1,3]benzodioxole-7,3'-indol]-1'(2'H)-yl)acetic acid To a suspension of ethyl (2'-oxospiro[furo[2,3-f][1,3]benzodioxole-7,3'-indol]-1'(2'H)-yl)acetate (10.5 g, 24.5 mmol)

in THF (200 mL) and water (100 mL) was added lithium hydroxide monohydrate (3.98 g, 95.0 mmol) at 0° C. The reaction mixture was stirred at 0° C. for 30 min and at ambient temperature for 17 h. The mixture was neutralized with of 4 M HCl (15.0 mL). The residue obtained upon removing the solvent was acidified by the addition of 4 M HCl (6.2 mL) to pH 3. The solid was filtered, washed with water and hexane, and dried under the reduced pressure to give the title compound (8.48 g, 87%) as a white solid: $^1$H NMR (300 MHz, CDCl$_3$) δ 7.32-7.06 (m, 4H), 6.79 (d, 1H), 6.49 (s, 1H), 6.23 (s, 1H), 5.84 (m, 2H), 4.92 (m, 1H), 4.69-4.63 (m, 2H), 4.45 (m, 1H); $^{13}$C NMR (75 MHz, CDCl$_3$) δ 177.8, 171.8, 155.8, 149.0, 142.4, 141.2, 132.0, 129.0, 124.1, 124.0, 119.2, 108.3, 103.4, 101.5, 93.5, 80.2, 58.2, 41.1; MS (ES−) m/z 338.2 (M−1).

Example 2.1

Synthesis of (2'-oxo-6,7-dihydro-5H-spiro[indeno[5,6-b']furan-3,3'-indol]-1'(2'H)-yl)acetic acid Following the procedure as described in EXAMPLE 2, and making non-critical variations using ethyl (2'-oxo-6,7-dihydro-5H-spiro[indeno[5,6-b']furan-3,3'-indol]-1'(2'H)-yl)acetate to replace ethyl (2'-oxospiro[furo[2,3-f][1,3]benzodioxole-7,3'-indol]-1'(2'H)-yl)acetate, the title compound was obtained in 74% yield; MS (ES−) m/z 354 (M−1).

Example 2.2

Synthesis of (4'-chloro-2'-oxo-5,6-dihydrospiro [benzo[1,2-b:5,4-b']difuran-3,3'-indol]-1'(2'H)-yl) acetic acid Following the procedure as described in EXAMPLE 2, and making non-critical variations using ethyl (4'-chloro-2'-oxo-5,6-dihydrospiro[benzo[1,2-b:5,4-b']difuran-3,3'-indol]-1' (2'H)-yl)acetate to replace ethyl (2'-oxospiro[furo[2,3-f][1,3] benzodioxole-7,3'-indol]-1'(2'H)-yl)acetate, the title compound was obtained in 92% yield as a colorless solid: mp 228-229° C.; $^1$H NMR (300 MHz, CDCl$_3$) δ 7.26-7.21 (m, 1H), 7.03 (dd, 1H), 6.71 (dd, 1H), 6.52 (s, 1H), 6.36 (s, 1H), 4.93 (dd, 2H), 4.69-4.63 (m, 1H), 4.54-4.51 (m, 3H), 2.95 (t, 2H); $^{13}$C NMR (75 MHz, CDCl$_3$) δ 177.8, 170.9, 162.1, 162.1, 143.1, 131.7, 130.0, 128.6, 124.7, 119.6, 118.7, 117.0, 106.7, 92.8, 77.2, 72.3, 58.1, 41.2, 28.9; MS (ES−) m/z 370.4 (M−1).

Example 2.3

Synthesis of (4'-bromo-2'-oxo-5,6-dihydrospiro [benzo[1,2-b:5,4-b']difuran-3,3'-indol]-1'(2'H)-yl) acetic acid Following the procedure as described in EXAMPLE 2, and making non-critical variations using ethyl (4'-bromo-2'-oxo-5,6-dihydrospiro[benzo[1,2-b:5,4-b']difuran-3,3'-indol]-1' (2'H)-yl)acetate to replace ethyl (2'-oxospiro[furo[2,3-f][1,3] benzodioxole-7,3'-indol]-1'(2'H)-yl)acetate, the title compound was obtained (98%) as a colorless solid: MS (ES−) m/z 415.2 (M−1).

Example 2.4

Synthesis of (5'-chloro-2'-oxo-5,6-dihydrospiro [benzo[1,2-b:5,4-b']difuran-3,3'-indol]-1'(2'H)-yl) acetic acid Following the procedure as described in EXAMPLE 2, and making non-critical variations using ethyl (5'-chloro-2'-oxo-5,6-dihydrospiro[benzo[1,2-b:5,4-b']difuran-3,3'-indol]-1' (2'H)-yl)acetate to replace ethyl (2'-oxospiro[furo[2,3-f][1,3] benzodioxole-7,3'-indol]-1'(2'H)-yl)acetate, the title compound was obtained in 98% yield as a colorless solid: $^1$H NMR (300 MHz, CDCl$_3$) δ 7.27-7.25 (m, 1H), 7.16 (d, 1H), 6.72 (d, 1H), 6.54 (s, 1H), 6.39 (s, 1H), 4.93 (dd, 2H), 4.69-4.63 (m, 1H), 4.54-4.51 (m, 3H), 2.95 (t, 2H); $^{13}$C NMR (75 MHz, CDCl$_3$) δ 177.8, 170.9, 162.1, 162.1, 143.1, 131.7, 130.0, 128.6, 124.7, 119.6, 118.7, 117.0, 106.7, 92.8, 77.2, 72.3, 58.1, 41.2, 28.9; MS (ES−) m/z 370.4 (M−1).

Example 2.5

Synthesis of (2-oxo-5',6',7',8'-tetrahydrospiro[indole-3,3'-naphtho[2,3-b']furan]-1(2H)-yl)acetic acid Following the procedure as described in Example 2, and making non-critical variations using ethyl (2-oxo-5',6',7',8'-tetrahydrospiro[indole-3,3'-naphtho[2,3-b']furan]-1(2H)-yl) acetate to replace ethyl (2'-oxospiro[furo[2,3-f][1,3]benzodioxole-7,3'-indol]-1'(2'H)-yl)acetate, the title compound was obtained (99%): MS (ES−) m/z 348 (M−1).

Example 2.6

Synthesis of (2'-oxo-5,6-dihydrospiro[benzo[1,2-b:5,4-b']difuran-3,3'-indol]-1'(2'H)-yl)acetic acid A mixture of ethyl (2'-oxo-5,6-dihydrospiro[benzo[1,2-b:5,4-b']difuran-3,3'-indol]-1'(2'H)-yl)acetate (0.23 g, 0.63 mmol) and LiOH (0.10 g, 4.20 mmol) in MeOH/H$_2$O (1/1, 20.0 mL) was stirred at ambient temperature for 20 hours. The mixture was acidified with 0.1 M HCl until pH 2-3. The solid was filtered off and dried to give the title compound (0.15 g, 70%): MS (ES−) m/z 336.3 (M−1).

Example 3

Synthesis of N-(4-chlorobenzyl)-2-(2'-oxospiro[furo [2,3-f][1,3]benzodioxole-7,3'-indol]-1'(2'H)-yl)acetamide A. Preparation of stock solution of isobutyl (2'-oxospiro[furo[2,3-f][1,3]benzodioxole-7,3'-indol]-1' (2'H)-yl)acetyl carbonate To a solution of (2'-oxospiro[furo[2,3-f][1,3]benzodioxole-7,3'-indol]-1'(2'H)-yl)acetic acid (0.30 g, 0.88 mmol) in dichloromethane (12.5 mL) was added N-methylmorpholine (0.09 g, 0.88 mmol) and iso-butyl chloroformate (0.12 g, 0.88 mmol) dropwise at 0° C. The mixture was stirred at 0° C. for 1.5 h and at ambient temperature for 3 h. This mixture was used as a mixed anhydride for the next step amide formation.

B. Synthesis of N-(4-chlorobenzyl)-2-(2'-oxospiro [furo[2,3-f][1,3]benzodioxole-7,3'-indol]-1'(2'H)-yl) acetamide To the above mixed anhydride stock solution (2.50 mL, 0.18 mmol) was added a solution of 4-chlorobenzylamine in dichloromethane (0.35 mL, 0.50 M, 0.18 mmol) at ambient temperature. The reaction mixture was stirred at ambient temperature for 23 h, washed with saturated aqueous sodium carbonate and water. After removal of the solvent, diethyl ether was added and the precipitate was collected by filtration to give the title compound (0.04 g, 46%): $^1$H NMR (300 MHz, CDCl$_3$) δ 7.39-6.97 (m, 8H), 6.49 (s, 1H), 6.29 (br, 1H), 6.01 (s, 1H), 5.85 (m, 2H), 4.87 (m, 1H), 4.65 (m, 1H), 4.53-4.29 (m, 4H); MS (ES+), m/z 485.2 (M+23).

Example 3.1

The compounds listed in the following table were synthesized using similar conditions as described in Example 3. The compound numbers listed below do not correspond to the compound numbers provided in the general Reaction Schemes above.

| Compound Number | Name | MS (m/z, M + 1) |
|---|---|---|
| 1 | N-(3-fluorophenyl)-2-(2'-oxospiro[furo[2,3-f][1,3]benzodioxole-7,3'-indol]-1'(2'H)-yl)acetamide | 433.2 |
| 2 | N-butyl-2-(2'-oxospiro[furo[2,3-f][1,3]benzodioxole-7,3'-indol]-1'(2'H)-yl)acetamide | 395.2 |
| 3 | 1'-(2-oxo-2-piperidin-1-ylethyl)spiro[furo[2,3-f][1,3]benzodioxole-7,3'-indol]-2'(1'H)-one | 407.2 |
| 4 | N-butyl-N-methyl-2-(2'-oxospiro[furo[2,3-f][1,3]benzodioxole-7,3'-indol]-1'(2'H)-yl)acetamide | 409.3 |
| 5 | 2-(2'-oxospiro[furo[2,3-f][1,3]benzodioxole-7,3'-indol]-1'(2'H)-yl)-N-phenylacetamide | 415.2 |
| 6 | N-(4-fluorophenyl)-2-(2'-oxospiro[furo[2,3-f][1,3]benzodioxole-7,3'-indol]-1'(2'H)-yl)acetamide | 433.3 |
| 7 | N-(3-fluorobenzyl)-2-(2'-oxospiro[furo[2,3-f][1,3]benzodioxole-7,3'-indol]-1'(2'H)-yl)acetamide | 447.3 |
| 8 | N-(3-chlorophenyl)-2-(2'-oxospiro[furo[2,3-f][1,3]benzodioxole-7,3'-indol]-1'(2'H)-yl)acetamide | 449.2 |
| 9 | N-(2-fluorophenyl)-2-(2'-oxospiro[furo[2,3-f][1,3]benzodioxole-7,3'-indol]-1'(2'H)-yl)acetamide | 433.3 |
| 10 | N-(2-ethylphenyl)-2-(2'-oxospiro[furo[2,3-f][1,3]benzodioxole-7,3'-indol]-1'(2'H)-yl)acetamide | 443.2 |
| 11 | N-(4-ethylphenyl)-2-(2'-oxospiro[furo[2,3-f][1,3]benzodioxole-7,3'-indol]-1'(2'H)-yl)acetamide | 443.3 |
| 12 | N-(3-methylphenyl)-2-(2'-oxospiro[furo[2,3-f][1,3]benzodioxole-7,3'-indol]-1'(2'H)-yl)acetamide | 429.3 |
| 13 | N-(2,3-dimethylphenyl)-2-(2'-oxospiro[furo[2,3-f][1,3]benzodioxole-7,3'-indol]-1'(2'H)-yl)acetamide | 443.3 |
| 14 | N-(3,5-dimethylphenyl)-2-(2'-oxospiro[furo[2,3-f][1,3]benzodioxole-7,3'-indol]-1'(2'H)-yl)acetamide | 443.4 |
| 15 | 2-(2'-oxospiro[furo[2,3-f][1,3]benzodioxole-7,3'-indol]-1'(2'H)-yl)-N-pentylacetamide | 409.4 |
| 16 | 2-(2'-oxospiro[furo[2,3-f][1,3]benzodioxole-7,3'-indol]-1'(2'H)-yl)-N-propylacetamide | 381.3 |
| 17 | N-isopropyl-2-(2'-oxospiro[furo[2,3-f][1,3]benzodioxole-7,3'-indol]-1'(2'H)-yl)acetamide | 381.4 |
| 18 | N-(3-methylbutyl)-2-(2'-oxospiro[furo[2,3-f][1,3]benzodioxole-7,3'-indol]-1'(2'H)-yl)acetamide | 409.3 |
| 19 | N-isobutyl-2-(2'-oxospiro[furo[2,3-f][1,3]benzodioxole-7,3'-indol]-1'(2'H)-yl)acetamide | 395.3 |
| 20 | N-hexyl-2-(2'-oxospiro[furo[2,3-f][1,3]benzodioxole-7,3'-indol]-1'(2'H)-yl)acetamide | 423.4 |
| 21 | N-cyclohexyl-2-(2'-oxospiro[furo[2,3-f][1,3]benzodioxole-7,3'-indol]-1'(2'H)-yl)acetamide | 421.4 |
| 22 | N-cyclopentyl-2-(2'-oxospiro[furo[2,3-f][1,3]benzodioxole-7,3'-indol]-1'(2'H)-yl)acetamide | 407.3 |
| 23 | N-heptyl-2-(2'-oxospiro[furo[2,3-f][1,3]benzodioxole-7,3'-indol]-1'(2'H)-yl)acetamide | 437.5 |
| 24 | N-(2-chlorobenzyl)-2-(2'-oxospiro[furo[2,3-f][1,3]benzodioxole-7,3'-indol]-1'(2'H)-yl)acetamide | 463.2 |
| 25 | N-(2,6-dimethylphenyl)-2-(2'-oxospiro[furo[2,3-f][1,3]benzodioxole-7,3'-indol]-1'(2'H)-yl)acetamide | 443.3 |
| 26 | N-(2-methoxyphenyl)-2-(2'-oxospiro[furo[2,3-f][1,3]benzodioxole-7,3'-indol]-1'(2'H)-yl)acetamide | 445.3 |
| 27 | N-[(5-methyl-2-furyl)methyl]-2-(2'-oxospiro[furo[2,3-f][1,3]benzodioxole-7,3'-indol]-1'(2'H)-yl)acetamide | 433.2 |
| 28 | N-ethyl-2-(2'-oxospiro[furo[2,3-f][1,3]benzodioxole-7,3'-indol]-1'(2'H)-yl)acetamide | 367.4 |
| 29 | N-methyl-2-(2'-oxospiro[furo[2,3-f][1,3]benzodioxole-7,3'-indol]-1'(2'H)-yl)acetamide | 353.3 |
| 30 | N-(2-fluorobenzyl)-2-(2'-oxospiro[furo[2,3-f][1,3]benzodioxole-7,3'-indol]-1'(2'H)-yl)acetamide | 447.2 |
| 31 | N-[2-(3-methoxyphenyl)ethyl]-2-(2'-oxospiro[furo[2,3-f][1,3]benzodioxole-7,3'-indol]-1'(2'H)-yl)acetamide | 473.3 |
| 32 | N-(2-ethoxyethyl)-2-(2'-oxospiro[furo[2,3-f][1,3]benzodioxole-7,3'-indol]-1'(2'H)-yl)acetamide | 411.3 |
| 33 | N-(4-methoxybenzyl)-2-(2'-oxospiro[furo[2,3-f][1,3]benzodioxole-7,3'-indol]-1'(2'H)-yl)acetamide | 459.3 |
| 34 | N-(2,4-dimethylphenyl)-2-(2'-oxospiro[furo[2,3-f][1,3]benzodioxole-7,3'-indol]-1'(2'H)-yl)acetamide | 443.3 |
| 35 | N-(3-isopropoxypropyl)-2-(2'-oxospiro[furo[2,3-f][1,3]benzodioxole-7,3'-indol]-1'(2'H)-yl)acetamide | 439.4 |

-continued

| Compound Number | Name | MS (m/z, M + 1) |
| --- | --- | --- |
| 36 | N-(2-furylmethyl)-2-(2'-oxospiro[furo[2,3-f][1,3]benzodioxole-7,3'-indol]-1'(2'H)-yl)acetamide | 419.3 |
| 37 | N-(cyclohexylmethyl)-2-(2'-oxospiro[furo[2,3-f][1,3]benzodioxole-7,3'-indol]-1'(2'H)-yl)acetamide | 435.3 |
| 38 | N-(3-fluoro-2-methylphenyl)-2-(2'-oxospiro[furo[2,3-f][1,3]benzodioxole-7,3'-indol]-1'(2'H)-yl)acetamide | 447.3 |
| 39 | N-(4-methoxyphenyl)-2-(2'-oxospiro[furo[2,3-f][1,3]benzodioxole-7,3'-indol]-1'(2'H)-yl)acetamide | 445.3 |
| 40 | N-cyclobutyl-2-(2'-oxospiro[furo[2,3-f][1,3]benzodioxole-7,3'-indol]-1'(2'H)-yl)acetamide | 393.4 |
| 41 | N-(2,5-difluorophenyl)-2-(2'-oxospiro[furo[2,3-f][1,3]benzodioxole-7,3'-indol]-1'(2'H)-yl)acetamide | 451.3 |
| 42 | N-benzyl-2-(2'-oxospiro[furo[2,3-f][1,3]benzodioxole-7,3'-indol]-1'(2'H)-yl)acetamide | 429.3 |
| 43 | N-(cyclopropylmethyl)-2-(2'-oxospiro[furo[2,3-f][1,3]benzodioxole-7,3'-indol]-1'(2'H)-yl)acetamide | 393.2 |
| 44 | N-butyl-N-ethyl-2-(2'-oxospiro[furo[2,3-f][1,3]benzodioxole-7,3'-indol]-1'(2'H)-yl)acetamide | 423.3 |
| 45 | N-octyl-2-(2'-oxospiro[furo[2,3-f][1,3]benzodioxole-7,3'-indol]-1'(2'H)-yl)acetamide | 451.2 |
| 46 | N-(3,3-dimethylbutyl)-2-(2'-oxospiro[furo[2,3-f][1,3]benzodioxole-7,3'-indol]-1'(2'H)-yl)acetamide | 423.2 |
| 47 | N-(4-chloro-2-methylphenyl)-2-(2'-oxospiro[furo[2,3-f][1,3]benzodioxole-7,3'-indol]-1'(2'H)-yl)acetamide | 463.1 |
| 48 | N-(3-methoxyphenyl)-2-(2'-oxospiro[furo[2,3-f][1,3]benzodioxole-7,3'-indol]-1'(2'H)-yl)acetamide | 445.0 |
| 49 | N-(2-fluoro-4-methylphenyl)-2-(2'-oxospiro[furo[2,3-f][1,3]benzodioxole-7,3'-indol]-1'(2'H)-yl)acetamide | 447.0 |
| 50 | N-(3,4-dimethylphenyl)-2-(2'-oxospiro[furo[2,3-f][1,3]benzodioxole-7,3'-indol]-1'(2'H)-yl)acetamide | 443.1 |
| 51 | N-(3-chlorobenzyl)-2-(2'-oxospiro[furo[2,3-f][1,3]benzodioxole-7,3'-indol]-1'(2'H)-yl)acetamide | 463.1 |
| 52 | N-(3-methoxybenzyl)-2-(2'-oxospiro[furo[2,3-f][1,3]benzodioxole-7,3'-indol]-1'(2'H)-yl)acetamide | 459.1 |
| 53 | N-(3,4-difluorophenyl)-2-(2'-oxospiro[furo[2,3-f][1,3]benzodioxole-7,3'-indol]-1'(2'H)-yl)acetamide | 451.1 |
| 54 | N-(3-methylbenzyl)-2-(2'-oxospiro[furo[2,3-f][1,3]benzodioxole-7,3'-indol]-1'(2'H)-yl)acetamide | 443.1 |
| 55 | N-(2-methoxybenzyl)-2-(2'-oxospiro[furo[2,3-f][1,3]benzodioxole-7,3'-indol]-1'(2'H)-yl)acetamide | 459.2 |
| 56 | N-(4-isopropylphenyl)-2-(2'-oxospiro[furo[2,3-f][1,3]benzodioxole-7,3'-indol]-1'(2'H)-yl)acetamide | 457.2 |
| 57 | N-(2,3-difluorophenyl)-2-(2'-oxospiro[furo[2,3-f][1,3]benzodioxole-7,3'-indol]-1'(2'H)-yl)acetamide | 451.1 |
| 58 | 2-(2'-oxospiro[furo[2,3-f][1,3]benzodioxole-7,3'-indol]-1'(2'H)-yl)-N-(tetrahydrofuran-2-ylmethyl)acetamide | 423.1 |
| 59 | N-[2-(4-methylphenyl)ethyl]-2-(2'-oxospiro[furo[2,3-f][1,3]benzodioxole-7,3'-indol]-1'(2'H)-yl)acetamide | 457.1 |
| 60 | N-[2-(3-chlorophenyl)ethyl]-2-(2'-oxospiro[furo[2,3-f][1,3]benzodioxole-7,3'-indol]-1'(2'H)-yl)acetamide | 477.1 |
| 61 | N-(4-cyanophenyl)-2-(2'-oxospiro[furo[2,3-f][1,3]benzodioxole-7,3'-indol]-1'(2'H)-yl)acetamide | 440.1 |
| 62 | N-(2,3-dihydro-1H-inden-1-yl)-2-(2'-oxospiro[furo[2,3-f][1,3]benzodioxole-7,3'-indol]-1'(2'H)-yl)acetamide | 455.1 |
| 63 | N-(2-methoxyethyl)-2-(2'-oxospiro[furo[2,3-f][1,3]benzodioxole-7,3'-indol]-1'(2'H)-yl)acetamide | 397.1 |
| 64 | N-[2-(4-methoxyphenyl)ethyl]-2-(2'-oxospiro[furo[2,3-f][1,3]benzodioxole-7,3'-indol]-1'(2'H)-yl)acetamide | 473.1 |
| 65 | N-(2-cyanoethyl)-2-(2'-oxospiro[furo[2,3-f][1,3]benzodioxole-7,3'-indol]-1'(2'H)-yl)acetamide | 392.1 |
| 66 | N-(2,4-dichlorobenzyl)-2-(2'-oxospiro[furo[2,3-f][1,3]benzodioxole-7,3'-indol]-1'(2'H)-yl)acetamide | 497.0 |
| 67 | N-(3,5-difluorobenzyl)-2-(2'-oxospiro[furo[2,3-f][1,3]benzodioxole-7,3'-indol]-1'(2'H)-yl)acetamide | 465.0 |
| 68 | N-(2,4-difluorobenzyl)-2-(2'-oxospiro[furo[2,3-f][1,3]benzodioxole-7,3'-indol]-1'(2'H)-yl)acetamide | 465.0 |
| 69 | N-(2-methylbenzyl)-2-(2'-oxospiro[furo[2,3-f][1,3]benzodioxole-7,3'-indol]-1'(2'H)-yl)acetamide | 443.1 |
| 70 | N-(3,4-difluorobenzyl)-2-(2'-oxospiro[furo[2,3-f][1,3]benzodioxole-7,3'-indol]-1'(2'H)-yl)acetamide | 465.1 |
| 71 | N-(2,5-difluorobenzyl)-2-(2'-oxospiro[furo[2,3-f][1,3]benzodioxole-7,3'-indol]-1'(2'H)-yl)acetamide | 465.1 |
| 72 | 2-(2'-oxospiro[furo[2,3-f][1,3]benzodioxole-7,3'-indol]-1'(2'H)-yl)-N,N-dipropylacetamide | 423.2 |
| 73 | N,N-dibutyl-2-(2'-oxospiro[furo[2,3-f][1,3]benzodioxole-7,3'-indol]-1'(2'H)-yl)acetamide | 451.2 |

-continued

| Compound Number | Name | MS (m/z, M + 1) |
|---|---|---|
| 74 | N-(2,6-difluorobenzyl)-2-(2'-oxospiro[furo[2,3-f][1,3]benzodioxole-7,3'-indol]-1'(2'H)-yl)acetamide | 465.1 |
| 75 | N-[2-(methylthio)phenyl]-2-(2'-oxospiro[furo[2,3-f][1,3]benzodioxole-7,3'-indol]-1'(2'H)-yl)acetamide | 461.1 |
| 76 | N-(2-isopropylphenyl)-2-(2'-oxospiro[furo[2,3-f][1,3]benzodioxole-7,3'-indol]-1'(2'H)-yl)acetamide | 457.2 |
| 77 | N-(4-bromophenyl)-2-(2'-oxospiro[furo[2,3-f][1,3]benzodioxole-7,3'-indol]-1'(2'H)-yl)acetamide | 493.0 |
| 78 | N-(4-chlorophenyl)-2-(2'-oxospiro[furo[2,3-f][1,3]benzodioxole-7,3'-indol]-1'(2'H)-yl)acetamide | 449.0 |
| 79 | N-(2,4-dichlorophenyl)-2-(2'-oxospiro[furo[2,3-f][1,3]benzodioxole-7,3'-indol]-1'(2'H)-yl)acetamide | 483.0 |
| 80 | N-(3,5-dichlorophenyl)-2-(2'-oxospiro[furo[2,3-f][1,3]benzodioxole-7,3'-indol]-1'(2'H)-yl)acetamide | 483.1 |
| 81 | N,N-diethyl-2-(2'-oxospiro[furo[2,3-f][1,3]benzodioxole-7,3'-indol]-1'(2'H)-yl)acetamide | 395.1 |
| 82 | N-methyl-2-(2'-oxospiro[furo[2,3-f][1,3]benzodioxole-7,3'-indol]-1'(2'H)-yl)-N-phenylacetamide | 429.1 |
| 83 | N-(4-hydroxybutyl)-2-(2'-oxospiro[furo[2,3-f][1,3]benzodioxole-7,3'-indol]-1'(2'H)-yl)acetamide | 411.1 |
| 84 | N-allyl-2-(2'-oxospiro[furo[2,3-f][1,3]benzodioxole-7,3'-indol]-1'(2'H)-yl)acetamide | 379.1 |
| 85 | N-(2-fluoro-5-methylphenyl)-2-(2'-oxospiro[furo[2,3-f][1,3]benzodioxole-7,3'-indol]-1'(2'H)-yl)acetamide | 447.1 |
| 86 | N-(1,3-benzodioxol-5-ylmethyl)-2-(2'-oxospiro[furo[2,3-f][1,3]benzodioxole-7,3'-indol]-1'(2'H)-yl)acetamide | 473.1 |
| 87 | N-cyclopropyl-2-(2'-oxospiro[furo[2,3-f][1,3]benzodioxole-7,3'-indol]-1'(2'H)-yl)acetamide | 379.1 |
| 88 | N-(2-cyclopropylethyl)-2-(2'-oxospiro[furo[2,3-f][1,3]benzodioxole-7,3'-indol]-1'(2'H)-yl)acetamide | 407.2 |
| 89 | N-(3,4-dichlorobenzyl)-2-(2'-oxospiro[furo[2,3-f][1,3]benzodioxole-7,3'-indol]-1'(2'H)-yl)acetamide | 497.1 |
| 90 | N-(2,3-dichlorobenzyl)-2-(2'-oxospiro[furo[2,3-f][1,3]benzodioxole-7,3'-indol]-1'(2'H)-yl)acetamide | 497.1 |
| 91 | N-(2,5-dimethylphenyl)-2-(2'-oxospiro[furo[2,3-f][1,3]benzodioxole-7,3'-indol]-1'(2'H)-yl)acetamide | 443.1 |
| 92 | N-(3,4-dichlorophenyl)-2-(2'-oxospiro[furo[2,3-f][1,3]benzodioxole-7,3'-indol]-1'(2'H)-yl)acetamide | 483.3 |
| 93 | N,N-dimethyl-2-(2'-oxospiro[furo[2,3-f][1,3]benzodioxole-7,3'-indol]-1'(2'H)-yl)acetamide | 367.2 |
| 94 | N-methyl-2-(2'-oxospiro[furo[2,3-f][1,3]benzodioxole-7,3'-indol]-1'(2'H)-yl)-N-(2-phenylethyl)acetamide | 457.2 |
| 95 | 2-(2'-oxospiro[furo[2,3-f][1,3]benzodioxole-7,3'-indol]-1'(2'H)-yl)-N-(2-phenylpropyl)acetamide | 457.2 |
| 96 | N-[(1R)-1-cyclohexylethyl]-2-(2'-oxospiro[furo[2,3-f][1,3]benzodioxole-7,3'-indol]-1'(2'H)-yl)acetamide | 449.2 |
| 97 | N-[(1S)-1-cyclohexylethyl]-2-(2'-oxospiro[furo[2,3-f][1,3]benzodioxole-7,3'-indol]-1'(2'H)-yl)acetamide | 449.2 |
| 98 | 2-(2'-oxospiro[furo[2,3-f][1,3]benzodioxole-7,3'-indol]-1'(2'H)-yl)-N-(2-piperidin-1-ylethyl)acetamide | 451.4 |
| 99 | 2-(2'-oxospiro[furo[2,3-f][1,3]benzodioxole-7,3'-indol]-1'(2'H)-yl)-N-[3-(trifluoromethyl)phenyl]acetamide | 483.1 |
| 100 | N-(3-cyanophenyl)-2-(2'-oxospiro[furo[2,3-f][1,3]benzodioxole-7,3'-indol]-1'(2'H)-yl)acetamide | 440.1 |
| 101 | 1'-(2-morpholin-4-yl-2-oxoethyl)spiro[furo[2,3-f][1,3]benzodioxole-7,3'-indol]-2'(1'H)-one | 409.1 |
| 102 | 2-(2'-oxospiro[furo[2,3-f][1,3]benzodioxole-7,3'-indol]-1'(2'H)-yl)-N-(2-phenylethyl)acetamide | 443.1 |
| 103 | N-(4-bromo-2-chlorophenyl)-2-(2'-oxospiro[furo[2,3-f][1,3]benzodioxole-7,3'-indol]-1'(2'H)-yl)acetamide | 527.0 |
| 104 | N-(2-biphenyl-4-ylethyl)-2-(2'-oxospiro[furo[2,3-f][1,3]benzodioxole-7,3'-indol]-1'(2'H)-yl)acetamide | 519.2 |

Example 3.2

Synthesis of N-(2-fluorophenyl)-2-(2'-oxo-6,7-dihydro-5H-spiro[indeno[5,6-b']furan-3,3'-indol]-1'(2'H)-yl)acetamide To a solution of 2'-oxo-6,7-dihydro-5H-spiro[indeno[5,6-b']furan-3,3'-indol]-1'(2'H)-yl)acetic acid (0.18 g, 0.54 mmol) in chloroform (5.00 mL) was added oxalyl chloride (0.09 mL, 1.07 mmol) with one drop of DMF. The mixture was refluxed for 2 hours, and evaporated under reduced vacuum to dryness. To the above residue were added $Et_3N$ (0.66 mL, 4.72 mmol), 2-fluoroaniline (0.10 mL, 1.00 mmol) and THF (5.00 mL). The reaction mixture was stirred at ambient temperature overnight, evaporated to dryness. The residue was subjected to column chromatography (25% ethyl acetate in hexane) to yield the title compound (0.04 g, 17%): $^1$H NMR (300 MHz, $CDCl_3$) δ 8.26 (t, 1H), 8.05-7.90 (br, 1H), 7.33 (td, 1H), 7.26-6.96 (m, 6H), 6.83 (s, 1H), 6.61 (s, 1H), 4.98 (d, 1H), 4.73 (d, 1H), 4.71 (d, 1H), 4.52 (d, 1H), 2.85 (t, 2H), 2.69 (t, 2H), 2.12-1.94 (m, 2H); $^{13}$C NMR (75 MHz, $CDCl_3$) δ 178.6, 165.0, 159.8, 146.9, 141.5, 137.5, 132.5, 129.2, 126.3, 125.2, 124.8, 124.4, 124.3, 121.9, 118.9, 115.2, 114.9, 109.0, 106.8, 79.9, 58.2, 45.3, 33.2, 32.0, 26.1; MS (ES+) m/z 429 (M+1), 451 (M+23).

Example 3.3

Synthesis of N-(2-fluorophenyl)-2-(2-oxo-5',6',7',8'-tetrahydrospiro[indole-3,3'-naphtho[2,3-b']furan]-1(2H)-yl)acetamide Following the procedure as described in EXAMPLE 3.2, and making non-critical variations using (2-oxo-5',6',7',8'-tetrahydrospiro[indole-3,3'-naphtho[2,3-b']furan]-1(2H)-yl) acetic acid to replace 2'-oxo-6,7-dihydro-5H-spiro[indeno[5,6-b']furan-3,3'-indol]-1'(2'H)-yl)acetic acid, the title compound was obtained in 5% yield: $^1$H NMR (300 MHz, CDCl$_3$) δ 8.27 (t, 1H), 8.04-7.90 (br, 1H), 7.33 (td, 1H), 7.26-6.97 (m, 6H), 6.69 (s, 1H), 6.48 (s, 1H), 4.94 (d, 1H), 4.69 (d, 1H), 4.71 (d, 1H), 4.52 (d, 1H), 2.81-2.45 (m, 4H), 1.82-1.60 (m, 4H); MS (ES+) m/z 443 (M+1), 465 (M+23).

Example 3.4

Synthesis of 2-(4'-bromo-5,6-difluoro-2'-oxospiro[1-benzofuran-3,3'-indol]-1'(2'H)-yl)-N-(2-fluorophenyl)acetamide A. Synthesis of (4'-bromo-5,6-difluoro-2'-oxospiro[1-benzofuran-3,3'-indol]-1'(2'H)-yl)acetic acid Following the procedure as described in EXAMPLE 2, and making non-critical variations using ethyl (4'-bromo-5,6-difluoro-2'-oxospiro[1-benzofuran-3,3'-indol]-1'(2'H)-yl)acetate to replace ethyl (2'-oxospiro[furo[2,3-f][1,3]benzodioxole-7,3'-indol]-1'(2'H)-yl)acetate, the title compound was obtained in 100% yield. The product was used directly in the next step.

B. Synthesis of 2-(4'-bromo-5,6-difluoro-2'-oxospiro[1-benzofuran-3,3'-indol]-1'(2'H)-yl)-N-(2-fluorophenyl)acetamide To a solution of (4'-bromo-5,6-difluoro-2'-oxospiro[1-benzofuran-3,3'-indol]-1'(2'H)-yl)acetic acid (0.24 g, 0.59 mmol) and oxalyl chloride (0.15 mL, 1.76 mmol) in toluene (7.00 mL) was added one drop of DMF and the resulted mixture was stirred at ambient temperature overnight. The mixture was concentrated under vacuum. The residue was dissolved in dichloromethane (5.00 mL) and 2-fluoroaniline (0.18 mL, 1.89 mmol) was added at ambient temperature. The mixture was stirred at ambient temperature for one hour. More dichloromethane (100 mL) was added. The organic layer was washed with water, dried over anhydrous sodium sulfate and filtered. The filtrate was concentrated in vacuo. The residue was subjected to column chromatography (ethyl acetate/hexane, 1/5) to give the title compound (0.23 g, 76%): $^1$H NMR (300 MHz, CDCl$_3$) δ 8.20 (t, 1H), 7.80 (br, 1H), 7.27-7.17 (m, 2H), 7.16-7.03 (m, 3H), 6.97-6.88 (m, 1H), 6.78-6.60 (m, 2H), 5.08 (d, 1H), 4.93 (d, 1H), 4.68 (d, 1H), 4.49 (d, 1H); $^{13}$C NMR (75 MHz, CDCl$_3$) δ 177.1, 163.9, 157.8, 143.6, 131.0, 128.8, 128.1, 124.7, 121.8, 120.0, 115.0, 111.6, 108.1, 99.8, 77.5, 59.2, 44.7; MS (ES+) m/z 503.4 (M+1), 505.4 (M+1).

Example 3.5

Synthesis of 2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide A. Synthesis of (4'-bromo-6,6-dimethyl-2'-oxo-5,6-dihydrospiro[benzo[1,2-b:5,4-b']difuran-3,3'-indol]-1'(2'H)-yl)acetic acid Following the procedure as described in EXAMPLE 2, and making non-critical variations using ethyl (4'-bromo-6,6-dimethyl-2'-oxo-5,6-dihydrospiro[benzo[1,2-b:5,4-b']difuran-3,3'-indol]-1'(2'H)-yl)acetate to replace ethyl (2'-oxospiro[furo[2,3-f][1,3]benzodioxole-7,3'-indol]-1'(2'H)-yl) acetate, the title compound was obtained. The product was used directly in the next step.

B. Synthesis of 2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B, and making non-critical variations using (4'-bromo-6,6-dimethyl-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (61% for two steps): MS (ES+) m/z 537.4 (M+1), 539.4 (M+1).

Example 3.6

Synthesis of 2-(4'-chloro-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B, and making non-critical variations using (4'-chloro-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (69%) as a colorless solid: mp 243-245° C.; $^1$H NMR (300 MHz, CDCl$_3$) δ 8.19 (t, 1H), 7.96 (s, 1H), 7.21-7.27 (m, 1H), 7.10-7.02 (m, 4H), 6.88 (d, 1H), 6.55 (s, 1H), 6.35 (s, 1H), 4.96 (dd, 2H), 4.70 (d, 1H), 4.57-4.53 (m, 3H), 2.97 (t, 2H); $^{13}$C NMR (75 MHz, CDCl$_3$) δ 178.2, 164.4, 162.2, 162.1, 143.2, 131.6, 130.2, 128.5, 125.2, 125.1, 124.9, 124.6, 121.9, 119.7, 118.6, 116.8, 115.1, 114.8, 107.3, 92.9, 77.2, 72.4, 58.2, 44.9, 28.9; MS (ES+) m/z 465.5 (M+1).

Example 3.7

Synthesis of 2-(5'-chloro-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B, and making non-critical variations using (5'-chloro-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (91%) as a colorless solid: mp 229-230° C.; $^1$H NMR (300 MHz, CDCl$_3$) δ 8.21 (t, 1H), 7.88 (s, 1H), 7.28-7.25 (m, 1H), 7.18 (d, 1H), 7.13-7.04 (m, 3H), 6.90 (d, 1H), 6.57 (s, 1H), 6.40 (s, 1H), 4.95 (d, 1H), 4.70-4.66 (m, 2H), 4.56-4.43 (m, 3H), 2.99 (t, 2H); $^{13}$C NMR (75 MHz, CDCl$_3$) δ 177.8, 170.9, 162.1, 162.1, 143.1, 131.7, 130.0, 128.6, 124.7, 119.6, 118.7, 117.0, 106.7, 92.8, 77.2, 72.3, 58.1, 41.2, 28.9; MS (ES+) m/z 465.4 (M+1).

Example 3.8

Synthesis of 2-(6-chloro-2'-oxospiro[1-benzofuran-3,3'-indol]-1'(2'H)-yl)-N-(2-fluorophenyl)acetamide Following the procedure as described in EXAMPLE 3.4B, and making non-critical variations using (6-chloro-2'-oxospiro[1-benzofuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (10%) as a white solid: mp 70-75° C.; $^1$H NMR (300 MHz, CDCl$_3$) δ 8.21 (t, 1H), 7.99 (br, 1H), 7.32 (dt, 1H), 7.19-6.93 (m, 7H), 6.80 (dd, 1H), 6.73 (d, 1H), 5.01 (d, 1H), 4.75 (d, 1H), 4.69 (d, 1H), 4.50 (d, 1H); $^{13}$C NMR (75 MHz, CDCl$_3$) δ 177.7, 164.6, 161.4, 141.4, 135.5, 131.6, 129.4, 127.3, 125.2, 125.0, 124.7, 124.6, 124.4, 124.3, 124.1, 121.9, 121.8, 115.1, 114.8, 111.3, 109.0, 80.3, 57.6, 44.9; MS (ES+) m/z 423.4 (M+1).

Example 3.9

Synthesis of 2-(5,6-difluoro-2'-oxospiro[1-benzofuran-3,3'-indol]-1'(2'H)-yl)-N-(2-fluorophenyl)acetamide Following the procedure as described in EXAMPLE 3.4B, and making non-critical variations using (5,6-difluoro-2'-oxospiro[1-benzofuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (35%) as a white solid: mp 97-100° C.; $^1$H NMR (300 MHz, CDCl$_3$) δ 8.20-8.10 (m, 2H), 7.31 (dt, 1H), 7.19-7.00 (m, 5H), 6.95 (d, 1H), 6.77-6.40 (m, 2H), 5.02 (d, 1H), 4.74 (d, 1H), 4.69 (d, 1H), 4.51 (d, 1H); $^{13}$C NMR (75 MHz, CDCl$_3$) δ 177.4, 164.3, 141.4, 131.2, 129.7, 125.6, 125.5, 125.3, 125.2, 125.1, 124.7, 124.4, 124.1, 121.8, 115.1, 114.9, 112.1, 111.8, 109.1, 100.3, 100.0, 80.7, 57.9; MS (ES+) m/z 425.5 (M+1).

Example 3.10

Synthesis of 2-(5-bromo-2'-oxospiro[1-benzofuran-3,3'-indol]-1'(2'H)-yl)-N-(2-fluorophenyl)acetamide Following the procedure as described in EXAMPLE 3.4B, and making non-critical variations using (5-bromo-2'-oxospiro[1-benzofuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (94%) as a light yellow solid: mp 100-103° C.; $^1$H NMR (300 MHz, CDCl$_3$) δ 8.26 (dd, 1H), 7.92 (br, 1H), 7.39-7.31 (m, 2H), 7.22-7.01 (m, 6H), 6.91 (d, 1H), 6.87 (d, 1H), 5.02 (d, 1H), 4.76 (d, 1H), 4.67 (d, 1H), 4.57 (d, 1H); MS (ES+) m/z 467.3 (M+1).

Example 3.11

Synthesis of 2-(4'-fluoro-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B, and making non-critical variations using (4'-fluoro-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained: $^1$H NMR (300 MHz, CDCl$_3$) δ 8.20 (t, 1H), 7.91 (s, 1H), 7.29 (dt, 1H), 7.13-7.04 (m, 3H), 6.81-6.75 (m, 2H), 6.61 (s, 1H), 6.39 (s, 1H), 4.95-4.87 (m, 2H), 4.70 (d, 1H), 4.55-4.44 (m, 3H), 2.98 (t, 2H); MS (ES+) m/z 449.5 (M+1)

Example 3.12

Synthesis of 2-(4'-bromo-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B, and making non-critical variations using (4'-bromo-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (75%) as a colorless solid: mp 245-246° C.; $^1$H NMR (300 MHz, CDCl$_3$) δ 8.20 (t, 1H), 7.90 (s, 1H), 7.20-7.03 (m, 5H), 6.92 (dd, 1H), 6.53 (s, 1H), 6.36 (s, 1H), 5.05 (d, 1H), 4.90 (d, 1H), 4.69 (d, 1H), 4.55-4.43 (m, 3H), 2.97 (t, 2H); $^{13}$C NMR (75 MHz, CDCl$_3$) δ 178.3, 164.3, 162.4, 162.2, 143.4, 130.4, 130.0, 128.0, 125.5, 125.2, 124.7, 121.9, 120.0, 119.7, 118.6, 116.7, 115.1, 114.8, 107.8, 92.8, 77.2, 72.4, 59.1, 44.9, 28.9; MS (ES+) m/z 509 (M+1), 511 (M+1).

Example 3.13

Synthesis of N-(2-fluorophenyl)-2-(2'-oxo-5,6-dihydrospiro[benzo[1,2-b:5,4-b']difuran-3,3'-indol]-1'(2'H)-yl)acetamide Following the procedure as described in EXAMPLE 3.4B, and making non-critical variations using (2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (68%) as a white solid: mp 210-212° C.; $^1$H NMR (300 MHz, DMSO-d$_6$) δ 10.18 (s, 1H), 8.17-7.67 (m, 1H), 7.55-6.90 (m, 7H), 6.54 (s, 1H), 6.38 (s, 1H), 4.68 (m, 4H), 4.46 (t, 2H), 2.93 (t, 2H); MS (ES+) m/z 431.4 (M+1).

Example 3.14

Synthesis of 2-(4'-fluoro-7'-methyl-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B and making non-critical variations using (4'-fluoro-7'-methyl-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (21%) as a white solid: mp 250-255° C.; $^1$H NMR (300 MHz, DMSO-d$_6$) δ 10.23 (s, 1H), 7.99-7.69 (m, 1H), 7.36-7.01 (m, 4H), 6.74 (t, 1H), 6.63 (s, 1H), 6.42 (s, 1H), 5.90 (d, 2H), 4.88 (t, 2H), 4.76 (ABq, 2H), 3.30 (s, 3H); MS (ES+) m/z 463.4 (M+1).

Example 4

Synthesis of 4'-[6-(dimethylamino)pyridin-3-yl]-1'-pentylspiro[furo[2,3-f][1,3]benzodioxole-7,3'-indol]-2'(1'H)one To an oven-dried flask was charged with [6-(dimethylamino)pyridin-3-yl]boronic acid (37.0 mg, 0.17 mmol), Pd(PPh$_3$)$_4$ (13.5 mg, 0.012 mmol) followed by flashing with nitrogen. To the flask was added a solution of 4'-bromo-1'-pentylspiro[furo[2,3-f][1,3]benzodioxole-7,3'-indol]-2'(1'H)-one (50.0 mg, 0.12 mmol) in anhydrous dioxane (2.00 mL) followed by the addition of 2.0 M Na$_2$CO$_3$ (0.24 mL). The reaction mixture was heated at reflux for 48 h. After cooling down to ambient temperature, the solvent was removed under reduced pressure. The residue was diluted with ethyl acetate (2.00 mL), washed with saturated ammonium chloride (2.00 mL), and concentrated in vacuo to dryness. The residue was subjected to column chromatography to yield the title compounds: $^1$H NMR (300 MHz, CDCl$_3$) δ 7.77 (d, 1H), 7.32 (t, 1H), 6.87 (dd, 2H), 6.71 (dd, 1H), 6.23 (d, 1H), 6.20 (s, 1H), 5.88 (d, 2H), 4.56 (ABq, 2H), 3.89-3.80 (m, 1H), 3.69-3.59 (m, 1H), 3.05 (s, 6H), 1.78-1.69 (m, 2H), 1.39-1.35 (m, 4H), 0.90 (t, 3H); $^{13}$C NMR (75 MHz, CDCl$_3$) δ 177.9, 158.3, 156.1, 148.8, 147.3, 142.9, 142.0, 137.8, 137.2, 129.9, 128.9, 125.6, 122.0, 121.0, 107.6, 104.3, 102.5, 101.5, 93.6, 77.8, 58.5, 40.5, 38.2, 29.1, 27.2, 22.4, 14.0; MS (ES+, m/z) 472.0 (M+1).

Example 4.1

The compounds listed in the following table were synthesized using similar conditions as described in Example 4. As previously noted, the compound numbers listed below do not correspond to the compound numbers provided in the general Reaction Schemes above.

| Compound Number | Name | MS (m/z, M + 1) |
|---|---|---|
| 105 | 4'-(3,5-dimethoxyphenyl)-1'-pentylspiro[furo[2,3-f][1,3]benzodioxole-7,3'-indol]-2'(1'H)-one | 488.4 |
| 106 | 4'-(4-fluorophenyl)-1'-pentylspiro[furo[2,3-f][1,3]benzodioxole-7,3'-indol]-2'(1'H)-one | 447.3 |
| 107 | 4'-(3,5-dichlorophenyl)-1'-pentylspiro[furo[2,3-f][1,3]benzodioxole-7,3'-indol]-2'(1'H)-one | 496.3 |
| 108 | 4'-[4-(dimethylamino)phenyl]-1'-pentylspiro[furo[2,3-f][1,3]benzodioxole-7,3'-indol]-2'(1'H)-one | 471.3 |
| 109 | 1'-pentyl-4'-(3,4,5-trimethoxyphenyl)spiro[furo[2,3-f][1,3]benzodioxole-7,3'-indol]-2'(1'H)-one | 518.3 |
| 110 | 4-(2'-oxo-1'-pentyl-1',2'-dihydrospiro[furo[2,3-f][1,3]benzodioxole-7,3'-indol]-4'-yl)benzonitrile | 453.3 |
| 111 | 4'-dibenzo[b,d]furan-4-yl-1'-pentylspiro[furo[2,3-f][1,3]benzodioxole-7,3'-indol]-2'(1'H)-one | 518.3 |
| 112 | 4'-(1-benzyl-1H-pyrazol-4-yl)-1'-pentylspiro[furo[2,3-f][1,3]benzodioxole-7,3'-indol]-2'(1'H)-one | 508.4 |
| 113 | 4'-(2-methoxypyrimidin-5-yl)-1'-pentylspiro[furo[2,3-f][1,3]benzodioxole-7,3'-indol]-2'(1'H)-one | 460.3 |
| 114 | 4'-(2,4-dimethoxypyrimidin-5-yl)-1'-pentylspiro[furo[2,3-f][1,3]benzodioxole-7,3'-indol]-2'(1'H)-one | 490.4 |
| 115 | 4-(2'-oxo-1'-pentyl-1',2'-dihydrospiro[furo[2,3-f][1,3]benzodioxole-7,3'-indol]-4'-yl)benzamide | 471.3 |
| 116 | 4'-{4-[(dimethylamino)methyl]phenyl}-1'-pentylspiro[furo[2,3-f][1,3]benzodioxole-7,3'-indol]-2'(1'H)-one | 484.6 |
| 117 | 4'-(1-benzofuran-2-yl)-1'-pentylspiro[furo[2,3-f][1,3]benzodioxole-7,3'-indol]-2'(1'H)-one | 467.5 |
| 118 | 4'-(6-methoxypyridin-3-yl)-1'-pentylspiro[furo[2,3-f][1,3]benzodioxole-7,3'-indol]-2'(1'H)-one | 458.5 |
| 119 | N,N-dimethyl-4-(2'-oxo-1'-pentyl-1',2'-dihydrospiro[furo[2,3-f][1,3]benzodioxole-7,3'-indol]-4'-yl)benzamide | 498.6 |
| 120 | 4'-dibenzo[b,d]thien-4-yl-1'-pentylspiro[furo[2,3-f][1,3]benzodioxole-7,3'-indol]-2'(1'H)-one | 533.6 |
| 121 | 3-(2'-oxo-1'-pentyl-1',2'-dihydrospiro[furo[2,3-f][1,3]benzodioxole-7,3'-indol]-4'-yl)benzonitrile | 452.5 |
| 122 | 1'-pentyl-4'-pyridin-3-ylspiro[furo[2,3-f][1,3]benzodioxole-7,3'-indol]-2'(1'H)-one | 428.5 |
| 123 | 4'-(3-fluoro-4-methoxyphenyl)-1'-pentylspiro[furo[2,3-f][1,3]benzodioxole-7,3'-indol]-2'(1'H)-one | 475.5 |
| 124 | 1'-pentyl-4'-[2-(trifluoromethoxy)phenyl]spiro[furo[2,3-f][1,3]benzodioxole-7,3'-indol]-2'(1'H)-one | 511.5 |
| 125 | 4'-[3,5-bis(trifluoromethyl)phenyl]-1'-pentylspiro[furo[2,3-f][1,3]benzodioxole-7,3'-indol]-2'(1'H)-one | 563.5 |
| 126 | 1'-pentyl-4'-[4-(trifluoromethyl)pyridin-3-yl]spiro[furo[2,3-f][1,3]benzodioxole-7,3'-indol]-2'(1'H)-one | 496.5 |
| 127 | 4'-(2-fluoro-5-methoxyphenyl)-1'-pentylspiro[furo[2,3-f][1,3]benzodioxole-7,3'-indol]-2'(1'H)-one | 475.5 |
| 128 | 4'-(4-ethoxy-3-fluorophenyl)-1'-pentylspiro[furo[2,3-f][1,3]benzodioxole-7,3'-indol]-2'(1'H)-one | 489.5 |

| Compound Number | Name | MS (m/z, M + 1) |
|---|---|---|
| 129 | 4'-(1-benzothien-2-yl)-1'-pentylspiro[furo[2,3-f][1,3]benzodioxole-7,3'-indol]-2'(1'H)-one | 483.6 |
| 130 | 4'-isobutyl-1'-pentylspiro[furo[2,3-f][1,3]benzodioxole-7,3'-indol]-2'(1'H)-one | 407.5 |
| 131 | 1'-pentyl-4'-[4-(trifluoromethoxy)phenyl]spiro[furo[2,3-f][1,3]benzodioxole-7,3'-indol]-2'(1'H)-one | 511.5 |
| 132 | 4'-(5-fluoro-2-methoxyphenyl)-1'-pentylspiro[furo[2,3-f][1,3]benzodioxole-7,3'-indol]-2'(1'H)-one | 475.5 |
| 133 | 4'-(1,3-benzodioxol-5-yl)-1'-pentylspiro[furo[2,3-f][1,3]benzodioxole-7,3'-indol]-2'(1'H)-one | 471.5 |
| 134 | 1'-pentyl-4'-phenylspiro[furo[2,3-f][1,3]benzodioxole-7,3'-indol]-2'(1'H)-one | 427.5 |
| 135 | 1'-pentyl-4'-[2-(trifluoromethyl)phenyl]spiro[furo[2,3-f][1,3]benzodioxole-7,3'-indol]-2'(1'H)-one | 495.5 |
| 136 | 4'-(4-chlorophenyl)-1'-pentylspiro[furo[2,3-f][1,3]benzodioxole-7,3'-indol]-2'(1'H)-one | 461.9 |
| 137 | 4'-(2,3-dihydro-1,4-benzodioxin-6-yl)-1'-pentylspiro[furo[2,3-f][1,3]benzodioxole-7,3'-indol]-2'(1'H)-one | 485.5 |
| 138 | 1'-pentyl-4'-quinolin-3-ylspiro[furo[2,3-f][1,3]benzodioxole-7,3'-indol]-2'(1'H)-one | 478.5 |
| 139 | 4'-(3,5-difluorophenyl)-1'-pentylspiro[furo[2,3-f][1,3]benzodioxole-7,3'-indol]-2'(1'H)-one | 463.5 |
| 140 | 4'-isoquinolin-4-yl-1'-pentylspiro[furo[2,3-f][1,3]benzodioxole-7,3'-indol]-2'(1'H)-one | 478.5 |
| 141 | 4'-(6-methoxypyridin-2-yl)-1'-pentylspiro[furo[2,3-f][1,3]benzodioxole-7,3'-indol]-2'(1'H)-one | 458.5 |
| 142 | 4'-(1H-indol-5-yl)-1'-pentylspiro[furo[2,3-f][1,3]benzodioxole-7,3'-indol]-2'(1'H)-one | 466.5 |
| 143 | N-[2-(2'-oxo-1'-pentyl-1',2'-dihydrospiro[furo[2,3-f][1,3]benzodioxole-7,3'-indol]-4'-yl)phenyl]acetamide | 484.5 |
| 144 | 4'-(4-fluoro-2-methylphenyl)-1'-pentylspiro[furo[2,3-f][1,3]benzodioxole-7,3'-indol]-2'(1'H)-one | 459.5 |
| 145 | 1'-pentyl-4'-quinolin-6-ylspiro[furo[2,3-f][1,3]benzodioxole-7,3'-indol]-2'(1'H)-one | 478.5 |
| 146 | N-[4-(2'-oxo-1'-pentyl-1',2'-dihydrospiro[furo[2,3-f][1,3]benzodioxole-7,3'-indol]-4'-yl)phenyl]methanesulfonamide | 520.6 |
| 147 | 4'-(5-chloro-2-methoxyphenyl)-1'-pentylspiro[furo[2,3-f][1,3]benzodioxole-7,3'-indol]-2'(1'H)-one | 492.0 |
| 148 | 1'-pentyl-4'-[3-(trifluoromethoxy)phenyl]spiro[furo[2,3-f][1,3]benzodioxole-7,3'-indol]-2'(1'H)-one | 511.5 |
| 149 | 1'-pentyl-4'-(4-phenoxyphenyl)spiro[furo[2,3-f][1,3]benzodioxole-7,3'-indol]-2'(1'H)-one | 519.6 |
| 150 | 4'-(2,4-dimethoxyphenyl)-1'-pentylspiro[furo[2,3-f][1,3]benzodioxole-7,3'-indol]-2'(1'H)-one | 487.5 |
| 151 | 4'-(3-furyl)-1'-pentylspiro[furo[2,3-f][1,3]benzodioxole-7,3'-indol]-2'(1'H)-one | 417.5 |
| 152 | 4'-(3,4-dimethoxyphenyl)-1'-pentylspiro[furo[2,3-f][1,3]benzodioxole-7,3'-indol]-2'(1'H)-one | 487.5 |
| 153 | N-[4-(2'-oxo-1'-pentyl-1',2'-dihydrospiro[furo[2,3-f][1,3]benzodioxole-7,3'-indol]-4'-yl)phenyl]acetamide | 484.5 |
| 154 | 1'-pentyl-4'-[(E)-2-phenylvinyl]spiro[furo[2,3-f][1,3]benzodioxole-7,3'-indol]-2'(1'H)-one | 453.5 |
| 155 | 4'-(4-methoxyphenyl)-1'-pentylspiro[furo[2,3-f][1,3]benzodioxole-7,3'-indol]-2'(1'H)-one | 457.5 |
| 156 | 4'-(6-fluoropyridin-3-yl)-1'-pentylspiro[furo[2,3-f][1,3]benzodioxole-7,3'-indol]-2'(1'H)-one | 446.5 |
| 157 | 4'-(3-chloro-4-fluorophenyl)-1'-pentylspiro[furo[2,3-f][1,3]benzodioxole-7,3'-indol]-2'(1'H)-one | 479.9 |
| 158 | 4'-(3-chlorophenyl)-1'-pentylspiro[furo[2,3-f][1,3]benzodioxole-7,3'-indol]-2'(1'H)-one | 461.9 |
| 159 | 4'-(1-benzothien-3-yl)-1'-pentylspiro[furo[2,3-f][1,3]benzodioxole-7,3'-indol]-2'(1'H)-one | 483.6 |
| 160 | 1'-pentyl-4'-(2-phenoxyphenyl)spiro[furo[2,3-f][1,3]benzodioxole-7,3'-indol]-2'(1'H)-one | 519.6 |
| 161 | 4'-(4-isopropoxyphenyl)-1'-pentylspiro[furo[2,3-f][1,3]benzodioxole-7,3'-indol]-2'(1'H)-one | 485.6 |
| 162 | 4'-[(E)-2-(4-fluorophenyl)vinyl]-1'-pentylspiro[furo[2,3-f][1,3]benzodioxole-7,3'-indol]-2'(1'H)-one | 471.5 |
| 163 | 4'-(6-fluoropyridin-2-yl)-1'-pentylspiro[furo[2,3-f][1,3]benzodioxole-7,3'-indol]-2'(1'H)-one | 446.5 |
| 164 | 1'-pentyl-4'-[1-(phenylsulfonyl)-1H-indol-3-yl]spiro[furo[2,3-f][1,3]benzodioxole-7,3'-indol]-2'(1'H)-one | 606.7 |

-continued

| Compound Number | Name | MS (m/z, M + 1) |
|---|---|---|
| 165 | 4'-(3-fluorophenyl)-1'-pentylspiro[furo[2,3-f][1,3]benzodioxole-7,3'-indol]-2'(1'H)-one | 445.5 |
| 166 | 4'-(3-acetylphenyl)-1'-pentylspiro[furo[2,3-f][1,3]benzodioxole-7,3'-indol]-2'(1'H)-one | 469.5 |
| 167 | 4'-(2-furyl)-1'-pentylspiro[furo[2,3-f][1,3]benzodioxole-7,3'-indol]-2'(1'H)-one | 417.5 |
| 168 | 4'-(4-methylphenyl)-1'-pentylspiro[furo[2,3-f][1,3]benzodioxole-7,3'-indol]-2'(1'H)-one | 441.5 |
| 169 | 4'-(1-methyl-1H-pyrrol-3-yl)-1'-pentylspiro[furo[2,3-f][1,3]benzodioxole-7,3'-indol]-2'(1'H)-one | 430.5 |
| 170 | 4'-(2,5-difluorophenyl)-1'-pentylspiro[furo[2,3-f][1,3]benzodioxole-7,3'-indol]-2'(1'H)-one | 463.5 |
| 171 | 4'-(2-fluorophenyl)-1'-pentylspiro[furo[2,3-f][1,3]benzodioxole-7,3'-indol]-2'(1'H)-one | 445.5 |
| 172 | 4'-(2-chlorophenyl)-1'-pentylspiro[furo[2,3-f][1,3]benzodioxole-7,3'-indol]-2'(1'H)-one | 461.9 |
| 173 | 4'-(2,4-difluorophenyl)-1'-pentylspiro[furo[2,3-f][1,3]benzodioxole-7,3'-indol]-2'(1'H)-one | 463.5 |
| 174 | 4'-(4-morpholin-4-ylphenyl)-1'-pentylspiro[furo[2,3-f][1,3]benzodioxole-7,3'-indol]-2'(1'H)-one | 512.6 |
| 175 | tert-butyl 5-methoxy-3-(2'-oxo-1'-pentyl-1',2'-dihydrospiro[furo[2,3-f][1,3]benzodioxole-7,3'-indol]-4'-yl)-1H-indole-1-carboxylate | 596.7 |
| 176 | 1'-pentyl-4'-pyrimidin-5-ylspiro[furo[2,3-f][1,3]benzodioxole-7,3'-indol]-2'(1'H)-one | 429.5 |
| 177 | tert-butyl 4-[2-(2'-oxo-1'-pentyl-1',2'-dihydrospiro[furo[2,3-f][1,3]benzodioxole-7,3'-indol]-4'-yl)phenyl]piperazine-1-carboxylate | 611.7 |
| 178 | 4'-(2-methoxypyridin-3-yl)-1'-pentylspiro[furo[2,3-f][1,3]benzodioxole-7,3'-indol]-2'(1'H)-one | 458.5 |
| 179 | 4'-(5-methoxypyridin-3-yl)-1'-pentylspiro[furo[2,3-f][1,3]benzodioxole-7,3'-indol]-2'(1'H)-one | 458.5 |
| 180 | 4'-(4-butoxy-3-fluorophenyl)-1'-pentylspiro[furo[2,3-f][1,3]benzodioxole-7,3'-indol]-2'(1'H)-one | 517.6 |
| 181 | 1'-pentyl-4'-pyridin-4-ylspiro[furo[2,3-f][1,3]benzodioxole-7,3'-indol]-2'(1'H)-one | 428.5 |
| 182 | 1'-pentyl-4'-phenoxathiin-4-ylspiro[furo[2,3-f][1,3]benzodioxole-7,3'-indol]-2'(1'H)-one | 549.6 |
| 183 | 4'-[(1Z)-3-chloroprop-1-en-1-yl]-1'-pentylspiro[furo[2,3-f][1,3]benzodioxole-7,3'-indol]-2'(1'H)-one | 425.9 |
| 184 | 1'-pentyl-4'-(3-thienyl)spiro[furo[2,3-f][1,3]benzodioxole-7,3'-indol]-2'(1'H)-one | 433.5 |
| 185 | 4'-(2,3-dimethoxyphenyl)-1'-pentylspiro[furo[2,3-f][1,3]benzodioxole-7,3'-indol]-2'(1'H)-one | 487.5 |
| 186 | 4'-(4-butylphenyl)-1'-pentylspiro[furo[2,3-f][1,3]benzodioxole-7,3'-indol]-2'(1'H)-one | 483.6 |
| 187 | 4'-(3-fluoro-5-methoxyphenyl)-1'-pentylspiro[furo[2,3-f][1,3]benzodioxole-7,3'-indol]-2'(1'H)-one | 475.5 |
| 188 | 4'-[3-fluoro-4-(pentyloxy)phenyl]-1'-pentylspiro[furo[2,3-f][1,3]benzodioxole-7,3'-indol]-2'(1'H)-one | 531.6 |
| 189 | 4'-(2-butoxy-5-fluorophenyl)-1'-pentylspiro[furo[2,3-f][1,3]benzodioxole-7,3'-indol]-2'(1'H)-one | 517.6 |
| 190 | 4'-(3-butoxyphenyl)-1'-pentylspiro[furo[2,3-f][1,3]benzodioxole-7,3'-indol]-2'(1'H)-one | 499.6 |
| 191 | 4'-(4-butoxyphenyl)-1'-pentylspiro[furo[2,3-f][1,3]benzodioxole-7,3'-indol]-2'(1'H)-one | 499.6 |
| 192 | 4'-(4-isobutoxyphenyl)-1'-pentylspiro[furo[2,3-f][1,3]benzodioxole-7,3'-indol]-2'(1'H)-one | 499.6 |
| 193 | 4'-{2-chloro-4-[(3,5-dimethoxybenzyl)oxy]phenyl}-1'-pentylspiro[furo[2,3-f][1,3]benzodioxole-7,3'-indol]-2'(1'H)-one | 628.1 |
| 194 | 4'-[4-(benzyloxy)-3-chlorophenyl]-1'-pentylspiro[furo[2,3-f][1,3]benzodioxole-7,3'-indol]-2'(1'H)-one | 568.1 |
| 195 | 4'-(1-methyl-1H-indol-5-yl)-1'-pentylspiro[furo[2,3-f][1,3]benzodioxole-7,3'-indol]-2'(1'H)-one | 480.6 |
| 196 | 4'-(4-methoxypyridin-3-yl)-1'-pentylspiro[furo[2,3-f][1,3]benzodioxole-7,3'-indol]-2'(1'H)-one | 458.5 |
| 197 | 4'-[(6-methoxypyridin-3-yl)amino]-1'-pentylspiro[furo[2,3-f][1,3]benzodioxole-7,3'-indol]-2'(1'H)-one | 473.5 |

Example 4.2

Synthesis of 2-(5,6-difluoro-2'-oxo-4'-pyrimidin-5-ylspiro[1-benzofuran-3,3'-indol]-1'(2'H)-yl)-N-(2-fluorophenyl)acetamide To a solution of 2-(4'-bromo-5,6-difluoro-2'-oxospiro[1-benzofuran-3,3'-indol]-1'(2'H)-yl)-N-(2-fluorophenyl)acetamide (0.15 g, 0.30 mmol) in anhydrous 1,4-dioxane (5.00 mL) was added Pd(PPh$_3$)$_4$ (0.03 g, 0.03 mmol) and stirred at ambient temperature for 10 min. Pyrimidine-5-boronic acid (0.06 g, 0.45 mmol) and sodium carbonate (0.90 mL of 2 M solution, 1.80 mmol) were added. The reaction mixture was reluxed at 120° C. for 16 h, diluted with ethyl acetate (50.0 mL). The organic layer was washed with water, dried over anhydrous sodium sulfate and filtered. The filtrate was concentrated in vacuo. The residue was subjected to column chromatography (ethyl acetate/hexane, 1/1) to give the title compound (0.13 g, 84%): $^1$H NMR (300 MHz, CDCl$_3$) δ 9.13 (s, 1H), 8.29-8.10 (m, 3H), 7.62 (s, 1H), 7.44 (t, 1H), 7.16-7.03 (m, 4H), 6.91 (d, 1H), 6.85-6.76 (m, 1H), 6.46-6.37 (m, 1H), 4.85-4.73 (m, 2H), 4.61-4.47 (m, 2H); $^{13}$C NMR (75 MHz, CDCl$_3$) δ 177.1, 163.9, 157.7, 156.4, 155.7, 141.9, 132.9, 130.0, 126.0, 124.7, 121.9, 115.0, 111.6, 109.8, 100.2, 79.4, 57.9, 44.7; MS (ES+) m/z 503.5 (M+1).

Example 4.3

Synthesis of 2-(6,6-dimethyl-2'-oxo-4'-pyrimidin-5-yl-5,6-dihydrospiro[benzo[1,2-b:5,4-b']difuran-3,3'-indol]-1'(2'H)-yl)-N-(2-fluorophenyl)acetamide Following the procedure as described in EXAMPLE 4.2, making variation using 2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide to replace 2-(4'-bromo-5,6-difluoro-2'-oxospiro[1-benzofuran-3,3'-indol]-1'(2'H)-yl)-N-(2-fluorophenyl)acetamide, the title compound was obtained (95%): mp >250° C.; $^1$H NMR (300 MHz, CDCl$_3$) δ 9.10 (s, 1H), 8.24 (t, 1H), 8.15 (s, 2H), 8.00 (s, 1H), 7.40 (t, 1H), 7.16-7.03 (m, 4H), 6.88 (d, 1H), 6.61 (s, 1H), 5.99 (s, 1H), 4.84-4.73 (m, 2H), 4.54 (d, 1H), 4.44 (d, 1H), 2.79 (s, 2H), 1.45 (s, 3H), 1.39 (s, 3H); $^{13}$C NMR (75 MHz, CDCl$_3$) δ 178.4, 164.5, 161.1, 157.4, 155.8, 154.1, 150.8, 141.7, 132.9, 132.2, 131.3, 129.4, 125.9, 125.5, 125.2, 124.7, 121.9, 120.8, 119.3, 118.8, 115.0, 109.5, 93.5, 88.5, 78.9, 58.0, 45.0, 42.0, 28.0, 27.9; MS (ES+) m/z 537.5 (M+1).

Example 4.4

Synthesis of 4'-(3-furyl)spiro[furo[2,3-f][1,3]benzodioxole-7,3'-indol]-2'(1'H)-one Following the procedure as described in EXAMPLE 4, making variations using 4'-bromospiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and 3-furanboronic acid to replace [6-(dimethylamino)pyridin-3-yl]boronic acid, the title compound was obtained (66%) as a colorless solid: mp 270-272° C.; $^1$H NMR (300 MHz, CDCl$_3$) δ 7.32 (t, 1H), 7.25 (d, 2H), 6.97 (d, 1H), 6.91 (d, 1H), 6.83 (s, 1H), 6.44 (s, 1H), 6.30 (s, 1H), 6.04 (d, 1H), 5.89 (dd, 2H), 4.68 (ABq, 2H); $^{13}$C NMR (75 MHz, CDCl$_3$) δ 180.4, 156.2, 149.2, 142.9, 142.1, 141.2, 140.4, 131.3, 129.2, 128.5, 125.3, 122.6, 120.6, 111.0, 109.5, 102.9, 101.6, 94.0, 77.2, 59.0; MS (ES+) m/z 348.4 (M+1).

Example 4.5

Synthesis of 4'-dibenzo[b,d]furan-4-ylspiro[furo[2,3-f][1,3]benzodioxole-7,3'-indol]-2'(1'H)-one Following the procedure as described in EXAMPLE 4, and making non-critical variations using 4'-bromospiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and dibenzo[b,d]furan-4-ylboronic acid to replace [6-(dimethylamino)pyridin-3-yl]boronic acid, the title compound was obtained (10%) as a colorless solid: mp >230° C.; $^1$H NMR (300 MHz, DMSO-d$_6$) δ 10.77 (s, 1H), 8.04 (d, 1H), 7.97 (dd, 1H), 7.43-7.42 (m, 3H), 7.34-7.29 (m, 3H), 7.16 (t, 1H), 6.98 (d, 1H), 6.89 (d, 1H), 6.25 (s, 1H), 5.69 (d, 2H), 4.41 (ABq, 2H); MS (ES+) m/z 448.5 (M+1).

Example 4.6

Synthesis of 4'-(6-methoxypyridin-3-yl)-1'-{[5-(trifluoromethyl)-2-furyl]methyl}spiro[furo[2,3-f][1,3]benzodioxole-7,3'-indol]-2'(1'H)-one Following the procedure as described in EXAMPLE 4, and making non-critical variations using 4'-bromo-1-{[5-(trifluoromethyl)-2-furyl]methyl}spiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and (6-methoxypyridin-3-yl)boronic acid to replace [6-(dimethylamino)pyridin-3-yl]boronic acid, the title compound was obtained (51%) as a colorless solid: mp 174-176° C.; $^1$H NMR (300 MHz, CDCl$_3$) δ 7.73 (d, 1H), 7.69 (d, 1H), 7.34 (t, 1H), 7.03 (d, 1H), 6.89-6.86 (m, 2H), 6.65 (d, 1H), 6.61 (d, 1H), 6.56 (d, 1H), 6.17 (d, 2H), 5.87 (d, 2H), 4.99 (ABq, 2H), 4.56 (ABq, 2H), 3.90 (s, 3H); $^{13}$C NMR (75 MHz, CDCl$_3$) δ 177.7, 163.5, 158.4, 156.1, 151.8, 151.8, 149.2, 147.8, 146.1, 142.3, 141.6, 138.8, 136.9, 132.6, 130.0, 129.1, 127.8, 127.2, 126.2, 119.9, 112.7, 112.7, 110.9, 109.6, 109.5, 108.5, 102.3, 101.6, 93.6, 78.2, 58.5, 53.6, 37.0; MS (ES+) m/z 537.4 (M+1).

Example 4.7

Synthesis of 4'-[6-(dimethylamino)pyridin-3-yl]-1'-{[5-(trifluoromethyl)-2-furyl]methyl}spiro[furo[2,3-f][1,3]benzodioxole-7,3'-indol]-2'(1'H)-one Following the procedure as described in EXAMPLE 4, and making non-critical variations using 4'-bromo-1-{[5-(trifluoromethyl)-2-furyl]methyl}spiro[furo[2,3-f][1,3]benzodioxole-7,3'-indol]-2'(1'H)-one to replace 4'-bromo-1-pentylspiro[furo[2,3-f][1,3]benzodioxole-7,3'-indol]-2'(1'H)-one, the title compound was obtained (37%) as a colorless solid: mp 174-176° C.; MS (ES+) m/z 550.4 (M+1).

Example 4.8

Synthesis of 4'-pyrimidin-5-ylspiro[furo[2,3-f][1,3]benzodioxole-7,3'-indol]-2'(1'H)-one Following the procedure as described in EXAMPLE 4, and making non-critical variations using 4'-bromospiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and pyrimidin-5-ylboronic acid to replace [6-(dimethylamino)pyridin-3-yl]boronic acid, the title compound was obtained (32%) as a colorless solid: mp 185-187°

C.; ¹H NMR (300 MHz, DMSO-d₆) δ 10.85 (s, 1H), 9.02 (s, 1H), 8.19 (s, 2H), 7.33 (t, 1H), 7.00 (d, 1H), 6.83 (d, 1H), 6.37 (s, 1H), 6.19 (s, 1H), 5.89 (d, 2H); ¹³C NMR (75 MHz, DMSO-d₆) δ 178.7, 157.5, 156.0, 155.6, 148.8, 142.3, 133.1, 132.6, 131.8, 129.5, 124.5, 120.3, 110.9, 103.2, 101.9, 93.3, 79.5, 66.8, 58.5; MS (ES+) m/z 360.4 (M+1).

Example 4.9

Synthesis of 4'-(3-furyl)-1'-(pyridin-2-ylmethyl)-5,6-dihydrospiro[benzo[1,2-b:5,4-b']difuran-3,3'-indol]-2'(1'H)-one Following the procedure as described in EXAMPLE 4, and making non-critical variations using 4'-bromo-4-(pyridin-2-ylmethyl)-5,6-dihydrospiro[benzo[1,2-b:5,4-b']difuran-3,3'-indol]-2'(1'H)-one to replace 4'-bromo-1-pentylspiro[furo[2,3-f][1,3]benzodioxole-7,3'-indol]-2'(1'H)-one, and 3-furanboronic acid to replace [6-(dimethylamino)pyridin-3-yl]boronic acid, the title compound was obtained (75%) as a colorless solid: mp 195-197° C.; ¹H NMR (300 MHz, CDCl₃) δ 8.58 (d, 1H), 7.68 (t, 1H), 7.32-7.21 (m, 4H), 6.97 (d, 1H), 6.92 (d, 1H), 6.77 (s, 1H), 6.60 (s, 1H), 6.35 (s, 1H), 5.99 (s, 1H), 5.12 (ABq, 2H), 4.71 (ABq, 2H), 4.57 (t, 2H), 3.03 (t, 2H); MS (ES+) m/z 437.4 (M+1).

Example 4.10

Synthesis of 1-(pyridin-2-ylmethyl)-4'-pyrimidin-5-yl-5,6-dihydrospiro[benzo[1,2-b:5,4-b']difuran-3,3'-indol]-2'(1'H)-one Following the procedure as described in EXAMPLE 4, and making non-critical variations using 4'-bromo-1'-(pyridin-2-ylmethyl)-5,6-dihydrospiro[benzo[1,2-b:5,4-b']difuran-3,3'-indol]-2'(1'H)-one to replace 4'-bromo-1-pentylspiro[furo[2,3-f][1,3]benzodioxole-7,3'-indol]-2'(1'H)-one, and pyrimidin-5-ylboronic acid to replace [6-(dimethylamino)pyridin-3-yl]boronic acid, the title compound was obtained (16%) as a colorless solid: mp >200° C.; ¹H NMR (300 MHz, CDCl₃) δ 9.09 (s, 1H), 8.59 (d, 1H), 8.14 (s, 2H), 7.74 (t, 1H), 7.67 (d, 1H), 7.63 (d, 1H), 7.52 (d, 1H), 7.47-7.42 (m, 1H), 7.37 (d, 1H), 7.30 (d, 1H), 7.09 (d, 1H), 6.82 (d, 1H), 6.62 (s, 1H), 6.07 (s, 1H), 5.18 (ABq, 2H), 4.62 (ABq, 2H), 4.62-4.48 (m, 2H), 3.02 (t, 2H); MS (ES+) m/z 449.5 (M+1).

Example 4.11

Synthesis of 4'-pyridin-3-yl-1'-(pyridin-2-ylmethyl)-5,6-dihydrospiro[benzo[1,2-b:5,4-b']difuran-3,3'-indol]-2'(1'H)-one Following the procedure as described in EXAMPLE 4, and making non-critical variations using 4'-bromo-1'-(pyridin-2-ylmethyl)-5,6-dihydrospiro[benzo[1,2-b:5,4-b']difuran-3,3'-indol]-2'(1'H)-one to replace 4'-bromo-1-pentylspiro[furo[2,3-f][1,3]benzodioxole-7,3'-indol]-2'(1'H)-one, and pyridin-3-ylboronic acid to replace [6-(dimethylamino)pyridin-3-yl]boronic acid, the title compound was obtained (9%) as a colorless solid: mp >200° C.; ¹H NMR (300 MHz, DMSO-d₆) δ 8.52 (d, 1H), 8.42 (d, 1H), 7.96 (s, 1H), 7.79 (t, 1H), 7.40 (d, 1H), 7.29 (t, 2H), 7.18-7.08 (m, 2H), 7.00 (d, 1H), 6.81 (d, 1H), 6.72 (s, 1H), 5.98 (s, 1H), 5.08 (ABq, 2H), 4.56-4.40 (m, 4H), 3.10-2.90 (m, 2H); MS (ES+) m/z 448.5 (M+1).

Example 4.12

Synthesis of 4'-(3-furyl)-1'-{[5-(trifluoromethyl)-2-furyl]methyl}-5,6-dihydrospiro[benzo[1,2-b:5,4-b']difuran-3,3'-indol]-2'(1'H)-one Following the procedure as described in EXAMPLE 4, and making non-critical variations using 4'-bromo-1-{[5-(trifluoromethyl)-2-furyl]methyl}-5,6-dihydrospiro[benzo[1,2-b:5,4-b']difuran-3,3'-indol]-2'(1'H)-one to replace 4'-bromo-1'-pentylspiro[furo[2,3-f][1,3]benzodioxole-7,3'-indol]-2'(1'H)-one, and 3-furylboronic acid to replace [6-(dimethylamino)pyridin-3-yl]boronic acid, the title compound was obtained (27%) as a colorless solid: mp 167-169° C.; ¹H NMR (300 MHz, CDCl₃) δ 7.34-7.29 (m, 2H), 7.01 (dd, 1H), 6.95 (dd, 1H), 6.77 (dd, 1H), 6.74 (dd, 1H), 6.51 (s, 1H), 6.41 (d, 1H), 6.34 (s, 1H), 6.00 (dd, 1H), 4.97 (ABq, 2H), 4.67 (ABq, 2H), 4.56 (t, 2H), 3.01 (t, 2H); MS (ES+) m/z 494.4 (M+1).

Example 4.13

Synthesis of 4'-quinolin-3-yl-1'-{[5-(trifluoromethyl)-2-furyl]methyl}spiro[furo[2,3-f][1,3]benzodioxole-7,3'-indol]-2'(1'H)-one Following the procedure as described in EXAMPLE 4, and making non-critical variations using 4'-bromo-1-{[5-(trifluoromethyl)-2-furyl]methyl}spiro[furo[2,3-f][1,3]benzodioxole-7,3'-indol]-2'(1'H)-one to replace 4'-bromo-1-pentylspiro[furo[2,3-f][1,3]benzodioxole-7,3'-indol]-2'(1'H)-one, quinolin-3-ylboronic acid to replace [6-(dimethylamino)pyridin-3-yl]boronic acid, the title compound was obtained (50%) as a colorless solid: ¹H NMR (300 MHz, CDCl₃) δ 8.52 (d, 1H), 8.09 (d, 1H), 7.74-7.68 (m, 1H), 7.56-7.50 (m, 1H), 7.42-7.39 (m, 2H), 7.32 (s, 1H), 7.09 (d, 1H), 7.01 (d, 1H), 6.78-6.77 (m, 1H), 6.45 (d, 1H), 6.26 (s, 1H), 5.94 (d, 1H), 5.91 (s, 1H), 5.89 (d, 1H), 5.03 (ABq, 2H), 4.52 (ABq, 2H); ¹³C NMR (75 MHz, CDCl₃) δ 177.4, 156.0, 151.8, 150.0, 149.3, 147.0, 142.4, 141.8, 136.8, 135.8, 131.1, 130.2, 129.9, 129.3, 129.0, 128.8, 128.0, 127.1, 127.0, 126.4, 126.0, 120.4, 112.7, 109.5, 108.8, 102.5, 101.7, 93.7, 78.3, 58.5, 37.1; MS (ES+) m/z 557.4 (M+1).

Example 4.14

Synthesis of 4'-pyrimidin-5-yl-1'-{[5-(trifluoromethyl)-2-furyl]methyl}-5,6-dihydrospiro[benzo[1,2-b:5,4-b']difuran-3,3'-indol]-2'(1'H)-one A mixture of 4'-bromo-1'-{[5-(trifluoromethyl)-2-furyl]methyl}-5,6-dihydrospiro[benzo[1,2-b:5,4-b']difuran-3,3'-indol]-2'(1'H)-one (0.11 g, 0.21 mmol), pyrimidine-5-boronic acid (0.04 g, 0.33 mmol), tetrakis(triphenylphosphine)palladium(0) (0.03 g, 0.02 mmol), 2.00 M sodium carbonate (1.00 mL) and 1,2-dimethoxyethane (10.0 mL) was heated at reflux for 16 h under nitrogen. After the organic solvent was evaporated in vacuo, the black residue was extracted with ethyl acetate (3×35.0 mL). The combined organic layers was dried over anhydrous sodium sulfate and filtered. The filtrate was concentrated in vacuo. The residue was subjected to column chromatography eluting with ethyl acetate:hexane (35%) to afford the title compound (0.03 g, 26%): mp 263-266° C.; ¹H NMR (300 MHz, CDCl₃) δ 9.10 (s, 1H), 8.14 (s, 2H), 7.39 (t, 1H), 7.10, (d, 1H), 6.87 (d, 1H), 6.76 (s, 1H), 6.51 (s, 1H), 6.46 (s, 1H), 6.07 (s, 1H), 5.03 (ABq, 2H), 4.62-4.48 (m, 21-1), 4.58 (ABq, 2H), 3.01 (t, 2H); ¹³C NMR (75 MHz, CDCl$_3$) δ 177.3, 162.5, 161.0, 157.4, 155.9, 151.6, 142.2, 141.7, 132.8, 132.3, 131.3, 129.3, 125.7, 120.6, 120.2, 118.3, 117.0, 112.7, 109.7, 109.4, 93.5, 78.9, 72.5, 57.7, 37.1, 28.9; MS (ES+) m/z 506.5 (M+1).

Example 4.15

Synthesis of tert-butyl 4-[(2'-oxo-4'-pyrimidin-5-ylspiro[furo[2,3-f][1,3]benzodioxole-7,3'-indol]-1'(2'H)-yl)methyl]piperidine-1-carboxylate Following the procedure as described in EXAMPLE 4.14, and making non-critical variations using tert-butyl 4-[(4'-bromo-2'-oxospiro[furo[2,3-f][1,3]benzodioxole-7,3'-indol]-1'(2'H)-yl)methyl]piperidine-1-carboxylate to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, the title compound was obtained (91%) as a colorless solid: $^1$H NMR (300 MHz, CDCl$_3$) δ 9.13 (s, 1H), 8.23 (s, 2H), 8.24-7.37 (m, 5H), 7.01 (d, 1H), 6.85 (d, 1H), 6.14 (dd2H), 5.91 (d, 2H), 4.55 (ABq, 2H), 4.15 (d, 2H), 3.84-3.58 (m, 3H), 2.69 (t, 2H), 1.44 (s, 9H); MS (ES+) m/z 557.5 (M+1).

Example 4.16

Synthesis of 1'-methyl-4'-pyrimidin-5-ylspiro[furo[2,3-f][1,3]benzodioxole-7,3'-indol]-2'(1'H)-one Following the procedure as described in EXAMPLE 4.14, and making non-critical variations using 4'-bromo-1-methylspiro[furo[2,3-f][1,3]benzodioxole-7,3'-indol]-2'(1'H)-one to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, the title compound was obtained (22%) as a colorless solid: $^1$H NMR (300 MHz, CDCl$_3$) δ 9.10 (s, 1H), 8.18 (s, 2H), 7.41 (t, 1H), 7.00 (d, 1H), 6.85 (d, 1H), 6.20 (s, 1H), 6.12 (s, 1H), 5.87 (d, 2H), 4.54 (ABq, 2H), 3.32 (s, 1H); MS (ES+) m/z 374.5 (M+1).

Example 4.17

Synthesis of 4'-(3-furyl)-1'-methylspiro[furo[2,3-f][1,3]benzodioxole-7,3'-indol]-2'(1'H)-one Following the procedure as described in EXAMPLE 4.14, and making non-critical variations using 4'-bromo-1'-methylspiro[furo[2,3-f][1,3]benzodioxole-7,3'-indol]-2'(1'H)-one to replace 4'-bromo-1'-{[5-(trifluoromethyl)-2-furyl]methyl}-5,6-dihydrospiro[benzo[1,2-b:5,4-b']difuran-3,3'-indol]-2'(1'H)one, and 3-furanboronic acid to replace pyrimidine-5-boronic acid, the title compound was obtained (81%) as a colorless solid: $^1$H NMR (300 MHz, CDCl$_3$) δ 7.40-7.28 (m, 2H), 7.05-6.95 (m, 1H), 6.90-6.78 (m, 2H), 6.45-6.38 (m, 1H), 6.23-6.16 (m, 1H), 6.07-5.97 (m, 1H), 5.97-5.80 (m, 2H), 4.75-4.50 (m, 2H), 3.30-3.22 (m, 3H); MS (ES+) m/z 362.4 (M+1).

Example 4.18

Synthesis of 4'-(6-fluoropyridin-3-yl)-1'-methylspiro[furo[2,3-f][1,3]benzodioxole-7,3'-indol]-2'(1'H)-one Following the procedure as described in EXAMPLE 4.14, and making non-critical variations using 4'-bromo-1'-methylspiro[furo[2,3-f][1,3]benzodioxole-7,3'-indol]-2'(1'H)-one to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, and (6-fluoropyridin-3-yl)boronic acid to replace pyrimidine-5-boronic acid, the title compound was obtained (100%) as a colorless solid: $^1$H NMR (300 MHz, CDCl$_3$) δ 7.75-7.65 (m, 1H), 7.42-7.30 (m, 1H), 7.19-7.05 (m, 1H), 7.00-6.90 (m, 1H), 6.90-6.80 (m, 1H), 6.78-6.64 (m, 1H), 6.24-6.12 (m, 2H), 5.92-5.79 (m, 2H), 4.74-4.63 (m, 1H), 4.40-4.29 (m, 1H), 3.34-3.26 (m, 3H); MS (ES+) m/z 391.4 (M+1).

Example 4.19

Synthesis of 1'-(2-cyclopropylethyl)-4'-quinolin-3-ylspiro[furo[2,3-f][1,3]benzodioxole-7,3'-indol]-2'(1'H)-one Following the procedure as described in EXAMPLE 4, and making non-critical variations using 4'-bromo-1'-(2-cyclopropylethyl)spiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and quinolin-3-ylboronic acid to replace [6-(dimethylamino)pyridin-3-yl]boronic acid, the title compound was obtained: MS (ES+) m/z 477.5 (M+1)

Example 4.20

Synthesis of N-(2-fluorophenyl)-2-(2'-oxo-4'-pyrimidin-5-yl-5,6-dihydrospiro[benzo[1,2-b:5,4-b']difuran-3,3'-indol]-1'(2'H)-yl)acetamide Following the procedure as described in EXAMPLE 4, and making non-critical variations using 2-(4'-bromo-2'-oxo-5,6-dihydrospiro[benzo[1,2-b:5,4-b']difuran-3,3'-indol]-1'(2'H)-yl)-N-(2-fluorophenyl)acetamide to replace 4'-bromo-1'-pentylspiro[furo[2,3-f][1,3]benzodioxole-7,3'-indol]-2'(1'H)-one, and pyrimidine-5-boronic acid to replace [6-(dimethylamino)pyridin-3-yl]boronic acid, the title compound was obtained (53%) as a colorless solid: mp 229-230° C.; $^1$H NMR (300 MHz, CDCl$_3$) δ 9.10 (s, 1H), 8.26-8.15 (m, 3H), 7.98 (s, 1H), 7.41 (t, 1H), 7.15-7.05 (m, 4H), 6.89 (d, 1H), 6.68 (s, 1H), 6.06 (s, 1H), 4.81-4.76 (m, 2H), 4.59-4.42 (m, 4H), 3.00 (t, 2H); $^{13}$C NMR (75 MHz, CDCl$_3$) δ 178.2, 164.4, 162.5, 161.0, 157.0, 155.8, 141.8, 132.6, 131.1, 129.4, 125.8, 125.5, 125.4, 125.2, 125.1, 124.7, 121.9, 120.6, 119.9, 118.7, 115.1, 114.8, 109.5, 93.4, 79.0, 72.4, 57.8, 44.9, 28.9; MS (ES+) m/z 509.5 (M+1).

Example 5

Synthesis of 4'-[(6-methoxypyridin-3-yl)amino]-1'-pentylspiro[furo[2,3-f][1,3]benzodioxole-7,3'-indol]-2'(1'H)-one To an oven-dried 2-neck 25 mL round bottom flask equipped with a condenser was charged with 4'-bromo-1'-pentylspiro-(6,7-dihydrofuro-[2,3-f][1,3]benzodioxole-7,3'-indole)-2'-(1H)-one (50.5 mg, 0.12 mmol), 5-amino-2-methoxypyridine (22.3 mg, 0.18 mmol), Pd$_2$(dba)$_3$ (10 mole %), BINAP (10 mole %) and sodium methoxide (12.9 mg, 0.24 mmol). The flask was flushed with nitrogen for 5 min followed by the addition of degassed toluene (5.00 mL). The reaction mixture was heated at reflux for 16 h. After cooling to ambient temperature, the reaction mixture was diluted with ethyl acetate (20.0 mL) and washed with saturated ammonium chloride (10.0 mL), brine (10.0 mL), dried over anhydrous sodium sulfate and filtered. The filtrate was concentrated in vacuo to dryness. The brown residue was subjected to column chromatography eluting with ethyl acetate-hexane (20% to 50%) to yield the title compound (30.0 mg) in 54% yield: MS (ES+), m/z 474.3 (M+1).

Example 5.1

The compounds listed in the following table were synthesized using similar conditions as described in EXAMPLE 5. As previously noted, the compound numbers listed below do not correspond to the compound numbers provided in the general Reaction Schemes above.

| Compound Number | Name | MS (m/z, M + 1) |
|---|---|---|
| 198 | 4'-[(3,5-difluorophenyl)amino]-1'-pentylspiro[furo[2,3-f][1,3]benzodioxole-7,3'-indol]-2'(1'H)-one | 479.1 |
| 199 | 4'-[(4,6-dimethylpyridin-2-yl)amino]-1'-pentylspiro[furo[2,3-f][1,3]benzodioxole-7,3'-indol]-2'(1'H)-one | 473.3 (M + 2) |
| 200 | 4'-[(4-methyl-1,3-thiazol-2-yl)amino]-1'-pentylspiro[furo[2,3-f][1,3]benzodioxole-7,3'-indol]-2'(1'H)-one | 464.1 |

Example 5.2

Synthesis of 4'-bromo-1'-pentylspiro[furo[2,3-f][1,3]benzodioxole-7,3'-indol]-2'(1'H)-one A mixture of 4'-bromo-1'-pentylspiro[furo[2,3-f][1,3]benzodioxole-7,3'-indol]-2'(1'H)-one (0.05 g, 0.12 mmol), 3-(trifluoromethyl)aniline (0.03 g, 0.17 mmol), $Pd_2(dba)_3$ (0.02 g, 0.01 mmol), xanthphos (0.007 g, 0.01 mmol), and sodium tert-butoxide (0.02 g, 0.17 mmol) in toluene (5.00 mL) was heated at 110° for 4 days. After cooling down to ambient temperature, the mixture was extracted with ethyl acetate. The organic phase was dried over anhydrous sodium sulfate and filtered. The filtrate was concentrated in vacuo to dryness. The residue was subjected to column chromatography eluting with ethyl acetate/hexane to give the title compound (0.06 g, 71%) as a solid: MS (ES+) m/z 511.5 (M+1).

Example 5.3

The compounds listed in the following table were synthesized using similar conditions as described in EXAMPLE 5.2. As previously noted, the compound numbers listed below do not correspond to the compound numbers provided in the general Reaction Schemes above.

| Compound Number | Name | MS (m/z, M + 1) |
|---|---|---|
| 201 | 4'-morpholino-1'-pentyl-6H-spiro[benzofuro[6,5-d][1,3]dioxole-7,3'-indolin]-2'-one | 437.5 |
| 202 | 4'-(4-methylpiperazin-1-yl)-1'-pentyl-6H-spiro[benzofuro[6,5-d][1,3]dioxole-7,3'-indolin]-2'-one | 450.5 |
| 203 | 1'-pentyl-4'-(pyrimidin-4-ylamino)-6H-spiro[benzofuro[6,5-d][1,3]dioxole-7,3'-indolin]-2'-one | 445.5 |
| 204 | 1'-pentyl-4'-(pyridin-3-ylamino)-6H-spiro[benzofuro[6,5-d][1,3]dioxole-7,3'-indolin]-2'-one | 444.5 |
| 205 | 4'-(4-chloro-2-(trifluoromethyl)phenylamino)-1'-pentyl-6H-spiro[benzofuro[6,5-d][1,3]dioxole-7,3'-indolin]-2'-one | 545.5 |
| 206 | 1'-pentyl-4'-(pyrimidin-2-ylamino)-6H-spiro[benzofuro[6,5-d][1,3]dioxole-7,3'-indolin]-2'-one | 444.5 |
| 207 | 4'-(benzo[d][1,3]dioxol-5-ylamino)-1'-pentyl-6H-spiro[benzofuro[6,5-d][1,3]dioxole-7,3'-indolin]-2'-one | 487.5 |
| 208 | 4'-(3-fluorophenylamino)-1'-pentyl-6H-spiro[benzofuro[6,5-d][1,3]dioxole-7,3'-indolin]-2'-one | 461.5 |
| 209 | 4'-(naphthalen-2-ylamino)-1'-pentyl-6H-spiro[benzofuro[6,5-d][1,3]dioxole-7,3'-indolin]-2'-one | 493.5 |
| 210 | 4'-(2-methoxyphenylamino)-1'-pentyl-6H-spiro[benzofuro[6,5-d][1,3]dioxole-7,3'-indolin]-2'-one | 473.2 |
| 211 | 4'-(4-methylthiazol-2-ylamino)-1'-pentyl-6H-spiro[benzofuro[6,5-d][1,3]dioxole-7,3'-indolin]-2'-one | 464.1 |
| 212 | 4'-(4,6-dimethylpyridin-2-ylamino)-1'-pentyl-6H-spiro[benzofuro[6,5-d][1,3]dioxole-7,3'-indolin]-2'-one | 473.3 |
| 213 | 4'-(3,5-difluorophenylamino)-1'-pentyl-6H-spiro[benzofuro[6,5-d][1,3]dioxole-7,3'-indolin]-2'-one | 479.1 |
| 214 | 4'-(6-methoxypyridin-3-ylamino)-1'-pentyl-6H-spiro[benzofuro[6,5-d][1,3]dioxole-7,3'-indolin]-2'-one | 474.3 |

Example 6

Synthesis of 2-[(2'-oxospiro[furo[2,3-f][1,3]benzodioxole-7,3'-indol]-1'(2'H)-yl)methyl]benzoic acid To a solution of methyl 2-[(2'-oxospiro[furo[2,3-f][1,3]benzodioxole-7,3'-indol]-1'(2'H)-yl)methyl]benzoate (7.56 g, 17.6 mmol) in a mixture of THF/water (2/1 v/v, 180 mL) was added lithium hydroxide monohydrate (1.48 g, 35.2 mmol). The resulting mixture was stirred at ambient temperature overnight and concentrated in vacuo followed by the addition of water (150 mL). The mixture was extracted with of ethyl acetate/hexanes, 1/3 v/v, 50.0 mL). The water layer was acidified with 1 N HCl solution until the pH value reached 2. The precipitate was filtered and dried to give the title compound (7.30 g, 100%) as a white solid: mp >250° C.; $^1$H NMR (300 MHz, DMSO-d$_6$) δ 13.25 (s, 1H), 7.95 (dd, 1H), 7.49 (dt, 1H), 7.37 (t, 1H), 7.24-7.16 (m, 2H), 7.11-6.98 (m, 2H), 6.80 (d, 1H), 6.68 (s, 1H), 6.36 (s, 1H), 5.91 (s, 2H), 5.37-5.19 (m, 2H), 4.88-4.68 (m, 2H); $^{13}$C NMR (75 MHz, DMSO-d$_6$) δ 177.6, 168.8, 156.0, 148.8, 143.0, 142.3, 137.6, 133.1, 132.1, 131.5, 129.9, 129.4, 127.7, 126.5, 124.2, 123.6, 120.1, 109.8, 103.8, 101.9, 93.8, 80.5, 58.0, 42.6.

Example 7

Synthesis of N-[2-(4-chlorophenyl)ethyl]-2-[(2'-oxospiro[furo[2,3-f][1,3]benzodioxole-7,3'-indol]-1' (2'H)-yl)methyl]benzamide

A. Preparation of stock solution of 2-[(2'-oxospiro[furo[2,3-f][1,3]benzodioxole-7,3'-indol]-1'(2'H)-yl)methyl]benzoyl chloride A solution of 2-[(2'-oxospiro[furo[2,3-f][1,3]benzodioxole-7,3'-indol]-1'(2'H)-yl)methyl]benzoic acid (0.21 g, 0.50 mmol), oxalyl chloride (0.09 mL, 1.00 mmol) and one drop of DMF in toluene (10.0 mL) was stirred at ambient temperature overnight. The mixture was concentrated under vacuum to afford a solid, which was dissolved in dichloromethane (5.00 mL) to form an acid chloride stock solution (0.10 mmol/mL) for use.

B. Synthesis of N-[2-(4-chlorophenyl)ethyl]-2-[(2'-oxospiro[furo[2,3-f][1,3]benzodioxole-7,3'-indol]-1' (2'H)-yl)methyl]benzamide The acid chloride stock solution obtained above (1.00 mL, 0.10 mmol) was added to a mixture of 2-(4-chlorophenyl)ethylamine (0.02 g, 0.13 mmol), triethylamine (0.14 mL, 1.00 mmol) in dichloromethane (1.00 mL). The resulting mixture was stirred at ambient temperature overnight and diluted with dichloromethane (5.00 mL). The mixture was washed with 1 N HCl, saturated sodium bicarbonate solution, dried over sodium sulfate and filtered. The filtrate was concentrated under vacuum to dryness to give the title compound as a white powder: $^1$H NMR (300 MHz, CDCl$_3$) δ 7.70-7.13 (m, 10H), 7.10-6.96 (m, 2H), 6.65-6.54 (br, 1H), 6.50 (s, 1H), 6.11 (s, 1H), 5.89-5.82 (m, 2H), 5.09-4.88 (m, 3H), 4.68 (d, 1H), 3.79-3.66 (m, 2H), 2.93 (t, 2H); MS (ES+), m/z 553.3 (M+1), 575.3 (M+23).

Example 7.1

The compounds listed in the following table were synthesized using similar conditions as described in EXAMPLE 7. As previously noted, the compound numbers listed below do not correspond to the compound numbers provided in the general Reaction Schemes above.

| Compound Number | Name | MS (m/z, M + 1) |
|---|---|---|
| 215 | N-(3-methylbutyl)-2-[(2'-oxospiro[furo[2,3-f][1,3]benzodioxole-7,3'-indol]-1'(2'H)-yl)methyl]benzamide | 485.3 |
| 216 | 2-[(2'-oxospiro[furo[2,3-f][1,3]benzodioxole-7,3'-indol]-1'(2'H)-yl)methyl]-N-phenylbenzamide | 491.2 |
| 217 | N,N-diisopropyl-2-[(2'-oxospiro[furo[2,3-f][1,3]benzodioxole-7,3'-indol]-1'(2'H)-yl)methyl]benzamide | 499.4 |
| 218 | N-(3-fluorophenyl)-2-[(2'-oxospiro[furo[2,3-f][1,3]benzodioxole-7,3'-indol]-1'(2'H)-yl)methyl]benzamide | 509.3 |
| 219 | N-(4-chlorobenzyl)-2-[(2'-oxospiro[furo[2,3-f][1,3]benzodioxole-7,3'-indol]-1'(2'H)-yl)methyl]benzamide | 539.3 |
| 220 | N-butyl-2-[(2'-oxospiro[furo[2,3-f][1,3]benzodioxole-7,3'-indol]-1'(2'H)-yl)methyl]benzamide | 471.3 |
| 221 | 2-[(2'-oxospiro[furo[2,3-f][1,3]benzodioxole-7,3'-indol]-1'(2'H)-yl)methyl]-N-pentylbenzamide | 485.3 |
| 222 | N-hexyl-2-[(2'-oxospiro[furo[2,3-f][1,3]benzodioxole-7,3'-indol]-1'(2'H)-yl)methyl]benzamide | 499.4 |
| 223 | 2-[(2'-oxospiro[furo[2,3-f][1,3]benzodioxole-7,3'-indol]-1'(2'H)-yl)methyl]-N-propylbenzamide | 457.3 |
| 224 | N-isopropyl-2-[(2'-oxospiro[furo[2,3-f][1,3]benzodioxole-7,3'-indol]-1'(2'H)-yl)methyl]benzamide | 457.3 |
| 225 | N-cyclohexyl-2-[(2'-oxospiro[furo[2,3-f][1,3]benzodioxole-7,3'-indol]-1'(2'H)-yl)methyl]benzamide | 497.3 |
| 226 | N-cyclopentyl-2-[(2'-oxospiro[furo[2,3-f][1,3]benzodioxole-7,3'-indol]-1'(2'H)-yl)methyl]benzamide | 483.3 |
| 227 | N-heptyl-2-[(2'-oxospiro[furo[2,3-f][1,3]benzodioxole-7,3'-indol]-1'(2'H)-yl)methyl]benzamide | 513.4 |
| 228 | N-(4-fluorophenyl)-2-[(2'-oxospiro[furo[2,3-f][1,3]benzodioxole-7,3'-indol]-1'(2'H)-yl)methyl]benzamide | 509.1 |

-continued

| Compound Number | Name | MS (m/z, M + 1) |
|---|---|---|
| 229 | N-(3-fluorobenzyl)-2-[(2'-oxospiro[furo[2,3-f][1,3]benzodioxole-7,3'-indol]-1'(2'H)-yl)methyl]benzamide | 523.1 |
| 230 | N-(3-chlorophenyl)-2-[(2'-oxospiro[furo[2,3-f][1,3]benzodioxole-7,3'-indol]-1'(2'H)-yl)methyl]benzamide | 525.0 |
| 231 | N-(2-fluorophenyl)-2-[(2'-oxospiro[furo[2,3-f][1,3]benzodioxole-7,3'-indol]-1'(2'H)-yl)methyl]benzamide | 509.1 |
| 232 | N-(2-ethylphenyl)-2-[(2'-oxospiro[furo[2,3-f][1,3]benzodioxole-7,3'-indol]-1'(2'H)-yl)methyl]benzamide | 519.1 |
| 233 | N-(4-ethylphenyl)-2-[(2'-oxospiro[furo[2,3-f][1,3]benzodioxole-7,3'-indol]-1'(2'H)-yl)methyl]benzamide | 519.2 |
| 234 | N-(3-methylphenyl)-2-[(2'-oxospiro[furo[2,3-f][1,3]benzodioxole-7,3'-indol]-1'(2'H)-yl)methyl]benzamide | 505.2 |
| 235 | N-(2,3-dimethylphenyl)-2-[(2'-oxospiro[furo[2,3-f][1,3]benzodioxole-7,3'-indol]-1'(2'H)-yl)methyl]benzamide | 519.2 |
| 236 | N-(3,5-dimethylphenyl)-2-[(2'-oxospiro[furo[2,3-f][1,3]benzodioxole-7,3'-indol]-1'(2'H)-yl)methyl]benzamide | 519.1 |
| 237 | 1'-[2-(piperidin-1-ylcarbonyl)benzyl]spiro[furo[2,3-f][1,3]benzodioxole-7,3'-indol]-2'(1'H)-one | 483.1 |
| 238 | N-isobutyl-2-[(2'-oxospiro[furo[2,3-f][1,3]benzodioxole-7,3'-indol]-1'(2'H)-yl)methyl]benzamide | 471.2 |
| 239 | N-(2-chlorobenzyl)-2-[(2'-oxospiro[furo[2,3-f][1,3]benzodioxole-7,3'-indol]-1'(2'H)-yl)methyl]benzamide | 539.1 |
| 240 | N-(2,6-dimethylphenyl)-2-[(2'-oxospiro[furo[2,3-f][1,3]benzodioxole-7,3'-indol]-1'(2'H)-yl)methyl]benzamide | 519.1 |
| 241 | N-(2-methoxyphenyl)-2-[(2'-oxospiro[furo[2,3-f][1,3]benzodioxole-7,3'-indol]-1'(2'H)-yl)methyl]benzamide | 521.1 |
| 242 | N-(3-methoxypropyl)-2-[(2'-oxospiro[furo[2,3-f][1,3]benzodioxole-7,3'-indol]-1'(2'H)-yl)methyl]benzamide | 487.2 |
| 243 | N-[2-(4-methylphenyl)ethyl]-2-[(2'-oxospiro[furo[2,3-f][1,3]benzodioxole-7,3'-indol]-1'(2'H)-yl)methyl]benzamide | 533.2 |
| 244 | 2-[(2'-oxospiro[furo[2,3-f][1,3]benzodioxole-7,3'-indol]-1'(2'H)-yl)methyl]-N-(tetrahydrofuran-2-ylmethyl)benzamide | 499.2 |
| 245 | N,N-dibenzyl-2-[(2'-oxospiro[furo[2,3-f][1,3]benzodioxole-7,3'-indol]-1'(2'H)-yl)methyl]benzamide | 595.2 |
| 246 | 2-[(2'-oxospiro[furo[2,3-f][1,3]benzodioxole-7,3'-indol]-1'(2'H)-yl)methyl]-N-(3-phenylpropyl)benzamide | 533.2 |
| 247 | N-[2-(3-chlorophenyl)ethyl]-2-[(2'-oxospiro[furo[2,3-f][1,3]benzodioxole-7,3'-indol]-1'(2'H)-yl)methyl]benzamide | 553.1 |
| 248 | N-[2-(4-fluorophenyl)ethyl]-2-[(2'-oxospiro[furo[2,3-f][1,3]benzodioxole-7,3'-indol]-1'(2'H)-yl)methyl]benzamide | 537.1 |
| 249 | N-(4-fluorobenzyl)-2-[(2'-oxospiro[furo[2,3-f][1,3]benzodioxole-7,3'-indol]-1'(2'H)-yl)methyl]benzamide | 523.1 |
| 250 | N-(3-ethoxypropyl)-2-[(2'-oxospiro[furo[2,3-f][1,3]benzodioxole-7,3'-indol]-1'(2'H)-yl)methyl]benzamide | 501.1 |
| 251 | N-hexyl-N-methyl-2-[(2'-oxospiro[furo[2,3-f][1,3]benzodioxole-7,3'-indol]-1'(2'H)-yl)methyl]benzamide | 513.2 |
| 252 | N-(3-isopropoxypropyl)-2-[(2'-oxospiro[furo[2,3-f][1,3]benzodioxole-7,3'-indol]-1'(2'H)-yl)methyl]benzamide | 515.2 |
| 253 | N-(4-methoxybenzyl)-2-[(2'-oxospiro[furo[2,3-f][1,3]benzodioxole-7,3'-indol]-1'(2'H)-yl)methyl]benzamide | 535.2 |
| 254 | N-(cyclopropylmethyl)-2-[(2'-oxospiro[furo[2,3-f][1,3]benzodioxole-7,3'-indol]-1'(2'H)-yl)methyl]benzamide | 469.1 |
| 255 | N-(2-ethoxyethyl)-2-[(2'-oxospiro[furo[2,3-f][1,3]benzodioxole-7,3'-indol]-1'(2'H)-yl)methyl]benzamide | 487.2 |

-continued

| Compound Number | Name | MS (m/z, M + 1) |
|---|---|---|
| 256 | N-(cyclohexylmethyl)-2-[(2'-oxospiro[furo[2,3-f][1,3]benzodioxole-7,3'-indol]-1'(2'H)-yl)methyl]benzamide | 511.2 |
| 257 | N-(2-furylmethyl)-2-[(2'-oxospiro[furo[2,3-f][1,3]benzodioxole-7,3'-indol]-1'(2'H)-yl)methyl]benzamide | 495.0 |
| 258 | N-(2,4-dimethylphenyl)-2-[(2'-oxospiro[furo[2,3-f][1,3]benzodioxole-7,3'-indol]-1'(2'H)-yl)methyl]benzamide | 519.2 |
| 259 | N-(4-cyanophenyl)-2-[(2'-oxospiro[furo[2,3-f][1,3]benzodioxole-7,3'-indol]-1'(2'H)-yl)methyl]benzamide | 516.2 |
| 260 | N-(3,5-dichlorophenyl)-2-[(2'-oxospiro[furo[2,3-f][1,3]benzodioxole-7,3'-indol]-1'(2'H)-yl)methyl]benzamide | 559.0 |
| 261 | N-(3-fluoro-2-methylphenyl)-2-[(2'-oxospiro[furo[2,3-f][1,3]benzodioxole-7,3'-indol]-1'(2'H)-yl)methyl]benzamide | 523.1 |
| 262 | N-(4-methoxyphenyl)-2-[(2'-oxospiro[furo[2,3-f][1,3]benzodioxole-7,3'-indol]-1'(2'H)-yl)methyl]benzamide | 521.1 |
| 263 | N-(5-chloro-2-methylphenyl)-2-[(2'-oxospiro[furo[2,3-f][1,3]benzodioxole-7,3'-indol]-1'(2'H)-yl)methyl]benzamide | 539.1 |
| 264 | 2-[(2'-oxospiro[furo[2,3-f][1,3]benzodioxole-7,3'-indol]-1'(2'H)-yl)methyl]-N-[3-(trifluoromethyl)phenyl]benzamide | 559.1 |
| 265 | 2-[(2'-oxospiro[furo[2,3-f][1,3]benzodioxole-7,3'-indol]-1'(2'H)-yl)methyl]-N-(pyridin-4-ylmethyl)benzamide | 506.1 |
| 266 | N-cyclobutyl-2-[(2'-oxospiro[furo[2,3-f][1,3]benzodioxole-7,3'-indol]-1'(2'H)-yl)methyl]benzamide | 469.1 |
| 267 | N-methyl-2-[(2'-oxospiro[furo[2,3-f][1,3]benzodioxole-7,3'-indol]-1'(2'H)-yl)methyl]benzamide | 429.1 |
| 268 | N-ethyl-2-[(2'-oxospiro[furo[2,3-f][1,3]benzodioxole-7,3'-indol]-1'(2'H)-yl)methyl]benzamide | 443.1 |
| 269 | 2-[(2'-oxospiro[furo[2,3-f][1,3]benzodioxole-7,3'-indol]-1'(2'H)-yl)methyl]-N-(2,2,2-trifluoroethyl)benzamide | 497.1 |
| 270 | N-(2,2-diphenylethyl)-2-[(2'-oxospiro[furo[2,3-f][1,3]benzodioxole-7,3'-indol]-1'(2'H)-yl)methyl]benzamide | 595.2 |
| 271 | N-[2-(diethylamino)ethyl]-2-[(2'-oxospiro[furo[2,3-f][1,3]benzodioxole-7,3'-indol]-1'(2'H)-yl)methyl]benzamide | 514.2 |
| 272 | N-(3,3-dimethylbutyl)-2-[(2'-oxospiro[furo[2,3-f][1,3]benzodioxole-7,3'-indol]-1'(2'H)-yl)methyl]benzamide | 499.2 |
| 273 | N-(2-ethylbutyl)-2-[(2'-oxospiro[furo[2,3-f][1,3]benzodioxole-7,3'-indol]-1'(2'H)-yl)methyl]benzamide | 499.2 |
| 274 | 2-[(2'-oxospiro[furo[2,3-f][1,3]benzodioxole-7,3'-indol]-1'(2'H)-yl)methyl]-N-(2-pyrrolidin-1-ylethyl)benzamide | 512.4 |
| 275 | N-[(1-ethylpyrrolidin-2-yl)methyl]-2-[(2'-oxospiro[furo[2,3-f][1,3]benzodioxole-7,3'-indol]-1'(2'H)-yl)methyl]benzamide | 526.4 |
| 276 | 2-[(2'-oxospiro[furo[2,3-f][1,3]benzodioxole-7,3'-indol]-1'(2'H)-yl)methyl]-N-(2-piperidin-1-ylethyl)benzamide | 526.5 |
| 277 | N-(2-morpholin-4-ylethyl)-2-[(2'-oxospiro[furo[2,3-f][1,3]benzodioxole-7,3'-indol]-1'(2'H)-yl)methyl]benzamide | 528.4 |
| 278 | N-[(1S)-1-cyclohexylethyl]-2-[(2'-oxospiro[furo[2,3-f][1,3]benzodioxole-7,3'-indol]-1'(2'H)-yl)methyl]benzamide | 525.5 |
| 279 | N-(2-fluoro-5-methylphenyl)-2-[(2'-oxospiro[furo[2,3-f][1,3]benzodioxole-7,3'-indol]-1'(2'H)-yl)methyl]benzamide | 523.4 |
| 280 | N-(2,4-difluorophenyl)-2-[(2'-oxospiro[furo[2,3-f][1,3]benzodioxole-7,3'-indol]-1'(2'H)-yl)methyl]benzamide | 527.3 |
| 281 | 2-[(2'-oxospiro[furo[2,3-f][1,3]benzodioxole-7,3'-indol]-1'(2'H)-yl)methyl]-N-(4-propylphenyl)benzamide | 533.4 |
| 282 | N-(3,3-diphenylpropyl)-2-[(2'-oxospiro[furo[2,3-f][1,3]benzodioxole-7,3'-indol]-1'(2'H)-yl)methyl]benzamide | 609.4 |
| 283 | N-(2-methoxyethyl)-2-[(2'-oxospiro[furo[2,3-f][1,3]benzodioxole-7,3'-indol]-1'(2'H)-yl)methyl]benzamide | 473.4 |

-continued

| Compound Number | Name | MS (m/z, M + 1) |
|---|---|---|
| 284 | N-(2,5-difluorobenzyl)-2-[(2'-oxospiro[furo[2,3-f][1,3]benzodioxole-7,3'-indol]-1'(2'H)-yl)methyl]benzamide | 541.3 |
| 285 | 2-[(2'-oxospiro[furo[2,3-f][1,3]benzodioxole-7,3'-indol]-1'(2'H)-yl)methyl]-N-(2-thienylmethyl)benzamide | 511.4 |
| 286 | N-[4-chloro-2-(trifluoromethyl)phenyl]-2-[(2'-oxospiro[furo[2,3-f][1,3]benzodioxole-7,3'-indol]-1'(2'H)-yl)methyl]benzamide | 593.3 |
| 287 | N-[2-(4-methoxyphenyl)ethyl]-2-[(2'-oxospiro[furo[2,3-f][1,3]benzodioxole-7,3'-indol]-1'(2'H)-yl)methyl]benzamide | 549.4 |
| 288 | N-(3,5-dichlorobenzyl)-2-[(2'-oxospiro[furo[2,3-f][1,3]benzodioxole-7,3'-indol]-1'(2'H)-yl)methyl]benzamide | 573.2 |
| 289 | N-(3-chlorobenzyl)-2-[(2'-oxospiro[furo[2,3-f][1,3]benzodioxole-7,3'-indol]-1'(2'H)-yl)methyl]benzamide | 539.3 |
| 290 | 2-[(2'-oxospiro[furo[2,3-f][1,3]benzodioxole-7,3'-indol]-1'(2'H)-yl)methyl]-N-[2-(2-thienyl)ethyl]benzamide | 525.4 |
| 291 | N-(2,3-dihydro-1H-inden-1-yl)-2-[(2'-oxospiro[furo[2,3-f][1,3]benzodioxole-7,3'-indol]-1'(2'H)-yl)methyl]benzamide | 531.4 |
| 292 | 2-[(2'-oxospiro[furo[2,3-f][1,3]benzodioxole-7,3'-indol]-1'(2'H)-yl)methyl]-N-[4-(trifluoromethyl)benzyl]benzamide | 573.3 |
| 293 | N-[4-fluoro-2-(trifluoromethyl)phenyl]-2-[(2'-oxospiro[furo[2,3-f][1,3]benzodioxole-7,3'-indol]-1'(2'H)-yl)methyl]benzamide | 577.5 |
| 294 | 2-[(2'-oxospiro[furo[2,3-f][1,3]benzodioxole-7,3'-indol]-1'(2'H)-yl)methyl]-N-(pyridin-3-ylmethyl)benzamide | 506.4 |
| 295 | 2-[(2'-oxospiro[furo[2,3-f][1,3]benzodioxole-7,3'-indol]-1'(2'H)-yl)methyl]-N-[2-(trifluoromethyl)benzyl]benzamide | 573.3 |
| 296 | N-(3-methylpyridin-2-yl)-2-[(2'-oxospiro[furo[2,3-f][1,3]benzodioxole-7,3'-indol]-1'(2'H)-yl)methyl]benzamide | 506.4 |
| 297 | N-(1-benzylpiperidin-4-yl)-2-[(2'-oxospiro[furo[2,3-f][1,3]benzodioxole-7,3'-indol]-1'(2'H)-yl)methyl]benzamide | 588.4 |
| 298 | 2-[(2'-oxospiro[furo[2,3-f][1,3]benzodioxole-7,3'-indol]-1'(2'H)-yl)methyl]-N-[2-(trifluoromethyl)phenyl]benzamide | 559.4 |
| 299 | N-[(1R)-1-cyclohexylethyl]-2-[(2'-oxospiro[furo[2,3-f][1,3]benzodioxole-7,3'-indol]-1'(2'H)-yl)methyl]benzamide | 525.5 |
| 300 | N-(2-cyanoethyl)-2-[(2'-oxospiro[furo[2,3-f][1,3]benzodioxole-7,3'-indol]-1'(2'H)-yl)methyl]benzamide | 468.3 |
| 301 | N-(6-methoxypyridin-3-yl)-2-[(2'-oxospiro[furo[2,3-f][1,3]benzodioxole-7,3'-indol]-1'(2'H)-yl)methyl]benzamide | 522.4 |
| 302 | 2-[(2'-oxospiro[furo[2,3-f][1,3]benzodioxole-7,3'-indol]-1'(2'H)-yl)methyl]-N-1,3-thiazol-2-ylbenzamide | 498.3 |
| 303 | 2-[(2'-oxospiro[furo[2,3-f][1,3]benzodioxole-7,3'-indol]-1'(2'H)-yl)methyl]-N-1,3,4-thiadiazol-2-ylbenzamide | 499.3 |
| 304 | N-(4,6-dimethylpyridin-2-yl)-2-[(2'-oxospiro[furo[2,3-f][1,3]benzodioxole-7,3'-indol]-1'(2'H)-yl)methyl]benzamide | 520.3 |
| 305 | N-(2,3-dihydro-1H-inden-5-yl)-2-[(2'-oxospiro[furo[2,3-f][1,3]benzodioxole-7,3'-indol]-1'(2'H)-yl)methyl]benzamide | 531.4 |
| 306 | 1'-{2-[(4-pyrimidin-2-ylpiperazin-1-yl)carbonyl]benzyl}spiro[furo[2,3-f][1,3]benzodioxole-7,3'-indol]-2'(1'H)-one | 562.4 |
| 307 | 1'-(2-{[4-(1,3-benzodioxol-5-ylmethyl)piperazin-1-yl]carbonyl}benzyl)spiro[furo[2,3-f][1,3]benzodioxole-7,3'-indol]-2'(1'H)-one | 618.4 |
| 308 | N-2-adamantyl-2-[(2'-oxospiro[furo[2,3-f][1,3]benzodioxole-7,3'-indol]-1'(2'H)-yl)methyl]benzamide | 549.5 |
| 309 | N-1-adamantyl-2-[(2'-oxospiro[furo[2,3-f][1,3]benzodioxole-7,3'-indol]-1'(2'H)-yl)methyl]benzamide | 549.5 |
| 310 | N-1-naphthyl-2-[(2'-oxospiro[furo[2,3-f][1,3]benzodioxole-7,3'-indol]-1'(2'H)-yl)methyl]benzamide | 541.4 |
| 311 | N-(3,5-difluorophenyl)-2-[(2'-oxospiro[furo[2,3-f][1,3]benzodioxole-7,3'-indol]-1'(2'H)-yl)methyl]benzamide | 527.3 |

| Compound Number | Name | MS (m/z, M + 1) |
|---|---|---|
| 312 | 1'-[2-(morpholin-4-ylcarbonyl)benzyl]spiro[furo[2,3-f][1,3]benzodioxole-7,3'-indol]-2'(1'H)-one | 485.4 |
| 313 | N-[3-(dimethylamino)propyl-N-methyl-2-[(2'-oxospiro[furo[2,3-f][1,3]benzodioxole-7,3'-indol]-1'(2'H)-yl)methyl]benzamide | 514.4 |

Example 8

Synthesis of 3-[(2'-oxospiro[furo[2,3-f][1,3]benzodioxole-7,3'-indol]-1'(2'H)-yl)methyl]benzoic acid Following the procedure described in EXAMPLE 6, and making non-critical variations using methyl 3-[(2'-oxospiro[furo[2,3-f][1,3]benzodioxole-7,3'-indol]-1'(2'H)-yl)methyl]benzoate to replace methyl 2-[(2'-oxospiro[furo[2,3-f][1,3]benzodioxole-7,3'-indol]-1'(2'H)-yl)methyl]benzoate, the title compound was obtained (100%): $^1$H NMR (300 MHz, CDCl$_3$) δ 13.03 (s, 1H), 7.86-7.80 (m, 2H), 7.59-7.57 (m, 1H), 7.48-7.44 (m, 1H), 7.25-7.16 (m, 2H), 7.03-6.95 (m, 2H), 6.68 (s, 1H), 6.18 (s, 1H), 5.90 (s, 2H), 5.05 (ABq, 2H), 4.75 (ABq, 2H); $^{13}$C NMR (75 MHz, CDCl$_3$) δ 177.4, 167.5, 155.9, 148.9, 142.5, 142.3, 137.3, 132.2, 131.7, 129.6, 129.4, 128.8, 128.1, 124.3, 123.7, 120.1, 109.9, 103.3, 101.9, 93.9, 80.3, 58.0, 43.2; MS (ES+) m/z 416.2 (M+1).

Example 9

Synthesis of N-[2-(3-chlorophenyl)ethyl]-3-[(2'-oxospiro[furo[2,3-f][1,3]benzodioxole-7,3'-indol]-1'(2'H)-yl)methyl]benzamide A. Preparation of stock solution of 3-[(2'-oxospiro[furo[2,3-f][1,3]benzodioxole-7,3'-indol]-1'(2'H)-yl)methyl]benzoyl chloride To a stirred slurry of 3-[(2'-oxospiro[furo[2,3-f][1,3]benzodioxole-7,3'-indol]-1'(2'H)-yl)methyl]benzoic acid (2.08 g, 5.00 mmol) in dry chloroform (50.0 mL) was added oxalyl chloride (0.95 g, 7.5 mmol) at ambient temperature followed by 1 drop of DMF. The mixture was stirred at ambient temperature overnight and evaporated to dryness in vacuo. The residue was dissolved in dry dichlormethane (60.0 mL) to form an acid chloride stock solution for use.

B. Synthesis of N-[2-(3-Chlorophenyl)ethyl]-3-[(2'-oxospiro[furo[2,3-f][1,3]benzodioxole-7,3'-indol]-1'(2'H)-yl)methyl]benzamide To a solution of 2-(3-chlorophenyl)ethylamine (0.02 mL, 0.24 mmol) in dry dichloromethane (2.00 mL) and triethylamine (0.05 mL, 0.32 mmol) was added the acid chloride stock solution (2.0 mL, 0.081 M in dichloromethane) obtained above at ambient temperature. The mixture was stirred for 2 h, washed with 15% HCl solution and water. The organic layer was separated, dried over Na$_2$SO$_4$ and filtered. The filtrate was concentrated in vacuo to dryness. The residue was dissolved in ethyl acetate, and the product was precipitated by the addition of hexane. The white solid was filtered and collected to yield the title compound (0.06 g) in 65% yield: $^1$H NMR (300 MHz, CDCl$_3$) δ 7.97-7.95 (m, 2H), 7.53-7.50 (m, 1H), 7.45-7.40 (m, 1H), 7.21-7.15 (m, 2H), 7.04-6.99 (m, 1H), 6.73-6.71 (m, 1H), 6.52 (s, 1H), 6.20 (s, 1H), 5.86 (s, 1H), 5.18 (d, 1H), 4.72 (d, 1H), 4.80 (d, 1H), 4.69 (d, 1H), 3.89 (s, 1H); MS (ES+) m/z 554.0 (M+1).

Example 9.1

The compounds listed in the following table were synthesized using the similar procedure as described in EXAMPLE 9. As previously noted, the compound numbers listed below do not correspond to the compound numbers provided in the general Reaction Schemes above.

| Compound Number | Name | MS (m/z, M + 1) |
|---|---|---|
| 314 | N-(3-methylbutyl)-3-[(2'-oxospiro[furo[2,3-f][1,3]benzodioxole-7,3'-indol]-1'(2'H)-yl)methyl]benzamide | 485.5 |
| 315 | 3-[(2'-oxospiro[furo[2,3-f][1,3]benzodioxole-7,3'-indol]-1'(2'H)-yl)methyl]-N-phenylbenzamide | 491.5 |
| 316 | N,N-diisopropyl-3-[(2'-oxospiro[furo[2,3-f][1,3]benzodioxole-7,3'-indol]-1'(2'H)-yl)methyl]benzamide | 499.6 |
| 317 | N-(3-fluorophenyl)-3-[(2'-oxospiro[furo[2,3-f][1,3]benzodioxole-7,3'-indol]-1'(2'H)-yl)methyl]benzamide | 509.5 |
| 318 | N-(4-chlorobenzyl)-3-[(2'-oxospiro[furo[2,3-f][1,3]benzodioxole-7,3'-indol]-1'(2'H)-yl)methyl]benzamide | 540.0 |
| 319 | N-butyl-3-[(2'-oxospiro[furo[2,3-f][1,3]benzodioxole-7,3'-indol]-1'(2'H)-yl)methyl]benzamide | 471.5 |
| 320 | N-(3-fluorobenzyl)-3-[(2'-oxospiro[furo[2,3-f][1,3]benzodioxole-7,3'-indol]-1'(2'H)-yl)methyl]benzamide | 523.5 |
| 321 | N-(3-chlorophenyl)-3-[(2'-oxospiro[furo[2,3-f][1,3]benzodioxole-7,3'-indol]-1'(2'H)-yl)methyl]benzamide | 526.0 |

| Compound Number | Name | MS (m/z, M + 1) |
|---|---|---|
| 322 | N-(2-fluorophenyl)-3-[(2'-oxospiro[furo[2,3-f][1,3]benzodioxole-7,3'-indol]-1'(2'H)-yl)methyl]benzamide | 509.5 |
| 323 | N-(2-ethylphenyl)-3-[(2'-oxospiro[furo[2,3-f][1,3]benzodioxole-7,3'-indol]-1'(2'H)-yl)methyl]benzamide | 519.6 |
| 324 | N-(4-ethylphenyl)-3-[(2'-oxospiro[furo[2,3-f][1,3]benzodioxole-7,3'-indol]-1'(2'H)-yl)methyl]benzamide | 519.6 |
| 325 | N-(3-methylphenyl)-3-[(2'-oxospiro[furo[2,3-f][1,3]benzodioxole-7,3'-indol]-1'(2'H)-yl)methyl]benzamide | 505.5 |
| 326 | N-(2,3-dimethylphenyl)-3-[(2'-oxospiro[furo[2,3-f][1,3]benzodioxole-7,3'-indol]-1'(2'H)-yl)methyl]benzamide | 519.6 |
| 327 | N-(3,5-dimethylphenyl)-3-[(2'-oxospiro[furo[2,3-f][1,3]benzodioxole-7,3'-indol]-1'(2'H)-yl)methyl]benzamide | 519.6 |
| 328 | 3-[(2'-oxospiro[furo[2,3-f][1,3]benzodioxole-7,3'-indol]-1'(2'H)-yl)methyl]-N-pentylbenzamide | 485.5 |
| 329 | 3-[(2'-oxospiro[furo[2,3-f][1,3]benzodioxole-7,3'-indol]-1'(2'H)-yl)methyl]-N-propylbenzamide | 457.5 |
| 330 | N-isopropyl-3-[(2'-oxospiro[furo[2,3-f][1,3]benzodioxole-7,3'-indol]-1'(2'H)-yl)methyl]benzamide | 457.5 |
| 331 | 1'-[3-(piperidin-1-ylcarbonyl)benzyl]spiro[furo[2,3-f][1,3]benzodioxole-7,3'-indol]-2'(1'H)-one | 483.5 |
| 332 | N-isobutyl-3-[(2'-oxospiro[furo[2,3-f][1,3]benzodioxole-7,3'-indol]-1'(2'H)-yl)methyl]benzamide | 471.5 |
| 333 | N-hexyl-3-[(2'-oxospiro[furo[2,3-f][1,3]benzodioxole-7,3'-indol]-1'(2'H)-yl)methyl]benzamide | 499.6 |
| 334 | N-cyclohexyl-3-[(2'-oxospiro[furo[2,3-f][1,3]benzodioxole-7,3'-indol]-1'(2'H)-yl)methyl]benzamide | 497.6 |
| 335 | N-cyclopentyl-3-[(2'-oxospiro[furo[2,3-f][1,3]benzodioxole-7,3'-indol]-1'(2'H)-yl)methyl]benzamide | 483.5 |
| 336 | N-heptyl-3-[(2'-oxospiro[furo[2,3-f][1,3]benzodioxole-7,3'-indol]-1'(2'H)-yl)methyl]benzamide | 513.6 |
| 337 | N-(2-methoxybenzyl)-3-[(2'-oxospiro[furo[2,3-f][1,3]benzodioxole-7,3'-indol]-1'(2'H)-yl)methyl]benzamide | 535.6 |
| 338 | N-(2-methoxyphenyl)-3-[(2'-oxospiro[furo[2,3-f][1,3]benzodioxole-7,3'-indol]-1'(2'H)-yl)methyl]benzamide | 521.5 |
| 339 | N-cyclopropyl-3-[(2'-oxospiro[furo[2,3-f][1,3]benzodioxole-7,3'-indol]-1'(2'H)-yl)methyl]benzamide | 455.5 |
| 340 | N-(3-methoxypropyl)-3-[(2'-oxospiro[furo[2,3-f][1,3]benzodioxole-7,3'-indol]-1'(2'H)-yl)methyl]benzamide | 487.5 |
| 341 | N-(2,4-dimethylphenyl)-3-[(2'-oxospiro[furo[2,3-f][1,3]benzodioxole-7,3'-indol]-1'(2'H)-yl)methyl]benzamide | 519.6 |
| 342 | 3-[(2'-oxospiro[furo[2,3-f][1,3]benzodioxole-7,3'-indol]-1'(2'H)-yl)methyl]-N-(tetrahydrofuran-2-ylmethyl)benzamide | 499.5 |
| 343 | N,N-dibenzyl-3-[(2'-oxospiro[furo[2,3-f][1,3]benzodioxole-7,3'-indol]-1'(2'H)-yl)methyl]benzamide | 595.7 |
| 344 | N-[2-(diethylamino)ethyl]-3-[(2'-oxospiro[furo[2,3-f][1,3]benzodioxole-7,3'-indol]-1'(2'H)-yl)methyl]benzamide | 514.6 |
| 345 | N-methyl-3-[(2'-oxospiro[furo[2,3-f][1,3]benzodioxole-7,3'-indol]-1'(2'H)-yl)methyl]benzamide | 429.4 |
| 346 | 3-[(2'-oxospiro[furo[2,3-f][1,3]benzodioxole-7,3'-indol]-1'(2'H)-yl)methyl]-N-[3-(trifluoromethyl)phenyl]benzamide | 559.5 |
| 347 | N-ethyl-3-[(2'-oxospiro[furo[2,3-f][1,3]benzodioxole-7,3'-indol]-1'(2'H)-yl)methyl]benzamide | 443.5 |
| 348 | N-(3-ethoxypropyl)-3-[(2'-oxospiro[furo[2,3-f][1,3]benzodioxole-7,3'-indol]-1'(2'H)-yl)methyl]benzamide | 501.5 |
| 349 | N-(4-methoxybenzyl)-3-[(2'-oxospiro[furo[2,3-f][1,3]benzodioxole-7,3'-indol]-1'(2'H)-yl)methyl]benzamide | 535.6 |

-continued

| Compound Number | Name | MS (m/z, M + 1) |
|---|---|---|
| 350 | N-(3,5-dichlorophenyl)-3-[(2'-oxospiro[furo[2,3-f][1,3]benzodioxole-7,3'-indol]-1'(2'H)-yl)methyl]benzamide | 560.4 |
| 351 | 3-[(2'-oxospiro[furo[2,3-f][1,3]benzodioxole-7,3'-indol]-1'(2'H)-yl)methyl]-N-pyridin-3-ylbenzamide | 492.5 |
| 352 | 3-[(2'-oxospiro[furo[2,3-f][1,3]benzodioxole-7,3'-indol]-1'(2'H)-yl)methyl]-N-(pyridin-4-ylmethyl)benzamide | 506.5 |
| 353 | N-(2-furylmethyl)-3-[(2'-oxospiro[furo[2,3-f][1,3]benzodioxole-7,3'-indol]-1'(2'H)-yl)methyl]benzamide | 495.5 |
| 354 | N-(3-fluoro-2-methylphenyl)-3-[(2'-oxospiro[furo[2,3-f][1,3]benzodioxole-7,3'-indol]-1'(2'H)-yl)methyl]benzamide | 523.5 |
| 355 | N-hexyl-N-methyl-3-[(2'-oxospiro[furo[2,3-f][1,3]benzodioxole-7,3'-indol]-1'(2'H)-yl)methyl]benzamide | 513.6 |
| 356 | N-(3-isopropoxypropyl)-3-[(2'-oxospiro[furo[2,3-f][1,3]benzodioxole-7,3'-indol]-1'(2'H)-yl)methyl]benzamide | 515.6 |
| 357 | N-(2-ethoxyethyl)-3-[(2'-oxospiro[furo[2,3-f][1,3]benzodioxole-7,3'-indol]-1'(2'H)-yl)methyl]benzamide | 487.5 |
| 358 | N-(cyclopropylmethyl)-3-[(2'-oxospiro[furo[2,3-f][1,3]benzodioxole-7,3'-indol]-1'(2'H)-yl)methyl]benzamide | 469.5 |
| 359 | N-(4-methoxyphenyl)-3-[(2'-oxospiro[furo[2,3-f][1,3]benzodioxole-7,3'-indol]-1'(2'H)-yl)methyl]benzamide | 521.5 |
| 360 | N-cyclobutyl-3-[(2'-oxospiro[furo[2,3-f][1,3]benzodioxole-7,3'-indol]-1'(2'H)-yl)methyl]benzamide | 469.5 |
| 361 | N-[2-(4-fluorophenyl)ethyl]-3-[(2'-oxospiro[furo[2,3-f][1,3]benzodioxole-7,3'-indol]-1'(2'H)-yl)methyl]benzamide | 537.5 |
| 362 | N-(cyclohexylmethyl)-3-[(2'-oxospiro[furo[2,3-f][1,3]benzodioxole-7,3'-indol]-1'(2'H)-yl)methyl]benzamide | 511.6 |
| 363 | N-[2-(4-methylphenyl)ethyl]-3-[(2'-oxospiro[furo[2,3-f][1,3]benzodioxole-7,3'-indol]-1'(2'H)-yl)methyl]benzamide | 533.6 |
| 364 | N-(2-ethylbutyl)-3-[(2'-oxospiro[furo[2,3-f][1,3]benzodioxole-7,3'-indol]-1'(2'H)-yl)methyl]benzamide | 499.6 |
| 365 | N-benzyl-3-[(2'-oxospiro[furo[2,3-f][1,3]benzodioxole-7,3'-indol]-1'(2'H)-yl)methyl]benzamide | 505.5 |
| 366 | N-(2-methoxyethyl)-3-[(2'-oxospiro[furo[2,3-f][1,3]benzodioxole-7,3'-indol]-1'(2'H)-yl)methyl]benzamide | 473.5 |
| 367 | 1'-[3-(morpholin-4-ylcarbonyl)benzyl]spiro[furo[2,3-f][1,3]benzodioxole-7,3'-indol]-2'(1'H)-one | 485.5 |
| 368 | N-(1-benzylpiperidin-4-yl)-3-[(2'-oxospiro[furo[2,3-f][1,3]benzodioxole-7,3'-indol]-1'(2'H)-yl)methyl]benzamide | 588.7 |
| 369 | N-[2-(4-methoxyphenyl)ethyl]-3-[(2'-oxospiro[furo[2,3-f][1,3]benzodioxole-7,3'-indol]-1'(2'H)-yl)methyl]benzamide | 549.6 |
| 370 | 3-[(2'-oxospiro[furo[2,3-f][1,3]benzodioxole-7,3'-indol]-1'(2'H)-yl)methyl]-N-(2-piperidin-1-ylethyl)benzamide | 526.6 |
| 371 | N-(1-cyclohexylethyl)-3-[(2'-oxospiro[furo[2,3-f][1,3]benzodioxole-7,3'-indol]-1'(2'H)-yl)methyl]benzamide | 525.6 |
| 372 | 3-[(2'-oxospiro[furo[2,3-f][1,3]benzodioxole-7,3'-indol]-1'(2'H)-yl)methyl]-N-(2-thienylmethyl)benzamide | 511.6 |
| 373 | 3-[(2'-oxospiro[furo[2,3-f][1,3]benzodioxole-7,3'-indol]-1'(2'H)-yl)methyl]-N-(4-propylphenyl)benzamide | 533.6 |
| 374 | N-(2,4-difluorobenzyl)-3-[(2'-oxospiro[furo[2,3-f][1,3]benzodioxole-7,3'-indol]-1'(2'H)-yl)methyl]benzamide | 541.5 |
| 375 | N-(3,5-difluorophenyl)-3-[(2'-oxospiro[furo[2,3-f][1,3]benzodioxole-7,3'-indol]-1'(2'H)-yl)methyl]benzamide | 527.5 |
| 376 | N-(2,3-dihydro-1H-inden-5-yl)-3-[(2'-oxospiro[furo[2,3-f][1,3]benzodioxole-7,3'-indol]-1'(2'H)-yl)methyl]benzamide | 531.6 |

-continued

| Compound Number | Name | MS (m/z, M + 1) |
|---|---|---|
| 377 | 3-[(2'-oxospiro[furo[2,3-f][1,3]benzodioxole-7,3'-indol]-1'(2'H)-yl)methyl]-N-[4-(trifluoromethyl)benzyl]benzamide | 573.5 |
| 378 | 3-[(2'-oxospiro[furo[2,3-f][1,3]benzodioxole-7,3'-indol]-1'(2'H)-yl)methyl]-N-[2-(2-thienyl)ethyl]benzamide | 525.6 |
| 379 | 3-[(2'-oxospiro[furo[2,3-f][1,3]benzodioxole-7,3'-indol]-1'(2'H)-yl)methyl]-N-(pyridin-3-ylmethyl)benzamide | 506.5 |
| 380 | 3-[(2'-oxospiro[furo[2,3-f][1,3]benzodioxole-7,3'-indol]-1'(2'H)-yl)methyl]-N-[2-(trifluoromethyl)benzyl]benzamide | 573.5 |
| 381 | N-[2-(4-chlorophenyl)ethyl]-3-[(2'-oxospiro[furo[2,3-f][1,3]benzodioxole-7,3'-indol]-1'(2'H)-yl)methyl]benzamide | 554.0 |
| 382 | 3-[(2'-oxospiro[furo[2,3-f][1,3]benzodioxole-7,3'-indol]-1'(2'H)-yl)methyl]-N-(2-pyrrolidin-1-ylethyl)benzamide | 512.6 |
| 383 | N-(3-methylpyridin-2-yl)-3-[(2'-oxospiro[furo[2,3-f][1,3]benzodioxole-7,3'-indol]-1'(2'H)-yl)methyl]benzamide | 506.5 |
| 384 | N-1,3-benzodioxol-5-yl-3-[(2'-oxospiro[furo[2,3-f][1,3]benzodioxole-7,3'-indol]-1'(2'H)-yl)methyl]benzamide | 535.5 |
| 385 | N-(2-morpholin-4-ylethyl)-3-[(2'-oxospiro[furo[2,3-f][1,3]benzodioxole-7,3'-indol]-1'(2'H)-yl)methyl]benzamide | 528.6 |
| 386 | 1'-{3-[(4-pyrimidin-2-ylpiperazin-1-yl)carbonyl]benzyl}spiro[furo[2,3-f][1,3]benzodioxole-7,3'-indol]-2'(1'H)-one | 562.6 |
| 387 | 3-[(2'-oxospiro[furo[2,3-f][1,3]benzodioxole-7,3'-indol]-1'(2'H)-yl)methyl]-N-1,3-thiazol-2-ylbenzamide | 498.5 |
| 388 | N-(6-methoxypyridin-3-yl)-3-[(2'-oxospiro[furo[2,3-f][1,3]benzodioxole-7,3'-indol]-1'(2'H)-yl)methyl]benzamide | 522.5 |
| 389 | N-(3,5-dichlorobenzyl)-3-[(2'-oxospiro[furo[2,3-f][1,3]benzodioxole-7,3'-indol]-1'(2'H)-yl)methyl]benzamide | 574.4 |
| 390 | N-1-naphthyl-3-[(2'-oxospiro[furo[2,3-f][1,3]benzodioxole-7,3'-indol]-1'(2'H)-yl)methyl]benzamide | 541.6 |
| 391 | N-(4,6-dimethylpyridin-2-yl)-3-[(2'-oxospiro[furo[2,3-f][1,3]benzodioxole-7,3'-indol]-1'(2'H)-yl)methyl]benzamide | 520.5 |
| 392 | 3-[(2'-oxospiro[furo[2,3-f][1,3]benzodioxole-7,3'-indol]-1'(2'H)-yl)methyl]-N-pyrimidin-4-ylbenzamide | 493.5 |
| 393 | N-(5-methyl-1,3-thiazol-2-yl)-3-[(2'-oxospiro[furo[2,3-f][1,3]benzodioxole-7,3'-indol]-1'(2'H)-yl)methyl]benzamide | 512.5 |
| 394 | N-(4-methylbenzyl)-3-[(2'-oxospiro[furo[2,3-f][1,3]benzodioxole-7,3'-indol]-1'(2'H)-yl)methyl]benzamide | 519.6 |
| 395 | N-[3-(1H-imidazol-1-yl)propyl]-3-[(2'-oxospiro[furo[2,3-f][1,3]benzodioxole-7,3'-indol]-1'(2'H)-yl)methyl]benzamide | 523.6 |
| 396 | 1'-{3-[(4-methylpiperazin-1-yl)carbonyl]benzyl}spiro[furo[2,3-f][1,3]benzodioxole-7,3'-indol]-2'(1'H)-one | 498.5 |
| 397 | N-(5-cyclopropyl-1,3,4-thiadiazol-2-yl)-3-[(2'-oxospiro[furo[2,3-f][1,3]benzodioxole-7,3'-indol]-1'(2'H)-yl)methyl]benzamide | 539.6 |
| 398 | 3-[(2'-oxospiro[furo[2,3-f][1,3]benzodioxole-7,3'-indol]-1'(2'H)-yl)methyl]-N-1,3,4-thiadiazol-2-ylbenzamide | 499.5 |
| 399 | N-(3,3-dimethylbutyl)-3-[(2'-oxospiro[furo[2,3-f][1,3]benzodioxole-7,3'-indol]-1'(2'H)-yl)methyl]benzamide | 499.6 |
| 400 | N-(4-morpholin-4-ylphenyl)-3-[(2'-oxospiro[furo[2,3-f][1,3]benzodioxole-7,3'-indol]-1'(2'H)-yl)methyl]benzamide | 576.6 |
| 401 | N-[(1-ethylpyrrolidin-2-yl)methyl]-3-[(2'-oxospiro[furo[2,3-f][1,3]benzodioxole-7,3'-indol]-1'(2'H)-yl)methyl]benzamide | 526.6 |
| 402 | N-(2-cyanoethyl)-3-[(2'-oxospiro[furo[2,3-f][1,3]benzodioxole-7,3'-indol]-1'(2'H)-yl)methyl]benzamide | |

-continued

| Compound Number | Name | MS (m/z, M + 1) |
|---|---|---|
| 403 | N-(2,2-diphenylethyl)-3-[(2'-oxospiro[furo[2,3-f][1,3]benzodioxole-7,3'-indol]-1'(2'H)-yl)methyl]benzamide | 595.4 |

Example 10

Synthesis of 1'-(4-fluorobenzyl)spiro[furo[2,3-f][1,3]benzodioxole-7,3'-indol]-2'(1'H)-one To a solution of spiro[furo[2,3-f][1,3]benzodioxole-7,3'-indol]-2'(1'H)-one (0.16 g, 0.57 mmol) in ethylmethylketone (5.00 mL) was added $Cs_2CO_3$ (0.40 g, 1.20 mmol). The reaction mixture was stirred at ambient temperature for 15 min followed by the addition of 4-fluorobenzyl bromide (0.20 g, 1.0 mmol). The reaction mixture was refluxed for 4 h. After the completion of the reaction, the mixture was filtered and the solvent was removed under reduced pressure. The residue was recrystallized from EtOAc/Hexane to yield the title compound (0.111 g) as a white solid in 50% yield: MS (ES+) m/z 390.3 (M+1).

Example 10.1

The compounds listed in the following table were synthesized using the similar procedure as described in EXAMPLE 10. As previously noted, the compound numbers listed below do not correspond to the compound numbers provided in the general Reaction Schemes above.

| Compound Number | Name | MS (m/z, M + 1) |
|---|---|---|
| 404 | 1'-{[1-(2,6-difluorobenzyl)-1H-1,2,3-triazol-4-yl]methyl}spiro[furo[2,3-f][1,3]benzodioxole-7,3'-indol]-2'(1'H)-one | 489.3 |
| 405 | 1'-prop-2-yn-1-ylspiro[furo[2,3-f][1,3]benzodioxole-7,3'-indol]-2'(1'H)-one | 320.3 |
| 406 | 1'-benzylspiro[furo[2,3-f][1,3]benzodioxole-7,3'-indol]-2'(1'H)-one | 372.2 |
| 407 | 1'-{[6-(trifluoromethyl)pyridin-3-yl]methyl}spiro[furo[2,3-f][1,3]benzodioxole-7,3'-indol]-2'(1'H)-one | 441.2 |
| 408 | 1'-(3,5-difluorobenzyl)spiro[furo[2,3-f][1,3]benzodioxole-7,3'-indol]-2'(1'H)-one | 408.3 |
| 409 | 1'-(3-nitrobenzyl)spiro[furo[2,3-f][1,3]benzodioxole-7,3'-indol]-2'(1'H)-one | 417.2 |
| 410 | 1'-[(6-chloropyridin-3-yl)methyl]spiro[furo[2,3-f][1,3]benzodioxole-7,3'-indol]-2'(1'H)-one | 407.2 |
| 411 | 1'-(tetrahydro-2H-pyran-2-ylmethyl)spiro[furo[2,3-f][1,3]benzodioxole-7,3'-indol]-2'(1'H)-one | 380.2 |
| 412 | 1'-(3-fluorobenzyl)spiro[furo[2,3-f][1,3]benzodioxole-7,3'-indol]-2'(1'H)-one | 390.3 |
| 413 | 1'-(tetrahydrofuran-2-ylmethyl)spiro[furo[2,3-f][1,3]benzodioxole-7,3'-indol]-2'(1'H)-one | 365.2 |
| 414 | 3-[(2'-oxospiro[furo[2,3-f][1,3]benzodioxole-7,3'-indol]-1'(2'H)-yl)methyl]benzonitrile | 397.2 |
| 415 | 1'-(2,3-dihydro-1,4-benzodioxin-2-ylmethyl)spiro[furo[2,3-f][1,3]benzodioxole-7,3'-indol]-2'(1'H)-one | 430.3 |
| 416 | 1'-(2-ethoxyethyl)spiro[furo[2,3-f][1,3]benzodioxole-7,3'-indol]-2'(1'H)-one | 354.2 |
| 417 | 1'-[(2E)-pent-2-en-1-yl]spiro[furo[2,3-f][1,3]benzodioxole-7,3'-indol]-2'(1'H)-one | 350.2 |
| 418 | 1'-hex-5-en-1-ylspiro[furo[2,3-f][1,3]benzodioxole-7,3'-indol]-2'(1'H)-one | 364.3 |
| 419 | 1'-(cyclobutylmethyl)spiro[furo[2,3-f][1,3]benzodioxole-7,3'-indol]-2'(1'H)-one | 350.2 |
| 420 | 1'-pent-2-yn-1-ylspiro[furo[2,3-f][1,3]benzodioxole-7,3'-indol]-2'(1'H)-one | 348.2 |
| 421 | 1'-(5-chloropentyl)spiro[furo[2,3-f][1,3]benzodioxole-7,3'-indol]-2'(1'H)-one | 386.2 |
| 422 | 1'-[4-(1H-pyrazol-1-yl)benzyl]spiro[furo[2,3-f][1,3]benzodioxole-7,3'-indol]-2'(1'H)-one | 438.3 |
| 423 | 1'-[(7-methoxy-2-oxo-2H-1,4-benzoxazin-3-yl)methyl]spiro[furo[2,3-f][1,3]benzodioxole-7,3'-indol]-2'(1'H)-one | 471.3 |
| 424 | 1'-(4-fluorobutyl)spiro[furo[2,3-f][1,3]benzodioxole-7,3'-indol]-2'(1'H)-one | 356.2 |
| 425 | 1'-(5-methylhexyl)spiro[furo[2,3-f][1,3]benzodioxole-7,3'-indol]-2'(1'H)-one | 380.3 |
| 426 | 1'-[(3Z)-4-methylhex-3-en-1-yl]spiro[furo[2,3-f][1,3]benzodioxole-7,3'-indol]-2'(1'H)-one | 378.2 |

-continued

| Compound Number | Name | MS (m/z, M + 1) |
|---|---|---|
| 427 | 1'-[(5-methyl-2-phenyl-2H-1,2,3-triazol-4-yl)methyl]spiro[furo[2,3-f][1,3]benzodioxole-7,3'-indol]-2'(1'H)-one | 453.2 |
| 428 | 1'-{[5-(trifluoromethyl)-2-furyl]methyl}spiro[furo[2,3-f][1,3]benzodioxole-7,3'-indol]-2'(1'H)-one | 430.2 |
| 429 | 1'-(3,4-dihydro-2H-1,5-benzodioxepin-7-ylmethyl)spiro[furo[2,3-f][1,3]benzodioxole-7,3'-indol]-2'(1'H)-one | 444.3 |
| 430 | 1'-(biphenyl-4-ylmethyl)spiro[furo[2,3-f][1,3]benzodioxole-7,3'-indol]-2'(1'H)-one | 448.2 |
| 431 | 4'-[(2'-oxospiro[furo[2,3-f][1,3]benzodioxole-7,3'-indol]-1'(2'H)-yl)methyl]biphenyl-2-carbonitrile | 473.3 |
| 432 | 1'-(2-bromoethyl)spiro[furo[2,3-f][1,3]benzodioxole-7,3'-indol]-2'(1'H)-one | 389.1 |
| 433 | 1'-(1H-1,2,3-triazol-4-ylmethyl)spiro[furo[2,3-f][1,3]benzodioxole-7,3'-indol]-2'(1'H)-one | 363.2 |
| 434 | 1'-(biphenyl-2-ylmethyl)spiro[furo[2,3-f][1,3]benzodioxole-7,3'-indol]-2'(1'H)-one | 448.3 |
| 435 | 1'-(diphenylmethyl)spiro[furo[2,3-f][1,3]benzodioxole-7,3'-indol]-2'(1'H)-one | 448.3 |
| 436 | 5-(2'-oxospiro[furo[2,3-f][1,3]benzodioxole-7,3'-indol]-1'(2'H)-yl)pentanenitrile | 363.2 |
| 437 | 1'-[2-(2-methoxyethoxy)ethyl]spiro[furo[2,3-f][1,3]benzodioxole-7,3'-indol]-2'(1'H)-one | 384.2 |
| 438 | 1'-(cyclopropylmethyl)spiro[furo[2,3-f][1,3]benzodioxole-7,3'-indol]-2'(1'H)-one | 336.2 |
| 439 | 1'-(4,4,4-trifluorobutyl)spiro[furo[2,3-f][1,3]benzodioxole-7,3'-indol]-2'(1'H)-one | 392.2 |
| 440 | ethyl 1-[2-(2'-oxospiro[furo[2,3-f][1,3]benzodioxole-7,3'-indol]-1'(2'H)-yl)ethyl]-1H-1,2,3-triazole-5-carboxylate | 449.3 |
| 441 | ethyl 1-[2-(2'-oxospiro[furo[2,3-f][1,3]benzodioxole-7,3'-indol]-1'(2'H)-yl)ethyl]-1H-1,2,3-triazole-4-carboxylate | 449.3 |
| 442 | diethyl [2-(2'-oxospiro[furo[2,3-f][1,3]benzodioxole-7,3'-indol]-1'(2'H)-yl)ethyl]phosphonate | 446.1 |
| 443 | 1'-(1,3-thiazol-4-ylmethyl)spiro[furo[2,3-f][1,3]benzodioxole-7,3'-indol]-2'(1'H)-one | 379.3 |
| 444 | 1'-[(5-chloro-1-benzothien-3-yl)methyl]spiro[furo[2,3-f][1,3]benzodioxole-7,3'-indol]-2'(1'H)-one | 462.1 |
| 445 | 1'-(pyridin-2-ylmethyl)spiro[furo[2,3-f][1,3]benzodioxole-7,3'-indol]-2'(1'H)-one | 373.1 |
| 446 | 1'-(pyridin-4-ylmethyl)spiro[furo[2,3-f][1,3]benzodioxole-7,3'-indol]-2'(1'H)-one | 373.1 |
| 447 | 1'-(pyridin-3-ylmethyl)spiro[furo[2,3-f][1,3]benzodioxole-7,3'-indol]-2'(1'H)-one | 373.1 |
| 448 | 1'-[2-(1H-pyrrol-1-yl)ethyl]spiro[furo[2,3-f][1,3]benzodioxole-7,3'-indol]-2'(1'H)-one | 375.2 |
| 449 | 1'-{[4-chloro-2-(trifluoromethyl)quinolin-6-yl]methyl}spiro[furo[2,3-f][1,3]benzodioxole-7,3'-indol]-2'(1'H)-one | 525.1 |
| 450 | 1'-(4-fluoro-3-methylbenzyl)spiro[furo[2,3-f][1,3]benzodioxole-7,3'-indol]-2'(1'H)-one | 404.3 |
| 451 | 1'-(5-fluoro-2-methylbenzyl)spiro[furo[2,3-f][1,3]benzodioxole-7,3'-indol]-2'(1'H)-one | 404.3 |
| 452 | 1'-[(2-methyl-1,3-thiazol-4-yl)methyl]spiro[furo[2,3-f][1,3]benzodioxole-7,3'-indol]-2'(1'H)-one | 393.2 |
| 453 | 1'-(1,3-benzothiazol-2-ylmethyl)spiro[furo[2,3-f][1,3]benzodioxole-7,3'-indol]-2'(1'H)-one | 329.3 |
| 454 | 1'-(2,5-difluorobenzyl)spiro[furo[2,3-f][1,3]benzodioxole-7,3'-indol]-2'(1'H)-one | 408.2 |
| 455 | 1'-[4-(1H-pyrrol-1-yl)benzyl]spiro[furo[2,3-f][1,3]benzodioxole-7,3'-indol]-2'(1'H)-one | 437.3 |
| 456 | 1'-[3-(1H-pyrrol-1-yl)benzyl]spiro[furo[2,3-f][1,3]benzodioxole-7,3'-indol]-2'(1'H)-one | 437.3 |
| 457 | 1'-(2,1,3-benzothiadiazol-4-ylmethyl)spiro[furo[2,3-f][1,3]benzodioxole-7,3'-indol]-2'(1'H)-one | 430.3 |
| 458 | 1'-(2,1,3-benzothiadiazol-5-ylmethyl)spiro[furo[2,3-f][1,3]benzodioxole-7,3'-indol]-2'(1'H)-one | 430.3 |
| 459 | 1'-[(1-methyl-1H-1,2,3-benzotriazol-5-yl)methyl]spiro[furo[2,3-f][1,3]benzodioxole-7,3'-indol]-2'(1'H)-one | 427.2 |
| 460 | 1'-[(4-chlorophenoxy)methyl]spiro[furo[2,3-f][1,3]benzodioxole-7,3'-indol]-2'(1'H)-one | 422.2 |
| 461 | 1'-[2-fluoro-3-(trifluoromethyl)benzyl]spiro[furo[2,3-f][1,3]benzodioxole-7,3'-indol]-2'(1'H)-one | 458.1 |

-continued

| Compound Number | Name | MS (m/z, M + 1) |
|---|---|---|
| 462 | 1'-[2-fluoro-6-(trifluoromethyl)benzyl]spiro[furo[2,3-f][1,3]benzodioxole-7,3'-indol]-2'(1'H)-one | 458.1 |
| 463 | 1'-[3-fluoro-4-(trifluoromethyl)benzyl]spiro[furo[2,3-f][1,3]benzodioxole-7,3'-indol]-2'(1'H)-one | 458.1 |
| 464 | 1'-[4-fluoro-3-(trifluoromethyl)benzyl]spiro[furo[2,3-f][1,3]benzodioxole-7,3'-indol]-2'(1'H)-one | 458.1 |
| 465 | 1'-[2-fluoro-5-(trifluoromethyl)benzyl]spiro[furo[2,3-f][1,3]benzodioxole-7,3'-indol]-2'(1'H)-one | 458.1 |
| 466 | 1'-[4-fluoro-2-(trifluoromethyl)benzyl]spiro[furo[2,3-f][1,3]benzodioxole-7,3'-indol]-2'(1'H)-one | 458.1 |
| 467 | 1'-[5-fluoro-2-(trifluoromethyl)benzyl]spiro[furo[2,3-f][1,3]benzodioxole-7,3'-indol]-2'(1'H)-one | 458.1 |
| 468 | 1'-[2-fluoro-4-(trifluoromethyl)benzyl]spiro[furo[2,3-f][1,3]benzodioxole-7,3'-indol]-2'(1'H)-one | 458.1 |
| 469 | 1'-[3-(1H-pyrrol-1-yl)propyl]spiro[furo[2,3-f][1,3]benzodioxole-7,3'-indol]-2'(1'H)-one | 389.2 |
| 470 | 1'-[(2,2,3,3-tetrafluorocyclobutyl)methyl]spiro[furo[2,3-f][1,3]benzodioxole-7,3'-indol]-2'(1'H)-one | 422.1 |
| 471 | 1'-[(3-methyl-5-phenylisoxazol-4-yl)methyl]spiro[furo[2,3-f][1,3]benzodioxole-7,3'-indol]-2'(1'H)-one | 453.3 |
| 472 | 1'-[2-(diethylamino)ethyl]spiro[furo[2,3-f][1,3]benzodioxole-7,3'-indol]-2'(1'H)-one | 381.2 |
| 473 | 1'-(2,3-difluorobenzyl)spiro[furo[2,3-f][1,3]benzodioxole-7,3'-indol]-2'(1'H)-one | 408.1 |
| 474 | 1'-[(1-bromo-2-naphthyl)methyl]spiro[furo[2,3-f][1,3]benzodioxole-7,3'-indol]-2'(1'H)-one | 501.2 |
| 475 | 1'-[(7-methoxy-2-oxo-2H-chromen-4-yl)methyl]spiro[furo[2,3-f][1,3]benzodioxole-7,3'-indol]-2'(1'H)-one | 470.3 |
| 476 | 1'-[(benzyloxy)methyl]spiro[furo[2,3-f][1,3]benzodioxole-7,3'-indol]-2'(1'H)-one | 402.3 |
| 477 | 1'-[2-(2,5,5-trimethyl-1,3-dioxan-2-yl)ethyl]spiro[furo[2,3-f][1,3]benzodioxole-7,3'-indol]-2'(1'H)-one | 438.2 |
| 478 | 1'-[(6-fluoro-4H-1,3-benzodioxin-8-yl)methyl]spiro[furo[2,3-f][1,3]benzodioxole-7,3'-indol]-2'(1'H)-one | 448.2 |
| 479 | 1'-allylspiro[furo[2,3-f][1,3]benzodioxole-7,3'-indol]-2'(1'H)-one | 322.3 |
| 480 | 1'-(1-naphthylmethyl)spiro[furo[2,3-f][1,3]benzodioxole-7,3'-indol]-2'(1'H)-one | 423.3 |
| 481 | 1'-[3-fluoro-5-(trifluoromethyl)benzyl]spiro[furo[2,3-f][1,3]benzodioxole-7,3'-indol]-2'(1'H)-one | 458.1 |
| 482 | 1'-(2,4-difluorobenzyl)spiro[furo[2,3-f][1,3]benzodioxole-7,3'-indol]-2'(1'H)-one | 408.1 |
| 483 | 1'-(2,6-difluorobenzyl)spiro[furo[2,3-f][1,3]benzodioxole-7,3'-indol]-2'(1'H)-one | 408.3 |
| 484 | 1'-[(5-phenyl-1,3-oxazol-4-yl)methyl]spiro[furo[2,3-f][1,3]benzodioxole-7,3'-indol]-2'(1'H)-one | 439.2 |
| 485 | 1'-(3,5,5-trimethylhexyl)spiro[furo[2,3-f][1,3]benzodioxole-7,3'-indol]-2'(1'H)-one | 408.3 |
| 486 | 1'-(2-ethylbutyl)spiro[furo[2,3-f][1,3]benzodioxole-7,3'-indol]-2'(1'H)-one | 366.3 |
| 487 | 1'-(4-methylpentyl)spiro[furo[2,3-f][1,3]benzodioxole-7,3'-indol]-2'(1'H)-one | 366.3 |
| 488 | 1'-(3-methoxybenzyl)spiro[furo[2,3-f][1,3]benzodioxole-7,3'-indol]-2'(1'H)-one | 402.3 |
| 489 | 1'-(3-methylbutyl)spiro[furo[2,3-f][1,3]benzodioxole-7,3'-indol]-2'(1'H)-one | 352.2 |
| 490 | 1'-(3-methylbut-2-en-1-yl)spiro[furo[2,3-f][1,3]benzodioxole-7,3'-indol]-2'(1'H)-one | 350.2 |
| 491 | 1'-pent-4-en-1-ylspiro[furo[2,3-f][1,3]benzodioxole-7,3'-indol]-2'(1'H)-one | 350.2 |
| 492 | 4-(2'-oxospiro[furo[2,3-f][1,3]benzodioxole-7,3'-indol]-1'(2'H)-yl)butanenitrile | 349.1 |
| 493 | 1'-[4-(1H-1,2,4-triazol-1-yl)benzyl]spiro[furo[2,3-f][1,3]benzodioxole-7,3'-indol]-2'(1'H)-one | 439.2 |
| 494 | 1'-(1,3-benzodioxol-5-ylmethyl)spiro[furo[2,3-f][1,3]benzodioxole-7,3'-indol]-2'(1'H)-one | 416.2 |
| 495 | 1'-[4,4-bis(4-fluorophenyl)butyl]spiro[furo[2,3-f][1,3]benzodioxole-7,3'-indol]-2'(1'H)-one | 526.2 |
| 496 | 1'-[(2-methylcyclopropyl)methyl]spiro[furo[2,3-f][1,3]benzodioxole-7,3'-indol]-2'(1'H)-one | 350.4 |
| 497 | 1'-(3-cyclopropylpropyl)spiro[furo[2,3-f][1,3]benzodioxole-7,3'-indol]-2'(1'H)-one | 364.3 |

-continued

| Compound Number | Name | MS (m/z, M + 1) |
|---|---|---|
| 498 | 1'-hexylspiro[furo[2,3-f][1,3]benzodioxole-7,3'-indol]-2'(1'H)-one | 366.3 |
| 499 | 1'-[(2-cyclopropyl-6-hydroxypyrimidin-4-yl)methyl]spiro[furo[2,3-f][1,3]benzodioxole-7,3'-indol]-2'(1'H)-one | 430.3 |

Example 10.2

Synthesis of 1'-(piperidin-4-ylmethyl)spiro[furo[2,3-f][1,3]benzodioxole-7,3'-indol]-2'(1'H)-one Following the procedure as described in EXAMPLE 10, and making non-critical variations using tert-butyl 4-(bromomethyl)peridine-1-carboxylate to replace 4-fluorobenzyl bromide, the title compound was obtained in 67% yield as a white solid upon acidification of the intermediate with 33% HBr: MS (ES+) m/z 379.3 (M+1).

Example 10.3

Synthesis of 1'-[(1-methylpiperidin-4-yl)methyl]spiro[furo[2,3-f][1,3]benzodioxole-7,3'-indol]-2'(1'H)-one hydrochloride To a solution of 1'-(piperidin-4-ylmethyl)spiro[furo[2,3-f][1,3]benzodioxole-7,3'-indol]-2'(1'H)-one (0.19 g, 0.50 mmol) in dichloroethane (5.00 mL) was added formaldehyde (0.10 mL, 33% solution, 0.03 g, 1.10 mmol) and sodium triacetoxyborohydride (0.30 g, 1.40 mmol). After stirring at ambient temperature for 20 hours, the reaction mixture was diluted with of dichloromethane (20.0 mL) and washed with water (2×20.0 mL). The organic layer was dried over sodium sulfate and filtered. The filtrate was concentrated in vacuo to dryness. The residue was subjected to column chromatography and the product was dissolved in dichloromethane (5.00 mL) and excess of HCl in ether was added. The precipitate was filtered to give the title compound in 20% yield: MS (ES+) m/z 393.3 (M+1).

Example 10.4

Synthesis of 1'-[(1-ethylpiperidin-4-yl)methyl]spiro[furo[2,3-f][1,3]benzodioxole-7,3'-indol]-2'(1'H)-one hydrochloride Following the procedure as described in EXAMPLE 10.3, and making non-critical variations using acetaldehyde to replace formalin, the title compound was obtained in 20% yield as a white solid: MS (ES+) m/z 407.3 (M+1).

Example 10.5

Synthesis of 1'-[(1-cyclohexyl)piperidin-4-yl)methyl]spiro[furo[2,3-f][1,3]benzodioxole-7,3'-indol]-2'(1'H)-one hydrochloride Following the procedure as described in EXAMPLE 10.3, and making non-critical variations using cyclohexanone to replace formalin, the title compound was obtained 24% yield as a white solid: MS (ES+) m/z 461.5 (M+1).

Example 10.6

Synthesis of 1'-{[1-cyclopropylmethyl)piperidin-4-yl]methyl}spiro[furo[2,3-f][1,3]benzodioxole-7,3'-indol]-2'(1'H)one hydrochloride Following the procedure as described in EXAMPLE 10.3, and making non-critical variations using cyclopropanecarbaldehyde to replace formalin, the title compound was obtained in 14% yield as a white solid: MS (ES+) m/z 433.5 (M+1).

Example 10.7

Synthesis of 1'-[(1-cyclopentylpiperidin-4-yl)methyl]spiro[furo[2,3-f][1,3]benzodioxole-7,3'-indol]-2'(1'H)-one hydrochloride Following the procedure as described in EXAMPLE 10.3, and making non-critical variations using cyclopentanone to replace formalin, the title compound was obtained in 37% yield as a white solid: MS (ES+) m/z 447.3 (M+1).

Example 10.8

Synthesis of 1'-{[1-(pyridine-3-ylmethyl)piperidin-4-yl]methyl}spiro[furo[2,3-f][1,3]benzodioxole-7,3'-indol]-2'(1'H)-one hydrochloride Following the procedure as described in EXAMPLE 10.3, and making non-critical variations using nicotinaldehyde to replace formalin, the title compound was obtained in 11% yield as a white solid: MS (ES+) m/z 470.4 (M+1).

Example 10.9

Synthesis of 1'-{[1-(3-methylbutyl)piperidin-4-yl]methyl}spiro[furo[2,3-f][1,3]benzodioxole-7,3'-indol]-2'(1'H)-one hydrochloride Following the procedure as described in EXAMPLE 10.3, and making non-critical variations using 3-methylbutanal to replace formalin, the title compound was obtained in 15% yield as a white solid: MS (ES+) m/z 449.5 (M+1).

Example 10.10

Synthesis of 1'-{[1-(1-ethylpropyl)piperidin-4-yl]methyl}spiro[furo[2,3-f][1,3]benzodioxole-7,3'-indol]-2'(1'H)-one hydrochloride Following the procedure as described in EXAMPLE 10.3, and making non-critical variations using pentan-3-one to replace formalin, the title compound was obtained in 17% yield as a white solid: MS (ES+) m/z 449.4 (M+1).

Example 10.11

Synthesis of 1'-[(1-cyclobutylpiperidin-4-yl)methyl] spiro[furo[2,3-f][1,3]benzodioxole-7,3'-indol]-2' (1'H)one hydrochloride Following the procedure as described in EXAMPLE 10.3, and making non-critical variations using cyclobutanone to replace formalin, the title compound was obtained in 31% yield as a white solid: MS (ES+) m/z 433.4 (M+1).

Example 10.12

Synthesis of 1'-[(1-isopropylpiperidin-4-yl)methyl] spiro[furo[2,3-f][1,3]benzodioxole-7,3'-indol]-2' (1'H)-one hydrochloride Following the procedure as described in Example 10.3, and making non-critical variations using acetone to replace formalin, the title compound was obtained in 31% yield as a white solid: $^1$H NMR (300 MHz, DMSO-$d_6$) δ 10.36 (s, 1H), 7.79-6.87 (m, 4H), 6.82-6.48 (m, 1H), 6.38-6.15 (m, 1H), 5.89 (s, 2H), 4.67 (ABq, 2H), 4.12 (s, 1H), 3.79-0.60 (m, 16H); MS (ES+) m/z 421.4 (M+1).

Example 10.13

Synthesis of 1'-{[1-(pyridin-2-ylmethyl)piperidin-4-yl]methyl}spiro[furo[2,3-f][1,3]benzodioxole-7,3'-indol]-2'(1'H)-one hydrochloride Following the procedure as described in EXAMPLE 10.3, and making non-critical variations using picolinaldehyde to replace formalin, the title compound was obtained in 15% yield as a white solid: MS (ES+) m/z 470.4 (M+1).

Example 10.14

Synthesis of 1'-{[1-(2-thienylmethyl)piperidin-4-yl] methyl}spiro[furo[2,3-f][1,3]benzodioxole-7,3'-indol]-2'(1'H)-one hydrochloride Following the procedure as described in EXAMPLE 10.3, and making non-critical variations using thiophene-2-carbaldehyde to replace formalin, the title compound was obtained in 21% yield as a white solid: MS (ES+) m/z 475.3 (M+1).

Example 10.15

Synthesis of 1'-({1-[3-(methylthio)propyl]piperidin-4-yl}methyl)spiro[furo[2,3-f][1,3]benzodioxole-7,3'-indol]-2'(1'H)-one hydrochloride Following the procedure as described in EXAMPLE 10.3, and making non-critical variations using 3-(methylthio)propanal to replace formalin, the title compound was obtained in 7% yield as a white solid: MS (ES+) m/z 467.5 (M+1).

Example 10.16

Synthesis of 1'-{[1-(tetrahydro-2H-pyran-4-yl)piperidin-4-yl]methyl}spiro[furo[2,3-f][1,3]benzodioxole-7,3'-indol]-2'(1'H)one hydrochloride Following the procedure as described in EXAMPLE 10.3, and making non-critical variations using tetrahydro-4H-pyran-4-one to replace formalin, the title compound was obtained in 33% yield as a white solid: MS (ES+) m/z 463.4 (M+1).

Example 10.17

Synthesis of 1-{[1-(3,3-dimethylbutyl)piperidin-4-yl]methyl}spiro[furo[2,3-f][1,3]benzodioxole-7,3'-indol]-2'(1'H)-one hydrochloride Following the procedure as described in EXAMPLE 10.3, and making non-critical variations using 3,3-dimethylbutanal to replace formalin, the title compound was obtained in 19% yield as a white solid: MS (ES+) m/z 463.5 (M+1).

Example 10.18

Synthesis of tert-butyl 4-[(5,5-dimethyl-2'-oxo-5,6-dihydrospiro[benzo[1,2-b:5,4-b']difuran-3,3'-indol]-1'(2'H)-yl)methyl]piperidine-1-carboxylate Following the procedure as described in EXAMPLE 10, and making non-critical variations using 5,5-dimethyl-5,6-dihydrospiro[benzo[1,2-b:5,4-b']difuran-3,3'-indol]-2'(1'H)-one to replace spiro[furo[2,3-f][1,3]benzodioxole-7,3'-indol]-2'(1'H)-one, and tert-butyl 4-(tosyloxymethyl)piperidine-1-carboxylate to replace 4-fluorobenzyl bromide, the title compound was obtained in 70% yield: mp 65-75° C.; $^1$H NMR (300 MHz, CDCl$_3$) δ 7.30 (td, 1H), 7.18 (d, 1H), 7.05 (t, 1H), 6.89 (d, 1H), 6.38 (s, 1H), 6.28 (s, 1H), 4.88 (d, 1H), 4.64 (d, 1H), 4.18 (s, 2H), 4.17-4.01 (br, 2H), 3.74-3.53 (m, 2H), 2.74-2.59 (m, 2H), 2.11-1.92 (m, 1H), 1.70-1.59 (m, 2H), 1.43 (s, 9H), 1.37-1.19 (m, 2H), 1.17 (s, 3H), 1.14 (s, 3H); $^{13}$C NMR (75 MHz, CDCl$_3$) δ 178.0, 161.3, 161.0, 154.7, 142.8, 132.6, 129.9, 128.7, 124.2, 123.3, 120.3, 116.2, 108.5, 93.4, 85.4, 80.6, 79.5, 57.7, 45.7, 41.3, 35.0, 30.0, 28.4, 27.8, 27.5; MS (ES+) m/z 527.5 (M+23).

Example 10.19

Synthesis of 5,5-dimethyl-1'-(piperidin-4-ylmethyl)-5,6-dihydrospiro[benzo[1,2-b:5,4-b']difuran-3,3'-indol]-2'(1'H)-one hydrochloride To a stirred solution of tert-butyl 4-[(5,5-dimethyl-2'-oxo-5,6-dihydrospiro[benzo[1,2-b:5,4-b']difuran-3,3'-indol]-1' (2'H)-yl)methyl]piperidine-1-carboxylate (80 mg, 0.16 m mol) in 10.0 mL dichloromethane was added hydrobromic acid (0.50 mL of hydrobromic acid ≧33% in glacial acetic acid, 1.60 mmol) slowly at 0° C. The mixture was stirred at ambient temperature for one hour and concentrated in vacuo to dryness. The residue was treated with 10.0 mL of 2 N sodium hydroxide solution and extracted with dichloromethane (3×30.0 mL). The combined organic layers was washed with brine (100 mL), dried over anhydrous sodium sulfate and filtered. The filtrate was concentrated in vacuo to dryness. The residue was subjected to column chromatography (2% methanol in ethyl acetate) to give 5,5-dimethyl-1'-(piperidin-4-ylmethyl)-5,6-dihydrospiro[benzo[1,2-b:5,4-b']difuran-3,3'-indol]-2'(1'H)-one (0.03 g, 46%), which was treated with 2.0 M HCl in diethyl ether to give the title compound: $^1$H NMR (300 MHz, CD$_3$OD) δ 7.41 (td, 1H), 7.25-7.12 (m, 3H), 6.43 (s, 1H), 6.37 (s, 1H), 4.87 (d, 1H), 4.72 (d, 1H), 4.23 (s, 2H), 3.80 (d, 2H), 3.51-3.38 (m, 2H), 3.11-2.94 (m, 2H), 2.39-2.19 (m, 1H), 2.06-1.94 (m, 2H), 1.67-1.49 (m, 2H), 1.22 (s, 3H), 1.19 (s, 3H); $^{13}$C NMR (75 MHz, CD$_3$OD) δ 181.4, 163.9, 163.4, 144.7, 134.7, 132.3, 131.0, 125.9, 125.8, 122.6, 118.4, 111.3, 94.9, 87.4, 82.6, 60.2, 46.7, 45.7, 45.6, 43.3, 34.6, 28.8, 28.7, 28.6; MS (ES+) m/z 405.4 (M+1).

Example 10.20

Synthesis of 7'-fluoro-1'-[(1-isopropylpiperidin-4-yl) methyl]spiro[furo[2,3-f][1,3]benzodioxole-7,3'-indol]-2'(1'H)one hydrochloride A. Following the procedure as described in EXAMPLES 10.18 and 10.19, and making non-critical variations using 7'-fluorospiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, 7'-fluoro-1'-(piperidin-4-ylmethyl)spiro[furo[2,3-f][1,3]benzodioxole-7,3'-indol]-2'(1'H)-one was obtained and used in the next step.

B. To a stirred solution of 7'-fluoro-1'-(piperidin-4-ylmethyl)spiro[furo[2,3-f][1,3]benzodioxole-7,3'-indol]-2'(1'H)-one (120 mg, 0.28 mmol) and triethylamine (3.9 pt, 0.028 mmol) in 5.00 mL dichloromethane was added acetone (4.1 µL, 0.56 mmol) followed with sodium triacetoxyborohydride (124 mg, 0.56 mmol) at ambient temperature. The mixture was stirred at ambient temperature overnight, quenched with water (10.0 mL). The mixture was extracted with dichloromethane (3×30.0 mL). The combined organic layers was dried over anhydrous sodium sulfate and filtered. The filtrate was concentrated in vacuo. The residue was subjected to column chromatography (2% methanol in ethyl acetate/hexane) to give 7'-fluoro-1'-[(1-isopropylpiperidin-4-yl)methyl]spiro[furo[2,3-f][1,3]benzodioxole-7,3'-indol]-2'(1'H)-one (85 mg, 69%) as a white solid, which was treated with 2.0 M HCl in diethyl ether to give the title compound: mp 157-160° C.; $^1$H NMR (300 MHz, CD$_3$OD) δ 7.22-7.05 (m, 2H), 7.05-6.98 (m, 1H), 6.52 (s, 1H), 6.21 (s, 1H), 5.86 (s, 2H), 4.83 (d, 1H), 4.68 (d, 1H), 3.95-3.77 (m, 2H), 3.55-3.42 (m, 3H), 3.12-2.96 (m, 2H), 2.30-2.10 (m, 1H), 2.10-1.97 (m, 2H), 1.76-1.52 (m, 2H), 1.34 (d, 6H); $^{13}$C NMR (75 MHz, CD$_3$OD) δ 179.7, 157.6, 150.6, 150.4, 147.1, 143.9, 136.6, 125.8, 121.2, 120.3, 118.0, 103.9, 103.0, 94.3, 81.8, 60.1, 59.7, 47.6, 35.33, 35.30, 28.6, 28.5, 16.98, 16.96; MS (ES+) m/z 439.27 (M+1).

Example 10.21

Synthesis of 5,5-dimethyl-1'-{[5-(trifluoromethyl)-2-furyl]methyl}-5,6-dihydrospiro[benzo[1,2-b:5,4-b']difuran-3,3'-indol]-2'(1'H)-one To a solution of 5,5-dimethyl-5,6-dihydrospiro[benzo[1,2-b:5,4-b']difuran-3,3'-indol]-2'(1'H)-one (0.09 g, 0.29 mmol) in 2-butanone (10.0 mL) was added 2-bromomethyl-5-(trifluoromethyl)furan (0.08 g, 0.35 mmol) followed by cesium carbonate (0.19 g, 0.58 mmol) at 0° C. The mixture was stirred at ambient temperature overnight. The reaction mixture was filtered and the filtrate was concentrated in vacuo. The residue was subjected to column chromatography (ethyl acetate/hexane, 1/5) to give the title compound (0.06 g, 45%): mp 155-160° C.; $^1$H NMR (300 MHz, CDCl$_3$,) δ 7.29 (t, 1H), 7.19 (d, 1H), 7.07 (t, 1H), 6.97 (d, 1H), 6.73 (t, 1H), 6.42-6.37 (m, 2H), 6.30 (s, 1H), 5.08 (d, 1H), 4.94-4.84 (m, 2H), 4.65 (d, 1H), 4.18 (s, 2H), 1.19 (s, 3H), 1.14 (s, 3H); $^{13}$C NMR (75 MHz, CDCl$_3$) δ 177.5, 161.2, 161.0, 152.0, 141.4, 132.5, 130.1, 128.8, 124.2, 123.8, 120.1, 116.4, 112.6, 109.3, 108.7, 93.4, 85.5, 80.6, 57.7, 41.4, 36.9, 27.6, 27.5; MS (ES+) m/z 456.5 (M+1).

Example 10.22

Synthesis of 5,5-dimethyl-1'-(pyridin-3-ylmethyl)-5,6-dihydrospiro[benzo[1,2-b:5,4-b']difuran-3,3'-indol]-2'(1'H)-one hydrochloride To a solution of 5,5-dimethyl-5,6-dihydrospiro[benzo[1,2-b:5,4-b']difuran-3,3'-indol]-2'(1'H)-one (0.08 g, 0.26 mmol) in DMF (10 mL) was added sodium hydride (0.03 g, 0.78 mmol) slowly at 0° C. After 30 min, 3-(bromomethyl)-pyridine hydrobromide (0.10 g, 0.39 mmol) was added. The mixture was stirred at ambient temperature overnight, quenched with saturated ammonium chloride (10.0 mL). The mixture was extracted with ethyl acetate (3×20.0 mL). The combined organic layers was dried over anhydrous sodium sulfate and filtered. The filtrate was concentrated in vacuo. The residue was subjected to column chromatography (ethyl acetate/hexane, 2/1) to give 5,5-dimethyl-1'-(pyridin-3-ylmethyl)-5,6-dihydrospiro[benzo[1,2-b:5,4-b']difuran-3,3'-indol]-2'(1'H)-one as a white solid (0.05 g, 48%), which was treated with 2.0 M HCl in diethyl ether to give the title compound: mp 124-126° C.; $^1$H NMR (300 MHz, CD$_3$OD) δ 8.96 (br, 1H), 8.82 (br, 1H), 8.62 (d, 1H), 7.3 (t, 1H), 7.32 (td, 1H), 7.23-7.17 (m, 1H), 7.16-7.08 (m, 2H), 6.42 (s, 1H), 6.32 (s, 1H), 5.35-5.14 (m, 2H), 4.93-4.84 (m, 1H), 4.74 (d, 1H), 4.18 (s, 2H), 1.18 (s, 3H), 1.14 (s, 3H); $^{13}$C NMR (75 MHz, CD$_3$OD) δ 178.9, 161.6, 161.1, 145.4, 141.3, 141.1, 132.5, 130.1, 128.8, 124.0, 123.9, 120.1, 116.2, 108.8, 92.6, 85.1, 80.2, 57.8, 41.0, 40.5, 26.5, 26.4; MS (ES+) m/z 399.5 (M+1).

Example 10.23

Synthesis of 5,5-dimethyl-1'-(pyridin-2-ylmethyl)-5,6-dihydrospiro[benzo[1,2-b:5,4-b']difuran-3,3'-indol]-2'(1'H)-one hydrochloride Following the procedure as described in EXAMPLE 10.22, and making non-critical variations using 2-(bromomethyl)-pyridine hydrobromide to replace 3-(bromomethyl)-pyridine hydrobromide, the title compound was obtained (45%): mp 145-147° C.; $^1$H NMR (300 MHz, CD$_3$OD) δ 8.86 (dd, 1H), 8.56 (td, 1H), 8.05-7.97 (m, 2H), 7.37 (td, 1H), 7.31-7.25 (m, 1H), 7.24-7.16 (m, 1H), 7.11 (d, 1H), 6.55 (s, 1H), 6.37 (s, 1H), 5.52 (d, 1H), 5.38 (d, 1H), 4.97 (d, 1H), 4.79 (d, 1H), 4.23 (s, 2H), 1.24 (s, 3H), 1.20 (s, 3H); $^{13}$C NMR (75 MHz, CD$_3$OD) δ 177.4, 160.0, 159.6, 150.3, 144.7, 141.0, 139.7, 131.0, 128.6, 127.2, 124.3, 123.7, 122.6, 122.4, 118.5, 114.8, 107.2, 91.0, 83.6, 78.7, 56.3, 40.1, 39.4, 24.9, 24.8; MS (ES+) m/z 399.5 (M+1).

Example 10.24

Synthesis of 1'-[(6-methylpyridin-3-yl)methyl]spiro[furo[2,3-f][1,3]benzodioxole-7,3'-indol]-2'(1'H)-one hydrochloride Following the procedure as described in EXAMPLE 10.21, and making non-critical variations using (6-methylpyridin-3-yl)methyl 4-methylbenzenesulfonate to replace 2-bromomethyl-5-(trifluoromethyl)furan, and spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, 1'-[(6-methylpyridin-3-yl)methyl]spiro[furo[2,3-f][1,3]benzodioxole-7,3'-indol]-2'(1'H)-one was obtained (56%), which was treated with 2.0 M HCl in diethyl ether to give the title compound: $^1$H NMR (300 MHz, CD$_3$OD) δ 8.77 (s, 1H), 8.46 (dd, 1H), 7.91 (d, 1H), 7.33 (t, 1H), 7.24-7.09 (m, 3H), 6.52 (s, 1H), 6.14 (s, 1H), 5.86 (s, 2H), 5.18 (s, 2H), 4.93-4.85 (m, 1H), 4.71 (d, 1H), 2.77 (s, 3H); $^{13}$C NMR (75 MHz, CD$_3$OD) δ 180.0, 157.6, 155.1, 150.6, 146.6, 143.8, 142.7, 141.2, 135.7, 133.5, 130.3, 129.5, 125.3, 125.2, 120.5, 110.3, 103.8, 103.0, 94.3, 81.5, 59.7, 41.5, 19.5; MS (ES+) m/z 387.4 (M+1).

Example 10.25

Synthesis of 1'-[(6-methoxypyridin-3-yl)methyl] spiro[furo[2,3-f][1,3]benzodioxole-7,3'-indol]-2'(1'H)-one Following the procedure as described in EXAMPLE 10.21, and making non-critical variations using (6-methoxypyridin-3-yl)methyl 4-methylbenzenesulfonate to replace 2-bromomethyl-5-(trifluoromethyl)furan, and spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, the title compound was obtained (45%): $^1$H NMR (300 MHz, CDCl$_3$) δ 8.19 (d, 1H), 7.59 (dd, 1H), 7.26-7.12 (m, 2H), 7.02 (t, 1H), 6.83 (d, 1H), 6.74 (d, 1H), 6.50 (s, 1H), 6.07 (s, 1H), 5.89-5.82 (m, 2H), 5.00-4.90 (m, 2H), 4.76 (d, 1H), 4.65 (d, 1H), 3.93 (s, 3H); $^{13}$C NMR (75 MHz, CDCl$_3$) δ 177.6, 163.7, 155.9, 149.0, 145.3, 142.4, 141.6, 138.9, 132.2, 129.0, 124.4, 124.1, 123.7, 119.2, 111.7, 109.0, 102.9, 101.5, 93.7, 80.4, 58.2, 53.9, 41.1; MS (ES+) m/z 403.2 (M+1).

Example 10.26

Synthesis of 1'-[(6-chloropyridin-3-yl)methyl]spiro[furo[2,3-f][1,3]benzodioxole-7,3'-indol]-2'(1'H)-one Following the procedure described in EXAMPLE 10.21, and making non-critical variations using 2-chloro-5-(chloromethyl)pyridine to replace 2-bromomethyl-5-(trifluoromethyl)furan, and spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, the title compound was obtained (69%): $^1$H NMR (300 MHz, CDCl$_3$) δ 8.42 (d, 1H), 7.63 (dd, 1H), 7.34-7.14 (m, 3H), 7.05 (t, 1H), 6.77 (d, 1H), 6.51 (s, 1H), 6.06 (s, 1H), 5.89-5.84 (m, 2H), 5.07-4.78 (m, 3H), 4.66 (d, 1H); MS (ES+) m/z 407.3 (M+1).

Example 10.27

Synthesis of 1'-{[6-(dimethylamino)pyridin-3-yl]methyl}spiro[furo[2,3-f][1,3]benzodioxole-7,3'-indol]-2'(1'H)-one hydrochloride To a seal tube was added 1'-((6-chloropyridin-3-yl)methyl)-6H-spiro[benzofuro[6,5-d][1,3]dioxole-7,3'-indolin]-2'-one (0.10 g, 0.25 mmol) and dimethylamine (2.00 mL of 2 M THF solution, 4.00 mmol). The mixture was stirred at 130° C. overnight. After cooling down to ambient temperature, the mixture was concentrated in vacuo. The residue was subjected to column chromatography (ethyl acetate/hexane, 1/2) to give 1'-{[6-(dimethylamino)pyridin-3-yl]methyl}spiro[furo[2,3-f][1,3]benzodioxole-7,3'-indol]-2'(1'H)one as a white solid (50 mg, 48%), which was treated with 2.0 M HCl in diethyl ether to give the title compound: mp 146-150° C.; $^1$H NMR (300 MHz, CD$_3$OD) δ 8.03 (d, 1H), 7.95 (dd, 1H), 7.36 (td, 1H), 7.25-7.12 (m, 4H), 6.57 (s, 1H), 6.09 (s, 1H), 5.90 (s, 2H), 5.07-4.87 (m, 3H), 4.72 (d, 1H), 3.27 (s, 6H); $^{13}$C NMR (75 MHz, CD$_3$OD) δ 179.9, 157.6, 154.6, 150.5, 143.8, 143.4, 142.9, 137.7, 133.5, 130.2, 125.1, 121.8, 120.6, 113.2, 110.4, 103.7, 103.0, 94.3, 81.4, 59.7, 41.1, 39.5; MS (ES+) m/z 416.5 (M+1).

Example 10.28

Synthesis of 1'-[(6-morpholin-4-ylpyridin-3-yl)methyl]spiro[furo[2,3-f][1,3]benzodioxole-7,3'-indol]-2'(1'H)-one hydrochloride Following the procedure as described in EXAMPLE 10.27, and making non-critical variations using morpholine to replace dimethylamine solution, the title compound was obtained (52%): mp 185-200° C.; $^1$H NMR (300 MHz, CD$_3$OD) δ 8.13-8.04 (m, 2H), 7.45 (d, 1H), 7.37 (t, 1H), 7.26-7.14 (m, 3H), 6.56 (s, 1H), 6.10 (s, 1H), 5.89 (s, 2H), 5.10-4.87 (m, 3H), 4.72 (d, 1H), 3.91-3.84 (m, 4H), 3.73-3.67 (m, 4H); $^{13}$C NMR (75 MHz, CD$_3$OD) δ 180.0, 157.6, 153.7, 150.5, 145.1, 143.8, 142.8, 136.3, 133.5, 130.3, 125.2, 125.1, 123.6, 120.6, 114.6, 110.4, 103.7, 103.0, 94.3, 81.5, 66.7, 59.7, 47.2, 40.9; MS (ES+) m/z 458.5 (M+1).

Example 10.29

Synthesis of 1'-[(6-pyrrolidin-1-ylpyridin-3-yl)methyl]spiro[furo[2,3-f][1,3]benzodioxole-7,3'-indol]-2'(1'H)-one hydrochloride Following the procedure as described in EXAMPLE 10.27, and making non-critical variations using pyrrolidine to replace dimethylamine solution, the title compound was obtained (45%): mp 160-165° C.; $^1$H NMR (300 MHz, CD$_3$OD) δ 7.99-7.91 (m, 2H), 7.33 (td, 1H), 7.22-7.06 (m, 4H), 6.53 (s, 1H), 6.05 (s, 1H), 5.86 (s, 2H), 5.04-4.82 (m, 3H), 4.68 (d, 1H), 3.57 (t, 4H), 2.13 (t, 4H); $^{13}$C NMR (75 MHz, CD$_3$OD) δ 177.0, 154.6, 148.0, 147.6, 141.1, 140.8, 139.9, 132.5, 130.5, 127.3, 122.2, 118.8, 117.6, 112.0, 107.4, 100.7, 100.0, 91.3, 78.5, 56.7, 38.0, 23.2; MS (ES+) m/z 442.2 (M+1).

Example 10.30

Synthesis of 1'-(2-chloro-4-fluorobenzyl)spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and 1-(bromomethyl)-2-chloro-4-fluorobenzene to replace 2-(bromomethyl)-5-(trifluoromethyl)furan, the title compound was obtained (54%) as a white solid: mp 174-175° C.; MS (ES+) m/z 424.2 (M+1).

Example 10.31

Synthesis of 1'-[(2-methylcyclopropyl)methyl]spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-(bromomethyl)-2-methylcyclopropane to replace 2-(bromomethyl)-5-

Example 10.32

Synthesis of 1'-(3-cyclopropylpropyl)spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and (3-bromopropyl)cyclopropane to replace 2-(bromomethyl)-5-(trifluoromethyl)furan, the title compound was obtained (51%) as a white solid: mp 111-113° C.; MS (ES+) m/z 364.3 (M+1).

Example 10.33

Synthesis of 1'-butylspiro[furo[2,3-f][1,3]benzodioxole-7,3'-indol]-2'(1'H)-one

Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and 1-bromobutane to replace 2-(bromomethyl)-5-(trifluoromethyl)furan, the title compound was obtained (62%) as a white solid: mp 119-120° C.; MS (ES+) m/z 338.3 (M+1).

Example 10.34

Synthesis of 1'-[(5-methylisoxazol-4-yl)methyl]spiro[furo[2,3-f][1,3]benzodioxole-7,3'indol]-2'(1'H)-one Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 4-(bromomethyl)-5-methylisoxazole to replace 2-(bromomethyl)-5-(trifluoromethyl)furan, the title compound was obtained (25%) as a white solid: mp 159-161° C.; $^1$H NMR (300 MHz, DMSO-$d_6$) δ 7.39-6.91 (m, 4H), 6.50 (s, 1H), 6.11 (s, 1H), 5.94 (d, 1H), 5.85 (ABq, 2H), 4.95 (ABq, 2H), 4.78 (ABq, 2H), 2.37 (s, 3H); MS (ES+) m/z 377.3 (M+1).

Example 10.35

Synthesis of 1'-(tetrahydro-2H-pyran-4-ylmethyl)spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and 4-(bromomethyl)tetrahydro-2H-pyran to replace 2-(bromomethyl)-5-(trifluoromethyl)furan, the title compound was obtained (25%) as a white solid: mp 142-144° C.; $^1$H NMR (300 MHz, DMSO-$d_6$) δ 7.34-6.85 (m, 4H), 6.50 (s, 1H), 6.08 (s, 1H), 5.85 (ABq, 2H), 4.76 (ABq, 2H), 4.18-3.86 (m, 2H), 3.63 (ddd, 2H), 3.34 (t, 2H), 2.38-1.92 (m, 1H), 1.70-1.36 (m, 4H); MS (ES+) m/z 380.3 (M+1).

Example 10.36

Synthesis of 1'[2-(trifluoromethoxy)benzyl]spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and 1-(bromomethyl)-2-(trifluoromethoxy)benzene to replace 2-(bromomethyl)-5-(trifluoromethyl)furan, the title compound was obtained (77%) as a white solid: mp 130-135° C.; MS (ES+) m/z 456.3 (M+1).

Example 10.37

Synthesis of 1'[3-(trifluoromethoxy)benzyl]spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1H)-one to replace 5,5-dimethyl-5,6-dihydrospiro[benzo[1,2-b:5,4-b']difuran-3,3'-indol]-2'(1'H)-one, and 1-(bromomethyl)-3-(trifluoromethoxy)benzene to replace 2-(bromomethyl)-5-(trifluoromethyl)furan, the title compound was obtained (65%) as a white solid: mp 88-91° C.; MS (ES+) m/z 456.3 (M+1).

Example 10.38

Synthesis of 1'[4-(trifluoromethoxy)benzyl]spiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and 1-(bromomethyl)-4-(trifluoromethoxy)benzene to replace 2-(bromomethyl)-5-(trifluoromethyl)furan, the title compound was obtained (50%) as a white solid: mp 99-101° C.; MS (ES+) m/z 456.3 (M+1).

Example 10.39

Synthesis of 1'-methylspiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and iodomethane to replace 2-(bromomethyl)-5-(trifluoromethyl)furan, the title compound was obtained (72%) as a white solid: mp 142-144° C.; MS (ES+) m/z 296.2 (M+1).

Example 10.40

Synthesis of 1'-Propylspiro[furo[2,3-f][1,3]benzodioxole-7,3'-indol]-2'(1'H)-one Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-bromopropane to replace 2-(bromomethyl)-5-(trifluoromethyl)furan, the title compound was obtained (64%) as a white solid: mp 158-160° C.; MS (ES+) m/z 324.4 (M+1).

Example 10.41

Synthesis of 1'-(2,1,3-benzoxadiazol-5-ylmethyl) spiro[furo2,3-f][1,3]benzodioxole-7,3'-indol]-2' (1'H)-one Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 5-(bromomethyl)benzo[c][1,2,5]oxadiazole to replace 2-(bromomethyl)-5-(trifluoromethyl)furan, the title compound was obtained (17%) as a white solid: mp 163-165° C.; MS (ES+) m/z 414.4 (M+1).

Example 10.42

Synthesis of 1'-[(1-methyl-1H-benzotriazol-6-yl)methyl]spiro[furo-2,3-f][1,3]benzodioxole-7,3'-indol]-2' (1'H)-one Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 6-(bromomethyl)-1-methyl-1H-benzotriazole to replace 2-(bromomethyl)-5-(trifluoromethyl)furan, the title compound was obtained (17%) as a white solid: mp 230-235° C.; MS (ES+) m/z 427.3 (M+1).

Example 10.43

Synthesis of tert-butyl 4-[(2'-oxo-5,6-dihydrospiro [benzo[1,2-b:5,4-b']difuran-3,3'-indol]-1'(2'H)-yl) methyl]piperidine 1-carboxylate Following the procedure described in EXAMPLE 10.21, and making non-critical variations using 5,6-dihydrospiro [benzo[1,2-b:5,4-b']difuran-3,3'-indol]-2'(1'H)-one to replace 5,5-dimethyl-5,6-dihydrospiro[benzo[1,2-b:5,4-b'] difuran-3,3'-indol]-2'(1'H)-one, and tert-butyl 4-(bromomethyl)peridine-1-carboxylate to replace 2-(bromomethyl)-5-(trifluoromethyl)furan, the title compound was obtained (58%) as a white solid: mp 96-98° C.; $^1$H NMR (300 MHz, DMSO-d$_6$) δ 7.84-6.85 (m, 4H), 6.40 (s, 1H), 6.37 (s, 1H), 4.68 (ABq, 2H), 4.46 (t, 2H), 4.06-3.73 (m, 2H), 3.68-3.45 (m, 2H), 2.92 (t, 2H), 2.63 (s, 2H), 2.04-1.82 (m, 1H), 1.76-0.66 (m, 13H); MS (ES+) m/z 477.4 (M+1).

Example 10.44

Synthesis of 1'-(2,3-difluorobenzyl)-5,6-dihydrospyro[benzo[1,2-b:5,4-b']difuran-3,3'-indol]-2' (1'H)-one Following the procedure described in EXAMPLE 10.21, and making non-critical variations using 5,6-dihydrospiro [benzo[1,2-b:5,4-b']difuran-3,3'-indol]-2'(1'H)-one to replace 5,5-dimethyl-5,6-dihydrospiro[benzo[1,2-b:5,4-b'] difuran-3,3'-indol]-2'(1'H)-one, and 1-(bromomethyl)-2,3-difluorobenzene to replace 2-(bromomethyl)-5-(trifluoromethyl)furan, the title compound was obtained (67%) as a white solid: mp 156-158° C.; $^1$H NMR (300 MHz, DMSO-d$_6$) δ 7.50-6.85 (m, 7H), 6.43 (s, 1H), 6.39 (s, 1H), 5.01 (q, 2H), 4.75 (dd, 2H), 4.46 (t, 2H), 2.92 (t, 2H); MS (ES+) m/z 406.2 (M+1).

Example 10.45

Synthesis of 1'-(pyridin-2-ylmethyl)-5,6-dihydrospiro[benzo[1,2-b:5,4-b']difuran-3,3'-indol]-2' (1'H)-one hydrochloride Following the procedure described in EXAMPLE 10.21, and making non-critical variations using 5,6-dihydrospiro [benzo[1,2-b:5,4-b']difuran-3,3'-indol]-2'(1'H)-one to replace 5,5-dimethyl-5,6-dihydrospiro[benzo[1,2-b:5,4-b'] difuran-3,3'-indol]-2'(1'H)-one, and 2-(bromomethyl)pyridine hydrobromide to replace 2-(bromomethyl)-5-(trifluoromethyl)furan, 1'-(pyridin-2-ylmethyl)-5,6-dihydrospyro [benzo[1,2-b:5,4-b']difuran-3,3'-indol]2'(1'H)-one was obtained (27%) as a white solid, which was treated in CH$_2$Cl$_2$ with excess of HCl in ether to give the title compound: mp 208-210° C.; $^1$H NMR (300 MHz, DMSO-d$_6$) δ 8.78-8.53 (m, 1H), 8.05 (t, 1H), 7.64-7.47 (m, 2H), 7.30-6.92 (m, 4H), 6.59 (s, 1H), 6.38 (s, 1H), 5.24-5.06 (m, 2H), 4.78 (ABq, 2H), 4.46 (t, 2H), 2.94 (t, 2H); MS (ES+) m/z 371.4 (M+1).

Example 10.46

Synthesis of 1'-(4-methoxybenzyl)-5,6-dihydrospiro [benzo[1,2-b:5,4-b']difuran-3,3'-indol]-2'(1'H)-one Following the procedure described in EXAMPLE 10.21, and making non-critical variations using 5,6-dihydrospiro [benzo[1,2-b:5,4-b']difuran-3,3'-indol]-2'(1'H)-one to replace 5,5-dimethyl-5,6-dihydrospiro[benzo[1,2-b:5,4-b'] difuran-3,3'-indol]-2'(1'H)-one, and 1-(chloromethyl)-4-methoxybenzene to replace 2-(bromomethyl)-5-(trifluoromethyl)furan, the title compound was obtained (56%) as a white solid: mp 120-121° C.; MS (ES+) m/z 400.2 (M+1).

Example 10.47

Synthesis of 4'-bromo-1'-{[5-(trifluoromethyl)-2-furyl]methyl}spiro[furo[2,3-f][1,3]benzodioxole-7,3'-indol]-2'(1'H)-one To a solution of 4'-bromospiro[furo[2,3-f][1,3]benzodioxole-7,3'-indol]-2'(1'H)-one (0.48 g, 1.33 mmol) in N,N-dimethylformamide (5.00 mL) was added sodium hydride (0.08 g, 1.98 mmol, 60% dispersion in mineral oil) in one portion at 0° C. The reaction mixture was stirred for 0.5 h followed by the addition of a solution of 2-(bromomethyl)-5-trifluoromethyl)furan in N,N-dimethylformamide (1.00 mL). The reaction mixture was stirred at ambient temperature for 16 h and quenched by slow addition of water (5.00 mL). The reaction mixture was extracted with ethyl acetate (3×20.0 mL), washed with brine, dried over anhydrous sodium sulfate and filtered. The filtrate was concentrated in vacuo to dryness. The residue was subjected to column chromatography eluting with ethyl acetate:hexane (35%) to afford the title compound (0.46 g, 69%) as a colorless solid: $^1$H NMR (300 MHz, CDCl$_3$) δ 7.22-7.14 (m, 2H), 6.94 (dd, 1H), 6.73 (d, 1H), 6.46 (s, 1H), 6.39 (d, 1H), 6.04 (s, 1H) 5.86 (dd, 2H), 4.94 (ABq, 2H), 4.92 (ABq, 2H); $^{13}$C NMR (75 MHz, CDCl$_3$) δ 177.0, 157.2, 151.6, 151.5, 149.3, 143.4, 142.2, 130.5, 127.8, 129.6, 120.1, 116.0, 112.7, 109.5, 107.9, 102.5, 101.6, 93.3, 77.1, 59.6, 37.1; MS (ES+) m/z 508.2 (M+2).

Example 10.48

Synthesis of 4'-bromo-1'-{[5-(trifluoromethyl)-2-furyl]methyl}-5,6-dihydrospiro[benzo[1,2-b:5,4-b']difuran-3,3'-indol]-2'(1'H)-one Following the procedure described in EXAMPLE 10.47, and making non-critical variations using 4'-bromo-5,6-dihydrospiro[benzo[1,2-b:5,4-b']difuran-3,3'-indol]-2'(1'H)-one to replace 4'-bromospiro[furo[2,3-f][1,3]benzodioxole-7,3'-indol]-2'(1'H)-one, the title compound was obtained (76%) as a colorless solid: mp 182-184° C.; $^1$H NMR (300 MHz, CDCl$_3$) δ 7.21-7.11 (m, 2H), 6.92 (dd, 1H), 6.74 (d1H), 6.41 (d, 1H), 6.38 (s, 1H), 6.37 (s, 1H), 5.10 (d, 1H), 5.02 (d, 1H), 4.87 (d, 1H), 4.81 (d, 1H), 4.53 (t, 2H), 2.98 (t, 2H); $^{13}$C NMR (75 MHz, CDCl$_3$) δ 177.3, 162.4, 162.2, 151.5, 143.4, 130.2, 127.7, 120.5, 120.0, 119.7, 118.4, 117.0, 112.7, 112.6, 109.5, 107.8, 92.9, 77.1, 72.4, 59.1, 37.0, 28.9; MS (ES+) m/z 506.3 (M+1).

Example 10.49

Synthesis of 4'-bromo-1'-methylspiro[furo[2,3-f][1,3]benzodioxole-7,3'-indol]-2'(1'H)-one Following the procedure described in EXAMPLE 10.47, and making non-critical variations using iodomethane to replace 2-(bromomethyl)-5-(trifluoromethyl)furan, the title compound was obtained (79%) as a colorless solid: mp 155-157° C.; $^1$H NMR (300 MHz, CDCl$_3$) δ 7.19 (d, 1H), 7.17 (s, 1H), 6.84 (dd, 1H), 6.46 (s, 1H), 6.08 (s, 1H), 5.86 (dd, 2H), 4.90 (ABq, 2H), 3.25 (s, 3H); $^{13}$C NMR (75 MHz, CDCl$_3$) δ 177.3, 157.2, 149.2, 145.1, 142.0, 130.4, 129.9, 127.3, 119.9, 116.3, 107.3, 102.7, 101.5, 93.3, 77.3, 59.7, 26.9; MS (ES+) m/z 376.4 (M+2).

Example 10.50

Synthesis of tert-butyl 4-[(4'-bromo-2'-oxospiro[furo[2,3-f][1,3]benzodioxole-7,3'-indol]-1'(2'H)-yl)methyl]piperidine-1-carboxylate Following the procedure described in EXAMPLE 10.47, and making non-critical variations using tert-butyl 4-({[(4-methylphenyl)sulfonyl]oxy}methyl)piperidine-1-carboxylate to replace 2-(bromomethyl)-5-(trifluoromethyl)furan, the title compound was obtained (43%) as a colorless solid: $^1$H NMR (300 MHz, CDCl$_3$) δ 7.17 (d, 2H), 6.83 (t, 1H), 6.46 (s, 1H), 6.04 (s, 1H), 5.87 (d, 2H), 4.89 (ABq, 2H), 4.11 (d, 2H), 3.73-3.42 (m, 3H), 2.66 (t, 2H), 2.03-1.90 (m, 1H), 1.43 (s, 9H); $^{13}$C NMR (75 MHz, CDCl$_3$) δ 177.6, 157.3, 154.7, 149.2, 144.8, 142.1, 130.3, 129.8, 127.3, 120.2, 116.3, 107.6, 102.4, 101.6, 93.4, 79.6, 77.2, 59.6, 46.1, 43.4, 34.9, 28.4; MS (ES+) m/z 581.4 (M+23), 579.4 (M+23), 503.3 (M−57), 501.3 (M−57).

Example 10.51

Synthesis of 1'-[(3,5-dimethylisoxazol-4-yl)methyl]spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 4-(chloromethyl)-3,5-dimethylisoxazole to replace 2-(bromomethyl)-5-(trifluoromethyl)furan, the title compound was obtained (35%) as a colorless solid: mp 165-167° C.; $^1$H NMR (300 MHz, CDCl$_3$) δ 7.24 (t, 1H), 7.16 (d, 1H), 7.05 (t, 1H), 6.72 (d, 1H), 6.50 (s, 1H), 6.05 (s, 1H), 5.85 (d, 2H), 4.75 (ABq, 2H), 4.67 (ABq, 2H), 2.46 (s, 3H), 2.22 (s, 3H); $^{13}$C NMR (75 MHz, CDCl$_3$) δ 177.5, 167.1, 159.1, 156.1, 149.1, 142.4, 141.7, 131.8, 129.0, 124.3, 123.8, 118.9, 108.8, 108.6, 102.9, 101.6, 93.8, 80.6, 58.2, 33.3, 11.5, 10.7; MS (ES+) m/z 391.3 (M+1).

Example 10.52

Synthesis of 1'-(2-furylmethyl)spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 2-chloromethylfuran to replace 2-(bromomethyl)-5-(trifluoromethyl)furan, the title compound (40%) as a colorless solid: mp 110-112° C.; $^1$H NMR (300 MHz, CDCl$_3$) δ 7.35-7.33 (m, 1H), 7.29-7.23 (m, 1H), 7.15 (d, 1H), 7.06-7.00 (m, 2H), 6.50 (s, 1H), 6.34-6.31 (m, 2H), 6.10 (s, 1H), 5.85 (dd, 2H), 4.92 (ABq, 2H), 4.79 (ABq, 2H); $^{13}$C NMR (75 MHz, CDCl$_3$) δ 177.1, 155.9, 149.0, 148.9, 142.6, 142.3, 141.8, 132.2, 128.9, 123.8, 123.5, 119.5, 110.6, 109.3, 108.7, 103.1, 101.5, 93.6, 80.4, 58.2, 37.1; MS (ES+) m/z 362.5 (M+1).

Example 10.53

Synthesis of ethyl 5-(2'-oxospiro[furo[2,3-f][1,3]benzodioxole-7,3'-indol]-1'(2'H)-yl)pentanoate Following the procedure described in EXAMPLE 10.47, and making non-critical variations using spiro[furo[2,3-f][1,3]benzodioxole-7,3'-indol]-2'(1'H)one to replace 4'-bromospiro[furo[2,3-f][1,3]benzodioxole-7,3'-indol]-2'(1'H)-one, and ethyl 5-bromovalerate to replace 2-(bromomethyl)-5-(trifluoromethyl)furan, the title compound was obtained (62%) as a gummy material: $^1$H NMR (300 MHz, CDCl$_3$) δ 7.28 (t, 1H), 7.14 (d, 1H), 7.03 (t, 1H), 6.88 (d, 1H), 6.48 (s, 1H), 6.13 (s, 1H), 5.84 (d, 2H), 4.76 (ABq, 2H), 4.07 (q, 2H), 3.87-3.65 (m, 2H), 2.35 (t, 2H), 1.80-1.64 (m, 4H), 1.20 (t, 3H); $^{13}$C NMR (75 MHz, CDCl$_3$) δ 177.4, 173.1, 155.9, 148.8, 142.3, 142.2, 132.5, 128.9, 124.04, 123.3, 119.5, 108.6, 103.0, 101.5, 93.6, 80.5, 60.4, 58.2, 39.9, 33.7, 26.8, 22.2, 14.2; MS (ES+) m/z 432.09 (M+23).

Example 10.54

Synthesis of ethyl 4-(2'-oxospiro[furo[2,3-f][1,3]benzodioxole-7,3'-indol]-1'(2'H)-yl)butanoate Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and ethyl 4-bromobutyrate to replace 2-(bromomethyl)-5-(trifluoromethyl)furan, the title compound was obtained (80%) as a gummy material: $^1$H NMR (300 MHz, CDCl$_3$) δ 7.29 (t, 1H), 7.14 (d, 1H), 7.04 (d, 1H), 6.99 (d, 1H), 6.48 (s, 1H), 6.18 (s, 1H), 5.84 (d, 2H), 4.76 (ABq, 2H), 4.11 (q, 2H), 3.88-3.71 (m, 2H), 2.40 (t, 2H), 2.03 (t, 2H), 1.21 (t, 3H); $^{13}$C NMR (75 MHz, CDCl$_3$) δ 177.4, 172.8, 156.0, 148.9, 142.4, 142.2, 132.4, 129.0, 124.0, 123.3, 119.4, 108.7, 103.0, 101.5, 93.6, 80.5, 60.7, 58.2, 39.6, 31.2, 22.6, 14.3; MS (ES+) m/z 418.08 (M+23), 396.1 (M+1).

Example 10.55

Synthesis of 1'-(1,2,4-oxadiazol-3-ylmethyl)spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 3-(chloromethyl)-1,2,4-oxadiazole to replace 2-(bromomethyl)-5-(trifluoromethyl)furan, the title compound was obtained (36%)) as a colorless solid: mp 160-162° C.; $^1$H NMR (300 MHz, CDCl$_3$) δ 7.39 (dt, 1H), 7.20-7.13 (m, 3H), 7.05 (d, 1H), 6.50 (s, 1H), 6.12 (s, 1H), 5.86 (dd, 2H), 4.78 (ABq, 2H), 4.68 (s, 2H); $^{13}$C NMR (75 MHz, CDCl$_3$) δ 176.7, 156.0, 149.3, 142.5, 139.6, 131.6, 129.4, 124.8, 124.5, 118.4, 113.6, 108.7, 103.0, 101.7, 93.7, 80.3, 58.2, 29.7, 28.0; MS (ES+) m/z 365.2 (M+1).

Example 10.56

Synthesis of 1'-{[5-(3-chlorophenyl)-2-furyl]methyl}spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 2-(chloromethyl)-5-[3-chlorophenyl]furan to replace 2-(bromomethyl)-5-(trifluoromethyl)furan, the title compound was obtained (22%) as a colorless solid: mp 205-207° C.; $^1$H NMR (300 MHz, CDCl$_3$) δ 7.55 (t, 1H), 7.46 (dt, 1H), 7.28 (d, 2H), 7.21-7.14 (m, 2H), 7.09-7.04 (m, 2H), 6.59 (d, 1H), 6.50 (s, 1H), 6.40 (d, 1H), 6.10 (s, 1H), 5.84 (dd, 2H), 4.98 (ABq, 2H), 4.80 (ABq, 2H); $^{13}$C NMR (75 MHz, CDCl$_3$) δ 177.2, 155.9, 152.5, 149.2, 148.9, 142.4, 141.7, 134.8, 132.1, 132.0, 130.1, 128.9, 127.5, 124.0, 123.7, 123.6, 121.7, 119.4, 110.8, 109.2, 106.9, 103.0, 101.5, 93.6, 80.4, 58.2, 37.3; MS (ES+) m/z 472.2 (M+1).

Example 10.57

Synthesis of 1'-(3-chloropropyl)spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)one to replace 4'-bromospiro[furo[2,3-f][1,3]benzodioxole-7,3'-indol]-2'(1'H)-one, and 1-bromo-3-chloropropane to replace 2-(bromomethyl)-5-(trifluoromethyl)furan, the title compound was obtained (22%) as a colorless solid: mp 144-146° C.; $^1$H NMR (300 MHz, CDCl$_3$) δ 7.31 (dt, 1H), 7.14-7.12 (m, 2H), 7.01 (t, 1H), 6.65 (s, 1H), 6.23 (s, 1H), 5.89 (s, 2H), 4.68 (ABq, 2H), 3.85-3.79 (m, 2H), 3.67 (t, 2H), 2.06 (t, 1H); $^{13}$C NMR (75 MHz, DMSO-d$_6$) δ 177.2, 155.8, 148.7, 142.9, 142.2, 132.4, 129.3, 124.1, 123.3, 120.3, 109.3, 103.6, 101.7, 80.3, 57.8, 43.4, 30.6; MS (ES+) m/z 358.2 (M+1).

Example 10.58

Synthesis of 1'-[(2-isopropyl-1,3-oxazol-4-yl)methyl]spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 4-chloromethyl-2-isopropyloxazole to replace 2-(bromomethyl)-5-(trifluoromethyl)furan, the title compound was obtained (22%) as a colorless solid: mp 118-120° C.; $^1$H NMR (300 MHz, DMSO-d$_6$) δ 7.97 (s, 1H), 7.24 (t, 1H), 7.13 (d, 1H), 7.05 (d, 1H), 6.98 (t, 1H), 6.65 (s, 1H), 6.26 (s, 1H), 5.88 (d, 2H), 4.85 (d, 1H), 4.77 (d, 1H), 4.71-4.66 (m, 2H), 3.04-2.95 (m, 1H), 1.18 (dd, 6H); $^{13}$C NMR (75 MHz, DMSO-d$_6$) δ 176.9, 169.1, 155.6, 148.7, 142.4, 142.2, 136.8, 135.2, 132.4, 129.2, 123.9, 123.4, 120.5, 109.9, 103.6, 101.9, 93.7, 79.9, 57.9, 36.2, 28.1, 20.7, 20.6; MS (ES+) m/z 405.2 (M+1).

Example 10.59

Synthesis of 1'-[(1-methyl-1H-benzimidazol-2-yl)methyl]spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)one to replace 4'-bromospiro[furo[2,3-f][1,3]benzodioxole-7,3'-indol]-2'(1'H)-one, and 2-(bromomethyl)-1-methyl-1H-benzimidozole to replace 2-(bromomethyl)-5-(trifluoromethyl)furan, the title compound was obtained (22%) as a colorless solid: mp >250° C.; $^1$H NMR (300 MHz, CDCl$_3$) δ 7.71 (d, 1H), 7.65 (d, 1H), 7.54 (t, 1H), 7.39 (t, 1H), 7.30-7.24 (m, 1H), 7.16 (d, 1H), 7.05 (d, 2H), 6.63 (s, 1H), 6.49 (s, 1H), 6.44 (d, 1H), 6.11 (s, 1H), 5.83 (d, 2H), 4.99 (ABq, 2H), 4.80 (ABq, 2H); $^{13}$C NMR (75 MHz, CDCl$_3$) δ 177.2, 155.9, 150.6, 149.6, 148.9, 142.3, 141.7, 132.1, 131.8, 129.8, 128.9, 127.9, 126.8, 126.7, 126.6, 123.9, 123.6, 119.4, 111.0, 110.9, 110.6, 109.3, 103.1, 101.5, 93.6, 80.4, 58.2, 37.3; MS (ES+) m/z 506.3 (M+1).

Example 10.60

Synthesis of 1'-[(2-oxo-1,3-benzothiazol-3(2H)-yl)methyl]spiro[furo[2,3-f][1,3]benzodioxole-7,3'-indol]-2'(1'H)one Following the procedure described in EXAMPLE 10.47, and making non-critical variations using spiro[furo[2,3-f][1,3]benzodioxole-7,3"-indol]-2"(1"H)-one to replace 4"-bromospiro[furo[2,3-f][1,3]benzodioxole-7,3"-indol]-2"(1"H)-one, and 3-(bromomethyl)-benzo[d]thiazol-2(3H)-one to replace 2-(bromomethyl)-5-(trifluoromethyl)furan, the title compound was obtained (31%) as a colorless solid: $^1$H NMR (300 MHz, DMSO-d$_6$) δ 7.67 (d, 1H), 7.41 (d, 1H), 7.35-7.29 (m, 3H), 7.23-7.14 (m, 2H), 7.05 (t, 1H), 6.68 (s, 1H), 5.94-5.85 (m, 5H), 4.69 (td, 1H); $^{13}$C NMR (75 MHz, DMSO-d$_6$) δ 178.1, 170.6, 155.9, 148.9, 142.2, 141.0, 136.1, 131.8, 129.6, 127.3, 124.5, 124.4, 124.3, 123.7, 121.5, 119.8, 112.1, 110.0, 103.4, 101.9, 93.8, 80.3, 58.3, 47.9; MS (ES+) m/z 467.2 (M+23).

Example 10.61

Synthesis of 1'-[(5-chloro-2-thienyl)methyl]-5'-fluorospiro[furo[2,3-f][1,3]benzodioxole-7,3'-indol]-2'(1'H)-one Following the procedure described in EXAMPLE 10.47, and making non-critical variations using 5'-fluorospiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 5-chloro-2-(chloromethyl)thiophene to replace 2-(bromomethyl)-5-(trifluoromethyl)furan, the title compound was obtained (76%) as a colorless solid: mp 142-144° C.; $^1$H NMR (300 MHz, DMSO-d$_6$) δ 7.22-7.17 (m, 1H), 7.14-7.13 (m, 1H), 7.12-7.10 (m, 2H), 6.96 (d, 1H), 6.68 (s, 1H), 6.13 (s, 1H), 5.91 (d, 2H), 5.02 (ABq, 2H), 4.73 (ABq, 2H); $^{13}$C NMR (75 MHz, DMSO-d$_6$) δ 176.9, 161.0, 157.8, 156.0, 149.0, 142.2, 138.3, 138.2 (d, $^4J_{CF}$=7.0 Hz) 133.6 (d, $^3J_{CF}$=33 Hz), 128.3, 127.8, 127.1, 119.5, 115.6 (d, $^1J_{CF}$=93 Hz), 112.5 (d, $^1J_{CF}$=100 Hz), 110.8 (d, $^3J_{CF}$=32 Hz), 103.2, 102.0, 93.9, 79.8, 58.2 (d, $^4J_{CF}$=7.0 Hz), 39.0; MS (ES+) m/z 430.1 (M+1).

Example 10.62

Synthesis of 1'-[(5-chloro-2-furyl)methyl]spiro[furo[2,3-f][1,3]benzodioxole-7,3'-indol]-2'(1'H)-one To an ice-cooled solution of (5-chloro-2-furyl)methanol (2.03 g, 15.3 mmol) in anhydrous dichloromethane (50.0 mL) was added triethylamine (4.64 g, 45.9 mmol) followed by thionyl chloride (3.64 g, 30.6 mmol). The reaction mixture was stirred at 0° C. for 30 min and quenched with saturated ammonium chloride (25.0 mL). After the aqueous layer was separated, the organic layer was washed with 10% aqueous HCl (20.0 mL), brine (20 mL), dried over anhydrous sodium sulfate and filtered. The filtrate was concentrated in vacuo to dryness to give 5-chloro-2-chloromethylfuran as a yellow oil. A solution of this oil in anhydrous N,N-dimethylformamide (3.00 mL) was added directly without any further purification to a mixture of spiro[furo[2,3-f][1,3]benzodioxole-7,3'-indol]-2'(1'H)-one (0.84 g, 3.00 mmol) and sodium hydroxide (0.48 g, 12.0 mmol) in anhydrous N,N-dimethylformamide (9.00 mL). The reaction mixture was heated at 70° C. for 16 h, cooled to ambient temperature followed by the addition of saturated ammonium chloride (5.0). N,N-Dimethylformamide was removed under high vacuum. The residue was diluted with ethyl acetate (100 mL), washed with 10% aqueous HCl (25.0 mL), brine (25.0 mL), dried over anhydrous sodium sulfate and filtered. The filtrate was concentrated in vacuo to dryness. The brown residue was subjected to column chromatography eluting with ethyl acetate/hexane (35%) to afford the title compound (0.74 g, 62%) as a colorless solid: mp 148-150° C.; $^1$H NMR (300 MHz, DMSO-d$_6$) δ 7.29 (t, 1H), 7.15-7.12 (m, 2H), 7.01 (d, 1H), 6.67 (s, 1H), 6.60 (d, 1H), 6.39 (d, 1H), 6.10 (s, 1H), 5.89 (d, 2H), 4.89 (ABq, 2H), 4.72 (ABq, 2H); $^{13}$C NMR (75 MHz, DMSO-d$_6$) δ 176.9 155.8 149.7, 148.8, 142.2, 142.1, 134.8, 132.1, 129.3 124.1, 123.7 120.2, 112.0, 109.9, 108.2 103.2, 101.9, 93.8, 80.0, 57.9 37.0; MS (ES+) m/z 396 (M+1).

Example 10.63

Synthesis of 1'-[(4-hydroxy-1,2,2,6,6-pentamethylpiperidin-4-yl)methyl]spiro[furo[2,3-f][1,3]benzodioxole-7,3'-indol]-2'(1'H)-one Following the procedure described in EXAMPLE 10.62, and making non-critical variations using 5,5,6,7,7-pentamethyl-1-oxa-6-azaspiro[2.5]octane to replace (5-chloro-2-furyl)methanol, the title compound was obtained (70%) as a colorless solid: mp 210-214° C.; $^1$H NMR (300 MHz, DMSO-d$_6$) δ 7.29 (d, 1H), 7.24 (t, 1H), 7.10 (d, 1H), 7.01 (t, 1H), 6.66 (s, 1H), 6.45 (s, 1H), 5.90 (d, 2H), 5.20 (br, 1H), 4.70 (ABq, 2H), 3.57 (q, 2H), 3.30 (s, 3H), 2.01-1.83 (m, 4H), 1.45 (s, 6H), 1.34 (s, 6H); $^{13}$C NMR (75 MHz, DMSO-d$_6$) δ 178.5, 156.0, 148.7, 144.5, 142.2, 132.3, 128.9, 123.8, 123.2, 120.3, 110.9, 104.1, 101.9, 93.7, 80.9, 71.6, 65.3, 57.8, 52.6, 30.2, 28.7, 22.1; MS (ES+) m/z 465.4 (M+1).

Example 10.64

Synthesis of 1'-{[5-(2-chlorophenyl)-2-furyl]methyl}spiro[furo[2,3-f][1,3]benzodioxole-7,3'-indol]-2'(1'H)-one Following the procedure described in EXAMPLE 10.62, and making non-critical variations using [5-(2-chlorophenyl)-2-furyl]methanol to replace (5-chloro-2-furyl)methanol, the title compound was obtained (48%) as a colorless solid: mp 148-150° C.; $^1$H NMR (300 MHz, CDCl$_3$) δ 7.74 (d, 1H), 7.39 (d, 1H), 7.29 (d, 1H), 7.24 (d, 1H), 7.19-7.15 (m, 2H), 7.08-7.04 (m, 3H), 6.51 (s, 1H), 6.45 (d, 1H), 6.12 (s, 1H), 6.84 (s, 2H), 4.99 (ABq, 2H), 4.78 (ABq, 2H); $^{13}$C NMR (75 MHz, CDCl$_3$) δ 177.2, 155.9, 150.3, 149.0, 148.6, 142.4, 141.8, 132.1, 130.8, 130.0, 128.9, 128.7, 128.2, 127.7, 126.9, 123.9, 123.6, 119.4, 111.8, 110.7, 109.2, 103.1, 101.5, 93.6, 80.4, 58.2, 37.3; MS (ES+) m/z 472.2 (M+1).

Example 10.65

Synthesis of 1'-[(5-methyl-2-furyl)methyl]spiro[furo[2,3-f][1,3]benzodioxole-7,3'-indol]-2'(1'H)-one Following the procedure described in EXAMPLE 10.62, and making non-critical variations using (5-methyl-2-furyl)methanol to replace (5-chloro-2-furyl)methanol, the title compound was obtained (70%) as a colorless solid: mp 117-119° C.; $^1$H NMR (300 MHz, DMSO-d$_6$) δ 7.26 (t, 1H), 7.12 (t, 2H), 6.99 (t, 1H), 6.67 (s, 1H), 6.32 (d, 1H), 6.07 (s, 1H), 5.97 (d, 1H), 5.89 (d, 2H), 4.84 (ABq, 2H), 4.72 (ABq, 2H); $^{13}$C NMR (75 MHz, DMSO-d$_6$) δ 176.8, 155.7, 151.9, 148.8, 147.7, 142.3, 142.2, 132.1, 129.2, 124.0, 123.5, 120.4, 110.1, 110.0, 107.0, 103.2, 101.9, 93.8, 79.9, 57.9, 37.2, 13.7; MS (ES+) m/z 376 (M+1).

Example 10.66

Synthesis of 1'-[(5-bromo-2-furyl)methyl]spiro[furo[2,3-f][1,3]benzodioxole-7,3'-indol]-2'(1'H)-one Following the procedure described in EXAMPLE 10.62, and making non-critical variations using (5-bromo-2-furyl)methanol to replace (5-chloro-2-furyl)methanol, the title compound was obtained (76%) as colorless solid: $^1$H NMR (300 MHz, DMSO-d$_6$) δ 9.29 (s, 1H), 7.69 (dt, 1H), 7.32-7.26 (m, 2H), 7.04 (d, 1H), 6.99 (d, 1H), 6.71 (d, 1H), 6.02 (s, 1H), 4.91 (ABq, 2H), 4.47 (t, 2H), 3.08 (t, 2H); $^{13}$C NMR (75 MHz, DMSO-d$_6$) δ 176.9, 160.4, 156.3, 153.8, 149.7, 146.1, 137.5, 130.9, 130.8, 126.5, 125.8, 123.1, 121.5, 118.8, 116.4, 108.3, 96.7, 76.6, 71.9, 45.7, 29.1; MS (ES+) m/z 440.1 (M+1), 442.1 (M+1).

Example 10.67

Synthesis of 1'-[(5-chloro-2-thienyl)methyl]spiro[furo[2,3-f][1,3]benzodioxole-7,3'-indol]-2'(1'H)-one Following the procedure described in EXAMPLE 10.62, and making non-critical variations using (5-chloro-2-thienyl)methanol to replace (5-chloro-2-furyl)methanol, the title compound was obtained (77%) as a colorless solid: mp 145-146° C.; $^1$H NMR (300 MHz, DMSO-d$_6$) δ 7.28 (t, 1H), 7.20-7.14 (m, 2H), 7.10 (d, 1H), 7.01 (t, 1H), 6.95 (d, 1H), 6.67 (s, 1H), 6.09 (s, 1H), 5.89 (d, 2H), 5.02 (ABq, 2H), 4.71 (ABq, 2H); MS (ES+) m/z 411.9 (M+1).

Example 10.68

Synthesis of 1'-{[3-hydroxy-5-(trifluoromethyl)-2-thienyl]methyl}spiro[furo[2,3-f][1,3]benzodioxole-7,3'-indol]-2'(1'H)-one Following the procedure described in EXAMPLE 10.62, and making non-critical variations using 2-(hydroxymethyl)-5-(trifluoromethyl)thiophene-3-ol to replace (5-chloro-2-furyl)methanol, the title compound was obtained (48%) as a colorless solid: mp 225-227° C.; $^1$H NMR (300 MHz, DMSO-d$_6$) δ 10.4 (s, 1H), 7.29 (dt, 1H), 7.16-7.10 (m, 3H), 7.01 (dt, 1H), 6.68 (s, 1H), 6.09 (s, 1H), 5.89 (d, 2H), 4.94 (ABq, 2H), 4.70 (ABq, 2H); $^{13}$C NMR (75 MHz, DMSO-d$_6$) δ 176.9, 155.8, 152.3, 148.9, 142.2, 141.9, 132.1, 129.4, 125.9, 125.4, 124.5, 124.2, 123.8, 122.6, 120.9, 120.0, 116.5, 109.5, 103.3, 101.9, 93.8, 80.2, 57.9, 34.9; MS (ES+) m/z 460.38 (M−1).

Example 10.69

Synthesis of 1'-{[5-(2-trifluoromethylphenyl)-2-furyl]methyl}-4H-spiro[furo[2,3-g][1,3]benzodioxine-8,3'-indol]-2'(1'H)-one Following the procedure described in EXAMPLE 10.62, and making non-critical variations using {5-[2-(trifluoromethyl)phenyl]-2-furyl}methanol to replace (5-chloro-2-furyl)methanol, the title compound was obtained (28%) as a colorless solid: mp 124-126° C.; $^1$H NMR (300 MHz, CDCl$_3$) δ 7.71 (d, 1H), 7.65 (d, 1H), 7.54 (t, 1H), 7.39 (t, 1H), 7.30-7.24 (m, 1H), 7.16 (d, 1H), 7.05 (d, 2H), 6.63 (s, 1H), 6.49 (s, 1H), 6.44 (d, 1H), 6.11 (s, 1H), 5.83 (d, 2H), 4.99 (ABq, 2H), 4.80 (ABq, 2H); $^{13}$C NMR (75 MHz, CDCl$_3$) δ 177.2, 155.9, 150.6, 149.6, 148.9, 142.3, 141.7, 132.1, 131.8, 129.8, 128.9, 127.9, 126.8, 126.7, 126.6, 123.9, 123.6, 119.4, 111.0, 110.9, 110.6, 109.3, 103.1, 101.5, 93.6, 80.4, 58.2, 37.3; MS (ES+) m/z 506.27 (M+1).

Example 10.70

Synthesis of 1'[(2-chloro-1,3-thiazol-5-yl)methyl]spiro[furo[2,3-f][1,3]benzodioxole-7,3'-indol]-2'(1'H)one To a solution of (2-chloro-1,3-thiazol-5-yl)methanol (0.30 g, 2.00 mmol) in anhydrous CH$_2$Cl$_2$ (20.0 mL) was added thionyl chloride (0.50 g, 4.20 mmol) followed by triethylamine (0.40 g, 4.00 mmol) at 0° C. After stirring at 0° C. for one hour and ambient temperature for one hour, the reaction mixture was diluted with CH$_2$Cl$_2$ (50.0 mL) and extracted with water (2×20 mL). The organic phase was dried over Na$_2$SO$_4$ and filtered. The filtrate was concentrated in vacuo to dryness. The residue was dissolved in methyl-ethyl ketone (10.0 mL) followed by the additions of spiro[furo[2,3-f][1,3]benzodioxole-7,3'-indol]-2'(1'H)-one (0.36 g, 2.00 mmol) and cesium carbonate (1.95 g, 6.00 mmol). The reaction mixture was heated at 70° C. overnight, cooled, filtered and the filtrate was concentrated in vacuo to dryness. The residue was subjected to column chromatography to yield the title compound (0.032 g, 3.4%) as a colorless solid: mp 195-198° C.; $^1$H NMR (300 MHz, DMSO-d$_6$) δ 7.81 (s, 1H), 7.39-6.93 (m, 5H), 6.66 (s, 1H), 6.15-6.12 (m, 1H), 5.89 (d, 2H), 5.10 (s, 2H), 4.70 (dd, 2H); MS (ES+) m/z 413.1 (M+1).

Example 10.71

Synthesis of 1'-{[5-(trifluoromethyl)-2-furyl]methyl}-6,7-dihydrospiro[benzo[1,2-b:4,5-b']difuran-3,3'-indol]-2'(1'H)-one Following the procedure as described in EXAMPLE 10.21, and making non-critical variations using 6,7-dihydrospiro[benzo[1,2-b:4,5-b']difuran-3,3'-indol]-2'(1'H)-one to replace 5,5-dimethyl-5,6-dihydrospiro[benzo[1,2-b:5,4-b']difuran-3,3'-indol]-2'(1'H)-one, the title compound was obtained (19%) as a white solid: mp 174-177° C.; $^1$H NMR (300 MHz, DMSO-d$_6$) δ 7.33-6.95 (m, 5H), 6.84 (s, 1H), 6.71 (d, 1H), 5.88 (s, 1H), 5.03 (ABq, 2H), 4.70 (ABq, 2H), 4.46-4.31 (m, 2H), 3.07 (t, 2H); MS (ES+) m/z 428.0 (M+1).

Example 10.72

Synthesis of 1'{[5-(trifluoromethyl)-2-furyl]methyl}5,6-dihydrospyro[benzo[1,2-b:5,4-b']difuran-3,3'-indol]2'(1'H)-one Following the procedure described in EXAMPLE 10.21, and making non-critical variations using 5,6-dihydrospyro[benzo[1,2-b:5,4-b']difuran-3,3'-indol]2'(1'H)-one to replace 5,5-dimethyl-5,6-dihydrospiro[benzo[1,2-b:5,4-b']difuran-3,3'-indol]-2'(1'H)-one, the title compound was obtained (71%) as a white solid: mp 173-176° C.; $^1$H NMR (300 MHz, DMSO-d$_6$) δ 7.50-6.90 (m, 5H), 6.73 (d, 1H), 6.38 (s, 1H), 6.32 (s, 1H), 5.04 (ABq, 2H), 4.75 (ABq, 2H), 4.55-4.36 (m, 2H), 2.88 (t, 2H); $^{13}$C NMR (75 MHz, DMSO-d$_6$) δ 177.2, 161.7, 161.0, 153.5, 142.0, 140.3, 139.7, 139.2, 132.6, 129.1, 124.1, 123.8, 121.2, 121.0, 120.3, 119.1, 117.7, 114.6, 114.5, 110.4, 109.6, 93.0, 80.0, 72.5, 57.3, 36.8, 28.7; MS (ES+) m/z 428.2 (M+1).

Example 10.73

Synthesis of 1'-{[5-(trifluoromethyl)-2-thienyl]methyl}spiro[furo[2,3-f][1,3]benzodioxole-7,3'-indol]-2'(1'H)-one To a solution of 1'-{[3-hydroxy-5-(trifluoromethyl)-2-thienyl]methyl}spiro[furo[2,3-f][1,3]benzodioxole-7,3'-indol]-2'(1'H)-one (0.75 g, 1.62 mmol) in anhydrous dichloromethane (12.0 mL) was added triethylamine (0.49 g, 0.70 mL, 4.85 mmol) and trifluoromethanesulfonic anhydride (0.91 g, 0.50 mL, 3.24 mmol) at 0° C. under nitrogen. The reaction mixture was stirred for 30 min and quenched with saturated ammonium chloride (15.0 mL). After the aqueous layer was separated, the organic layer was washed with 10% HCl (10.0 mL), brine (10.0 mL), dried over anhydrous sodium sulfate and filtered. The filtrate was concentrated in vacuo to dryness. The residue was subjected to column chromatography to provide brown gummy material as the triflate.

A mixture of this triflate (15.3 mmol), tetrakis(triphenylphosphine)palladium(0) (0.19 g, 0.17 mmol), triethylamine (1.66 g, 2.30 mL, 16.5 mmol), and formic acid (0.76 mg, 0.60 mL, 16.5 mmol) in anhydrous dioxane (24 mL) was heated at reflux for 16 h. After the reaction mixture was cooled down to ambient temperature, the solvent was removed under reduced pressure. The black residue was diluted with ethyl acetate (50.0 mL), washed with 10% HCl (20.0 mL), saturated ammonium chloride (20.0 mL), brine (20.0 mL), dried over anhydrous sodium sulfate and filtered. The filtrate was concentrated in vacuo to dryness. The residue was subjected to column chromatography eluting with ethyl acetate:hexane (35%) to afford the title compound (0.65 g, 89%) as a colorless solid: mp 127-130° C.; $^1$NMR (300 MHz, DMSO-$d_6$) δ 7.58-7.56 (m, 1H), 7.32-7.27 (m, 2H), 7.22 (s, 1H), 7.18 (d, 1H), 7.16 (s, 1H), 7.09 (dt, 1H), 6.68 (s, 1H), 6.10 (s, 1H), 5.89 (d, 2H), 5.17 (ABq, 2H), 4.72 (ABq, 2H); $^{13}$C NMR (75 MHz, DMSO-$d_6$) δ 177.0, 155.9, 148.9, 144.7, 142.2, 141.8, 132.1, 130.6, 130.5, 129.3, 128.7, 128.0, 124.3, 123.9, 120.0, 109.8, 103.3, 102.0, 93.9, 80.2, 57.8, 38.7; MS (ES+) m/z 446.1 (M+1).

Example 10.74

Synthesis of 1'-{[3-methoxy-5-(trifluoromethyl)-2-thienyl]methyl}spiro[furo[2,3-f][1,3]benzodioxole-7,3'-indol]-2'(1'H)-one A mixture of 1'-{[3-hydroxy-5-(trifluoromethyl)-2-thienyl]methyl}spiro[furo[2,3-f][1,3]benzodioxole-7,3'-indol]-2'(1'H)-one (0.18 g, 0.39 mmol), NaOH (0.08 g, 1.96 mmol) and iodomethane (0.17 g, 1.18 mmol) in anhydrous N,N-dimethylformamide (2.00 mL) was stirred at ambient temperature for 16 h. The reaction was quenched by addition of saturated ammonium chloride (10.0 mL) and extracted with ethyl acetate (3×50.0 mL). The combined organic layers was washed with water (3×20.0 mL), brine (20.0 mL), dried over anhydrous sodium sulfate and filtered. The filtrate was concentrated in vacuo to dryness. The colorless solid was triturated with ether to give the title compound (0.15 g, 81%): mp 178-180° C.; $^1$H NMR (300 MHz, DMSO-$d_6$) δ 7.71 (s, 1H), 7.30 (dt, 1H), 7.15 (d, 1H), 7.07-7.02 (m, 2H), 6.68 (s, 1H), 6.08 (s, 1H), 5.89 (d, 2H), 4.95 (ABq, 2H), 4.70 (ABq, 2H), 3.90 (s, 3H); $^{13}$C NMR (75 MHz, DMSO-$d_6$) δ 177.0, 155.8, 154.9, 148.9, 142.2, 141.8, 132.1, 129.4, 125.7, 124.3, 123.8, 120.4, 120.3, 120.0, 119.5, 109.4, 103.2, 102.0, 93.9, 80.1, 59.9, 57.9, 34.9; MS (ES+) m/z 476.3 (M+1).

Example 10.75

Synthesis of 4'-methyl-1'-{[5-(trifluoromethyl)-2-furyl]methyl}spiro[furo[2,3-f][1,3]benzodioxole-7,3'-indol]-2'(1'H)-one A mixture of 4'-bromo-1'-((5-(trifluoromethyl)furan-2-yl)methyl)-6H-spiro[benzofuro[6,5-d][1,3]dioxole-7,3'-indolin]-2'-one (0.51 g, 1.00 mmol), lithium chloride (0.09 mg, 2.00 mmol), Pd$_2$(dba)$_3$ (0.09 mg, 10 mole %) was flushed with nitrogen. To the above mixture was added anhydrous 1-methyl-2-pyrrolidinone (5.00 mL) and tetramethyltin (0.27 mg, 0.20 mL, 1.50 mmol). The reaction mixture was heated at 60° C. for 16 h and quenched with saturated ammonium chloride (10.0 mL). The reaction mixture was extracted with ethyl acetate (3×10.0 mL). The combined organic layers was dried over anhydrous sodium sulfate and filtered. The filtrate was concentrated in vacuo to dryness. The residue was subjected to column chromatography eluting with ethyl acetate: hexane (20%) to afford the title compound (0.07 g, 16%) as a colorless solid: mp 117-119° C.; $^1$H NMR (300 MHz, CDCl$_3$) δ 7.18 (t, 1H), 6.82 (t, 2H), 6.72 (d, 1H), 6.47 (s, 1H), 6.37 (d, 1H), 6.09 (s, 1H), 5.86 (d, 2H), 4.95 (ABq, 2H), 4.83 (ABq, 2H), 2.03 (s, 3H); $^{13}$C NMR (75 MHz, CDCl$_3$) δ 177.6, 156.2, 152.0, 149.1, 142.3, 141.3, 135.6, 129.4, 128.9, 126.0, 120.6, 117.2, 112.7, 112.6, 109.2, 106.5, 102.9, 101.6, 93.3, 78.4, 58.3, 37.0, 17.1; MS (ES+) m/z 444.1 (M+1).

Example 10.76

Synthesis of 5'-methyl-1'-{[5-(trifluoromethyl)-2-furyl]methyl}spiro[furo[2,3-f][1,3]benzodioxole-7,3'-indol]-2'(1'H)-one Following the procedure described in EXAMPLE 10.47, and making non-critical variations using 5'-methylspiro[furo[2,3-f][1,3]benzodioxole-7,3'-indol]-2'(1'H)-one to replace 4'-bromospiro[furo[2,3-f][1,3]benzodioxole-7,3'-indol]-2' (1'H)-one, the title compound was obtained (77%): mp 96-98° C.; $^1$H NMR (300 MHz, CDCl$_3$) δ 7.09 (d, 1H), 7.00 (s, 1H), 6.87 (d, 1H), 6.74 (d, 1H), 6.52 (s, 1H), 6.38 (d, 1H), 6.11 (s, 1H), 5.88 (d, 2H), 4.96 (ABq, 2H), 4.80 (ABq, 2H), 2.29 (s, 3H); MS (ES+) m/z 444.2 (M+1).

Example 10.77

Synthesis of 1'-({5-[4-(trifluoromethyl)phenyl]-1,2,4-oxadiazol-3-yl}methyl)spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and 3-chloromethyl-5-[4-(trifluoromethyl)phenyl]-1,2,4-oxadiazole to replace 2-(bromomethyl)-5-(trifluoromethyl)furan, the title compound was obtained (44%): $^1$H NMR (300 MHz, CDCl$_3$) δ 8.22 (d, 2H), 7.76 (d, 2H), 7.30-7.18 (m, 2H), 7.06 (t, 1H), 6.91 (d, 1H), 6.51 (s, 1H), 6.40 (s, 1H), 5.88 (s, 2H), 5.17 (ABq, 2H), 4.86 (ABq, 2H); MS (ES+) m/z 508.1 (M+1).

Example 10.78

Synthesis of 1'-(2-thienylmethyl)spiro[furo[2,3-f][1,3]benzodioxole-7,3'-indol]-2'(1'H)-one Following the procedure described in EXAMPLE 10.62, and making non-critical variations using 2-thiophenemethanol to replace (5-chloro-2-furyl)methanol, the title compound was obtained (37%) as a colorless solid: $^1$H NMR (300 MHz, CDCl$_3$) δ 7.26-7.20 (m, 2H), 7.18-7.13 (m, 1H), 7.10-6.98 (m, 2H), 6.97-6.90 (m, 2H), 6.50 (s, 1H), 6.12 (s, 1H), 5.85 (d, 2H), 5.10 (ABq, 2H), 4.79 (ABq, 2H); MS (ES+) m/z 378.19 (M+1).

Example 10.79

Synthesis of 5-[(2'-oxospiro[furo[2,3-f][1,3]benzodioxole-7,3'-indol]-1'(2'H)-yl)methyl]thiophene-2-carbonitrile A mixture of 1'-[(5-bromo-2-thienyl)methyl]spiro[furo[2,3-f][1,3]benzodioxole-7,3'-indol]-2'(1'H)-one (0.23 g, 0.49 mmol), zinc cyanide (0.07 g, 0.59 mmol), tris(dibenzylideneacetone)dipalladium(0) (0.10 g, 0.11 mmol), 1,1'-bis (diphenylphosphino)ferrocene (0.06 g, 0.11 mmol), N,N-dimethylformamide (6.00 mL) and a catalytic amount of water (2 drops) was heated at 120° C. for 24 hours. After cooling down to ambient temperature, the organic solvent was evaporated in vacuo. The residue was extracted with ethyl acetate (5×15.0 mL) and the combined organic solution was passed through a bed of celite. The filtrate was successively washed with saturated aqueous ammonium chloride (25.0 mL), water (2×35.0 mL) and brine (40.0 mL). The organic layer was dried over sodium sulfate and filtered. The filtrate was concentrated in vacuo to dryness. The residue was subjected to column chromatography eluted with 20-35% ethyl acetate in hexanes to afford solid which was further purified by preparative thin layer chromatography, eluted with 20% ethyl acetate in hexanes to afford the title compound (0.09 g, 44%): $^1$H NMR (300 MHz, CDCl$_3$) δ 7.50 (d, 1H), 7.32-7.16 (m, 2H), 7.12-7.04 (m, 2H), 6.86 (d, 1H), 6.51 (s, 1H), 6.08 (s, 1H), 5.87 (d, 2H), 5.10 (ABq, 2H), 4.78 (ABq, 2H); MS (ES+) m/z 403.0 (M+1).

Example 10.80

Synthesis of 5-[(2'-oxospiro[furo[2,3-f][1,3]benzodioxole-7,3'-indol]-1'(2'H)-yl)methyl]-2-furonitrile Following the procedure described in EXAMPLE 10.79, and making non-critical variations using 1'-[(5-bromo-2-furyl)methyl]spiro[furo[2,3-f][1,3]benzodioxole-7,3'-indol]-2'(1'H)-one to replace 1'-[(5-bromo-2-thienyl)methyl]spiro[furo[2,3-f][1,3]benzodioxole-7,3'-indol]-2'(1'H)-one, the title compound was obtained (44%) as a colorless solid: mp 167-169° C.; $^1$H NMR (300 MHz, CDCl$_3$) δ 7.34-7.27 (m, 1H), 7.21-7.17 (m, 1H), 7.12-7.08 (m, 1H), 7.07-7.03 (m, 1H), 6.95 (d, 1H), 6.51 (s, 1H), 6.44 (d, 1H), 6.08 (s, 1H), 5.86 (q, 2H), 4.96 (ABq, 2H), 4.78 (ABq, 2H); MS (ES+) m/z 387.2 (M+1).

Example 10.81

Synthesis of 1'-{[5-(methylsulfonyl)-2-furyl]methyl}spiro[furo[2,3-f][1,3]benzodioxole-7,3'-indol]-2'(1'H)-one A mixture of 1'-[(5-bromo-2-furyl)methyl]spiro[furo[2,3-f][1,3]benzodioxole-7,3'-indol]-2'(1'H)-one (0.70 g, 1.59 mmol), sodium methanesulfinate (85%, 0.23 g, 1.91 mmol), copper (I) iodide (0.04 g, 0.22 mmol), L-proline (0.04 g, 0.35 mmol) and dimethyl sulfoxide (4.00 mL) was heated at 100° C. After 3 days, the reaction mixture was cooled down to ambient temperature, quenched with water (50.0 mL) and extracted with ethyl acetate (3×40.0 mL). The combined organic layers was washed with brine (2×50.0 mL), dried over sodium sulfate and filtered. The filtrate was concentrated in vacuo to dryness. The residue was subjected to column chromatography eluting with ethyl acetate:hexane (30-50%) to afford the title compound (0.50 g, 71%): mp 177-179° C.; $^1$H NMR (300 MHz, CDCl$_3$) δ 7.29 (t, 1H), 7.19 (d, 1H), 7.12-7.04 (m, 2H), 6.94 (d, 1H), 6.50 (s, 1H), 6.42 (d, 1H), 6.11 (s, 1H), 5.86 (s, 2H), 5.00 (ABq, 2H), 4.79 (ABq, 2H), 3.11 (s, 3H); $^{13}$C NMR (75 MHz, CDCl$_3$) δ 177.3, 155.9, 154.5, 149.1, 149.1, 142.4, 141.1, 131.9, 129.1, 124.2, 124.1, 119.0, 118.4, 109.9, 108.7, 102.9, 101.6, 93.7, 80.3, 58.2, 43.4, 37.2; MS (ES+) m/z 440.0 (M+1).

Example 10.82

Synthesis of 1'-[(6-oxo-1,6-dihydropyridin-3-yl)methyl]spiro[furo[2,3-f][1,3]benzodioxole-7,3'-indol]-2'(1'H)-one To a mixture of 1'-[(6-methoxypyridin-3-yl)methyl]spiro[furo[2,3-f][1,3]benzodioxole-7,3'-indol]-2'(1'H)-one (0.23 g, 0.57 mmol), sodium iodide (0.28 g, 1.87 mmol), water (2 drops) in anhydrous acetonitrile (5.00 mL) was added chlorotrimethylsilane (0.19 g, 1.78 mmol) at 0° C. The reaction mixture was stirred at ambient temperature for 16 h and quenched with sodium bisulfite (0.20 g). The reaction mixture was diluted with ethyl acetate (100 mL) and washed with brine (2×25.0 mL), dried over anhydrous sodium sulfate and filtered. The filtrate was concentrated in vacuo to dryness. The residue was triturated with ether (2×10.0 mL) to give the title compound (0.16 g, 72%) as light yellow solid: mp 247-250° C.; $^1$H NMR (300 MHz, DMSO-d$_6$,) δ 11.50 (br, 1H), 7.50 (bd, 1H), 7.36-7.24 (m, 2H), 7.17-7.12 (m, 2H), 7.01 (dt, 1H), 6.67 (s, 1H), 6.28 (d, 1H), 6.09 (s, 1H), 5.91-5.88 (m, 2H), 4.78 (d, 1H), 4.67-4.62 (m, 3H); MS (ES+) m/z 389.15 (M+1).

Example 10.83

Synthesis of 1'-[(1-methyl-6-oxo-1,6-dihydropyridin-3-yl)methyl]spiro[furo[2,3-f][1,3]benzodioxole-7,3'-indol]-2'(1'H)-one Following the procedure described in PREPARATION 1A, and making non-critical variations using 1'-[(6-oxo-1,6-dihydropyridin-3-yl)methyl]spiro[furo[2,3-f][1,3]benzodioxole-7,3'-indol]-2'(1'H)-one to replace 4-bromoindole, and methyl iodide to replace 1-bromopentane, the title compound was obtained (78%): mp 115-118° C.; $^1$H NMR (300 MHz, CDCl$_3$) δ 7.39-7.23 (m, 3H), 7.18 (d, 1H), 7.06 (t, 1H), 6.87 (d, 1H), 6.57-6.48 (m, 2H), 6.02 (s, 1H), 5.87-5.83 (m, 2H), 4.90 (d, 1H), 4.75-4.52 (m, 3H), 3.51 (s, 3H); $^{13}$C NMR (75 MHz, CDCl$_3$) δ 177.8, 162.5, 155.9, 149.1, 142.4, 141.6, 139.7, 137.6, 132.1, 129.1, 124.4, 123.9, 121.3, 119.1, 114.0, 108.6, 102.8, 101.6, 93.7, 80.3, 58.2, 40.8, 38.0; MS (ES+) m/z 403.3 (M+1).

Example 10.84

Synthesis of 5-bromo-1'-[(5-chloro-2-thienyl)methyl]spiro[1-benzofuran-3,3'-indol]-2'(1'H)-one Following the procedure described in EXAMPLE 10, and making non-critical variations using 5-bromospiro[1-benzofuran-3,3'-indol]-2'(1'H)-one to replace spiro[furo[2,3-f][1,3]benzodioxole-7,3'-indol]-2'(1'H)one, and 2-chloro-5-(chloromethyl)thiophene to replace 4-fluorobenzyl bromide, the title compound was obtained (95%) as a white solid: mp 140-142° C.; $^1$H NMR (300 MHz, CDCl$_3$) δ 7.33-7.26 (m, 2H), 7.16-7.02 (m, 2H), 6.94 (d, 1H), 6.97-6.75 (m, 4H), 5.07-4.91 (m, 3H), 4.68 (d, 1H); MS (ES+) m/z 446.7 (M+1), 448.7 (M+1).

Example 10.85

Synthesis of 1'-[(5-chloro-1,3,4-thiadiazol-2-yl)methyl]spiro[furo[2,3-f][1,3]benzodioxole-7,3'-indol]-2'(1'H)-one To a solution of spiro[furo[2,3-f][1,3]benzodioxole-7,3'-indol]-2'(1'H)one (0.56 g, 1.99 mmol) and (5-chloro-1,3,4-thiadiazol-2-yl)methanol (0.30 g, 1.99 mmol) in anhydrous tetrahydrofuran (12.0 mL) was added tributylphosphine (0.60 g, 2.99 mmol) at 0° C. The reaction mixture was stirred for 15 min followed by the addition of N,N,N',N'-tetramethylazodicarboxamide (0.51 g, 2.99 mmol). The reaction mixture was stirred at ambient temperature overnight, quenched with aqueous ammonium chloride (10.0 mL) and diluted with ethyl acetate (350 mL). The organic layer was washed with aqueous saturated sodium chloride (2×25.0 mL), dried over anhydrous sodium sulfate and filtered. The filtrate was concentrated in vacuo to dryness. The residue was subjected to column chromatography (ethyl acetate/hexane, 1/2) to give the title compound (0.20 g, 24%) as a yellowish solid: mp 194-197° C.; $^1$H NMR (300 MHz, DMSO-$d_6$) δ 7.30 (dt, 1H), 7.20-7.12 (m, 2H), 7.05 (dt, 1H), 6.67 (s, 1H), 6.28 (s, 1H), 5.90 (s, 2H), 5.43 (d, 1H), 5.34 (d, 1H), 4.78 (d, 1H), 4.67 (d, 1H); $^{13}$C NMR (75 MHz, DMSO-$d_6$) δ 177.2, 168.3, 155.8, 155.4, 148.9, 142.2, 141.9, 132.2, 129.4, 124.2, 124.0, 120.1, 109.8, 103.7, 101.9, 93.8, 80.1, 67.5, 57.9, 25.6; MS (ES+) m/z 414.2 (M+1), 416.2 (M+1).

Example 10.86

Synthesis of 1'-[(1-pyridin-2-ylpiperidin-4-yl)methyl]spiro[furo[2,3-f][1,3]benzodioxole-7,3'-indol]-2'(1'H)-one A mixture of 1'-(piperidin-4-ylmethyl)spiro[furo[2,3-f][1,3]benzodioxole-7,3'-indol]-2'(1'H)-one hydrobromide (0.20 g, 0.44 mmol), 2-bromopyridine (0.16 mL, 0.65 mmol), tetrabutyl ammonium iodide (0.05 g) and DBU (0.16 mL, 1.09 mmol) in DMF (5.00 mL) was heated at 120° C. for 15 hrs. After cooling down to ambient temperature, water (30.0 mL) was added. The above mixture was extracted twice with ethyl acetate (50.0 mL), the combined organic phase was dried over $Na_2SO_4$ and filtered. The filtrate was concentrated in vacuo to dryness. The residue was subjected to flash chromatography eluting with 30% ethyl acetate in hexane to give a white solid (0.05 g, 27%): mp 95-97° C.; $^1$H NMR (300 MHz, CDCl$_3$) δ 8.17 (d, 1H), 7.47 (td, 1H), 7.31 (t, 1H), 7.18 (d, 1H), 7.06 (t, 1H), 6.92 (d, 1H), 6.66 (d, 1H), 6.59 (dd, 1H), 6.52 (s, 1H), 6.12 (s, 1H), 5.91-5.84 (m, 2H), 4.91 (d, 1H), 4.66 (d, 1H), 4.42-4.27 (m, 2H), 3.82-3.53 (m, 2H), 2.85 (t, 2H), 2.22-2.05 (m, 1H), 1.85-1.70 (m, 2H), 1.53-1.35 (m, 2H); $^{13}$C NMR (75 MHz, CDCl$_3$) δ 177.9, 158.8, 156.1, 149.0, 147.4, 142.8, 142.5, 138.0, 132.4, 129.1, 124.2, 123.5, 119.5, 112.9, 108.8, 107.7, 103.1, 101.7, 93.8, 80.7, 58.3, 46.0, 45.5, 45.4, 35.2, 29.8, 29.7; MS (ES+) m/z 456 (M+1).

Example 10.87

Synthesis of 1'-[(1-phenyl-2-ylpiperidin-4-yl)methyl]spiro[furo[2,3-f][1,3]benzodioxole-7,3'-indol]-2'(1'H)-one A mixture of 1'-(piperidin-4-ylmethyl)spiro[furo[2,3-f][1,3]benzodioxole-7,3'-indol]-2'(1'H)-one hydrobromide (0.20 g, 0.44 mmol), 2-bromobenzene (0.07 mL, 0.65 mmol), $Pd_2(dba)_3$ (0.03 g, 0.03 mmol), BINAP (0.06 g, 0.10 mmol) and NaOBu$^t$ (0.13 g, 1.30 mmol) in toluene was heated at 100° C. for 15 hrs under nitrogen. After cooling down to ambient temperature, water (30.0 mL) was added. The above mixture was extracted twice with ethyl acetate (50.0 mL), the combined organic phase was dried over $Na_2SO_4$ and filtered. The filtrate was concentrated in vacuo to dryness. The residue was subjected to flash chromatography eluting 30% ethyl acetate in hexane to give a white solid (0.10 g, 48%): mp 76-78° C.; $^1$H NMR (300 MHz, CDCl$_3$) δ 7.37-7.16 (m, 4H), 7.12-6.80 (m, 5H), 6.53 (s, 1H), 6.14 (s, 1H), 5.87 (dd, 2H), 4.92 (d, 1H), 4.66 (d, 1H), 3.87-3.55 (m, 4H), 2.72 (t, 2H), 2.12-1.94 (m, 1H), 1.89-1.73 (m, 2H), 1.71-1.45 (m, 2H); $^{13}$C NMR (75 MHz, CDCl$_3$) δ 177.9, 156.1, 149.0, 142.9, 142.5, 132.4, 129.2, 129.1, 124.2, 123.4, 119.9, 119.5, 116.9, 108.8, 103.1, 101.6, 93.8, 80.8, 60.5, 58.3, 49.8, 46.1, 34.8, 30.1, 30.0; MS (ES+) m/z 455 (M+1).

Example 10.88

Synthesis of 1'-(pyridin-2-ylmethyl)-6-(trifluoromethoxy)spiro[1-benzofuran-3,3'-indol]-2'(1'H)-one hydrochloride Following the procedure described in EXAMPLE 10.47, and making non-critical variations using 6-(trifluoromethoxy)spiro[1-benzofuran-3,3'-indol]-2'(1'H)one to replace 4'-bromospiro[furo[2,3-f][1,3]benzodioxole-7,3'-indol]-2'(1'H)-one, and 2-(bromomethyl)pyridine hydrobromide to replace 2-(bromomethyl)-2-(trifluoromethyl)furan, 1'-(pyridin-2-ylmethyl)-6-(trifluoromethoxy)spiro[1-benzofuran-3,3'-indol]-2'(1'H)-one was obtained, which was treated with 4.0 M HCl in dioxane to give the title compound (39%): mp 150-152° C.; $^1$H NMR (300 MHz, CD$_3$OD) δ 8.89-8.78 (m, 1H), 8.62-8.47 (m, 1H), 8.07-7.00 (m, 2H), 7.42-6.70 (m, 7H), 5.52-5.31 (m, 2H), 5.05 (d, 1H), 4.89 (d, 1H); $^{13}$C NMR (75 MHz, CD$_3$OD) δ 179.4, 163.5, 153.1, 152.7, 148.2, 143.8, 142.8, 133.1, 130.6, 129.3, 127.4, 126.8, 125.7, 125.6, 125.4, 114.9, 110.4, 104.9, 82.0, 58.9, 43.0; MS (ES+) m/z 413 (M+1).

Example 10.89

Synthesis of 1'-(pyridin-3-ylmethyl)-6-(trifluoromethoxy)spiro[1-benzofuran-3,3'-indol]-2'(1'H)-one hydrochloride Following the procedure described in EXAMPLE 10.47, and making non-critical variations using 6-(trifluoromethoxy)spiro[1-benzofuran-3,3'-indol]-2'(1'H)one to replace 4'-bromospiro[furo[2,3-f][1,3]benzodioxole-7,3'-indol]-2'(1'H)-one, and 3-(bromomethyl)pyridine hydrobromide to replace 2-(bromomethyl)-5-(trifluoromethyl)furan, 1'-(pyridin-3-ylmethyl)-6-(trifluoromethoxy)spiro[1-benzofuran-3,3'-indol]-2'(1'H)-one was obtained, which was treated with 4.0 M HCl in dioxane to give the title compound (70%) as a white solid: mp 151-153° C.; $^1$H NMR (300 MHz, CD$_3$OD) δ 9.07-8.61 (m, 3H), 8.19-8.04 (m, 1H), 7.42-6.71 (m, 7H), 5.28 (s, 2H), 5.05 (d, 1H), 4.86 (d, 1H); $^{13}$C NMR (75 MHz, CD$_3$OD) δ 179.43, 163.5, 151.8, 147.0, 142.9, 142.4, 142.2, 133.0, 130.6, 129.3, 128.9, 125.5, 125.4, 125.3, 114.9, 110.5, 104.9, 82.0, 58.9, 42.0; MS (ES+) m/z 413 (M+1).

Example 10.90

Synthesis of 6-(trifluoromethoxy)-1'-{[5-(trifluoromethyl)-2-furyl]methyl}spiro[1-benzofuran-3,3'-indol]-2'(1'H)-one Following the procedure described in EXAMPLE 10.47, and making non-critical variations using 6-(trifluoromethoxy)spiro[1-benzofuran-3,3'-indol]-2'(1'H)one to replace 4'-bromospiro[furo[2,3-f][1,3]benzodioxole-7,3'-indol]-2'(1'H)-one, the title compound was obtained (82%) as a white solid: mp 78-80° C.; $^1$H NMR (300 MHz, CDCl$_3$) δ 7.33 (td, 1H), 7.21-6.98 (m, 3H), 6.86-6.73 (m, 2H), 6.67 (s, 2H), 6.42 (d, 1H), 5.09 (d, 1H), 5.04 (d, 1H), 4.88 (d, 1H), 4.77 (d, 1H); $^{13}$C NMR (75 MHz, CDCl$_3$) 176.7, 161.7, 151.9, 150.6, 141.5, 131.7, 129.5, 127.5, 124.2, 124.2, 124.0, 114.1, 112.8, 112.8, 109.6, 109.2, 104.3, 80.7, 57.6, 37.1; MS (ES+) m/z 470 (M+1).

Example 10.91

Synthesis of 1'-(4-methoxybenzyl)-6-(trifluoromethoxy)spiro[1-benzofuran-3,3'-indol]-2'(1'H)-one Following the procedure described in EXAMPLE 10.47, and making non-critical variations using 6-(trifluoromethoxy)spiro[1-benzofuran-3,3'-indol]-2'(1'H)one to replace 4'-bromospiro[furo[2,3-f][1,3]benzodioxole-7,3'-indol]-2'(1'H)-one, and 4-methoxybenzyl chloride to replace 2-(bromomethyl)-5-(trifluoromethyl)furan, the title compound was obtained (91%) as a white solid: mp 82-84° C.; $^1$H NMR (300 MHz, CDCl$_3$) δ 7.32-6.80 (m, 9H), 6.68 (s, 2H), 5.06 (d, 1H), 5.03 (d, 1H), 4.80 (d, 1H), 4.77 (d, 1H), 3.80 (s, 3H); $^{13}$C NMR (75 MHz, CDCl$_3$) δ 171.1, 161.8, 159.4, 150.5, 142.3, 132.0, 129.2, 128.9, 127.7, 124.1, 124.0, 123.7, 122.2, 118.8, 114.4, 114.1, 109.7, 104.3, 80.9, 57.6, 55.4, 43.9; MS (ES+) m/z 442 (M+1).

Example 10.92

Synthesis of 1'-(cyclohexylmethyl)spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)one to replace 4'-bromospiro[furo[2,3-f][1,3]benzodioxole-7,3'-indol]-2'(1'H)-one, and bromomethyl cyclohexane to replace 2-(bromomethyl)-5-(trifluoromethyl)furan, the title compound was obtained (74%) as a white solid: mp 153-154° C.; $^1$H NMR (300 MHz, CDCl$_3$) δ 7.30 (td, 1H), 7.16 (d, 1H), 7.04 (t, 1H), 6.90 (d, 1H), 6.51 (s, 1H), 6.14 (s, 1H), 5.90-5.84 (m, 2H), 4.91 (d, 1H), 4.65 (d, 1H), 3.72-3.44 (m, 2H), 1.94-1.60 (m, 6H), 1.32-0.99 (m, 5H); $^{13}$C NMR (75 MHz, CDCl$_3$) δ 177.8, 156.1, 148.9, 143.0, 142.4, 132.5, 128.9, 124.0, 123.2, 119.7, 109.0, 103.2, 101.6, 93.7, 80.8, 58.3, 46.8, 36.3, 31.1, 31.0, 26.4, 25.9, 25.8; MS (ES+) m/z 378 (M+1), 400 (M+23).

Example 10.93

Synthesis of 1'-(methylsulfonyl)spiro[furo[2,3-f][1,3]benzodioxole-7,3'-indol]-2'(1'H)-one Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and methanesulfonyl chloride to replace 2-(bromomethyl)-5-(trifluoromethyl)furan, the title compound was obtained (51%) as a white solid: mp 215-217° C.; $^1$H NMR (300 MHz, CDCl$_3$) δ 7.83 (d, 1H), 7.42-7.31 (m, 1H), 7.25-7.17 (m, 2H), 6.52 (s, 1H), 6.20 (s, 1H), 5.93-5.87 (m, 2H), 4.98 (d, 1H), 4.68 (d, 1H), 3.46 (s, 3H); $^{13}$C NMR (75 MHz, CDCl$_3$) δ 176.9, 155.8, 149.5, 142.7, 138.1, 130.5, 129.7, 125.9, 124.3, 118.5, 113.8, 102.9, 101.8, 93.8, 80.6, 58.8, 41.8; MS (ES+) m/z 360 (M+1), 382 (M+23).

Example 10.94

Synthesis of 1'-(2-piperidin-1-ylethyl)spiro[furo[2,3-f][1,3]benzodioxole-7,3'-indol]-2'(1'H)-one hydrochloride A mixture of 1'-(2-aminoethyl)spiro[furo[2,3-f][1,3]benzodioxole-7,3'-indol]-2'(1'H)-one (0.20 g, 0.62 mmol), 1,5-dibromopentane (0.08 mL, 0.62 mmol) and triethyl amine (0.17 mL, 1.23 mmol) in THF (10.0 mL) was refluxed for 15 hrs and concentrated in vacuo to dryness. The residue was subjected to flash chromatography eluting with 10% methanol in ethyl acetate to give 1-(2-piperidin-1-ylethyl)spiro[furo[2,3-f][1,3]benzodioxole-7,3'-indol]-2'(1'H)-one, which was treated with 4.0 M HCl in dioxane to give the title compound (28%): mp >240° C.; $^1$H NMR (300 MHz, CD$_3$OD) δ 7.40 (t, 1H), 7.27-7.11 (m, 3H), 6.51 (s, 1H), 6.17 (s, 1H), 5.86 (s, 2H), 4.91 (d, 1H), 4.71 (d, 1H), 4.40-4.13 (m, 2H), 3.95-3.84 (m, 1H), 3.66-3.37 (m, 3H), 3.14-2.96 (m, 2H), 2.06-1.45 (m, 6H); $^{13}$C NMR (75 MHz, CD$_3$OD) δ 180.4, 157.5, 150.5, 143.8, 142.5, 133.9, 130.3, 125.3, 125.1, 120.6, 110.2, 103.9, 102.9, 94.2, 81.4, 59.7, 55.4, 54.9, 53.9, 36.4, 24.2, 22.6; MS (ES+) m/z 393 (M+1).

Example 10.95

Synthesis of 1'-[2-(pyridin-2-ylamino)ethyl]spiro[furo[2,3-f][1,3]benzodioxole-7,3'-indol]-2'(1'H)-one and 1'-[2-(dipyridin-2-ylamino)ethyl]spiro[furo[2,3-f][1,3]benzodioxole-7,3'-indol]-2'(1'H)-one and Following the procedure described in EXAMPLE 10.87, and making non-critical variations using 1'-(2-aminoethyl)spiro[furo[2,3-f][1,3]benzodioxole-7,3'-indol]-2'(1'H)-one to replace 1'-(piperidin-4-ylmethyl)spiro[furo[2,3-f][1,3]benzodioxole-7,3'-indol]-2'(1'H)-one, and 2-bromopyridine to replace 2-bromobenzene, 1'-(2-(pyridin-2-ylamino)ethyl)-spiro[furo[2,3-f][1,3]benzodioxole-7,3'-indol]-2'(1'H)-one was obtained as the first fraction from the chromatography as a white solid (5%): mp 61-63° C.; $^1$H NMR (300 MHz, CDCl$_3$) δ 8.05 (d, 1H), 7.50-6.97 (m, 5H), 6.57 (dd, 1H), 6.50 (s, 1H), 6.38 (d, 1H), 6.03 (s, 1H), 5.85 (s, 1H), 5.84 (s, 1H), 4.84 (d, 1H), 4.79 (t, 1H), 4.60 (d, 1H), 4.15-3.94 (m, 2H), 3.81-3.64 (m, 2H); $^{13}$C NMR (75 MHz, CDCl$_3$) δ 178.4, 158.2, 156.0, 149.0, 148.0, 142.4, 142.38, 137.4, 132.3, 129.1, 124.0, 123.5, 119.5, 113.3, 109.0, 108.3, 103.2, 101.6, 93.7, 80.5, 58.3, 40.1, 39.9; MS (ES+) m/z 402 (M+1). 1'-(2-(dipyridin-2-ylamino)ethyl)-spiro[furo[2,3-f][1,3]benzodioxole-7,3'-indol]-2'(1'H)-one was obtained as the second fraction from the chromatography (31%): mp 165-167° C.; $^1$H NMR (300 MHz, CDCl$_3$) δ 8.31 (dd, 2H), 7.48 (d, 2H), 7.23 (t, 1H), 7.09-6.83 (m, 7H), 6.47 (s, 1H), 5.95 (s, 1H), 5.88-5.81 (m, 2H), 4.73 (d, 1H), 4.67-4.49 (m, 2H), 4.46 (d, 1H), 4.20 (t, 2H); $^{13}$C NMR (75 MHz, CDCl$_3$) δ 177.6, 157.0, 156.0, 148.8, 148.4, 143.1, 142.3, 137.4, 132.3, 128.9, 123.6, 123.1, 119.6, 117.5, 114.5, 109.3, 103.4, 101.6, 93.6, 80.7, 58.2, 45.9, 39.5; MS (ES+) m/z 479 (M+1).

Example 10.96

Synthesis of tert-butyl 4-[2-(2'-oxospiro[furo[2,3-f][1,3]benzodioxole-7,3'-indol]-1'(2'H)-yl)ethyl]piperidine-1-carboxylate Following the procedure as described in EXAMPLE 10, and making non-critical variations using tert-butyl 4-(2-{[(4-methylphenyl)sulfonyl]oxy}ethyl)piperidine-1-carboxylate to replace 4-fluorobenzyl bromide, the title compound was obtained in 95% yield: mp 173-175° C.; $^1$H NMR (300 MHz, CDCl$_3$) δ 7.31 (t, 1H), 7.17 (d, 1H), 7.06 (t, 1H), 6.88 (d, 1H), 6.51 (s, 1H), 6.10 (s, 1H), 5.90-5.84 (m, 2H), 4.90 (d, 1H), 4.65 (d, 1H), 4.0-3.64 (m, 4H), 2.75-2.58 (m, 2H), 1.85-1.09 (m, 16H); $^{13}$C NMR (75 MHz, CDCl$_3$) δ 177.5, 156.0, 155.0, 149.0, 142.4, 142.2, 132.6, 129.0, 124.2, 123.4, 119.5, 108.6, 103.0, 101.6, 93.8, 80.5, 79.5, 58.3, 38.0, 34.0, 33.9, 32.1, 31.9, 28.6; MS (ES+) m/z 515 (M+23), 393 (M−100).

Example 10.97

Synthesis of 1'-(2-piperidin-4-ylethyl)spiro[furo[2,3-f][1,3]benzodioxole-7,3'-indol]-2'(1'H)-one hydrochloride To a solution of tert-butyl 4-[2-(2'-oxospiro[furo[2,3-f][1,3]benzodioxole-7,3'-indol]-1'(2'H)-yl)ethyl]piperidine-1-carboxylate (0.94 g, 1.91 mmol) in dioxane (5.00 mL) was added 4.0 M HCl in dioxane (2.00 mL, 8.00 mmol). The mixture was stirred at ambient temperature for 30 min followed by the addition of anhydrous ether (40.0 mL). The precipitated white solid was filtered, washed with ether and dried to give the title compound (0.75 g, 91%): $^1$H NMR (300 MHz, CD$_3$OD) δ 7.37 (t, 1H), 7.20-7.07 (m, 3H), 6.52 (s, 1H), 6.10 (s, 1H), 5.86 (s, 2H), 4.83 (d, 1H), 4.67 (d, 1H), 3.97-3.75 (m, 2H), 3.45-3.33 (m, 2H), 3.01-2.85 (m, 2H), 2.15-2.01 (m, 2H), 1.82-1.37 (m, 5H); $^{13}$C NMR (75 MHz, CD$_3$OD) δ 179.8, 157.6, 150.4, 143.7, 143.4, 133.6, 130.3, 124.9, 124.8, 120.8, 110.3, 103.7, 102.9, 94.3, 81.4, 59.8, 45.2, 38.5, 34.4, 32.6, 29.8, 29.7; MS (ES+) m/z 393 (M+1).

Example 10.98

Synthesis of 1'-[2-(1-cyclopentylpiperidin-4-yl)ethyl]spiro[furo[2,3-f][1,3]benzodioxole-7,3'-indol]-2'(1'H)-one hydrochloride To a solution of cyclopentanone (0.04 mL, 0.45 mmol) and triethyl amine (0.12 mL, 0.84 mmol) in dichloroethane (5.00 mL) was added 1'-(2-piperidin-4-ylethyl)spiro[furo[2,3-f][1,3]benzodioxole-7,3'-indol]-2'(1'H)-one hydrochloride (0.12 g, 0.28 mmol) and sodium triacetoxyborohydride (0.10 g, 0.45 mmol). The reaction mixture was stirred for 16 hrs and concentrated in vacuo to dryness. The residue was subjected to flash chromatography eluting with ethyl acetate/methanol/ammonium hydroxide (15/1/0.1) to give 1'-[2-(1-cyclopentylpiperidin-4-yl)ethyl]spiro[furo[2,3-f][1,3]benzodioxole-7,3'-indol]-2'(1'H)-one as a white solid, which was treated with 4.0 M HCl in dioxane to give the title compound (0.05 g, 32% yield): mp 153-155° C.; $^1$H NMR (300 MHz, CD$_3$OD) δ 7.37 (td, 1H), 7.21-7.08 (m, 3H), 6.53 (s, 1H), 6.11 (s, 1H), 5.88 (s, 1H), 5.87 (s, 1H), 4.83 (d, 1H), 4.69 (d, 1H), 3.98-3.75 (m, 2H), 3.68-3.38 (m, 3H), 3.01-2.83 (m, 2H), 2.25-2.08 (m, 4H), 1.92-1.37 (m, 11H); $^{13}$C NMR (75 MHz, CD$_3$OD) δ 179.8, 157.6, 150.4, 143.8, 143.4, 133.6, 130.3, 124.9, 124.8, 120.8, 110.3, 103.7, 103.0, 94.3, 81.4, 69.1, 59.8, 53.2, 38.6, 34.3, 32.5, 30.6, 30.5, 29.4, 24.7; MS (ES+) m/z 461 (M+1).

Example 10.99

Synthesis of 1'-[2-(1-isopropylpiperidin-4-yl)ethyl]spiro[furo[2,3-f][1,3]benzodioxole-7,3'-indol]-2'(1'H)-one hydrochloride Following the procedure as described in EXAMPLE 10.98, and making non-critical variations using acetone to replace cyclopentanone, the title compound was obtained (42%) as a white solid: mp 155-156° C.; $^1$H NMR (300 MHz, CD$_3$OD) δ 7.37 (t, 1H), 7.21-7.08 (m, 3H), 6.53 (s, 1H), 6.11 (s, 1H), 5.87 (s, 1H), 4.84 (d, 1H), 4.69 (d, 1H), 3.98-3.75 (m, 2H), 3.58-3.38 (m, 3H), 3.05-2.85 (m, 2H), 2.23-2.09 (m, 2H), 1.82-1.44 (m, 5H), 1.35 (d, 6H); $^{13}$C NMR (75 MHz, CD$_3$OD) δ 179.8, 157.6, 150.5, 143.8, 143.4, 133.6, 130.3, 125.0, 124.8, 120.8, 110.3, 103.7, 103.0, 94.3, 81.4, 59.8, 59.6, 38.6, 34.2, 32.7, 30.6, 30.5, 24.2, 16.9. 15.4; MS (ES+) m/z 435 (M+1).

Example 10.100

Synthesis of 1'-[2-(1-cyclobutylpiperidin-4-yl)ethyl]spiro[furo[2,3-f][1,3]benzodioxole-7,3'-indol]-2' (1'H)-one hydrochloride Following the procedure as described in EXAMPLE 10.98, and making non-critical variations using cyclobutanone to replace cyclopentanone, the title compound was obtained (81%) as a white solid: mp 158-160° C.; $^1$H NMR (300 MHz, CD$_3$OD) δ 7.37 (t, 1H), 7.21-7.05 (m, 3H), 6.52 (s, 1H), 6.10 (s, 1H), 5.86 (s, 2H), 4.83 (d, 1H), 4.67 (d, 1H), 3.98-3.39 (m, 5H), 2.85-2.59 (m, 2H), 2.43-1.42 (m, 13H); $^{13}$C NMR (75 MHz, CD$_3$OD) δ 179.8, 157.6, 150.4, 143.7, 143.4, 133.6, 130.3, 124.9, 124.8, 120.8, 110.4, 103.8, 103.0, 94.2, 81.5, 60.5, 59.8, 50.8, 38.6, 34.4, 32.5, 30.1, 26.8, 14.4; MS (ES+) m/z 447 (M+1).

Example 10.101

Synthesis of 1'-{2-[1-(tetrahydro-2H-pyran-4-yl)piperidin-4-yl]ethyl}spiro[furo[2,3-f][1,3]benzodioxole-7,3'-indol]-2'(1'H)one hydrochloride Following the procedure as described in EXAMPLE 10.98, and making non-critical variations using tetrahydro-4H-pyran-4-one to replace cyclopentanone, the title compound was obtained (45%) as a white solid: mp 168-170° C.; $^1$H NMR (300 MHz, CD$_3$OD) δ 7.37 (t, 1H), 7.21-7.06 (m, 3H), 6.52 (s, 1H), 6.11 (s, 1H), 5.86 (s, 2H), 4.83 (d, 1H), 4.67 (d, 1H), 4.12-3.31 (m, 9H), 3.05-2.85 (m, 2H), 2.25-1.45 (m, 11H); $^{13}$C NMR (75 MHz, CD$_3$OD) δ 179.8, 157.6, 150.4, 143.7, 143.4, 133.6, 130.3, 125.0, 124.8, 120.8, 110.3, 103.8, 102.9, 94.3, 81.4, 67.2, 64.1, 59.8, 50.7, 38.6, 34.2, 32.7, 30.6, 30.5, 28.7; MS (ES+) m/z 477 (M+1).

Example 11

Synthesis of 4-[(2'-oxospiro[furo[2,3-f][1,3]benzodioxole-7,3'-indol]-1'(2'H)-yl)methyl]benzoic acid Following the procedure described in EXAMPLE 6, and making non-critical variations using methyl 4-[(2'-oxospiro[furo[2,3-f][1,3]benzodioxole-7,3'-indol]-1'(2'H)-yl)methyl]benzoate to replace methyl 2-[(2'-oxospiro[furo[2,3-f][1,3]benzodioxole-7,3'-indol]-1'(2'H)-yl)methyl]benzoate, the title compound was obtained (100%): $^1$H NMR (300 MHz, CDCl$_3$) δ 12.96 (s, 1H), 7.90 (d, 2H), 7.43 (d, 2H), 7.22 (t, 1H), 7.17 (d, 1H), 7.00 (t, 1H), 6.94 (d, 1H), 6.68 (s, 1H), 6.21 (s, 1H), 5.90 (s, 2H), 4.98 (s, 2H), 4.76 (ABq, 2H); $^{13}$C NMR (75 MHz, CDCl$_3$) δ 177.4, 167.5, 156.0, 148.9, 142.6, 142.3, 141.8, 132:1, 130.5, 130.3, 129.3, 127.7, 124.2, 123.7, 120.1, 109.9, 103.5, 101.9, 93.8, 80.4, 58.0, 43.4.

Example 12

Synthesis of N-(3-fluorophenyl)-4-[(2'-oxospiro[furo[2,3-f][1,3]benzodioxole-7,3'-indol]-1'(2'H)-yl)methyl]benzamide A. Preparation of stock solution of 4-[(2'-oxospiro[furo[2,3-f][1,3]benzodioxole-7,3'-indol]-1'(2'H)-yl)methyl]benzoyl chloride To a stirred slurry of 4-[(2'-oxospiro[furo[2,3-f][1,3]benzodioxole-7,3'-indol]-1'(2'H)-yl)methyl]benzoic acid (2.08 g, 5.00 mmol) in dry chloroform (50.0 mL) was added oxalyl chloride (0.95 g, 7.50 mmol) at ambient temperature followed by 1 drop of DMF. The mixture was stirred at ambient temperature for 2 h and evaporated to dryness in vacuo. The residue was dissolved in dry dichlormethane (60.0 mL) to form an acid chloride stock solution for use.

B. Synthesis of N-(3-fluorophenyl)-4-[(2'-oxospiro [furo[2,3-f][1,3]benzodioxole-7,3'-indol]-1'(2'H)-yl) methyl]benzamide To a solution of 3-fluorophenylamine (0.02 mL, 0.24 mmol) in dry dichloromethane (2.00 mL) and triethylamine (0.05 mL, 0.32 mmol) was added the acid chloride stock solution (2.0 mL, 0.081 M in dichloromethane) obtained above at ambient temperature. The mixture was stirred for 2 h, washed with 15% HCl solution and water. The organic layer was separated, dried over $Na_2SO_4$ and filtered. The filtrate was concentrated in vacuo to dryness. The residue was dissolved in ethyl acetate, and the product was precipitated by the addition of hexane. The white solid was filtered and collected to yield the title compound (0.06 g) in 70% yield: $^1$H NMR (300 MHz, $CDCl_3$) δ 8.30 (s, 1H), 7.83 (d, 2H), 7.58 (ddd, 1H), 7.38 (d, 2H), 7.27-7.23 (m, 2H), 7.21-7.16 (m, 2H), 7.04 (dt, 1H), 6.85-6.78 (m, 1H), 6.74 (d, 1H), 6.46 (s, 1H), 6.10 (s, 1H), 5.77 (d, 1H), 5.68 (d, 1H), 4.97 (ABq, 2H), 4.76 (ABq, 2H); MS (ES+), m/z 509.1 (M+1).

Example 12.1

The compounds listed in the following table were prepared using the similar procedure as described in EXAMPLE 12. As previously noted, the compound numbers listed below do not correspond to the compound numbers provided in the general Reaction Schemes above.

| Compound Number | Name | MS (m/z, M + 1) |
|---|---|---|
| 500 | N-butyl-4-[(2'-oxospiro[furo[2,3-f][1,3]benzodioxole-7,3'-indol]-1'(2'H)-yl)methyl]benzamide | 471.2 |
| 501 | N-(3-fluorobenzyl)-4-[(2'-oxospiro[furo[2,3-f][1,3]benzodioxole-7,3'-indol]-1'(2'H)-yl)methyl]benzamide | 523.1 |
| 502 | 1'-[4-(piperidin-1-ylcarbonyl)benzyl]spiro[furo[2,3-f][1,3]benzodioxole-7,3'-indol]-2'(1'H)-one | 483.2 |
| 503 | N,N-diisopropyl-4-[(2'-oxospiro[furo[2,3-f][1,3]benzodioxole-7,3'-indol]-1'(2'H)-yl)methyl]benzamide | 499.1 |
| 504 | N-(4-chlorobenzyl)-4-[(2'-oxospiro[furo[2,3-f][1,3]benzodioxole-7,3'-indol]-1'(2'H)-yl)methyl]benzamide | 540.1 |
| 505 | N-(3-chlorophenyl)-4-[(2'-oxospiro[furo[2,3-f][1,3]benzodioxole-7,3'-indol]-1'(2'H)-yl)methyl]benzamide | 526.1 |
| 506 | N-(2-fluorophenyl)-4-[(2'-oxospiro[furo[2,3-f][1,3]benzodioxole-7,3'-indol]-1'(2'H)-yl)methyl]benzamide | 509.2 |
| 507 | N-(2-ethylphenyl)-4-[(2'-oxospiro[furo[2,3-f][1,3]benzodioxole-7,3'-indol]-1'(2'H)-yl)methyl]benzamide | 519.2 |
| 508 | N-(4-ethylphenyl)-4-[(2'-oxospiro[furo[2,3-f][1,3]benzodioxole-7,3'-indol]-1'(2'H)-yl)methyl]benzamide | 519.2 |
| 509 | N-(4-methylphenyl)-4-[(2'-oxospiro[furo[2,3-f][1,3]benzodioxole-7,3'-indol]-1'(2'H)-yl)methyl]benzamide | 505.2 |
| 510 | N-(3,5-dimethylphenyl)-4-[(2'-oxospiro[furo[2,3-f][1,3]benzodioxole-7,3'-indol]-1'(2'H)-yl)methyl]benzamide | 519.2 |
| 511 | N-(2,3-dimethylphenyl)-4-[(2'-oxospiro[furo[2,3-f][1,3]benzodioxole-7,3'-indol]-1'(2'H)-yl)methyl]benzamide | 519.2 |
| 512 | 4-[(2'-oxospiro[furo[2,3-f][1,3]benzodioxole-7,3'-indol]-1'(2'H)-yl)methyl]-N-pentylbenzamide | 485.1 |
| 513 | 4-[(2'-oxospiro[furo[2,3-f][1,3]benzodioxole-7,3'-indol]-1'(2'H)-yl)methyl]-N-propylbenzamide | 457.1 |
| 514 | N-isopropyl-4-[(2'-oxospiro[furo[2,3-f][1,3]benzodioxole-7,3'-indol]-1'(2'H)-yl)methyl]benzamide | 457.1 |
| 515 | N-isobutyl-4-[(2'-oxospiro[furo[2,3-f][1,3]benzodioxole-7,3'-indol]-1'(2'H)-yl)methyl]benzamide | 471.1 |
| 516 | N-hexyl-4-[(2'-oxospiro[furo[2,3-f][1,3]benzodioxole-7,3'-indol]-1'(2'H)-yl)methyl]benzamide | 499.2 |
| 517 | N-cyclohexyl-4-[(2'-oxospiro[furo[2,3-f][1,3]benzodioxole-7,3'-indol]-1'(2'H)-yl)methyl]benzamide | 497.2 |
| 518 | N-cyclopentyl-4-[(2'-oxospiro[furo[2,3-f][1,3]benzodioxole-7,3'-indol]-1'(2'H)-yl)methyl]benzamide | 483.2 |
| 519 | N-heptyl-4-[(2'-oxospiro[furo[2,3-f][1,3]benzodioxole-7,3'-indol]-1'(2'H)-yl)methyl]benzamide | 513.2 |

-continued

| Compound Number | Name | MS (m/z, M + 1) |
| --- | --- | --- |
| 520 | N-(2-methoxybenzyl)-4-[(2'-oxospiro[furo[2,3-f][1,3]benzodioxole-7,3'-indol]-1'(2'H)-yl)methyl]benzamide | 535.2 |
| 521 | N-(2,6-dimethylphenyl)-4-[(2'-oxospiro[furo[2,3-f][1,3]benzodioxole-7,3'-indol]-1'(2'H)-yl)methyl]benzamide | 519.2 |
| 522 | N-(2-methoxyphenyl)-4-[(2'-oxospiro[furo[2,3-f][1,3]benzodioxole-7,3'-indol]-1'(2'H)-yl)methyl]benzamide | 521.2 |
| 523 | N-cyclopropyl-4-[(2'-oxospiro[furo[2,3-f][1,3]benzodioxole-7,3'-indol]-1'(2'H)-yl)methyl]benzamide | 455.1 |
| 524 | N-(3-methoxypropyl)-4-[(2'-oxospiro[furo[2,3-f][1,3]benzodioxole-7,3'-indol]-1'(2'H)-yl)methyl]benzamide | 487.2 |
| 525 | 4-[(2'-oxospiro[furo[2,3-f][1,3]benzodioxole-7,3'-indol]-1'(2'H)-yl)methyl]-N-phenylbenzamide | 491.2 |
| 526 | N-(2,4-dimethylphenyl)-4-[(2'-oxospiro[furo[2,3-f][1,3]benzodioxole-7,3'-indol]-1'(2'H)-yl)methyl]benzamide | 519.2 |
| 527 | 4-[(2'-oxospiro[furo[2,3-f][1,3]benzodioxole-7,3'-indol]-1'(2'H)-yl)methyl]-N-(tetrahydrofuran-2-ylmethyl)benzamide | 499.2 |
| 528 | N,N-dibenzyl-4-[(2'-oxospiro[furo[2,3-f][1,3]benzodioxole-7,3'-indol]-1'(2'H)-yl)methyl]benzamide | 595.2 |
| 529 | N-[2-(diethylamino)ethyl]-4-[(2'-oxospiro[furo[2,3-f][1,3]benzodioxole-7,3'-indol]-1'(2'H)-yl)methyl]benzamide | 514.2 |
| 530 | N-methyl-4-[(2'-oxospiro[furo[2,3-f][1,3]benzodioxole-7,3'-indol]-1'(2'H)-yl)methyl]benzamide | 429.2 |
| 531 | 4-[(2'-oxospiro[furo[2,3-f][1,3]benzodioxole-7,3'-indol]-1'(2'H)-yl)methyl]-N-[3-(trifluoromethyl)phenyl]benzamide | 559.1 |
| 532 | N-ethyl-4-[(2'-oxospiro[furo[2,3-f][1,3]benzodioxole-7,3'-indol]-1'(2'H)-yl)methyl]benzamide | 443.1 |
| 533 | N-(3-ethoxypropyl)-4-[(2'-oxospiro[furo[2,3-f][1,3]benzodioxole-7,3'-indol]-1'(2'H)-yl)methyl]benzamide | 501.2 |
| 534 | N-(4-methoxybenzyl)-4-[(2'-oxospiro[furo[2,3-f][1,3]benzodioxole-7,3'-indol]-1'(2'H)-yl)methyl]benzamide | 535.2 |
| 535 | N-(3,5-dichlorophenyl)-4-[(2'-oxospiro[furo[2,3-f][1,3]benzodioxole-7,3'-indol]-1'(2'H)-yl)methyl]benzamide | 560.2 |
| 536 | 4-[(2'-oxospiro[furo[2,3-f][1,3]benzodioxole-7,3'-indol]-1'(2'H)-yl)methyl]-N-pyridin-3-ylbenzamide | 492.2 |
| 537 | N-(4-cyanophenyl)-4-[(2'-oxospiro[furo[2,3-f][1,3]benzodioxole-7,3'-indol]-1'(2'H)-yl)methyl]benzamide | 516.2 |
| 538 | N-(4-methylpentyl)-4-[(2'-oxospiro[furo[2,3-f][1,3]benzodioxole-7,3'-indol]-1'(2'H)-yl)methyl]benzamide | 499.2 |
| 539 | 4-[(2'-oxospiro[furo[2,3-f][1,3]benzodioxole-7,3'-indol]-1'(2'H)-yl)methyl]-N-(2,2,2-trifluoroethyl)benzamide | 497.2 |
| 540 | 4-[(2'-oxospiro[furo[2,3-f][1,3]benzodioxole-7,3'-indol]-1'(2'H)-yl)methyl]-N-(pyridin-4-ylmethyl)benzamide | 506.1 |
| 541 | N-[2-(3-chlorophenyl)ethyl]-4-[(2'-oxospiro[furo[2,3-f][1,3]benzodioxole-7,3'-indol]-1'(2'H)-yl)methyl]benzamide | 554 |
| 542 | N-(2-furylmethyl)-4-[(2'-oxospiro[furo[2,3-f][1,3]benzodioxole-7,3'-indol]-1'(2'H)-yl)methyl]benzamide | 495.1 |
| 543 | N-(3-fluoro-2-methylphenyl)-4-[(2'-oxospiro[furo[2,3-f][1,3]benzodioxole-7,3'-indol]-1'(2'H)-yl)methyl]benzamide | 523.1 |
| 544 | N-hexyl-N-methyl-4-[(2'-oxospiro[furo[2,3-f][1,3]benzodioxole-7,3'-indol]-1'(2'H)-yl)methyl]benzamide | 513.1 |
| 545 | N-(3-isopropoxypropyl)-4-[(2'-oxospiro[furo[2,3-f][1,3]benzodioxole-7,3'-indol]-1'(2'H)-yl)methyl]benzamide | 515.2 |
| 546 | N-(2-ethoxyethyl)-4-[(2'-oxospiro[furo[2,3-f][1,3]benzodioxole-7,3'-indol]-1'(2'H)-yl)methyl]benzamide | 487.2 |

-continued

| Compound Number | Name | MS (m/z, M + 1) |
|---|---|---|
| 547 | N-(cyclopropylmethyl)-4-[(2'-oxospiro[furo[2,3-f][1,3]benzodioxole-7,3'-indol]-1'(2'H)-yl)methyl]benzamide | 469.1 |
| 548 | N-(4-methoxyphenyl)-4-[(2'-oxospiro[furo[2,3-f][1,3]benzodioxole-7,3'-indol]-1'(2'H)-yl)methyl]benzamide | 521.1 |
| 549 | N-cyclobutyl-4-[(2'-oxospiro[furo[2,3-f][1,3]benzodioxole-7,3'-indol]-1'(2'H)-yl)methyl]benzamide | 469.1 |
| 550 | N-(2,2-diphenylethyl)-4-[(2'-oxospiro[furo[2,3-f][1,3]benzodioxole-7,3'-indol]-1'(2'H)-yl)methyl]benzamide | 595.2 |
| 551 | N-[2-(4-fluorophenyl)ethyl]-4-[(2'-oxospiro[furo[2,3-f][1,3]benzodioxole-7,3'-indol]-1'(2'H)-yl)methyl]benzamide | 537.2 |
| 552 | N-(cyclohexylmethyl)-4-[(2'-oxospiro[furo[2,3-f][1,3]benzodioxole-7,3'-indol]-1'(2'H)-yl)methyl]benzamide | 511.2 |
| 553 | N-(2-fluoro-4-methylphenyl)-4-[(2'-oxospiro[furo[2,3-f][1,3]benzodioxole-7,3'-indol]-1'(2'H)-yl)methyl]benzamide | 523.2 |
| 554 | N-[2-(4-methylphenyl)ethyl]-4-[(2'-oxospiro[furo[2,3-f][1,3]benzodioxole-7,3'-indol]-1'(2'H)-yl)methyl]benzamide | 533.2 |
| 555 | N-(2-ethylbutyl)-4-[(2'-oxospiro[furo[2,3-f][1,3]benzodioxole-7,3'-indol]-1'(2'H)-yl)methyl]benzamide | 499.2 |
| 556 | N-benzyl-4-[(2'-oxospiro[furo[2,3-f][1,3]benzodioxole-7,3'-indol]-1'(2'H)-yl)methyl]benzamide | 505.1 |
| 557 | N-(2-methoxyethyl)-4-[(2'-oxospiro[furo[2,3-f][1,3]benzodioxole-7,3'-indol]-1'(2'H)-yl)methyl]benzamide | 473.1 |
| 558 | 1'-[4-(morpholin-4-ylcarbonyl)benzyl]spiro[furo[2,3-f][1,3]benzodioxole-7,3'-indol]-2'(1'H)-one | 485.1 |
| 559 | N-(1-benzylpiperidin-4-yl)-4-[(2'-oxospiro[furo[2,3-f][1,3]benzodioxole-7,3'-indol]-1'(2'H)-yl)methyl]benzamide | 588.2 |
| 560 | N-[2-(4-methoxyphenyl)ethyl]-4-[(2'-oxospiro[furo[2,3-f][1,3]benzodioxole-7,3'-indol]-1'(2'H)-yl)methyl]benzamide | 549.2 |
| 561 | 4-[(2'-oxospiro[furo[2,3-f][1,3]benzodioxole-7,3'-indol]-1'(2'H)-yl)methyl]-N-[2-(trifluoromethyl)phenyl]benzamide | 559.1 |
| 562 | N-[4-chloro-2-(trifluoromethyl)phenyl]-4-[(2'-oxospiro[furo[2,3-f][1,3]benzodioxole-7,3'-indol]-1'(2'H)-yl)methyl]benzamide | 594.1 |
| 563 | N-[4-fluoro-2-(trifluoromethyl)phenyl]-4-[(2'-oxospiro[furo[2,3-f][1,3]benzodioxole-7,3'-indol]-1'(2'H)-yl)methyl]benzamide | 577.1 |
| 564 | N-(2-cyanoethyl)-4-[(2'-oxospiro[furo[2,3-f][1,3]benzodioxole-7,3'-indol]-1'(2'H)-yl)methyl]benzamide | 468.1 |
| 565 | N-[(1S)-1-cyclohexylethyl]-4-[(2'-oxospiro[furo[2,3-f][1,3]benzodioxole-7,3'-indol]-1'(2'H)-yl)methyl]benzamide | 525.2 |
| 566 | N-[(1R)-1-cyclohexylethyl]-4-[(2'-oxospiro[furo[2,3-f][1,3]benzodioxole-7,3'-indol]-1'(2'H)-yl)methyl]benzamide | 525.2 |
| 567 | N-(2,4-difluorophenyl)-4-[(2'-oxospiro[furo[2,3-f][1,3]benzodioxole-7,3'-indol]-1'(2'H)-yl)methyl]benzamide | 527.1 |
| 568 | N-(2,3-dihydro-1H-inden-1-yl)-4-[(2'-oxospiro[furo[2,3-f][1,3]benzodioxole-7,3'-indol]-1'(2'H)-yl)methyl]benzamide | 531.2 |
| 569 | 4-[(2'-oxospiro[furo[2,3-f][1,3]benzodioxole-7,3'-indol]-1'(2'H)-yl)methyl]-N-(2-thienylmethyl)benzamide | 511.2 |
| 570 | N-[(1-ethylpyrrolidin-2-yl)methyl]-4-[(2'-oxospiro[furo[2,3-f][1,3]benzodioxole-7,3'-indol]-1'(2'H)-yl)methyl]benzamide | 526.2 |
| 571 | 4-[(2'-oxospiro[furo[2,3-f][1,3]benzodioxole-7,3'-indol]-1'(2'H)-yl)methyl]-N-(4-propylphenyl)benzamide | 533.2 |
| 572 | N-(2,5-difluorobenzyl)-4-[(2'-oxospiro[furo[2,3-f][1,3]benzodioxole-7,3'-indol]-1'(2'H)-yl)methyl]benzamide | 541.1 |
| 573 | N-(2,3-dihydro-1H-inden-5-yl)-4-[(2'-oxospiro[furo[2,3-f][1,3]benzodioxole-7,3'-indol]-1'(2'H)-yl)methyl]benzamide | 531.2 |

| Compound Number | Name | MS (m/z, M + 1) |
|---|---|---|
| 574 | N-(2,5-difluorophenyl)-4-[(2'-oxospiro[furo[2,3-f][1,3]benzodioxole-7,3'-indol]-1'(2'H)-yl)methyl]benzamide | 527.1 |
| 575 | 4-[(2'-oxospiro[furo[2,3-f][1,3]benzodioxole-7,3'-indol]-1'(2'H)-yl)methyl]-N-[4-(trifluoromethyl)benzyl]benzamide | 573.1 |
| 576 | 4-[(2'-oxospiro[furo[2,3-f][1,3]benzodioxole-7,3'-indol]-1'(2'H)-yl)methyl]-N-[2-(2-thienyl)ethyl]benzamide | 525.1 |
| 577 | 4-[(2'-oxospiro[furo[2,3-f][1,3]benzodioxole-7,3'-indol]-1'(2'H)-yl)methyl]-N-(pyridin-3-ylmethyl)benzamide | 506.2 |
| 578 | 4-[(2'-oxospiro[furo[2,3-f][1,3]benzodioxole-7,3'-indol]-1'(2'H)-yl)methyl]-N-[2-(trifluoromethyl)benzyl]benzamide | 573.1 |
| 579 | N-[2-(4-chlorophenyl)ethyl]-4-[(2'-oxospiro[furo[2,3-f][1,3]benzodioxole-7,3'-indol]-1'(2'H)-yl)methyl]benzamide | 554 |
| 580 | 4-[(2'-oxospiro[furo[2,3-f][1,3]benzodioxole-7,3'-indol]-1'(2'H)-yl)methyl]-N-(2-pyrrolidin-1-ylethyl)benzamide | 512.2 |
| 581 | N-(3-methylpyridin-2-yl)-4-[(2'-oxospiro[furo[2,3-f][1,3]benzodioxole-7,3'-indol]-1'(2'H)-yl)methyl]benzamide | 506.1 |
| 582 | N-[3-(dimethylamino)propyl]-N-methyl-4-[(2'-oxospiro[furo[2,3-f][1,3]benzodioxole-7,3'-indol]-1'(2'H)-yl)methyl]benzamide | 514.2 |
| 583 | N-1,3-benzodioxol-5-yl-4-[(2'-oxospiro[furo[2,3-f][1,3]benzodioxole-7,3'-indol]-1'(2'H)-yl)methyl]benzamide | 535.1 |
| 584 | N-(2-morpholin-4-ylethyl)-4-[(2'-oxospiro[furo[2,3-f][1,3]benzodioxole-7,3'-indol]-1'(2'H)-yl)methyl]benzamide | 528.2 |
| 585 | 1'-{4-[(4-pyrimidin-2-ylpiperazin-1-yl)carbonyl]benzyl}spiro[furo[2,3-f][1,3]benzodioxole-7,3'-indol]-2'(1'H)-one | 562.2 |
| 586 | 4-[(2'-oxospiro[furo[2,3-f][1,3]benzodioxole-7,3'-indol]-1'(2'H)-yl)methyl]-N-1,3-thiazol-2-ylbenzamide | 498.1 |
| 587 | N-(6-methoxypyridin-3-yl)-4-[(2'-oxospiro[furo[2,3-f][1,3]benzodioxole-7,3'-indol]-1'(2'H)-yl)methyl]benzamide | 522.1 |
| 588 | N-(3,5-dichlorobenzyl)-4-[(2'-oxospiro[furo[2,3-f][1,3]benzodioxole-7,3'-indol]-1'(2'H)-yl)methyl]benzamide | 574.1 |
| 589 | N-1-naphthyl-4-[(2'-oxospiro[furo[2,3-f][1,3]benzodioxole-7,3'-indol]-1'(2'H)-yl)methyl]benzamide | 541.2 |
| 590 | 1'-(4-{[4-(1,3-benzodioxol-5-ylmethyl)piperazin-1-yl]carbonyl}benzyl)spiro[furo[2,3-f][1,3]benzodioxole-7,3'-indol]-2'(1'H)-one | 618.2 |
| 591 | N-(4,6-dimethylpyridin-2-yl)-4-[(2'-oxospiro[furo[2,3-f][1,3]benzodioxole-7,3'-indol]-1'(2'H)-yl)methyl]benzamide | 520.2 |
| 592 | 4-[(2'-oxospiro[furo[2,3-f][1,3]benzodioxole-7,3'-indol]-1'(2'H)-yl)methyl]-N-pyrimidin-4-ylbenzamide | 493.1 |
| 593 | N-(5-methyl-1,3-thiazol-2-yl)-4-[(2'-oxospiro[furo[2,3-f][1,3]benzodioxole-7,3'-indol]-1'(2'H)-yl)methyl]benzamide | 512.2 |
| 594 | N-(2-cyano-6-fluorophenyl)-4-[(2'-oxospiro[furo[2,3-f][1,3]benzodioxole-7,3'-indol]-1'(2'H)-yl)methyl]benzamide | 534.1 |
| 595 | N-(4-methylbenzyl)-4-[(2'-oxospiro[furo[2,3-f][1,3]benzodioxole-7,3'-indol]-1'(2'H)-yl)methyl]benzamide | 519.1 |
| 596 | N-[3-(1H-imidazol-1-yl)propyl]-4-[(2'-oxospiro[furo[2,3-f][1,3]benzodioxole-7,3'-indol]-1'(2'H)-yl)methyl]benzamide | 523.1 |
| 597 | N-(4-morpholin-4-ylphenyl)-4-[(2'-oxospiro[furo[2,3-f][1,3]benzodioxole-7,3'-indol]-1'(2'H)-yl)methyl]benzamide | 576.2 |
| 598 | 1'-{4-[(4-methylpiperazin-1-yl)carbonyl]benzyl}spiro[furo[2,3-f][1,3]benzodioxole-7,3'-indol]-2'(1'H)-one | 498.2 |
| 599 | N-(5-cyclopropyl-1,3,4-thiadiazol-2-yl)-4-[(2'-oxospiro[furo[2,3-f][1,3]benzodioxole-7,3'-indol]-1'(2'H)-yl)methyl]benzamide | 539.2 |

Example 13

Synthesis of 1'-(3-hydroxypropyl)spiro[furo[2,3-f][1,3]benzodioxole-7,3'-indol]-2'(1'H)-one A suspension of 1'-[3-(benzyloxy)propyl]spiro[furo[2,3-f][1,3]benzodioxole-7,3'-indol]-2'(1'H)-one (6.27 g, 14.5 mmol) and 10% Pd/C (0.5 g) in MeOH (150 mL) was hydrogenated under the normal pressure of hydrogen overnight and filtered through a pad of celite. The filtrate was concentrated in vacuo to dryness. The residue was crystallized from ether to yield the title compound (4.82 g) as a white solid in 98% yield: $^1$H NMR (300 MHz, CDCl$_3$) δ 7.38-6.93 (m, 4H), 6.49 (s, 1H), 6.10 (s, 1H), 4.87 (m, 1H), 4.63 (m, 1H), 4.01-3.81 (m, 2H), 3.62 (t, 2H), 2.89 (br, 1H), 1.99-1.91 (m, 2H); $^{13}$C NMR (75 MHz, CDCl$_3$) δ 178.8, 156.0, 148.9, 142.4, 142.1, 132.3, 129.0, 128.9, 124.1, 123.9, 119.0, 108.6, 103.0, 101.5, 93.6, 80.4, 58.3, 37.8, 29.8; MS (ES+) m/z 340.2 (M+1).

Example 14

Synthesis of 3-(2'-oxospiro[furo[2,3-f][1,3]benzodioxole-7,3'-indol]-1'(2'H)-yl)propanal To a solution of 1'-(3-hydroxypropyl)spiro[furo[2,3-f][1,3]benzodioxole-7,3'-indol]-2'(1'H)-one (4.82 g, 14.2 mmol) in dichloromethane (150 mL) was added 1,1,1-triacetoxy-1,1-dihydro-1,2-benziodoxol-3(1H)-one (7.00 g, 16.7 mmol) at 0° C. The resulting mixture was stirred at 0° C. for 4 h, diluted with ethyl acetate, washed sequentially with 10% Na$_2$S$_2$O$_3$ solution, saturated NaHCO$_3$ and brine, dried over anhydrous Na$_2$SO$_4$ and filtered. The filtrate was concentrated in vacuo to dryness. The residue was subjected to flash chromatography and the product was recrystallized from ethyl acetate/hexanes to afford the title compound (3.86 g) in 80% yield: $^1$H NMR (300 MHz, CDCl$_3$) δ 9.83 (s, 1H), 7.33-6.92 (m, 4H), 6.48 (s, 1H), 6.08 (s, 1H), 4.86 (m, 1H), 4.61 (m, 1H), 4.15-3.98 (m, 2H), 2.97-2.84 (m, 2H); MS (ES+, m/z) 338.1 (M+1).

Example 15

Synthesis of 1'-{3-[(cyclopropylmethyl)amino]propyl}spiro[furo[2,3-f][1,3]benzodioxole-7,3'-indol]-2'(1'H)-one To a solution of 3-(2'-oxospiro[furo[2,3-f][1,3]benzodioxole-7,3'-indol]-1'(2'H)-yl)propanal (0.07 g, 0.20 mmol) in THF (5.00 mL) was added (aminomethyl)cyclopropane (0.30 mmol) and MP-triacetoxyborohydride (0.26 g, 0.60 mmol). After overnight shaking, the polymer-bound 4-phenyloxybenzaldehyde (0.25 g, 0.18 mmol) was added. After another overnight shaking, the mixture was diluted with ether (10.0 mL) and filtered. The filtrate was concentrated in vacuo to dryness. The residue was recrystallized to give the title compound (0.05 g) in 62% yield as a white solid: $^1$H NMR (300 MHz, CDCl$_3$) δ 7.32-6.92 (m, 4H), 6.49 (s, 1H), 6.12 (s, 1H), 5.83 (m, 2H), 4.86 (m, 1H), 4.64 (m, 1H), 3.97-3.77 (m, 2H), 2.87-2.80 (m, 2H), 2.66-2.56 (m, 2H), 1.02-0.94 (m, 1H), 0.56-0.47 (m, 2H), 0.25-0.18 (m, 2H); MS (ES+) m/z 393.3 (M+1).

Example 15.1

The compounds listed in the following table were prepared using the similar procedure as described in EXAMPLE 15. As previously noted, the compound numbers listed below do not correspond to the compound numbers provided in the general Reaction Schemes above.

| Compound Number | Name | MS (m/z, M + 1) |
|---|---|---|
| 600 | 1'-{3-[(4-fluorobenzyl)amino]propyl}spiro[furo[2,3-f][1,3]benzodioxole-7,3'-indol]-2'(1'H)-one | 447.0 |
| 601 | 1'-{3-[(4-chlorophenyl)amino]propyl}spiro[furo[2,3-f][1,3]benzodioxole-7,3'-indol]-2'(1'H)-one | 449.2 |
| 602 | 1'-[3-(pentylamino)propyl]spiro[furo[2,3-f][1,3]benzodioxole-7,3'-indol]-2'(1'H)-one | 409.1 |
| 603 | 1'-{3-[(2-ethoxyethyl)amino]propyl}spiro[furo[2,3-f][1,3]benzodioxole-7,3'-indol]-2'(1'H)-one | 411.1 |
| 604 | 1'-{3-[(3-methoxypropyl)amino]propyl}spiro[furo[2,3-f][1,3]benzodioxole-7,3'-indol]-2'(1'H)-one | 411.1 |
| 605 | 1'-{3-[(3-methylbutyl)amino]propyl}spiro[furo[2,3-f][1,3]benzodioxole-7,3'-indol]-2'(1'H)-one | 409.6 |
| 606 | 1'-{3-[(3-ethoxypropyl)amino]propyl}spiro[furo[2,3-f][1,3]benzodioxole-7,3'-indol]-2'(1'H)-one | 425.6 |
| 607 | 1'-{3-[(2,2-dimethylpropyl)amino]propyl}spiro[furo[2,3-f][1,3]benzodioxole-7,3'-indol]-2'(1'H)-one | 409.1 |
| 608 | 3-{[3-(2'-oxospiro[furo[2,3-f][1,3]benzodioxole-7,3'-indol]-1'(2'H)-yl)propyl]amino}propanenitrile | 392.4 |
| 609 | 1'-{3-[(2,2,2-trifluoroethyl)amino]propyl}spiro[furo[2,3-f][1,3]benzodioxole-7,3'-indol]-2'(1'H)-one | 421.1 |
| 610 | 1'-[3-(cyclopropylamino)propyl]spiro[furo[2,3-f][1,3]benzodioxole-7,3'-indol]-2'(1'H)-one | 379.1 |
| 611 | 1'-[3-(cyclobutylamino)propyl]spiro[furo[2,3-f][1,3]benzodioxole-7,3'-indol]-2'(1'H)-one | 393.1 |
| 612 | 1'-{3-[(2-cyclopropylethyl)amino]propyl}spiro[furo[2,3-f][1,3]benzodioxole-7,3'-indol]-2'(1'H)-one | 407.1 |
| 613 | 1'-[3-(isobutylamino)propyl]spiro[furo[2,3-f][1,3]benzodioxole-7,3'-indol]-2'(1'H)-one | 395.1 |
| 614 | 1'-[3-(hexylamino)propyl]spiro[furo[2,3-f][1,3]benzodioxole-7,3'-indol]-2'(1'H)-one | 423.5 |
| 615 | 1'-[3-(heptylamino)propyl]spiro[furo[2,3-f][1,3]benzodioxole-7,3'-indol]-2'(1'H)-one | 437.1 |

-continued

| Compound Number | Name | MS (m/z, M + 1) |
|---|---|---|
| 616 | 1'-[3-(isopropylamino)propyl]spiro[furo[2,3-f][1,3]benzodioxole-7,3'-indol]-2'(1'H)-one | 381.7 |
| 617 | 1'-{3-[(tetrahydrofuran-2-ylmethyl)amino]propyl}spiro[furo[2,3-f][1,3]benzodioxole-7,3'-indol]-2'(1'H)-one | 423.1 |
| 618 | 1'-[3-(benzylamino)propyl]spiro[furo[2,3-f][1,3]benzodioxole-7,3'-indol]-2'(1'H)-one | 429.1 |
| 619 | 1'-{3-[(2-phenylethyl)amino]propyl}spiro[furo[2,3-f][1,3]benzodioxole-7,3'-indol]-2'(1'H)-one | 443.1 |
| 620 | 1'-[3-(dibenzylamino)propyl]spiro[furo[2,3-f][1,3]benzodioxole-7,3'-indol]-2'(1'H)-one | 519.4 |
| 621 | 1'-[3-(propylamino)propyl]spiro[furo[2,3-f][1,3]benzodioxole-7,3'-indol]-2'(1'H)-one | 381.1 |
| 622 | 1'-(3-{[2-(3-fluorophenyl)ethyl]amino}propyl)spiro[furo[2,3-f][1,3]benzodioxole-7,3'-indol]-2'(1'H)-one | 461.5 |
| 623 | 1'-{3-[(3-phenylpropyl)amino]propyl}spiro[furo[2,3-f][1,3]benzodioxole-7,3'-indol]-2'(1'H)-one | 457.5 |
| 624 | 1'-{3-[(2,2-diphenylethyl)amino]propyl}spiro[furo[2,3-f][1,3]benzodioxole-7,3'-indol]-2'(1'H)-one | 519.4 |
| 625 | 1'-(3-{[2-(4-methylphenyl)ethyl]amino}propyl)spiro[furo[2,3-f][1,3]benzodioxole-7,3'-indol]-2'(1'H)-one | 457.5 |
| 626 | 1'-(3-{[2-(3-chlorophenyl)ethyl]amino}propyl)spiro[furo[2,3-f][1,3]benzodioxole-7,3'-indol]-2'(1'H)-one | 477.3 |
| 627 | 1'-{3-[(2-pyridin-4-ylethyl)amino]propyl}spiro[furo[2,3-f][1,3]benzodioxole-7,3'-indol]-2'(1'H)-one | 444.2 |
| 628 | 1'-{3-[(pyridin-4-ylmethyl)amino]propyl}spiro[furo[2,3-f][1,3]benzodioxole-7,3'-indol]-2'(1'H)-one | 430.5 |
| 629 | 1'-(3-{[2-(4-fluorophenyl)ethyl]amino}propyl)spiro[furo[2,3-f][1,3]benzodioxole-7,3'-indol]-2'(1'H)-one | 461.0 |
| 630 | 1'-{3-[(pyridin-2-ylmethyl)amino]propyl}spiro[furo[2,3-f][1,3]benzodioxole-7,3'-indol]-2'(1'H)-one | 430.2 |
| 631 | 1'-(3-{[(1R)-1-cyclohexylethyl]amino}propyl)spiro[furo[2,3-f][1,3]benzodioxole-7,3'-indol]-2'(1'H)-one | 449.1 |
| 632 | 1'-{3-[(2-furylmethyl)amino]propyl}spiro[furo[2,3-f][1,3]benzodioxole-7,3'-indol]-2'(1'H)-one | 419.4 |
| 633 | 1'-{3-[(4-chlorobenzyl)amino]propyl}spiro[furo[2,3-f][1,3]benzodioxole-7,3'-indol]-2'(1'H)-one | 463.1 |
| 634 | 1'-{3-[(4-methoxybenzyl)amino]propyl}spiro[furo[2,3-f][1,3]benzodioxole-7,3'-indol]-2'(1'H)-one | 459.4 |
| 635 | 1'-{3-[(3-isopropoxypropyl)amino]propyl}spiro[furo[2,3-f][1,3]benzodioxole-7,3'-indol]-2'(1'H)-one | 439.1 |
| 636 | 1'-(3-{[2-(2-fluorophenyl)ethyl]amino}propyl)spiro[furo[2,3-f][1,3]benzodioxole-7,3'-indol]-2'(1'H)-one | 461.0 |
| 637 | 1'-{3-[(3,3-dimethylbutyl)amino]propyl}spiro[furo[2,3-f][1,3]benzodioxole-7,3'-indol]-2'(1'H)-one | 423.5 |
| 638 | 1'-{3-[(cyclohexylmethyl)amino]propyl}spiro[furo[2,3-f][1,3]benzodioxole-7,3'-indol]-2'(1'H)-one | 435.0 |
| 639 | 1'-(3-{[(1S)-1-cyclohexylethyl]amino}propyl)spiro[furo[2,3-f][1,3]benzodioxole-7,3'-indol]-2'(1'H)-one | 436.5 |
| 640 | 1'-{3-[(2-piperidin-1-ylethyl)amino]propyl}spiro[furo[2,3-f][1,3]benzodioxole-7,3'-indol]-2'(1'H)-one | 449.1 |
| 641 | 1'-{3-[(2-pyrrolidin-1-ylethyl)amino]propyl}spiro[furo[2,3-f][1,3]benzodioxole-7,3'-indol]-2'(1'H)-one | 450.5 |
| 642 | 1'-{3-[(2-morpholin-4-ylethyl)amino]propyl}spiro[furo[2,3-f][1,3]benzodioxole-7,3'-indol]-2'(1'H)-one | 452.4 |
| 643 | 1'-[3-(cyclohexylamino)propyl]spiro[furo[2,3-f][1,3]benzodioxole-7,3'-indol]-2'(1'H)-one | 421.5 |
| 644 | 1'-[3-(cyclopentylamino)propyl]spiro[furo[2,3-f][1,3]benzodioxole-7,3'-indol]-2'(1'H)-one | 407.3 |
| 645 | 1'-{3-[(2-chlorobenzyl)amino]propyl}spiro[furo[2,3-f][1,3]benzodioxole-7,3'-indol]-2'(1'H)-one | 463.2 |
| 646 | 1'-(3-pyrrolidin-1-ylpropyl)spiro[furo[2,3-f][1,3]benzodioxole-7,3'-indol]-2'(1'H)-one | 393.5 |
| 647 | 1'-[3-(dibutylamino)propyl]spiro[furo[2,3-f][1,3]benzodioxole-7,3'-indol]-2'(1'H)-one | 451.5 |
| 648 | 1'-(3-piperidin-1-ylpropyl)spiro[furo[2,3-f][1,3]benzodioxole-7,3'-indol]-2'(1'H)-one | 407.0 |
| 649 | 1'-[3-(dipropylamino)propyl]spiro[furo[2,3-f][1,3]benzodioxole-7,3'-indol]-2'(1'H)-one | 423.2 |
| 650 | 1'-(3-{[2-(dimethylamino)ethyl]amino}propyl)spiro[furo[2,3-f][1,3]benzodioxole-7,3'-indol]-2'(1'H)-one | 410.5 |
| 651 | 1'-(3-{[2-(diethylamino)ethyl](methyl)amino}propyl)spiro[furo[2,3-f][1,3]benzodioxole-7,3'-indol]-2'(1'H)-one | 452.1 |
| 652 | 1'-(3-{[2-(diisopropylamino)ethyl]amino}propyl)spiro[furo[2,3-f][1,3]benzodioxole-7,3'-indol]-2'(1'H)-one | 466.1 |

-continued

| Compound Number | Name | MS (m/z, M + 1) |
|---|---|---|
| 653 | 1'-[3-(diisopropylamino)propyl]spiro[furo[2,3-f][1,3]benzodioxole-7,3'-indol]-2'(1'H)-one | 423.0 |
| 654 | 1'-[3-(methylamino)propyl]spiro[furo[2,3-f][1,3]benzodioxole-7,3'-indol]-2'(1'H)-one | 353.0 |
| 655 | 1'-[3-(ethylamino)propyl]spiro[furo[2,3-f][1,3]benzodioxole-7,3'-indol]-2'(1'H)-one | 367.0 |
| 656 | 1'-{3-[bis(2-methoxyethyl)amino]propyl}spiro[furo[2,3-f][1,3]benzodioxole-7,3'-indol]-2'(1'H)-one | 455.0 |
| 657 | 1'-{3-[(2-fluorobenzyl)amino]propyl}spiro[furo[2,3-f][1,3]benzodioxole-7,3'-indol]-2'(1'H)-one | 446.9 |
| 658 | 1'-{3-[(3,5-difluorobenzyl)amino]propyl}spiro[furo[2,3-f][1,3]benzodioxole-7,3'-indol]-2'(1'H)-one | 464.9 |
| 659 | 1'-(3-{[3-(dimethylamino)propyl]amino}propyl)spiro[furo[2,3-f][1,3]benzodioxole-7,3'-indol]-2'(1'H)-one | 424.0 |
| 660 | 1'-[3-(diethylamino)propyl]spiro[furo[2,3-f][1,3]benzodioxole-7,3'-indol]-2'(1'H)-one | 394.9 |
| 661 | 1'-[3-(octylamino)propyl]spiro[furo[2,3-f][1,3]benzodioxole-7,3'-indol]-2'(1'H)-one | 451.5 |
| 662 | 1'-{3-[(1-methylbutyl)amino]propyl}spiro[furo[2,3-f][1,3]benzodioxole-7,3'-indol]-2'(1'H)-one | 409.0 |
| 663 | 1'-{3-[butyl(methyl)amino]propyl}spiro[furo[2,3-f][1,3]benzodioxole-7,3'-indol]-2'(1'H)-one | 409.0 |
| 664 | 1'-{3-[(2-isopropoxyethyl)amino]propyl}spiro[furo[2,3-f][1,3]benzodioxole-7,3'-indol]-2'(1'H)-one | 425.0 |
| 665 | 1'-{3-[(2,4-difluorobenzyl)amino]propyl}spiro[furo[2,3-f][1,3]benzodioxole-7,3'-indol]-2'(1'H)-one | 464.9 |
| 666 | 1'-{3-[(2-methylbenzyl)amino]propyl}spiro[furo[2,3-f][1,3]benzodioxole-7,3'-indol]-2'(1'H)-one | 443.0 |
| 667 | 1'-{3-[(3-fluorobenzyl)amino]propyl}spiro[furo[2,3-f][1,3]benzodioxole-7,3'-indol]-2'(1'H)-one | 446.9 |
| 668 | 1'-{3-[(2,6-difluorobenzyl)amino]propyl}spiro[furo[2,3-f][1,3]benzodioxole-7,3'-indol]-2'(1'H)-one | 464.9 |
| 669 | 1'-{3-[(1,2-dimethylpropyl)amino]propyl}spiro[furo[2,3-f][1,3]benzodioxole-7,3'-indol]-2'(1'H)-one | 409.0 |
| 670 | 1'-(3-{[2-(1-methylpyrrolidin-2-yl)ethyl]amino}propyl)spiro[furo[2,3-f][1,3]benzodioxole-7,3'-indol]-2'(1'H)-one | 450.4 |
| 671 | 1'-{3-[(2-pyridin-3-ylethyl)amino]propyl}spiro[furo[2,3-f][1,3]benzodioxole-7,3'-indol]-2'(1'H)-one | 444.5 |
| 672 | 1'-{3-[(1-methyl-2-phenylethyl)amino]propyl}spiro[furo[2,3-f][1,3]benzodioxole-7,3'-indol]-2'(1'H)-one | 457.0 |
| 673 | 1'-(3-{[2-(2-chlorophenyl)ethyl]amino}propyl)spiro[furo[2,3-f][1,3]benzodioxole-7,3'-indol]-2'(1'H)-one | 476.9 |
| 674 | 1'-{3-[(2-cyclohexylethyl)amino]propyl}spiro[furo[2,3-f][1,3]benzodioxole-7,3'-indol]-2'(1'H)-one | 448.1 |
| 675 | 1'-{3-[(2-pyridin-2-ylethyl)amino]propyl}spiro[furo[2,3-f][1,3]benzodioxole-7,3'-indol]-2'(1'H)-one | 444.2 |
| 676 | 1'-{3-[(2-biphenyl-4-ylethyl)amino]propyl}spiro[furo[2,3-f][1,3]benzodioxole-7,3'-indol]-2'(1'H)-one | 519.6 |
| 677 | 1'-{3-[(3-morpholin-4-ylpropyl)amino]propyl}spiro[furo[2,3-f][1,3]benzodioxole-7,3'-indol]-2'(1'H)-one | 466.2 |
| 678 | 1'-(3-{[(5-methyl-2-furyl)methyl]amino}propyl)spiro[furo[2,3-f][1,3]benzodioxole-7,3'-indol]-2'(1'H)-one | 433.3 |
| 679 | 1'-{3-[(3-methylbenzyl)amino]propyl}spiro[furo[2,3-f][1,3]benzodioxole-7,3'-indol]-2'(1'H)-one | 443.4 |

Example 16

Synthesis of 1'-(3-aminopropyl)spiro[furo[2,3-f][1,3]benzodioxole-7,3'-indol]-2'(1'H)-one To a solution of 2-[3-(2'-oxospiro[furo[2,3-f][1,3]benzodioxole-7,3'-indol]-1'(2'H)-yl)propyl]-1H-isoindole-1,3(2H)-dione (3.20 g, 6.80 mmol) in ethanol (70.0 mL) was added hydrazine monohydrate (1.87 g, 37.0 mmol). The mixture was stirred at ambient temperature for 4 h. The solvent was removed under reduced pressure and the residue was re-dissolved in ethyl acetate. The solution was washed with sodium bicarbonate and brine solution, dried over $MgSO_4$ and filtered. The filtrate was concentrated in vacuo to dryness. The residue was crystallized from hexane to yield the title compound (2.50 g) in 75% yield: $^1$H NMR (300 MHz, $CDCl_3$) δ 7.31-7.24 (m, 1H), 7.16-7.14 (m, 1H), 7.06-7.01 (m, 1H), 6.94-6.91 (m, 1H), 6.48 (s, 1H), 6.10 (s, 1H), 5.82 (m, 2H), 4.90-4.87 (m, 1H), 4.61 (d, 1H), 3.98-3.71 (m, 2H), 2.77-2.73 (m, 2H), 1.97 (br, 2H), 1.84-1.81 (m, 2H); $^{13}$C NMR (75 MHz, $CDCl_3$) δ 177.8, 155.9, 148.9, 142.3, 142.2, 132.4, 129.0, 124.0, 123.4, 119.4, 108.7, 103.0, 101.5, 93.6, 80.5, 58.2, 38.8, 37.5, 30.6; MS (ES+) m/z 339.3 (M+1).

Example 17

Synthesis of 3-chloro-N-[3-(2'-oxospiro[furo[2,3-f][1,3]benzodioxole-7,3'-indol]-1'(2'H)-yl)propyl]thiophene-2-carboxamide To a solution of 1'-(3-aminopropyl)spiro[furo[2,3-f]-[1,3]benzodioxole-7,3'-indol]-2'(1'H)-one (0.05 g, 0.13 mmol) in dichloromethane (4.00 mL) was added triethylamine (0.03 g, 0.26 mmol) and 3-chlorothiophene-2-carbonyl chloride (0.02 g, 0.12 mmol) at 0° C. The mixture was stirred for 2 h, washed with 15% HCl solution and water. The organic layer was dried over MgSO$_4$ and filtered. The filtrate was concentrated in vacuo to dryness. The residue was dissolved in ethyl acetate, and the product was precipitated with the addition of hexane. The white solid was collected by filtration and dried in vacuo to yield the title compound (0.04 g) in 67% yield: $^1$H NMR (300 MHz, CDCl$_3$) δ 7.60 (t, 1H), 7.41 (d, 1H), 7.33-7.27- (m, 1H), 7.17 (d, 1H), 7.08-7.03- (m, 1H), 6.93 (t, 1H), 6.49 (s, 1H), 6.11 (s, 1H), 5.95 (m, 2H), 4.90 (d, 1H), 4.65 (d, 1H), 3.96-3.79- (m, 2H), 3.53-3.36- (m, 2H), 2.04-1.93- (m, 2H); $^{13}$C NMR (75 MHz, CDCl$_3$) 178.3, 160.6, 156.0, 149.0, 142.4, 141.8, 132.5, 129.4, 129.2, 129.1, 124.2, 123.7, 123.6, 119.2, 108.5, 102.9, 101.6, 93.7, 80.5, 58.3, 37.4, 36.5, 27.3; MS (ES+) m/z 483 (M+1).

Example 17.1

The compounds listed in the following table were synthesized using the similar procedure as described in EXAMPLE 17. As previously noted, the compound numbers listed below do not correspond to the compound numbers provided in the general Reaction Schemes above.

| Compound Number | Name | MS (m/z, M + 1) |
|---|---|---|
| 680 | N-[3-(2'-oxospiro[furo[2,3-f][1,3]benzodioxole-7,3'-indol]-1'(2'H)-yl)propyl]cyclopropanecarboxamide | 407.3 |
| 681 | N-[3-(2'-oxospiro[furo[2,3-f][1,3]benzodioxole-7,3'-indol]-1'(2'H)-yl)propyl]cyclobutanecarboxamide | 421.3 |
| 682 | 2-chloro-N-[3-(2'-oxospiro[furo[2,3-f][1,3]benzodioxole-7,3'-indol]-1'(2'H)-yl)propyl]nicotinamide | 478.3 |
| 683 | N-[3-(2'-oxospiro[furo[2,3-f][1,3]benzodioxole-7,3'-indol]-1'(2'H)-yl)propyl]cyclopentanecarboxamide | 435.3 |
| 684 | 2,2-dimethyl-N-[3-(2'-oxospiro[furo[2,3-f][1,3]benzodioxole-7,3'-indol]-1'(2'H)-yl)propyl]propanamide | 423.3 |
| 685 | 2-(4-methoxyphenyl)-N-[3-(2'-oxospiro[furo[2,3-f][1,3]benzodioxole-7,3'-indol]-1'(2'H)-yl)propyl]acetamide | 487.3 |
| 686 | 4-tert-butyl-N-[3-(2'-oxospiro[furo[2,3-f][1,3]benzodioxole-7,3'-indol]-1'(2'H)-yl)propyl]benzamide | 499.2 |
| 687 | 3,3-dimethyl-N-[3-(2'-oxospiro[furo[2,3-f][1,3]benzodioxole-7,3'-indol]-1'(2'H)-yl)propyl]butanamide | 437.3 |
| 688 | N-[3-(2'-oxospiro[furo[2,3-f][1,3]benzodioxole-7,3'-indol]-1'(2'H)-yl)propyl]biphenyl-4-carboxamide | 519.3 |
| 689 | 3-methyl-N-[3-(2'-oxospiro[furo[2,3-f][1,3]benzodioxole-7,3'-indol]-1'(2'H)-yl)propyl]-1-benzofuran-2-carboxamide | 497.2 |
| 690 | 2-(benzyloxy)-N-[3-(2'-oxospiro[furo[2,3-f][1,3]benzodioxole-7,3'-indol]-1'(2'H)-yl)propyl]acetamide | 487.3 |
| 691 | N-[3-(2'-oxospiro[furo[2,3-f][1,3]benzodioxole-7,3'-indol]-1'(2'H)-yl)propyl]-2-furamide | 433.3 |
| 692 | N-[3-(2'-oxospiro[furo[2,3-f][1,3]benzodioxole-7,3'-indol]-1'(2'H)-yl)propyl]-1,3-benzodioxole-5-carboxamide | 487.3 |
| 693 | N-[3-(2'-oxospiro[furo[2,3-f][1,3]benzodioxole-7,3'-indol]-1'(2'H)-yl)propyl]quinoline-2-carboxamide | 494.3 |
| 694 | N-[3-(2'-oxospiro[furo[2,3-f][1,3]benzodioxole-7,3'-indol]-1'(2'H)-yl)propyl]-2-phenylacetamide | 457.4 |
| 695 | N-[3-(2'-oxospiro[furo[2,3-f][1,3]benzodioxole-7,3'-indol]-1'(2'H)-yl)propyl]piperidine-1-carboxamide | 450.3 |
| 696 | 2-methoxy-N-[3-(2'-oxospiro[furo[2,3-f][1,3]benzodioxole-7,3'-indol]-1'(2'H)-yl)propyl]acetamide | 411.2 |
| 697 | 4-(dimethylamino)-N-[3-(2'-oxospiro[furo[2,3-f][1,3]benzodioxole-7,3'-indol]-1'(2'H)-yl)propyl]benzamide | 486.3 |
| 698 | 4-ethoxy-N-[3-(2'-oxospiro[furo[2,3-f][1,3]benzodioxole-7,3'-indol]-1'(2'H)-yl)propyl]benzamide | 487.3 |
| 699 | 2-methyl-N-[3-(2'-oxospiro[furo[2,3-f][1,3]benzodioxole-7,3'-indol]-1'(2'H)-yl)propyl]butanamide | 423.3 |
| 700 | N-[3-(2'-oxospiro[furo[2,3-f][1,3]benzodioxole-7,3'-indol]-1'(2'H)-yl)propyl]-2-phenoxyacetamide | 473.2 |
| 701 | N-[3-(2'-oxospiro[furo[2,3-f][1,3]benzodioxole-7,3'-indol]-1'(2'H)-yl)propyl]quinoxaline-2-carboxamide | 495.0 |
| 702 | N-[3-(2'-oxospiro[furo[2,3-f][1,3]benzodioxole-7,3'-indol]-1'(2'H)-yl)propyl]cyclohexanecarboxamide | 449.3 |

| Compound Number | Name | MS (m/z, M + 1) |
|---|---|---|
| 703 | 4-fluoro-N-[3-(2'-oxospiro[furo[2,3-f][1,3]benzodioxole-7,3'-indol]-1'(2'H)-yl)propyl]benzamide | 461.3 |
| 704 | 2-ethyl-N-[3-(2'-oxospiro[furo[2,3-f][1,3]benzodioxole-7,3'-indol]-1'(2'H)-yl)propyl]butanamide | 437.3 |
| 705 | 2-(4-fluorophenyl)-N-[3-(2'-oxospiro[furo[2,3-f][1,3]benzodioxole-7,3'-indol]-1'(2'H)-yl)propyl]acetamide | 475.3 |
| 706 | 6-chloro-N-[3-(2'-oxospiro[furo[2,3-f][1,3]benzodioxole-7,3'-indol]-1'(2'H)-yl)propyl]nicotinamide | 478.0 |
| 707 | 2-fluoro-N-[3-(2'-oxospiro[furo[2,3-f][1,3]benzodioxole-7,3'-indol]-1'(2'H)-yl)propyl]benzamide | 461.4 |
| 708 | N-[3-(2'-oxospiro[furo[2,3-f][1,3]benzodioxole-7,3'-indol]-1'(2'H)-yl)propyl]-2-phenylcyclopropanecarboxamide | 482.8 |
| 709 | 4-methyl-N-[3-(2'-oxospiro[furo[2,3-f][1,3]benzodioxole-7,3'-indol]-1'(2'H)-yl)propyl]benzamide | 457.7 |
| 710 | 1-(4-fluorophenyl)-5-methyl-N-[3-(2'-oxospiro[furo[2,3-f][1,3]benzodioxole-7,3'-indol]-1'(2'H)-yl)propyl]-1H-pyrazole-4-carboxamide | 541.2 |
| 711 | N-[3-(2'-oxospiro[furo[2,3-f][1,3]benzodioxole-7,3'-indol]-1'(2'H)-yl)propyl]-1-benzofuran-5-carboxamide | 483.1 |
| 712 | N-[3-(2'-oxospiro[furo[2,3-f][1,3]benzodioxole-7,3'-indol]-1'(2'H)-yl)propyl]-2,1,3-benzoxadiazole-5-carboxamide | 485.4 |
| 713 | 2,4-dichloro-N-[3-(2'-oxospiro[furo[2,3-f][1,3]benzodioxole-7,3'-indol]-1'(2'H)-yl)propyl]benzamide | 513.1 |
| 714 | 1-methyl-N-[3-(2'-oxospiro[furo[2,3-f][1,3]benzodioxole-7,3'-indol]-1'(2'H)-yl)propyl]-1H-1,2,3-benzotriazole-5-carboxamide | 498.4 |
| 715 | 5-fluoro-2-methyl-N-[3-(2'-oxospiro[furo[2,3-f][1,3]benzodioxole-7,3'-indol]-1'(2'H)-yl)propyl]benzamide | 475.1 |
| 716 | 2-chloro-N-[3-(2'-oxospiro[furo[2,3-f][1,3]benzodioxole-7,3'-indol]-1'(2'H)-yl)propyl]isonicotinamide | 478.1 |
| 717 | N-[3-(2'-oxospiro[furo[2,3-f][1,3]benzodioxole-7,3'-indol]-1'(2'H)-yl)propyl]-2,3-dihydro-1,4-benzodioxine-6-carboxamide | 501.1 |
| 718 | 5-methyl-N-[3-(2'-oxospiro[furo[2,3-f][1,3]benzodioxole-7,3'-indol]-1'(2'H)-yl)propyl]isoxazole-3-carboxamide | 448.2 |
| 719 | N-[3-(2'-oxospiro[furo[2,3-f][1,3]benzodioxole-7,3'-indol]-1'(2'H)-yl)propyl]-1-benzofuran-2-carboxamide | 483.1 |
| 720 | N-[3-(2'-oxospiro[furo[2,3-f][1,3]benzodioxole-7,3'-indol]-1'(2'H)-yl)propyl]-1-benzothiophene-2-carboxamide | 499.1 |
| 721 | N-[3-(2'-oxospiro[furo[2,3-f][1,3]benzodioxole-7,3'-indol]-1'(2'H)-yl)propyl]-2,3-dihydro-1,4-benzodioxine-2-carboxamide | 501.1 |
| 722 | N-[3-(2'-oxospiro[furo[2,3-f][1,3]benzodioxole-7,3'-indol]-1'(2'H)-yl)propyl]-4-(1H-pyrazol-1-yl)benzamide | 509.1 |
| 723 | 1,3-dimethyl-N-[3-(2'-oxospiro[furo[2,3-f][1,3]benzodioxole-7,3'-indol]-1'(2'H)-yl)propyl]-1H-pyrazole-5-carboxamide | 461.2 |
| 724 | 4-methyl-N-[3-(2'-oxospiro[furo[2,3-f][1,3]benzodioxole-7,3'-indol]-1'(2'H)-yl)propyl]-3,4-dihydro-2H-1,4-benzoxazine-7-carboxamide | 514.2 |
| 725 | N-[3-(2'-oxospiro[furo[2,3-f][1,3]benzodioxole-7,3'-indol]-1'(2'H)-yl)propyl]quinoxaline-6-carboxamide | 495.2 |
| 726 | N-[3-(2'-oxospiro[furo[2,3-f][1,3]benzodioxole-7,3'-indol]-1'(2'H)-yl)propyl]-2,3-dihydro-1-benzofuran-2-carboxamide | 485.2 |
| 727 | N-[3-(2'-oxospiro[furo[2,3-f][1,3]benzodioxole-7,3'-indol]-1'(2'H)-yl)propyl]-2,3-dihydro-1-benzothiophene-5-carboxamide | 499.1 |
| 728 | N-[3-(2'-oxospiro[furo[2,3-f][1,3]benzodioxole-7,3'-indol]-1'(2'H)-yl)propyl]-2-(trifluoromethoxy)benzamide | 526.9 |
| 729 | N-[3-(2'-oxospiro[furo[2,3-f][1,3]benzodioxole-7,3'-indol]-1'(2'H)-yl)propyl]pentanamide | 445.2 |
| 730 | N-[3-(2'-oxospiro[furo[2,3-f][1,3]benzodioxole-7,3'-indol]-1'(2'H)-yl)propyl]heptanamide | 473.2 |
| 731 | 3-cyclopentyl-N-[3-(2'-oxospiro[furo[2,3-f][1,3]benzodioxole-7,3'-indol]-1'(2'H)-yl)propyl]propanamide | 463.0 |
| 732 | 9-oxo-N-[3-(2'-oxospiro[furo[2,3-f][1,3]benzodioxole-7,3'-indol]-1'(2'H)-yl)propyl]-9H-fluorene-4-carboxamide | 545.0 |
| 733 | N-[3-(2'-oxospiro[furo[2,3-f][1,3]benzodioxole-7,3'-indol]-1'(2'H)-yl)propyl]-4-(trifluoromethyl)benzamide | 511.4 |

-continued

| Compound Number | Name | MS (m/z, M + 1) |
|---|---|---|
| 734 | 2,5-difluoro-N-[3-(2'-oxospiro[furo[2,3-f][1,3]benzodioxole-7,3'-indol]-1'(2'H)-yl)propyl]benzamide | 479.3 |
| 735 | 2,5-dimethyl-N-[3-(2'-oxospiro[furo[2,3-f][1,3]benzodioxole-7,3'-indol]-1'(2'H)-yl)propyl]-3-furamide | 461.4 |
| 736 | N-[3-(2'-oxospiro[furo[2,3-f][1,3]benzodioxole-7,3'-indol]-1'(2'H)-yl)propyl]-4-phenoxybutanamide | 523.3 |
| 737 | 4-fluoro-N-[3-(2'-oxospiro[furo[2,3-f][1,3]benzodioxole-7,3'-indol]-1'(2'H)-yl)propyl]-2-(trifluoromethyl)benzamide | 529.0 |
| 738 | N-[3-(2'-oxospiro[furo[2,3-f][1,3]benzodioxole-7,3'-indol]-1'(2'H)-yl)propyl]-2-(2-thienyl)acetamide | 463.3 |
| 739 | 2-chloro-5-fluoro-N-[3-(2'-oxospiro[furo[2,3-f][1,3]benzodioxole-7,3'-indol]-1'(2'H)-yl)propyl]benzamide | 495.0 |
| 740 | N-[3-(2'-oxospiro[furo[2,3-f][1,3]benzodioxole-7,3'-indol]-1'(2'H)-yl)propyl]-2-naphthamide | 493.0 |
| 741 | 2-(4-chlorophenoxy)-N-[3-(2'-oxospiro[furo[2,3-f][1,3]benzodioxole-7,3'-indol]-1'(2'H)-yl)propyl]acetamide | 507.3 |
| 742 | 2,4-dimethoxy-N-[3-(2'-oxospiro[furo[2,3-f][1,3]benzodioxole-7,3'-indol]-1'(2'H)-yl)propyl]benzamide | 503.4 |
| 743 | 2-nitro-N-[3-(2'-oxospiro[furo[2,3-f][1,3]benzodioxole-7,3'-indol]-1'(2'H)-yl)propyl]benzamide | 488.4 |
| 744 | 2-(4-chlorophenyl)-3-methyl-N-[3-(2'-oxospiro[furo[2,3-f][1,3]benzodioxole-7,3'-indol]-1'(2'H)-yl)propyl]butanamide | 533.4 |
| 745 | 4-amino-N-[3-(2'-oxospiro[furo[2,3-f][1,3]benzodioxole-7,3'-indol]-1'(2'H)-yl)propyl]benzamide | 458.4 |
| 746 | 3,4-dimethoxy-N-[3-(2'-oxospiro[furo[2,3-f][1,3]benzodioxole-7,3'-indol]-1'(2'H)-yl)propyl]benzamide | 503.3 |
| 747 | N-[3-(2'-oxospiro[furo[2,3-f][1,3]benzodioxole-7,3'-indol]-1'(2'H)-yl)propyl]-5H-dibenzo[b,f]azepine-5-carboxamide | 558.4 |
| 748 | N-[3-(2'-oxospiro[furo[2,3-f][1,3]benzodioxole-7,3'-indol]-1'(2'H)-yl)propyl]adamantane-1-carboxamide | 501.5 |
| 749 | 2-[(2-isopropyl-5-methylcyclohexyl)oxy]-N-[3-(2'-oxospiro[furo[2,3-f][1,3]benzodioxole-7,3'-indol]-1'(2'H)-yl)propyl]acetamide | 535.5 |
| 750 | N-[3-(2'-oxospiro[furo[2,3-f][1,3]benzodioxole-7,3'-indol]-1'(2'H)-yl)propyl]-3,5-bis(trifluoromethyl)benzamide | 579.3 |
| 751 | 2-(2,5-dimethoxyphenyl)-N-[3-(2'-oxospiro[furo[2,3-f][1,3]benzodioxole-7,3'-indol]-1'(2'H)-yl)propyl]acetamide | 517.4 |
| 752 | 2-chloro-N-[3-(2'-oxospiro[furo[2,3-f][1,3]benzodioxole-7,3'-indol]-1'(2'H)-yl)propyl]benzamide | 477.3 |
| 753 | 3-chloro-N-[3-(2'-oxospiro[furo[2,3-f][1,3]benzodioxole-7,3'-indol]-1'(2'H)-yl)propyl]benzamide | 477.3 |
| 754 | 4-chloro-N-[3-(2'-oxospiro[furo[2,3-f][1,3]benzodioxole-7,3'-indol]-1'(2'H)-yl)propyl]benzamide | 477.3 |
| 755 | N-[3-(2'-oxospiro[furo[2,3-f][1,3]benzodioxole-7,3'-indol]-1'(2'H)-yl)propyl]hexanamide | 437.4 |
| 756 | 2,6-difluoro-N-[3-(2'-oxospiro[furo[2,3-f][1,3]benzodioxole-7,3'-indol]-1'(2'H)-yl)propyl]benzamide | 479.4 |
| 757 | 2-chloro-N-[3-(2'-oxospiro[furo[2,3-f][1,3]benzodioxole-7,3'-indol]-1'(2'H)-yl)propyl]acetamide | 415.3 |
| 758 | N-[3-(2'-oxospiro[furo[2,3-f][1,3]benzodioxole-7,3'-indol]-1'(2'H)-yl)propyl]-2,5-bis(trifluoromethyl)benzamide | 579.4 |
| 759 | N-[3-(2'-oxospiro[furo[2,3-f][1,3]benzodioxole-7,3'-indol]-1'(2'H)-yl)propyl]pyrrolidine-1-carboxamide | 436.4 |
| 760 | 2-bromo-2,2-difluoro-N-[3-(2'-oxospiro[furo[2,3-f][1,3]benzodioxole-7,3'-indol]-1'(2'H)-yl)propyl]acetamide | 497.3 |
| 761 | 2,3,5-trifluoro-N-[3-(2'-oxospiro[furo[2,3-f][1,3]benzodioxole-7,3'-indol]-1'(2'H)-yl)propyl]benzamide | 497.3 |
| 762 | 5-fluoro-N-[3-(2'-oxospiro[furo[2,3-f][1,3]benzodioxole-7,3'-indol]-1'(2'H)-yl)propyl]-2-(trifluoromethyl)benzamide | 529.4 |
| 763 | 5-chloro-N-[3-(2'-oxospiro[furo[2,3-f][1,3]benzodioxole-7,3'-indol]-1'(2'H)-yl)propyl]-2-(trifluoromethyl)benzamide | 545.3 |

-continued

| Compound Number | Name | MS (m/z, M + 1) |
|---|---|---|
| 764 | N-[3-(2'-oxospiro[furo[2,3-f][1,3]benzodioxole-7,3'-indol]-1'(2'H)-yl)propyl]thiophene-2-carboxamide | 449.3 |
| 765 | N-[3-(2'-oxospiro[furo[2,3-f][1,3]benzodioxole-7,3'-indol]-1'(2'H)-yl)propyl]morpholine-4-carboxamide | 452.4 |
| 766 | 2-(1-naphthyl)-N-[3-(2'-oxospiro[furo[2,3-f][1,3]benzodioxole-7,3'-indol]-1'(2'H)-yl)propyl]acetamide | 507.4 |
| 767 | 2-methyl-N-[3-(2'-oxospiro[furo[2,3-f][1,3]benzodioxole-7,3'-indol]-1'(2'H)-yl)propyl]propanamide | 409.4 |
| 768 | N-[3-(2'-oxospiro[furo[2,3-f][1,3]benzodioxole-7,3'-indol]-1'(2'H)-yl)propyl]-N-propionylpropanamide | 451.4 |
| 769 | N-[3-(2'-oxospiro[furo[2,3-f][1,3]benzodioxole-7,3'-indol]-1'(2'H)-yl)propyl]-4-pentylbenzamide | 513.3 |
| 770 | 4,7,7-trimethyl-3-oxo-N-[3-(2'-oxospiro[furo[2,3-f][1,3]benzodioxole-7,3'-indol]-1'(2'H)-yl)propyl]-2-oxabicyclo[2.2.1]heptane-1-carboxamide | 519.4 |
| 771 | 2-bromo-N-[3-(2'-oxospiro[furo[2,3-f][1,3]benzodioxole-7,3'-indol]-1'(2'H)-yl)propyl]benzamide | 523.2 |
| 772 | 3-cyano-N-[3-(2'-oxospiro[furo[2,3-f][1,3]benzodioxole-7,3'-indol]-1'(2'H)-yl)propyl]benzamide | 468.3 |
| 773 | 4-cyano-N-[3-(2'-oxospiro[furo[2,3-f][1,3]benzodioxole-7,3'-indol]-1'(2'H)-yl)propyl]benzamide | 468.3 |

Example 18

Synthesis of 1'-(2-aminoethyl)spiro[furo[2,3-f][1,3]benzodioxole-7,3'-indol]-2'(1'H)-one To a suspension of 2-[2-(2'-oxospiro[furo[2,3-f][1,3]benzodioxole-7,3'-indol]-1'(2'H)-yl)ethyl]-1H-isoindole-1,3(2H)-dione (20.0 g, 44.0 mmol) in methanol (400 mL) was added hydrazine (8.00 mL). The mixture was stirred at ambient temperature for 48 h and filtered. The filtrate was concentrated in vacuo to dryness. The residue was subjected to flash chromatography eluting with ethyl acetate/methanol/ammonia (10/1/0.2) to afford the crude product which was recrystallized from ethyl acetate to yield the title compound (8.0 g) in 56% yield as a white solid: $^1$H NMR (300 MHz, CDCl$_3$) δ 7.34 (m, 1H), 7.17 (dd, 1H), 7.06 (dd, 1H), 6.95 (d, 1H), 6.51 (s, 1H), 6.18 (s, 1H), 5.89-5.82- (ABq, 2H), 4.93 (d, 1H), 4.66 (d, 1H), 3.95-3.74- (m, 2H), 3.06 (t, 2H), 1.59-1.35- (br, 2H); $^{13}$C NMR (75 MHz, CDCl$_3$) δ 178.0, 155.9, 148.8, 142.3, 132.4, 128.9, 124.0, 123.4, 119.5, 108.6, 103.1, 101.5, 93.6, 80.5, 58.2, 43.4, 39.8; MS (ES+) m/z 325 (M+1), 308 (M−16).

Example 19

Synthesis of 1-(4-fluorophenyl)-3-[2-(2'-oxospiro[furo[2,3-f][1,3]benzodioxole-7,3'-indol]-1'(2'H)-yl)ethyl]urea To a mixture of 1'-(2-aminoethyl)spiro[furo[2,3-f][1,3]benzodioxole-7,3'-indol]-2'(1'H)-one (0.15 mmol) and triethylamine (0.01 mmol) in anhydrous dichloromethane was added 1-fluoro-4-isocyanatobenzene (0.14 mmol) at ambient temperature. The mixture was stirred for 16 h, diluted with of dichloromethane (5.00 mL), washed with 10% HCl solution and brine, dried over Na$_2$SO$_4$ and filtered. The filtrate was concentrated in vacuo to dryness to give the title compound (0.05 g) in 82% yield: $^1$H NMR (300 MHz, DMSO-d$_6$) δ 8.54 (s, 1H), 7.35-7.25 (m, 3H), 7.19 (d, 1H), 7.11 (d, 1H), 7.06-6.91 (m, 3H), 6.67 (s, 1H), 6.52 (t, 1H), 5.94-5.84 (ABq, 2H), 4.74 (d, 1H), 4.61 (d, 1H), 3.91-3.69 (m, 2H), 3.49-3.34 (m, 2H); MS (ES+) m/z 462 (M+1), 484 (M+23).

Example 19.1

The compounds listed in the following table were synthesized using the similar procedure as described in EXAMPLE 19. As previously noted, the compound numbers listed below do not correspond to the compound numbers provided in the general Reaction Schemes above.

| Compound Number | Name | MS (m/z, M + 1) |
|---|---|---|
| 774 | 1-benzyl-3-[2-(2'-oxospiro[furo[2,3-f][1,3]benzodioxole-7,3'-indol]-1'(2'H)-yl)ethyl]urea | 458 |
| 775 | 1-[2-(2'-oxospiro[furo[2,3-f][1,3]benzodioxole-7,3'-indol]-1'(2'H)-yl)ethyl]-3-(4-phenoxyphenyl)urea | 536 |
| 776 | 1-butyl-3-[2-(2'-oxospiro[furo[2,3-f][1,3]benzodioxole-7,3'-indol]-1'(2'H)-yl)ethyl]urea | 424 |
| 777 | 1-cyclohexyl-3-[2-(2'-oxospiro[furo[2,3-f][1,3]benzodioxole-7,3'-indol]-1'(2'H)-yl)ethyl]urea | 450 |
| 778 | 1-ethyl-3-[2-(2'-oxospiro[furo[2,3-f][1,3]benzodioxole-7,3'-indol]-1'(2'H)-yl)ethyl]urea | 396 |
| 779 | 1-isopropyl-3-[2-(2'-oxospiro[furo[2,3-f][1,3]benzodioxole-7,3'-indol]-1'(2'H)-yl)ethyl]urea | 410 |
| 780 | 1-[2-(2'-oxospiro[furo[2,3-f][1,3]benzodioxole-7,3'-indol]-1'(2'H)-yl)ethyl]-3-propylurea | 410 |

| Compound Number | Name | MS (m/z, M + 1) |
|---|---|---|
| 781 | 1-tert-butyl-3-[2-(2'-oxospiro[furo[2,3-f][1,3]benzodioxole-7,3'-indol]-1'(2'H)-yl)ethyl]urea | 424 |
| 782 | 1-cyclopentyl-3-[2-(2'-oxospiro[furo[2,3-f][1,3]benzodioxole-7,3'-indol]-1'(2'H)-yl)ethyl]urea | 436 |
| 783 | 1-[2-(2'-oxospiro[furo[2,3-f][1,3]benzodioxole-7,3'-indol]-1'(2'H)-yl)ethyl]-3-pentylurea | 438 |
| 784 | 1-[2-(2'-oxospiro[furo[2,3-f][1,3]benzodioxole-7,3'-indol]-1'(2'H)-yl)ethyl]-3-phenylurea | 444 |
| 785 | 1-(2-furylmethyl)-3-[2-(2'-oxospiro[furo[2,3-f][1,3]benzodioxole-7,3'-indol]-1'(2'H)-yl)ethyl]urea | 448 |
| 786 | 1-hexyl-3-[2-(2'-oxospiro[furo[2,3-f][1,3]benzodioxole-7,3'-indol]-1'(2'H)-yl)ethyl]urea | 452 |
| 787 | ethyl N-({[2-(2'-oxospiro[furo[2,3-f][1,3]benzodioxole-7,3'-indol]-1'(2'H)-yl)ethyl]amino}carbonyl)glycinate | 454 |
| 788 | 1-(3-methylphenyl)-3-[2-(2'-oxospiro[furo[2,3-f][1,3]benzodioxole-7,3'-indol]-1'(2'H)-yl)ethyl]urea | 458 |
| 789 | 1-(4-methylphenyl)-3-[2-(2'-oxospiro[furo[2,3-f][1,3]benzodioxole-7,3'-indol]-1'(2'H)-yl)ethyl]urea | 458 |
| 790 | ethyl N-({[2-(2'-oxospiro[furo[2,3-f][1,3]benzodioxole-7,3'-indol]-1'(2'H)-yl)ethyl]amino}carbonyl)-beta-alaninate | 468 |
| 791 | 1-(4-cyanophenyl)-3-[2-(2'-oxospiro[furo[2,3-f][1,3]benzodioxole-7,3'-indol]-1'(2'H)-yl)ethyl]urea | 469 |
| 792 | N-({[2-(2'-oxospiro[furo[2,3-f][1,3]benzodioxole-7,3'-indol]-1'(2'H)-yl)ethyl]amino}carbonyl)benzamide | 472 |
| 793 | 1-[2-(2'-oxospiro[furo[2,3-f][1,3]benzodioxole-7,3'-indol]-1'(2'H)-yl)ethyl]-3-(2-phenylethyl)urea | 473 |
| 794 | 1-(4-methylbenzyl)-3-[2-(2'-oxospiro[furo[2,3-f][1,3]benzodioxole-7,3'-indol]-1'(2'H)-yl)ethyl]urea | 472 |
| 795 | 1-(2-methylbenzyl)-3-[2-(2'-oxospiro[furo[2,3-f][1,3]benzodioxole-7,3'-indol]-1'(2'H)-yl)ethyl]urea | 472 |
| 796 | 1-(4-ethylphenyl)-3-[2-(2'-oxospiro[furo[2,3-f][1,3]benzodioxole-7,3'-indol]-1'(2'H)-yl)ethyl]urea | 472 |
| 797 | 1-(3-methoxyphenyl)-3-[2-(2'-oxospiro[furo[2,3-f][1,3]benzodioxole-7,3'-indol]-1'(2'H)-yl)ethyl]urea | 474 |
| 798 | 1-(2-fluoro-5-methylphenyl)-3-[2-(2'-oxospiro[furo[2,3-f][1,3]benzodioxole-7,3'-indol]-1'(2'H)-yl)ethyl]urea | 476 |
| 799 | 1-(3-fluoro-4-methylphenyl)-3-[2-(2'-oxospiro[furo[2,3-f][1,3]benzodioxole-7,3'-indol]-1'(2'H)-yl)ethyl]urea | 476 |
| 800 | 1-(4-chlorophenyl)-3-[2-(2'-oxospiro[furo[2,3-f][1,3]benzodioxole-7,3'-indol]-1'(2'H)-yl)ethyl]urea | 479 |
| 801 | 2-[({[2-(2'-oxospiro[furo[2,3-f][1,3]benzodioxole-7,3'-indol]-1'(2'H)-yl)ethyl]amino}carbonyl)amino]ethyl 2-methylacrylate | 480 |
| 802 | 1-[2-(2'-oxospiro[furo[2,3-f][1,3]benzodioxole-7,3'-indol]-1'(2'H)-yl)ethyl]-3-(1,1,3,3-tetramethylbutyl)urea | 480 |
| 803 | ethyl 4-[({[2-(2'-oxospiro[furo[2,3-f][1,3]benzodioxole-7,3'-indol]-1'(2'H)-yl)ethyl]amino}carbonyl)amino]butanoate | 482 |
| 804 | 1-[4-(cyanomethyl)phenyl]-3-[2-(2'-oxospiro[furo[2,3-f][1,3]benzodioxole-7,3'-indol]-1'(2'H)-yl)ethyl]urea | 483 |
| 805 | 1-(2,3-dihydro-1H-inden-5-yl)-3-[2-(2'-oxospiro[furo[2,3-f][1,3]benzodioxole-7,3'-indol]-1'(2'H)-yl)ethyl]urea | 483 |
| 806 | 1-(3-acetylphenyl)-3-[2-(2'-oxospiro[furo[2,3-f][1,3]benzodioxole-7,3'-indol]-1'(2'H)-yl)ethyl]urea | 484 |
| 807 | 1-(4-acetylphenyl)-3-[2-(2'-oxospiro[furo[2,3-f][1,3]benzodioxole-7,3'-indol]-1'(2'H)-yl)ethyl]urea | 486 |
| 808 | 1-(4-isopropylphenyl)-3-[2-(2'-oxospiro[furo[2,3-f][1,3]benzodioxole-7,3'-indol]-1'(2'H)-yl)ethyl]urea | 486 |
| 809 | 1-(2-methoxybenzyl)-3-[2-(2'-oxospiro[furo[2,3-f][1,3]benzodioxole-7,3'-indol]-1'(2'H)-yl)ethyl]urea | 486 |
| 810 | 1-(4-methoxybenzyl)-3-[2-(2'-oxospiro[furo[2,3-f][1,3]benzodioxole-7,3'-indol]-1'(2'H)-yl)ethyl]urea | 488 |
| 811 | 1-(4-methoxy-2-methylphenyl)-3-[2-(2'-oxospiro[furo[2,3-f][1,3]benzodioxole-7,3'-indol]-1'(2'H)-yl)ethyl]urea | 4882 |
| 812 | 1-(4-chloro-2-methylphenyl)-3-[2-(2'-oxospiro[furo[2,3-f][1,3]benzodioxole-7,3'-indol]-1'(2'H)-yl)ethyl]urea | 488 |
| 813 | 1-(3-chloro-4-methylphenyl)-3-[2-(2'-oxospiro[furo[2,3-f][1,3]benzodioxole-7,3'-indol]-1'(2'H)-yl)ethyl]urea | 493 |
| 814 | 1-(3-chloro-2-methylphenyl)-3-[2-(2'-oxospiro[furo[2,3-f][1,3]benzodioxole-7,3'-indol]-1'(2'H)-yl)ethyl]urea | 493 |
| 815 | 1-(5-chloro-2-methylphenyl)-3-[2-(2'-oxospiro[furo[2,3-f][1,3]benzodioxole-7,3'-indol]-1'(2'H)-yl)ethyl]urea | 493 |
| 816 | 1-(2-chlorobenzyl)-3-[2-(2'-oxospiro[furo[2,3-f][1,3]benzodioxole-7,3'-indol]-1'(2'H)-yl)ethyl]urea | 493 |

| Compound Number | Name | MS (m/z, M + 1) |
|---|---|---|
| 817 | 1-(1-naphthyl)-3-[2-(2'-oxospiro[furo[2,3-f][1,3]benzodioxole-7,3'-indol]-1'(2'H)-yl)ethyl]urea | 493 |
| 818 | 1-(2-naphthyl)-3-[2-(2'-oxospiro[furo[2,3-f][1,3]benzodioxole-7,3'-indol]-1'(2'H)-yl)ethyl]urea | 494 |
| 819 | 1-(3-chloro-2-fluorophenyl)-3-[2-(2'-oxospiro[furo[2,3-f][1,3]benzodioxole-7,3'-indol]-1'(2'H)-yl)ethyl]urea | 494 |
| 820 | 1-[2-(2'-oxospiro[furo[2,3-f][1,3]benzodioxole-7,3'-indol]-1'(2'H)-yl)ethyl]-3-(5,6,7,8-tetrahydronaphthalen-1-yl)urea | 497 |
| 821 | 1-(4-tert-butylphenyl)-3-[2-(2'-oxospiro[furo[2,3-f][1,3]benzodioxole-7,3'-indol]-1'(2'H)-yl)ethyl]urea | 498 |
| 822 | 1-(4-butylphenyl)-3-[2-(2'-oxospiro[furo[2,3-f][1,3]benzodioxole-7,3'-indol]-1'(2'H)-yl)ethyl]urea | 500 |
| 823 | 1-[2-(4-ethylphenyl)ethyl]-3-[2-(2'-oxospiro[furo[2,3-f][1,3]benzodioxole-7,3'-indol]-1'(2'H)-yl)ethyl]urea | 500 |
| 824 | 1-(2,3-dihydro-1,4-benzodioxin-6-yl)-3-[2-(2'-oxospiro[furo[2,3-f][1,3]benzodioxole-7,3'-indol]-1'(2'H)-yl)ethyl]urea | 500 |
| 825 | methyl 4-[({[2-(2'-oxospiro[furo[2,3-f][1,3]benzodioxole-7,3'-indol]-1'(2'H)-yl)ethyl]amino}carbonyl)amino]benzoate | 502 |
| 826 | 1-(2-ethoxybenzyl)-3-[2-(2'-oxospiro[furo[2,3-f][1,3]benzodioxole-7,3'-indol]-1'(2'H)-yl)ethyl]urea | 502 |
| 827 | 1-(3,4-dimethoxyphenyl)-3-[2-(2'-oxospiro[furo[2,3-f][1,3]benzodioxole-7,3'-indol]-1'(2'H)-yl)ethyl]urea | 502 |
| 828 | 1-(3,5-dimethoxyphenyl)-3-[2-(2'-oxospiro[furo[2,3-f][1,3]benzodioxole-7,3'-indol]-1'(2'H)-yl)ethyl]urea | 504 |
| 829 | 1-(3-chloro-4-methoxyphenyl)-3-[2-(2'-oxospiro[furo[2,3-f][1,3]benzodioxole-7,3'-indol]-1'(2'H)-yl)ethyl]urea | 504 |
| 830 | 1-[4-(difluoromethoxy)phenyl]-3-[2-(2'-oxospiro[furo[2,3-f][1,3]benzodioxole-7,3'-indol]-1'(2'H)-yl)ethyl]urea | 509 |
| 831 | 1-[2-(difluoromethoxy)phenyl]-3-[2-(2'-oxospiro[furo[2,3-f][1,3]benzodioxole-7,3'-indol]-1'(2'H)-yl)ethyl]urea | 510 |
| 832 | 1-[2-(2'-oxospiro[furo[2,3-f][1,3]benzodioxole-7,3'-indol]-1'(2'H)-yl)ethyl]-3-[3-(trifluoromethyl)phenyl]urea | 510 |
| 833 | 1-[2-(2'-oxospiro[furo[2,3-f][1,3]benzodioxole-7,3'-indol]-1'(2'H)-yl)ethyl]-3-[2-(trifluoromethyl)phenyl]urea | 512 |
| 834 | 1-[2-(2'-oxospiro[furo[2,3-f][1,3]benzodioxole-7,3'-indol]-1'(2'H)-yl)ethyl]-3-[4-(trifluoromethyl)phenyl]urea | 512 |
| 835 | 1-(3,4-dichlorophenyl)-3-[2-(2'-oxospiro[furo[2,3-f][1,3]benzodioxole-7,3'-indol]-1'(2'H)-yl)ethyl]urea | 512 |
| 836 | 1-(2,3-dichlorophenyl)-3-[2-(2'-oxospiro[furo[2,3-f][1,3]benzodioxole-7,3'-indol]-1'(2'H)-yl)ethyl]urea | 513 |
| 837 | 1-(3,5-dichlorophenyl)-3-[2-(2'-oxospiro[furo[2,3-f][1,3]benzodioxole-7,3'-indol]-1'(2'H)-yl)ethyl]urea | 513 |
| 838 | ethyl 4-[({[2-(2'-oxospiro[furo[2,3-f][1,3]benzodioxole-7,3'-indol]-1'(2'H)-yl)ethyl]amino}carbonyl)amino]benzoate | 513 |
| 839 | ethyl 2-[({[2-(2'-oxospiro[furo[2,3-f][1,3]benzodioxole-7,3'-indol]-1'(2'H)-yl)ethyl]amino}carbonyl)amino]benzoate | 516 |
| 840 | 1-[2-(1,3-benzodioxol-5-yl)ethyl]-3-[2-(2'-oxospiro[furo[2,3-f][1,3]benzodioxole-7,3'-indol]-1'(2'H)-yl)ethyl]urea | 516 |
| 841 | methyl 2-methyl-3-[({[2-(2'-oxospiro[furo[2,3-f][1,3]benzodioxole-7,3'-indol]-1'(2'H)-yl)ethyl]amino}carbonyl)amino]benzoate | 516 |
| 842 | 1-(4-butoxyphenyl)-3-[2-(2'-oxospiro[furo[2,3-f][1,3]benzodioxole-7,3'-indol]-1'(2'H)-yl)ethyl]urea | 516 |
| 843 | 1-(2-methoxy-4-nitrophenyl)-3-[2-(2'-oxospiro[furo[2,3-f][1,3]benzodioxole-7,3'-indol]-1'(2'H)-yl)ethyl]urea | 516 |
| 844 | 1-biphenyl-2-yl-3-[2-(2'-oxospiro[furo[2,3-f][1,3]benzodioxole-7,3'-indol]-1'(2'H)-yl)ethyl]urea | 519 |
| 845 | 1-[4-methyl-3-(trifluoromethyl)phenyl]-3-[2-(2'-oxospiro[furo[2,3-f][1,3]benzodioxole-7,3'-indol]-1'(2'H)-yl)ethyl]urea | 520 |
| 846 | 1-(2,4-dichlorobenzyl)-3-[2-(2'-oxospiro[furo[2,3-f][1,3]benzodioxole-7,3'-indol]-1'(2'H)-yl)ethyl]urea | 526 |
| 847 | 1-[2-(2'-oxospiro[furo[2,3-f][1,3]benzodioxole-7,3'-indol]-1'(2'H)-yl)ethyl]-3-[2-(trifluoromethoxy)phenyl]urea | 527 |

| Compound Number | Name | MS (m/z, M + 1) |
|---|---|---|
| 848 | 1-[4-fluoro-2-(trifluoromethyl)phenyl]-3-[2-(2'-oxospiro[furo[2,3-f][1,3]benzodioxole-7,3'-indol]-1'(2'H)-yl)ethyl]urea | 528 |
| 849 | 1-(5-tert-butyl-2-methoxyphenyl)-3-[2-(2'-oxospiro[furo[2,3-f][1,3]benzodioxole-7,3'-indol]-1'(2'H)-yl)ethyl]urea | 530 |
| 850 | 1-[2-(3,5-dimethoxyphenyl)ethyl]-3-[2-(2'-oxospiro[furo[2,3-f][1,3]benzodioxole-7,3'-indol]-1'(2'H)-yl)ethyl]urea | 530 |
| 851 | 1-(9H-fluoren-2-yl)-3-[2-(2'-oxospiro[furo[2,3-f][1,3]benzodioxole-7,3'-indol]-1'(2'H)-yl)ethyl]urea | 532 |
| 852 | 1-(9H-fluoren-9-yl)-3-[2-(2'-oxospiro[furo[2,3-f][1,3]benzodioxole-7,3'-indol]-1'(2'H)-yl)ethyl]urea | 532 |
| 853 | 1-[2-(2'-oxospiro[furo[2,3-f][1,3]benzodioxole-7,3'-indol]-1'(2'H)-yl)ethyl]-3-(3,4,5-trimethoxyphenyl)urea | 532 |
| 854 | 1-(diphenylmethyl)-3-[2-(2'-oxospiro[furo[2,3-f][1,3]benzodioxole-7,3'-indol]-1'(2'H)-yl)ethyl]urea | 534 |
| 855 | 1-[2-(2'-oxospiro[furo[2,3-f][1,3]benzodioxole-7,3'-indol]-1'(2'H)-yl)ethyl]-3-(2-phenoxyphenyl)urea | 534 |
| 856 | 1-(2-biphenyl-4-ylethyl)-3-[2-(2'-oxospiro[furo[2,3-f][1,3]benzodioxole-7,3'-indol]-1'(2'H)-yl)ethyl]urea | 536 |
| 857 | 1-[2-(2'-oxospiro[furo[2,3-f][1,3]benzodioxole-7,3'-indol]-1'(2'H)-yl)ethyl]-3-(3,4,5-trimethoxybenzyl)urea | 548 |
| 858 | 1-(2-nitrophenyl)-3-[2-(2'-oxospiro[furo[2,3-f][1,3]benzodioxole-7,3'-indol]-1'(2'H)-yl)ethyl]urea | 548 |
| 859 | 1-(1,3-benzodioxol-5-yl)-3-[2-(2'-oxospiro[furo[2,3-f][1,3]benzodioxole-7,3'-indol]-1'(2'H)-yl)ethyl]urea | 489 |
| 860 | 1-[4-(dimethylamino)phenyl]-3-[2-(2'-oxospiro[furo[2,3-f][1,3]benzodioxole-7,3'-indol]-1'(2'H)-yl)ethyl]urea | 488 |
| 861 | 1-(2-fluorobenzyl)-3-[2-(2'-oxospiro[furo[2,3-f][1,3]benzodioxole-7,3'-indol]-1'(2'H)-yl)ethyl]urea | 487 |
| 862 | 1-(4-fluoro-3-methylphenyl)-3-[2-(2'-oxospiro[furo[2,3-f][1,3]benzodioxole-7,3'-indol]-1'(2'H)-yl)ethyl]urea | 476 |
| 863 | 1-(3-fluorobenzyl)-3-[2-(2'-oxospiro[furo[2,3-f][1,3]benzodioxole-7,3'-indol]-1'(2'H)-yl)ethyl]urea | 476 |
| 864 | 1-(cyclohexylmethyl)-3-[2-(2'-oxospiro[furo[2,3-f][1,3]benzodioxole-7,3'-indol]-1'(2'H)-yl)ethyl]urea | 476 |
| 865 | 1-(2-methylphenyl)-3-[2-(2'-oxospiro[furo[2,3-f][1,3]benzodioxole-7,3'-indol]-1'(2'H)-yl)ethyl]urea | 464 |
| 866 | 1-[4-(6-methyl-1,3-benzothiazol-2-yl)phenyl]-3-[2-(2'-oxospiro[furo[2,3-f][1,3]benzodioxole-7,3'-indol]-1'(2'H)-yl)ethyl]urea | 458 |

Example 20

Synthesis of 1'-pentyl-7H-spiro[furo[3,4-f][1,3]benzodioxole-5,3'-indol]-2'(1'H)-one Following the procedure as described in EXAMPLE 1, and making non-critical variations using 3-hydroxy-3-[6-(hydroxymethyl)-1,3-benzodioxol-5-yl]-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (45%) as a colorless solid: mp 113-115° C.; $^1$H NMR (300 MHz, CDCl$_3$) δ 7.24-7.33 (m, 1H), 7.12 (dd, 1H), 7.01 (t, 1H), 6.87 (d, 1H), 6.74 (s, 1H), 6.15 (s, 1H), 5.92 (dd, 2H), 5.48 (d, 1H), 5.27 (d, 1H), 3.76-3.56 (m, 2H), 1.71-1.64- (m, 2H), 1.37-1.27- (m, 4H), 0.89-0.84 (m, 3H); $^{13}$C NMR (75 MHz, CDCl$_3$) δ 175.9, 148.7, 148.1, 143.6, 133.7, 132.1, 130.3, 129.8, 125.3, 125.0, 123.1, 113.5, 109.1, 108.7, 101.9, 101.7, 88.7, 74.4, 40.0, 29.7, 29.0, 25.3, 13.3; MS (ES+) m/z 352.1 (M+1).

Example 21

Synthesis of 1'-pentylspiro[indeno[5,6-d][1,3]dioxole-5,3'-indole]-2',7(1'H,6H)-dione To a solution of [3-(1,3-benzodioxol-5-yl)-2-oxo-1-pentyl-2,3-dihydro-1H-indol-3-yl]acetic acid (0.28 g, 0.73 mmol) was added one drop of DMF and oxalyl chloride (0.32 mL, 3.7 mmol) in toluene (10 mL). The mixture was stirred at ambient temperature overnight and concentrated under vacuum to dryness to afford a brown oil. This substance was dissovled in dichloromethane (15.0 mL) followed by the addition of tin (IV) chloride (0.07 mL, 0.57 mmol) at 0° C. The mixture was stirred at ambient temperature overnight and quenched with ice water. The mixture was poured into water (100 mL), and the mixture was extracted with dichloromethane (150 mL). The organic layer was washed with water, dried over sodium sulfate and filtered. The filtrate was concentrated in vacuo to dryness. The residue was subjected to flash column chromatography to afford the title compound (0.09 g, 67%) as a white solid: $^1$H NMR (300 MHz, CDCl$_3$)

δ 7.31 (td, 1H), 7.14 (s, 1H), 7.02 (td, 1H), 6.97-6.92 (m, 2H), 6.22 (s, 1H), 6.03-5.98 (m, 2H), 3.87-3.63 (m, 2H), 3.17 (d, 1H), 2.85 (d, 1H), 1.79-1.66 (m, 2H), 1.41-1.30 (m, 4H), 0.88 (t, 3H); $^{13}$C NMR (75 MHz, CDCl$_3$) δ 201.4, 177.5, 154.8, 151.8, 149.6, 143.1, 132.5, 131.6, 128.9, 123.4, 123.2, 108.9, 103.5, 102.6, 102.5, 53.8, 47.7, 40.5, 29.0, 27.1, 22.3, 14.0; MS (ES+), m/z 386.1 (M+23), 364.1 (M+1).

Example 22

Synthesis of 1-pentyl-6'H-spiro[indole-3,5'-naphtho[2,3-d][1,3]dioxole]-2,8'(1'H,7'H)-dione Following the procedure as described in EXAMPLE 21, and making non-critical variations using 3-[3-(1,3-benzodioxol-5-yl)-2-oxo-1-pentyl-2,3-dihydro-1H-indol-3-yl]propanoic acid to replace [3-(1,3-benzodioxol-5-yl)-2-oxo-1-pentyl-2,3-dihydro-1H-indol-3-yl]acetic acid, the title compound was obtained (32%) as a white solid: $^{1}$H NMR (300 MHz, CDCl$_3$) δ 7.57 (s, 1H), 7.37-7.28 (m, 1H), 7.08-7.03 (m, 2H), 6.95 (d, 1H), 6.02 (s, 1H), 5.95-5.91 (m, 2H), 3.73 (t, 2H), 3.37-3.24 (m, 1H), 2.79-2.67 (m, 1H), 2.41-2.32 (m, 2H), 1.76-1.64 (m, 2H), 1.38-1.28 (m, 4H), 0.87 (t, 3H); $^{13}$C NMR (75 MHz, CDCl$_3$) δ 195.4, 177.4, 152.3, 148.0, 142.7, 138.9, 133.6, 128.8, 128.4, 124.1, 122.9, 108.9, 106.9, 106.6, 101.9, 51.7, 40.2, 33.1, 32.8, 29.0, 27.1, 22.3, 14.0; MS (ES+) m/z 400.1 (M+23), 378.1 (M+1).

Example 23

Synthesis of 1'-pentyl-6,7-dihydrospiro[indeno[5,6-d][1,3]dioxole-5,3'-indol]-2'(1'H)-one A mixture of 1'-pentylspiro[indeno[5,6-d][1,3]dioxole-5,3'-indole]-2',7(1'H,6H)-dione (0.04 g, 0.11 mmol), triethylsilane (1.50 mL) and trifluoroacetic acid (2.00 mL, excess) was stirred at ambient temperature overnight. The mixture was concentrated in vacuo to dryness. The residue was subjected to flash column chromatography to afford the title compound (0.02 g, 47%) as an oil: $^{1}$H NMR (300 MHz, CDCl$_3$) δ 7.25 (td, 1H), 7.06-6.95 (m, 2H), 6.88 (d, 1H), 6.77 (s, 1H), 6.05 (s, 1H), 5.88-5.82 (m, 2H), 3.81-3.60 (m, 2H), 3.37-3.24 (m, 1H), 3.13-3.01 (m, 1H), 2.70-2.59 (m, 1H), 2.44-2.32 (m, 1H), 1.76-1.64 (m, 2H), 1.39-1.28 (m, 4H), 0.88 (t, 3H); $^{13}$C NMR (75 MHz, CDCl$_3$) δ 179.5, 147.9, 147.0, 142.9, 138.2, 136.7, 134.7, 128.1, 123.5, 122.6, 108.3, 105.3, 103.6, 101.2, 59.9, 40.0, 38.3, 31.6, 29.0, 27.1, 22.6, 14.0; MS (ES+) m/z 372.1 (M+23), 350.1 (M+1).

Example 24

Synthesis of 1-pentyl-7',8'-dihydro-6'H-spiro[indole-3,5'-naphtho[2,3-d][1,3]dioxol]-2(1H)-one Following the procedure as described in EXAMPLE 23, and making non-critical variations using 1-pentyl-6'H-spiro[indole-3,5'-naphtho[2,3-d][1,3]dioxole]-2,8'(1'H,7'H)-dione to replace 1'-pentylspiro[indeno[5,6-d][1,3]dioxole-5,3'-indole]-2',7(1'H,6H)-dione, the title compound was obtained (69%) as an oil: $^{1}$H NMR (300 MHz, CDCl$_3$) δ 7.25 (td, 1H), 7.08-6.94 (m, 2H), 6.90 (d, 1H), 6.60 (s, 1H), 5.89 (s, 1H), 5.81-5.76 (m, 2H), 3.81-3.66 (m, 2H), 2.96-2.77 (m, 2H), 2.38-2.24 (m, 1H), 2.17-2.06 (m, 1H), 2.02-1.83 (m, 2H), 1.78-1.65 (m, 2H), 1.42-1.29 (m, 4H), 0.89 (t, 3H); $^{13}$C NMR (75 MHz, CDCl$_3$) δ 180.3, 146.7, 146.1, 142.4, 137.3, 131.6, 127.8, 127.8, 124.1, 122.5, 109.0, 108.3, 107.3, 100.7, 52.0, 40.0, 34.0, 29.4, 29.1, 27.1, 22.4, 18.8, 14.0; MS (ES+) m/z 364.1 (M+1).

Example 25

Synthesis of 8',8'-difluoro-1-pentyl-7',8'-dihydro-6'H-spiro[indole-3,5'-naphtho[2,3-d][1,3]dioxol]-2(1H)-one A mixture of 1-pentyl-6'H-spiro[indole-3,5'-naphtho[2,3-d][1,3]dioxole]-2,8'(1'H,7'H)-dione (0.02 g, 0.05 mmol), bis(2-methoxyethyl)aminosulfur trifluoride (0.50 mL) and one drop of ethanol was stirred at 85° C. for 72 hours in a Teflon bottle and quenched by slowly addition of water. The mixture was poured into water (100 mL) and extracted with ethyl acetate (100 mL). The organic layer was washed with water, dried over sodium sulfate and filtered. The filtrate was concentrated in vacuo to dryness. The residue was subjected to flash column chromatography to afford the title compound (0.01 g, 47%) as an oil: $^{1}$H NMR (300 MHz, CDCl$_3$) δ 7.57 (s, 1H), 7.38-7.28 (m, 1H), 7.09-7.01 (m, 2H), 6.95 (d, 1H), 6.03 (s, 1H), 5.96-5.90 (m, 2H), 3.73 (t, 2H), 3.38-3.24 (m, 1H), 2.79-2.67 (m, 1H), 2.41-2.32 (m, 2H), 1.77-1.63 (m, 2H), 1.39-1.28 (m, 4H), 0.90 (t, 3H); $^{13}$C NMR (75 MHz, CDCl$_3$) δ 195.4, 177.4, 152.3, 148.0, 142.7, 138.9, 133.6, 128.8, 128.4, 124.1, 122.9, 108.9, 106.9, 106.6, 101.9, 51.7, 40.2, 33.1, 32.8, 29.0, 27.1, 22.3, 14.0; MS (ES+) m/z 422.2 (M+23), 380.2 (M+1).

To a solution of 1-pentyl-6'H-spiro[indole-3,5'-naphtho[2,3-d][1,3]dioxole]-2,8'(1'H,7'H)-dione (0.20 g, 0.55 mmol) in methanol (10.0 mL) was added sodium borohydride (0.03 g, 0.83 mmol). The reaction mixture was stirred at ambient temperature for 2 h and poured into of water (100 mL) and extracted with ethyl acetate (100 mL). The organic layer was washed with water, dried over sodium sulfate and filtered. The filtrate was concentrated in vacuo to dryness. The residue was subjected to flash column chromatography to afford the title compound (0.18 g, 90%) as an oil: $^{1}$H NMR (300 MHz, CDCl$_3$) δ 7.36-7.29 (m, 1H), 7.11-6.99 (m, 3H), 6.93 (d, 1H), 5.98 (s, 1H), 5.94-5.87 (m, 2H), 5.16 (d, 1H), 3.80-3.61 (m, 2H), 2.69 (br, 1H), 2.39 (d, 1H), 1.75-1.62 (m, 2H), 1.38-1.22 (m, 4H), 0.87 (t, 3H); $^{13}$C NMR (75 MHz, CDCl$_3$) δ 180.5, 148.9, 148.5, 143.7, 140.5, 136.9, 132.1, 128.7, 123.7, 123.3, 108.8, 105.7, 103.2, 101.5, 74.8, 59.6, 40.4, 28.9, 27.0, 22.3, 14.0; MS (ES+) m/z 388.4 (M+23).

Example 27

Synthesis of 7-methoxy-1'-pentyl-6,7-dihydrospiro[indeno[5,6-d][1,3]dioxole-5,3'-indol]-2'(1'H)-one To a solution of 7-hydroxy-1'-pentyl-6,7-dihydrospiro[indeno[5,6-d][1,3]dioxole-5,3'-indol]-2'(1'H)-one (0.05 g, 0.14 mmol) in THF (10.0 mL) was added sodium hydride (0.01 mg, 0.21 mmol) at 0° C. The reaction mixture was stirred for half an hour followed by the addition of iodomethane (0.50 mL). The mixture was stirred at ambient temperature for two hours, then poured into water (100 mL), and extracted with ethyl acetate (100 mL). The organic layer was washed with water, dried over sodium sulfate and filtered. The filtrate was concentrated in vacuo to dryness. The residue was subjected to flash column chromatography to afford the title compound (0.03 g, 57%) as an oil: $^{1}$H NMR (300 MHz, CDCl$_3$) δ 7.26-7.18 (m, 1H), 6.98-6.82 (m, 4H), 6.10 (s, 1H), 5.88 (s, 2H), 5.26 t, 1H), 3.88-3.63 (m, 2H), 3.45 (s, 3H), 2.71-2.54 (m, 2H), 1.80-1.65 (m, 2H), 1.45-1.29 (m, 4H), 0.90 (t, 3H);

$^{13}$C NMR (75 MHz, CDCl$_3$) δ 178.3, 148.9, 148.4, 142.4, 136.8, 136.6, 135.1, 128.1, 123.1, 122.6, 108.5, 105.0, 103.2, 101.5, 82.7, 57.9, 55.6, 43.4, 40.3, 29.1, 27.2, 22.4, 14.0: MS (ES+) m/z 402.4 (M+23).

Example 28

Synthesis of 1'-pentyl-6,7-dihydro-5H-spiro[1,3-dioxolo[4,5-d]isoquinoline-8,3'-indole]-2',5(1'H)-dione A mixture of 1'-pentylspiro[indeno[5,6-d][1,3]dioxole-5,3'-indole]-2',7(1'H,6H)-dione (0.10 g, 0.28 mmol), sodium azide (0.09 g, 1.40 mmol) and trifluoroacetic acid (2.00 mL) was stirred at 50° C. overnight. The mixture was poured into water (100 mL) and extracted with ethyl acetate (100 mL). The organic layer was washed with water, dried over sodium sulfate and filtered. The filtrate was concentrated in vacuo to dryness. The residue was subjected to flash column chromatography to afford the title compound (0.08 g, 74%) as a white solid: $^1$H NMR (300 MHz, CDCl$_3$) δ 7.60 (s, 1H), 7.30 (td, 1H), 7.20 (dd, 1H), 6.98 (td, 1H), 6.93 (d, 1H), 6.32 (br, 1H), 6.21 (s, 1H), 5.97-5.92 (m, 2H), 4.02 (dd, 1H), 3.87-3.70 (m, 2H), 3.47 (dd, 1H), 1.80-1.66 (m, 2H), 1.42-4.30 (m, 4H), 0.90 (t, 3H); $^{13}$C NMR (75 MHz, CDCl$_3$) δ 175.8, 165.2, 151.6, 147.9, 141.7, 134.3, 130.9, 129.0, 124.5, 123.2, 122.9, 109.0, 108.5, 105.4, 101.9, 51.9, 48.2, 40.4, 29.1, 27.1, 22.3, 14.0; MS (ES+) m/z 379.3 (M+1).

Example 29

Synthesis of 2'-oxo-1'-pentyl-N-pyridin-2-yl-1',2'-dihydrospiro[furo[2,3-f][1,3]benzodioxole-7,3'-indole]-4'-carboxamide A mixture of 4'-bromo-1'-pentylspiro[furo[2,3-f][1,3]benzodioxole-7,3'-indol]-2'(1'H)-one (0.28 g, 0.65 mmol), tetrakis(triphenylphosphine)palladium(0) (0.08 g, 10 mole %), triethylamine (0.33 g, 0.50 mL, 3.25 mmol) and 2-aminopyridine (0.12 g, 1.30 mmol) in N,N-dimethylformamide (5.00 mL) was subjected to carbon monoxide (40 Psi). The reaction mixture was heated at 80° C. for 16 h. After cooling down to ambient temperature, the reaction mixture was diluted with ethyl acetate (20.0 mL), washed with water (3×20.0 mL), brine (2×20.0 mL), dried over anhydrous sodium sulfate and filtered. The filtrate was concentrated in vacuo to dryness. The residue was subjected to column chromatography to give the title compound (0.04 g, 14%) as a solid: $^1$H NMR (300 MHz, CDCl$_3$) δ 8.52 (d, 1H), 7.87 (br, 1H), 7.69-7.62 (m, 3H), 7.53-7.51 (m, 1H), 7.47-7.38 (m, 3H), 7.04-6.98 (m, 1H), 5.79 (d, 2H), 4.97 (ABq, 2H), 3.84-3.66 (m, 2H), 1.77-1.67 (m, 2H), 1.38-1.33 (m, 4H), 0.90 (t, 3H); $^{13}$C NMR (75 MHz, CDCl$_3$) δ 177.5, 158.2, 156.7, 149.2, 143.5, 142.1, 132.2, 132.0, 131.9, 131.8, 129.6, 128.6, 128.4, 121.8, 118.2, 110.7, 102.0, 101.4, 93.9, 79.5, 77.2, 58.5, 40.6, 29.0, 27.0, 22.3, 14.0; MS (ES+) m/z 473.2 (M+2).

Example 29.1

Synthesis of N-(3-methoxyphenyl)-2'-oxo-1'-pentyl-1',2'-dihydrospiro[furo[2,3-f][1,3]benzodioxole-7,3'-indole]-4'-carboxamide Following the procedure described in EXAMPLE 29, and making non-critical variations using 3-methoxyaniline to replace 2-aminopyridine, the title compound was obtained (20%) as a colorless solid: mp 173-175° C.; $^1$H NMR (300 MHz, CDCl$_3$) δ 7.42 (t, 1H), 7.30-7.27 (m, 1H), 7.14 (t, 1H), 7.04-6.97 (m, 2H), 7.23 (s, 1H), 6.74-6.62 (m, 2H), 6.31 (s, 1H), 6.16 (s, 1H), 5.83 (dd, 2H), 4.87-5.01 (m, 2H), 3.91-3.63 (m, 5H), 1.73-1.78 (m, 2H), 1.37-1.32 (m, 4H), 0.93-0.86 (m, 3H); $^{13}$C NMR (75 MHz, CDCl$_3$) δ 177.8, 165.1, 159.9, 149.3, 143.6, 143.5, 142.1, 138.1, 134.5, 129.7, 129.5, 127.9, 122.4, 118.3, 112.2, 110.7, 110.5, 105.6, 101.9, 101.6, 94.3, 79.2, 58.3, 55.3, 40.5, 28.9, 26.9, 22.3, 13.9; MS (ES+) m/z 501.5 (M+1).

Example 30

Synthesis of 2'-oxo-1'-pentyl-1',2'-dihydrospiro[furo[2,3-f][1,3]benzodioxole-7,3'-indole]-4'-carbonitrile A mixture of 4'-bromo-1-pentylspiro[furo[2,3-f][1,3]benzodioxole-7,3'-indol]-2'(1'H)-one (0.10 g, 0.23 mmol), tris(dibenzylideneacetone)dipalladium(0) (0.21 g, 0.23 mmol) and 2-(di-tert-butylphosphino)biphenyl (0.07, 0.23 mmol), tributyltin cyanide (0.07 g, 0.23 mmol) and potassium cyanide (0.02 g, 0.23 mmol) was purged with nitrogen and anhydrous acetonitrile (10.0 mL) was added. The reaction mixture was refluxed for 16 h. After cooling down to ambient temperature, the reaction mixture was diluted with ethyl acetate (20.0 mL), washed with water (20.0 mL), brine (20.0 mL), dried over anhydrous sodium sulfate and filtered. The filtrate was concentrated in vacuo to dryness. The brown residue was subjected to column chromatography eluting with ethyl acetate/hexane (65%) to give the title compound (0.03 g, 33%) which was recrystallized from ether to get a colorless solid: mp 128-129° C.; $^1$H NMR (300 MHz, CDCl$_3$) δ 9.10 (s, 1H), 7.42-7.37 (m, 1H), 7.29-7.27 (m, 1H), 7.09 (d, 1H), 6.53 (s, 1H), 6.03 (s, 1H), 5.87 (dd, 2H), 4.91 (q, 2H), 3.86-3.63 (m, 2H), 1.74-1.62 (m, 2H), 1.43-1.26 (m, 4H), 0.89 (t, 3H); $^{13}$C NMR (75 MHz, CDCl$_3$) δ 176.5, 157.1, 149.5, 143.5, 142.4, 135.4, 129.7, 128.3, 126.4, 116.3, 114.8, 112.3, 108.8, 102.2, 93.7, 78.7, 58.3, 40.6, 28.9, 26.7, 22.2, 13.9; MS (ES+) m/z 377.5 (M+1).

Example 31

Synthesis of 1'-hexylspiro[1,3-dioxolo[4,5-g]chromene-8,3'-indole]-2',6(1'H,7H)-dione To a solution of 2-(1-hexyl-3-(6-hydroxybenzo[d][1,3]dioxol-5-yl)-2-oxoindolin-3-yl)acetate (0.19 g, 0.43 mmol) in THF:H$_2$O (2:1) was added lithium hydroxide (0.04 g, 0.86 mmol). The mixture was stirred at ambient temperature for 4 hrs. The organic solvent was removed in vacuo and the pH of the aqueous residue was adjusted to 2 followed by extraction with ethyl acetate. The organic layer was dried over anhydrous sodium sulfate and filtered. The filtrate was concentrated in vacuo to dryness and the residue was subjected to column chromatography eluting with 25% ethyl acetate/hexane to yield the title compound (0.09 g, 53%) as a white solid: $^1$H NMR (300 MHz, CDCl$_3$) δ 7.33 (dt, 1H), 7.14-7.03 (m, 2H), 6.93 (d, 1H), 6.66 (s, 1H), 6.06 (s, 1H), 5.88 (dd, 2H), 3.76-3.63 (m, 2H), 2.94 (q, 2H), 1.69-1.62 (m, 2H) 1.34-1.22 (m, 6H), 0.83 (t, 3H); $^{13}$C NMR (75 MHz, CDCl$_3$) δ 175.9, 165.8, 148.3, 147.2, 144.6, 142.6, 129.9, 129.6, 123.8, 123.4, 114.7, 109.2, 105.1, 101.9, 99.8, 49.6, 40.3, 37.2, 31.2, 27.2, 26.4, 22.4, 13.9; MS (ES+) m/z 394.5 (M+1).

Example 32

Synthesis of 1'-pentylspiro[1-benzofuran-3,3'-indol]-2'(1'H)-one

A mixture of 6-bromo-1'-pentylspiro[1-benzofuran-3,3'-indol]-2'(1'H)-one (0.10 g, 0.27 mmol) and palladium/carbon (0.09 g, 0.01 mmol) in methanol/ethyl acetate (1/1, 4.00 mL) was stirred under hydrogen at atmospheric pressure for 16 h. The solvent was evaporated and the black residue was subjected to column chromatography (ethyl acetate/hexane, 1/6) to give the title compound (0.08 g, 97%) as a white solid: $^1$H NMR (300 MHz, CDCl$_3$) δ 7.30 (dd, 1H), 7.18 (dd, 1H), 7.20 (d, 1H), 7.02 (dd, 1H), 6.96-6.90 (m, 2H), 6.79 (dd, 1H), 6.69 (d, 1H), 4.93 (d, 1H), 4.67 (d, 1H), 3.89-3.64 (m, 2H), 1.81-1.66 (m, 2H), 1.44-1.31 (m, 4H), 0.92 (t, 3H); $^{13}$C NMR (75 MHz, CDCl$_3$) δ 177.2, 160.7, 142.5, 132.8, 129.7, 129.0, 128.8, 123.9, 123.3, 123.1, 121.3, 110.4, 108.6, 58.1, 40.4, 29.0, 27.2, 22.3, 14.0; MS (ES+) m/z 308.5 (M+1).

Example 33

Synthesis of 6-anilino-1'-pentylspiro[1-benzofuran-3,3'-indol]-2'(1'H)-one

To a solution of 6-bromo-1'-pentylspiro[1-benzofuran-3,3'-indol]-2'(1'H)-one (0.08 g, 0.19 mmol) in anhydrous toluene (4.00 mL) was added aniline (0.03 g, 0.29 mmol), xanthphos (0.02 g, 0.03 mmol) and tris(dibenzylideneacetone) dipalladium(0) (0.02 g, 0.02 mmol). The reaction mixture was refluxed for 16 h, cooled down to ambient temperature and concentrated in vacuo to dryness. The black residue was subjected to column chromatography (ethyl acetate/hexane, 1/7) to give the title compound (0.05 g, 62%) as a yellow oil: $^1$H NMR (300 MHz, CDCl$_3$) δ 7.40-7.25 (m, 6H), 7.18 (d, 1H), 7.12-7.05 (m, 3H), 6.98-6.90 (m, 2H), 6.71 (d, 1H), 6.57 (d, 1H), 6.48 (dd, 1H), 4.93 (d, 1H), 4.67 (d, 1H), 3.88-3.64 (m, 2H), 1.80-1.65 (m, 2H), 1.45-1.30 (m, 4H), 0.92 (t, 3H); MS (ES+) m/z 399.5 (M+1).

Example 34

Synthesis of 6-morpholin-4-yl-1'-pentylspiro[1-benzofuran-3,3'-indol]-2'(1'H)-one (1:1)

Following the procedure as described in EXAMPLE 33, and making non-critical variations using morphine to replace aniline, the title compound was obtained (42%) as a brown oil: $^1$H NMR (300 MHz, CDCl$_3$) δ 7.32 (d, 1H), 7.15 (d, 1H), 7.05 (dd, 1H), 6.91 (d, 1H), 6.59 (d, 1H), 6.50 (d, 1H), 6.35 (dd, 1H), 4.95 (d, 1H), 4.65 (d, 1H), 3.89-3.60 (m, 6H), 3.15-3.05 (m, 4H), 1.80-1.68 (m, 2H), 1.43-1.34 (m, 4H), 0.92 (t, 3H); $^{13}$C NMR (75 MHz, CDCl$_3$) δ 177.5, 162.2, 153.4, 142.6, 132.9, 128.7, 123.9, 123.4, 123.0, 120.1, 108.9, 108.5, 97.9, 80.3, 66.9, 57.7, 49.4, 40.3, 29.0, 27.1, 22.4, 14.0; MS (ES+) m/z 393.5 (M+1).

Example 35

Synthesis of 6-amino-1'-pentylspiro[1-benzofuran-3,3'-indol]-2'(1'H)-one

A. Synthesis of 6-[(diphenylmethylene)amino]-1'-pentylspiro[1-benzofuran-3,3'-indol]-2'(1'H)-one To a solution of 6-bromo-1'-pentylspiro[1-benzofuran-3,3'-indol]-2'(1'H)one (0.10 g, 0.26 mmol) in anhydrous toluene (5.00 mL) was added benzophenone imine (0.09 g, 0.52 mmol), sodium t-butoxide (0.03 g, 0.36 mmol), tris(dibenzylideneacetone) dipalladium(0) (0.01 g, 0.07 mmol) and (±)-2,2'-bis(diphenylphosphino)-1,1'-binaphthalene (0.12 g, 0.19 mmol). The reaction mixture was refluxed for 16 h, cooled down to ambient temperature, diluted with dichloromethane (50.0 mL) and filtered through a celite bed. The filtrate was concentrated in vacuo to dryness to give the title compound which was used in next step without purification.

B. Synthesis of 6-amino-1'-pentylspiro[1-benzofuran-3,3'-indol]-2'(1'H)-one

To a solution of 6-[(diphenylmethylene)amino]-1-pentylspiro[1-benzofuran-3,3'-indol]-2'(1'H)-one in anhydrous tetrahydrofuran (4.00 mL) was added aqueous 10% hydrochloric acid (2.00 mL). The reaction mixture was stirred for 15 min, diluted with aqueous sodium bicarbonate (5.00 mL) and extracted with ethyl acetate (3×25.0 mL). The combined organic solution was dried over sodium sulfate and filtered. The filtrate was concentrated in vacuo to dryness. The residue was subjected to column chromatography (ethyl acetate/hexane, 1/1) to give the title compound (0.02 g, 24% yield) as a yellow oil: $^1$H NMR (300 MHz, CDCl$_3$) δ 7.26 (td, 1H), 7.12 (d, 1H), 6.99 (dd, 1H), 6.89 (d, 1H), 6.43 (d, 1H), 6.23 (d, 1H), 6.08 (dd, 1H), 4.86 (d, 1H), 4.60 (d, 1H), 3.86-3.60 (m, 2H), 1.77-1.65 (m, 2H), 1.41-1.30 (m, 4H), 0.89 (t, 3H); $^{13}$C NMR (75 MHz, CDCl$_3$) δ 177.8, 171.2, 162.1, 148.7, 142.5, 133.1, 128.6, 127.8, 123.9, 123.7, 123.0, 118.5, 108.5, 108.4, 97.2, 80.2, 77.6, 77.4, 77.2, 76.8, 64.0, 60.4, 57.6, 40.3, 29.7, 29.0, 27.1, 22.6, 22.4, 22.1, 19.1, 14.2, 14.0, 13.7; MS (ES+) m/z 323.5 (M+1).

Example 36

Synthesis of 1'-pentyl-6-phenoxyspiro[1-benzofuran-3,3'-indol]-2'(1'H)-one

To a solution of 6-bromo-1'-pentylspiro[1-benzofuran-3,3'-indol]-2'(1'H)-one (0.08 g, 0.19 mmol) in anhydrous dioxane (4.00 mL) was added copper iodide (0.01 g, 0.01 mmol), N,N-dimethyl glycine hydrochloride (0.01 g, 0.01 mmol), cesium carbonate (0.17 g, 0.52 mmol) and phenol (0.03 g, 0.32 mmol). The resulted mixture was refluxed for 16 h under nitrogen, diluted with dichloromethane (50.0 mL) and filtered through a celite bed. The filtrate was concentrated in vacuo to dryness. The residue was subjected to column chromatography (ethyl acetate/hexane, 1/6) to give the title compound (0.07 g, 87%) as a colorless oil: $^1$H NMR (300 MHz, CDCl$_3$) δ 7.36-7.28 (m, 3H), 7.20-7.00 (m, 4H), 6.92 (d, 1H), 6.62 (dd, 1H), 6.58 (br, 1H), 6.44 (dd, 1H), 4.95 (d, 1H), 4.71 (d, 1H), 3.92-3.64 (m, 2H), 1.70-1.68 (m, 2H), 1.43-1.34 (m, 4H), 0.92 (t, 3H); MS (ES+) m/z 400.5 (M+1).

Example 37

Synthesis of 1'-pentyl-6-pyridin-3-ylspiro[1-benzofuran-3,3'-indol]-2'(1'H)-one

A mixture of 6-bromo-1'-pentylspiro[1-benzofuran-3,3'-indol]-2'(1'H)-one (0.08 g, 0.19 mmol), pyridine-3-boronic acid (0.05 g, 0.41 mmol), palladium acetate (0.002 g, 0.07 mmol), tri-O-tolylphosphine (0.0015 g, 0.005 mmol), 2 M sodium carbonate (1.00 mL) and 1,2-dimethoxyethane (9.00 mL) was heated at reflux for 16 hours under N$_2$. The solvent was evaporated and the black residue was extracted with ethyl acetate (4×15.0 mL). The combined organics was dried over sodium sulfate and filtered. The filtrate was concentrated in vacuo to dryness. The residue was subjected to column chromatography (ethyl acetate/hexane, 4/1) to give the title compound (0.07 g, 67% yield) as a white solid: $^1$H NMR (300 MHz, CDCl$_3$) δ 8.60 (br, 1H), 7.85 (d, 1H), 7.45-7.24 (m, 3H), 7.20-7.10 (m, 2H), 7.12-6.98 (m, 2H), 6.95 (d, 1H), 6.81 (d, 1H), 5.05 (d, 1H), 4.78 (d, 1H), 3.89-3.64 (m, 2H), 1.80-

1.68 (m, 2H), 1.43-1.34 (m, 4H), 0.92 (t, 3H); $^{13}$C NMR (75 MHz, CDCl$_3$) δ 176.9, 161.6, 149.5, 147.3, 142.6, 139.9, 136.4, 135.6, 133.4, 130.1, 129.2, 124.9, 121.7, 119.5, 110.3, 109.7, 107.7, 80.1, 57.8, 42.3, 28.8, 27.1, 22.3, 14.85; MS (ES+) m/z 385.5 (M+1).

Example 38

Synthesis of 1'-pentyl-6-pyridin-4-ylspiro[1-benzofuran-3,3'-indol]-2'(1'H)-one

Following the procedure as described in EXAMPLE 37, and making non-critical variations using 4-pyridine boronic acid to replace 3-pyridine boronic acid, the title compound was obtained (38%) as white solid: mp 107-110° C.; $^1$H NMR (300 MHz, CDCl$_3$) δ 8.64-8.58 (m, 2H), 7.45-7.40 (m, 2H), 7.31 (dt, 1H), 7.19-7.13 (m, 2H), 6.93 (d, 1H), 6.79 (d, 1H), 4.95 (d, 1H), 4.75 (d, 1H), 3.88-3.64 (m, 2H), 1.80-1.68 (m, 2H), 1.43-1.34 (m, 4H), 0.90 (t, 3H); MS (ES+) m/z 385.5 (M+1).

Example 39

Synthesis of 6-(methylsulfonyl)-1'-pentylspiro[1-benzofuran-3,3'-indol]-2'(1'H)-one A mixture of 6-bromo-1'-pentylspiro[1-benzofuran-3,3'-indol]-2'(1'H)-one (0.60 g, 1.55 mmol), sodium methanesulfinate (0.19 g, 1.86 mmol), copper iodide (0.03 g, 0.16 mmol), and L-proline (0.04 g, 0.31 mmol) in dimethyl sulfoxide (3.00 mL) was heated at 100° C. for 2 days under N$_2$. The reaction mixture was diluted with water (50.0 mL) and extracted with ethyl acetate (4×15.0 mL). The combined organics was dried over sodium sulfate and filtered. The filtrate was concentrated in vacuo to dryness. The residue was subjected to column chromatography (ethyl acetate/hexane, 2/3) to give the title compound (0.03 g, 46%) as a light yellow oil: $^1$H NMR (300 MHz, CDCl$_3$) δ 7.46-7.48 (m, 1H), 7.38 (dt, 1H), 7.34 (dt, 1H), 7.13-7.02 (m, 2H), 6.94 (d, 1H), 6.86 (d, 1H), 5.03 (d, 1H), 4.78 (d, 1H), 3.87-3.64 (m, 2H), 3.02 (s, 3H), 1.79-1.68 (m, 2H), 1.41-1.32 (m, 4H), 0.90 (t, 3H); $^{13}$C NMR (75 MHz, CDCl$_3$) δ 176.1, 161.2, 142.6, 142.1, 135.4, 131.5, 129.5, 124.3, 124.0, 123.5, 120.7, 109.5, 109.0, 80.5, 57.7, 44.5, 40.6, 29.0, 27.1, 22.3, 14.0; MS (ES+) m/z 386.5 (M+1).

Example 40

Synthesis of 1'-pentyl-6-(phenylsulfonyl)spiro[1-benzofuran-3,3'-indol]-2'(1'H)-one Following the procedure as described in EXAMPLE 39, and making non-critical variations using sodium phenyl sulfinate to replace sodium methanesulfinate, the title compound was obtained (50%) as a yellowish oil: $^1$H NMR (300 MHz, CDCl$_3$,) δ 7.94-7.88 (m, 2H), 7.60-7.44 (m, 4H), 7.40 (dd, 1H), 7.31 (dt, 1H), 7.10-6.99 (m, 2H), 6.92 (d, 1H), 6.78 (d, 1H), 4.98 (d, 1H), 4.72 (d, 1H), 3.84-3.61 (m, 2H), 1.75-1.65 (m, 2H), 1.39-1.30 (m, 4H), 0.88 (t, 3H); $^{13}$C NMR (75 MHz, CDCl$_3$) δ 176.1, 161.2, 143.2, 142.5, 141.2, 134.9, 133.3, 129.4, 129.3, 127.8, 124.1, 124.0, 123.5, 121.1, 109.8, 108.9, 80.5, 57.7, 40.5, 29.0, 27.1, 22.3, 14.0; MS (ES+) m/z 448.5 (M+1).

Example 41

Synthesis of 1'-pentyl-5-phenoxyspiro[1-benzofuran-3,3'-indol]-2'(1'H)-one

Following the procedure as described in EXAMPLE 36, and making non-critical variations using 5-bromo-1'-pentyl-spiro[1-benzofuran-3,3'-indol]-2'(1'H)-one to replace 6-bromo-1'-pentylspiro[1-benzofuran-3,3'-indol]-2'(1'H)-one, the title compound was obtained (10% yield) as a colorless oil: $^1$H NMR (300 MHz, CDCl$_3$) δ 7.32-7.10 (m, 5H), 7.06-6.82 (m, 6H), 6.42 (d, 1H), 4.95 (d, 1H), 4.71 (d, 1H), 3.82-3.62 (m, 2H), 1.75-1.63 (m, 2H), 1.43-1.34 (m, 4H), 0.85 (t, 3H); MS (ES+) m/z 400.4 (M+1).

Example 42

Synthesis of 1'-(diphenylmethyl)-5-(4,4,5,5-tetramethyl-1,3,2-dioxaborolan-2-yl)spiro[1-benzofuran-3,3'-indol]-2'(1'H)-one A mixture of 5-bromo-1'-(diphenylmethyl)spiro[1-benzofuran-3,3'-indol]-2'(1'H)-one (3.00 g, 6.22 mmol), bis(pinacolato)diboron (1.80 g, 7.09 mmol), (1,1'-bis(diphenylphosphino)ferrocene)dichloropalladium(II) (0.45 g, 9 mole %), and potassium acetate (5.49 g, 56.0 mmol) in anhydrous dimethyl sulfoxide (40.0 mL) was stirred at 100° C. under N$_2$ for 16 h. The reaction mixture was diluted with water (600 mL). The aqueous mixture was extracted with ethyl acetate (3×200 mL). The combined organic layers was dried over anhydrous sodium sulfate and filtered. The filtrate was concentrated in vacuo. The residue was subjected to column chromatography (ethyl acetate/hexane, 1/6) to give the title compound (1.00 g, 30%) as a white solid: $^1$H NMR (300 MHz, CDCl$_3$) δ 7.68 (dd, 1H), 7.40-7.25 (m, 10H), 7.18 (br, 1H), 7.11 (dd, 1H), 7.06-6.91 (m, 4H), 6.50 (d, 1H), 4.99 (d, 1H), 4.74 (d, 1H), 1.27 (d, 12H); MS (ES+) m/z 530.32 (M+1).

Example 43

Synthesis of 1'-(diphenylmethyl)-5-hydroxyspiro[1-benzofuran-3,3'-indol]-2'(1'H)-one A mixture of 1'-(diphenylmethyl)-5-(4,4,5,5-tetramethyl-1,3,2-dioxaborolan-2-yl)spiro[1-benzofuran-3,3'-indol]-2'(1'H)one (4.50 g, 8.50 mmol), hydrogen peroxide (4.86 mL, 30% solution, 42.5 mmol), sodium hydroxide (16.38 mL, 10% solution, 40.82 mmol) in methanol was stirred at 0° C. for 30 min and ambient temperature for 16 h. The reaction mixture was quenched with sodium bisulfite. The pH of the reaction mixture was adjusted to 4 using 14% hydrochloric acid. The mixture was extracted with ethyl acetate (3×250 mL). The combined organic layers was dried over anhydrous sodium sulfate and filtered. The filtrate was concentrated in vacuo. The residue was triturated with hexane (20.0 mL), followed by ether (15.0 mL) to give the title compound (3.20 g, 90%) as a white solid: $^1$H NMR (300 MHz, CDCl$_3$) δ 7.45-7.38 (m, 10H), 7.13 (dd, 1H), 7.07-6.91 (m, 3H), 6.79 (d, 1H), 6.63 (dd, 1H), 6.50 (d, 1H), 6.12 (d, 1H), 4.96 (d, 1H), 4.69 (d, 1H); MS (ES+) m/z 420.23 (M+1).

Example 44

Synthesis of 5-hydroxyspiro[1-benzofuran-3,3'-indol]-2'(1'H)-one

Following the procedure as described in EXAMPLE 1.28, and making non-critical variations using 1'-(diphenylmethyl)-5-hydroxyspiro[1-benzofuran-3,3'-indol]-2'(1'H)-one to replace 1'-(diphenylmethyl)-5'-methylspiro[furo[2,3-f][1,3]benzodioxole-7,3'-indol]-2'(1'H)-one, the title compound was obtained (48%) as a white solid: $^1$H NMR (300 MHz, DMSO-d$_6$) δ 10.58 (s, 1H), 8.85 (s, 1H), 7.21 (dt, 1H), 7.06 (d, 1H), 6.94 (dd, 1H), 6.89 (d, 1H), 6.72 (d, 1H), 6.54 (dd, 1H), 6.02 (d, 1H), 4.70 (d, 1H), 4.57 (d, 1H); MS (ES+) m/z 254.2 (M+1).

Example 45

Synthesis of 2'-oxo-1',2'-dihydrospiro[1-benzofuran-3,3'-indol]-5-yl trifluoromethanesulfonate To a mixture of 5-hydroxyspiro[1-benzofuran-3,3'-indol]-2'(1'H)one (0.18 g, 0.70 mmol) and trifluoromethane sulfonic anhydride (0.26 g, 0.91 mmol) in dichloromethane (5.00 mL) was added triethylamine (0.14 g, 1.93 mmol) at 0° C. The reaction mixture was stirred at ambient temperature for 16 h and diluted with dichloromethane (100 mL). After washing with aqueous saturated sodium chloride (2×20.0 mL), the organic layer was dried over anhydrous sodium sulfate and filtered. The filtrate was concentrated in vacuo. The residue was subjected to column chromatography (ethyl acetate/hexane, 1/2) to give the title compound (0.07 g, 25%) as a light yellow solid: $^1$H NMR (300 MHz, CDCl$_3$) δ 7.92 (br, 1H), 7.29 (dt, 1H), 7.15-7.03 (m, 3H), 7.99-6.94 (m, 2H), 6.69 (d, 1H), 5.03 (d, 1H), 4.76 (d, 1H); MS (ES+) m/z 386.5 (M+1).

Example 46

Synthesis of 2'-oxo-1'-{[5-(trifluoromethyl)-2-furyl]methyl}-1',2'-dihydrospiro[1-benzofuran-3,3'-indol]-5-yl trifluoromethanesulfonate To a mixture of 2'-oxo-1',2'-dihydrospiro[1-benzofuran-3,3'-indol]-5-yl trifluoromethanesulfonate (0.42 g, 1.10 mmol) and sodium hydroxide (0.07 g, 1.65 mmol) in N,N-dimethylformamide (5.00 mL) was added 2-(bromomethyl)-5-(trifluoromethyl)furan (0.50 g, 2.20 mmol) at 0° C. The reaction mixture was stirred at ambient temperature for 16 h and diluted with ethyl acetate (200 mL). After washing with aqueous saturated sodium chloride (2×20.0 mL), the organic layer was dried over anhydrous sodium sulfate and filtered. The filtrate was concentrated in vacuo. The residue was subjected to column chromatography (ethyl acetate/hexane, 1/3) to give the title compound (0.47 g, 80%) as a clear oil: $^1$H NMR (300 MHz, CDCl$_3$) δ 7.34 (t, 1H), 7.18-6.94 (m, 5H), 6.74 (dd, 1H), 6.55 (dd, 1H), 6.40 (d, 1H), 5.09-4.72 (m, 4H); MS (ES+) m/z 534.4 (M+1).

Example 47

Synthesis of 5-pyridin-3-yl-1'-{[5-(trifluoromethyl)-2-furyl]methyl}spiro[1-benzofuran-3,3'-indol]-2'(1'H)-one hydrochloride Following the procedure as described in EXAMPLE 4.2, and making non-critical variations using 2'-oxo-1'-{[5-(trifluoromethyl)-2-furyl]methyl}-1',2'-dihydrospiro[1-benzofuran-3,3'-indol]-5-yl trifluoromethanesulfonate to replace 2-(4'-bromo-5,6-difluoro-2'-oxospiro[1-benzofuran-3,3'-indol]-1'(2'H)-yl)-N-(2-fluorophenyl)acetamide, and pyridin-3-ylboronic acid to replace pyrimidine-5-boronic acid, 5-pyridin-3-yl-1-{[5-(trifluoromethyl)-2-furyl]methyl}spiro[1-benzofuran-3,3'-indol]-2'(1'H)-one was obtained (74%) as a white solid, which was treated with HCl in ether to give the title compound: mp 98-100° C.; $^1$H NMR (300 MHz, CD$_3$OD) δ 8.96 (br, 1H), 8.74-8.65 (m, 2H), 8.04 (dd, 1H), 7.73 (dd, 1H), 7.37 (dt, 1H), 7.25-7.09 (m, 5H), 6.95 (dd, 1H), 6.67 (d, 1H), 5.20-4.83 (m, 4H); $^{13}$C NMR (75 MHz, CD$_3$OD). δ 175.7, 161.3, 151.1, 142.1, 140.2, 138.6, 137.5, 137.4, 130.0, 129.4, 128.1, 127.5, 125.6, 125.5, 122.3, 122.1, 120.8, 111.4, 111.3, 109.7, 108.1, 107.7, 78.7, 58.3, 34.9; MS (ES+) m/z 463.1 (M+1).

Example 48

Synthesis of 1'-pentyl-5-pyridin-3-ylspiro[1-benzofuran-3,3'-indol]-2'(1'H)-one

Following the procedure as described in EXAMPLE 4.2, and making non-critical variations using 5-bromo-1'-pentylspiro[1-benzofuran-3,3'-indol]-2'(1'H)one to replace 2-(4'-bromo-5,6-difluoro-2'-oxospiro[1-benzofuran-3,3'-indol]-1'(2'H)-yl)-N-(2-fluorophenyl)acetamide, and pyridin-3-ylboronic acid to replace pyrimidine-5-boronic acid, the title compound was obtained (70%) was obtained as a white solid: $^1$H NMR (300 MHz, CDCl$_3$) δ 8.55 (br, 1H), 7.65 (d, 1H), 7.45-6.98 (m, 7H), 6.92 (d, 1H), 6.85 (d, 1H), 4.98 (d, 1H), 4.72 (d, 1H), 3.89-3.64 (m, 2H), 1.80-1.68 (m, 2H), 1.43-1.34 (m, 4H), 0.86 (t, 3H); MS (ES+) m/z 385.5 (M+1).

Example 49

Synthesis of 1'-pentyl-5-pyrimidin-5-ylspiro[1-benzofuran-3,3'-indol]-2'(1'H)-one Following the procedure as described in EXAMPLE 4.2, and making non-critical variations using 5-bromo-1'-pentylspiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, the title compound was obtained (40%) was obtained as a white solid: mp 115-117° C.; $^1$H NMR (300 MHz, CDCl$_3$) δ 9.08 (s, 1H), 8.74 (s, 1H), 7.41 (dd, 1H), 7.33 (dt, 1H), 7.16 (dd, 1H), 7.11-7.01 (m, 2H), 6.95 (d, 1H), 6.86 (d, 1H), 5.01 (d, 1H), 4.75 (d, 1H), 3.89-3.64 (m, 2H), 1.80-1.68 (m, 2H), 1.43-1.34 (m, 4H), 0.88 (t, 3H); MS (ES+) m/z 386.4 (M+1).

Example 50

Synthesis of 1'-pentyl-5-pyridin-4-ylspiro[1-benzofuran-3,3'-indol]-2'(1'H)-one

Following the procedure as described in EXAMPLE 4.2, and making non-critical variations using 5-bromo-1'-pentylspiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, and pyridin-4-ylboronic acid to replace pyrimidine-5-boronic acid, the title compound was obtained (95%) as a white solid: $^1$H NMR (300 MHz, CDCl$_3$) δ 8.55-8.47 (m, 2H), 7.52-7.46 (dd, 1H), 7.35-7.26 (m, 3H), 7.15 (dd, 1H), 7.07-7.00 (m, 2H), 6.97-6.92 (m, 2H), 4.99 (d, 1H), 4.73 (d, 1H), 3.89-3.67 (m, 2H), 1.80-1.68 (m, 2H), 1.43-1.34 (m, 4H), 0.92 (t, 3H); MS (ES+) m/z 385.5 (M+1).

Example 51

Synthesis of 2'-oxo-1'-pentyl-1',2'-dihydrospiro[1-benzofuran-3,3'-indole]-5-carbonitrile Following the procedure as described in EXAMPLE 30, and making non-critical variations using 5-bromo-1'-pentylspiro[1-benzofuran-3,3'-indol]-2'(1'H)-one to replace 4'-bromo-1'-pentylspiro[furo[2,3-f][1,3]benzodioxole-7,3'-indol]-2'(1'H)-one, the title compound was obtained (78%) as a white solid: $^1$H NMR (300 MHz, CDCl$_3$) δ 7.51 (dt, 1H), 7.34 (dt, 1H), 7.12-6.91 (m, 5H), 5.01 (d, 1H), 4.76 (d, 1H), 3.86-3.63 (m, 2H), 1.80-1.68 (m, 2H), 1.43-1.32 (m, 4H), 0.92 (t, 3H); $^{13}$C NMR (75 MHz, CDCl$_3$) δ 176.2, 164.1, 142.6, 134.8, 131.4, 130.8, 129.6, 127.8, 123.9, 123.5, 118.8, 111.5, 109.1, 104.7, 80.6, 57.3, 40.6, 29.0, 27.1, 22.3, 14.0; MS (ES+) m/z 333.5 (M+1).

Example 52

Synthesis of N-(2-fluorophenyl)-2-(2'-oxo-5-pyridin-3-ylspiro[1-benzofuran-3,3'-indol]-1'(2'H)-yl)acetamide Following the procedure as described in EXAMPLE 37, and making non-critical variations using 2-(5-bromo-2'-oxospiro[1-benzofuran-3,3'-indol]-1'(2'H)-yl)-N-(2-fluorophenyl)acetamide to replace 6-bromo-1'-pentylspiro[1-benzofuran-3,3'-indol]-2'(1'H)-one, the title compound was obtained (55% yield) was obtained as a white solid: mp 98-100° C.; $^1$H NMR (300 MHz, CDCl$_3$) δ 8.60-8.53 (m, 2H), 8.14 (dd, 1H), 7.65 (dd, 1H), 7.41 (dd, 1H), 7.32-6.90 (m, 11H), 5.02 (d, 1H), 4.76 (d, 1H), 4.72 (d, 1H), 4.56 (d, 1H); $^{13}$C NMR (75 MHz, CDCl$_3$) δ 177.9, 164.8, 160.9, 154.2, 151.0, 147.1, 141.7, 134.2, 131.7, 131.5, 129.9, 129.4, 129.1, 125.1, 124.6, 124.5, 124.2, 124.0, 122.5, 122.2, 115.1, 114.8, 111.0, 109.1, 80.0, 58.1, 44.6; MS (ES+) m/z 466.4 (M+1).

Example 53

Synthesis of 1'-[(5-fluoro-1H-benzimidazol-2-yl)methyl]spiro[furo[2,3-f][1,3]benzodioxole-7,3'-indol]-2'(1'H)-one A mixture of (2'-oxospiro[furo[2,3-f][1,3]benzodioxole-7,3'-indol]-1'(2'H)-yl)acetic acid (0.50 g, 1.47 mmol) and 4-fluorobenzene-1,2-diamine (0.15 g, 1.18 mmol) in anhydrous toluene (20.0 mL) was refluxed overnight under N$_2$. The reaction mixture was diluted with water (250 mL) and extracted with ethyl acetate (2×200 mL). The combined organic extracts was dried over anhydrous sodium sulfate and filtered. The filtrate was concentrated in vacuo to dryness. The residue was subjected to column chromatography (ethyl acetate/hexane, 2/1) to give the title compound (0.13 g, 22%): mp 138-142° C.; $^1$H NMR (300 MHz, CDCl$_3$) δ 7.47-7.39 (m, 1H), 7.32-7.22 (m, 2H), 7.16-6.93 (m, 3H), 6.18 (s, 1H), 6.07 (s, 1H), 5.84-5.78 (m, 2H), 5.20-5.14 (m, 2H), 4.98 (d, 1H), 4.60 (d, 1H); $^{13}$C NMR (75 MHz, CDCl$_3$) δ 179.2, 161.3, 158.1, 156.2, 149.2, 149.1, 142.5, 141.2, 131.5, 129.5, 124.4, 124.0, 118.0, 111.6, 111.2, 109.9, 103.1, 101.7, 93.5, 80.5, 58.5, 38.9; MS (ES+) m/z 430.2 (M+1).

Example 54

Synthesis of 1'-(diphenylmethyl)-5-pyridin-3-ylspiro[1-benzofuran-3,3'-indol]-2'(1'H)-one Following the procedure as described in EXAMPLE 4.2, and making non-critical variations using 5-bromo-1'-(diphenylmethyl)spiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, and pyridin-3-ylboronic acid to replace pyrimidine-5-boronic acid, the title compound was obtained (74%) as a white solid: mp 204-207° C.; $^1$H NMR (300 MHz, CDCl$_3$) δ 8.62-8.46 (m, 2H), 7.62 (d, 1H), 7.43-7.26 (m, 11H), 7.16 (dd, 1H), 7.03-6.94 (m, 4H), 6.76 ((d, 1H), 6.54 (d, 1H), 5.09 (d, 1H), 4.82 (d, 1H); MS (ES+) m/z 481.5 (M+1).

Example 55

Synthesis of tert-butyl 3-(2'-oxo-1',2'-dihydrospiro[1-benzofuran-3,3'-indol]-5-yl)piperidine-1-carboxylate A. Synthesis of 5-piperidin-3-ylspiro[1-benzofuran-3,3'-indol]-2'(1'H)-one Following the procedure as described in EXAMPLE 1.28, and making non-critical variations using 1'-(diphenylmethyl)-5-pyridin-3-ylspiro[1-benzofuran-3,3'-indol]-2'(1'H)-one to replace 1'-(diphenylmethyl)-5'-methylspiro[furo[2,3-f][1,3]benzodioxole-7,3'-indol]-2'(1'H)-one, the title compound was obtained that was used in the next step.

B. Synthesis of tert-butyl 3-(2'-oxo-1',2'-dihydrospiro[1-benzofuran-3,3'-indol]-5-yl)piperidine-1-carboxylate To a mixture of 5-piperidin-3-ylspiro[1-benzofuran-3,3'-indol]-2'(1'H)-one, triethylamine (0.95 g, 9.36 mmol) in anhydrous dichloromethane (15.0 mL) was added di-tert-butyl dicarbonate (1.02 g, 4.68 mmol) at 0° C. The reaction mixture was stirred at ambient temperature and stirred over night under N$_2$, diluted with dichloromethane (100 mL) and filtered through celite. The filtrate was concentrated in vacuo to dryness. The brown residue was subjected to column chromatography (ethyl acetate/hexane, 1/1) to give the title compound (0.50 g, 40%) as a white solid: mp 120-123° C.; $^1$H NMR (300 MHz, CDCl$_3$) δ 7.82 (br, 1H), 7.23-7.21 (m, 2H), 7.14-6.86 (m, 5H), 6.63 (br, 1H), 4.95 (d, 1H), 4.69 (d, 1H), 4.10-4.00 (m, 2H), 2.70-2.45 (m, 2H), 1.95-1.80 (m, 2H), 1.48-1.38 (m, 11H); MS (ES+) m/z 443.4 (M+1).

Example 56

Synthesis of tert-butyl 3-(2'-oxo-1-{[5-(trifluoromethyl)-2-furyl]methyl}-1',2'-dihydrospiro[1-benzofuran-3,3'-indol]-5-yl)piperidine-1-carboxylate Following the procedure as described in PREPARATION 1A, and making non-critical variations using tert-butyl 3-(2'-oxo-1,2'-dihydrospiro[1-benzofuran-3,3'-indol]-5-yl)piperidine-1-carboxylate to replace 4-bromoindole, and 2-(bromomethyl)-5-(trifluoromethyl)furan to replace 1-bromopentane, the title compound was obtained (10%) as a white solid: mp 59-61° C.; $^1$H NMR (300 MHz, CDCl$_3$) δ 7.34-7.23 (m, 2H), 7.12 (d, 1H), 7.04-6.96 (m, 2H), 6.89 (d, 1H), 6.75 (s, 1H), 6.50 (s, 1H), 6.41 (s, 1H), 5.10-4.86 (m, 3H), 4.66 (d, 1H), 4.16-3.94 (m, 2H), 2.68-2.38 (m, 2H), 1.90-1.60 (m, 3H), 1.40 (s, 10H), 1.27-1.21 (m, 1H); MS (ES+) m/z 591.2 (M+23).

Example 57

Synthesis of 5-pyridin-4-yl-1'-{[5-(trifluoromethyl)-2-furyl]methyl}spiro[1-benzofuran-3,3'-indol]-2'(1'H)-one hydrochloride Following the procedure as described in EXAMPLE 4.2, and making non-critical variations using 2'-oxo-1'-{[5-(trifluoromethyl)-2-furyl]methyl}-1',2'-dihydrospiro[1-benzofuran-3,3'-indol]-5-yl trifluoromethanesulfonate to replace 2-(4'-bromo-5,6-difluoro-2'-oxospiro[1-benzofuran-3,3'-indol]-1'(2'H)-yl)-N-(2-fluorophenyl)acetamide, and pyridin-4-ylboronic acid to replace pyrimidine-5-boronic acid, 5-pyridin-4-yl-1-{[5-(trifluoromethyl)-2-furyl]methyl}spiro[1-benzofuran-3,3'-indol]-2'(1'H)-one was obtained as a white solid, which was treated with HCl in ether to give the title compound (54%): mp 108-110° C.; $^1$H NMR (300 MHz, CDCl$_3$) δ 8.57-8.47 (m, 2H), 7.52 (dd, 1H), 7.37-7.29 (m, 3H), 7.18 (dd, 1H), 7.12-7.00 (m, 3H), 6.92 (d, 1H), 6.75 (dd, 1H), 6.43 (d, 1H), 5.11 4.83 (m, 3H), 4.75 (d, 1H); $^{13}$C NMR (75 MHz, CDCl$_3$) δ 176.2, 164.3, 156.7, 151.5, 141.5, 140.8, 131.5, 131.1, 130.7, 129.8, 127.7, 124.3, 124.1, 123.4, 123.1, 112.9, 112.2, 110.0, 109.4, 80.9, 57.5, 37.3; MS (ES+) m/z 466.4 (M+1).

Example 58

Synthesis of 5-methoxy-1'-methylspiro[1-benzofuran-3,3'-indol]-2'(1'H)one

To a mixture of 5-hydroxyspiro[1-benzofuran-3,3'-indol]-2'(1'H)-one (0.10 g, 0.39 mmol), triphenylphosphine (0.20 g, 0.76 mmol) and methanol (0.05 g, 1.6 mmol) in anhydrous tetrahydrofuran was added diethyl azodicarboxylate (0.14 g, 0.80 mmol) at 0° C. The reaction mixture was stirred at ambient temperature under N$_2$ for 16 h and concentrated in vacuo to dryness. The brown residue was subjected to column chromatography (ethyl acetate/hexane, 1/1) to give the title compound (0.02 g, 14% yield) as a yellowish solid: mp 159-161° C.; $^1$H NMR (300 MHz, CDCl$_3$) δ 7.32 (dt, 1H), 7.14 (d, 1H), 7.05 (t, 1H), 6.93-6.83 (m, 2H), 6.74 (dd, 1H), 6.25 (d, 1H), 4.89 (d, 1H), 4.63 (d, 1H), 3.63 (s, 3H), 3.28 (s, 3H); MS (ES+) 282.3 (M+1).

Example 59

Synthesis of N-[2-(2'-oxospiro[furo[2,3-f][1,3]benzodioxole-7,3'-indol]-1'(2'H)-yl)ethyl]-2-(trifluoromethoxy)benzamide Following the procedure as described in EXAMPLE 17, and making non-critical variations using 1'-(2-aminoethyl)spiro[furo[2,3-f][1,3]benzodioxole-7,3'-indol]-2'(1'H)-one to replace 1'-(3-aminopropyl)spiro[furo[2,3-f][1,3]benzodioxole-7,3'-indol]-2'(1'H)-one, and 2-(trifluoromethoxy)benzoyl chloride to replace 3-chlorothiophene-2-carbonyl chloride, the title compound was obtained (91%) as a colorless solid: mp 183-184° C.; $^1$H NMR (300 MHz, CDCl$_3$) δ 7.86-7.83 (m, 1H), 7.50-7.45 (m, 1H), 7.37-7.27 (m, 3H), 7.16-7.11 (m, 2H), 7.07-7.02 (m, 1H), 6.84 (t, 1H), 6.47 (s, 1H), 6.10 (s, 1H), 5.82 (dd, 2H), 4.87 (d, 1H), 4.64 (d, 1H), 4.10-3.94 (m, 2H), 3.90-3.68 (m, 2H); $^{13}$C NMR (75 MHz, CDCl$_3$) δ 178.2, 165.0, 155.9, 148.8, 145.9, 142.3, 141.9, 132.4, 132.1, 131.3, 129.2, 127.6, 127.3, 124.0, 123.6, 121.2, 121.1, 119.2, 108.7, 103.0, 101.4, 93.6, 80.4, 58.2, 39.5, 38.2; MS (ES+) m/z 513.4 (M+1).

Biological Assays

Various techniques are known in the art for testing the activity of compounds of the invention. In order that the invention described herein may be more fully understood, the following biological assays are set forth. It should be understood that these examples are for illustrative purposes only and are not to be construed as limiting this invention in any manner.

Biological Example 1

Guanidine Influx Assay (In Vitro Assay)

This example describes an in vitro assay for testing and profiling test agents against human or rat sodium channels stably expressed in cells of either an endogenous or recombinant origin. The assay is also useful for determining the IC$_{50}$ of a sodium channel blocking compound. The assay is based on the guanidine flux assay described by Reddy, N. L., et al., *J Med Chem* (1998), 41(17):3298-302.

The guanidine influx assay is a radiotracer flux assay used to determine ion flux activity of sodium channels in a high-throughput microplate-based format. The assay uses $^{14}$C-guanidine hydrochloride in combination with various known sodium channel modulators, to assay the potency of test agents. Potency is determined by an IC$_{50}$ calculation. Selectivity is determined by comparing potency of the compound for the channel of interest to its potency against other sodium channels (also called 'selectivity profiling').

Each of the test agents is assayed against cells that express the sodium channel of interest. Voltage gated sodium channels are either TTX sensitive or insensitive. This property is useful when evaluating the activities of a channel of interest when it resides in a mixed population with other sodium channels. The following Table 1 lists certain cell lines which are useful in screening for a certain sodium channel activity in the presence or absence of TTX.

TABLE 1

| CELL LINE | mRNA Expression | Functional Characterization |
| --- | --- | --- |
| CHO-K1 (Chinese Hamster Ovary; recommended host cell line) ATTC accession number CCL-61 | Na$_v$1.4 expression has been shown by RT-PCR No other Na$_v$ expression has been detected | The 18-20-fold increase in [$^{14}$C] Guanidine influx was completely blocked using TTX. (Na$_v$1.4 is a TTX sensitive channel) |
| L6 (rat myoblast cell) ATTC Number CRL-1458 | Expression of Na$_v$1.4 and 1.5 | The 10-15 fold increase in [$^{14}$C] Guanidine influx was only partially blocked by TTX (Na$_v$1.5 is TTX resistant) |
| SH-SY5Y (Human neuroblastoma) ATTC Number CRL-2266 | Published Expression of Na$_v$1.9 and Na$_v$1.7 (Blum et al) | The 10-16-fold increase in [$^{14}$C] Guanidine influx above background. was partially blocked by TTX (Na$_v$1.9 is TTX resistant) |

TABLE 1-continued

| CELL LINE | mRNA Expression | Functional Characterization |
|---|---|---|
| SK-N-BE2C (a human neuroblastoma cell line ATCC Number CRL-2268) | Expression of $Na_v1.8$ | Stimulation of BE2C cells with pyrethroids results in a 6 fold increase in [$^{14}$C] Guanidine influx above background. TTX partially blocked influx ($Na_v1.8$ is TTX resistant) |
| PC12 (rat pheochromocytoma) ATTC Number CRL-1721 | Expression of $Na_v1.2$ expression | The 8-12-fold increase in [$^{14}$C] Guanidine influx was completely blocked using TTX. ($Na_v1.2$ is a TTX sensitive channel) |

It is also possible to employ recombinant cells expressing these sodium channels. Cloning and propagation of recombinant cells are known to those skilled in the art (see, for example, Klugbauer, N, et al., *EMBO J.* (1995), 14(6):1084-90; and Lossin, C., et al., *Neuron* (2002), 34, pp. 877-884)

Cells expressing the channel of interest are grown according to the supplier or in the case of a recombinant cell in the presence of selective growth media such as G418 (Gibco/Invitrogen). The cells are disassociated from the culture dishes with an enzymatic solution (1x) Trypsin/EDTA (Gibco/Invitrogen) and analyzed for density and viability using haemocytometer (Neubauer). Disassociated cells are washed and resuspended in their culture media then plated into Scintiplates (Beckman Coulter Inc.) (approximately 100,000 cells/well) and incubated at 37° C./5% $CO_2$ for 20-24 hours. After an extensive wash with Low sodium HEPES-buffered saline solution (LNHBSS) (150 mM Choline Chloride, 20 nM HEPES (Sigma), 1 mM Calcium Chloride, 5 mM Potassium Chloride, 1 mM Magnesium Chloride, 10 mM Glucose) agents diluted with LNHBSS are added to each well. (Varying concentrations of test agent may be used). The activation/radiolabel mixture contains aconitine (Sigma), and $^{14}$C-guanidine hydrochloride (ARC).

After loading the cells with test agent and activation/radiolabel mixture, the Scintiplates are incubated at ambient temperature. Following the incubation, the Scintplates are extensively washed with LNHBSS supplemented with guanidine (Sigma). The Scintiplates are dried and then counted using a Wallac MicroBeta TriLux (Perkin-Elmer Life Sciences). The ability of the test agent to block sodium channel activity is determined by comparing the amount of $^{14}$C-guanidine present inside the cells expressing the different sodium channels. Based on this data, a variety of calculations, as set out elsewhere in this specification, may be used to determine whether a test agent is selective for a particular sodium channel.

$IC_{50}$ value of a test agent for a specific sodium channel may be determined using the above general method. $IC_{50}$ may be determined using a 3, 8, 10, 12 or 16 point curve in duplicate or triplicate with a starting concentration of 1, 5 or 10 µM diluted serially with a final concentration reaching the sub-nanomolar, nanomolar and low micromolar ranges. Typically the mid-point concentration of test agent is set at 1 µM, and sequential concentrations of half dilutions greater or smaller are applied (e.g. 0.5 µM; 5 µM and 0.25 µM; 10 µM and 0.125 µM; 20 µM etc.). The $IC_{50}$ curve is calculated using the 4 Parameter Logistic Model or Sigmoidal Dose-Response Model formula (fit=$(A+((B-A)/(1+((C/x)^D))))$.

The fold selectivity, factor of selectivity or multiple of selectivity, is calculated by dividing the $IC_{50}$ value of the test sodium channel by the reference sodium channel, for example, $Na_v1.5$.

Representative compounds of the invention, when tested in the above assay using a known cell line that expresses a sodium channel, demonstrated an $IC_{50}$ (nM) activity level as set forth below in Table 2 wherein "A" refers to an $IC_{50}$ activity level of from 1 nM to 10 nM, "B" refers to an $IC_{50}$ activity level from 10 nM to 100 nM, "C" refers to an $IC_{50}$ activity level from 100 nM to 1000 nM, and "D" refers to an $IC_{50}$ activity level equal to or greater than 1000 nM. The Example numbers provided in Table 2 correspond to the Example numbers herein:

TABLE 2

| Example Number | Compound Name | $IC_{50}$ Activity Data (nM) |
|---|---|---|
| Example 1 | 1'-(2-cyclopropylethyl)spiro[furo[2,3-f][1,3]benzodioxole-7,3'-indol]-2'(1'H)-one | A |
| Example 2 | (2'-oxospiro[furo[2,3-f][1,3]benzodioxole-7,3'-indol]-1'(2'H)-yl)acetic acid | D |
| Example 3 | N-(4-chlorobenzyl)-2-(2'-oxospiro[furo[2,3-f][1,3]benzodioxole-7,3'-indol]-1'(2'H)-yl)acetamide | C |
| Example 4 | 4'-[6-(dimethylamino)pyridin-3-yl]-1'-pentylspiro[furo[2,3-f][1,3]benzodioxole-7,3'-indol]-2'(1'H)-one | C |
| Example 5 | 4'-[(6-methoxypyridin-3-yl)amino]-1'-pentylspiro[furo[2,3-f][1,3]benzodioxole-7,3'-indol]-2'(1'H)-one | C |
| Example 6 | 2-[(2'-oxospiro[furo[2,3-f][1,3]benzodioxole-7,3'-indol]-1'(2'H)-yl)methyl]benzoic acid | D |
| Example 7 | N-[2-(4-chlorophenyl)ethyl]-2-[(2'-oxospiro[furo[2,3-f][1,3]benzodioxole-7,3'-indol]-1'(2'H)-yl)methyl]benzamide | C |
| Example 8 | 3-[(2'-oxospiro[furo[2,3-f][1,3]benzodioxole-7,3'-indol]-1'(2'H)-yl)methyl]benzoic acid | C |

TABLE 2-continued

| Example Number | Compound Name | IC$_{50}$ Activity Data (nM) |
|---|---|---|
| Example 9 | N-[2-(3-chlorophenyl)ethyl]-3-[(2'-oxospiro[furo[2,3-f][1,3]benzodioxole-7,3'-indol]-1'(2'H)-yl)methyl]benzamide | C |
| Example 10 | 1'-(4-fluorobenzyl)spiro[furo[2,3-f][1,3]benzodioxole-7,3'-indol]-2'(1'H)-one | B |
| Example 11 | 4-[(2'-oxospiro[furo[2,3-f][1,3]benzodioxole-7,3'-indol]-1'(2'H)-yl)methyl]benzoic acid | D |
| Example 12 | N-(3-fluorophenyl)-4-[(2'-oxospiro[furo[2,3-f][1,3]benzodioxole-7,3'-indol]-1'(2'H)-yl)methyl]benzamide | C |
| Example 13 | 1'-(3-hydroxypropyl)spiro[furo[2,3-f][1,3]benzodioxole-7,3'-indol]-2'(1'H)-one | B |
| Example 15 | 1'-{3-[(cyclopropylmethyl)amino]propyl}spiro[furo[2,3-f][1,3]benzodioxole-7,3'-indol]-2'(1'H)-one | D |
| Example 16 | 1'-(3-aminopropyl)spiro[furo[2,3-f][1,3]benzodioxole-7,3'-indol]-2'(1'H)-one | D |
| Example 17 | 3-chloro-N-[3-(2'-oxospiro[furo[2,3-f][1,3]benzodioxole-7,3'-indol]-1'(2'H)-yl)propyl]thiophene-2-carboxamide | B |
| Example 18 | 1'-(2-aminoethyl)spiro[furo[2,3-f][1,3]benzodioxole-7,3'-indol]-2'(1'H)-one | D |
| Example 19 | 1-(4-fluorophenyl)-3-[2-(2'-oxospiro[furo[2,3-f][1,3]benzodioxole-7,3'-indol]-1'(2'H)-yl)ethyl]urea | D |
| Example 20 | 1'-pentyl-7H-spiro[furo[3,4-f][1,3]benzodioxole-5,3'-indol]-2'(1'H)-one | A |
| Example 21 | 1'-pentylspiro[indeno[5,6-d][1,3]dioxole-5,3'-indole]-2',7(1'H,6H)-dione | A |
| Example 22 | 1-pentyl-6'H-spiro[indole-3,5'-naphtho[2,3-d][1,3]dioxole]-2,8'(1H,7'H)-dione | A |
| Example 23 | 1'-pentyl-6,7-dihydrospiro[indeno[5,6-d][1,3]dioxole-5,3'-indol]-2'(1'H)-one | C |
| Example 24 | 1-pentyl-7',8'-dihydro-6'H-spiro[indole-3,5'-naphtho[2,3-d][1,3]dioxol]-2(1H)-one | A |
| Example 26 | 7-hydroxy-1'-pentyl-6,7-dihydrospiro[indeno[5,6-d][1,3]dioxole-5,3'-indol]-2'(1'H)-one | D |
| Example 27 | 7-methoxy-1'-pentyl-6,7-dihydrospiro[indeno[5,6-d][1,3]dioxole-5,3'-indol]-2'(1'H)-one | D |
| Example 28 | 1'-pentyl-6,7-dihydro-5H-spiro[1,3-dioxolo[4,5-g]isoquinoline-8,3'-indole]-2',5(1'H)-dione | D |
| Example 29 | 2'-oxo-1'-pentyl-N-pyridin-2-yl-1',2'-dihydrospiro[furo[2,3-f][1,3]benzodioxole-7,3'-indole]-4'-carboxamide | D |
| Example 30 | 2'-oxo-1'-pentyl-1',2'-dihydrospiro[furo[2,3-f][1,3]benzodioxole-7,3'-indole]-4'-carbonitrile | B |
| Example 31 | 1'-hexylspiro[1,3-dioxolo[4,5-g]chromene-8,3'-indole]-2',6(1'H,7H)-dione | D |
| Example 32 | 1'-pentylspiro[1-benzofuran-3,3'-indol]-2'(1'H)-one | B |
| Example 33 | 6-anilino-1'-pentylspiro[1-benzofuran-3,3'-indol]-2'(1'H)-one | D |
| Example 34 | 6-morpholin-4-yl-1'-pentylspiro[1-benzofuran-3,3'-indol]-2'(1'H)-one | D |
| Example 36 | 1'-pentyl-6-phenoxyspiro[1-benzofuran-3,3'-indol]-2'(1'H)-one | D |
| example 37 | 1'-pentyl-6-pyridin-3-ylspiro[1-benzofuran-3,3'-indol]-2'(1'H)-one | D |
| Example 38 | 1'-pentyl-6-pyridin-4-ylspiro[1-benzofuran-3,3'-indol]-2'(1'H)-one | C |
| Example 39 | 6-(methylsulfonyl)-1'-pentylspiro[1-benzofuran-3,3'-indol]-2'(1'H)-one | D |
| Example 40 | 1'-pentyl-6-(phenylsulfonyl)spiro[1-benzofuran-3,3'-indol]-2'(1'H)-one | C |
| Example 41 | 1'-pentyl-5-phenoxyspiro[1-benzofuran-3,3'-indol]-2'(1'H)-one | D |
| Example 48 | 1'-pentyl-5-pyridin-3-ylspiro[1-benzofuran-3,3'-indol]-2'(1'H)-one | C |
| Example 49 | 1'-pentyl-5-pyrimidin-5-ylspiro[1-benzofuran-3,3'-indol]-2'(1'H)-one | C |
| Example 50 | 1'-pentyl-5-pyridin-4-ylspiro[1-benzofuran-3,3'-indol]-2'(1'H)-one | C |
| Example 51 | 2'-oxo-1'-pentyl-1',2'-dihydrospiro[1-benzofuran-3,3'-indole]-5-carbonitrile | C |
| Example 52 | N-(2-fluorophenyl)-2-(2'-oxo-5-pyridin-3-ylspiro[1-benzofuran-3,3'-indol]-1'(2'H)-yl)acetamide | C |
| Example 54 | 1'-(diphenylmethyl)-5-pyridin-3-ylspiro[1-benzofuran-3,3'-indol]-2'(1'H)-one | D |
| Example 55 | tert-butyl 3-(2'-oxo-1',2'-dihydrospiro[1-benzofuran-3,3'-indol]-5-yl)piperidine-1-carboxylate | D |

TABLE 2-continued

| Example Number | Compound Name | $IC_{50}$ Activity Data (nM) |
|---|---|---|
| Example 59 | N-[2-(2'-oxospiro[furo[2,3-f][1,3]benzodioxole-7,3'-indol]-1'(2'H)-yl)ethyl]-2-(trifluoromethoxy)benzamide | C |

Biological Example 2

Electrophysiological Assay (In Vitro Assay)

Cells expressing the channel of interest are cultured in DMEM growth media (Gibco) with 0.5 mg/mL G418, +/−1% PSG, and 10% heat-inactivated fetal bovine serum at 37 C.° and 5% $CO_2$. For electrophysiological recordings, cells are plated on 10 mm dishes.

Whole cell recordings are examined by established methods of whole cell voltage clamp (Bean et al., op. cit.) using an Axopatch 200B amplifier and Clampex software (Axon Instruments, Union City, Calif.). All experiments are performed at ambient temperature. Electrodes are fire-polished to resistances of 2-4 Mohms Voltage errors and capacitance artifacts are minimized by series resistance compensation and capacitance compensation, respectively. Data are acquired at 40 kHz and filtered at 5 kHz. The external (bath) solution consists of: NaCl (140 mM), KCl (5 mM), $CaCl_2$ (2 mM), $MgCl_2$ (1 mM), HEPES (10 mM) at pH 7.4. The internal (pipette) solution consists of (in mM): NaCl (5), $CaCl_2$ (0.1) $MgCl_2$ (2), CsCl (10), CsF (120), HEPES (10), EGTA (10), at pH 7.2.

To estimate the steady-state affinity of compounds for the resting and inactivated state of the channel ($K_r$ and $K_i$, respectively), 12.5 ms test pulses to depolarizing voltages from −60 to +90 mV from a holding potential of −110 mV is used to construct current-voltage relationships (I-V curves). A voltage near the peak of the IV-curve (−30 to 0 mV) is used as the test pulse throughout the remainder of the experiment. Steady-state inactivation (availability) curves is then constructed by measuring the current activated during a 8.75 ms test pulse following 1 second conditioning pulses to potentials ranging from −110 to −10 mV. To monitor channels at steady-state, a single "diary" protocol with a holding potential of −110 mV is created to record the resting state current (10 ms test pulse), the current after fast inactivation (5 ms pre-pulse of −80 to −50 mV followed by a 10 ms test pulse), and the current during various holding potentials (35 ms ramp to test pulse levels). Compounds are applied during the "diary" protocol and the block is monitored at 15 s intervals.

After the compounds equilibrate, the voltage-dependence of the steady-state inactivation in the presence of the compound is determined. Compounds that block the resting state of the channel decrease the current elicited during test pulses from all holding potentials, whereas compounds that primarily block the inactivated state decrease the current elicited during test pulses at more depolarized potentials. The currents at the resting state ($I_{rest}$) and the currents during the inactivated state ($I_{inactivated}$) are used to calculate steady-state affinity of compounds. Based on the Michaelis-Menton model of inhibition, the $K_r$ and $K_i$ is calculated as the concentration of compound needed to cause 50% inhibition of the $I_{rest}$ or the $I_{inactivated}$, respectively.

$$\% \text{ inhibition} = \frac{V_{max} * [\text{Drug}]^h}{[\text{Drug}]^h + K_m^h}$$

$V_{max}$ is the rate of inhibition, h is the Hill coefficient (for interacting sites), $K_m$ is Michaelis-Menten constant, and [Drug] is the concentration of the test compound. At 50% inhibition ($½V_{max}$) of the $I_{rest}$ or $I_{inactivated}$, the drug concentration is numerically equal to $K_m$ and approximates the $K_r$ and $K_i$, respectively.

Biological Example 3

In Vivo Assay for Benign Prostate Hyperplasia (BPH)

The effectiveness of the compounds of the present invention for treating BPH can be demonstrated by the following in vivo assay.

Dogs are dosed orally with test compounds at oral doses of between 0 mg/kg and 100 mg/kg for a period of 4 weeks. A control group receives placebo. The animals are sacrificed and the prostate glands dissected out, dabbed dry and then weighed. Test compounds are efficacious in a dose dependent manner within a range of 5 mg/kg and 100 mg/kg if they significantly reduce the weight of the prostate in dogs when compared to the vehicle treated (0 mg/kg) controls.

Biological Example 4

In Vivo Assay for Antihypercholesterlemia Efficacy and Antiatherosclerotic Efficacy The effectiveness of the compounds of the present invention for treating hypercholesterolemia can be demonstrated by the following in vivo assay.

Dogs have cardiovascular systems similar to that of humans, making them ideal for studying the effects of medicinal compounds designed to treat cardiovascular disorders.

Dogs are dosed orally at a range of 0 mg/kg to 100 mg/kg daily with test compounds for a period of 2-4 weeks. After 2 and 4 weeks the animals are bled and their serum collected for total cholesterol analysis and compared to the animals dosed with vehicle alone (0 mg/kg).

The measurement of cholesterol is one of the most common tests performed in the clinical laboratory setting. Simple fluorometric methods for the sensitive quantitation of total cholesterol in plasma or serum are commonly used. In one assay, cholesteryl esters in the sample are first hydrolyzed by cholesterol esterase. All cholesterol, whether previously esterified or existing free in the circulation, is then oxidized by cholesterol oxidase to the corresponding ketone and hydrogen peroxide. ADHP (10-acetyl-3,7-dihydroxyphenoxazine) is utilized as a highly sensitive and stable probe for hydrogen peroxide. Horseradish peroxidase catalyzes the reaction of ADHP with hydrogen peroxide to yield the highly fluorescent product resorufin, which can be monitored using excitation wavelengths of 565-580 nm and emission wavelengths of 585-595 nm.

Biological Example 5

In Vivo Assay for Treatment of Pruritis

The compounds of the invention can be evaluated for their activity as antipruritic agents by in vivo test using rodent models. One established model for peripherally elicited pruritus is through the injection of serotonin into the rostral back area (neck) in hairless rats. Prior to serotonin injections (e.g., 2 mg/ml, 50 µL), a dose of a compound of the present invention can be applied systemically through oral, intravenous or intraperitoneal routes or topically to a circular area fixed diameter (e.g. 18 mm). Following dosing, the serotonin injections are given in the area of the topical dosing. After serotonin injection the animal behaviour is monitored by video recording for 20 min-1.5 h, and the number of scratches in this time compared to vehicle treated animals. Thus, application of a compound of the current invention could suppress serotonin-induced scratching in rats.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of treating pruritus in a mammal, wherein the methods comprises administering to the mammal in need thereof a therapeutically effective amount of a compound of formula (I):

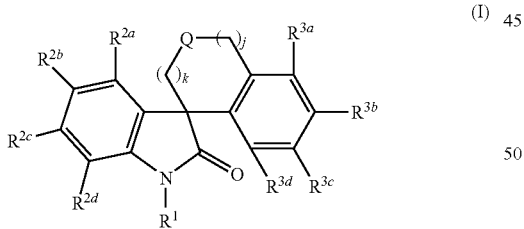

wherein:
j and k are each independently 0, 1, 2 or 3;
Q is;
$R^1$ is hydrogen, alkyl, alkenyl, alkynyl, haloalkyl, aryl, cycloalkyl, cycloalkylalkyl, heteroaryl, heterocyclyl, $-R^8-C(O)R^5$, $-R^8-C(O)OR^5$, $-R^8-C(O)N(R^4)R^5$, $-S(O)_2-R^5$, $-R^9-S(O)_m-R^5$ (where m is 0, 1 or 2), $-R^8-OR^5$, $-R^8-CN$, $-R^9-P(O)(OR^5)_2$, or $-R^9-O-R^9-OR^5$;
or $R^1$ is aralkyl substituted by $-C(O)N(R^6)R^7$ where:
$R^6$ is hydrogen, alkyl, aryl or aralkyl; and
$R^7$ is hydrogen, alkyl, haloalkyl, $-R^9-CN$, $-R^9-OR^5$, $-R^9-N(R^4)R^5$, aryl, aralkyl, cycloalkyl, cycloalkylalkyl, heterocyclyl, heterocyclylalkyl, heteroaryl, or heteroarylalkyl;
or $R^6$ and $R^7$, together with the nitrogen to which they are attached, may form a heterocyclyl or heteroaryl;
and wherein each aryl, aralkyl, cycloalkyl, cycloalkylalkyl, heterocyclyl, heterocyclylalkyl, heteroaryl and heteroarylalkyl groups for $R^6$ and $R^7$ may be optionally substituted by one or more substituents selected from the group consisting of alkyl, cycloalkyl, aryl, aralkyl, halo, haloalkyl, $-R^8-CN$, $-R^8-OR^5$, heterocyclyl and heteroaryl;
or $R^1$ is aralkyl optionally substituted by one or more substituents selected from the group consisting of $-R^8-OR^5$, $-C(O)OR^5$, halo, haloalkyl, alkyl, nitro, cyano, aryl, aralkyl, heterocyclyl and heteroaryl;
or $R^1$ is $-R^9-N(R^{10})R^{11}$, $-R^9-N(R^{12})C(O)R^{11}$ or $-R^9-N(R^{10})C(O)N(R^{10})R^{11}$ where:
each $R^{10}$ is hydrogen, alkyl, aryl, aralkyl or heteroaryl;
each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, $-R^9-OC(O)R^5$, $-R^9-C(O)OR^5$, $-R^9-C(O)N(R^4)R^5$, $-R^9-C(O)R^5$, $-R^9-N(R^4)R^5$, $-R^9-OR^5$, or $-R^9-CN$; and
$R^{12}$ is hydrogen, alkyl, aryl, aralkyl or $-C(O)R^5$;
and wherein each aryl, aralkyl, cycloalkyl, cycloalkylalkyl, heterocyclyl, heterocyclylalkyl, heteroaryl and heteroarylalkyl groups for $R^{10}$ and $R^{11}$ may be optionally substituted by one or more substituents selected from the group consisting of alkyl, cycloalkyl, aryl, aralkyl, halo, haloalkyl, nitro, $-R^8-CN$, $-R^8-OR^5$, $-R^8-C(O)R^5$, heterocyclyl and heteroaryl;
or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, $-R^8-OR^5$, $-R^8-C(O)OR^5$, $-R^8-N(R^4)R^5$, $-R^8-C(O)N(R^4)R^5$, $-R^8-N(R^5)C(O)R^4$, $-R^8-S(O)_m R^4$ (where m is 0, 1 or 2), $-R^8-CN$, or $-R^8-NO_2$;
$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-N=C(R^4)R^5$, $-S(O)_m R^4$, $-OS(O)_2 CF_3$, $-R^8-C(O)R^4$, $-C(S)R^4$, $-C(R^4)_2 C(O)R^5$, $-R^8-C(O)OR^4$, $-C(S)OR^4$, $-R^8-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_n R^4$, $-N(R^5)S(O)_n N(R^4)R^5$, $-R^8-S(O)_n N(R^4)R^5$, $-N(R^5)C(=NR^5)N(R^4)R^5$, and $-N(R^5)C(=N-CN)N(R^4)R^5$, wherein each m is independently 0, 1, or 2 and each n is independently 1 or 2;
and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-S(O)_m R^4$, —$R^8$—$S(O)_nN(R^4)R^5$, —$R^8$—$C(O)R^4$, —$R^8$—$C(O)OR^4$, —$R^8$—$C(O)N(R^4)R^5$, —$N(R^5)C(O)R^4$, and —$N(R^5)S(O)_nR^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2b}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m$R$^4$, —OS(O)$_2$CF$_3$, —$R^8$—C(O)$R^4$, —C(S)$R^4$, —C($R^4$)$_2$C(O)$R^5$, —$R^8$—C(O)OR$^4$, —C(S)OR$^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)OR$^4$, —N($R^5$)C(S)OR$^4$, —N($R^5$)C(O)N($R^4$)$R^5$, —N($R^5$)C(S)N($R^4$)$R^5$, —N($R^5$)S(O)$_n$R$^4$, —N($R^5$)S(O)$_n$N($R^4$)$R^5$, —$R^8$—S(O)$_n$N($R^4$)$R^5$, —N($R^5$)C(=NR$^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3a}$ and $R^{3b}$, together with the carbon ring atoms to which they are directly attached, may form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain;

as a stereoisomer, enantiomer, tautomer thereof or mixtures thereof;

or a pharmaceutically acceptable salt, solvate or prodrug thereof.

\* \* \* \* \*

UNITED STATES PATENT AND TRADEMARK OFFICE
CERTIFICATE OF CORRECTION

PATENT NO. : 8,466,188 B2  
APPLICATION NO. : 12/445264  
DATED : June 18, 2013  
INVENTOR(S) : Mikhail Chafeev et al.

Page 1 of 1

It is certified that error appears in the above-identified patent and that said Letters Patent is hereby corrected as shown below:

On the Title Page

Item (45):
"Jun. 18, 2013" should read, --***Jun. 18, 2013--.

Item (*):
--This patent is subject to a terminal disclaimer.-- was omitted from the face of the patent.

Item (56):
--Official Action from European Patent Office, dated 11/27/08, for Patent Application No. 06 740 804.7, 3 pages-- was omitted from the face of the patent.

Item (56):
--Response to Official Action from European Patent Office, dated 02/11/09, for Patent Application No. 06 740 804.7, 3 pages-- was omitted from the face of the patent.

Item (56):
--International Search Report and Written Opinion, mailed 06/09/11, for PCTAN PCT/US2011/026359, 14 pages-- was omitted from the face of the patent.

In the Claims

Column 299, Line 57:
"Q is;" should read, --Q is -O-;--.

Column 301, Lines 7-8:
"selected from cycloalkyl, aryl, heterocyclyl and heteroaryl, and $R^{2b}$ and $R^{2d}$ are as defined above;" should read, --selected from cycloalkyl, aryl, heterocyclyl and heteroaryl, and $R^{2c}$ and $R^{2d}$ are as defined above;--.

Signed and Sealed this  
Twenty-eighth Day of October, 2014

Michelle K. Lee  
*Deputy Director of the United States Patent and Trademark Office*